US010604514B2

(12) United States Patent
KC et al.

(10) Patent No.: US 10,604,514 B2
(45) Date of Patent: Mar. 31, 2020

(54) 6-(5-MEMBERED HETEROARYL)ISOQUINOLIN-3-YL CARBOXAMIDES AND PREPARATION AND USE THEREOF

(71) Applicant: Samumed, LLC, San Diego, CA (US)

(72) Inventors: Sunil Kumar KC, San Diego, CA (US); Gopi Kumar Mittapalli, San Diego, CA (US); Chandramouli Chiruta, San Diego, CA (US); Brian Joseph Hofilena, San Diego, CA (US); Chi Ching Mak, San Diego, CA (US); Brian Walter Eastman, San Diego, CA (US); Venkataiah Bollu, San Diego, CA (US)

(73) Assignee: Samumed, LLC, San Diego, CA (US)

( * ) Notice: Subject to any disclaimer, the term of this patent is extended or adjusted under 35 U.S.C. 154(b) by 0 days.

(21) Appl. No.: 16/164,447

(22) Filed: Oct. 18, 2018

(65) Prior Publication Data
US 2019/0119263 A1 Apr. 25, 2019

Related U.S. Application Data

(60) Provisional application No. 62/574,568, filed on Oct. 19, 2017, provisional application No. 62/578,691, filed on Oct. 30, 2017.

(51) Int. Cl.
| C07D 413/04 | (2006.01) |
| C07D 413/14 | (2006.01) |
| C07D 401/14 | (2006.01) |
| C07D 417/04 | (2006.01) |
| C07D 487/04 | (2006.01) |
| A61P 35/00 | (2006.01) |
| C07D 451/04 | (2006.01) |
| C07D 401/04 | (2006.01) |
| C07D 417/14 | (2006.01) |
| C07D 487/08 | (2006.01) |

(52) U.S. Cl.
CPC ............ *C07D 413/04* (2013.01); *A61P 35/00* (2018.01); *C07D 401/04* (2013.01); *C07D 401/14* (2013.01); *C07D 413/14* (2013.01); *C07D 417/04* (2013.01); *C07D 417/14* (2013.01); *C07D 451/04* (2013.01); *C07D 487/04* (2013.01); *C07D 487/08* (2013.01); *C07B 2200/05* (2013.01)

(58) Field of Classification Search
CPC .. C07D 413/04; C07D 413/14; C07D 401/14; C07D 417/04; C07D 487/04
USPC ................................................ 546/143, 139
See application file for complete search history.

(56) References Cited

U.S. PATENT DOCUMENTS

| 4,164,559 | A | 8/1979 | Miyata et al. |
| 4,474,752 | A | 10/1984 | Haslam et al. |
| 6,120,484 | A | 9/2000 | Silverstein |
| 6,377,849 | B1 | 4/2002 | Lenarz |
| 6,440,102 | B1 | 8/2002 | Arenberg |
| 6,648,873 | B2 | 11/2003 | Arenberg et al. |
| 6,911,211 | B2 | 6/2005 | Eini |
| 7,998,978 | B2 * | 8/2011 | Huang ................. C07D 239/84 514/310 |
| 2013/0079329 | A1 | 3/2013 | Hood |
| 2017/0247365 | A1 * | 8/2017 | Jones ................... C07D 403/12 |
| 2017/0313681 | A1 * | 11/2017 | KC ...................... C07D 401/04 |
| 2017/0313682 | A1 * | 11/2017 | KC ...................... C07D 471/08 |
| 2019/0119263 | A1 | 4/2019 | Kc et al. |
| 2019/0125740 | A1 | 5/2019 | Kc et al. |
| 2019/0125741 | A1 | 5/2019 | Kc et al. |

FOREIGN PATENT DOCUMENTS

| WO | WO 1987/005297 | 2/1987 |
| WO | WO 2001/053268 | 7/2001 |
| WO | WO 2005/009997 | 2/2005 |
| WO | WO 2007/125405 | 11/2007 |
| WO | WO 2017/151786 | 11/2007 |
| WO | WO 2012/080284 | 6/2012 |
| WO | WO 2013/040215 | 3/2013 |
| WO | 2013169793 | * 11/2013 |
| WO | WO 2013/16793 | 11/2013 |
| WO | WO 2013/169793 | 2/2014 |
| WO | WO 2016/046530 | 3/2016 |
| WO | WO 2017/005137 | 1/2017 |
| WO | WO 2017/189823 | 11/2017 |
| WO | WO 2017/189829 | 11/2017 |

(Continued)

OTHER PUBLICATIONS

U.S. Appl. No. 11/337,815, filed Jan. 24, 2006, Lobi et al.
U.S. Appl. No. 13/614,296, filed Sep. 13, 2012, Hood & Kumar.
U.S. Appl. No. 14/019,229, filed Sep. 5, 2013, Hood & Kumar.
U.S. Appl. No. 14/664,517, filed Mar. 20, 2015, Hood et al.
Chou and Talalay, "Quantitative analysis of dose-effect relationships: the combined effects of multiple drugs or enzyme inhibitors," Advances in Enzyme Regulation, 1984, 22:27-55.
King et al, "Build-3: a randomized, controlled trial of bosentan in idiopathic pulmonary fibrosis," American Journal of Respiratory and Critical Care Medicine, Jul. 1, 2011, 184:92-99.

(Continued)

Primary Examiner — Niloofar Rahmani
(74) Attorney, Agent, or Firm — Fish & Richardson P.C.

(57) ABSTRACT

Isoquinoline compounds for treating various diseases and pathologies are disclosed. More particularly, the present disclosure concerns the use of an isoquinoline compound or analogs thereof, in the treatment of disorders characterized by the activation of Wnt pathway signaling (e.g., cancer, abnormal cellular proliferation, angiogenesis, Alzheimer's disease, lung disease, inflammation, auto-immune diseases and osteoarthritis), the modulation of cellular events mediated by Wnt pathway signaling, as well as neurological conditions/disorders/diseases linked to overexpression of DYRK1A.

35 Claims, No Drawings

(56) References Cited

FOREIGN PATENT DOCUMENTS

WO    WO 2018/183964    10/2018

OTHER PUBLICATIONS

Datta et al, "Novel therapeutic approaches for pulmonary fibrosis," British Journal of Pharmacology, Jan. 26, 2011, 163:141-172.
Leyns et al, "Frzb-1 is a secreted antagonist of Wnt signaling expressed in the spemann organizer," Cell, Mar. 21, 1997, 88:747-756.
Liu et al., "Fibrotic lung fibroblasts show blunted inhibition by cAMP due to deficient cAMP response element-binding protein phosphorylation," Journal of Pharmacology and Experimental Therapeutics, 2005, 315(2):678-687.
PCT International Search Report and Written Opinion in International Appln. No. PCT/US2018/056560, dated Dec. 6, 2018, 15 pages.
Watts et al, "RhoA signaling modulates cyclin DI expression in human lung fibroblasts; implications for idiopathic pulmonary fibrosis," Respiratory Research, Jun. 15, 2006, pp. 1-14.
PCT Internationa Search Report and Written Opinion in International Appln. No. PCT/US2018/057853, dated Dec. 19, 2018, 19 pages.
U.S. Appl. No. 16/172,553, filed Oct. 26, 2018, Kumar et al.
U.S. Appl. No. 16/172,589, filed Oct. 26, 2018, Kumar et al.
U.S. Appl. No. 16/177,149, filed Oct. 31, 2018, Kumar et al.
He et al, "Synthesis and SAR of novel quinazolines as potent and brain-penetrant c-jun N-terminal kinase (JNK) inhibiotrs," Bioorganic & Medicinal Chemistry Letters, Jan. 19, 2011, 21:6:1719-1723.
Liang et al, "Identification of an imidazopyridine scaffold to generate patent and selective TYK2 inhibitors that demonstrate activity in as in vivo psoriasis model," Bioorganic & Medicinal Chemistry Letters, Aug. 12, 2017, 27:18:4370-4376.
PCT Internationa Search Report and Written Opinion in International Appln. No. PCT/US2018/057854, dated Jan. 4, 2019, 15 pages.
PCT Internationa Search Report and Written Opinion in International Appln. No. PCT/US2018/058564, dated Feb. 4, 2019, 16 pages.
U.S. Appl. No. 16/528,023, Kc et al., filed Jul. 31, 2019.

* cited by examiner

6-(5-MEMBERED HETEROARYL)ISOQUINOLIN-3-YL CARBOXAMIDES AND PREPARATION AND USE THEREOF

RELATED APPLICATIONS

This application claims the benefit of U.S. Provisional Application Nos. 62/574,568, filed Oct. 19, 2017, and 62/578,691, filed Oct. 30, 2017, which are incorporated herein by reference in their entirety.

BACKGROUND

Technical Field

This disclosure relates to inhibitors of one or more proteins in the Wnt pathway, including inhibitors of one or more Wnt proteins, and compositions comprising the same. More particularly, it concerns the use of an isoquinoline compound or salts or analogs thereof, in the treatment of disorders characterized by the activation of Wnt pathway signaling (e.g., cancer, abnormal cellular proliferation, angiogenesis, Alzheimer's disease, lung disease, inflammation, auto-immune diseases fibrotic disorders, cartilage (chondral) defects, and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states, as well as neurological conditions/disorders/diseases linked to overexpression of DYRK1A.

Background

The Wnt growth factor family includes more than 10 genes identified in the mouse and at least 19 genes identified in the human. Members of the Wnt family of signaling molecules mediate many short- and long-range patterning processes during invertebrate and vertebrate development. The Wnt signaling pathway is known for its role in the inductive interactions that regulate growth and differentiation, and it also plays roles in the homeostatic maintenance of post-embryonic tissue integrity. Wnt stabilizes cytoplasmic β-catenin, which stimulates the expression of genes including c-myc, c jun, fra-1, and cyclin Dl. In addition, misregulation of Wnt signaling can cause developmental defects and is implicated in the genesis of several human cancers. The Wnt pathway has also been implicated in the maintenance of stem or progenitor cells in a growing list of adult tissues including skin, blood, gut, prostate, muscle, and the nervous system.

Dual specificity tyrosine-phosphorylation-regulated kinase 1A is an enzyme that in humans is encoded by the DYRK1A gene. DYRK1A is a member of the dual-specificity tyrosine phosphorylation-regulated kinase (DYRK) family. DYRK1A contains a nuclear targeting signal sequence, a protein kinase domain, a leucine zipper motif, and a highly conservative 13-consecutive-histidine repeat. It catalyzes its autophosphorylation on serine/threonine and tyrosine residues. It may play a significant role in a signaling pathway regulating cell proliferation and may be involved in brain development. DYRK1A is localized in the Down syndrome critical region of chromosome 21, and is considered to be a candidate gene for learning defects associated with Down syndrome. DYRK1A is also expressed in adult brain neurons, indicating that DYRK1A may play a role in the mature central nervous system. Thus, several lines of evidence point to some synaptic functions of DYRK1A. For instance, it has been found that DYRK1A phosphorylates and modulates the interaction of several components of the endocytic protein complex machinery (Dynamin 1, Amphiphysin, and Synaptojanin), suggesting a role in synaptic vesicle recycling. In addition, a polymorphism (SNP) in DYRK1A was found to be associated with HIV-1 replication in monocyte-derived macrophages, as well as with progression to AIDS in two independent cohorts of HIV-1-infected individuals.

SUMMARY

The present disclosure provides methods and reagents, involving contacting a cell with an agent, such as an isoquinoline compound, in a sufficient amount to antagonize a Wnt activity, e.g., to reverse or control an aberrant growth state or correct a genetic disorder due to mutations in Wnt signaling components.

The present disclosure also provides methods and reagents, involving contacting a cell with an agent, such as an isoquinoline compound, in a sufficient amount to antagonize DYRK1A activity, e.g., i) to normalize prenatal and early postnatal brain development; ii) to improve cognitive function in youth and adulthood; and/or iii) to attenuate Alzheimer's-type neurodegeneration.

Some embodiments disclosed herein include Wnt and/or DYRK1A inhibitors containing an isoquinoline core. Other embodiments disclosed herein include pharmaceutical compositions and methods of treatment using these compounds.

One embodiment disclosed herein includes a compound having the structure of Formula I:

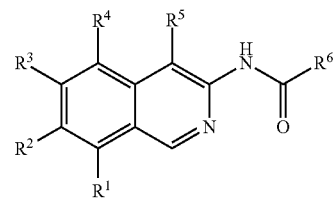

as well as prodrugs and pharmaceutically acceptable salts thereof.

In some embodiments of Formula (I):

$R^1$, $R^2$, $R^4$, and $R^5$ are independently selected from the group consisting of H and halide;

$R^3$ is a 5-membered heteroaryl optionally substituted with 1-4 $R^{26}$;

with the proviso that $R^3$ is not

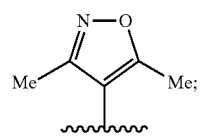

$R^6$ is selected from the group consisting of —$CH_2$phenyl substituted with 1-5 $R^{41}$, —CH═CHphenyl optionally substituted with halide, —$(C_{1-4}$ alkylene$)_p$heterocyclyl optionally substituted with 1-5 $R^{27}$, -carbocyclyl substituted with 1-5 $R^{28}$, and

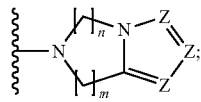

wherein —$(C_{1-4}$ alkylene) is, optionally substituted with one or more substituents as defined anywhere herein; wherein n is 1-4, m is 0-2 and each Z is independently selected from the group consisting of $CR^{32}$ and N;

each $R^{26}$ is independently unsubstituted —$(C_{1-5}$ alkyl);

each $R^{27}$ is independently selected from the group consisting of halide and —$N(R^{43})(R^{44})$ with the proviso that if one or more $R^{27}$ is halide, at least one $R^{27}$ is —$N(R^{43})(R^{44})$;

each $R^{28}$ is independently —$N(R^{33})(R^{34})$;

each $R^{32}$ is independently selected from the group consisting of H, unsubstituted —$(C_{1-5}$ alkyl), unsubstituted —$(C_{2-5}$ alkenyl), unsubstituted —$(C_{2-5}$ alkynyl), and unsubstituted —$(C_{1-5}$ haloalkyl);

$R^{33}$ is attached to the nitrogen and selected from the group consisting of H, unsubstituted —$(C_{1-5}$ alkyl), unsubstituted —$(C_{2-5}$ alkenyl), unsubstituted —$(C_{2-5}$ alkynyl), and unsubstituted —$(C_{1-5}$ haloalkyl);

$R^{34}$ is attached to the nitrogen and is selected from the group consisting of unsubstituted —$(C_{1-5}$ haloalkyl), —$(C_{1-4}$ alkylene$)_p$heterocyclyl optionally substituted with 1-10 $R^{38}$, —$(C_{1-4}$ alkylene$)_p$carbocyclyl optionally substituted with 1-12 $R^{39}$, —$(C_{1-4}$ alkylene$)OR^{35}$; wherein each —$(C_{1-4}$ alkylene) is, independently, optionally substituted with one or more substituents as defined anywhere herein;

each $R^{35}$ is independently selected from the group consisting of H and unsubstituted —$(C_{1-5}$ alkyl);

each $R^{38}$ is independently selected from the group consisting of halide and unsubstituted —$(C_{1-5}$ alkyl);

each $R^{39}$ is independently selected from the group consisting of halide, unsubstituted —$(C_{1-5}$ alkyl), unsubstituted —$(C_{2-5}$ alkenyl), unsubstituted —$(C_{2-5}$ alkynyl), unsubstituted —$(C_{1-5}$ haloalkyl), —CN, and —$(C_{1-4}$ alkylene$)_p$carbocyclyl optionally substituted with 1-12 $R^{40}$; wherein each —$(C_{1-4}$ alkylene) is, independently, optionally substituted with one or more substituents as defined anywhere herein;

each $R^{40}$ is independently selected from the group consisting of halide, unsubstituted —$(C_{1-5}$ alkyl), unsubstituted —$(C_{2-5}$ alkenyl), unsubstituted —$(C_{2-5}$ alkynyl), unsubstituted —$(C_{1-5}$ haloalkyl), and —CN;

each $R^{41}$ is independently selected from the group consisting of halide and —OMe;

each $R^{43}$ is attached to the nitrogen and selected from the group consisting of H, unsubstituted —$(C_{1-5}$ alkyl), unsubstituted —$(C_{2-5}$ alkenyl), unsubstituted —$(C_{2-5}$ alkynyl), and unsubstituted —$(C_{1-5}$ haloalkyl);

each $R^{44}$ is attached to the nitrogen and is selected from the group consisting of H, unsubstituted —$(C_{1-5}$ alkyl), unsubstituted —$(C_{2-5}$ alkenyl), unsubstituted —$(C_{2-5}$ alkynyl), unsubstituted —$(C_{1-5}$ haloalkyl), —$(C_{1-4}$ alkylene$)_p$heterocyclyl optionally substituted with 1-10 $R^{38}$, —$(C_{1-4}$ alkylene$)_p$carbocyclyl optionally substituted with 1-12 $R^{39}$, —$(C_{1-4}$ alkylene$)OR^{35}$; wherein each —$(C_{1-4}$ alkylene) is, independently, optionally substituted with one or more substituents as defined anywhere herein;

each p is independently 0 or 1; and wherein one or more H are optionally replaced by D.

In another embodiment of Formula (I):

$R^1$, $R^2$, $R^4$, and $R^5$ are independently selected from the group consisting of H and halide;

$R^3$ is selected from the group consisting of:

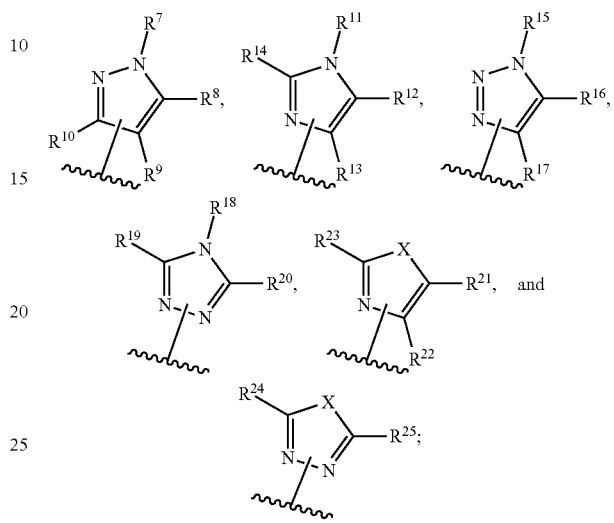

wherein each of $R^7$-$R^{25}$ is, independently, a substituent or a single bond connecting $R^3$ to the isoquinoline ring; wherein only one of $R^7$-$R^{10}$ (when present) is a bond, only one of $R^{11}$-$R^{14}$ (when present) is a bond, only one of $R^{15}$-$R^{17}$ (when present) is a bond, only one of $R^{18}$-$R^{20}$ (when present) is a bond, only one of $R^{21}$-$R^{23}$ (when present) is a bond, and only one of $R^{24}$-$R^{25}$ (when present) is a bond; for purposes of clarification, any one of the nitrogen atoms attached to $R^7$, $R^{11}$, $R^{15}$, or $R^{18}$ can serve as the point of attachment of $R^3$ to the isoquinoline ring; likewise, any one of the carbon atoms attached to $R^8$, $R^9$, $R^{10}$, $R^{12}$, $R^{13}$, $R^{14}$, $R^{16}$, $R^{17}$, $R^{19}$, $R^{20}$, $R^{21}$, $R^{22}$, $R^{23}$, $R^{24}$, and $R^{25}$, can serve as the point of attachment of $R^3$ to the isoquinoline ring; so that:

when the nitrogen atom to which $R^7$ is attached serves as the point of attachment of $R^3$ to the isoquinoline ring, then $R^7$ is a single bond connecting $R^3$ to the isoquinoline ring;

when the carbon atom to which $R^8$ is attached serves as the point of attachment of $R^3$ to the isoquinoline ring, then $R^8$ is a single bond connecting $R^3$ to the isoquinoline ring;

when the carbon atom to which $R^9$ is attached serves as the point of attachment of $R^3$ to the isoquinoline ring, then $R^9$ is a single bond connecting $R^3$ to the isoquinoline ring;

when the carbon atom to which $R^{10}$ is attached serves as the point of attachment of $R^3$ to the isoquinoline ring, then $R^{10}$ is a single bond connecting $R^3$ to the isoquinoline ring;

when the nitrogen atom to which $R^{11}$ is attached serves as the point of attachment of $R^3$ to the isoquinoline ring, then $R^{11}$ is a single bond connecting $R^3$ to the isoquinoline ring;

when the carbon atom to which $R^{12}$ is attached serves as the point of attachment of $R^3$ to the isoquinoline ring, then $R^{12}$ is a single bond connecting $R^3$ to the isoquinoline ring;

when the carbon atom to which $R^{13}$ is attached serves as the point of attachment of $R^3$ to the isoquinoline ring, then $R^{13}$ is a single bond connecting $R^3$ to the isoquinoline ring;

when the carbon atom to which $R^{14}$ is attached serves as the point of attachment of $R^3$ to the isoquinoline ring, then $R^{14}$ is a single bond connecting $R^3$ to the isoquinoline ring;

when the nitrogen atom to which $R^{15}$ is attached serves as the point of attachment of $R^3$ to the isoquinoline ring, then $R^{15}$ is a single bond connecting $R^3$ to the isoquinoline ring;

when the carbon atom to which $R^{16}$ is attached serves as the point of attachment of $R^3$ to the isoquinoline ring, then $R^{16}$ is a single bond connecting $R^3$ to the isoquinoline ring;

when the carbon atom to which $R^{17}$ is attached serves as the point of attachment of $R^3$ to the isoquinoline ring, then $R^{17}$ is a single bond connecting $R^3$ to the isoquinoline ring;

when the nitrogen atom to which $R^{18}$ is attached serves as the point of attachment of $R^3$ to the isoquinoline ring, then $R^{18}$ is a single bond connecting $R^3$ to the isoquinoline ring;

when the carbon atom to which $R^{19}$ is attached serves as the point of attachment of $R^3$ to the isoquinoline ring, then $R^{19}$ is a single bond connecting $R^3$ to the isoquinoline ring;

when the carbon atom to which $R^{20}$ is attached serves as the point of attachment of $R^3$ to the isoquinoline ring, then $R^{20}$ is a single bond connecting $R^3$ to the isoquinoline ring;

when the carbon atom to which $R^{21}$ is attached serves as the point of attachment of $R^3$ to the isoquinoline ring, then $R^{21}$ is a single bond connecting $R^3$ to the isoquinoline ring;

when the carbon atom to which $R^{22}$ is attached serves as the point of attachment of $R^3$ to the isoquinoline ring, then $R^{22}$ is a single bond connecting $R^3$ to the isoquinoline ring;

when the carbon atom to which $R^{23}$ is attached serves as the point of attachment of $R^3$ to the isoquinoline ring, then $R^{23}$ is a single bond connecting $R^3$ to the isoquinoline ring;

when the carbon atom to which $R^{24}$ is attached serves as the point of attachment of $R^3$ to the isoquinoline ring, then $R^{24}$ is a single bond connecting $R^3$ to the isoquinoline ring;

when the carbon atom to which $R^{25}$ is attached serves as the point of attachment of $R^3$ to the isoquinoline ring, then $R^{25}$ is a single bond connecting $R^3$ to the isoquinoline ring;

$R^6$ is selected from the group consisting of —$CH_2$phenyl substituted with 1-5 $R^{41}$, —CH=CHphenyl optionally substituted with halide, —$(C_{1-4}$ alkylene$)_p$heterocyclyl optionally substituted with 1-5 $R^{27}$, -carbocyclyl substituted with 1-5 $R^{28}$, and

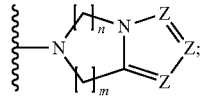

wherein —$(C_{1-4}$ alkylene) is, optionally substituted with one or more substituents as defined anywhere herein; wherein n is 1-4, m is 0-2 and each Z is independently selected from the group consisting of $CR^{32}$ and N;

$R^7$ is selected from the group consisting of a single bond, H, and unsubstituted —$(C_{1-5}$ alkyl);

$R^8$, $R^9$, and $R^{10}$ are independently selected from the group consisting of a single bond, H, and unsubstituted —$(C_{1-5}$ alkyl);

$R^{11}$ is selected from the group consisting of a single bond, H, and unsubstituted —$(C_{1-5}$ alkyl);

$R^{12}$, $R^{13}$, and $R^{14}$ are independently selected from the group consisting of a single bond, H, and unsubstituted —$(C_{1-5}$ alkyl);

$R^{15}$ is selected from the group consisting of a single bond, H, and unsubstituted —$(C_{1-5}$ alkyl);

$R^{16}$ and $R^{17}$ are independently selected from the group consisting of a single bond, H, and unsubstituted —$(C_{1-5}$ alkyl);

$R^{18}$ is selected from the group consisting of a single bond, H, and unsubstituted —$(C_{1-5}$ alkyl);

$R^{19}$ and $R^{20}$ are independently selected from the group consisting of a single bond, H, and unsubstituted —$(C_{1-5}$ alkyl);

$R^{21}$, $R^{22}$, and $R^{23}$ are independently selected from the group consisting of a single bond, H, and unsubstituted —$(C_{1-5}$ alkyl);

$R^{24}$ and $R^{25}$ are independently selected from the group consisting of a single bond, H, and unsubstituted —$(C_{1-5}$ alkyl);

each $R^{27}$ is independently selected from the group consisting of halide, and —$N(R^{43})(R^{44})$ with the proviso that if one or more $R^{27}$ is halide, at least one $R^{27}$ is —$N(R^{43})(R^{44})$;

each $R^{28}$ is independently —$N(R^{33})(R^{34})$;

each $R^{32}$ is independently selected from the group consisting of H, unsubstituted —$(C_{1-5}$ alkyl), unsubstituted —$(C_{2-5}$ alkenyl), unsubstituted —$(C_{2-5}$ alkynyl), and unsubstituted —$(C_{1-5}$ haloalkyl);

$R^{33}$ is attached to the nitrogen and selected from the group consisting of H, unsubstituted —$(C_{1-5}$ alkyl), unsubstituted —$(C_{2-5}$ alkenyl), unsubstituted —$(C_{2-5}$ alkynyl), and unsubstituted —$(C_{1-5}$ haloalkyl);

$R^{34}$ is attached to the nitrogen and is selected from the group consisting of unsubstituted —$(C_{1-5}$ haloalkyl), —$(C_{1-4}$ alkylene$)_p$heterocyclyl optionally substituted with 1-10 $R^{38}$, —$(C_{1-4}$ alkylene$)_p$carbocyclyl optionally substituted with 1-12 $R^{39}$, —$(C_{1-4}$ alkylene)$OR^{35}$; wherein each —$(C_{1-4}$ alkylene) is, independently, optionally substituted with one or more substituents as defined anywhere herein;

each $R^{35}$ is independently selected from the group consisting of H and unsubstituted —$(C_{1-5}$ alkyl);

each $R^{38}$ is independently selected from the group consisting of halide and unsubstituted —$(C_{1-5}$ alkyl);

each $R^{39}$ is independently selected from the group consisting of halide, unsubstituted —$(C_{1-5}$ alkyl), unsubstituted —$(C_{2-5}$ alkenyl), unsubstituted —$(C_{2-5}$ alkynyl), unsubstituted —$(C_{1-5}$ haloalkyl), —CN, and —$(C_{1-4}$ alkylene$)_p$carbocyclyl optionally substituted with 1-12 $R^{40}$; wherein each —$(C_{1-4}$ alkylene) is, independently, optionally substituted with one or more substituents as defined anywhere herein;

each $R^{40}$ is independently selected from the group consisting of halide, unsubstituted —$(C_{1-5}$ alkyl), unsubstituted —$(C_{2-5}$ alkenyl), unsubstituted —$(C_{2-5}$ alkynyl), unsubstituted —$(C_{1-5}$ haloalkyl), and —CN;

each $R^{41}$ is independently selected from the group consisting of halide and —OMe;

each $R^{43}$ is attached to the nitrogen and selected from the group consisting of H, unsubstituted —$(C_{1-5}$ alkyl), unsubstituted —$(C_{2-5}$ alkenyl), unsubstituted —$(C_{2-5}$ alkynyl), and unsubstituted —$(C_{1-5}$ haloalkyl);

each $R^{44}$ is attached to the nitrogen and is selected from the group consisting of H, unsubstituted —$(C_{1-5}$ alkyl), unsubstituted —$(C_{2-5}$ alkenyl), unsubstituted —$(C_{2-5}$ alkynyl), unsubstituted —$(C_{1-5}$ haloalkyl), —$(C_{1-4}$ alkylene$)_p$heterocyclyl optionally substituted with 1-10 $R^{38}$, —$(C_{1-4}$ alkylene$)_p$carbocyclyl optionally substituted with 1-12 $R^{39}$, —$(C_{1-4}$ alkylene)$OR^{35}$; wherein each —$(C_{1-4}$ alkylene) is, independently, optionally substituted with one or more substituents as defined anywhere herein;

each X is O or S;

each p is independently 0 or 1; and wherein one or more H are optionally replaced by D.

In another embodiment of Formula (I):

$R^1$, $R^2$, $R^4$, and $R^5$ are independently selected from the group consisting of H and halide;

$R^3$ is a 5-membered heteroaryl optionally substituted with 1-4 $R^{26}$;

with the proviso that $R^3$ is not

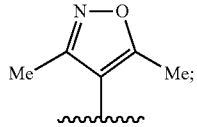

$R^6$ is selected from the group consisting of —$(C_{1-4}$ alkylene$)_p$heterocyclyl optionally substituted with 1-5 $R^{27}$, -carbocyclyl optionally substituted with 1-5 $R^{28}$, and —$N(R^{30})(R^{31})$; wherein —$(C_{1-4}$ alkylene) is, optionally substituted with one or more substituents as defined anywhere herein;

each $R^{26}$ is independently unsubstituted —$(C_{1-5}$ alkyl);

each $R^{27}$ is independently selected from the group consisting of halide, unsubstituted —$(C_{1-5}$ alkyl), unsubstituted —$(C_{1-9}$ haloalkyl), —$OR^{35}$, and —$(C_{1-4}$ alkylene$)_p$heterocyclyl optionally substituted with 1-5 $R^{36}$; wherein —$(C_{1-4}$ alkylene) is, optionally substituted with one or more substituents as defined anywhere herein;

each $R^{28}$ is independently selected from the group consisting of —$N(R^{33})_2$, —$(C_{1-4}$ alkylene)$OR^{35}$, —$C(=O)(R^{37})$, and —$(C_{1-4}$ alkylene$)_p$heterocyclyl optionally substituted with 1-5 $R^{36}$; wherein each —$(C_{1-4}$ alkylene) is independently, optionally substituted with one or more substituents as defined anywhere herein;

$R^{30}$ is attached to the nitrogen and is selected from the group consisting of H and unsubstituted —$(C_{1-5}$ alkyl);

$R^{31}$ is attached to the nitrogen and is heterocyclyl optionally substituted with 1-5 $R^{38}$;

$R^{33}$ is attached to the nitrogen and selected from the group consisting of H, unsubstituted —$(C_{1-5}$ alkyl), unsubstituted —$(C_{2-5}$ alkenyl), and unsubstituted —$(C_{2-5}$ alkynyl);

each $R^{35}$ is independently selected from the group consisting of H and unsubstituted —$(C_{1-5}$ alkyl);

each $R^{36}$ is selected from the group consisting of unsubstituted —$(C_{1-5}$ alkyl) and unsubstituted —$(C_{1-5}$ haloalkyl);

$R^{37}$ is -heterocyclyl optionally substituted with one or more halides or one or more unsubstituted —$(C_{1-5}$ alkyl);

each $R^{38}$ is independently selected from the group consisting of halide and unsubstituted —$(C_{1-5}$ alkyl);

each p is independently 0 or 1; and wherein one or more H are optionally replaced by D.

In another embodiment of Formula (I):

$R^1$, $R^2$, $R^4$, and $R^5$ are independently selected from the group consisting of H and halide;

$R^3$ is selected from the group consisting of:

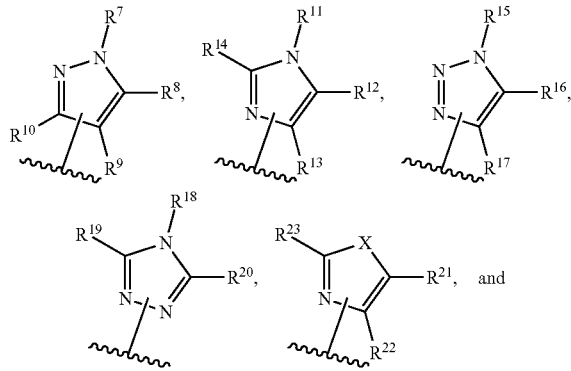

-continued

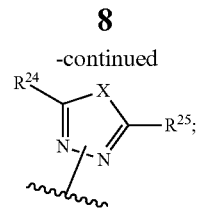

wherein each of $R^7$-$R^{25}$ is, independently, a substituent or a single bond connecting $R^3$ to the isoquinoline ring; wherein only one of $R^7$-$R^{10}$ (when present) is a bond, only one of $R^{11}$-$R^4$ (when present) is a bond, only one of $R^{15}$-$R^{17}$ (when present) is a bond, only one of $R^8$-$R^{20}$ (when present) is a bond, only one of $R^{21}$-$R^{23}$ (when present) is a bond, and only one of $R^{24}$-$R^{25}$ (when present) is a bond; for purposes of clarification, any one of the nitrogen atoms attached to $R^7$, $R^{11}$, $R^{15}$, or $R^{18}$ can serve as the point of attachment of $R^3$ to the isoquinoline ring; likewise, any one of the carbon atoms attached to $R^8$, $R^9$, $R^{10}$, $R^{12}$, $R^{13}$, $R^{14}$, $R^{16}$, $R^{17}$, $R^{19}$, $R^{20}$, $R^{21}$, $R^{22}$, $R^{23}$, $R^{24}$, and $R^{25}$, can serve as the point of attachment of $R^3$ to the isoquinoline ring; so that: when the nitrogen atom to which $R^7$ is attached serves as the point of attachment of $R^3$ to the isoquinoline ring, then $R^7$ is a single bond connecting $R^3$ to the isoquinoline ring;

when the carbon atom to which $R^8$ is attached serves as the point of attachment of $R^3$ to the isoquinoline ring, then $R^8$ is a single bond connecting $R^3$ to the isoquinoline ring;

when the carbon atom to which $R^9$ is attached serves as the point of attachment of $R^3$ to the isoquinoline ring, then $R^9$ is a single bond connecting $R^3$ to the isoquinoline ring;

when the carbon atom to which $R^{10}$ is attached serves as the point of attachment of $R^3$ to the isoquinoline ring, then $R^{10}$ is a single bond connecting $R^3$ to the isoquinoline ring;

when the nitrogen atom to which $R^{11}$ is attached serves as the point of attachment of $R^3$ to the isoquinoline ring, then $R^{11}$ is a single bond connecting $R^3$ to the isoquinoline ring;

when the carbon atom to which $R^{12}$ is attached serves as the point of attachment of $R^3$ to the isoquinoline ring, then $R^{12}$ is a single bond connecting $R^3$ to the isoquinoline ring;

when the carbon atom to which $R^{13}$ is attached serves as the point of attachment of $R^3$ to the isoquinoline ring, then $R^{13}$ is a single bond connecting $R^3$ to the isoquinoline ring;

when the carbon atom to which $R^{14}$ is attached serves as the point of attachment of $R^3$ to the isoquinoline ring, then $R^{14}$ is a single bond connecting $R^3$ to the isoquinoline ring;

when the nitrogen atom to which $R^{15}$ is attached serves as the point of attachment of $R^3$ to the isoquinoline ring, then $R^{15}$ is a single bond connecting $R^3$ to the isoquinoline ring;

when the carbon atom to which $R^{16}$ is attached serves as the point of attachment of $R^3$ to the isoquinoline ring, then $R^{16}$ is a single bond connecting $R^3$ to the isoquinoline ring;

when the carbon atom to which $R^{17}$ is attached serves as the point of attachment of $R^3$ to the isoquinoline ring, then $R^{17}$ is a single bond connecting $R^3$ to the isoquinoline ring;

when the nitrogen atom to which $R^{18}$ is attached serves as the point of attachment of $R^3$ to the isoquinoline ring, then $R^{18}$ is a single bond connecting $R^3$ to the isoquinoline ring;

when the carbon atom to which $R^{19}$ is attached serves as the point of attachment of $R^3$ to the isoquinoline ring, then $R^{19}$ is a single bond connecting $R^3$ to the isoquinoline ring;

when the carbon atom to which $R^{20}$ is attached serves as the point of attachment of $R^3$ to the isoquinoline ring, then $R^{20}$ is a single bond connecting $R^3$ to the isoquinoline ring;

when the carbon atom to which $R^{2'}$ is attached serves as the point of attachment of $R^3$ to the isoquinoline ring, then $R^{2'}$ is a single bond connecting $R^3$ to the isoquinoline ring;

when the carbon atom to which $R^{22}$ is attached serves as the point of attachment of $R^3$ to the isoquinoline ring, then $R^{22}$ is a single bond connecting $R^3$ to the isoquinoline ring;

when the carbon atom to which $R^{23}$ is attached serves as the point of attachment of $R^3$ to the isoquinoline ring, then $R^{23}$ is a single bond connecting $R^3$ to the isoquinoline ring;

when the carbon atom to which $R^{24}$ is attached serves as the point of attachment of $R^3$ to the isoquinoline ring, then $R^{24}$ is a single bond connecting $R^3$ to the isoquinoline ring;

when the carbon atom to which $R^{25}$ is attached serves as the point of attachment of $R^3$ to the isoquinoline ring, then $R^{25}$ is a single bond connecting $R^3$ to the isoquinoline ring;

$R^6$ is selected from the group consisting of —$(C_{1-4}$ alkylene$)_p$heterocyclyl optionally substituted with 1-5 $R^{27}$, -carbocyclyl optionally substituted with 1-5 $R^{28}$, and —$N(R^{30})(R^{31})$; wherein —$(C_{1-4}$ alkylene) is, optionally substituted with one or more substituents as defined anywhere herein;

$R^7$ is selected from the group consisting of a single bond, H, and unsubstituted —$(C_{1-5}$ alkyl);

$R^8$, $R^9$, and $R^{10}$ are independently selected from the group consisting of a single bond, H, and unsubstituted —$(C_{1-5}$ alkyl);

$R^{11}$ is selected from the group consisting of a single bond, H, and unsubstituted —$(C_{1-5}$ alkyl);

$R^{12}$, $R^{13}$, and $R^{14}$ are independently selected from the group consisting of a single bond, H, and unsubstituted —$(C_{1-5}$ alkyl);

$R^{15}$ is selected from the group consisting of a single bond, H, and unsubstituted —$(C_{1-5}$ alkyl);

$R^{16}$ and $R^{17}$ are independently selected from the group consisting of a single bond, H, and unsubstituted —$(C_{1-5}$ alkyl);

$R^{18}$ is selected from the group consisting of a single bond, H, and unsubstituted —$(C_{1-5}$ alkyl);

$R^{19}$ and $R^{20}$ are independently selected from the group consisting of a single bond, H, and unsubstituted —$(C_{1-5}$ alkyl);

$R^{21}$, $R^{22}$, and $R^{23}$ are independently selected from the group consisting of a single bond, H, and unsubstituted —$(C_{1-5}$ alkyl);

$R^{24}$ and $R^{25}$ are independently selected from the group consisting of a single bond, H, and unsubstituted —$(C_{1-5}$ alkyl);

each $R^{27}$ is independently selected from the group consisting of halide, unsubstituted —$(C_{1-5}$ alkyl), unsubstituted —$(C_{1-9}$ haloalkyl), —$OR^{35}$, and —$(C_{1-4}$ alkylene$)_p$heterocyclyl optionally substituted with 1-5 $R^{36}$; wherein —$(C_{1-4}$ alkylene) is, optionally substituted with one or more substituents as defined anywhere herein;

each $R^{28}$ is independently selected from the group consisting of —$N(R^{33})_2$, —$(C_{1-4}$ alkylene)$OR^{35}$, —$C(=O)(R^{37})$, and —$(C_{1-4}$ alkylene$)_p$heterocyclyl optionally substituted with 1-5 $R^{36}$; wherein each —$(C_{1-4}$ alkylene) is independently, optionally substituted with one or more substituents as defined anywhere herein;

$R^{30}$ is attached to the nitrogen and is selected from the group consisting of H and unsubstituted —$(C_{1-5}$ alkyl);

$R^{31}$ is attached to the nitrogen and is heterocyclyl optionally substituted with 1-5 $R^{38}$;

$R^{33}$ is attached to the nitrogen and selected from the group consisting of H, unsubstituted —$(C_{1-5}$ alkyl), unsubstituted —$(C_{2-5}$ alkenyl), and unsubstituted —$(C_{2-5}$ alkynyl); each $R^{35}$ is independently selected from the group consisting of H and unsubstituted —$(C_{1-5}$ alkyl);

each $R^{36}$ is selected from the group consisting of unsubstituted —$(C_{1-5}$ alkyl) and unsubstituted —$(C_{1-5}$ haloalkyl);

$R^{37}$ is -heterocyclyl optionally substituted with one or more halides or one or more unsubstituted —$(C_{1-5}$ alkyl);

each $R^{38}$ is independently selected from the group consisting of halide and unsubstituted —$(C_{1-5}$ alkyl);

each X is O or S; and each p is independently 0 or 1; and wherein one or more H are optionally replaced by D.

In another embodiment of Formula (I):

$R^1$, $R^2$, $R^4$, and $R^5$ are independently selected from the group consisting of H and halide;

$R^3$ is a 5-membered heteroaryl optionally substituted with 1-4 $R^{26}$;

$R^6$ is a selected from the group consisting of -phenyl substituted with 1-5 $R^{42}$ and 6-membered heteroaryl optionally substituted with 1-6 $R^{29}$;

each $R^{26}$ is independently unsubstituted —$(C_{1-5}$ alkyl);

each $R^{29}$ is independently selected from the group consisting of unsubstituted —$(C_{1-5}$ alkyl) and heterocyclyl optionally substituted with 1-5 $R^{36}$;

each $R^{36}$ is independently unsubstituted —$(C_{1-5}$ alkyl);

each $R^{42}$ is independently selected from the group consisting of halide, —OMe, and unsubstituted —$(C_{1-5}$ alkyl); and wherein one or more H are optionally replaced by D.

In another embodiment of Formula (I):

$R^1$, $R^2$, $R^4$, and $R^5$ are independently selected from the group consisting of H and halide;

$R^3$ is selected from the group consisting of:

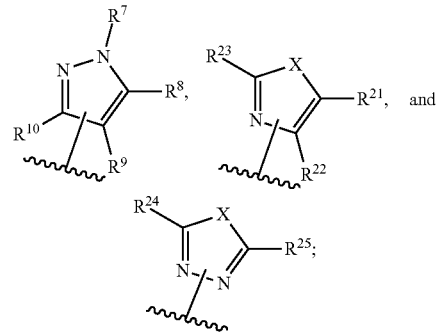

wherein each of $R^7$-$R^{10}$ and $R^{21}$-$R^{25}$ is, independently, a substituent or a single bond connecting $R^3$ to the isoquinoline ring; wherein only one of $R^7$-$R^{10}$ (when present) is a bond, only one of $R^{21}$-$R^{23}$ (when present) is a bond, and only one of $R^{24}$-$R^{25}$ (when present) is a bond; for purposes of clarification, any one of the nitrogen atoms attached to $R^7$ can serve as the point of attachment of $R^3$ to the isoquinoline ring; likewise, any one of the carbon atoms attached to $R^8$, $R^9$, $R^{10}$, $R^{21}$, $R^{22}$, $R^{23}$, $R^{24}$, or $R^{25}$ can serve as the point of attachment of $R^3$ to the isoquinoline ring; so that:

when the nitrogen atom to which $R^7$ is attached serves as the point of attachment of $R^3$ to the isoquinoline ring, then $R^7$ is a single bond connecting $R^3$ to the isoquinoline ring;

when the carbon atom to which $R^8$ is attached serves as the point of attachment of $R^3$ to the isoquinoline ring, then $R^8$ is a single bond connecting $R^3$ to the isoquinoline ring;

when the carbon atom to which $R^9$ is attached serves as the point of attachment of $R^3$ to the isoquinoline ring, then $R^9$ is a single bond connecting $R^3$ to the isoquinoline ring;

when the carbon atom to which $R^{10}$ is attached serves as the point of attachment of $R^3$ to the isoquinoline ring, then $R^{10}$ is a single bond connecting $R^3$ to the isoquinoline ring;

when the carbon atom to which $R^{21}$ is attached serves as the point of attachment of $R^3$ to the isoquinoline ring, then $R^{21}$ is a single bond connecting $R^3$ to the isoquinoline ring;

when the carbon atom to which $R^{22}$ is attached serves as the point of attachment of $R^3$ to the isoquinoline ring, then $R^{22}$ is a single bond connecting $R^3$ to the isoquinoline ring;

when the carbon atom to which $R^{23}$ is attached serves as the point of attachment of $R^3$ to the isoquinoline ring, then $R^{23}$ is a single bond connecting $R^3$ to the isoquinoline ring;

when the carbon atom to which $R^{24}$ is attached serves as the point of attachment of $R^3$ to the isoquinoline ring, then $R^{24}$ is a single bond connecting $R^3$ to the isoquinoline ring;

when the carbon atom to which $R^{25}$ is attached serves as the point of attachment of $R^3$ to the isoquinoline ring, then $R^{25}$ is a single bond connecting $R^3$ to the isoquinoline ring;

$R^6$ is a selected from the group consisting of -phenyl substituted with 1-5 $R^{42}$ and 6-membered heteroaryl optionally substituted with 1-6 $R^{29}$;

$R^7$ is selected from the group consisting of H, and unsubstituted —$(C_{1-5}$ alkyl);

$R^8$, $R^9$, and $R^{10}$ are independently selected from the group consisting of a single bond, H, unsubstituted —$(C_{1-5}$ alkyl);

$R^{21}$, $R^{22}$, and $R^{23}$ are independently selected from the group consisting of a single bond, H, halide, unsubstituted —$(C_{1-5}$ alkyl);

$R^{24}$ and $R^{25}$ are independently selected from the group consisting of a single bond, H, unsubstituted —$(C_{1-5}$ alkyl);

each $R^{29}$ is independently selected from the group consisting of unsubstituted —$(C_{1-5}$ alkyl) and heterocyclyl optionally substituted with 1-5 $R^{36}$;

each $R^{36}$ is independently unsubstituted —$(C_{1-5}$ alkyl);

each $R^{42}$ is independently selected from the group consisting of halide, —OMe, and unsubstituted —$(C_{1-5}$ alkyl);

each X is O or S: and wherein one or more H are optionally replaced by D.

In another embodiment of Formula (I):

$R^1$, $R^2$, $R^4$, and $R^5$ are independently selected from the group consisting of H and halide;

$R^3$ is a 5-membered heteroaryl optionally substituted with 1-4 $R^{26}$;

$R^6$ is a selected from the group consisting of -phenyl substituted with 1-5 $R^{42}$ and 6-membered heteroaryl optionally substituted with 1-6 $R^{29}$;

each $R^{26}$ is independently unsubstituted —$(C_{1-5}$ alkyl);

each $R^{29}$ is independently selected from the group consisting of unsubstituted —$(C_{1-5}$ alkyl), heterocyclyl optionally substituted with 1-5 $R^{36}$, and N-oxide;

each $R^{36}$ is independently selected from the group consisting of unsubstituted —$(C_{1-5}$ alkyl) and N-oxide;

each $R^{42}$ is independently selected from the group consisting of halide, —OMe, and unsubstituted —$(C_{1-5}$ alkyl); and wherein one or more H are optionally replaced by D.

In another embodiment of Formula (I):

$R^1$, $R^2$, $R^4$, and $R^5$ are independently selected from the group consisting of H and halide;

$R^3$ is selected from the group consisting of:

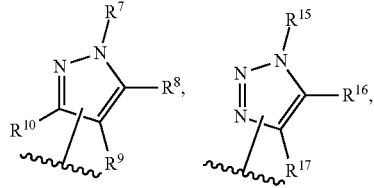

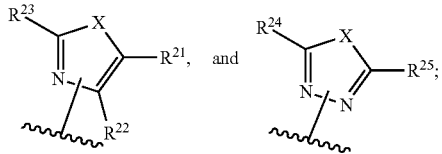

wherein each of $R^7$-$R^{10}$ and $R^{21}$-$R^{25}$ is, independently, a substituent or a single bond connecting $R^3$ to the isoquinoline ring; wherein only one of $R^7$-$R^{10}$ (when present) is a bond, only one of $R^{15}$-$R^{17}$ (when present) is a bond, only one of $R^{21}$-$R^{23}$ (when present) is a bond, and only one of $R^{24}$-$R^{25}$ (when present) is a bond; for purposes of clarification, any one of the nitrogen atoms attached to $R^7$ can serve as the point of attachment of $R^3$ to the isoquinoline ring; likewise, any one of the carbon atoms attached to $R^8$, $R^9$, $R^{10}$, $R^{15}$, $R^{16}$, $R^{17}$, $R^{21}$, $R^{22}$, $R^{23}$, $R^{24}$, or $R^{25}$ can serve as the point of attachment of $R^3$ to the isoquinoline ring; so that:

when the nitrogen atom to which $R^7$ is attached serves as the point of attachment of $R^3$ to the isoquinoline ring, then $R^7$ is a single bond connecting $R^3$ to the isoquinoline ring;

when the carbon atom to which $R^8$ is attached serves as the point of attachment of $R^3$ to the isoquinoline ring, then $R^8$ is a single bond connecting $R^3$ to the isoquinoline ring;

when the carbon atom to which $R^9$ is attached serves as the point of attachment of $R^3$ to the isoquinoline ring, then $R^9$ is a single bond connecting $R^3$ to the isoquinoline ring;

when the carbon atom to which $R^{10}$ is attached serves as the point of attachment of $R^3$ to the isoquinoline ring, then $R^{10}$ is a single bond connecting $R^3$ to the isoquinoline ring;

when the nitrogen atom to which $R^{15}$ is attached serves as the point of attachment of $R^3$ to the isoquinoline ring, then $R^{15}$ is a single bond connecting $R^3$ to the isoquinoline ring;

when the carbon atom to which $R^{16}$ is attached serves as the point of attachment of $R^3$ to the isoquinoline ring, then $R^{16}$ is a single bond connecting $R^3$ to the isoquinoline ring;

when the carbon atom to which $R^{17}$ is attached serves as the point of attachment of $R^3$ to the isoquinoline ring, then $R^{17}$ is a single bond connecting $R^3$ to the isoquinoline ring;

when the carbon atom to which $R^{21}$ is attached serves as the point of attachment of $R^3$ to the isoquinoline ring, then $R^{21}$ is a single bond connecting $R^3$ to the isoquinoline ring;

when the carbon atom to which $R^{22}$ is attached serves as the point of attachment of $R^3$ to the isoquinoline ring, then $R^{22}$ is a single bond connecting $R^3$ to the isoquinoline ring;

when the carbon atom to which $R^{23}$ is attached serves as the point of attachment of $R^3$ to the isoquinoline ring, then $R^{23}$ is a single bond connecting $R^3$ to the isoquinoline ring;

when the carbon atom to which $R^{24}$ is attached serves as the point of attachment of $R^3$ to the isoquinoline ring, then $R^{24}$ is a single bond connecting $R^3$ to the isoquinoline ring;

when the carbon atom to which $R^{25}$ is attached serves as the point of attachment of $R^3$ to the isoquinoline ring, then $R^{25}$ is a single bond connecting $R^3$ to the isoquinoline ring;

$R^6$ is a selected from the group consisting of -phenyl substituted with 1-5 $R^{42}$ and 6-membered heteroaryl optionally substituted with 1-6 $R^{29}$;

$R^7$ is selected from the group consisting of H, and unsubstituted —$(C_{1-5}$ alkyl);

$R^8$, $R^9$, and $R^{10}$ are independently selected from the group consisting of a single bond, H, unsubstituted —$(C_{1-5}$ alkyl);

$R^{15}$ is selected from the group consisting of a single bond, H, and unsubstituted —$(C_{1-5}$ alkyl);

$R^{16}$ and $R^{17}$ are independently selected from the group consisting of a single bond, H, and unsubstituted —($C_{1-5}$ alkyl);

$R^{21}$, $R^{22}$, and $R^{23}$ are independently selected from the group consisting of a single bond, H, halide, unsubstituted —($C_{1-5}$ alkyl);

$R^{24}$ and $R^{25}$ are independently selected from the group consisting of a single bond, H, unsubstituted —($C_{1-5}$ alkyl);

each $R^{29}$ is independently selected from the group consisting of unsubstituted —($C_{1-5}$ alkyl), heterocyclyl optionally substituted with 1-5 $R^{36}$, and N-oxide;

each $R^{36}$ is independently selected from the group consisting of unsubstituted —($C_{1-5}$ alkyl) and N-oxide;

each $R^{42}$ is independently selected from the group consisting of halide, —OMe, and unsubstituted —($C_{1-5}$ alkyl);

each X is O or S; and wherein one or more H are optionally replaced by D.

Some embodiments include stereoisomers and pharmaceutically acceptable salts of a compound of Formula (I). Some embodiments include pharmaceutically acceptable salts of a compound of Formula (I).

Some embodiments include pro-drugs of a compound of Formula (I).

Some embodiments of the present disclosure include pharmaceutical compositions comprising a compound of Formula (I) and a pharmaceutically acceptable carrier, diluent, or excipient.

Other embodiments disclosed herein include methods of inhibiting one or more members of the Wnt pathway, including one or more Wnt proteins by administering to a patient affected by a disorder or disease in which aberrant Wnt signaling is implicated, such as cancer and other diseases associated with abnormal angiogenesis, cellular proliferation, cell cycling and mutations in Wnt signaling components, a compound according to Formula (I). Accordingly, the compounds and compositions provided herein can be used to treat cancer, to reduce or inhibit angiogenesis, to reduce or inhibit cellular proliferation and correct a genetic disorder due to mutations in Wnt signaling components.

Other embodiments disclosed herein include methods of inhibiting DYRK1A by administering to a patient affected by a disorder or disease in which DYRK1A overexpression is implicated, such as Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor and Stroke.

Non-limiting examples of diseases which can be treated with the compounds and compositions provided herein include a variety of cancers, diabetic retinopathy, pulmonary fibrosis, rheumatoid arthritis, sepsis, ankylosing spondylitis, psoriasis, scleroderma, mycotic and viral infections, osteochondrodysplasia, Alzheimer's disease, lung disease, bone/osteoporotic (wrist, spine, shoulder and hip) fractures, articular cartilage (chondral) defects, degenerative disc disease (or intervertebral disc degeneration), polyposis *coli*, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Some embodiments of the present disclosure include methods to prepare compounds of Formula (I).

It is to be understood that both the foregoing general description and the following detailed description are exemplary and explanatory only and are not restrictive of the disclosure, as claimed.

DETAILED DESCRIPTION

Provided herein are compositions and methods for inhibiting one or more members of the Wnt pathway, including one or more Wnt proteins. Other Wnt inhibitors and methods for using the same are disclosed in U.S. application Ser. Nos. 13/614,296; 14/019,229; and Ser. No. 14/664,517, all of which are incorporated by reference in their entirety herein.

Provided herein are compositions and methods for inhibiting DYRK1A. Other DYRK1A inhibitors and methods for using the same are disclosed in U.S. application Ser. No. 14/664,517, which is incorporated by reference in its entirety herein.

Some embodiments provided herein relate to a method for treating a disease including, but not limited to, neurological diseases or disorders, cancers, chronic inflammation, diabetic retinopathy, pulmonary fibrosis, rheumatoid arthritis, sepsis, ankylosing spondylitis, psoriasis, scleroderma, mycotic and viral infections, bone and cartilage diseases, lung disease, osteoarthritis, articular cartilage (chondral) defects, degenerative disc disease (or intervertebral disc degeneration), polyposis *coli*, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease, and Rett syndrome.

In some embodiments, non-limiting examples of bone and cartilage diseases which can be treated with the compounds and compositions provided herein include bone spur (osteophytes), craniosynostosis, fibrodysplasia ossificans progressive, fibrous dysplasia, giant cell tumor of bone, hip labral tear, meniscal tears, osteoarthritis, articular cartilage (chondral) defects, degenerative disc disease (or intervertebral disc degeneration), osteochondritis dissecans, osteochondroma (bone tumor), osteopetrosis, relapsing polychondritis, and Salter-Harris fractures.

In some embodiments, non-limiting examples of a neurological disease or disorder associated with tau protein, amyloid or alpha-synuclein pathology which can be treated with the compounds and compositions provided herein include, but are not limited to, Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

In some embodiments, non-limiting examples of diseases in which chronic inflammation is involved which can be treated with the compounds and compositions provided herein include eye disorders, joint pain, arthritis (rheumatoid, osteo, psoriatic gout), cancers (colon, breast, lung, pancreas, and others), gastrointestinal disorders (ulcerative colitis and inflammatory bowel diseases), pulmonary disorders (chronic obstructive pulmonary disorder and asthma), allergies, skin disorders (atopic dermatitis and psoriasis), diabetes, pancreatitis, tendonitis, hepatitis, heart disease, myocarditis, stroke, lupus, and neurological disorders such as multiple sclerosis, Parkinson's and dementia including Alzheimer's disease.

In some embodiments, non-limiting examples of cancers which can be treated with the compounds and compositions provided herein include colon, ovarian, pancreatic, breast, liver, prostate, and hematologic cancers.

In some embodiments, pharmaceutical compositions are provided that are effective for treatment of a disease of an animal, e.g., a mammal, caused by either the pathological activation or mutations of the Wnt pathway or DYRK1A overexpression. The composition includes a pharmaceutically acceptable carrier and a compound as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "alkyl" means a branched, or straight chain chemical group containing only carbon and hydrogen, such as methyl, ethyl, n-propyl, iso-propyl, n-butyl, isobutyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

As used herein, "alkenyl" means a straight or branched chain chemical group containing only carbon and hydrogen and containing at least one carbon-carbon double bond, such as ethenyl, 1-propenyl, 2-propenyl, 2-methyl-1-propenyl, 1-butenyl, 2-butenyl, and the like. In various embodiments, alkenyl groups can either be unsubstituted or substituted with one or more substituents. Typically, alkenyl groups will comprise 2 to 9 carbon atoms (for example, 2 to 6 carbon atoms, 2 to 4 carbon atoms, or 2 carbon atoms).

As used herein, "alkynyl" means a straight or branched chain chemical group containing only carbon and hydrogen and containing at least one carbon-carbon triple bond, such as ethynyl, 1-propynyl, 1-butynyl, 2-butynyl, and the like. In various embodiments, alkynyl groups can either be unsubstituted or substituted with one or more substituents. Typically, alkynyl groups will comprise 2 to 9 carbon atoms (for example, 2 to 6 carbon atoms, 2 to 4 carbon atoms, or 2 carbon atoms).

As used herein, "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

As used herein, "alkenylene" means a bivalent branched, or straight chain chemical group containing only carbon and hydrogen and containing at least one carbon-carbon double bond, such as ethenylene, 1-propenylene, 2-propenylene, 2-methyl-1-propenylene, 1-butenylene, 2-butenylene, and the like. In various embodiments, alkenylene groups can either be unsubstituted or substituted with one or more substituents. Typically, alkenylene groups will comprise 2 to 9 carbon atoms (for example, 2 to 6 carbon atoms, 2 to 4 carbon atoms, or 2 carbon atoms).

As used herein, "alkynylene" means a bivalent branched, or straight chain chemical group containing only carbon and hydrogen and containing at least one carbon-carbon triple bond, such as ethynylene, 1-propynylene, 1-butynylene, 2-butynylene, and the like. In various embodiments, alkynylene groups can either be unsubstituted or substituted with one or more substituents. Typically, alkynylene groups will comprise 2 to 9 carbon atoms (for example, 2 to 6 carbon atoms, 2 to 4 carbon atoms, or 2 carbon atoms).

As used herein, "alkoxy" means an alkyl-O— group in which the alkyl group is as described herein. Exemplary alkoxy groups include methoxy, ethoxy, n-propoxy, i-propoxy, n-butoxy, s-butoxy, t-butoxy, pentoxy, hexoxy and heptoxy, and also the linear or branched positional isomers thereof.

As used herein, "haloalkoxy" means a haloalkyl-O— group in which the haloalkyl group is as described herein. Exemplary haloalkoxy groups include fluoromethoxy, difluoromethoxy, trifluoromethoxy, and also the linear or branched positional isomers thereof.

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that none of the rings in the ring system are aromatic. Carbocyclyl groups can either be unsubstituted or substituted with one or more substituents. In some embodiments, carbocyclyl groups include 3 to 10 carbon atoms, for example, 3 to 6 carbon atoms.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, 2,3-dihydro-1H-indenyl, and others. In some embodiments, the aryl is phenyl.

As used herein, "arylalkylene" means an aryl-alkylene-group in which the aryl and alkylene moieties are as previously described. In some embodiments, arylalkylene groups contain a $C_{1-4}$alkylene moiety. Exemplary arylalkylene groups include benzyl and 2-phenethyl.

As used herein, the term "heteroaryl" means a mono-, bi-, tri- or polycyclic group having 5 to 14 ring atoms, alternatively 5, 6, 9, or 10 ring atoms; and having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, and others. In some embodiments, the heteroaryl is selected from thienyl, pyridinyl, furyl, pyrazolyl, imidazolyl, isoindolinyl, pyranyl, pyrazinyl, and pyrimidinyl.

As used herein, "halo", "halide" or "halogen" is a chloro, bromo, fluoro, or iodo atom radical. In some embodiments, a halo is a chloro, bromo or fluoro. For example, a halide can be fluoro.

As used herein, "haloalkyl" means a hydrocarbon substituent, which is a linear or branched, alkyl, alkenyl or alkynyl substituted with one or more chloro, bromo, fluoro, and/or iodo atom(s). In some embodiments, a haloalkyl is a fluoroalkyls, wherein one or more of the hydrogen atoms have been substituted by fluoro. In some embodiments, haloalkyls are of 1 to about 3 carbons in length (e.g., 1 to about 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may include multiple fused rings. Heterocyclyls may be substituted or unsubstituted with one or more substituents. In some embodiments, heterocycles have 3-11 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others. In some embodiments, the heterocyclyl is selected from azetidinyl, morpholinyl, piperazinyl, pyrrolidinyl, and tetrahydropyridinyl.

As used herein, "monocyclic heterocyclyl" means a single nonaromatic cyclic ring comprising at least one heteroatom in the ring system backbone. Heterocyclyls may be substituted or unsubstituted with one or more substituents. In some embodiments, heterocycles have 3-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyls include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

As used herein, "bicyclic heterocyclyl" means a nonaromatic bicyclic ring system comprising at least one heteroatom in the ring system backbone. Bicyclic heterocyclyls may be substituted or unsubstituted with one or more substituents. In some embodiments, bicyclic heterocycles have 4-11 members with the heteroatom(s) being selected from one to five of O, N or S. Examples of bicyclic heterocyclyls include 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, and the like.

As used herein, "spirocyclic heterocyclyl" means a nonaromatic bicyclic ring system comprising at least one heteroatom in the ring system backbone and with the rings connected through just one atom. Spirocyclic heterocyclyls may be substituted or unsubstituted with one or more substituents. In some embodiments, spirocyclic heterocycles have 5-11 members with the heteroatom(s) being selected from one to five of O, N or S. Examples of spirocyclic heterocyclyls include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 2,5-diazaspiro[3.6]decane, and the like.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, —($C_{1-9}$ alkyl) optionally substituted with one or more of hydroxyl, —$NH_2$, —$NH(C_{1-3}$ alkyl), and —$N(C_{1-3}$ alkyl)$_2$; —($C_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; —($C_{1-9}$ alkoxy) optionally substituted with one or more of halide, hydroxyl, —$NH_2$, —$NH(C_{1-3}$ alkyl), and —$N(C_{1-3}$ alkyl)$_2$; —OPO(OH)$_2$; a phosphonate [such as —PO(OH)$_2$ and —PO(OR')$_2$]; —OPO(OR')R"; —NRR'; —C(O)NRR'; —C(NR)NR'R"; —C(NR')R"; a cyano; a nitro; an azido; —SH; —S—R; —OSO$_2$(OR); a sulfonate [such as —SO$_2$(OH) and —SO$_2$(OR)]; —SO$_2$NR'R"; and —SO$_2$R; in which each occurrence of R, R' and R" are independently selected from H; —($C_{1-9}$ alkyl); $C_{6-10}$ aryl optionally substituted with from 1-3R'''; 5-10 membered heteroaryl having from 1-4 heteroatoms independently selected from N, O, and S and optionally substituted with from 1-3 R'''; $C_{3-7}$ carbocyclyl optionally substituted with from 1-3 R'''; and 3-8 membered heterocyclyl having from 1-4 heteroatoms independently selected from N, O, and S and optionally substituted with from 1-3 R'''; wherein each R''' is independently selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl). In some embodiments, the substituent is selected from —($C_{1-6}$ alkyl), —($C_{1-6}$ haloalkyl), a halide (e.g., F), a hydroxyl, —C(O)OR, —C(O)R, —(C$_{1-6}$ alkoxyl), —NRR', —C(O)NRR', and a cyano, in which each occurrence of R and R' is independently selected from H and —(C$_{1-6}$ alkyl).

As used herein, when two groups are indicated to be "linked" or "bonded" to form a "ring", it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions. In some embodiments, such rings have from 3-7 members, for example, 5 or 6 members.

The skilled artisan will recognize that some chemical structures described herein may be represented on paper by one or more other resonance forms; or may exist in one or more other tautomeric forms, even when kinetically, the artisan recognizes that such tautomeric forms represent only a very small portion of a sample of such compound(s). Such compounds are clearly contemplated within the scope of this disclosure, though such resonance forms or tautomers are not explicitly represented herein.

The compounds provided herein may encompass various stereochemical forms. The compounds also encompass diastereomers as well as optical isomers, e.g., mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The present disclosure includes all pharmaceutically acceptable isotopically labeled compounds of Formula I wherein one or more atoms are replaced by atoms having the same atomic number, but an atomic mass or mass number different from the atomic mass or mass number which predominates in nature. Examples of isotopes suitable for inclusion in the compounds of the disclosure include, but are not limited to, isotopes of hydrogen, such as $^2$H (deuterium) and $^3$H (tritium), carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

The term "administration" or "administering" refers to a method of providing a dosage of a compound or pharmaceutical composition to a vertebrate or invertebrate, including a mammal, a bird, a fish, or an amphibian, where the method is, e.g., orally, subcutaneously, intravenously, intralymphatic, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The method of administration can vary depending on various factors, e.g., the components of the pharmaceutical composition, the site of the disease, the disease involved, and the severity of the disease.

A "diagnostic" as used herein is a compound, method, system, or device that assists in the identification or characterization of a health or disease state. The diagnostic can be used in standard assays as is known in the art.

The term "mammal" is used in its usual biological sense. Thus, it specifically includes humans, cattle, horses, monkeys, dogs, cats, mice, rats, cows, sheep, pigs, goats, and non-human primates, but also includes many other species.

The term "pharmaceutically acceptable carrier", "pharmaceutically acceptable diluent" or "pharmaceutically acceptable excipient" includes any and all solvents, co-solvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Brunton et al. (Eds.) (2017); *Goodman and Gilman's: The Pharmacological Basis of Therapeutics*, 13th Ed., The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Many such salts are known in the art, for example, as described in WO 87/05297. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

"Patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

A "therapeutically effective amount" of a compound as provided herein is one which is sufficient to achieve the desired physiological effect and may vary according to the nature and severity of the disease condition, and the potency of the compound. "Therapeutically effective amount" is also intended to include one or more of the compounds of Formula I in combination with one or more other agents that are effective to treat the diseases and/or conditions described herein. The combination of compounds can be a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease.

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

"Drug-eluting" and/or controlled release as used herein refers to any and all mechanisms, e.g., diffusion, migration, permeation, and/or desorption by which the drug(s) incorporated in the drug-eluting material pass therefrom over time into the surrounding body tissue.

"Drug-eluting material" and/or controlled release material as used herein refers to any natural, synthetic or semi-synthetic material capable of acquiring and retaining a desired shape or configuration and into which one or more drugs can be incorporated and from which incorporated drug(s) are capable of eluting over time.

"Elutable drug" as used herein refers to any drug or combination of drugs having the ability to pass over time from the drug-eluting material in which it is incorporated into the surrounding areas of the body.

Compounds

The compounds and compositions described herein can be used as anti-proliferative agents, e.g., anti-cancer and anti-angiogenesis agents, and/or as inhibitors of the Wnt signaling pathway, e.g., for treating diseases or disorders associated with aberrant Wnt signaling. In addition, the compounds can be used as inhibitors of one or more kinases, kinase receptors, or kinase complexes. Such compounds and compositions are also useful for controlling cellular proliferation, differentiation, and/or apoptosis.

The compounds and compositions described herein can be used to inhibit DYRK1A for treating a disorder or disease in which DYRK1A overexpression is implicated, such as Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

Some embodiments of the present disclosure include compounds of Formula I:

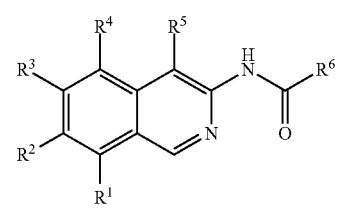

or salts, pharmaceutically acceptable salts, or prodrugs thereof.

In some embodiments, $R^1$, $R^2$, $R^4$, and $R^5$ are independently selected from the group consisting of H and halide (e.g., F, Cl, Br, I);

In some embodiments, $R^1$, $R^2$, $R^4$, and $R^5$ are independently selected from the group consisting of H and F.

In some embodiments, $R^1$, $R^2$, $R^4$, and $R^5$ are all H.

In some embodiments, $R^1$ is F, and $R^2$, $R^4$, and $R^5$ are all H.

In some embodiments, $R^2$ is F, and $R^1$, $R^4$, and $R^5$ are all H.

In some embodiments, $R^4$ is F, and $R^1$, $R^2$, and $R^5$ are all H.

In some embodiments, $R^5$ is F, and $R^1$, $R^2$, and $R^4$ are all H.

In some embodiments, $R^3$ is a 5-membered heteroaryl ring optionally substituted as defined anywhere herein.

In some embodiments, $R^3$ is 5-membered heteroaryl ring optionally substituted with 1-4 (e.g., 1-3, 1-2, 1) $R^{26}$;

In some embodiments, there is the proviso that $R^3$ is not

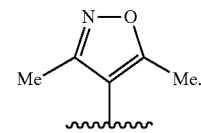

In some embodiments, $R^3$ is selected from the group consisting of: furanyl optionally substituted with 1-4 (e.g., 1-3, 1-2, 1) $R^{26}$, thiophenyl optionally substituted with 1-4 (e.g., 1-3, 1-2, 1) $R^{26}$, pyrrolyl optionally substituted with 1-4 (e.g., 1-3, 1-2, 1) $R^{26}$,

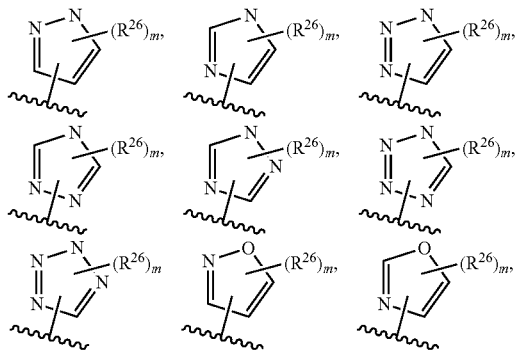

-continued

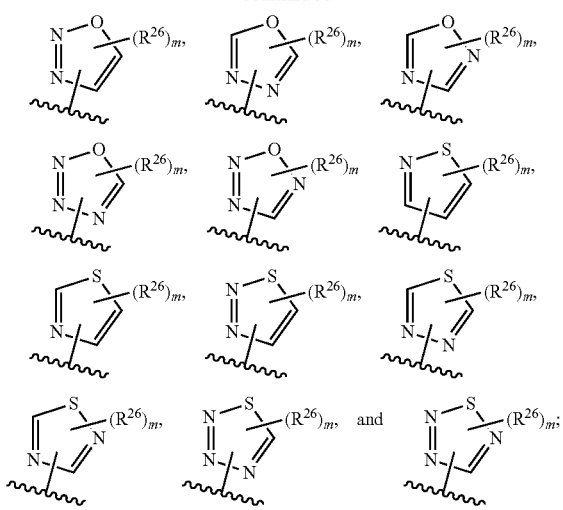

wherein each m is independently 1 to 4 (e.g., 1-3, 1-2, 1).

In some embodiments, $R^3$ is selected from the group consisting of:

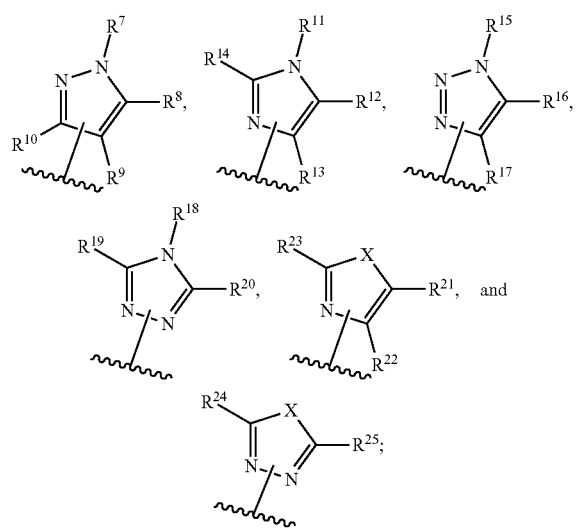

wherein each of $R^7$-$R^{25}$ is, independently, a substituent as defined anywhere herein or a single bond connecting $R^3$ to the isoquinoline ring; wherein only one of $R^7$-$R^{10}$ (when present) is a bond, only one of $R^{11}$-$R^{14}$ (when present) is a bond, only one of $R^{15}$-$R^{17}$ (when present) is a bond, only one of $R^{18}$-$R^{20}$ (when present) is a bond, only one of $R^{21}$-$R^{23}$ (when present) is a bond, and only one of $R^{24}$-$R^{25}$ (when present) is a bond; for purposes of clarification, any one of the nitrogen atoms attached to $R^7$, $R^{11}$, $R^{15}$, or $R^{18}$ can serve as the point of attachment of $R^3$ to the isoquinoline ring; likewise, any one of the carbon atoms attached to $R^8$, $R^9$, $R^{10}$, $R^{12}$, $R^{13}$, $R^{14}$, $R^{16}$, $R^{17}$, $R^{19}$, $R^{20}$, $R^{21}$, $R^{22}$, $R^{23}$, $R^{24}$, and $R^{25}$, can serve as the point of attachment of $R^3$ to the isoquinoline ring.

In some embodiments, $R^3$ is selected from the group consisting of:

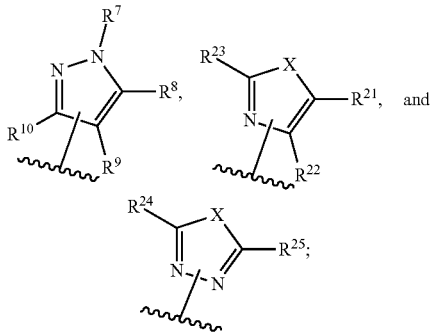

wherein each of $R^7$-$R^{10}$ and $R^{21}$-$R^{25}$ is, independently, a substituent as defined anywhere herein or a single bond connecting $R^3$ to the isoquinoline ring; wherein only one of $R^7$-$R^{10}$ (when present) is a bond, only one of $R^{21}$-$R^{23}$ (when present) is a bond, and only one of $R^{24}$-$R^{25}$ (when present) is a bond; for purposes of clarification, any one of the nitrogen atoms attached to $R^7$ can serve as the point of attachment of $R^3$ to the isoquinoline ring; likewise, any one of the carbon atoms attached to $R^8$, $R^9$, $R^{10}$, $R^{21}$, $R^{22}$, $R^{23}$, $R^{24}$, or $R^{25}$ can serve as the point of attachment of $R^3$ to the isoquinoline ring.

In some embodiment, —($C_{1-4}$ alkylene) is, optionally substituted with one or more substituents as defined anywhere herein, wherein one or more H are optionally replaced by D.

In some embodiment, —($C_{1-4}$ alkylene) is, optionally substituted with one or more halides (e.g., F, Cl, Br, I) or one or more unsubstituted —($C_{1-3}$ alkyl) (e.g., $C_{2-3, 1-2, 1}$ alkyl).

In some embodiment, —($C_{1-4}$ alkylene) is, optionally substituted with one or more halides (e.g., F, Cl, Br, I) and one or more unsubstituted —($C_{1-3}$ alkyl) (e.g., $C_{2-3, 1-2, 1}$ alkyl).

In some embodiment, —($C_{1-4}$ alkylene) is, optionally substituted with one or more F or one or more Me.

In some embodiment, —($C_{1-4}$ alkylene) is, optionally substituted with one or more F and one or more Me.

In some embodiment, —($C_{1-4}$ alkylene) is —$CH_2$—.

In some embodiment, —($C_{1-4}$ alkylene) is —$CD_2$-.

In some embodiment, —($C_{1-4}$ alkylene) is —$CH_2CH_2$—.

In some embodiment, —($C_{1-4}$ alkylene) is —$CH_2CH_2CH_2$—.

In some embodiments, $R^6$ is selected from the group consisting of —($C_{1-4}$ alkylene)$_p$heterocyclyl optionally substituted with 1-5 (e.g., 1-4, 1-3, 1-2, 1) $R^{27}$, -carbocyclyl optionally substituted with 1-5 (e.g., 1-4, 1-3, 1-2, 1) $R^{27}$, and —N($R^{30}$)($R^{31}$); wherein —($C_{1-4}$ alkylene) is, optionally substituted with one or more substituents as defined anywhere herein.

In some embodiments, $R^6$ is selected from the group consisting of:

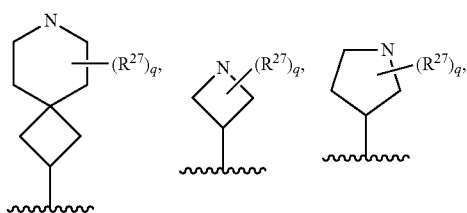

-continued

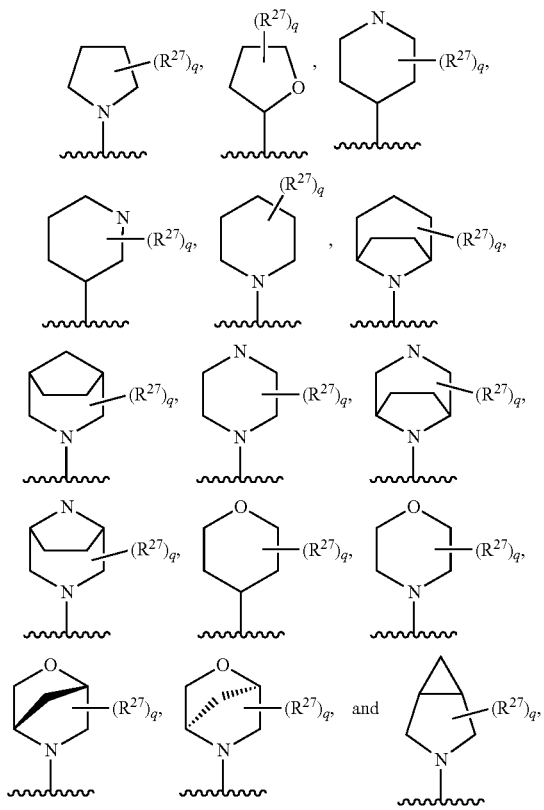

and q is 0 to 2, wherein one or more H on the heterocycle ring are optionally replaced by D.

In some embodiments, $R^6$ is selected from the group consisting of:

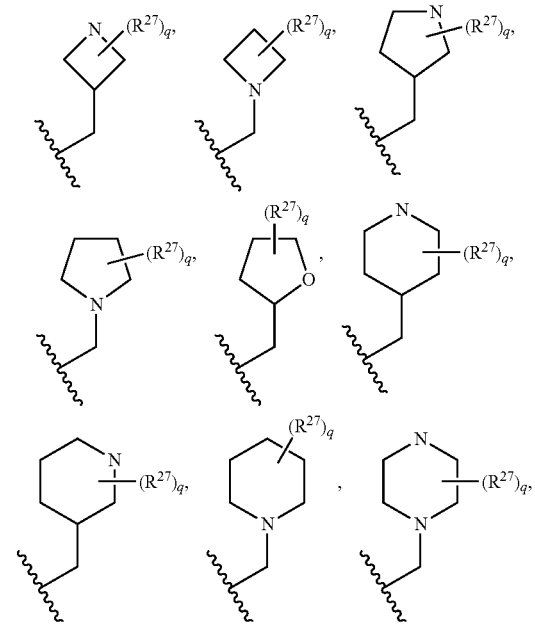

-continued

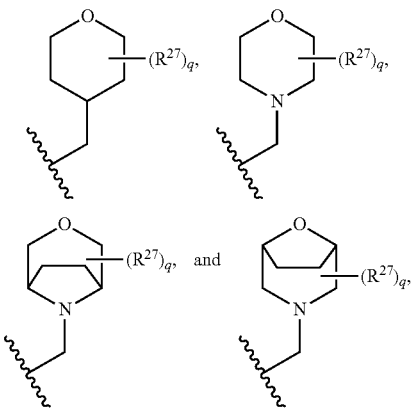

and q is 0 to 2, wherein one or more H on the heterocycle ring are optionally replaced by D.

In some embodiments, $R^6$ is

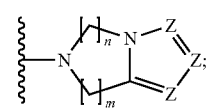

wherein n is 1-4 (e.g., 1-3, 1-2, 1), m is 0-2 (e.g., 0-1, 0) and each Z is independently selected from the group consisting of $CR^{32}$ and N.

In some embodiments, $R^6$ is selected from the group consisting of

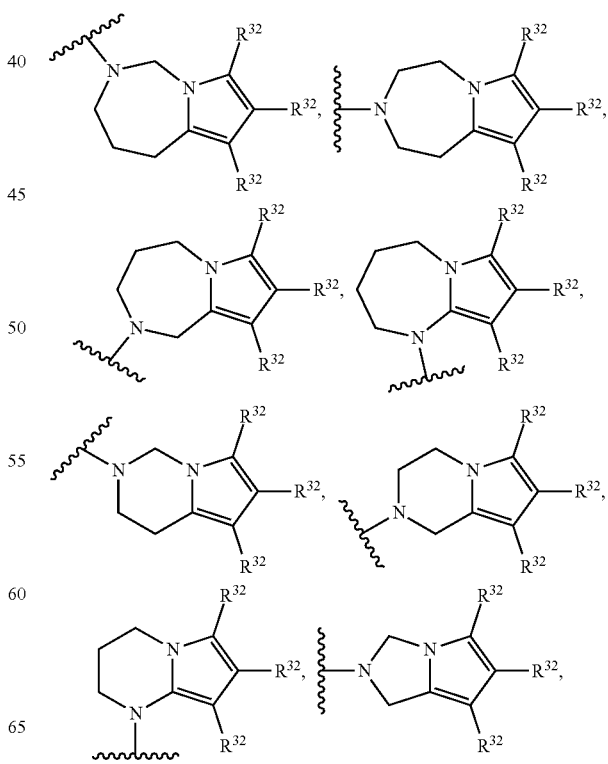

-continued
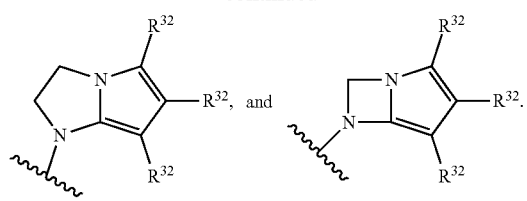
In some embodiments, $R^6$ is selected from the group consisting of
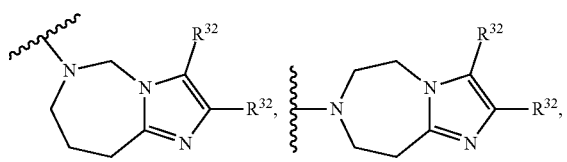
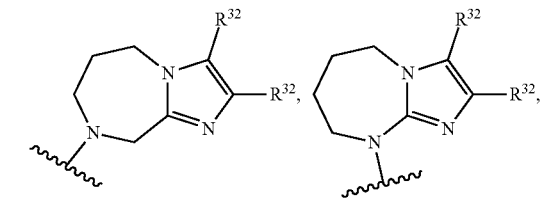
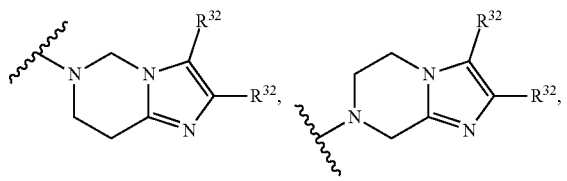
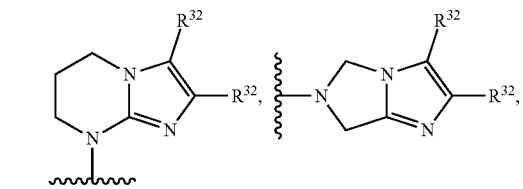
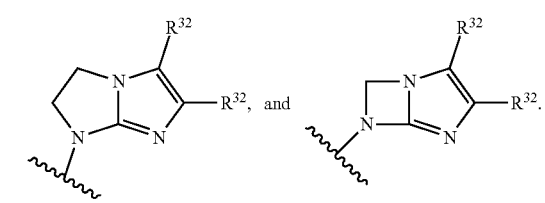
In some embodiments, $R^6$ is selected from the group consisting of
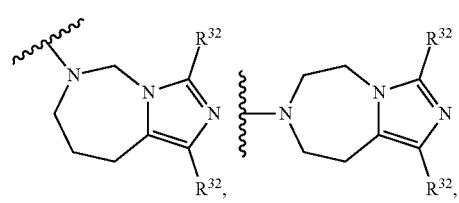
-continued
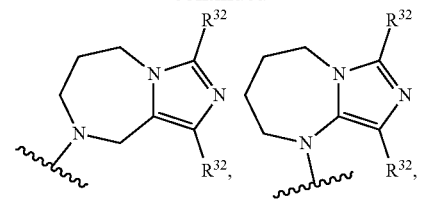
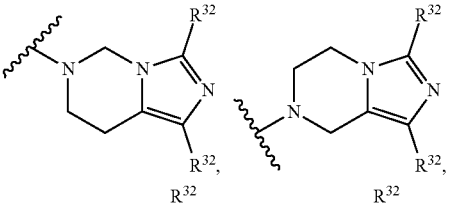
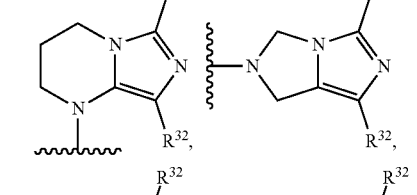
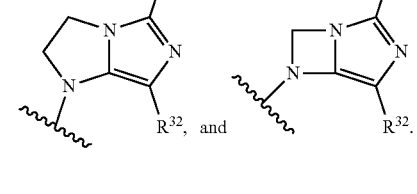
In some embodiments, $R^6$ is selected from the group consisting of
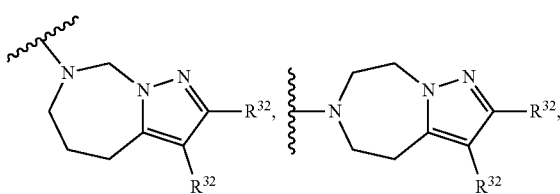
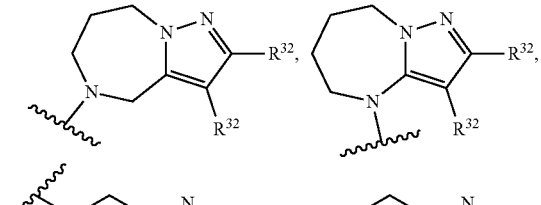
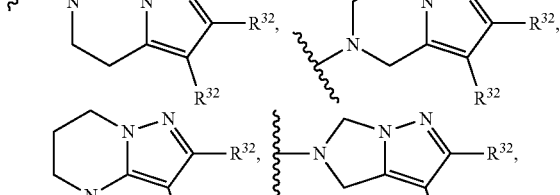
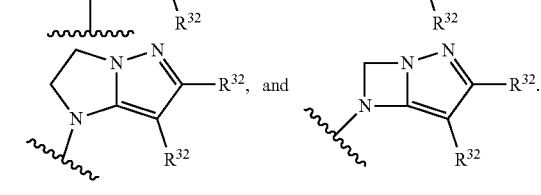

In some embodiments, $R^6$ is selected from the group consisting of

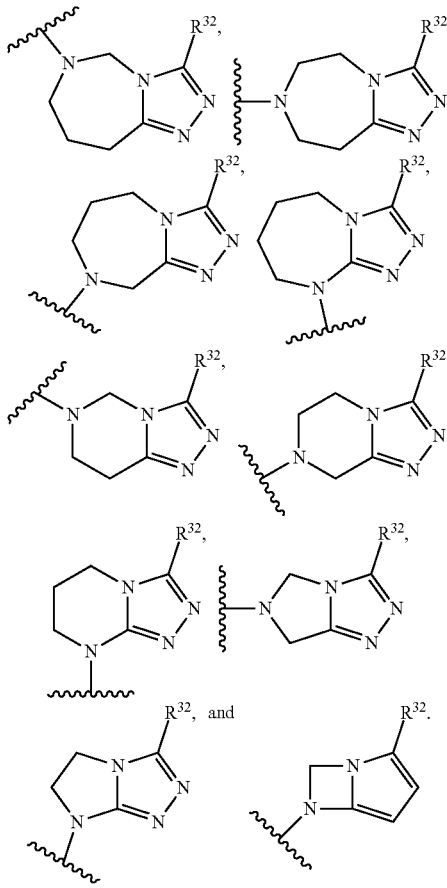

In some embodiments, $R^6$ is selected from the group consisting of

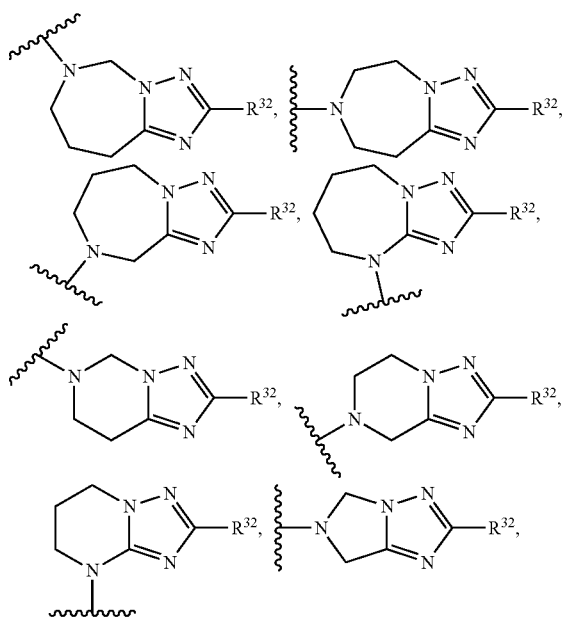

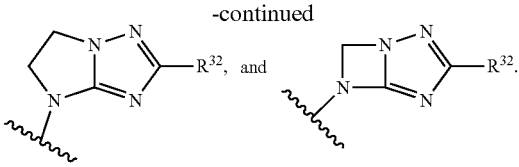

In some embodiments, $R^6$ is selected from the group consisting of

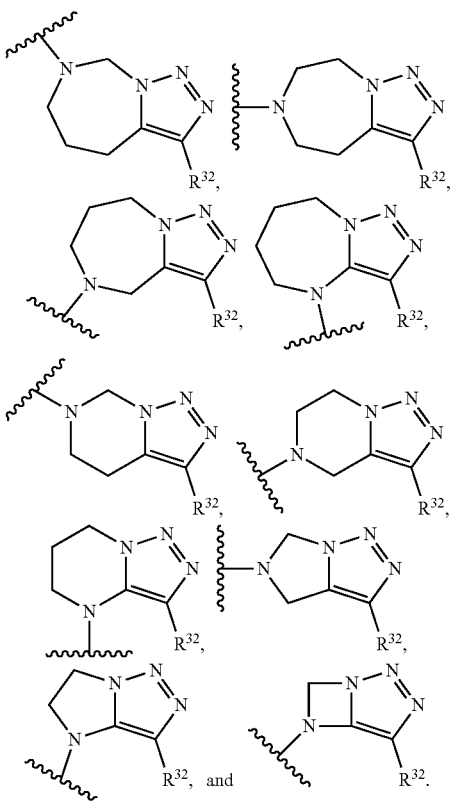

In some embodiments, $R^6$ is —N($R^3$)($R^{31}$).
In some embodiments, $R^6$ is —NH($R^{31}$).
In some embodiments, $R^6$ is selected from the group consisting of

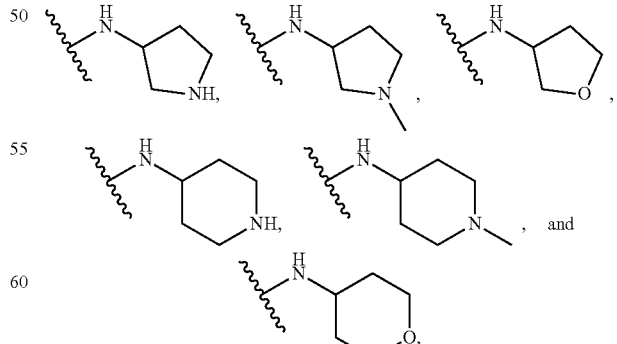

wherein one or more H on the heterocycle ring are optionally replaced by D.
In some embodiments, $R^6$ is —NMe($R^{31}$).

In some embodiments, $R^6$ is selected from the group consisting of

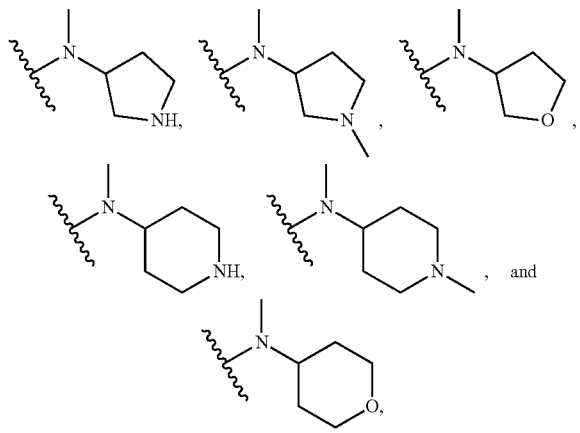

wherein one or more H on the heterocycle ring are optionally replaced by D.

In some embodiments, $R^6$ is selected from the group consisting of —$CH_2$phenyl substituted with 1-5 $R^{41}$, —CH=CHphenyl optionally substituted with halide (e.g., F, Cl, Br, I), —($C_{1-4}$ alkylene)$_p$heterocyclyl substituted with 1-5 (e.g., 1-4, 1-3, 1-2, 1) $R^{27}$, -carbocyclyl substituted with 1-5 (e.g., 1-4, 1-3, 1-2, 1) $R^{28}$, and

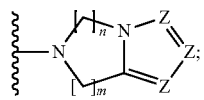

wherein —($C_{1-4}$ alkylene) is, optionally substituted with one or more substituents as defined anywhere herein; wherein n is 1-4 (e.g., 1-3, 1-2, 1), m is 0-2 (e.g., 2, 1, 0) and each Z is independently selected from the group consisting of $CR^{32}$ and N.

In some embodiments, $R^6$ is a selected from the group consisting of -phenyl substituted with 1-5 (e.g., 1-4, 1-3, 1-2, 1) $R^{42}$ and 6-membered heteroaryl optionally substituted with 1-6 (e.g., 1-5, 1-4, 1-3, 1-2, 1) $R^{29}$.

In some embodiments, $R^6$ is selected from the group consisting of -phenyl substituted with 1-2 $R^{42}$ and pyridinyl optionally substituted with 1-2 $R^{29}$.

In some embodiments, $R^6$ is a -phenyl substituted with 1-2 $R^{42}$, wherein one or more H on the phenyl ring are replaced by D.

In some embodiments, $R^6$ is selected from the group consisting of -phenyl substituted with 1-2 $R^{42}$ and pyridin-4-yl optionally substituted with 1-2 $R^{29}$.

In some embodiments, $R^3$ is R

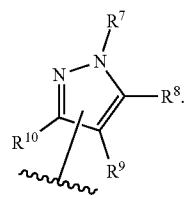

In certain embodiments, $R^9$ is a single bond connecting $R^3$ to the isoquinoline ring, i.e., $R^3$ has the following formula:

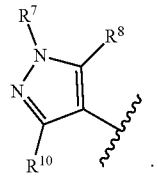

In certain embodiments, $R^9$ is a single bond connecting $R^3$ to the isoquinoline ring, i.e., $R^3$ has the following formula:

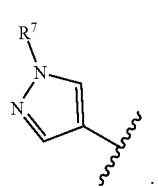

In some embodiments, $R^7$ is selected from the group consisting of a single bond, H, and unsubstituted —($C_{1-5}$ alkyl) (e.g., $C_{2-5, 3-5, 4-5, 2-4, 3-4, 2-3, 1-4, 1-3, 1-2, 1}$ alkyl).

In some embodiments, $R^7$ is selected from the group consisting of H and Me.

In some embodiments, $R^7$ is Me.

In some embodiments, $R^7$ is $CD_3$.

In some embodiments, $R^8$, $R^9$, and $R^{10}$ are independently selected from the group consisting of a single bond, H, and unsubstituted —($C_{1-5}$ alkyl) (e.g., $C_{2-5, 3-5, 4-5, 2-4, 3-4, 2-3, 1-4, 1-3, 1-2, 1}$ alkyl).

In some embodiments, $R^8$, $R^9$, and $R^{10}$ are independently selected from the group consisting of a single bond, H, and Me.

In some embodiments, $R^9$ is a single bond connecting $R^3$ to the isoquinoline ring and $R^8$ and $R^{10}$ are independently selected from the group consisting of H and Me.

In some embodiments, $R^9$ is a single bond and $R^8$ and $R^{10}$ are both H.

In some embodiments, $R^3$ is

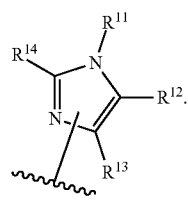

In certain embodiments, $R^{12}$ is a single bond connecting $R^3$ to the isoquinoline ring, i.e., $R^3$ has the following formula:

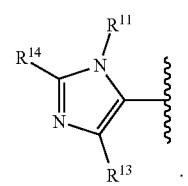

In certain embodiments, $R^{12}$ is a single bond connecting $R^3$ to the isoquinoline ring, i.e., $R^3$ has the following formula:

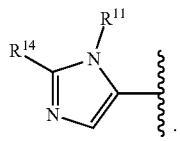

In some embodiments, $R^{11}$ is selected from the group consisting of a single bond, H, and unsubstituted —($C_{1-5}$ alkyl) (e.g., $C_{2-5, 3-5, 4-5, 2-4, 3-4, 2-3, 1-4, 1-3, 1-2, 1}$ alkyl).

In some embodiments, $R^{11}$ is selected from the group consisting of H and Me.

In some embodiments, $R^{11}$ is H.

In some embodiments, $R^{11}$ is Me.

In some embodiments, $R^{11}$ is $CD_3$.

In some embodiments, $R^{12}$, $R^{13}$, and $R^{14}$ are independently selected from the group consisting of a single bond, H, and unsubstituted —($C_{1-5}$ alkyl) (e.g., $C_{2-5, 3-5, 4-5, 2-4, 3-4, 2-3, 1-4, 1-3, 1-2, 1}$ alkyl).

In some embodiments, $R^{12}$, $R^{13}$, and $R^{14}$ are independently selected from the group consisting of a single bond, H, and Me.

In some embodiments, $R^{12}$ is a single bond connecting $R^3$ to the isoquinoline ring and $R^{13}$ and $R^{14}$ are independently selected from the group consisting of H and Me.

In some embodiments, $R^{12}$ is a single bond connecting $R^3$ to the isoquinoline ring and $R^{13}$ and $R^{14}$ are both H.

In some embodiments, $R^{12}$ is a single bond connecting $R^3$ to the isoquinoline ring; $R^{13}$ is H, and $R^{14}$ is Me.

In some embodiments, $R^3$ is

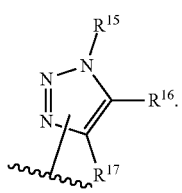

In certain embodiments, $R^{16}$ is a single bond connecting $R^3$ to the isoquinoline ring, i.e., $R^3$ has the following formula:

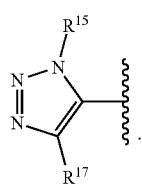

In certain embodiments, $R^{17}$ is a single bond connecting $R^3$ to the isoquinoline ring, i.e., $R^3$ has the following formula:

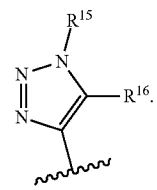

In certain embodiments, $R^{17}$ is a single bond connecting $R^3$ to the isoquinoline ring, i.e., $R^3$ has the following formula:

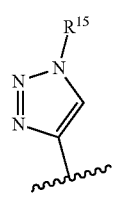

In some embodiments, $R^{15}$ is selected from the group consisting of a single bond, H, and unsubstituted —($C_{1-5}$ alkyl) (e.g., $C_{2-5, 3-5, 4-5, 2-4, 3-4, 2-3, 1-4, 1-3, 1-2, 1}$ alkyl).

In some embodiments, $R^{15}$ is selected from the group consisting of H and Me.

In some embodiments, $R^{15}$ is H.

In some embodiments, $R^{15}$ is Me.

In some embodiments, $R^{15}$ is $CD_3$.

In some embodiments, $R^{16}$ and $R^{17}$ are independently selected from the group consisting of a single bond, H, and unsubstituted —($C_{1-5}$ alkyl) (e.g., $C_{2-5, 3-5, 4-5, 2-4, 3-4, 2-3, 1-4, 1-3, 1-2, 1}$ alkyl).

In some embodiments, $R^{16}$ and $R^{17}$ are independently selected from the group consisting of a single bond, H, and Me.

In some embodiments, $R^{17}$ is a single bond connecting $R^3$ to the isoquinoline ring and $R^{16}$ is selected from the group consisting of H and Me.

In some embodiments, $R^{17}$ is a single bond connecting $R^3$ to the isoquinoline ring and $R^{16}$ is H.

In some embodiments, $R^3$ is

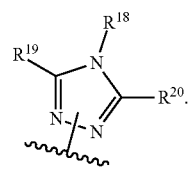

In certain embodiments, $R^{20}$ is a single bond connecting $R^3$ to the isoquinoline ring, i.e., $R^3$ has the following formula:

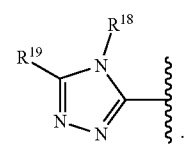

In certain embodiments, $R^{20}$ is a single bond connecting $R^3$ to the isoquinoline ring, i.e., $R^3$ has the following formula:

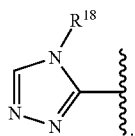

In some embodiments, $R^{18}$ is selected from the group consisting of a single bond, H, and unsubstituted —($C_{1-5}$ alkyl) (e.g., $C_{2-5, 3-5, 4-5, 2-4, 3-4, 2-3, 1-4, 1-3, 1-2, 1}$ alkyl).

In some embodiments, $R^{18}$ is selected from the group consisting of H and Me.

In some embodiments, $R^{18}$ is H.

In some embodiments, $R^{18}$ is Me.

In some embodiments, $R^{18}$ is $CD_3$.

In some embodiments, $R^{19}$ and $R^{20}$ are independently selected from the group consisting of a single bond, H, and unsubstituted —($C_{1-5}$ alkyl) (e.g., $C_{2-5, 3-5, 4-5, 2-4, 3-4, 2-3, 1-4, 1-3, 1-2, 1}$ alkyl).

In some embodiments, $R^{19}$ and $R^{20}$ are independently selected from the group consisting of a single bond, H, and Me.

In some embodiments, $R^{20}$ is a single bond connecting $R^3$ to the isoquinoline ring and $R^{19}$ is selected from the group consisting of H and Me.

In some embodiments, $R^{20}$ is a single bond connecting $R^3$ to the isoquinoline ring and $R^{19}$ is H.

In some embodiments, $R^3$ is

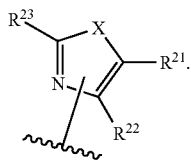

In some embodiments, $R^3$ is

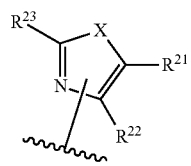

and X is S.

In some embodiments, $R^3$ is

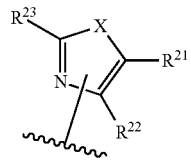

and X is O.

In certain embodiments, $R^{27}$ is a single bond connecting $R^3$ to the isoquinoline ring, i.e., $R^3$ has the following formula:

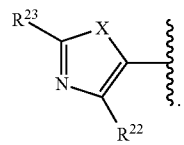

In some embodiments, $R^3$ is

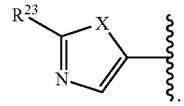

In certain embodiments, $R^{27}$ is a single bond connecting $R^3$ to the isoquinoline ring, i.e., $R^3$ has the following formula:

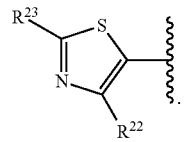

In some embodiments, $R^3$ is

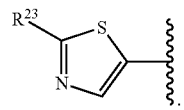

In some embodiments, $R^3$ is

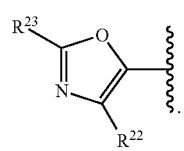

In some embodiments, $R^3$ is

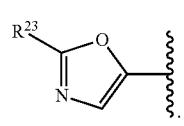

In some embodiments, $R^{21}$, $R^{22}$, and $R^{23}$ are independently selected from the group consisting of a single bond, H, and unsubstituted —($C_{1-5}$ alkyl) (e.g., $C_{2-5, 3-5, 4-5, 2-4, 3-4, 2-3, 1-4, 1-3, 1-2, 1}$ alkyl).

In some embodiments, X is O and $R^{21}$, $R^{22}$, and $R^{23}$ are independently selected from the group consisting of a single bond, H, and Me.

In some embodiments, X is O, $R^{21}$ is a single bond connecting $R^3$ to the isoquinoline ring and $R^{22}$ and $R^{23}$ are independently selected from the group consisting of H and Me.

In some embodiments, X is O, $R^{21}$ is a single bond connecting $R^3$ to the isoquinoline ring and $R^{22}$ and $R^{23}$ are both H.

In some embodiments, X is O, $R^{21}$ is a single bond connecting $R^3$ to the isoquinoline ring; $R^{22}$ is H, and $R^{23}$ is Me.

In some embodiments, X is S and $R^{21}$, $R^{22}$, and $R^{23}$ are independently selected from the group consisting of a single bond, H, and Me.

In some embodiments, X is S, $R^{21}$ is a single bond connecting $R^3$ to the isoquinoline ring and $R^{22}$ and $R^{23}$ are independently selected from the group consisting of H and Me.

In some embodiments, X is S, $R^{21}$ is a single bond connecting $R^3$ to the isoquinoline ring and $R^{22}$ and $R^{23}$ are both H.

In some embodiments, X is S, $R^{21}$ is a single bond connecting $R^3$ to the isoquinoline ring; $R^{22}$ is H, and $R^{23}$ is Me.

In some embodiments, $R^3$ is

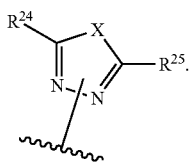

In some embodiments, $R^3$ is

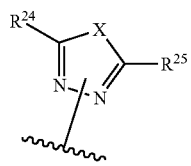

and X is S.

In some embodiments, $R^3$ is

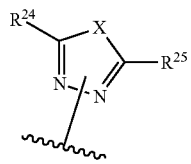

and X is O.

In certain embodiments, $R^{33}$ is a single bond connecting $R^3$ to the isoquinoline ring, i.e., $R^3$ has the following formula:

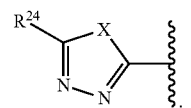

In some embodiments, $R^3$ is

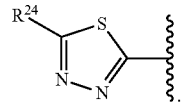

In some embodiments, $R^3$ is

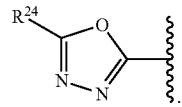

In some embodiments, $R^{24}$ and $R^{25}$ are independently selected from the group consisting of a single bond, H, and unsubstituted —($C_{1-5}$ alkyl) (e.g., $C_{2-5,\ 3-5,\ 4-5,\ 2-4,\ 3-4,\ 2-3,\ 1-4,\ 1-3,\ 1-2,\ 1}$ alkyl).

In some embodiments, X is O, $R^{24}$ and $R^{25}$ are independently selected from the group consisting of a single bond, H, and Me.

In some embodiments, X is O, $R^{25}$ is a single bond connecting $R^3$ to the isoquinoline ring and $R^{24}$ is Me.

In some embodiments, X is O, $R^{25}$ is a single bond connecting $R^3$ to the isoquinoline ring and $R^{24}$ is H.

In some embodiments, X is S, $R^{24}$ and $R^{25}$ are independently selected from the group consisting of a single bond, H, and Me.

In some embodiments, X is S, $R^{25}$ is a single bond connecting $R^3$ to the isoquinoline ring and $R^{24}$ is Me.

In some embodiments, X is S, $R^{25}$ is a single bond connecting $R^3$ to the isoquinoline ring and $R^{24}$ is H.

In some embodiments, each $R^{26}$ is independently unsubstituted —($C_{1-5}$ alkyl) (e.g., $C_{2-5,\ 3-5,\ 4-5,\ 2-4,\ 3-4,\ 2-3,\ 1-4,\ 1-3,\ 1-2,\ 1}$ alkyl).

In some embodiments, each $R^{26}$ is independently Me, Et, nPr, iPr, nBu, iBu, tBu.

In some embodiments, each $R^{27}$ is independently selected from the group consisting of halide (e.g., F, Cl, Br, I), unsubstituted —($C_{1-5}$ alkyl) (e.g., $C_{2-5,\ 3-5,\ 4-5,\ 2-4,\ 3-4,\ 2-3,\ 1-4,\ 1-3,\ 1-2,\ 1}$ alkyl), unsubstituted —($C_{1-5}$ haloalkyl) (e.g., $C_{2-5,\ 3-5,\ 4-5,\ 2-4,\ 3-4,\ 2-3,\ 1-4,\ 1-3,\ 1-2,\ 1}$ haloalkyl), —$OR^{35}$, and —($C_{1-4}$ alkylene)$_p$heterocyclyl optionally substituted with 1-5 (e.g., 1-4, 1-3, 1-2, 1) $R^{36}$; wherein —($C_{1-4}$ alkylene) is, optionally substituted with one or more substituents as defined anywhere herein.

In some embodiments, each $R^{27}$ is independently selected from the group consisting of F, Me, Et, nPr, iPr, nBu, iBu, tBu, —$CF_3$, —OMe, -OEt, -heterocyclyl optionally substituted with 1-2 (e.g., 1) $R^{36}$ and —$CH_2$heterocyclyl optionally substituted with 1-2 (e.g., 1) $R^{36}$.

In some embodiments, each $R^{27}$ is independently selected from the group consisting of halide (e.g., F, Cl, Br, I) and —$N(R^{43})(R^{44})$.

In some embodiments, if one or more $R^{27}$ is halide, at least one $R^{27}$ is —$N(R^{43})(R^{44})$.

In some embodiments, each $R^{27}$ is F.

In some embodiments, $R^{27}$ is —$N(R^{43})(R^{44})$.

In some embodiments, one $R^{27}$ is F and one $R^{27}$ is —$N(R^{43})(R^{44})$.

In some embodiments, $R^{27}$ is —$NMe_2$; in some embodiments, $R^{27}$ is —NH(Me); in some embodiments, $R^{27}$ is —NH(Et); in some embodiments, $R^{27}$ is —NH(nPr); in some embodiments, $R^{27}$ is —NH(iPr); in some embodiments, $R^{27}$ is —NH(nBu); in some embodiments, $R^{27}$ is —NH(iBu); in some embodiments, $R^{27}$ is —NH(tBu); wherein one or more H are optionally replaced by D.

In some embodiments, one $R^{27}$ is F and one $R^{27}$ is —NMe$_2$; in some embodiments, one $R^{27}$ is F and one $R^{27}$ is —NH(Me); in some embodiments, one $R^{27}$ is F and one $R^{27}$ is —NH(Et); in some embodiments, one $R^{27}$ is F and one $R^{27}$ is —NH(nPr); in some embodiments, one $R^{27}$ is F and one $R^{27}$ is —NH(iPr); in some embodiments, one $R^{27}$ is F and one $R^{27}$ is —NH(nBu); in some embodiments, one $R^{27}$ is F and one $R^{27}$ is —NH(iBu); in some embodiments, one $R^{27}$ is F and one $R^{27}$ is —NH(tBu); wherein one or more H are optionally replaced by D.

In some embodiments, $R^{27}$ is —NH($C_{1-5}$ haloalkyl); in some embodiments, $R^{27}$ is —NH($C_{1-4}$ haloalkyl); in some embodiments, $R^{27}$ is —NH($C_{1-3}$ haloalkyl); in some embodiments, $R^{27}$ is —NH($C_{1-2}$ haloalkyl); in some embodiments, $R^{27}$ is —NH(CH$_2$CH$_2$F); in some embodiments, $R^{27}$ is —NH(CH$_2$CHF$_2$); in some embodiments, $R^{27}$ is —NH(CH$_2$CF$_3$); in some embodiments, $R^{27}$ is —NH(CH$_2$CH$_2$CH$_2$F); in some embodiments, $R^{27}$ is —NH(CH$_2$CH$_2$CHF$_2$); in some embodiments, $R^{27}$ is —NH(CH$_2$CH$_2$CF$_3$); in some embodiments, $R^{27}$ is —NH(CH(CH$_2$F)$_2$); in some embodiments, $R^{27}$ is —NH(CH(CHF$_2$)$_2$); in some embodiments, $R^{27}$ is —NH(CH(CF$_3$)$_2$); in some embodiments, $R^{27}$ is —N($C_{1-5}$ haloalkyl)$_2$; in some embodiments, $R^{27}$ is —N($C_{1-4}$ haloalkyl)$_2$; in some embodiments, $R^{27}$ is —N($C_{1-3}$ haloalkyl)$_2$; in some embodiments, $R^{27}$ is —N($C_{1-2}$ haloalkyl)$_2$; in some embodiments, $R^{27}$ is —N(CH$_2$CH$_2$F)$_2$; in some embodiments, $R^{27}$ is —N(CH$_2$CHF$_2$)$_2$; in some embodiments, $R^{27}$ is —N(CH$_2$CF$_3$)$_2$; in some embodiments, $R^{27}$ is —N(CH$_2$CH$_2$CH$_2$F)$_2$; in some embodiments, $R^{27}$ is —N(CH$_2$CH$_2$CHF$_2$)$_2$; in some embodiments, $R^{27}$ is —N(CH$_2$CH$_2$CF$_3$)$_2$; in some embodiments, $R^{27}$ is —N(CH(CH$_2$F)$_2$)$_2$; in some embodiments, $R^{27}$ is —N(CH(CHF$_2$)$_2$)$_2$; in some embodiments, $R^{27}$ is —N(CH(CF$_3$)$_2$)$_2$; in some embodiments, $R^{27}$ is —NMe($C_{1-5}$ haloalkyl); in some embodiments, $R^{27}$ is —NMe($C_{1-4}$ haloalkyl); in some embodiments, $R^{27}$ is —NMe($C_{1-3}$ haloalkyl); in some embodiments, $R^{27}$ is —NMe($C_{1-2}$ haloalkyl); in some embodiments, $R^{27}$ is —NMe(CH$_2$CH$_2$F); in some embodiments, $R^{27}$ is —NMe(CH$_2$CHF$_2$); in some embodiments, $R^{27}$ is —NMe(CH$_2$CF$_3$); in some embodiments, $R^{27}$ is —NMe(CH$_2$CH$_2$CH$_2$F); in some embodiments, $R^{27}$ is —NMe(CH$_2$CH$_2$CHF$_2$); in some embodiments, $R^{27}$ is —NMe(CH$_2$CH$_2$CF$_3$); in some embodiments, $R^{27}$ is —NMe(CH(CH$_2$F)$_2$); in some embodiments, $R^{27}$ is —NMe(CH(CHF$_2$)$_2$); in some embodiments, $R^{27}$ is —NMe(CH(CF$_3$)$_2$); wherein one or more H are optionally replaced by D.

In some embodiments, $R^{27}$ is —NH(CF$_3$).

In some embodiments, one $R^{27}$ is F and one $R^{27}$ is —NH($C_{1-5}$ haloalkyl); in some embodiments, one $R^{27}$ is F and one $R^{27}$ is —NH($C_{1-4}$ haloalkyl); in some embodiments, one $R^{27}$ is F and one $R^{27}$ is —NH($C_{1-3}$ haloalkyl); in some embodiments, one $R^{27}$ is F and one $R^{27}$ is —NH($C_{1-2}$ haloalkyl); in some embodiments, one $R^{27}$ is F and one $R^{27}$ is —NH(CH$_2$CH$_2$F); in some embodiments, one $R^{27}$ is F and one $R^{27}$ is —NH(CH$_2$CHF$_2$); in some embodiments, one $R^{27}$ is F and one $R^{27}$ is —NH(CH$_2$CF$_3$); in some embodiments, one $R^{27}$ is F and one $R^{27}$ is —NH(CH$_2$CH$_2$CH$_2$F); in some embodiments, one $R^{27}$ is F and one $R^{27}$ is —NH(CH$_2$CH$_2$CHF$_2$); in some embodiments, one $R^{27}$ is F and one $R^{27}$ is —NH(CH$_2$CH$_2$CF$_3$); in some embodiments, one $R^{27}$ is F and one $R^{27}$ is —NH(CH(CH$_2$F)$_2$); in some embodiments, one $R^{27}$ is F and one $R^{27}$ is —NH(CH(CHF$_2$)$_2$); in some embodiments, one $R^{27}$ is F and one $R^{27}$ is —NH(CH(CF$_3$)$_2$); in some embodiments, one $R^{27}$ is F and one $R^{27}$ is —N($C_{1-5}$ haloalkyl)$_2$; in some embodiments, one $R^{27}$ is F and one $R^{27}$ is —N($C_{1-4}$ haloalkyl)$_2$; in some embodiments, one $R^{27}$ is F and one $R^{27}$ is —N($C_{1-3}$ haloalkyl)$_2$; in some embodiments, one $R^{27}$ is F and one $R^{27}$ is —N($C_{1-2}$ haloalkyl)$_2$; in some embodiments, one $R^{27}$ is F and one $R^{27}$ is —N(CH$_2$CH$_2$F)$_2$; in some embodiments, one $R^{27}$ is F and one $R^{27}$ is —N(CH$_2$CHF$_2$)$_2$; in some embodiments, one $R^{27}$ is F and one $R^{27}$ is —N(CH$_2$CF$_3$)$_2$; in some embodiments, one $R^{27}$ is F and one $R^{27}$ is —N(CH$_2$CH$_2$CH$_2$F)$_2$; in some embodiments, one $R^{27}$ is F and one $R^{27}$ is —N(CH$_2$CH$_2$CHF$_2$)$_2$; in some embodiments, one $R^{27}$ is F and one $R^{27}$ is —N(CH$_2$CH$_2$CF$_3$)$_2$; in some embodiments, one $R^{27}$ is F and one $R^{27}$ is —N(CH(CH$_2$F)$_2$)$_2$; in some embodiments, one $R^{27}$ is F and one $R^{27}$ is —N(CH(CHF$_2$)$_2$)$_2$; in some embodiments, one $R^{27}$ is F and one $R^{27}$ is —N(CH(CF$_3$)$_2$)$_2$; in some embodiments, one $R^{27}$ is F and one $R^{27}$ is —NMe($C_{1-5}$ haloalkyl); in some embodiments, one $R^{27}$ is F and one $R^{27}$ is —NMe($C_{1-4}$ haloalkyl); in some embodiments, one $R^{27}$ is F and one $R^{27}$ is —NMe($C_{1-3}$ haloalkyl); in some embodiments, one $R^{27}$ is F and one $R^{27}$ is —NMe($C_{1-2}$ haloalkyl); in some embodiments, one $R^{27}$ is F and one $R^{27}$ is —NMe(CH$_2$CH$_2$F); in some embodiments, one $R^{27}$ is F and one $R^{27}$ is —NMe(CH$_2$CHF$_2$); in some embodiments, one $R^{27}$ is F and one $R^{27}$ is —NMe(CH$_2$CF$_3$); in some embodiments, one $R^{27}$ is F and one $R^{27}$ is —NMe(CH$_2$CH$_2$CH$_2$F); in some embodiments, one $R^{27}$ is F and one $R^{27}$ is —NMe(CH$_2$CH$_2$CHF$_2$); in some embodiments, one $R^{27}$ is F and one $R^{27}$ is —NMe(CH$_2$CH$_2$CF$_3$); in some embodiments, one $R^{27}$ is F and one $R^{27}$ is —NMe(CH(CH$_2$F)$_2$); in some embodiments, one $R^{27}$ is F and one $R^{27}$ is —NMe(CH(CHF$_2$)$_2$); in some embodiments, one $R^{27}$ is F and one $R^{27}$ is —NMe(CH(CF$_3$)$_2$); wherein one or more H are optionally replaced by D.

In some embodiments, one $R^{27}$ is F and one $R^{27}$ is —NH(CF$_3$).

In some embodiments, each $R^{28}$ is independently selected from the group consisting of —N($R^{33}$)$_2$, —($C_{1-4}$ alkylene)OR$^{35}$, —C(=O)(R$^{37}$), and —($C_{1-4}$ alkylene)$_p$heterocyclyl optionally substituted with 1-5 (e.g., 1-4, 1-3, 1-2, 1) $R^{36}$; wherein each —($C_{1-4}$ alkylene) is independently, optionally substituted with one or more substituents as defined anywhere herein.

In some embodiments, each $R^{28}$ is independently selected from the group consisting of —NH$_2$, —NH(Me), —NMe$_2$, —CH$_2$OH, —CH$_2$OMe, —C(=O)(R$^{37}$), -heterocyclyl optionally substituted with 1-5 (e.g., 1-4, 1-3, 1-2, 1) $R^{36}$, and —CH$_2$heterocyclyl optionally substituted with 1-5 (e.g., 1-4, 1-3, 1-2, 1) $R^{36}$.

In some embodiments, each $R^{28}$ is independently selected from the group consisting of —NH$_2$, —NH(Me), —NMe$_2$, —CH$_2$OH, —CH$_2$OMe,

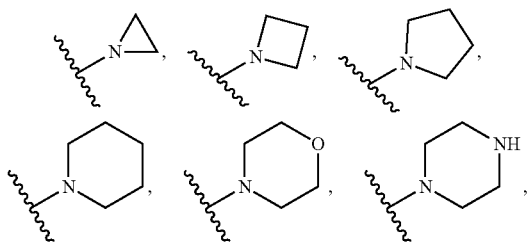

In some embodiments, each $R^{28}$ is —$N(R^{33})(R^{34})$.

In some embodiments, $R^{28}$ is —$NH_2$.

In some embodiments, $R^{28}$ is —$NMe_2$; wherein one or more H are optionally replaced by D.

In some embodiments, $R^{28}$ is —NH(Me); wherein one or more H are optionally replaced by D.

In some embodiments, $R^{28}$ is —NH($C_{1-5}$ haloalkyl); in some embodiments, $R^{28}$ is —NH(unsubstituted ($C_{1-4}$ haloalkyl)); in some embodiments, $R^{28}$ is —NH($C_{1-3}$ haloalkyl); in some embodiments, $R^{28}$ is —NH($C_{1-2}$ haloalkyl); in some embodiments, $R^{28}$ is —NH($CH_2CH_2F$); in some embodiments, $R^{28}$ is —NH($CH_2CHF_2$); in some embodiments, $R^{28}$ is —NH($CH_2CF_3$); in some embodiments, $R^{28}$ is —NH($CH_2CH_2CH_2F$); in some embodiments, $R^{28}$ is —NH($CH_2CH_2CHF_2$); in some embodiments, $R^{28}$ is —NH($CH_2CH_2CF_3$); in some embodiments, $R^{28}$ is —NH($CH(CH_2F)_2$); in some embodiments, $R^{28}$ is —NH($CH(CHF_2)_2$); in some embodiments, $R^{28}$ is —NH($CH(CF_3)_2$); in some embodiments, $R^{28}$ is —N($C_{1-5}$ haloalkyl)$_2$; in some embodiments, $R^{28}$ is —N($C_{1-4}$ haloalkyl)$_2$; in some embodiments, $R^{28}$ is —N($C_{1-3}$ haloalkyl)$_2$; in some embodiments, $R^{28}$ is —N($C_{1-2}$ haloalkyl)$_2$; in some embodiments, $R^{28}$ is —N($CH_2CH_2F$)$_2$; in some embodiments, $R^{28}$ is —N($CH_2CHF_2$)$_2$; in some embodiments, $R^{28}$ is —N($CH_2CF_3$)$_2$; in some embodiments, $R^{28}$ is —N($CH_2CH_2CH_2F$)$_2$; in some embodiments, $R^{28}$ is —N($CH_2CH_2CHF_2$)$_2$; in some embodiments, $R^{28}$ is —N($CH_2CH_2CF_3$)$_2$; in some embodiments, $R^{28}$ is —N($CH(CH_2F)_2$)$_2$; in some embodiments, $R^{28}$ is —N($CH(CHF_2)_2$)$_2$; in some embodiments, $R^{28}$ is —N($CH(CF_3)_2$)$_2$; in some embodiments, $R^{28}$ is —NMe($C_{1-5}$ haloalkyl); in some embodiments, $R^{28}$ is —NMe($C_{1-4}$ haloalkyl); in some embodiments, $R^{28}$ is —NMe($C_{1-3}$ haloalkyl); in some embodiments, $R^{28}$ is —NMe($C_{1-2}$ haloalkyl); in some embodiments, $R^{28}$ is —NMe($CH_2CH_2F$); in some embodiments, $R^{28}$ is —NMe($CH_2CHF_2$); in some embodiments, $R^{28}$ is —NMe($CH_2CF_3$); in some embodiments, $R^{28}$ is —NMe($CH_2CH_2CH_2F$); in some embodiments, $R^{28}$ is —NMe($CH_2CH_2CHF_2$); in some embodiments, $R^{28}$ is —NMe($CH_2CH_2CF_3$); in some embodiments, $R^{28}$ is —NMe($CH(CH_2F)_2$); in some embodiments, $R^{28}$ is —NMe($CH(CHF_2)_2$); in some embodiments, $R^{28}$ is —NMe(CH($CF_3$)$_2$); wherein one or more H are optionally replaced by D.

In some embodiments, $R^{28}$ is —NH($CF_3$).

In some embodiments, each $R^{28}$ is independently selected from the group consisting of —($C_{1-4}$ alkylene)$OR^{35}$, —C(=O)($R^{37}$), and —($C_{1-4}$ alkylene)$_p$heterocyclyl; wherein each —($C_{1-4}$ alkylene) is independently, optionally substituted with one or more substituents as defined anywhere herein.

In some embodiments, each $R^{29}$ is independently selected from the group consisting of unsubstituted —($C_{1-5}$ alkyl) (e.g., $C_{2-5, 3-5, 4-5, 2-4, 3-4, 2-3, 1-4, 1-3, 1-2, 1}$ alkyl) and heterocyclyl optionally substituted with 1-5 (e.g., 1-4, 1-3, 1-2, 1) $R^{36}$.

In some embodiments, each $R^{29}$ is independently selected from the group consisting of unsubstituted —($C_{1-5}$ alkyl) (e.g., $C_{2-5, 3-5, 4-5, 2-4, 3-4, 2-3, 1-4, 1-3, 1-2, 1}$ alkyl), heterocyclyl optionally substituted with 1-5 (e.g., 1-4, 1-3, 1-2, 1) $R^{36}$, and N-oxide.

In some embodiments, $R^{29}$ is selected from the group consisting of methyl, ethyl, n-propyl, isopropyl, N-oxide,

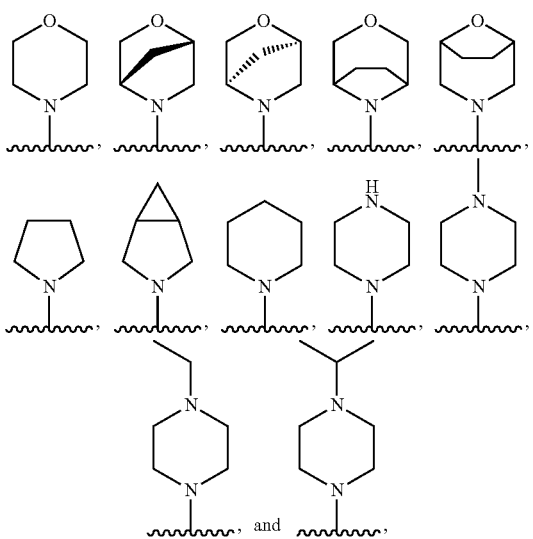

wherein one or more H on the heterocycle ring are optionally replaced by D.

In some embodiments, $R^{29}$ is selected from the group consisting of

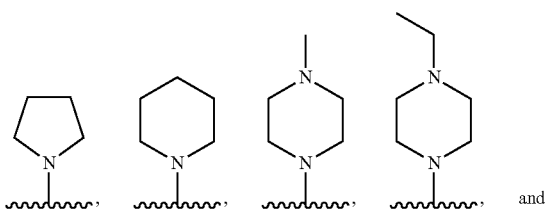

and

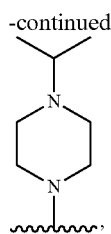

wherein one or more H on the heterocycle ring are optionally replaced by D.

In some embodiments, $R^{30}$ is attached to the nitrogen and is selected from the group consisting of H and unsubstituted —$(C_{1-5}$ alkyl) (e.g., $C_{2-5, 3-5, 4-5, 2-4, 3-4, 2-3, 1-4, 1-3, 1-2, 1}$ alkyl).

In some embodiments, In some embodiments, $R^{30}$ is attached to the nitrogen and is selected from the group consisting of H and Me.

In some embodiments, $R^{31}$ is attached to the nitrogen and is heterocyclyl optionally substituted with 1-5 (e.g., 1-4, 1-3, 1-2, 1) $R^{38}$.

In some embodiments, In some embodiments, $R^{31}$ is selected from the group consisting of

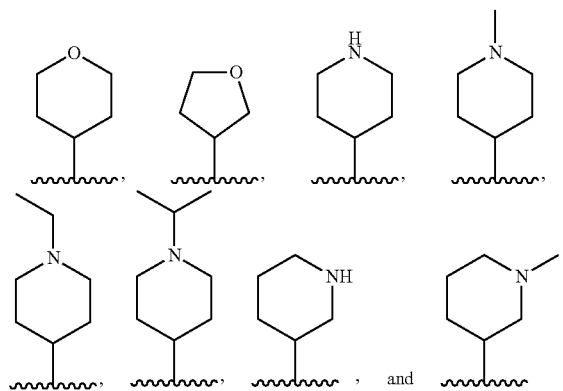

In some embodiments, each $R^{32}$ is independently selected from the group consisting of H, unsubstituted —$(C_{1-5}$ alkyl) (e.g., $C_{2-5, 3-5, 4-5, 2-4, 3-4, 2-3, 1-4, 1-3, 1-2, 1}$ alkyl), unsubstituted —$(C_{2-5}$ alkenyl) (e.g., $C_{3-5, 4-5, 2-4, 3-4, 2-3, 2}$ alkenyl), unsubstituted —$(C_{2-5}$ alkynyl) (e.g., $C_{3-5, 4-5, 2-4, 3-4, 2-3, 2}$ alkynyl), and unsubstituted —$(C_{1-5}$ haloalkyl) (e.g., $C_{2-5, 3-5, 4-5, 2-4, 3-4, 2-3, 1-4, 1-3, 1-2, 1}$ haloalkyl).

In some embodiments, each $R^{32}$ is independently selected from the group consisting of H, Me, —$CH_2F$, —$CHF_2$, and —$CF_3$.

In some embodiments, In some embodiments, each $R^{32}$ is H.

In some embodiments, $R^{33}$ is attached to the nitrogen and selected from the group consisting of H, unsubstituted —$(C_{1-5}$ alkyl) (e.g., $C_{2-5, 3-5, 4-5, 2-4, 3-4, 2-3, 1-4, 1-3, 1-2, 1}$ alkyl), unsubstituted —$(C_{2-5}$ alkenyl) (e.g., $C_{3-5, 4-5, 2-4, 3-4, 2-3, 2}$ alkenyl), unsubstituted —$(C_{2-5}$ alkynyl) (e.g., $C_{3-5, 4-5, 2-4, 3-4, 2-3, 2}$ alkynyl), and unsubstituted —$(C_{1-5}$ haloalkyl) (e.g., $C_{2-5, 3-5, 4-5, 2-4, 3-4, 2-3, 1-4, 1-3, 1-2, 1}$ haloalkyl).

In some embodiments, $R^{33}$ is attached to the nitrogen and selected from the group consisting of H, unsubstituted —$(C_{1-5}$ alkyl) (e.g., $C_{2-5, 3-5, 4-5, 2-4, 3-4, 2-3, 1-4, 1-3, 1-2, 1}$ alkyl), unsubstituted —$(C_{2-5}$ alkenyl) (e.g., $C_{3-5, 4-5, 2-4, 3-4, 2-3, 2}$ alkenyl), unsubstituted —$(C_{2-5}$ alkynyl) (e.g., $C_{3-5, 4-5, 2-4, 3-4, 2-3, 2}$ alkynyl).

In some embodiments, $R^{33}$ is selected from the group consisting of H, Me, Et, nPr, and iPr.

In some embodiments, $R^{33}$ is selected from the group consisting of H and Me.

In some embodiments, $R^{33}$ is selected from the group consisting of H, Me, Et, nPr, iPr, —$CH_2CH_2F$, —$CH_2CHF_2$, —$CH_2CF_3$, —$CH(CH_2F)_2$, —$CH(CHF_2)_2$, and —$CH(CF_3)_2$.

In some embodiments, $R^{34}$ is attached to the nitrogen and is selected from the group consisting of unsubstituted —$(C_{1-5}$ haloalkyl) (e.g., $C_{2-5, 3-5, 4-5, 2-4, 3-4, 2-3, 1-4, 1-3, 1-2, 1}$ haloalkyl), —$(C_{1-4}$ alkylene)$_p$heterocyclyl optionally substituted with 1-10 (e.g., 1-9, 1-8, 1-7, 1-6, 1-5, 1-4, 1-3, 1-2, 1) $R^{38}$, —$(C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{39}$, —$(C_{1-4}$ alkylene)$OR^{35}$; wherein each —$(C_{1-4}$ alkylene) is, independently, optionally substituted with one or more substituents as defined anywhere herein.

In some embodiments, $R^{34}$ is attached to the nitrogen and is selected from the group consisting of —$CH_2CH_2F$, —$CH_2CHF_2$, —$CH_2CF_3$, —$CH(CH_2F)_2$, —$CH(CHF_2)_2$, —$CH(CF_3)_2$,

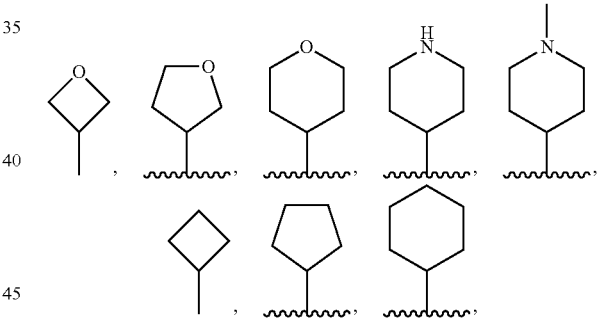

—$CH_2CH_2OH$, and —$CH_2CH_2OMe$.

In some embodiments, each $R^{35}$ is independently selected from the group consisting of H and unsubstituted —$(C_{1-5}$ alkyl) (e.g., $C_{2-5, 3-5, 4-5, 2-4, 3-4, 2-3, 1-4, 1-3, 1-2, 1}$ alkyl).

In some embodiments, $R^{35}$ is selected from the group consisting of H and Me.

In some embodiments, each $R^{36}$ is selected from the group consisting of unsubstituted —$(C_{1-5}$ alkyl) (e.g., $C_{2-5, 3-5, 4-5, 2-4, 3-4, 2-3, 1-4, 1-3, 1-2, 1}$ alkyl) and unsubstituted —$(C_{1-5}$ haloalkyl) (e.g., $C_{2-5, 3-5, 4-5, 2-4, 3-4, 2-3, 1-4, 1-3, 1-2, 1}$ haloalkyl).

In some embodiments, each $R^{36}$ is selected from the group consisting of Me, Et, nPr, iPr, —$CH_2F$, —$CHF_2$, and —$CF_3$.

In some embodiments, each $R^{36}$ is selected from the group consisting of Me, —$CH_2F$, —$CHF_2$, and —$CF_3$.

In some embodiments, each $R^{36}$ is unsubstituted —$(C_{1-5}$ alkyl) (e.g., $C_{2-5, 3-5, 4-5, 2-4, 3-4, 2-3, 1-4, 1-3, 1-2, 1}$ alkyl);

In some embodiments, $R^{36}$ is selected from the group consisting of Me, Et, nPr, and iPr.

In some embodiments, $R^{36}$ is Me.

In some embodiments, each $R^{36}$ is independently selected from the group consisting of unsubstituted —($C_{1-5}$ alkyl) (e.g., $C_{2-5, 3-5, 4-5, 2-4, 3-4, 2-3, 1-4, 1-3, 1-2, 1}$ alkyl) and N-oxide.

In some embodiments, $R^{36}$ is selected from the group consisting of Me, Et, nPr, iPr, and N-oxide.

In some embodiments, $R^{36}$ is selected from the group consisting of Me and N-oxide.

In some embodiments, $R^{36}$ is N-oxide.

In some embodiments, $R^{37}$ is -heterocyclyl optionally substituted with one or more halides (e.g., F, Cl, Br, I) or one or more unsubstituted —($C_{1-5}$ alkyl) (e.g., $C_{2-5, 3-5, 4-5, 2-4, 3-4, 2-3, 1-4, 1-3, 1-2, 1}$ alkyl).

In some embodiments, $R^{37}$ is selected from the group consisting of

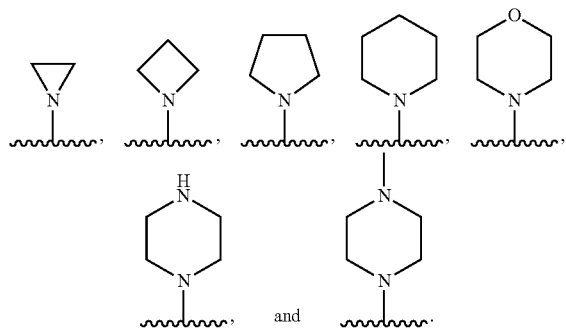

In some embodiments, each $R^{38}$ is independently selected from the group consisting of halide (e.g., F, Cl, Br, I) and unsubstituted —($C_{1-5}$ alkyl) (e.g., $C_{2-5, 3-5, 4-5, 2-4, 3-4, 2-3, 1-4, 1-3, 1-2, 1}$ alkyl).

In some embodiments, $R^{38}$ is selected from the group consisting of F, Me, Et, nPr, and iPr.

In some embodiments, $R^{38}$ is Me.

In some embodiments, each $R^{39}$ is independently selected from the group consisting of halide (e.g., F, Cl, Br, I), unsubstituted —($C_{1-5}$ alkyl) (e.g., $C_{2-5, 3-5, 4-5, 2-4, 3-4, 2-3, 1-4, 1-3, 1-2, 1}$ alkyl), unsubstituted —($C_{2-5}$ alkenyl) (e.g., $C_{3-5, 4-5, 2-4, 3-4, 2-3, 2}$ alkenyl), unsubstituted —($C_{2-5}$ alkynyl) (e.g., $C_{3-5, 4-5, 2-4, 3-4, 2-3, 2}$ alkynyl), and unsubstituted —($C_{1-5}$ haloalkyl) (e.g., $C_{2-5, 3-5, 4-5, 2-4, 3-4, 2-3, 1-4, 1-3, 1-2, 1}$ haloalkyl), —CN, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{40}$; wherein each —($C_{1-4}$ alkylene) is, independently, optionally substituted with one or more substituents as defined anywhere herein.

In some embodiments, $R^{39}$ is selected from the group consisting of F, Me, Et, nPr, and iPr.

In some embodiments, each $R^{40}$ is independently selected from the group consisting of halide (e.g., F, Cl, Br, I), unsubstituted —($C_{1-5}$ alkyl) (e.g., $C_{2-5, 3-5, 4-5, 2-4, 3-4, 2-3, 1-4, 1-3, 1-2, 1}$ alkyl), unsubstituted —($C_{2-5}$ alkenyl) (e.g., $C_{3-5, 4-5, 2-4, 3-4, 2-3, 2}$ alkenyl), unsubstituted —($C_{2-5}$ alkynyl) (e.g., $C_{3-5, 4-5, 2-4, 3-4, 2-3, 2}$ alkynyl), and unsubstituted —($C_{1-5}$ haloalkyl) (e.g., $C_{2-5, 3-5, 4-5, 2-4, 3-4, 2-3, 1-4, 1-3, 1-2, 1}$ haloalkyl), and —CN;

In some embodiments, $R^{39}$ is selected from the group consisting of F, Me, Et, nPr, and iPr.

In some embodiments, each $R^{41}$ is independently selected from the group consisting of halide (e.g., F, Cl, Br, I) and —OMe.

In some embodiments, each $R^{42}$ is independently selected from the group consisting of halide (e.g., F, Cl, Br, I), —OMe, and unsubstituted —($C_{1-5}$ alkyl) (e.g., $C_{2-5, 3-5, 4-5, 2-4, 3-4, 2-3, 1-4, 1-3, 1-2, 1}$ alkyl), wherein one or more H on the —OMe and/or alkyl are optionally replaced by D.

In some embodiments, $R^{42}$ is selected from the group consisting of F, Cl, —OMe, and Me, wherein one or more H on the —OMe and/or Me are optionally replaced by D.

In some embodiments, $R^{43}$ is attached to the nitrogen and selected from the group consisting of H, unsubstituted —($C_{1-5}$ alkyl) (e.g., $C_{2-5, 3-5, 4-5, 2-4, 3-4, 2-3, 1-4, 1-3, 1-2, 1}$ alkyl), and unsubstituted —($C_{1-5}$ haloalkyl) (e.g., $C_{2-5, 3-5, 4-5, 2-4, 3-4, 2-3, 1-4, 1-3, 1-2, 1}$ haloalkyl).

In some embodiments, $R^{44}$ is attached to the nitrogen and is selected from the group consisting of H, unsubstituted —($C_{1-5}$ alkyl) (e.g., $C_{2-5, 3-5, 4-5, 2-4, 3-4, 2-3, 1-4, 1-3, 1-2, 1}$ alkyl), unsubstituted —($C_{1-5}$ haloalkyl) (e.g., $C_{2-5, 3-5, 4-5, 2-4, 3-4, 2-3, 1-4, 1-3, 1-2, 1}$ haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{38}$, —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{39}$, —($C_{1-4}$ alkylene)$OR^{35}$; wherein each —($C_{1-4}$ alkylene) is, independently, optionally substituted with one or more substituents as defined anywhere herein.

In some embodiments, each p is independently 0 or 1.

In some embodiments, p is 0.

In some embodiments, p is 1.

In some embodiments, there is the proviso that Formula I is not a structure selected from the group consisting of:

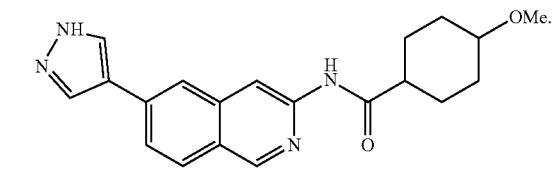 [SMILES: COC1CCC(C(=O)Nc2cc3cc(-c4cn[nH]c4)ccc3cn2)CC1]

In some embodiments, each X is O or S.

Illustrative compounds of Formula (I) are shown in Table 1.

TABLE 1

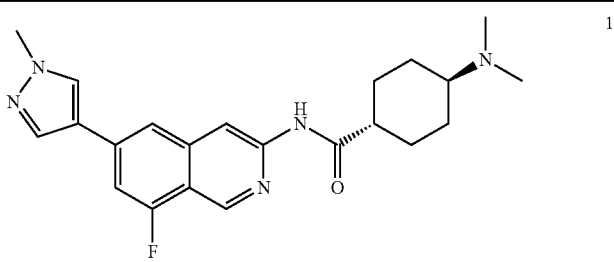

1

TABLE 1-continued
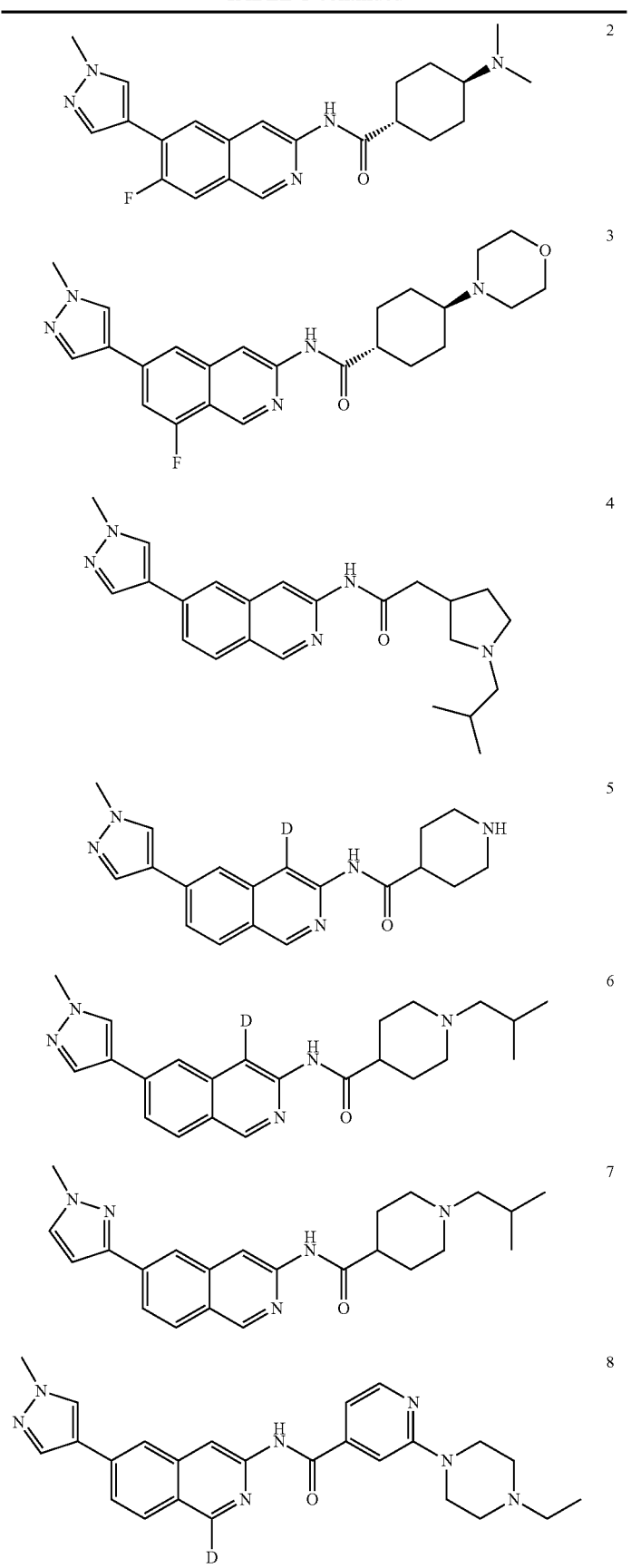

TABLE 1-continued
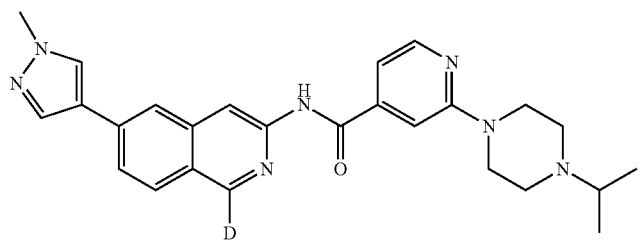 [SMILES: [2H]c1nc(NC(=O)c2ccnc(N3CCN(C(C)C)CC3)c2)cc2cc(-c3cnn(C)c3)ccc12]
9
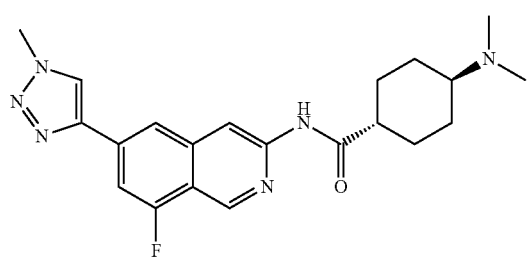 [SMILES: Cn1cc(-c2cc(F)c3cnc(NC(=O)[C@H]4CC[C@H](N(C)C)CC4)cc3c2)nn1]
10
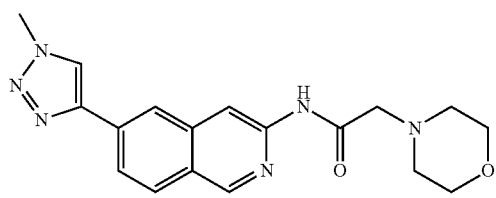 [SMILES: Cn1cc(-c2ccc3cnc(NC(=O)CN4CCOCC4)cc3c2)nn1]
11
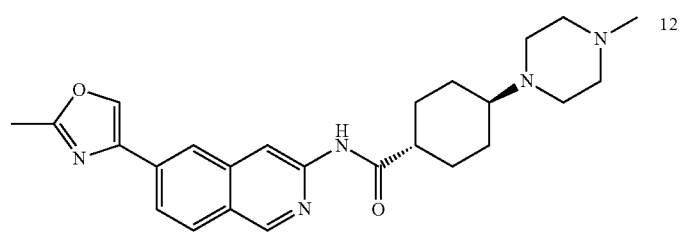
12
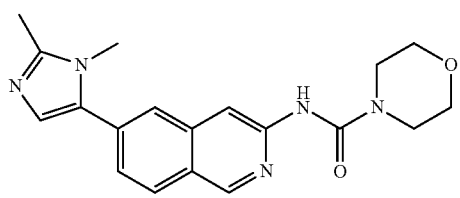 [SMILES: Cc1ncc(-c2ccc3cnc(NC(=O)N4CCOCC4)cc3c2)n1C]
13
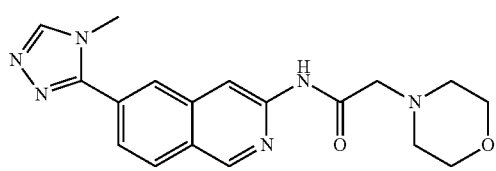 [SMILES: Cn1cnnc1-c1ccc2cnc(NC(=O)CN3CCOCC3)cc2c1]
14
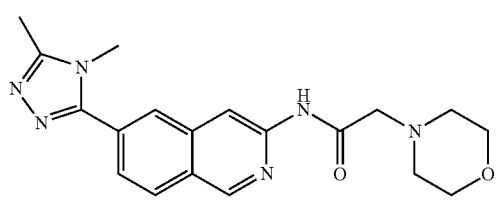 [SMILES: Cc1nnc(-c2ccc3cnc(NC(=O)CN4CCOCC4)cc3c2)n1C]
15

TABLE 1-continued
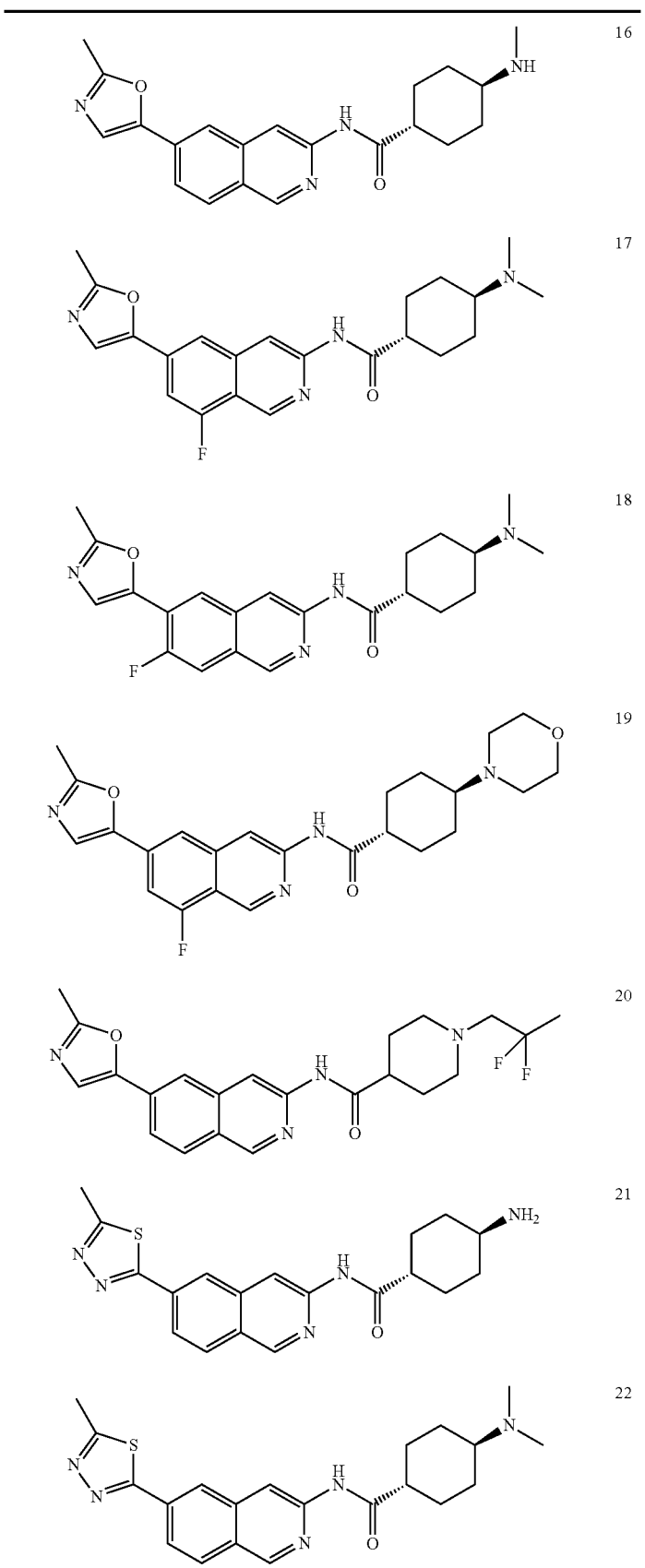

TABLE 1-continued
| | |
|---|---|
| 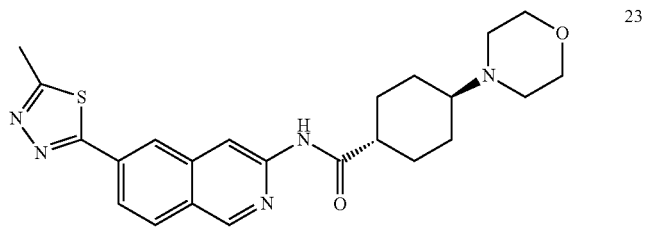 | 23 |
| 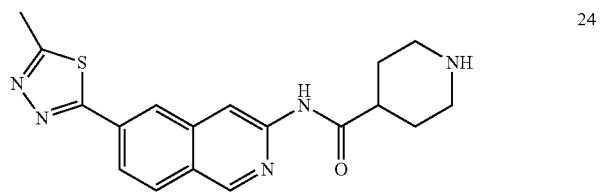 | 24 |
| 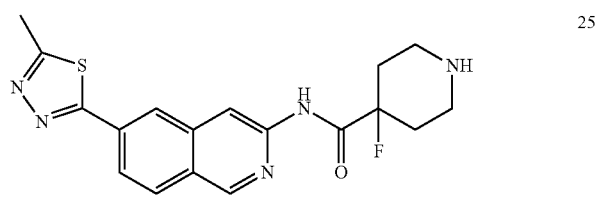 | 25 |
| 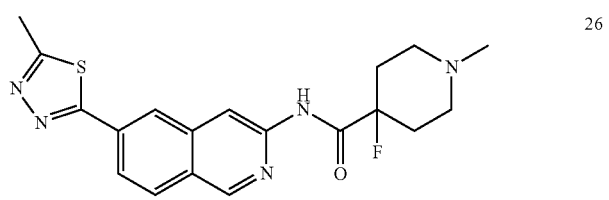 | 26 |
| 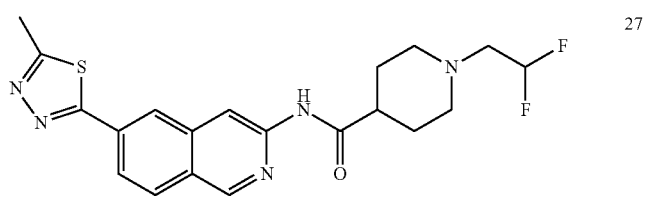 | 27 |
| 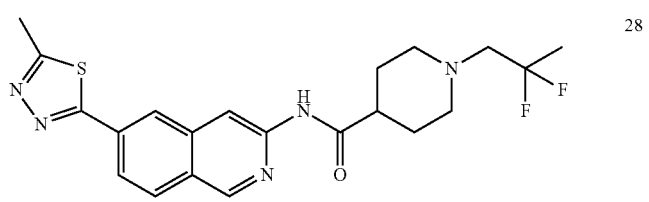 | 28 |
| 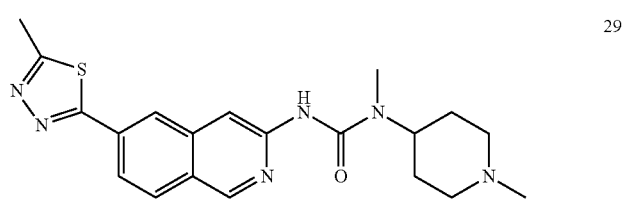 | 29 |
| 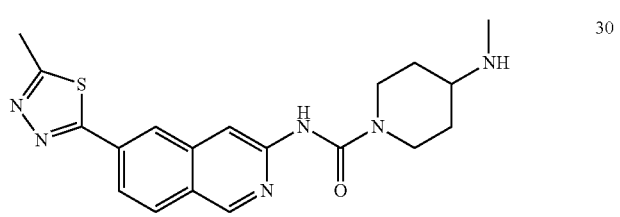 | 30 |

TABLE 1-continued
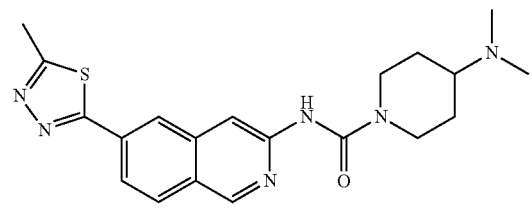 [SMILES: Cc1nnc(-c2ccc3cnc(NC(=O)N4CCC(N(C)C)CC4)cc3c2)s1]
31
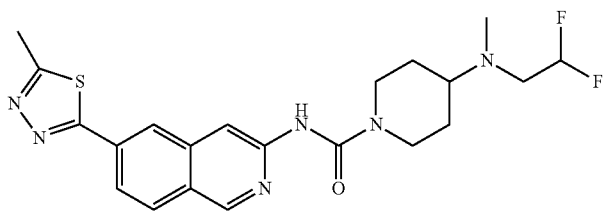 [SMILES: Cc1nnc(-c2ccc3cnc(NC(=O)N4CCC(N(C)CC(F)F)CC4)cc3c2)s1]
32
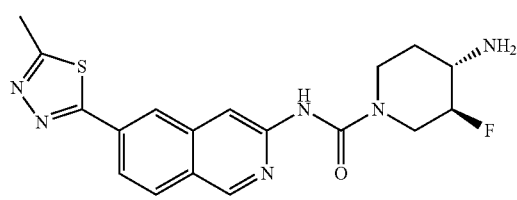 [SMILES: Cc1nnc(-c2ccc3cnc(NC(=O)N4CC[C@H](N)[C@@H](F)C4)cc3c2)s1]
33
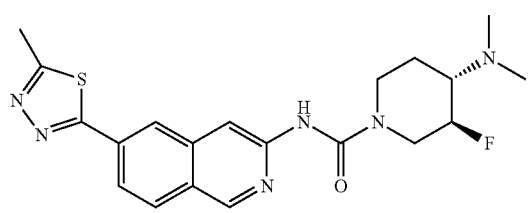 [SMILES: Cc1nnc(-c2ccc3cnc(NC(=O)N4CC[C@H](N(C)C)[C@@H](F)C4)cc3c2)s1]
34
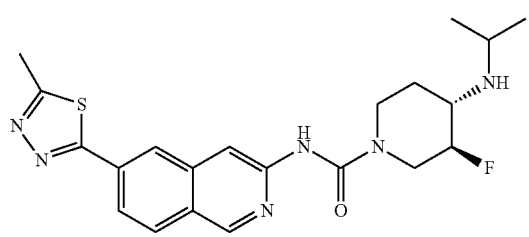 [SMILES: Cc1nnc(-c2ccc3cnc(NC(=O)N4CC[C@H](NC(C)C)[C@@H](F)C4)cc3c2)s1]
35
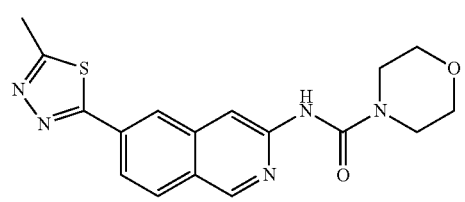 [SMILES: Cc1nnc(-c2ccc3cnc(NC(=O)N4CCOCC4)cc3c2)s1]
36
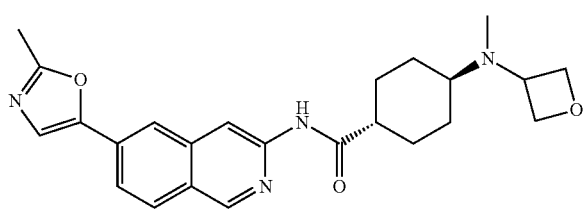 [SMILES: Cc1ncc(-c2ccc3cnc(NC(=O)[C@H]4CC[C@H](N(C)C5COC5)CC4)cc3c2)o1]
37

TABLE 1-continued
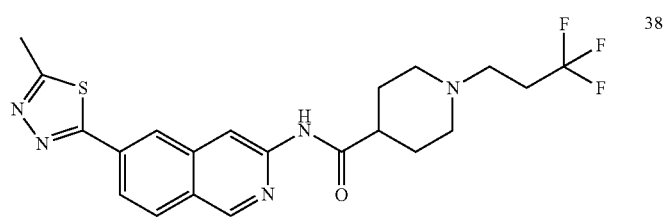
38
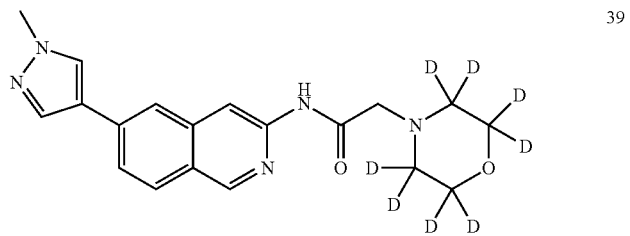
39
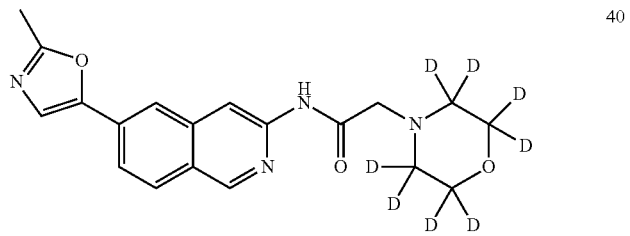
40
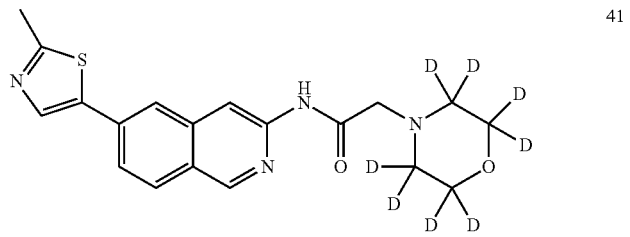
41
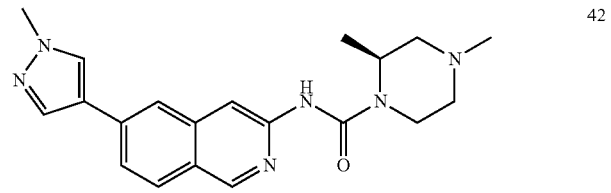
42
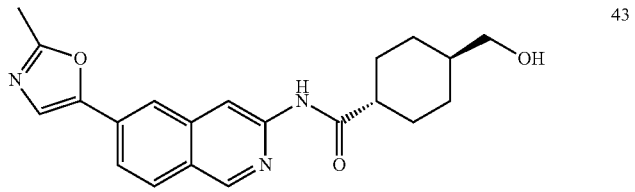
43
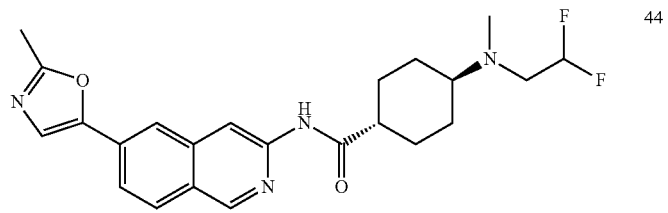
44

TABLE 1-continued
| | |
|---|---|
| 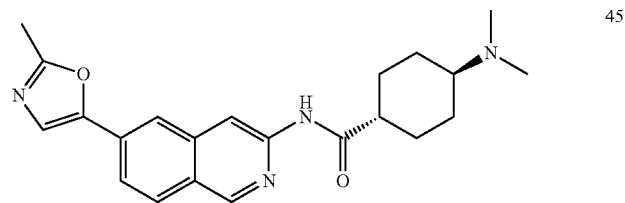 | 45 |
| 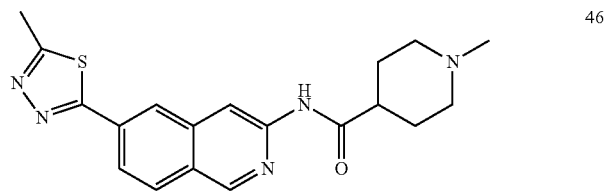 | 46 |
| 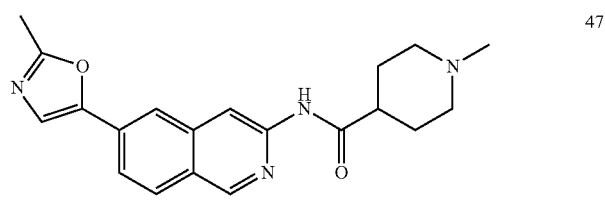 | 47 |
| 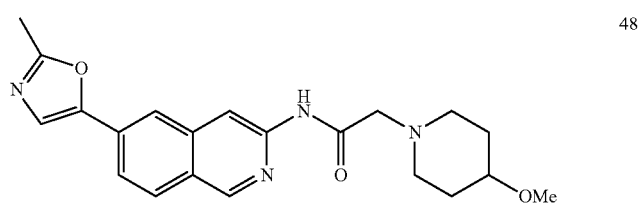 | 48 |
| 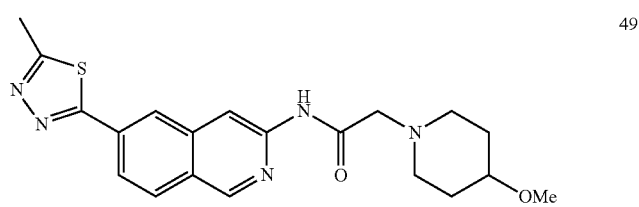 | 49 |
| 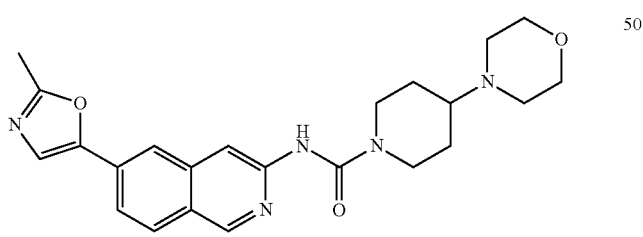 | 50 |
| 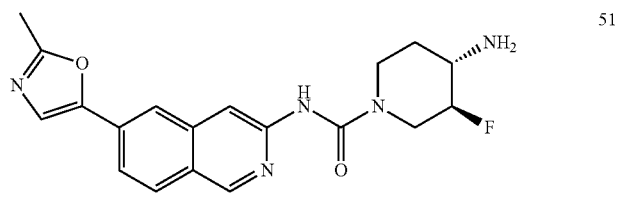 | 51 |

TABLE 1-continued
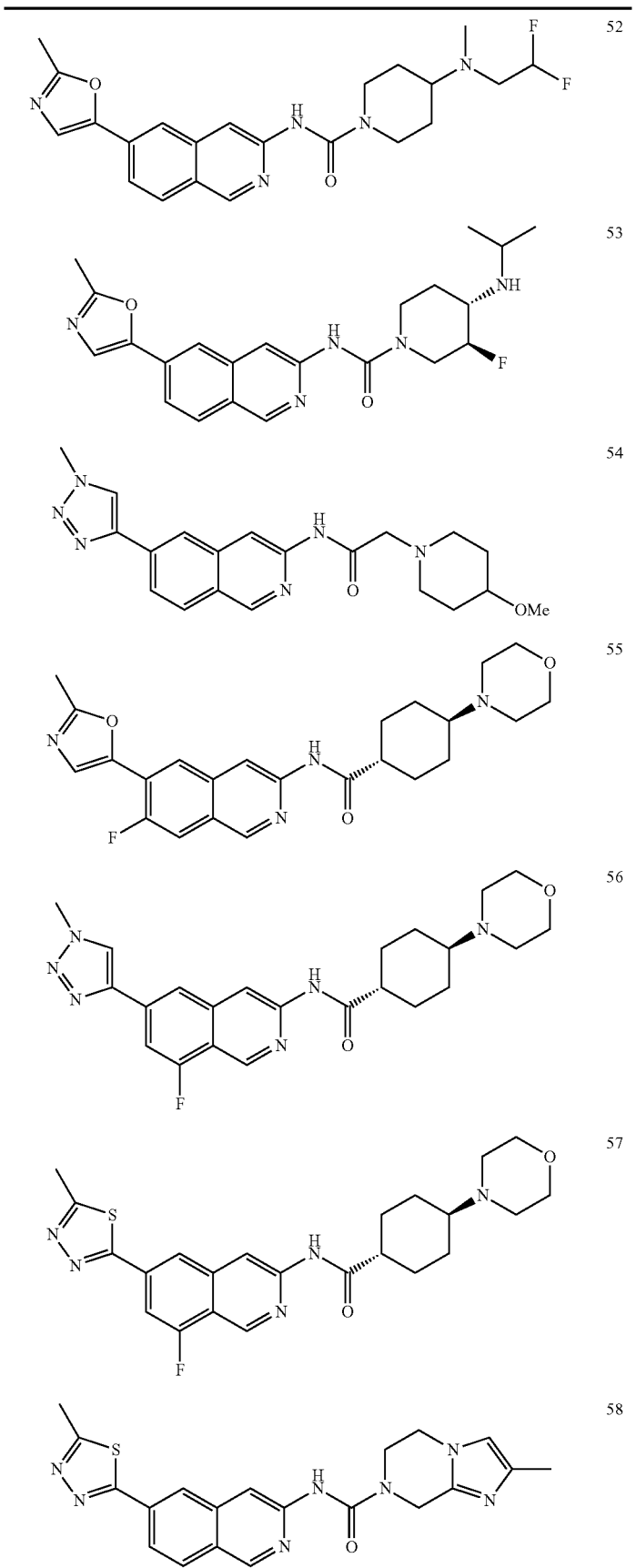

TABLE 1-continued
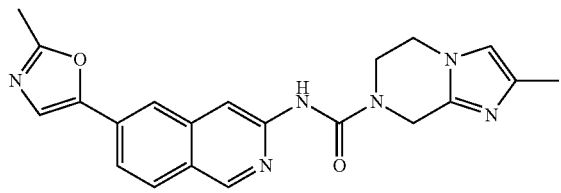 [SMILES: Cc1cn2c(n1)CN(C(=O)Nc1cc3cc(-c4cnc(C)o4)ccc3cn1)CC2]
59
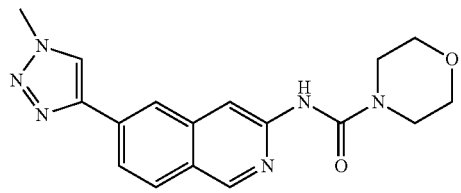
60
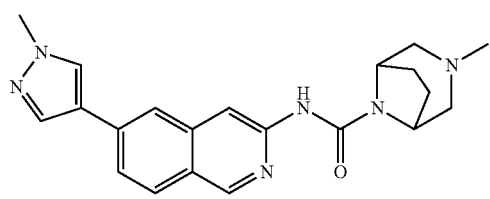 [SMILES: CN1CC2CCC(C1)N2C(=O)Nc1cc2cc(-c3cnn(C)c3)ccc2cn1]
61
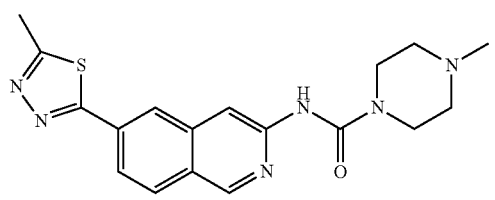
62
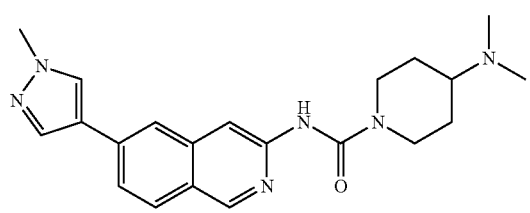 [SMILES: CN(C)C1CCN(C(=O)Nc2cc3cc(-c4cnn(C)c4)ccc3cn2)CC1]
63
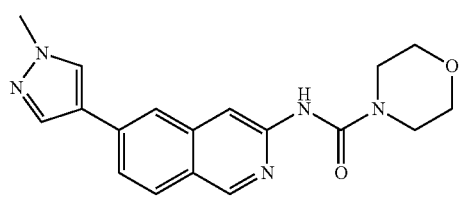 [SMILES: Cn1cc(-c2ccc3cnc(NC(=O)N4CCOCC4)cc3c2)cn1]
64
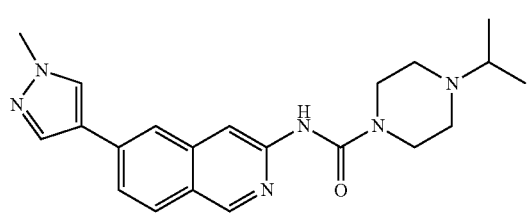 [SMILES: CC(C)N1CCN(C(=O)Nc2cc3cc(-c4cnn(C)c4)ccc3cn2)CC1]
65
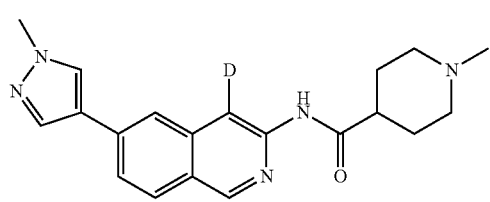 [SMILES: [2H]c1c(NC(=O)C2CCN(C)CC2)ncc2ccc(-c3cnn(C)c3)cc12]
66

TABLE 1-continued
| | |
|---|---|
| 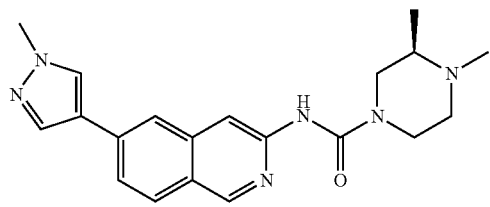 [SMILES: C[C@@H]1CN(C(=O)Nc2cc3cc(-c4cnn(C)c4)ccc3cn2)CCN1C] | 67 |
| 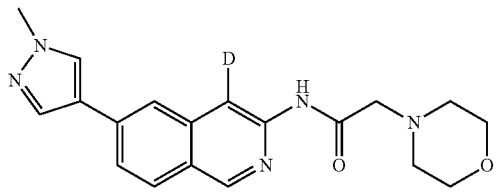 [SMILES: [2H]c1c(NC(=O)CN2CCOCC2)ncc2ccc(-c3cnn(C)c3)cc12] | 68 |
| 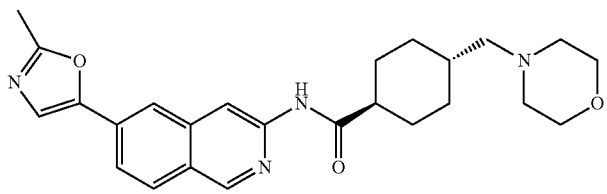 [SMILES: Cc1ncc(-c2ccc3cnc(NC(=O)[C@H]4CC[C@H](CN5CCOCC5)CC4)cc3c2)o1] | 69 |
| 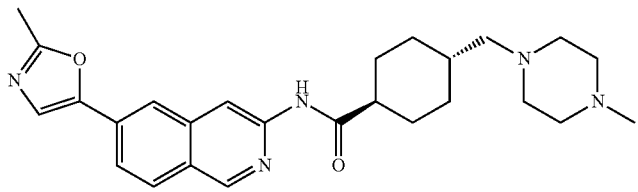 [SMILES: Cc1ncc(-c2ccc3cnc(NC(=O)[C@H]4CC[C@H](CN5CCN(C)CC5)CC4)cc3c2)o1] | 70 |
| 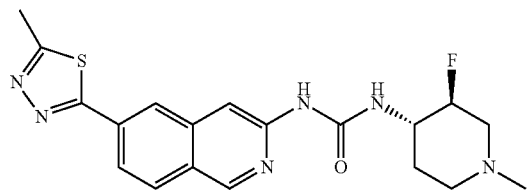 [SMILES: Cc1nnc(-c2ccc3cnc(NC(=O)N[C@H]4CCN(C)C[C@@H]4F)cc3c2)s1] | 71 |
| 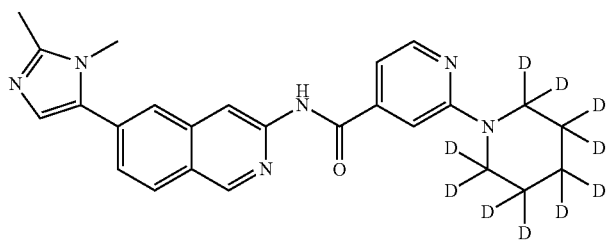 [SMILES: [2H]C1([2H])N(c2cc(C(=O)Nc3cc4cc(-c5cnc(C)n5C)ccc4cn3)ccn2)C([2H])([2H])C([2H])([2H])C([2H])([2H])C1([2H])[2H]] | 72 |
| 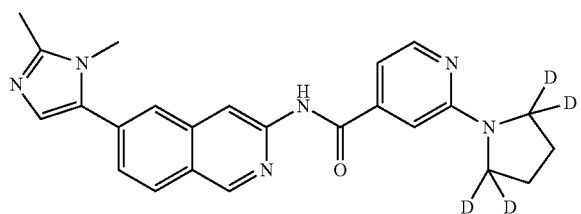 [SMILES: [2H]C1([2H])CCC([2H])([2H])N1c1cc(C(=O)Nc2cc3cc(-c4cnc(C)n4C)ccc3cn2)ccn1] | 73 |

TABLE 1-continued
| | |
|---|---|
| 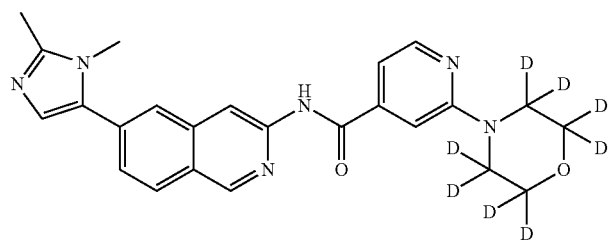 [SMILES: [2H]C1([2H])OC([2H])([2H])C([2H])([2H])N(c2cc(C(=O)Nc3cc4cc(-c5cnc(C)n5C)ccc4cn3)ccn2)C1([2H])[2H]] | 74 |
| 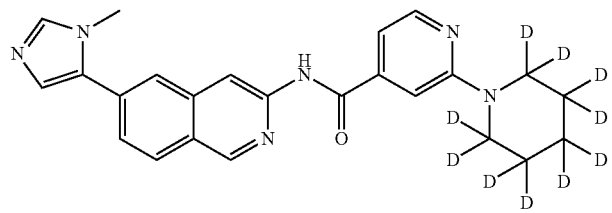 [SMILES: [2H]C1([2H])N(c2cc(C(=O)Nc3cc4cc(-c5cncn5C)ccc4cn3)ccn2)C([2H])([2H])C([2H])([2H])C([2H])([2H])C1([2H])[2H]] | 75 |
| 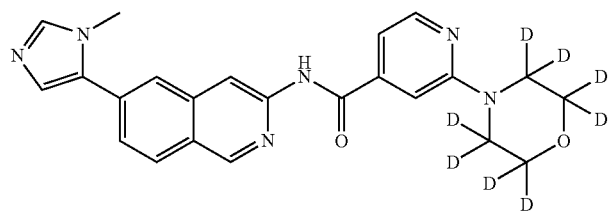 [SMILES: [2H]C1([2H])OC([2H])([2H])C([2H])([2H])N(c2cc(C(=O)Nc3cc4cc(-c5cncn5C)ccc4cn3)ccn2)C1([2H])[2H]] | 76 |
| 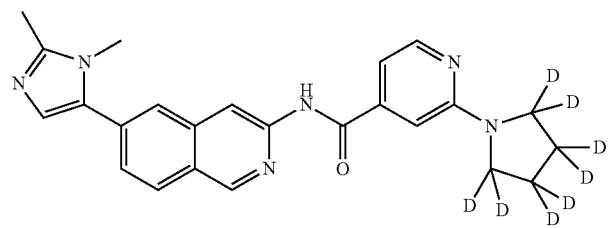 [SMILES: [2H]C1([2H])N(c2cc(C(=O)Nc3cc4cc(-c5cnc(C)n5C)ccc4cn3)ccn2)C([2H])([2H])C([2H])([2H])C1([2H])[2H]] | 77 |
| 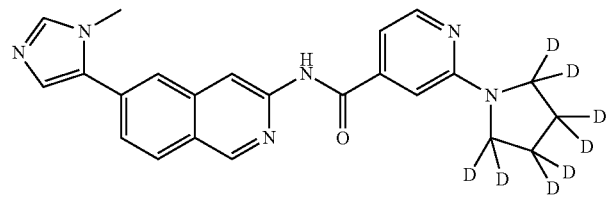 [SMILES: [2H]C1([2H])N(c2cc(C(=O)Nc3cc4cc(-c5cncn5C)ccc4cn3)ccn2)C([2H])([2H])C([2H])([2H])C1([2H])[2H]] | 78 |
| 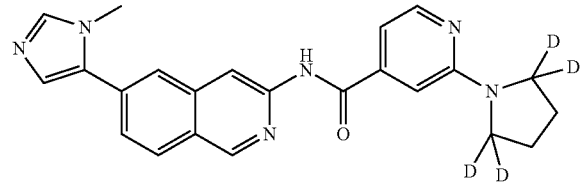 [SMILES: [2H]C1([2H])CCC([2H])([2H])N1c1cc(C(=O)Nc2cc3cc(-c4cncn4C)ccc3cn2)ccn1] | 79 |
| 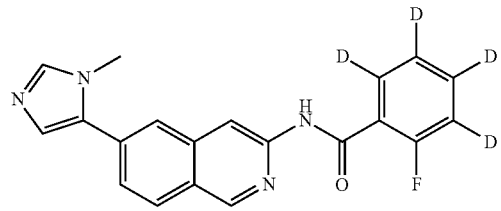 [SMILES: [2H]c1c([2H])c([2H])c(C(=O)Nc2cc3cc(-c4cncn4C)ccc3cn2)c(F)c1[2H]] | 80 |

TABLE 1-continued
| | |
|---|---|
| 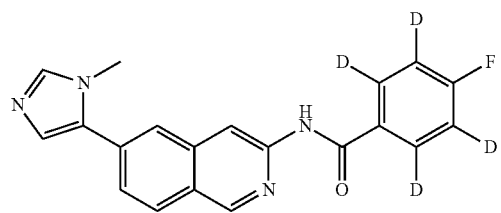 [SMILES: [2H]c1c([2H])c(C(=O)Nc2cc3cc(-c4cncn4C)ccc3cn2)c([2H])c([2H])c1F] | 81 |
| 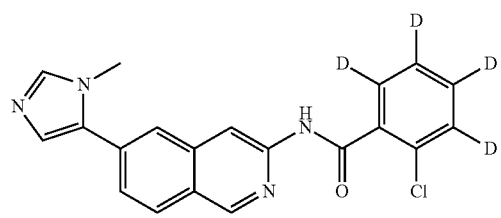 [SMILES: [2H]c1c([2H])c([2H])c(C(=O)Nc2cc3cc(-c4cncn4C)ccc3cn2)c(Cl)c1[2H]] | 82 |
| 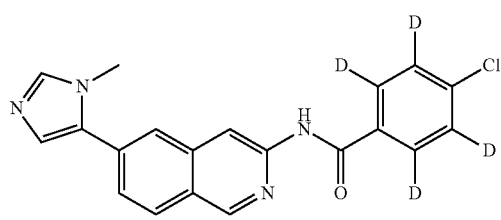 [SMILES: [2H]c1c([2H])c(C(=O)Nc2cc3cc(-c4cncn4C)ccc3cn2)c([2H])c([2H])c1Cl] | 83 |
| 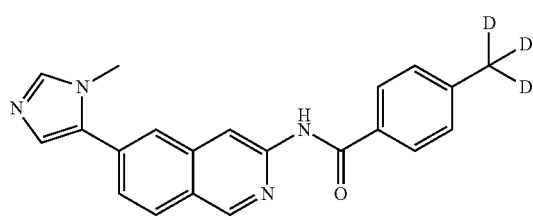 [SMILES: [2H]C([2H])([2H])c1ccc(C(=O)Nc2cc3cc(-c4cncn4C)ccc3cn2)cc1] | 84 |
| 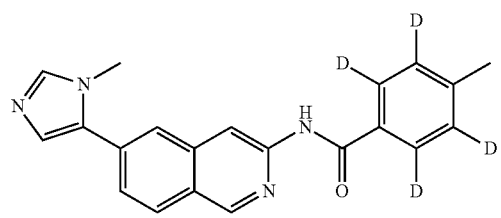 [SMILES: [2H]c1c([2H])c(C(=O)Nc2cc3cc(-c4cncn4C)ccc3cn2)c([2H])c([2H])c1C] | 85 |
| 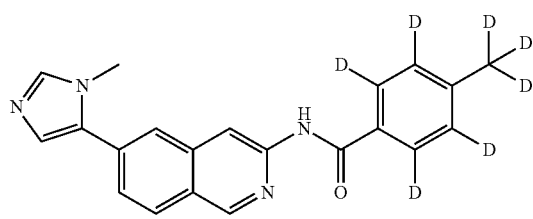 [SMILES: [2H]c1c([2H])c(C([2H])([2H])[2H])c([2H])c([2H])c1C(=O)Nc1cc2cc(-c3cncn3C)ccc2cn1] | 86 |
| 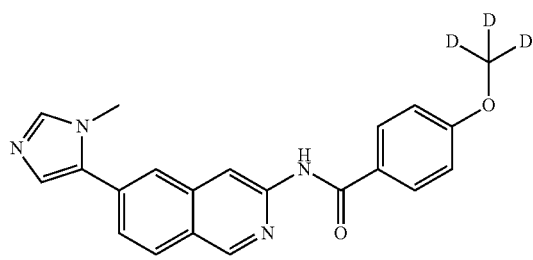 [SMILES: [2H]C([2H])([2H])Oc1ccc(C(=O)Nc2cc3cc(-c4cncn4C)ccc3cn2)cc1] | 87 |

TABLE 1-continued
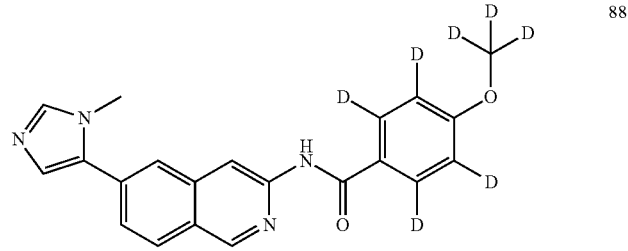 88
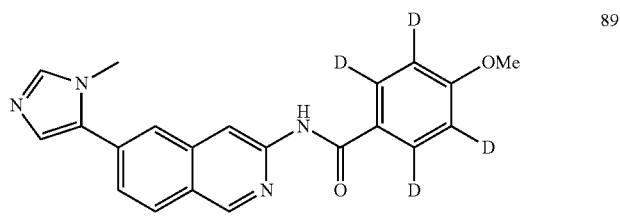 89
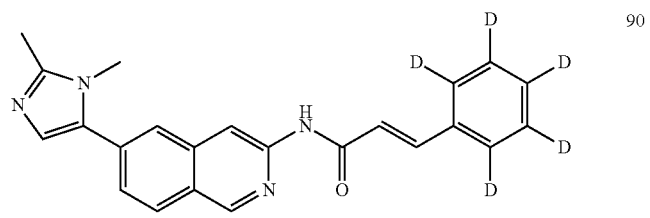 90
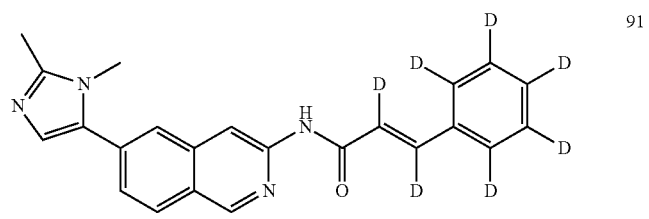 91
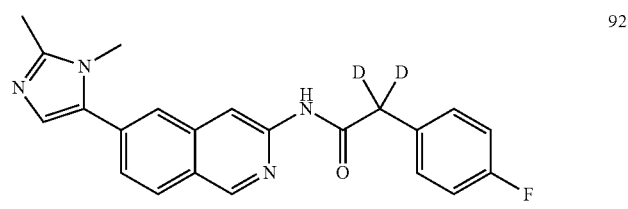 92
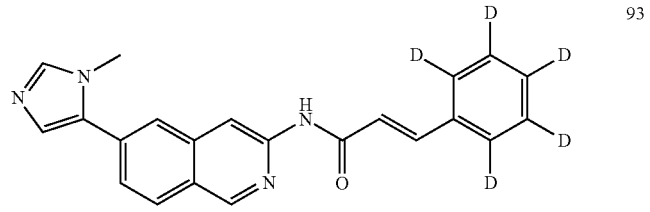 93
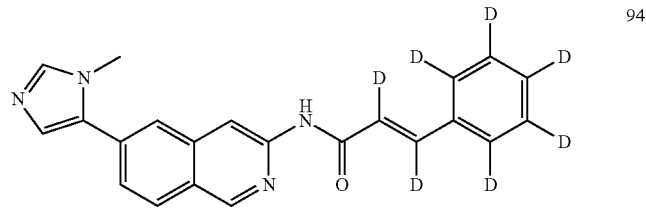 94

TABLE 1-continued
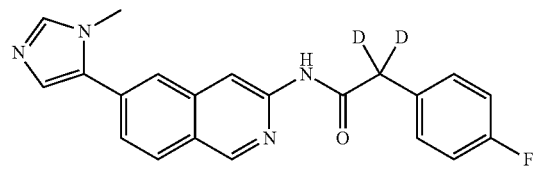 [SMILES: [2H]C([2H])(C(=O)Nc1cc2cc(-c3cncn3C)ccc2cn1)c1ccc(F)cc1] 95
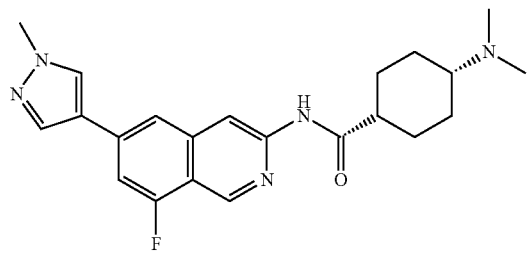 96
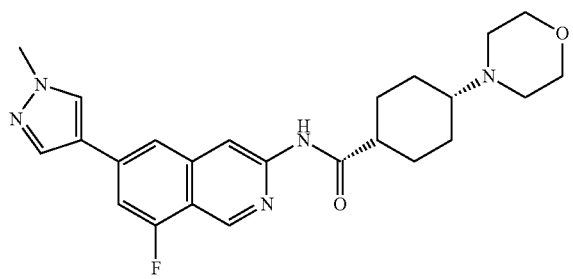 97
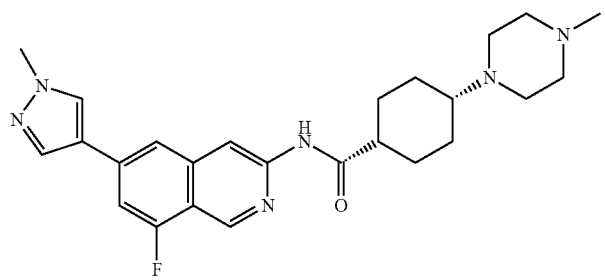 98
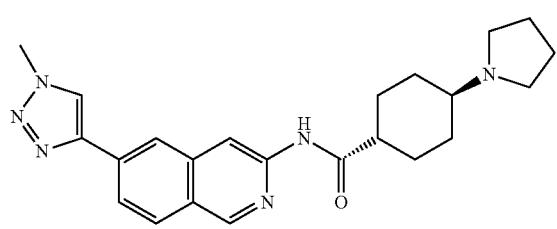 99
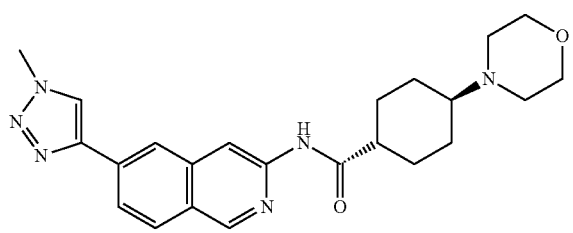 100

TABLE 1-continued
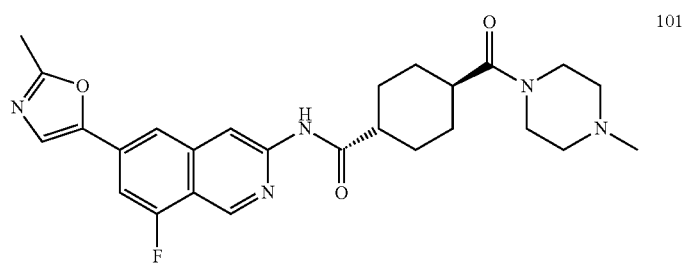
101
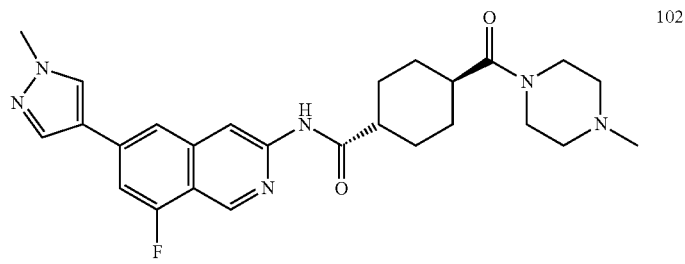
102
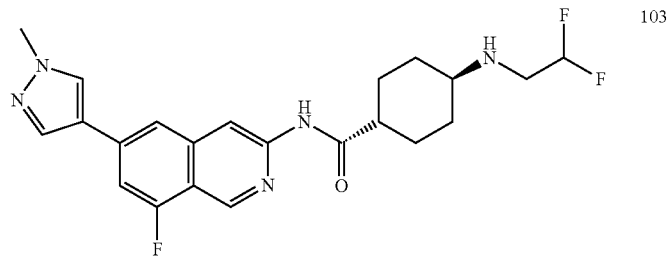
103
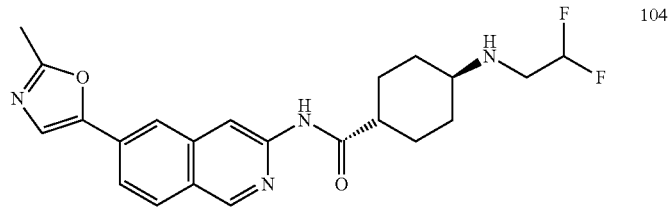
104
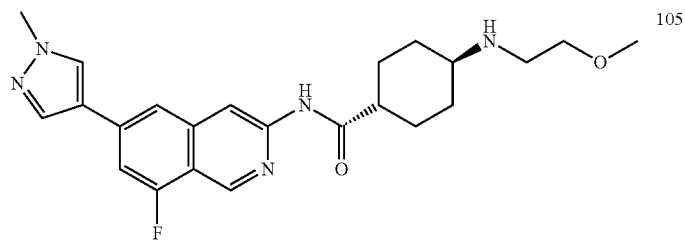
105
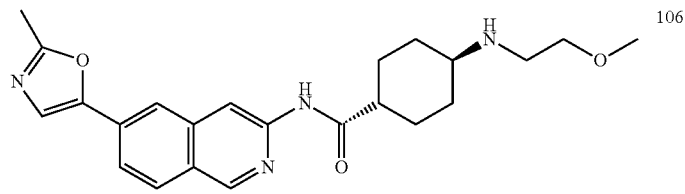
106

TABLE 1-continued
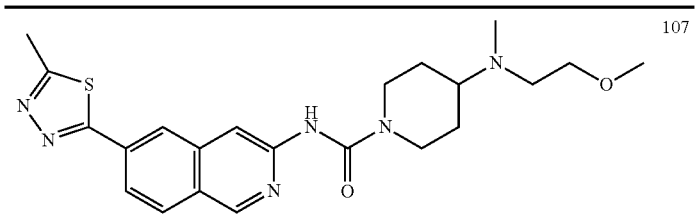 107
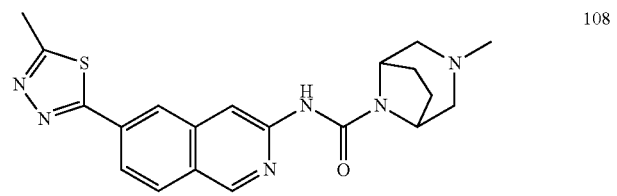 108
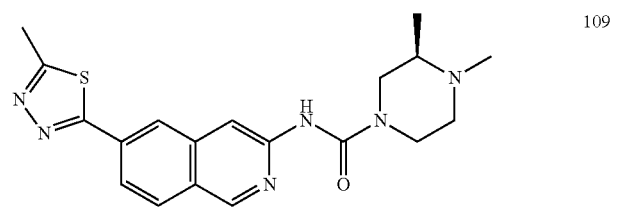 109
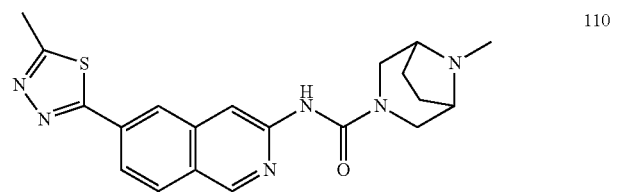 110
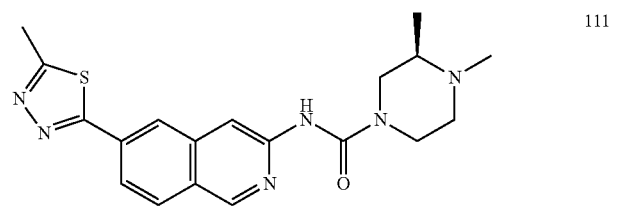 111
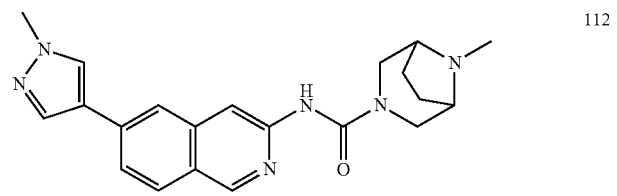 112
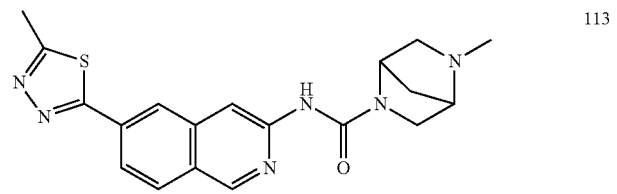 113
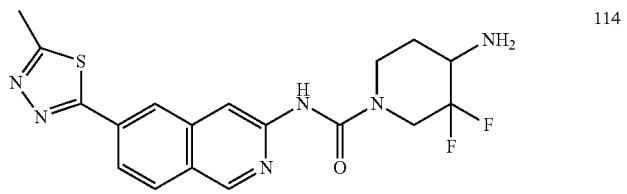 114

TABLE 1-continued
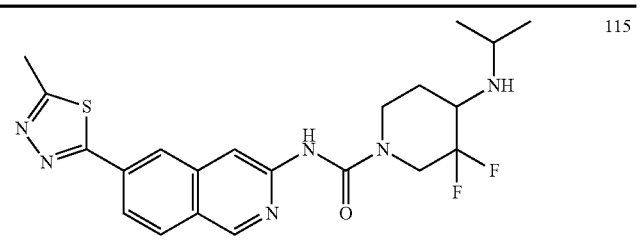 115
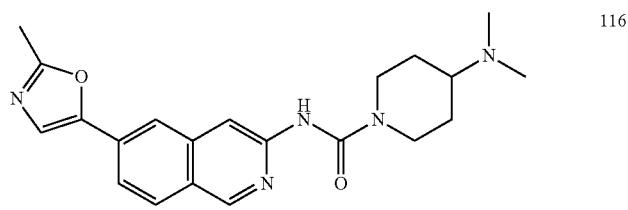 116
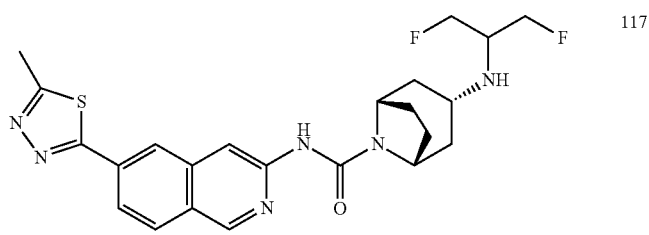 117
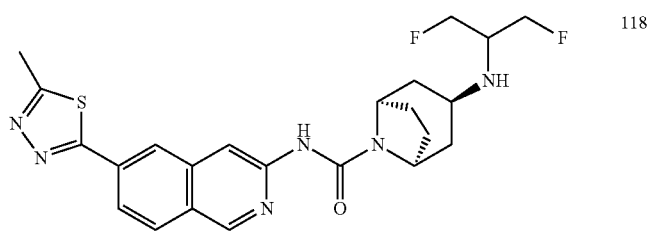 118
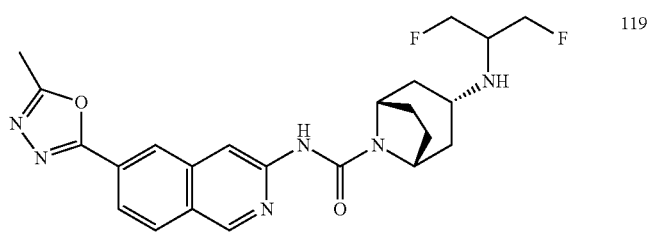 119
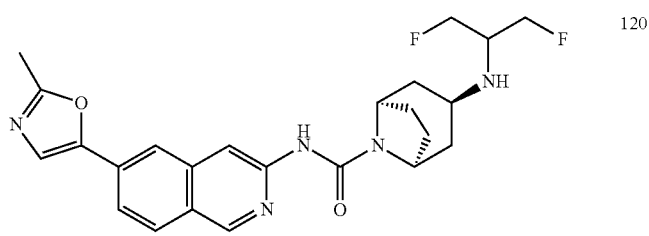 120
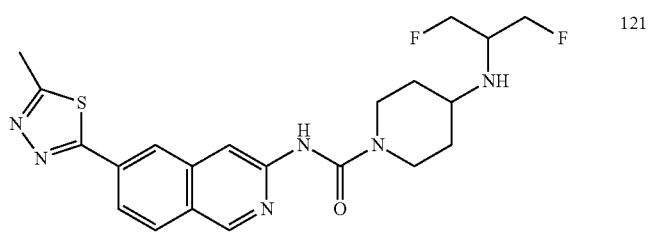 121

TABLE 1-continued
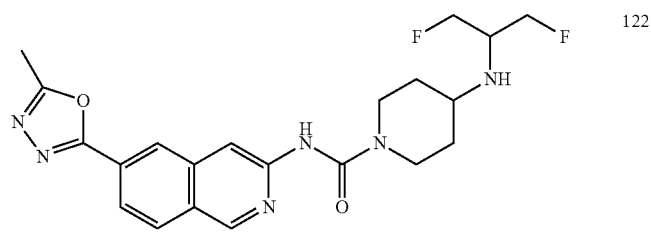 122
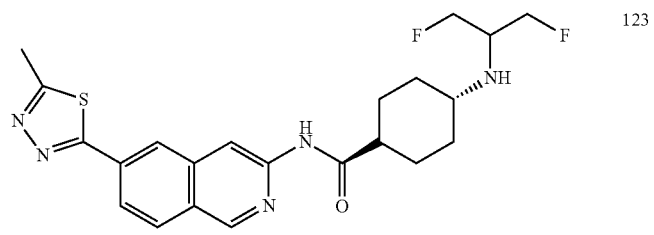 123
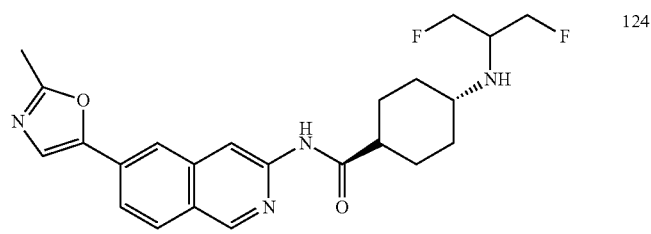 124
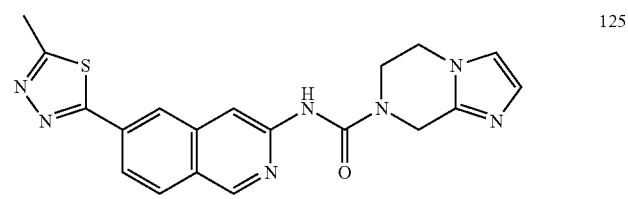 125
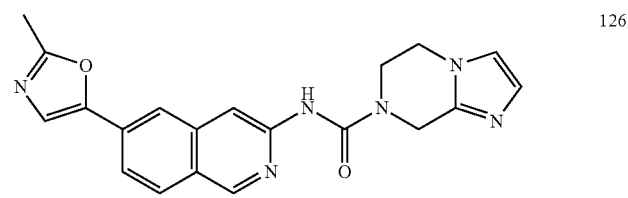 126
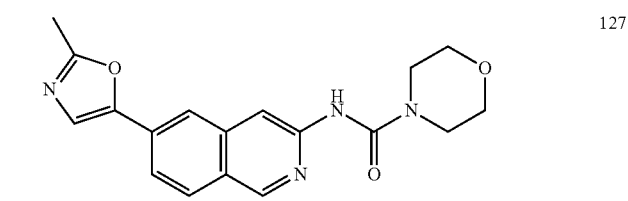 127
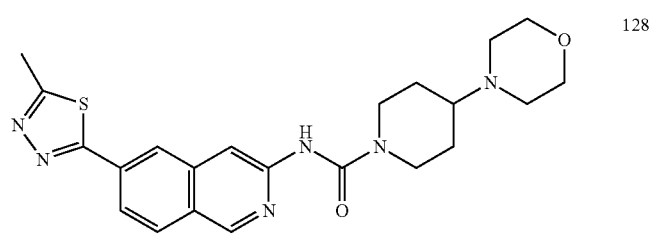 128

TABLE 1-continued
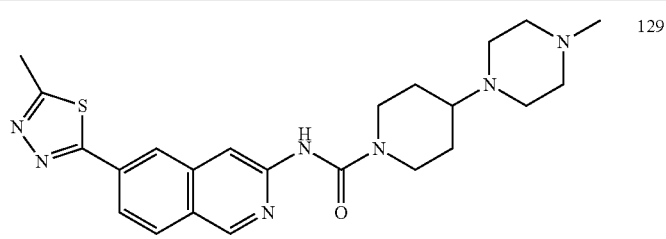
129
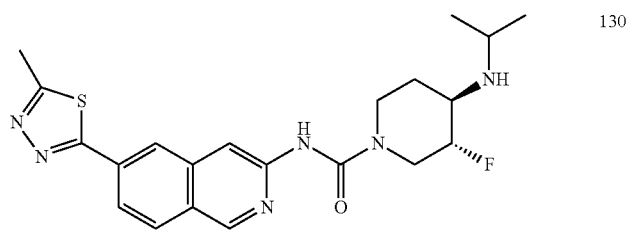
130
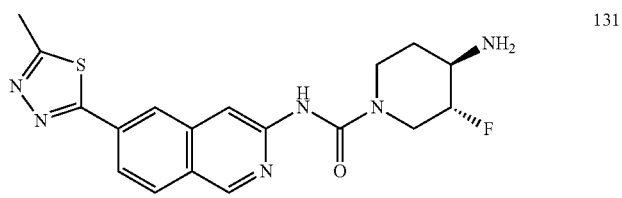
131
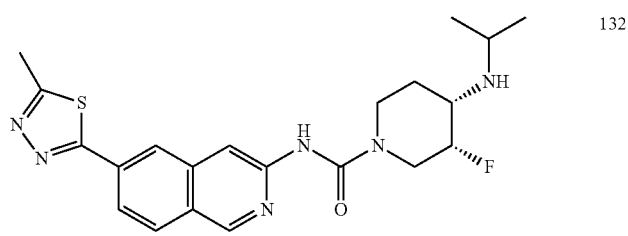
132
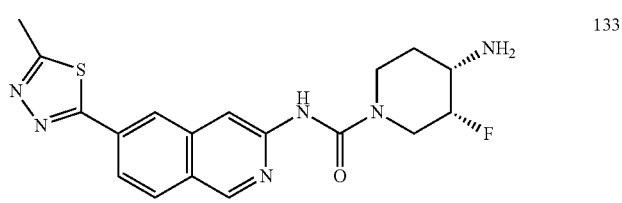
133
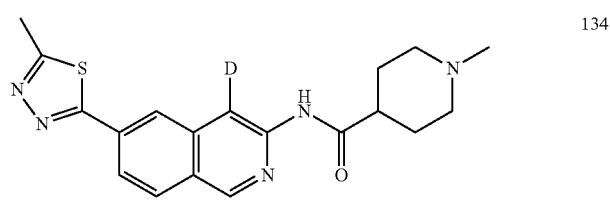
134
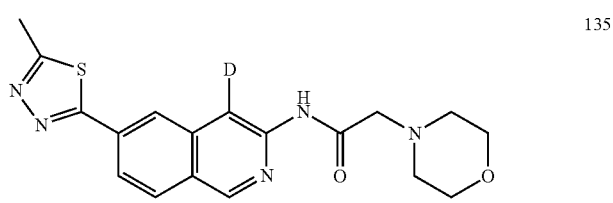
135

TABLE 1-continued
| | |
|---|---|
| 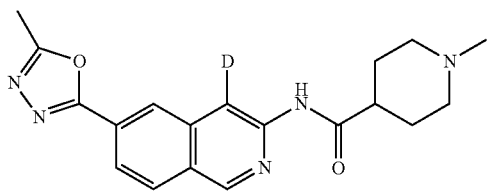 [SMILES: [2H]c1c(NC(=O)C2CCN(C)CC2)ncc2ccc(-c3nnc(C)o3)cc12] | 136 |
| 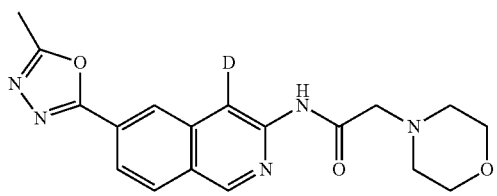 [SMILES: [2H]c1c(NC(=O)CN2CCOCC2)ncc2ccc(-c3nnc(C)o3)cc12] | 137 |
| 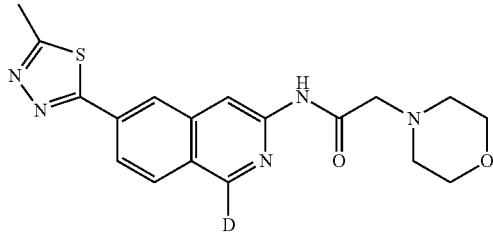 [SMILES: [2H]c1nc(NC(=O)CN2CCOCC2)cc2cc(-c3nnc(C)s3)ccc12] | 138 |
| 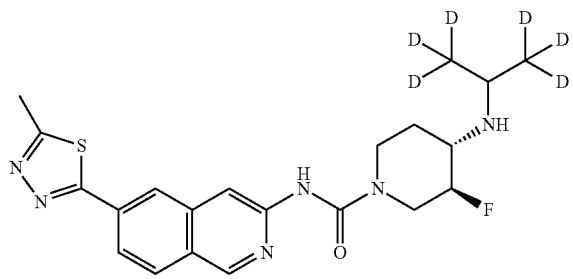 [SMILES: [2H]C([2H])([2H])C(N[C@H]1CCN(C(=O)Nc2cc3cc(-c4nnc(C)s4)ccc3cn2)C[C@@H]1F)C([2H])([2H])[2H]] | 139 |
| 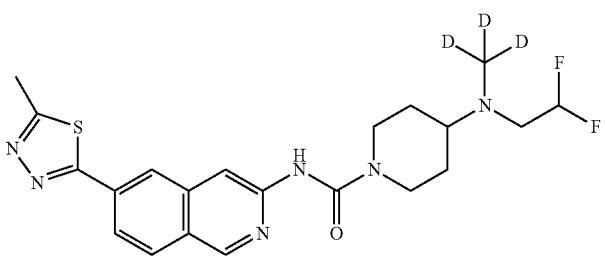 [SMILES: [2H]C([2H])([2H])N(CC(F)F)C1CCN(C(=O)Nc2cc3cc(-c4nnc(C)s4)ccc3cn2)CC1] | 140 |
| 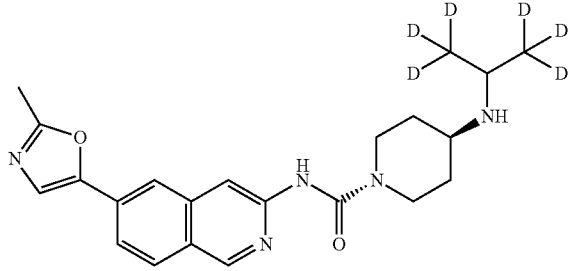 | 141 |

TABLE 1-continued
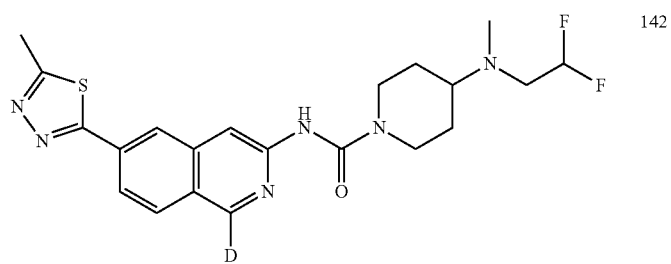
142
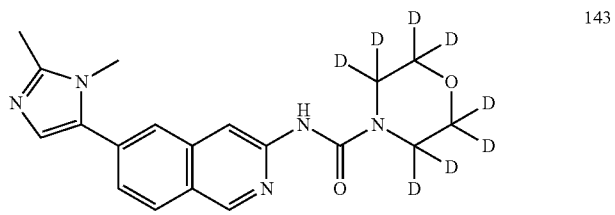
143
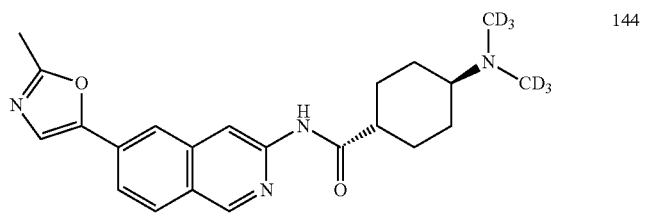
144
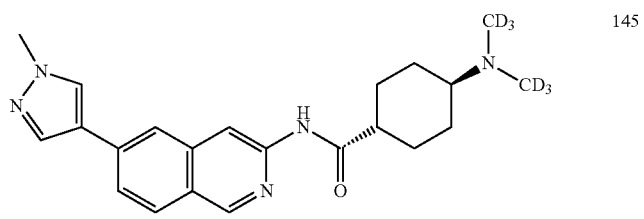
145
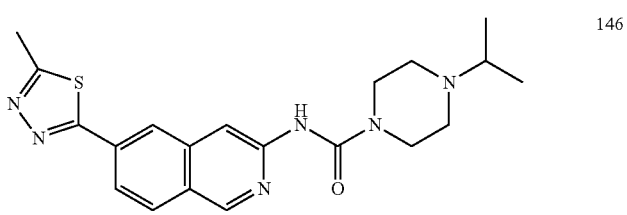
146
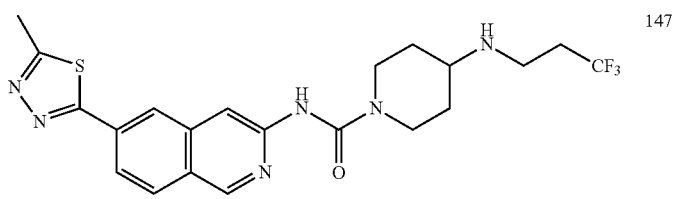
147
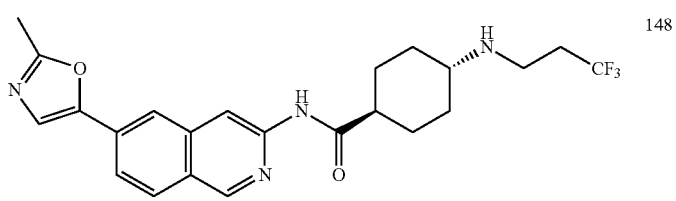
148

TABLE 1-continued
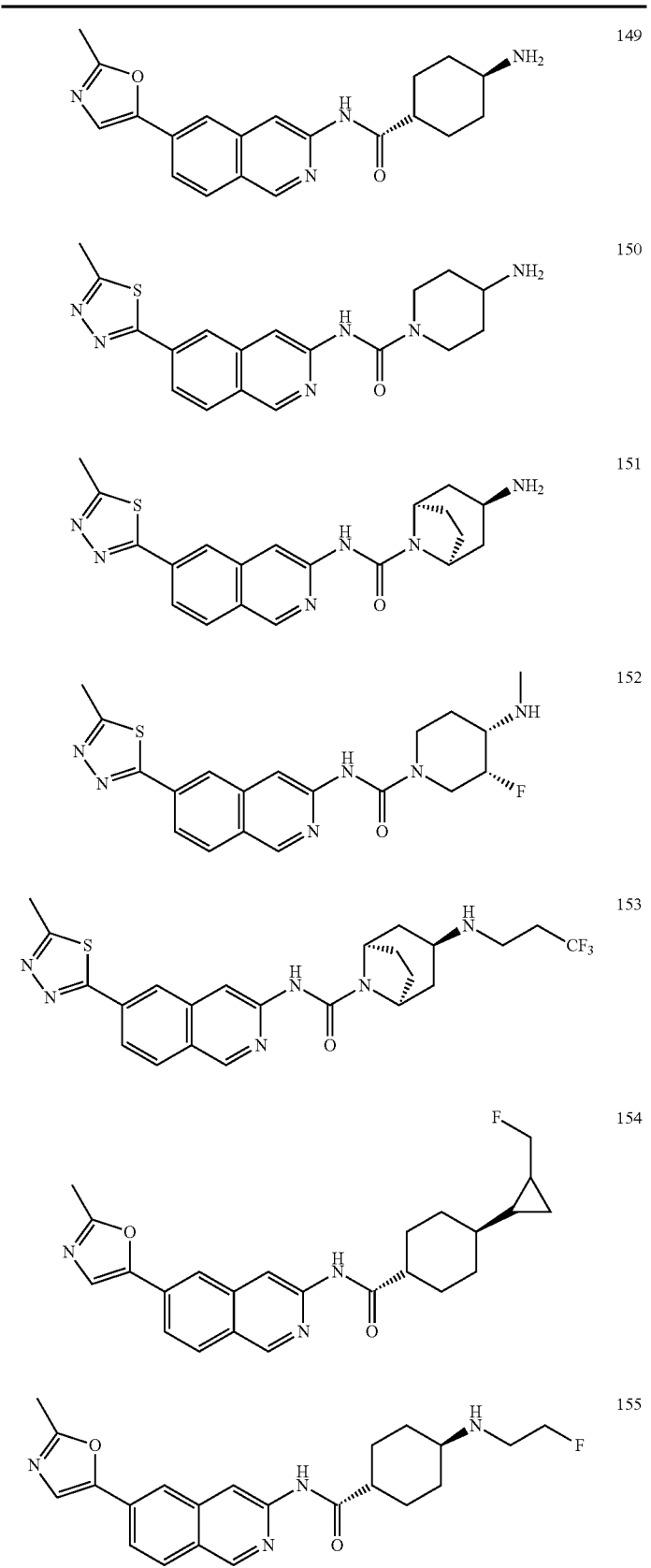

TABLE 1-continued
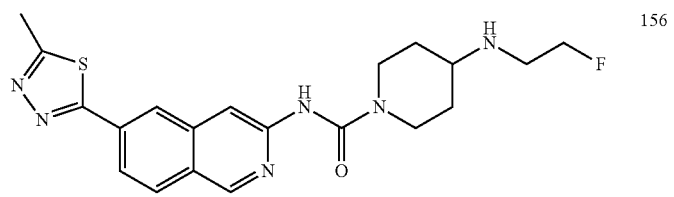
156
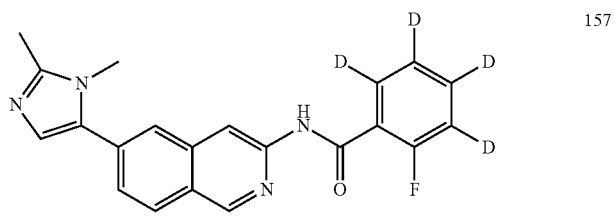
157
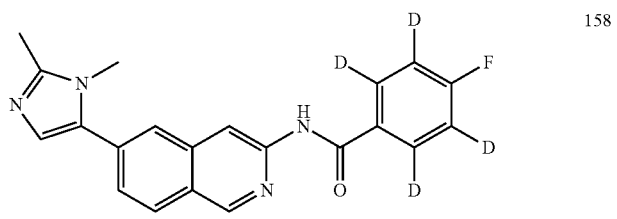
158
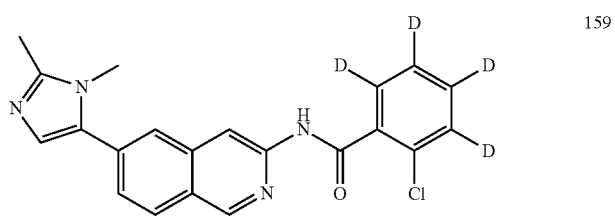
159
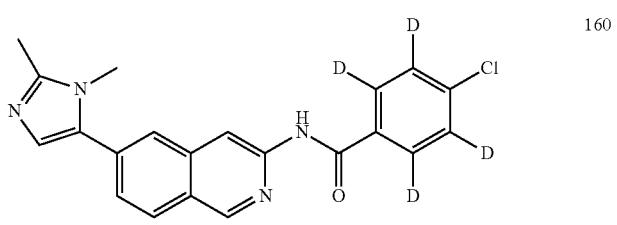
160
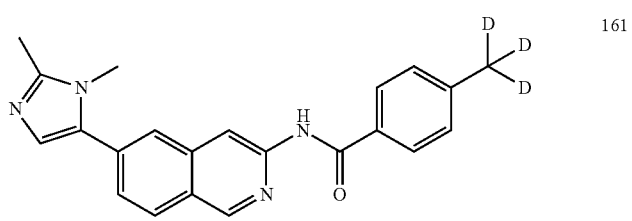
161
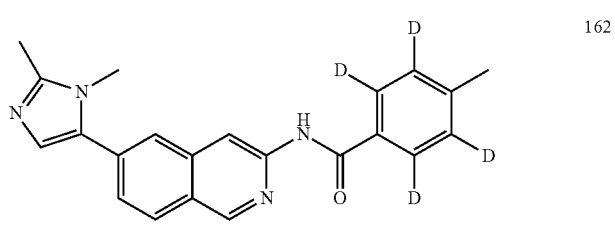
162

TABLE 1-continued

| | |
|---|---|
| (structure) | 163 |
| (structure) | 164 |
| (structure) | 165 |
| (structure) | 166 |
| (structure) | 167 |
| (structure) | 168 |
| (structure) | 169 |

TABLE 1-continued
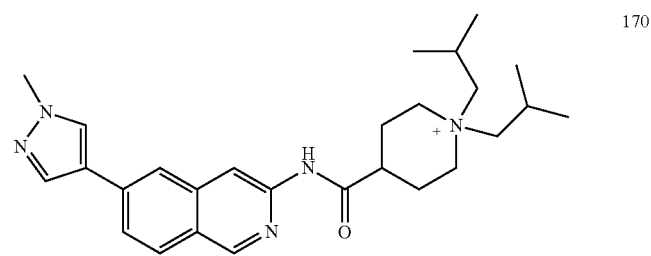
170
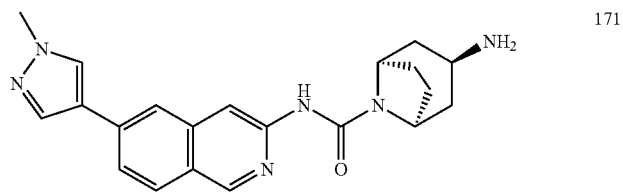
171
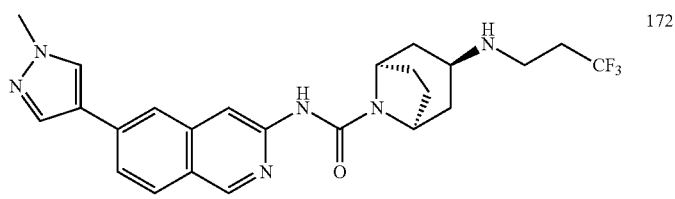
172
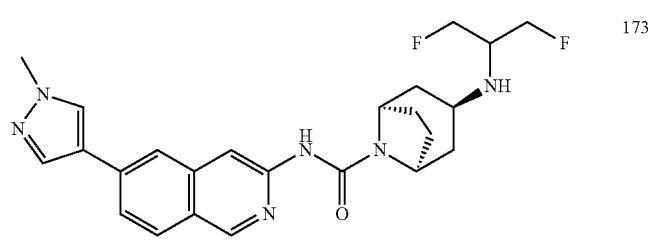
173
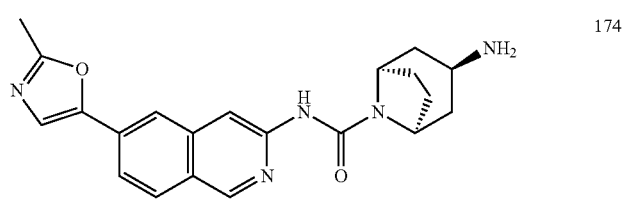
174
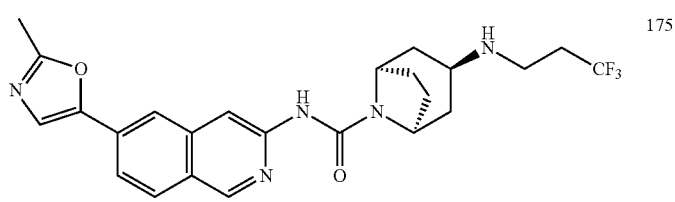
175
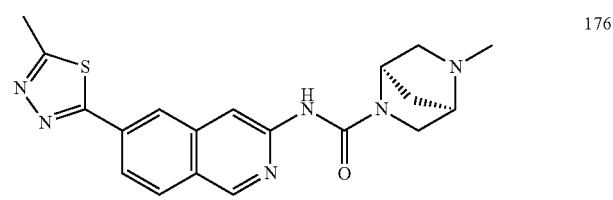
176

TABLE 1-continued
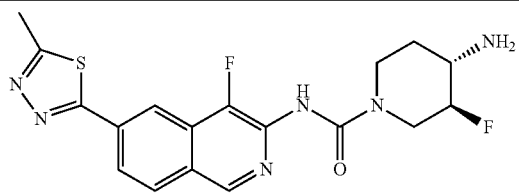
177
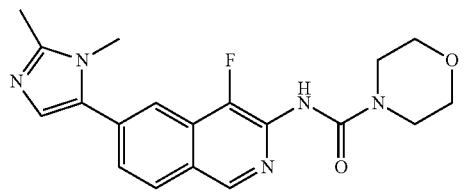 [SMILES: Cc1ncc(-c2ccc3cnc(NC(=O)N4CCOCC4)c(F)c3c2)n1C]
178
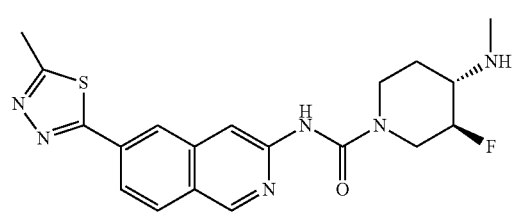
179
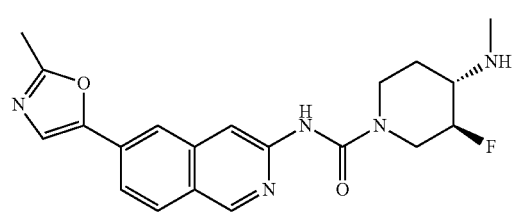 [SMILES: CN[C@H]1CCN(C(=O)Nc2cc3cc(-c4cnc(C)o4)ccc3cn2)C[C@@H]1F]
180
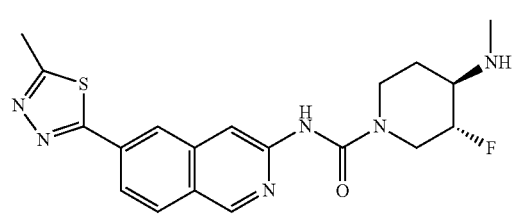 [SMILES: CN[C@@H]1CCN(C(=O)Nc2cc3cc(-c4nnc(C)s4)ccc3cn2)C[C@H]1F]
181
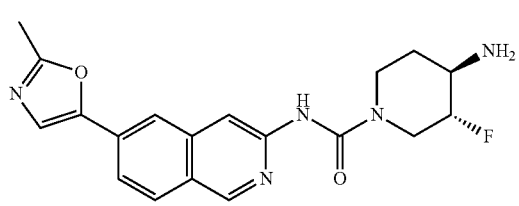 [SMILES: Cc1ncc(-c2ccc3cnc(NC(=O)N4CC[C@@H](N)[C@H](F)C4)cc3c2)o1]
182
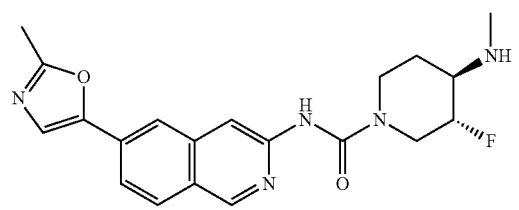
183
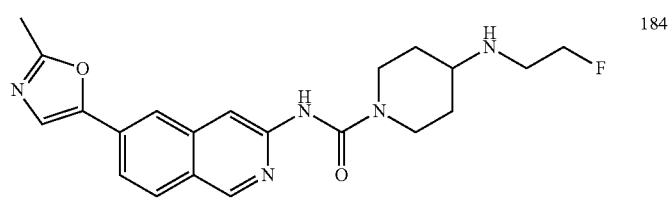
184

TABLE 1-continued
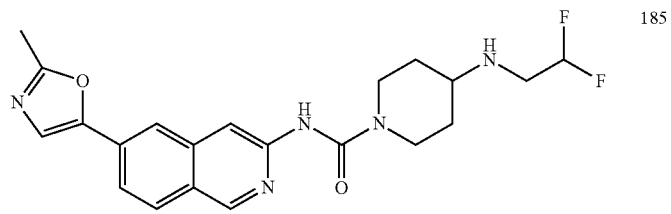 185
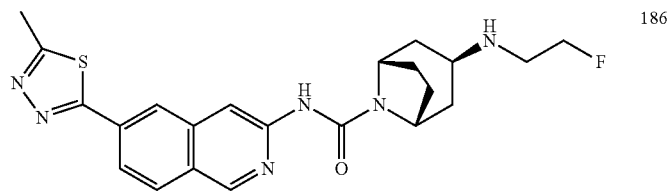 186
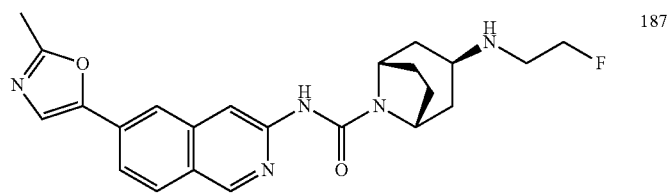 187
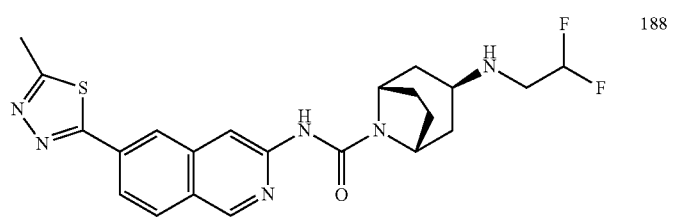 188
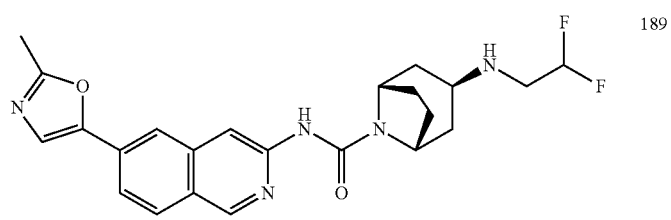 189
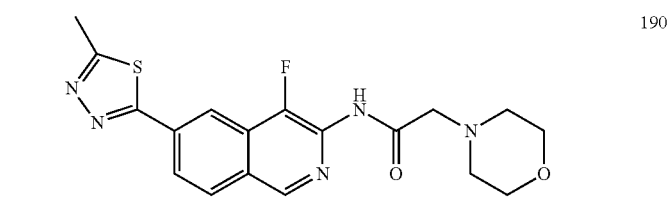 190
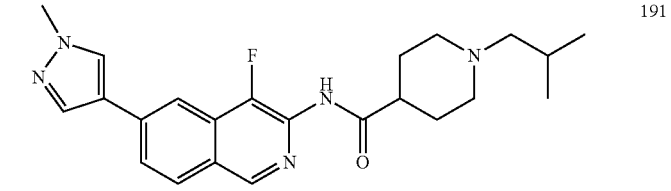 191

TABLE 1-continued
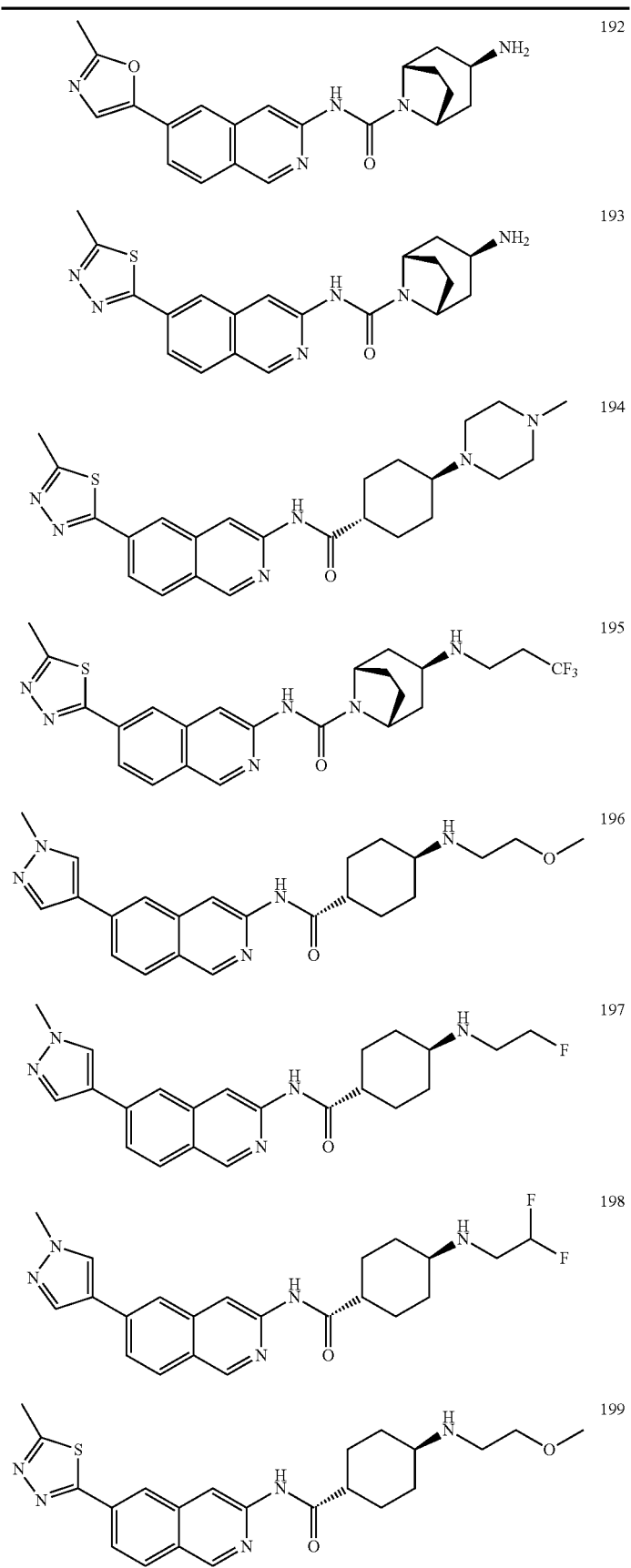

TABLE 1-continued
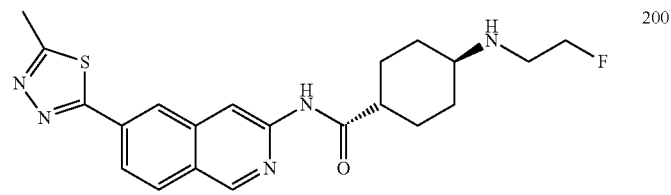 200
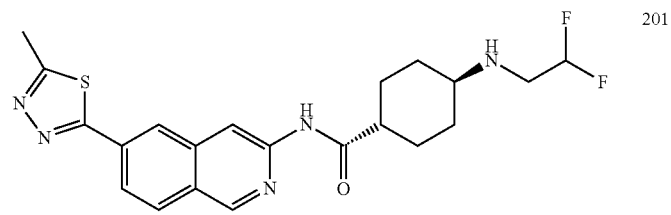 201
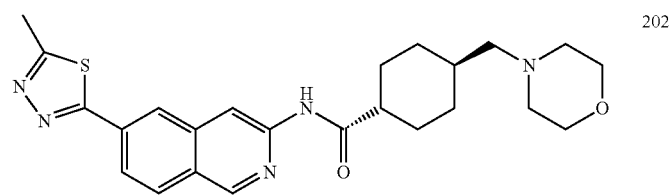 202
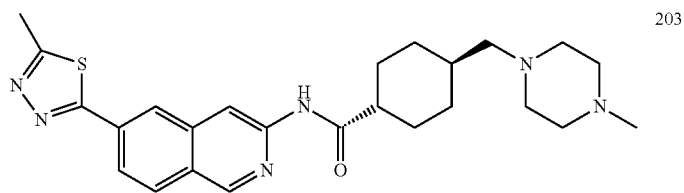 203
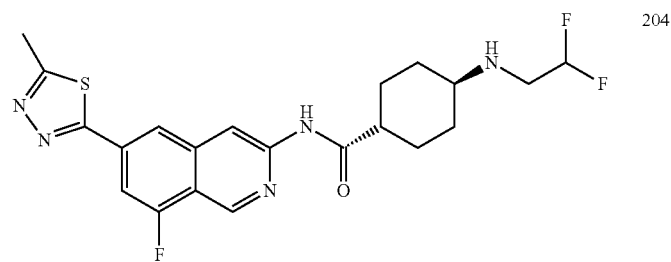 204
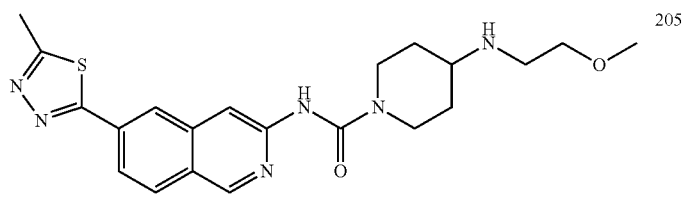 205
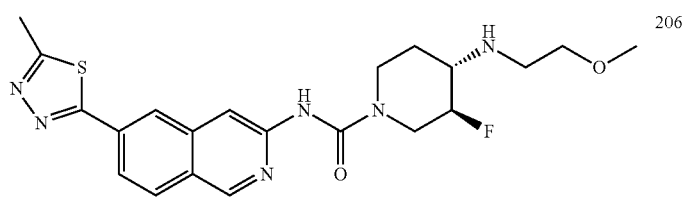 206

TABLE 1-continued
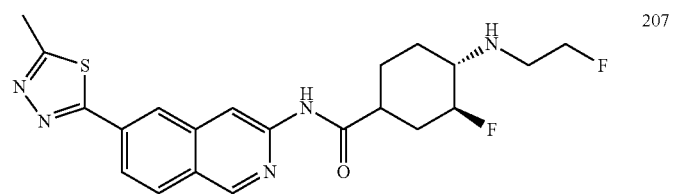 207
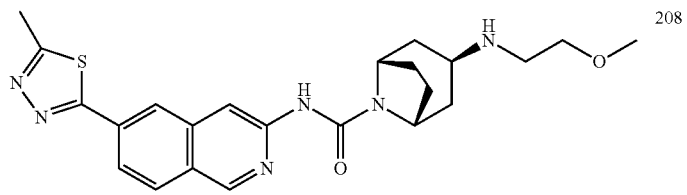 208
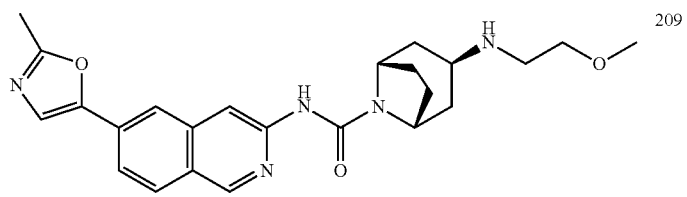 209
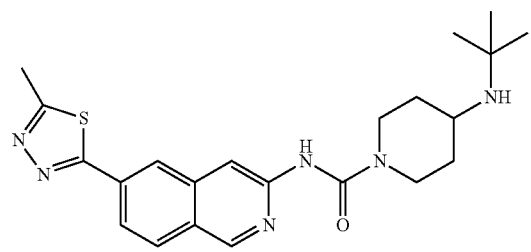 [SMILES: Cc1nnc(-c2ccc3cnc(NC(=O)N4CCC(NC(C)(C)C)CC4)cc3c2)s1] 210
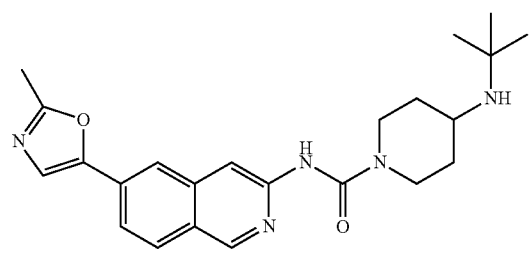 [SMILES: Cc1ncc(-c2ccc3cnc(NC(=O)N4CCC(NC(C)(C)C)CC4)cc3c2)o1] 211
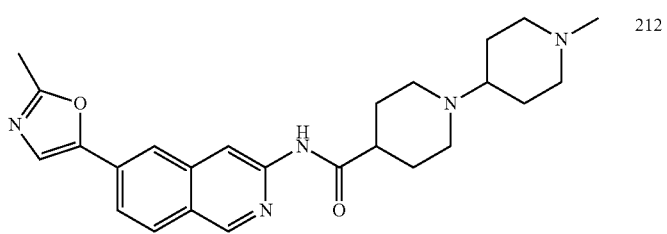 212
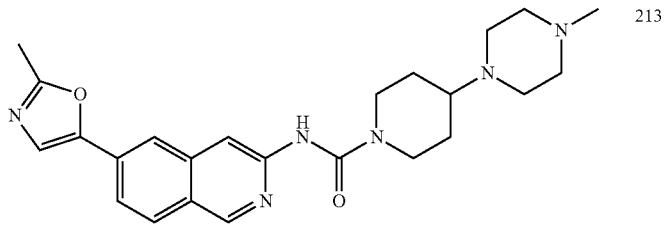 213

TABLE 1-continued
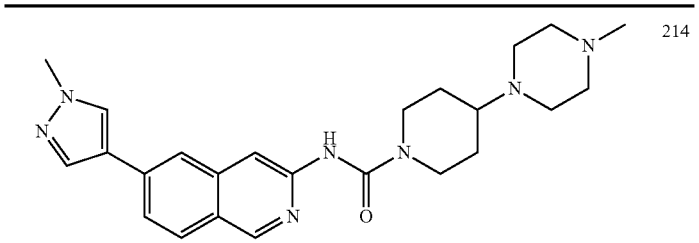
214
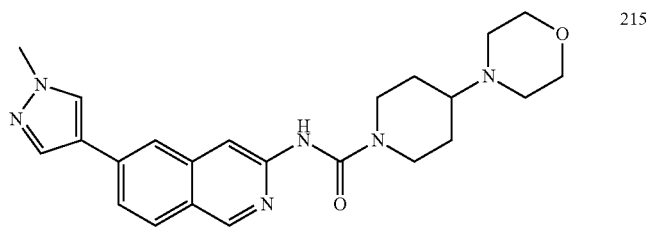
215
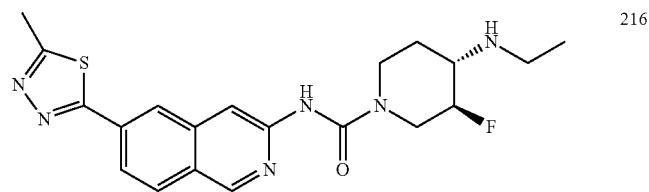
216
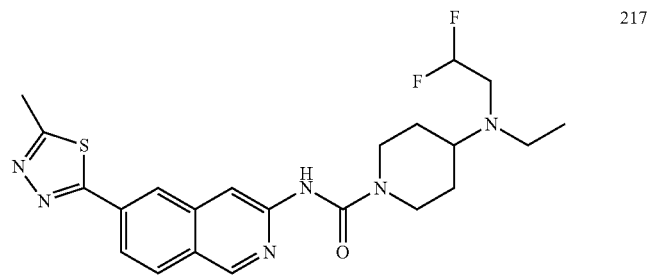
217
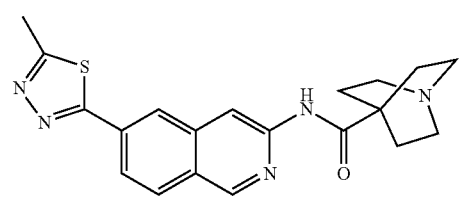 [SMILES: Cc1nnc(-c2ccc3cnc(NC(=O)C45CCN(CC4)CC5)cc3c2)s1]
218
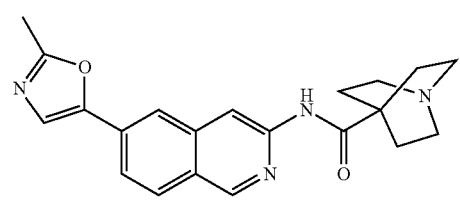
219
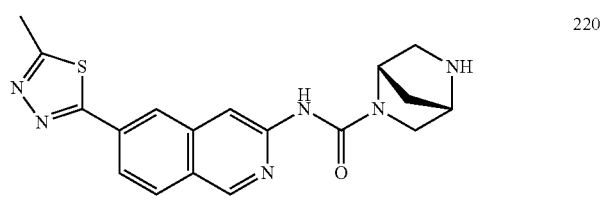
220

TABLE 1-continued
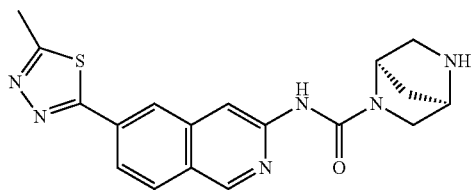 [SMILES: Cc1nnc(-c2ccc3cnc(NC(=O)N4C[C@H]5C[C@@H]4CN5)cc3c2)s1]
221
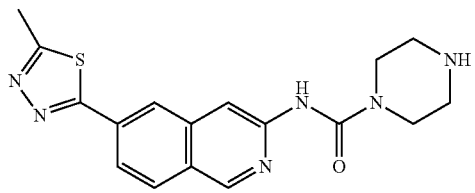 [SMILES: Cc1nnc(-c2ccc3cnc(NC(=O)N4CCNCC4)cc3c2)s1]
222
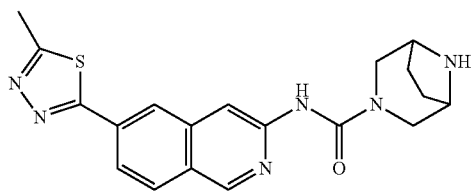 [SMILES: Cc1nnc(-c2ccc3cnc(NC(=O)N4CC5CCC(C4)N5)cc3c2)s1]
223
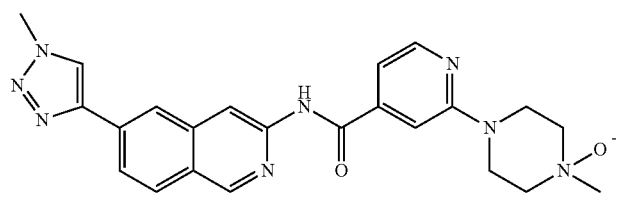
224
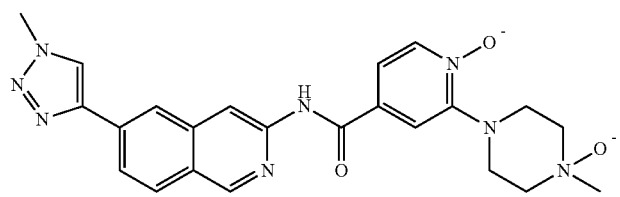
225
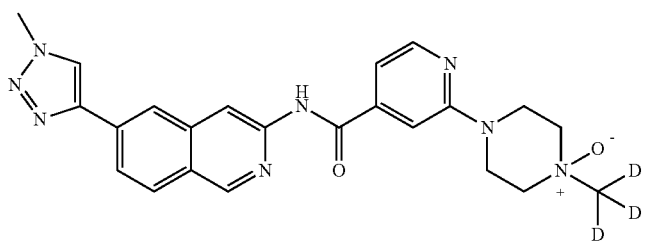
226
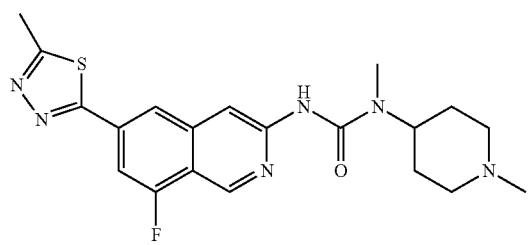 [SMILES: Cc1nnc(-c2cc(F)c3cnc(NC(=O)N(C)C4CCN(C)CC4)cc3c2)s1]
227

TABLE 1-continued

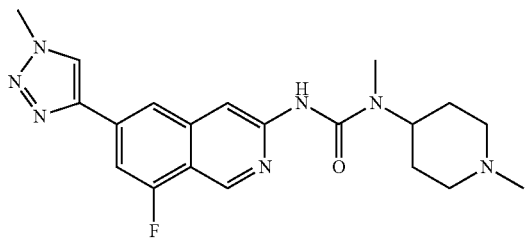 [SMILES: CN1CCC(N(C)C(=O)Nc2cc3cc(-c4cn(C)nn4)cc(F)c3cn2)CC1]
228

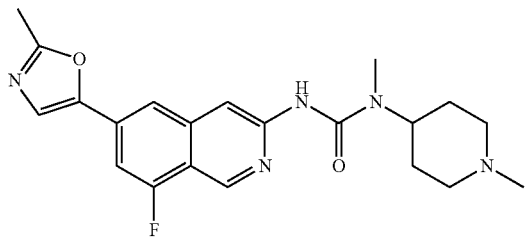 [SMILES: Cc1ncc(-c2cc(F)c3cnc(NC(=O)N(C)C4CCN(C)CC4)cc3c2)o1]
229

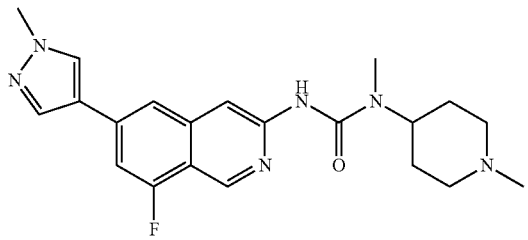 [SMILES: CN1CCC(N(C)C(=O)Nc2cc3cc(-c4cnn(C)c4)cc(F)c3cn2)CC1]
230

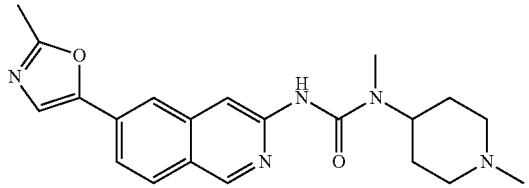 [SMILES: Cc1ncc(-c2ccc3cnc(NC(=O)N(C)C4CCN(C)CC4)cc3c2)o1]
231

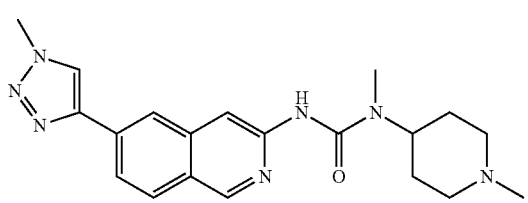 [SMILES: CN1CCC(N(C)C(=O)Nc2cc3cc(-c4cn(C)nn4)ccc3cn2)CC1]
232

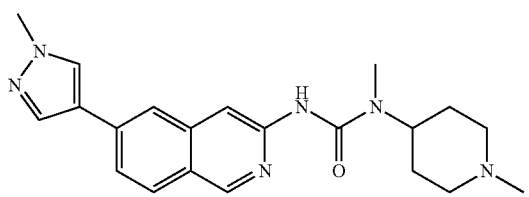 [SMILES: CN1CCC(N(C)C(=O)Nc2cc3cc(-c4cnn(C)c4)ccc3cn2)CC1]
233

Administration and Pharmaceutical Compositions

Some embodiments include pharmaceutical compositions comprising: (a) a therapeutically effective amount of a compound provided herein, or its corresponding enantiomer, diastereoisomer or tautomer, or pharmaceutically acceptable salt; and (b) a pharmaceutically acceptable carrier.

The compounds provided herein may also be useful in combination (administered together or sequentially) with other known agents.

Non-limiting examples of diseases which can be treated with a combination of a compound of Formula (I) and other another active agent are colorectal cancer, ovarian cancer, chronic inflammation, diabetic retinopathy, pulmonary fibrosis, and osteoarthritis. For example, a compound of Formula (I) can be combined with one or more chemotherapeutic compounds.

In some embodiments, colorectal cancer can be treated with a combination of a compound of Formula (I) and one or more of the following drugs: 5-Fluorouracil (5-FU), which can be administered with the vitamin-like drug leucovorin (also called folinic acid); capecitabine (XELODA®), irinotecan (CAMPOSTAR®), oxaliplatin (ELOXATIN®). Examples of combinations of these drugs which could be further combined with a compound of Formula (I) are FOLFOX (5-FU, leucovorin, and oxaliplatin), FOLFIRI (5-FU, leucovorin, and irinotecan), FOLFOXIRI (leucovorin, 5-FU, oxaliplatin, and irinotecan) and CapeOx (Capecitabine and oxaliplatin). For rectal cancer, chemo with 5-FU or capecitabine combined with radiation may be given before surgery (neoadjuvant treatment).

In some embodiments, ovarian cancer can be treated with a combination of a compound of Formula (I) and one or more of the following drugs: Topotecan, Liposomal doxorubicin (DOXIL®), Gemcitabine (GEMZAR®), Cyclophosphamide (CYTOXAN®), Vinorelbine (NAVELBINE®), Ifosfamide (IFEX®), Etoposide (VP-16), Altretamine (HEXALEN®), Capecitabine (XELODA®), Irinotecan (CPT-11, CAMPTOSAR®), Melphalan, Pemetrexed (ALIMTA®) and Albumin bound paclitaxel (nab-paclitaxel, ABRAXANE®). Examples of combinations of these drugs which could be further combined with a compound of Formula (I) are TIP (paclitaxel [Taxol], ifosfamide, and cisplatin), VeIP (vinblastine, ifosfamide, and cisplatin) and VIP (etoposide [VP-16], ifosfamide, and cisplatin).

In some embodiments, a compound of Formula (I) can be used to treat cancer in combination with any of the following methods: (a) Hormone therapy such as aromatase inhibitors, LHRH [luteinizing hormone-releasing hormone] analogs and inhibitors, and others; (b) Ablation or embolization procedures such as radiofrequency ablation (RFA), ethanol (alcohol) ablation, microwave thermotherapy and cryosurgery (cryotherapy); (c) Chemotherapy using alkylating agents such as cisplatin and carboplatin, oxaliplatin, mechlorethamine, cyclophosphamide, chlorambucil and ifosfamide; (d) Chemotherapy using anti-metabolites such as azathioprine and mercaptopurine; (e) Chemotherapy using plant alkaloids and terpenoids such as *vinca* alkaloids (i.e. Vincristine, Vinblastine, Vinorelbine and Vindesine) and taxanes; (f) Chemotherapy using podophyllotoxin, etoposide, teniposide and docetaxel; (g) Chemotherapy using topoisomerase inhibitors such as irinotecan, topotecan, amsacrine, etoposide, etoposide phosphate, and teniposide; (h) Chemotherapy using cytotoxic antibiotics such as actinomycin, anthracyclines, doxorubicin, daunorubicin, valrubicin, idarubicin, epirubicin, bleomycin, plicamycin and mitomycin; (i) Chemotherapy using tyrosine-kinase inhibitors such as Imatinib mesylate (GLEEVEC®, also known as STI-571), Gefitinib (Iressa, also known as ZD1839), Erlotinib (marketed as TARCEVA®), Bortezomib (VELCADE®), tamoxifen, tofacitinib, crizotinib, Bcl-2 inhibitors (e.g. obatoclax in clinical trials, ABT-263, and Gossypol), PARP inhibitors (e.g. Iniparib, Olaparib in clinical trials), PI3K inhibitors (e.g. perifosine in a phase III trial), VEGF Receptor 2 inhibitors (e.g. Apatinib), AN-152, (AEZS-108), Braf inhibitors (e.g. vemurafenib, dabrafenib and LGX818), MEK inhibitors (e.g. trametinib and MEK162), CDK inhibitors, (e.g. PD-0332991), salinomycin and Sorafenib; (j) Chemotherapy using monoclonal antibodies such as Rituximab (marketed as MABTHERA® or RITUXAN®), Trastuzumab (Herceptin also known as ErbB2), Cetuximab (marketed as ERBITUX®), and Bevacizumab (marketed as AVASTIN®); and (k) radiation therapy.

In some embodiments, diabetic retinopathy can be treated with a combination of a compound of Formula (I) and one or more of the following natural supplements: Bilberry, Butcher's broom, Ginkgo, Grape seed extract, and Pycnogenol (Pine bark).

In some embodiments, idiopathic pulmonary fibrosis/pulmonary fibrosis can be treated with a combination of a compound of Formula (I) and one or more of the following drugs: pirfenidone (pirfenidone was approved for use in 2011 in Europe under the brand name Esbriet®), prednisone, azathioprine, N-acetylcysteine, interferon-γ 1b, bosentan (bosentan is currently being studied in patients with IPF, [*The American Journal of Respiratory and Critical Care Medicine* (2011), 184(1), 92-9]), Nintedanib (BIBF 1120 and Vargatef), QAX576 [*British Journal of Pharmacology* (2011), 163(1), 141-172], and anti-inflammatory agents such as corticosteroids.

In some embodiments, a compound of Formula (I) can be used to treat idiopathic pulmonary fibrosis/pulmonary fibrosis in combination with any of the following methods: oxygen therapy, pulmonary rehabilitation and surgery.

In some embodiments, a compound of Formula (I) can be used to treat osteoarthritis in combination with any of the following methods: (a) Nonsteroidal anti-inflammatory drugs (NSAIDs) such as ibuprofen, naproxen, aspirin and acetaminophen; (b) physical therapy; (c) injections of corticosteroid medications; (d) injections of hyaluronic acid derivatives (e.g. Hyalgan, Synvisc); (e) narcotics, like codeine; (f) in combination with braces and/or shoe inserts or any device that can immobilize or support your joint to help you keep pressure off it (e.g., splints, braces, shoe inserts or other medical devices); (g) realigning bones (osteotomy); (h) joint replacement (arthroplasty); and (i) in combination with a chronic pain class.

In some embodiments, macular degeneration can be treated with a combination of a compound of Formula (I) and one or more of the following drugs: Bevacizumab (Avastin®), Ranibizumab (Lucentis®), Pegaptanib (Macugen), Aflibercept (Eylea®), verteporfin (Visudyne®) in combination with photodynamic therapy (PDT) or with any of the following methods: (a) in combination with laser to destroy abnormal blood vessels (photocoagulation); and (b) in combination with increased vitamin intake of antioxidant vitamins and zinc.

In some embodiments, retinitis pigmentosa can be treated with a combination of a compound of Formula (I) and one or more of the following drugs: UF-021 (Ocuseva™), vitamin A palmitate and pikachurin or with any of the following methods: (a) with the *Argus*® II retinal implant; and (b) with stem cell and/or gene therapy.

Administration of the compounds disclosed herein or the pharmaceutically acceptable salts thereof can be via any of the accepted modes of administration, including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. In some embodiments, the administration method includes oral or parenteral administration.

Compounds provided herein intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release or the like. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants and the like, for prolonged and/or timed, pulsed administration at a predetermined rate.

The compounds can be administered either alone or in combination with a conventional pharmaceutical carrier, excipient or the like. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a compound as described herein in the range of 0.005% to 100% with the balance made up from non-toxic carrier may be prepared. The contemplated compositions may contain 0.001%-100% of a compound provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy,* 22$^{nd}$ Edition (Pharmaceutical Press, London, U K. 2012).

In one embodiment, the compositions will take the form of a unit dosage form such as a pill or tablet and thus the composition may contain, along with a compound provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more compounds provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. a compound provided herein and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrin derivatives, sorbitan monolaurate, triethanolamine acetate, triethanolamine oleate, and the like).

In some embodiments, the unit dosage of compounds of Formula (I) is about 0.25 mg/Kg to about 50 mg/Kg in humans.

In some embodiments, the unit dosage of compounds of Formula (I) is about 0.25 mg/Kg to about 20 mg/Kg in humans.

In some embodiments, the unit dosage of compounds of Formula (I) is about 0.50 mg/Kg to about 19 mg/Kg in humans.

In some embodiments, the unit dosage of compounds of Formula (I) is about 0.75 mg/Kg to about 18 mg/Kg in humans.

In some embodiments, the unit dosage of compounds of Formula (I) is about 1.0 mg/Kg to about 17 mg/Kg in humans.

In some embodiments, the unit dosage of compounds of Formula (I) is about 1.25 mg/Kg to about 16 mg/Kg in humans.

In some embodiments, the unit dosage of compounds of Formula (I) is about 1.50 mg/Kg to about 15 mg/Kg in humans.

In some embodiments, the unit dosage of compounds of Formula (I) is about 1.75 mg/Kg to about 14 mg/Kg in humans.

In some embodiments, the unit dosage of compounds of Formula (I) is about 2.0 mg/Kg to about 13 mg/Kg in humans.

In some embodiments, the unit dosage of compounds of Formula (I) is about 3.0 mg/Kg to about 12 mg/Kg in humans.

In some embodiments, the unit dosage of compounds of Formula (I) is about 4.0 mg/Kg to about 11 mg/Kg in humans.

In some embodiments, the unit dosage of compounds of Formula (I) is about 5.0 mg/Kg to about 10 mg/Kg in humans.

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

Injectables can be prepared in conventional forms, either as liquid solutions, colloid, liposomes, complexes, coacervate or suspensions, as emulsions, or in solid forms suitable for reconstitution in liquid prior to injection. The percentage of a compound provided herein contained in such parenteral compositions is highly dependent on the specific nature thereof, as well as the activity of the compound and the needs of the patient. However, percentages of active ingredient of 0.01% to 10% in solution are employable, and could be higher if the composition is a solid or suspension, which could be subsequently diluted to the above percentages.

In some embodiments, the composition will comprise about 0.1-10% of the active agent in solution.

In some embodiments, the composition will comprise about 0.1-5% of the active agent in solution.

In some embodiments, the composition will comprise about 0.1-4% of the active agent in solution.

In some embodiments, the composition will comprise about 0.15-3% of the active agent in solution.

In some embodiments, the composition will comprise about 0.2-2% of the active agent in solution.

In some embodiments, the compositions are provided in dosage forms suitable for continuous dosage by intravenous infusion over a period of about 1-96 hours.

In some embodiments, the compositions are provided in dosage forms suitable for continuous dosage by intravenous infusion over a period of about 1-72 hours.

In some embodiments, the compositions are provided in dosage forms suitable for continuous dosage by intravenous infusion over a period of about 1-48 hours.

In some embodiments, the compositions are provided in dosage forms suitable for continuous dosage by intravenous infusion over a period of about 1-24 hours.

In some embodiments, the compositions are provided in dosage forms suitable for continuous dosage by intravenous infusion over a period of about 1-12 hours.

In some embodiments, the compositions are provided in dosage forms suitable for continuous dosage by intravenous infusion over a period of about 1-6 hours.

In some embodiments, these compositions can be administered by intravenous infusion to humans at doses of about 5 mg/m$^2$ to about 300 mg/m$^2$.

In some embodiments, these compositions can be administered by intravenous infusion to humans at doses of about 5 mg/m$^2$ to about 200 mg/m$^2$.

In some embodiments, these compositions can be administered by intravenous infusion to humans at doses of about 5 mg/m$^2$ to about 100 mg/m$^2$.

In some embodiments, these compositions can be administered by intravenous infusion to humans at doses of about 10 mg/m$^2$ to about 50 mg/m$^2$.

In some embodiments, these compositions can be administered by intravenous infusion to humans at doses of about 50 mg/m$^2$ to about 200 mg/m$^2$.

In some embodiments, these compositions can be administered by intravenous infusion to humans at doses of about 75 mg/m$^2$ to about 175 mg/m$^2$.

In some embodiments, these compositions can be administered by intravenous infusion to humans at doses of about 100 mg/m$^2$ to about 150 mg/m$^2$.

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size may be desired to maximize impaction on the nasal mucosa and to minimize or prevent pulmonary deposition of the administered formulation. In some embodiments, aerosols intended for delivery to the lung are provided for inhalation through the nose or the mouth. For delivery to the lung, inhaled aerodynamic particle sizes of about less than 10 μm are useful (e.g., about 1 to about 10 microns). Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formula (I) disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates, or as dry powders. Aqueous formulations may be aerosolized by liquid nebulizers employing either hydraulic or ultrasonic atomization or by modified micropump systems (like the soft mist inhalers, the Aerodose® or the AERx® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formula (I) disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the disclosure can be incorporated into a gel formulation (e.g., U.S. Pat. Nos. 4,474,752 and 6,911,211).

In some embodiments, compounds of Formula (I) disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments the acidic or basic solid compound of Formula (I) can be delivered from the reservoir of an external or internal implanted pumping system.

Formulations of the disclosure also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the *crista* fenestrae *cochleae*.

In some embodiments, the compounds of Formula (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing a compound provided herein with a suitable non-irritating excipient that is solid at ordinary temperatures but liquid at the rectal temperature and will therefore melt or erode/dissolve in the rectum and release the compound. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter, is first melted.

Solid compositions can be provided in various different types of dosage forms, depending on the physicochemical properties of the compound provided herein, the desired dissolution rate, cost considerations, and other criteria. In one of the embodiments, the solid composition is a single unit. This implies that one unit dose of the compound is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In one embodiment, the solid composition is a highly porous lyophilized form. Such lyophilizates, sometimes also called wafers or lyophilized tablets, are particularly useful for their rapid disintegration, which also enables the rapid dissolution of the compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with a compound provided herein so that the compound is located at the outer surface of the individual particles. In this type of system, the water-soluble low molecular weight excipient may be useful for preparing the cores of such coated particles, which can be subsequently coated with a coating composition comprising the compound and, for example, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of hepatocellular carcinoma, colon cancer, leukemia, lymphoma, sarcoma, ovarian cancer, diabetic retinopathy, pulmonary fibrosis, rheumatoid arthritis, sepsis, ankylosing spondylitis, psoriasis, scleroderma, mycotic and viral infections, bone and cartilage diseases, Alzheimer's disease, lung disease, bone/osteoporotic (wrist, spine, shoulder and hip) fractures, articular cartilage (chondral) defects, degenerative disc disease (or intervertebral disc degeneration), polyposis *coli*, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Methods of Treatment

The compounds and compositions provided herein can be used as inhibitors and/or modulators of one or more components of the Wnt pathway, which may include one or more Wnt proteins, and thus can be used to treat a variety of disorders and diseases in which aberrant Wnt signaling is implicated, such as cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation, to correct a genetic disorder, and/or to treat a neurological condition/disorder/disease due to mutations or dysregulation of the Wnt pathway and/or of one or more of Wnt signaling components. Non-limiting examples of diseases which can be treated with the compounds and compositions provided herein include a variety of cancers, diabetic retinopathy, pulmonary fibrosis, rheumatoid arthritis, scleroderma, mycotic and viral infections, bone and cartilage diseases, neurological conditions/diseases such as Alzheimer's disease, amyotrophic lateral sclerosis (ALS), motor neuron disease, multiple sclerosis or autism, lung disease, bone/osteoporotic (wrist, spine, shoulder and hip) fractures, polyposis *coli*, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

With respect to cancer, the Wnt pathway is known to be constitutively activated in a variety of cancers including, for example, colon cancer, hepatocellular carcinoma, lung cancer, ovarian cancer, prostate cancer, pancreatic cancer and leukemias such as CML, CLL and T-ALL. Accordingly, the compounds and compositions described herein may be used to treat these cancers in which the Wnt pathway is constitutively activated. In certain embodiments, the cancer is chosen from hepatocellular carcinoma, colon cancer, leukemia, lymphoma, sarcoma and ovarian cancer.

Other cancers can also be treated with the compounds and compositions described herein.

More particularly, cancers that may be treated by the compounds, compositions and methods described herein include, but are not limited to, the following:

1) Breast cancers, including, for example $ER^+$ breast cancer, $ER^-$ breast cancer, $her2^-$ breast cancer, $her2^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative (her2-). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, oligodendrocytoma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia.

11) Skin cancers and skin disorders, including, for example, malignant melanoma and metastatic melanoma, basal cell carcinoma, squamous cell carcinoma, Kaposi's sarcoma, moles dysplastic nevi, lipoma, angioma, dermatofibroma, keloids, and scleroderma.

12) Adrenal gland cancers, including, for example, neuroblastoma.

More particularly, tumors of the central nervous system that may be treated by the compounds, compositions and methods described herein include:

1) Astrocytic tumors, e.g., diffuse astrocytoma (fibrillary, protoplasmic, gemistocytic, mixed), anaplastic (malignant) astrocytoma, glioblastoma multiforme (giant cell glioblastoma and gliosarcoma), pilocytic astrocytoma (pilomyxoid astrocytoma), pleomorphic xanthoastrocytoma, subependymal giant cell astrocytoma, and gliomatosis cerebri.

2) Oligodendroglial tumors, e.g., oligodendroglioma and anaplastic oligodendroglioma.

3) Oligoastrocytic tumors, e.g., oligoastrocytoma and anaplastic oligoastrocytoma.

4) Ependymal tumors, e.g., subependymoma, myxopapillary ependymoma, ependymoma, (cellular, papillary, clear cell, tanycytic), and anaplastic (malignant) ependymoma.

5) Choroid plexus tumors, e.g., choroid plexus papilloma, atypical choroid plexus papilloma, and choroid plexus carcinoma.

6) Neuronal and mixed neuronal-glial tumors, e.g., gangliocytoma, ganglioglioma, dysembryoplastic neuroepithelial tumor (DNET), dysplastic gangliocytoma of the cerebellum (Lhermitte-Duclos), desmoplastic infantile astrocytoma/ganglioglioma, central neurocytoma, anaplastic ganglioglioma, extraventricular neurocytoma, cerebellar liponeurocytoma, Papillary glioneuronal tumor, Rosette-forming glioneuronal tumor of the fourth ventricle, and paraganglioma of the filum *terminale*.

7) Pineal tumors, e.g., pineocytoma, pineoblastoma, papillary tumors of the pineal region, and pineal parenchymal tumor of intermediate differentiation.

8) Embryonal tumors, e.g., medulloblastoma (medulloblastoma with extensive nodularity, anaplastic medulloblastoma, desmoplastic, large cell, melanotic, medullomyoblastoma), medulloepithelioma, supratentorial primitive neuroectodermal tumors, and primitive neuroectodermal tumors (PNETs) such as neuroblastoma, ganglioneuroblastoma, ependymoblastoma, and atypical teratoid/rhabdoid tumor.

9) Neuroblastic tumors, e.g., olfactory (esthesioneuroblastoma), olfactory neuroepithelioma, and neuroblastomas of the adrenal gland and sympathetic nervous system.

10) Glial tumors, e.g., astroblastoma, chordoid glioma of the third ventricle, and angiocentric glioma.

11) Tumors of cranial and paraspinal nerves, e.g., schwannoma, neurofibroma Perineurioma, and malignant peripheral nerve sheath tumor.

12) Tumors of the meninges such as tumors of meningothelial cells, e.g., meningioma (atypical meningioma and anaplastic meningioma); mesenchymal tumors, e.g., lipoma, angiolipoma, hibernoma, liposarcoma, solitary fibrous tumor, fibrosarcoma, malignant fibrous histiocytoma, leiomyoma, leiomyosarcoma, rhabdomyoma, rhabdomyosarcoma, chondroma, chondrosarcoma, osteoma, osteosarcoma, osteochondroma, haemangioma, epithelioid hemangioendothelioma, haemangiopericytoma, anaplastic haemangiopericytoma, angiosarcoma, Kaposi Sarcoma, and Ewing Sarcoma; primary melanocytic lesions, e.g., diffuse melanocytosis, melanocytoma, malignant melanoma, meningeal melanomatosis; and hemangioblastomas.

13) Tumors of the hematopoietic system, e.g., malignant Lymphomas, plasmocytoma, and granulocytic sarcoma.

14) Germ cell tumors, e.g., germinoma, embryonal carcinoma, yolk sac tumor, choriocarcinoma, teratoma, and mixed germ cell tumors.

15) Tumors of the sellar region, e.g., craniopharyngioma, granular cell tumor, pituicytoma, and spindle cell oncocytoma of the adenohypophysis.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

The compounds and compositions described herein can be used as anti-angiogenesis agents and as agents for modulating and/or inhibiting the activity of protein kinases, thus providing treatments for cancer and other diseases associated with cellular proliferation mediated by protein kinases. For example, the compounds described herein can inhibit the activity of one or more kinases. Accordingly, provided herein is a method of treating cancer or preventing or reducing angiogenesis through kinase inhibition.

In addition, and including treatment of cancer, the compounds and compositions described herein can function as cell-cycle control agents for treating proliferative disorders in a patient. Disorders associated with excessive proliferation include, for example, cancers, scleroderma, immunological disorders involving undesired proliferation of leukocytes, and restenosis and other smooth muscle disorders. Furthermore, such compounds may be used to prevent de-differentiation of post-mitotic tissue and/or cells.

Diseases or disorders associated with uncontrolled or abnormal cellular proliferation include, but are not limited to, the following:

a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma and Kaposi's sarcoma.

a disease process which features abnormal cellular proliferation, e.g., benign prostatic hyperplasia, familial adenomatosis polyposis, neurofibromatosis, atherosclerosis, arthritis, glomerulonephritis, restenosis following angioplasty or vascular surgery, inflammatory bowel disease, transplantation rejection, endotoxic shock, and fungal infections. Fibrotic disorders such as skin fibrosis; scleroderma; progressive systemic fibrosis; lung fibrosis; muscle fibrosis; kidney fibrosis; glomerulosclerosis; glomerulonephritis; hypertrophic scar formation; uterine fibrosis; renal fibrosis; cirrhosis of the liver, liver fibrosis; fatty liver disease (FLD); adhesions, such as those occurring in the abdomen, pelvis, spine or tendons; chronic obstructive pulmonary disease; fibrosis following myocardial infarction; pulmonary fibrosis; fibrosis and scarring associated with diffuse/interstitial lung disease; central nervous system fibrosis, such as fibrosis following stroke; fibrosis associated with neuro-degenerative disorders such as Alzheimer's Disease or multiple sclerosis; fibrosis associated with proliferative vitreoretinopathy (PVR); restenosis; endometriosis; ischemic disease and radiation fibrosis.

defective apoptosis-associated conditions, such as cancers (including but not limited to those types mentioned herein), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, sepsis, ankylosing spondylitis, psoriasis, scleroderma, autoimmune mediated glomerulonephritis, inflammatory bowel disease and autoimmune diabetes mellitus), neuro-degenerative disorders (including but not limited to Alzheimer's disease, lung disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis), tendinopathies such as tendinitis and tendinosis, aspirin-sensitive rhinosinusitis, cystic fibrosis, multiple sclerosis, kidney diseases and cancer pain.

genetic diseases due to mutations in Wnt signaling components, such as polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

The compounds and compositions provided herein have been found to possess immunomodulatory activities and are expected to control the innate and adaptive immune system (e.g. macrophages, microglia, dendritic cells, B and T cells) and suppress pro-inflammatory cytokine release (e.g. TNF, IL-6, IL-1, IFN) which is well known to be involved in chronic inflammation in a wide variety of disease areas. Therefore compounds and compositions provided herein can used to treat chronic inflammation associated with disorders and diseases including but not limited to eye disorders, joint pain, arthritis (rheumatoid, osteo, psoriatic gout), cancers (colon, breast, lung, pancreas, and others), gastrointestinal disorders (ulcerative colitis and inflammatory bowel diseases), pulmonary disorders (chronic obstructive pulmonary disorder and asthma), allergies, skin disorders (atopic dermatitis and psoriasis), diabetes, pancreatitis, tendonitis, hepatitis, heart disease, myocarditis, stroke, lupus, and neurological disorders such as multiple sclerosis, Parkinson's and dementia including Alzheimer's disease.

The compounds and compositions provided herein can be used as inhibitors and/or modulators of the enzyme DYRK1A, and thus can be used to treat a variety of disorders and diseases associated with tau protein, amyloid, alpha-synuclein, TDP-43 or FUS pathology including, but not limited to, Alzheimer's disease, amyotrophic lateral sclerosis (ALS), down syndrome, frontotemporal dementia (FTD) including FTD with Parkinsonism-17 (FTDP-17), behavioural variant frontotemporal dementia (bvFTD), FTD in patients with motor neuron disease (MND) (typically amyotrophic lateral sclerosis, also called FTD-ALS), corticobasal degeneration (CBD) (also called corticobasal ganglionic degeneration), progressive supranuclear palsy, primary progressive aphasia (PPA), globular glial tauopathy (GGT), myotonic dystrophy type 1 (DM1) (also called Steinert disease), myotonic dystrophy type 2 (DM2) (also called proximal myotonic myopathy), Guam complex, argyrophilic grain disease, dementia pugilistica, post-encephalitic parkinsonism, Lewy body dementia, Parkinson's disease, Pick's disease, and additional diseases with pronounced neurodegeneration such as autism, dementia, epilepsy, Huntington's disease, multiple sclerosis; diseases and disorders associated with acquired brain injury such as chronic traumatic encephalopathy, traumatic brain injury, tumor, and stroke.

Non-limiting examples of neurological disorders (e.g., neurological conditions and neurological diseases) which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, De Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barre syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Meniere's disease, meningitis, Menkes disease, metachromatic leukodystrophy, microcephaly, micropsia, Miller Fisher syndrome, misophonia, mitochondrial myopathy, Mobius syndrome, monomelic amyotrophy, motor neuron disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia Congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjögren's syndrome, snatiation, Sotos syndrome, spasticity, spina *bifida*, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease, and Zellweger syndrome.

The compounds and compositions may also be useful in the inhibition of the development of invasive cancer, tumor angiogenesis and metastasis.

In some embodiments, the disclosure provides a method for treating a disease or disorder associated with aberrant cellular proliferation by administering to a patient in need of such treatment an effective amount of one or more of the compounds of Formula (I), in combination (simultaneously or sequentially) with at least one other agent.

In some embodiments, the disclosure provides a method of treating or ameliorating in a patient a disorder or disease selected from the group consisting of: cancer, pulmonary fibrosis, idiopathic pulmonary fibrosis (IPF), degenerative disc disease, bone/osteoporotic fractures, bone or cartilage disease, and osteoarthritis, the method comprising administering to the patient a therapeutically effective amount of a compound according to Formula (I), or a pharmaceutically acceptable salt thereof.

In some embodiments, the disclosure provides a method of treating or ameliorating in a patient a disorder or disease selected from the group consisting of: chronic inflammation, systemic inflammation, diabetes, cancer, pulmonary fibrosis, idiopathic pulmonary fibrosis (IPF), degenerative disc disease, bone/osteoporotic fractures, a bone or cartilage disease, a neurological condition/disorder/disease, osteoarthritis, lung disease, a fibrotic disorder.

In some embodiments, the pharmaceutical composition comprises a therapeutically effective amount of a compound of Formula (I), or a pharmaceutically acceptable salt thereof, and a pharmaceutically acceptable excipient.

In some embodiments, the method of treats a disorder or disease in which aberrant Wnt signaling is implicated in a patient, the method comprises administering to the patient a therapeutically effective amount of a compound of Formula (I), or a pharmaceutically acceptable salt thereof.

In some embodiments, the disorder or disease is the pain and inflammation associated with cancer.

In some embodiments, the disorder or disease is the pain and inflammation associated with a joint.

In some embodiments, the disorder or disease is the pain and inflammation associated with the knee.

In some embodiments, the disorder or disease is the pain and inflammation associated with the hip.

In some embodiments, the disorder or disease is the pain and inflammation associated with the shoulder.

In some embodiments, the disorder or disease is the pain and inflammation associated with arthritis.

In some embodiments, the disorder or disease is the pain and inflammation associated with gastrointestinal disorders.

In some embodiments, the disorder or disease is the pain and inflammation associated with pulmonary disorders.

In some embodiments, the disorder or disease is the pain and inflammation associated with allergies.

In some embodiments, the disorder or disease is the pain and inflammation associated with skin disorders.

In some embodiments, the disorder or disease is the pain and inflammation associated with diabetes.

In some embodiments, the disorder or disease is the pain and inflammation associated with pancreatitis.

In some embodiments, the disorder or disease is the pain and inflammation associated with tendonitis.

In some embodiments, the disorder or disease is the pain and inflammation associated with heart disease.

In some embodiments, the disorder or disease is the pain and inflammation associated with lupus.

In some embodiments, the disorder or disease is the pain and inflammation associated with a neurological disorder.

In some embodiments, the disorder or disease is the pain and inflammation associated with multiple sclerosis.

In some embodiments, the disorder or disease is the pain and inflammation associated with Parkinson's.

In some embodiments, the disorder or disease is cancer.

In some embodiments, the disorder or disease is systemic inflammation.

In some embodiments, the disorder or disease is metastatic melanoma.

In some embodiments, the disorder or disease is fatty liver disease.

In some embodiments, the disorder or disease is liver fibrosis.

In some embodiments, the disorder or disease is tendon regeneration.

In some embodiments, the disorder or disease is diabetes.

In some embodiments, the disorder or disease is degenerative disc disease.

In some embodiments, the disorder or disease is osteoarthritis.

In some embodiments, the disorder or disease is diabetic retinopathy.

In some embodiments, the disorder or disease is pulmonary fibrosis.

In some embodiments, the disorder or disease is idiopathic pulmonary fibrosis (IPF).

In some embodiments, the disorder or disease is degenerative disc disease.

In some embodiments, the disorder or disease is rheumatoid arthritis.

In some embodiments, the disorder or disease is scleroderma.

In some embodiments, the disorder or disease is a mycotic or viral infection.

In some embodiments, the disorder or disease is a bone or cartilage disease.

In some embodiments, the disorder or disease is a neurological disorder.

In some embodiments, the disorder or disease is Alzheimer's disease.

In some embodiments, the disorder or disease is osteoarthritis.

In some embodiments, the disorder or disease is lung disease.

In some embodiments, the disorder or disease is a genetic disease caused by mutations in Wnt signaling components, wherein the genetic disease is selected from: polyposis *coli*, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

In some embodiments, the patient is a human.

In some embodiments, the cancer is chosen from: hepatocellular carcinoma, colon cancer, breast cancer, pancreatic cancer, chronic myeloid leukemia (CML), chronic myelomonocytic leukemia, chronic lymphocytic leukemia (CLL), acute myeloid leukemia, acute lymphocytic leukemia, Hodgkin lymphoma, lymphoma, sarcoma and ovarian cancer.

In some embodiments, the cancer is chosen from: lung cancer—non-small cell, lung cancer—small cell, multiple myeloma, nasopharyngeal cancer, neuroblastoma, osteosarcoma, penile cancer, pituitary tumors, prostate cancer, retinoblastoma, rhabdomyosarcoma, salivary gland cancer, skin cancer—basal and squamous cell, skin cancer—melanoma, small intestine cancer, stomach (gastric) cancers, testicular cancer, thymus cancer, thyroid cancer, uterine sarcoma, vaginal cancer, vulvar cancer, laryngeal or hypopharyngeal cancer, kidney cancer, Kaposi sarcoma, gestational trophoblastic disease, gastrointestinal stromal tumor, gastrointestinal carcinoid tumor, gallbladder cancer, eye cancer (melanoma and lymphoma), Ewing tumor, esophagus cancer, endometrial cancer, colorectal cancer, cervical cancer, brain or spinal cord tumor, bone metastasis, bone cancer, bladder cancer, bile duct cancer, anal cancer and adrenal cortical cancer.

In some embodiments, the cancer is hepatocellular carcinoma.

In some embodiments, the cancer is colon cancer.

In some embodiments, the cancer is colorectal cancer.

In some embodiments, the cancer is breast cancer.

In some embodiments, the cancer is pancreatic cancer.

In some embodiments, the cancer is chronic myeloid leukemia (CML).

In some embodiments, the cancer is chronic myelomonocytic leukemia.

In some embodiments, the cancer is chronic lymphocytic leukemia (CLL).

In some embodiments, the cancer is acute myeloid leukemia.

In some embodiments, the cancer is acute lymphocytic leukemia.

In some embodiments, the cancer is Hodgkin lymphoma.

In some embodiments, the cancer is lymphoma.

In some embodiments, the cancer is sarcoma.

In some embodiments, the cancer is ovarian cancer.

In some embodiments, the cancer is lung cancer—non-small cell.

In some embodiments, the cancer is lung cancer—small cell.

In some embodiments, the cancer is multiple myeloma.

In some embodiments, the cancer is nasopharyngeal cancer.

In some embodiments, the cancer is neuroblastoma.

In some embodiments, the cancer is osteosarcoma.

In some embodiments, the cancer is penile cancer.

In some embodiments, the cancer is pituitary tumors.

In some embodiments, the cancer is prostate cancer.

In some embodiments, the cancer is retinoblastoma.

In some embodiments, the cancer is rhabdomyosarcoma.

In some embodiments, the cancer is salivary gland cancer.

In some embodiments, the cancer is skin cancer—basal and squamous cell.

In some embodiments, the cancer is skin cancer—melanoma.

In some embodiments, the cancer is small intestine cancer.

In some embodiments, the cancer is stomach (gastric) cancers.

In some embodiments, the cancer is testicular cancer.

In some embodiments, the cancer is thymus cancer.

In some embodiments, the cancer is thyroid cancer.

In some embodiments, the cancer is uterine sarcoma.

In some embodiments, the cancer is vaginal cancer.

In some embodiments, the cancer is vulvar cancer.

In some embodiments, the cancer is Wilms tumor.

In some embodiments, the cancer is laryngeal or hypopharyngeal cancer.

In some embodiments, the cancer is kidney cancer.

In some embodiments, the cancer is Kaposi sarcoma.

In some embodiments, the cancer is gestational trophoblastic disease.

In some embodiments, the cancer is gastrointestinal stromal tumor.

In some embodiments, the cancer is gastrointestinal carcinoid tumor.

In some embodiments, the cancer is gallbladder cancer.

In some embodiments, the cancer is eye cancer (melanoma and lymphoma).

In some embodiments, the cancer is Ewing tumor.

In some embodiments, the cancer is esophagus cancer.

In some embodiments, the cancer is endometrial cancer.

In some embodiments, the cancer is colorectal cancer.

In some embodiments, the cancer is cervical cancer.

In some embodiments, the cancer is brain or spinal cord tumor.

In some embodiments, the cancer is bone metastasis.

In some embodiments, the cancer is bone cancer.

In some embodiments, the cancer is bladder cancer.

In some embodiments, the cancer is bile duct cancer.

In some embodiments, the cancer is anal cancer.

In some embodiments, the cancer is adrenal cortical cancer.

In some embodiments, the disorder or disease is a neurological condition/disorder/disease, wherein the neurological condition/disorder/disease is selected from: Alzheimer's disease, frontotemporal dementias, dementia with Lewy bodies, prion diseases, Parkinson's disease, Huntington's disease, progressive supranuclear palsy, corticobasal degeneration, multiple system atrophy, amyotrophic lateral sclerosis (ALS), inclusion body myositis, autism, degenerative myopathies, diabetic neuropathy, other metabolic neuropathies, endocrine neuropathies, orthostatic hypotension, multiple sclerosis and Charcot-Marie-Tooth disease.

In some embodiments, the disorder or disease is a neurological condition/disorder/disease associated with tau protein, amyloid, alpha-synuclein pathology, Tar DNA-binding Protein of 43 KDa (TDP-43), Prion protein PrP or fused in sarcoma (FUS).

In some embodiments, the disorder or disease is a neurological condition/disorder/disease, wherein the neurological condition/disorder/disease is selected from the group consisting of: Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

In some embodiments, the disorder or disease is a fibrotic disorder, wherein the fibrotic disorder is selected from the group consisting of: skin fibrosis; scleroderma; progressive systemic fibrosis; lung fibrosis; muscle fibrosis; kidney fibrosis; glomerulosclerosis; glomerulonephritis; hypertrophic scar formation; uterine fibrosis; renal fibrosis; cirrhosis of the liver, liver fibrosis; adhesions; chronic obstructive pulmonary disease; fibrosis following myocardial infarction; pulmonary fibrosis; fibrosis and scarring associated with diffuse/interstitial lung disease; central nervous system fibrosis; fibrosis associated with proliferative vitreoretinopathy (PVR); restenosis; endometriosis; ischemic disease, and radiation fibrosis.

In some embodiments, the disorder or disease is chronic inflammation associated with eye disorders, joint pain, arthritis (rheumatoid, osteo, psoriatic gout), cancers (colon, breast, lung, pancreas, and others), gastrointestinal disorders (ulcerative colitis and inflammatory bowel diseases), pulmonary disorders (chronic obstructive pulmonary disorder and asthma), allergies, skin disorders (atopic dermatitis and psoriasis), diabetes, pancreatitis, tendonitis, hepatitis, heart disease, myocarditis, stroke, lupus, and neurological disorders such as multiple sclerosis, Parkinson's and dementia including Alzheimer's disease.

In some embodiments, a compound of Formula (I) inhibits DYRK1A.

In some embodiments, a compound of Formula (I) inhibits GSK3.

In some embodiments, a compound of Formula (I) inhibits GSK3β.

In some embodiments, a compound of Formula (I) inhibits DYRK1A and GSK3β.

In some embodiments, the compound of Formula (I) inhibits one or more proteins in the Wnt pathway.

In some embodiments, the compound of Formula (I) inhibits signaling induced by one or more Wnt proteins.

In some embodiments, the Wnt proteins are chosen from: WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, and WNT16.

In some embodiments, the compound of Formula (I) inhibits a kinase activity.

In some embodiments, the method treats a disease or disorder mediated by the Wnt pathway in a patient, the method comprises administering to the patient a therapeutically effective amount of a compound (or compounds) of Formula (I), or a pharmaceutically acceptable salt thereof.

In some embodiments, the compound of Formula (I) inhibits one or more Wnt proteins.

In some embodiments, the method treats a disease or disorder mediated by kinase activity in a patient, the method comprises administering to the patient a therapeutically effective amount of a compound (or compounds) of Formula (I), or a pharmaceutically acceptable salt thereof.

In some embodiments, the disease or disorder comprises tumor growth, cell proliferation, or angiogenesis.

In some embodiments, the method inhibits the activity of a protein kinase receptor, the method comprises contacting the receptor with an effective amount of a compound (or compounds) of Formula (I), or a pharmaceutically acceptable salt thereof.

In some embodiments, the method treats a disease or disorder associated with aberrant cellular proliferation in a patient; the method comprises administering to the patient a therapeutically effective amount of a compound (or compounds) of Formula (I), or a pharmaceutically acceptable salt thereof.

In some embodiments, the method prevents or reduces angiogenesis in a patient; the method comprises administering to the patient a therapeutically effective amount of a compound (or compounds) of Formula (I), or a pharmaceutically acceptable salt thereof.

In some embodiments, the method prevents or reduces abnormal cellular proliferation in a patient; the method comprises administering to the patient a therapeutically effective amount of a compound (or compounds) of Formula (I), or a pharmaceutically acceptable salt thereof.

In some embodiments, the method treats a disease or disorder associated with aberrant cellular proliferation in a patient, the method comprises administering to the patient a pharmaceutical composition comprising one or more of the compounds of Formula (I) in combination with a pharmaceutically acceptable carrier and one or more other agents.

Moreover, the compounds and compositions, for example, as inhibitors of the cyclin-dependent kinases (CDKs), can modulate the level of cellular RNA and DNA synthesis and therefore are expected to be useful in the treatment of viral infections such as HIV, human papilloma virus, herpes virus, Epstein-Barr virus, adenovirus, Sindbis virus, pox virus and the like.

Compounds and compositions described herein can inhibit the kinase activity of, for example, CDK/cyclin complexes, such as those active in the $G_0$ or $G_1$ stage of the cell cycle, e.g., CDK2, CDK4, and/or CDK6 complexes.

Evaluation of Biological Activity

The biological activity of the compounds described herein can be tested using any suitable assay known to those of skill in the art, see, e.g., WO 2001/053268 and WO 2005/009997. For example, the activity of a compound may be tested using one or more of the test methods outlined below.

In one example, tumor cells may be screened for Wnt independent growth. In such a method, tumor cells of interest are contacted with a compound (i.e. inhibitor) of interest, and the proliferation of the cells, e.g. by uptake of tritiated thymidine, is monitored. In some embodiments, tumor cells may be isolated from a candidate patient who has been screened for the presence of a cancer that is associated with a mutation in the Wnt signaling pathway. Candidate cancers include, without limitation, those listed above.

In another example, one may utilize in vitro assays for Wnt biological activity, e.g. stabilization of γ-catenin and promoting growth of stem cells. Assays for biological activity of Wnt include stabilization of β-catenin, which can be measured, for example, by serial dilutions of a candidate inhibitor composition. An exemplary assay for Wnt biological activity contacts a candidate inhibitor with cells containing constitutively active Wnt/β-catenin signaling. The cells are cultured for a period of time sufficient to stabilize β-catenin, usually at least about 1 hour, and lysed. The cell lysate is resolved by SDS PAGE, then transferred to nitrocellulose and probed with antibodies specific for γ-catenin.

In a further example, the activity of a candidate compound can be measured in a *Xenopus* secondary axis bioassay (Leyns, L. et al. *Cell* (1997), 88(6), 747-756).

In another example, in vitro assays for DYRK1A biological activity may be used, e.g. regulation of microtubule-associated protein tau (MAPT/Tau) phosphorylation in neuronal cell line such as the human SH-SY5Y neuroblastoma cell line. Assays for DYRK1A-regulated level of phosphorylation can include monitoring levels of basal pSer396 Tau, which can be measured, for example, by serial dilutions of a candidate inhibitor composition using a ten micromolar top concentration and detected by ELISA or Western Blotting. An exemplary assay for DYRK-1A-regulated phosphorylation uses the SH-SY5Y cells cultured in a 96 well plate format for a period of time sufficient to stabilize microtubules and Tau phosphorylation, usually at least 2 days, then treated with a ⅓ serial dilution of compounds overnight and lysed. The cell lysate is resolved by SDS PAGE, then transferred to nitrocellulose and probed with an antibody specific for pSer396 Tau. The chemiluminescence signal for HRP-linked antibodies used in western blotting is detected using a Carestream Image Station and blot densitometry for pSer396 and beta-actin are analyzed using ImageJ (NIH).

In a further example, the activity of a candidate compound can be measured by ELISA by adding the lysate mentioned above onto total Tau-coated plates and detected with a specific pSer396 antibody. Colorimetric detection of ELISA signal is performed by Cytation3 plate reader (Biotek).

To further illustrate this disclosure, the following examples are included. The examples should not, of course, be construed as specifically limiting the disclosure. Variations of these examples within the scope of the claims are within the purview of one skilled in the art and are considered to fall within the scope of the disclosure as described, and claimed herein. The reader will recognize that the skilled artisan, armed with the present disclosure, and skill in the art is able to prepare and use the disclosure without exhaustive examples.

EXAMPLES

Compound Preparation

The starting materials used in preparing the compounds of the disclosure are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* 7th Ed., John Wiley & Sons (2013), Carey and Sundberg, *Advanced Organic Chemistry* 5th Ed., Springer (2007), *Comprehensive Organic Transformations: A Guide to Functional Group Transformations,* 2nd Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in P. Wuts *Greene's Protective Groups in Organic Synthesis,* 5th Ed., John Wiley & Sons (2014), incorporated herein by reference in its entirety.

Trademarks used herein are examples only and reflect illustrative materials used at the time of the disclosure. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the disclosure.

($^1$H) nuclear magnetic resonance spectra (NMR) were measured in the indicated solvents on a Bruker NMR spectrometer (Avance™ DRX300, 300 MHz for $^1$H or Avance™ DRX500, 500 MHz for $^1$H) or Varian NMR spectrometer (Mercury 400BB, 400 MHz for $^1$H). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; ddd, doublet of doublets of doublets; d/ABq, doublet of AB quartet; dt, doublet of triplets; td, triplet of doublets; dq, doublet of quartets; m, multiplet.

The following abbreviations have the indicated meanings:
brine=saturated aqueous sodium chloride
$CDCl_3$=deuterated chloroform
DCE=dichloroethane
DCM=dichloromethane
DIPEA=N,N-diisopropylethylamine
DMA=dimethylacetamide
DMAP=4-dimethylaminopyridine DMF=N,N-dimethylformamide
DMSO-$d_6$=deuterated dimethylsulfoxide
ESIMS=electron spray mass spectrometry
EtOAc=ethyl acetate
HATU=1-[Bis(dimethylamino)methylene]-1H-1,2,3-triazolo [4,5-b]pyridinium 3-oxid hexafluorophosphate
HCl=hydrochloric acid
HOAc=acetic acid
ISCO=Teledyne ISCO, Inc brand CombiFlash® Rf 200
KOAc=potassium acetate
LC/MS=Liquid chromatography-mass spectrometry
MCPBA=meta-chloroperoxybenzoic acid
MeCN=acetonitrile
MeOH=methanol
$MgSO_4$=magnesium sulfate
MW=microwave irradiation
$NaBH_3CN$=sodium cyanoborohydride
$NaHCO_3$=sodium bicarbonate
$Na(OAc)_3BH$=Sodium triacetoxyborohydride
NMR=nuclear magnetic resonance
ON=overnight
Pd(dppf)$Cl_2$=1,1'-bis(diphenylphosphino)ferrocene-palladium(II)dichloride
Pd(PPh$_3$)$_4$=tetrakis(triphenylphosphine)palladium(0)
r.t.=room temperature SPhos Pd G4=Methanesulfonato(2-dicyclohexylphosphino-3,6-dimethoxy-2',4',6'-tri-i-propyl-1,1'-biphenyl)(2'-methylamino-1,1'-biphenyl-2-yl)palladium(II)
TBAF=tetra-n-butylammonium fluoride,
TEA=triethylamine
TFA=trifluoroacetic acid
THF=tetrahydrofuran
TLC=thin layer chromatography The following example schemes are provided for the guidance of the reader, and collectively represent an example method for making the compounds provided herein. Furthermore, other methods for preparing compounds of the disclosure will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Unless otherwise indicated, all variables are as defined above.

General Procedures

Compounds of Formula I of the present disclosure can be prepared as depicted in Scheme 1.

Scheme 1

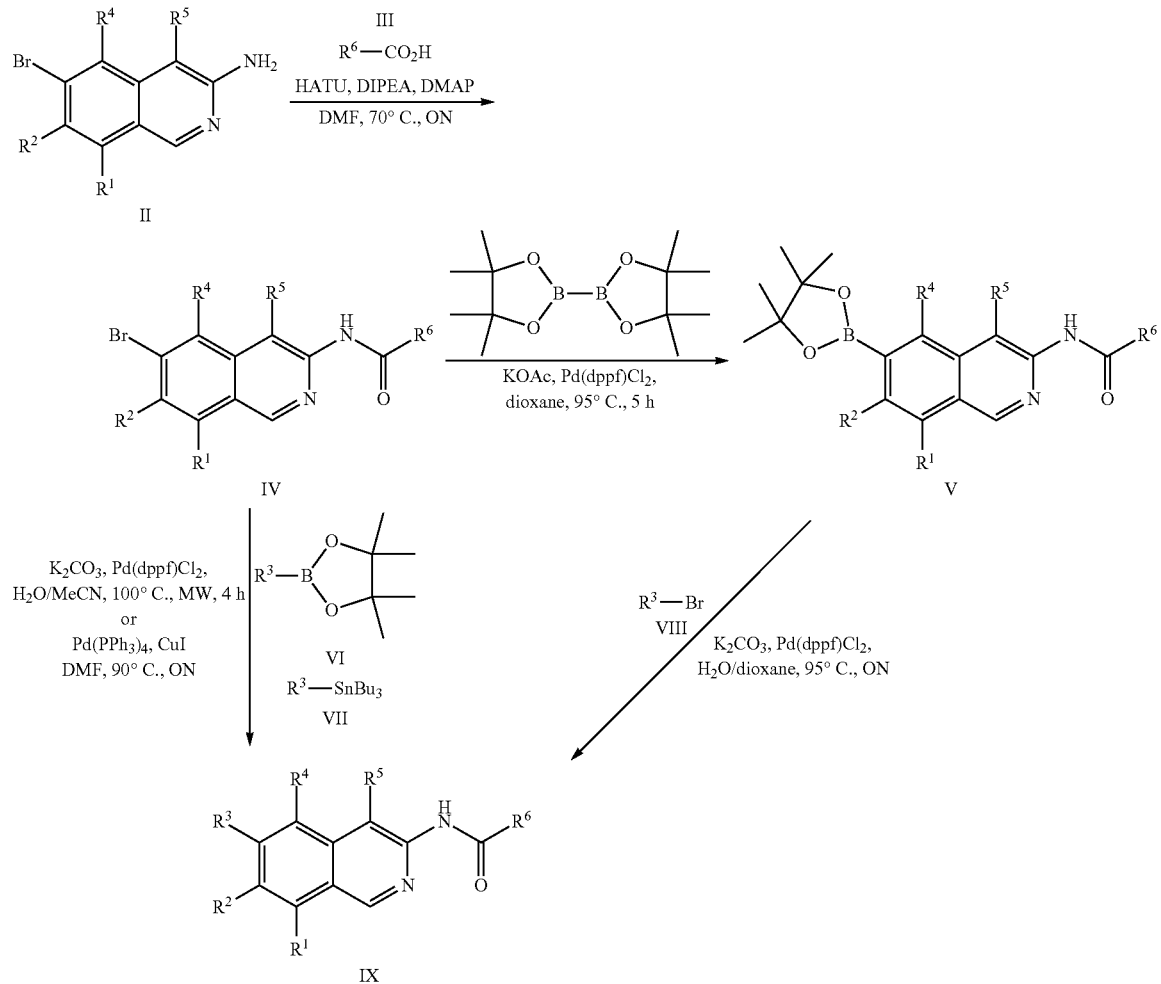

Scheme 1 describes a method for preparation of isoquinoline-3-carboxamide derivatives (IX) by first coupling the amine with a variety of acids (III) to produce amide IV. The bromo derivative IV is then reacted with bis(pinacolato)diboron to give the pinacol ester (V). Suzuki coupling with a variety of 5-membered heteroaryl bromides (VIII) yields the desired $R^3$ substituted isoquinoline IX. Alternatively, the bromo derivative IV is Suzuki coupled with a variety of 5-membered heteroaryl pinacol esters (VI) or coupled to a variety of 5-membered heteroaryl stannanes (VII) to produce the final $R^3$ substituted isoquinoline IX.

In some embodiments, compounds of Formula I of the present disclosure can be prepared as depicted in Scheme 2.

Scheme 2

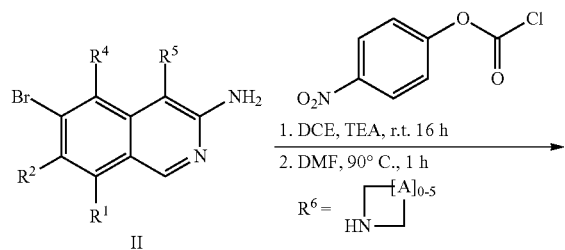

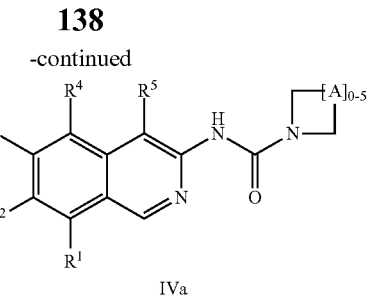

A = C, N, O, or S,
wherein C or N may be substituted as defined for $R^6$ herein Scheme 2 describes a method for preparation of isoquinoline-3-carboxamide intermediate (IVa) by first coupling the amine 4-nitrophenyl carbonochloridate followed by coupling with a variety of $R^6$NH heterocyclyls. Intermediate IVa could then be used in place of IV in Scheme 1 or 3.

In some embodiments, compounds of Formula I of the present disclosure can be prepared as depicted in Scheme 3.

Scheme 3

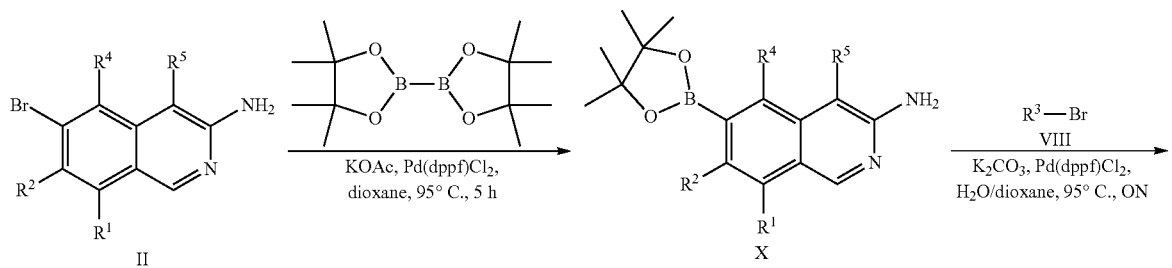

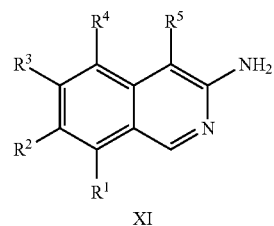

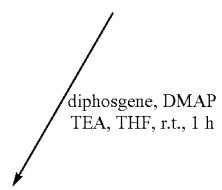

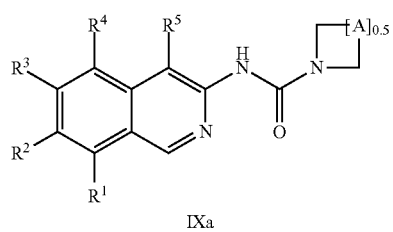

IXa

A = C, N, O, or S,
wherein C or N may be substituted
as defined for R⁶ herein

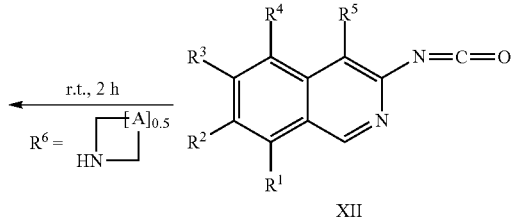

XII

Scheme 3 describes a method for preparation of isoquinoline-3-carboxamide derivatives (IXa) by first reacting with bis(pinacolato)diboron to give the pinacol ester (X). Suzuki coupling with a variety of 5-membered heteroaryl bromides (VIII) yields the desired $R^3$ substituted isoquinoline amine XI. The amine (XI) is then reacted with diphosgene to form the isocyanate (XII) which is then reacted with a variety of a variety of $R^6NH$ heterocyclyls produce the final $R^3$ and $R^6$ substituted isoquinoline IXa.

In other embodiments, compounds of Formula I of the present disclosure can be prepared as depicted in Scheme 4.

Scheme 4

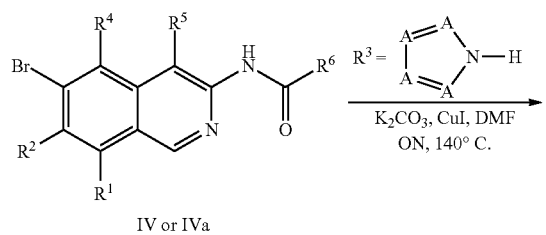

IV or IVa

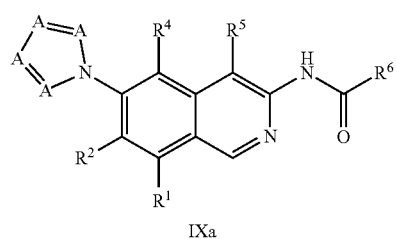

IXa

A = N or C, wherein N or C may be substituted as defined for $R^3$ herein

Scheme 4 describes a method for preparation of isoquinoline-3-carboxamide derivatives (IXa) starting with bromo intermediate IV or IVa and couple with the nitrogen of a variety of $R^3NH$ heteroaryls to produce the final $R^3$ substituted isoquinoline IXa.

Illustrative Compound Examples

Preparation of intermediate 6-bromoisoquinolin-1-d-3-amine (XIV) is depicted below in Scheme 5.

Scheme 5

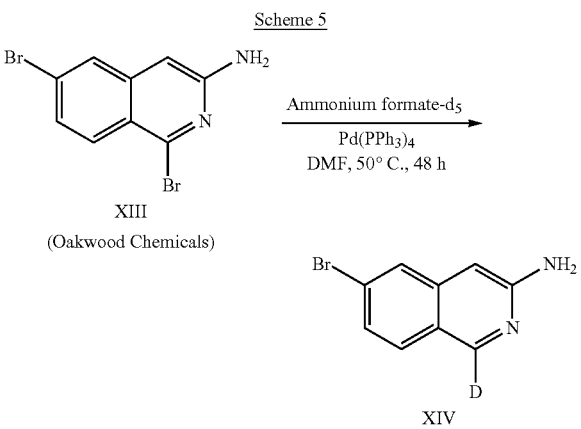

XIII
(Oakwood Chemicals)

XIV

Step 1

To a mixture of 1,6-dibromoisoquinolin-3-amine (XIII) (0.5 g, 1.66 mmol), ammonium formate-d₅ (0.56 g, 8.28 mmol) and Pd(PPh₃)₄ (191.3 mg, 0.170 mmol) in DMF (5 mL) was heated to 50° C. for 48 h. The solvents were concentrated and the residue was suspended in chloroform. The solid was collected by filtration and washed with water and EtOAc. The solid were dried under high vacuo to obtain 6-bromo-1-deuterio-isoquinolin-3-amine (XIV) (115 mg, 0.513 mmol, 31.0% yield) as a pale yellow solid. ¹H NMR (500 MHz, DMSO-d₆) δ ppm 6.11 (2H, s), 6.55 (1H, s), 7.22 (1H, dd, J=8.78, 1.92 Hz), 7.73 (1H, d, J=8.51 Hz), 7.79 (1H, d, J=1.92 Hz); ESIMS found for C₉H₆DBrN₂ m/z 224.0 (⁷⁹BrM+H).

Preparation of intermediate 6-bromo-4-chloroisoquinolin-3-amine (XVI) is depicted below in Scheme 6.

Scheme 6

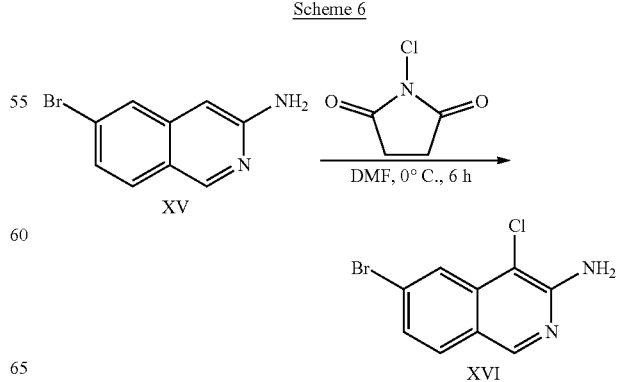

Step 1

To a stirred suspension of 6-bromoisoquinolin-3-amine (XV) (1.0 g, 4.48 mmol) in DMF (15 mL) at 0° C. was added 1-chloropyrrolidine-2,5-dione (598.6 mg, 4.48 mmol) portionwise. The mixture was stirred at 0° C. for 6 h. The reaction mixture was added to water (150 mL), stirred for 1 h and the resulting solids were collected by filtration and air dried overnight to obtain 6-bromo-4-chloro-isoquinolin-3-amine (XVI) (922 mg, 3.58 mmol, 79.9% yield) as a beige solid which was used for next step without purification. $^1$H NMR (499 MHz, DMSO-$d_6$) δ ppm 6.55 (2H, s), 7.40 (1H, dd, J=8.64, 1.78 Hz), 7.88 (1H, d, J=8.51 Hz), 7.90 (1H, d, J=1.10 Hz), 8.86 (1H, s); ESIMS found for $C_9H_6BrClN_2$ m/z 256.9 ($^{79}$BrM+H).

Preparation of intermediate 6-bromo-4-methylisoquinolin-3-amine (XVIII) is depicted below in Scheme 7.

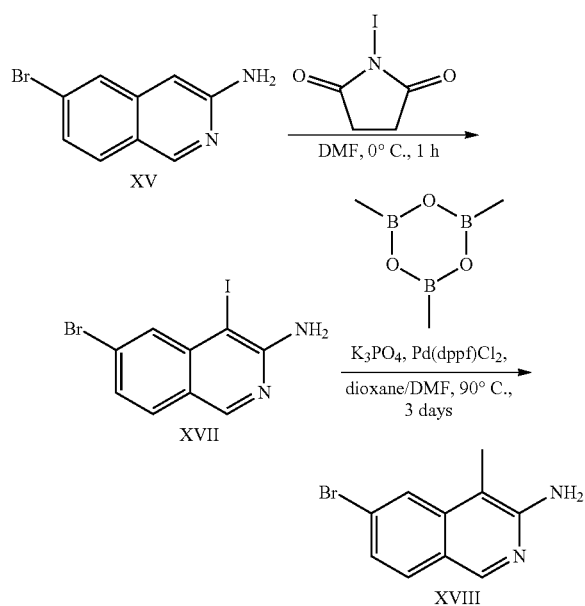

Step 1

To a stirred suspension of 6-bromoisoquinolin-3-amine (XV) (2.0 g, 8.97 mmol) in DMF (25.1 mL) at 0° C. was added 1-iodopyrrolidine-2,5-dione (2.02 g, 8.97 mmol) portionwise, The mixture was stirred at 0° C. for 1 hr. LC-MS of the mixture showed completion of the reaction and the desired product. The solvent was removed under vacuum, the residue was purified by C18 Silica gel (240 g) [0-→100% H$_2$O/MeCN (0.1% Formic acid)] to produce 6-bromo-4-iodo-isoquinolin-3-amine (XVII) (1.95 g, 5.58 mmol, 62.2% yield) as a brown solid. $^1$H NMR (499 MHz, DMSO-$d_6$) δ ppm 6.41 (2H, br s), 7.40 (1H, dd, J=8.64, 1.78 Hz), 7.76-7.81 (1H, m), 7.82 (1H, d, J=8.51 Hz), 8.81 (1H, s); ESIMS found for $C_9H_6BrIN_2$ m/z 348.9 ($^{79}$BrM+H).

Step 2

A stirred solution of 6-bromo-4-iodo-isoquinolin-3-amine (XVII) (1.0 g, 2.87 mmol), 2,4,6-trimethyl-1,3,5,2,4,6-trioxatriborinane (0.72 g, 2.87 mmol), Pd(dppf)Cl$_2$ (0.23 g, 0.29 mmol), and K$_3$PO$_4$ (5.73 mL, 5.73 mmol) in 1,4-dioxane (10 mL) was heated to 90° C. for 3 days. The solvent was removed under high vacuum and the residue was purified by C18 silica gel (240 g) [0-20% H$_2$O/MeCN (0.1% Formic acid)] to produce 6-bromo-4-methyl-isoquinolin-3-amine (XVIII) (74 mg, 0.312 mmol, 10.9% yield) as an off-white solid. $^1$H NMR (499 MHz, DMSO-$d_6$) δ ppm 2.23 (3H, br s), 5.91 (2H, br s), 7.27 (1H, br d, J=2.20 Hz), 7.71-7.82 (1H, m), 7.92 (1H, br s), 8.72 (1H, br s); ESIMS found for $C_{10}H_9BrN_2$ m/z 239.0 ($^{81}$BrM+H).

Preparation of intermediate 6-bromo-7-fluoroisoquinolin-3-amine (XXI) is depicted below in Scheme 8.

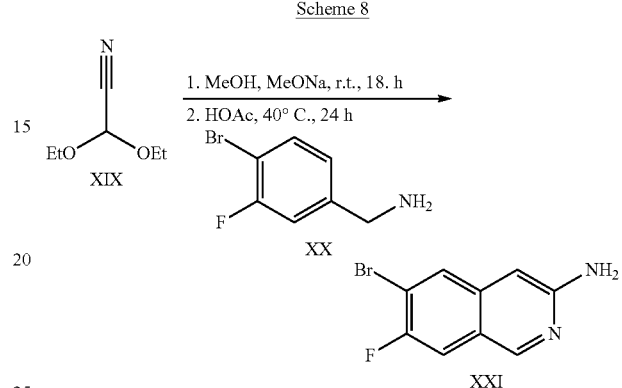

Step 1

To a vial was added 2,2-diethoxyacetonitrile (XIX) (1.0 g, 7.74 mmol) dissolved MeOH (7.74 mL) followed by addition of MeONa/MeOH (0.18 mL, 0.77 mmol) dropwise. The reaction was stirred at room temperature for 20 h. HOAc (44.3 µL, 0.77 mmol) was added until pH=7-8 (using pH strips). (4-Bromo-3-fluoro-phenyl)methanamine hydrochloride (XX) (1.86 g, 7.74 mmol) was added and stirred at 40° C. for 4 h. The solvent was removed under vacuum. Sulfuric acid (12.6 mL, 232.3 mmol) was added and stirred at 40° C. for 16 h. NH$_4$OH (30.8 mL, 240.0 mmol) was added dropwise at 0° C. The solvent was removed under vacuum and the residue was purified by C18 silica gel (240 g) [0-50% H$_2$O/MeCN (0.1% Formic acid)] to produce 6-bromo-7-fluoro-isoquinolin-3-amine (XXI) (1.33 g, 5.50 mmol, 71.1% yield) as an off-white solid. $^1$H NMR (499 MHz, DMSO-$d_6$) δ ppm 6.07 (2H, s), 6.61 (1H, s), 7.76 (1H, d, J=9.33 Hz), 8.01 (1H, d, J=6.86 Hz), 8.80 (1H, s); ESIMS found for $C_9H_6BrFN_2$ m/z 242.9 ($^{81}$BrM+H).

Preparation of intermediates 6-bromo-7-chloroisoquinolin-3-amine (XXIII) and 6-bromo-5-chloroisoquinolin-3-amine (XXIV) is depicted below in Scheme 9.

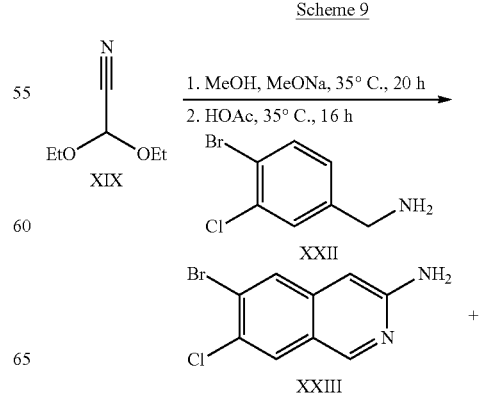

-continued

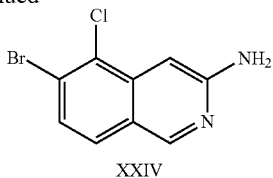

XXIV

Step 1

To a stirred solution of 2,2-diethoxyacetonitrile (XIX) (0.59 g, 4.57 mmol) in a vial containing MeOH (4.57 mL) was added MeONa (0.1 mL, 0.46 mmol) dropwise. The reaction was stirred at 35° C. for 20 h. HOAc was added (26.1 µL, 0.46 mmol) (checked that the pH is 7-8 using pH strips) followed by (4-bromo-3-chloro-phenyl)methanamine (XXII) (1.01 g, 4.57 mmol). The mixture was stirred at 35° C. for 40 h. The solvent was removed under vacuum. Sulfuric Acid (7.43 mL, 137.0 mmol) was then added and stirred at 35° C. for 16 h. NH$_4$OH (60.6 mL, 141.6 mmol) was added at 0° C. The reaction was filtered through Celite and purified by C18 silica gel (240 g) [0→30% H$_2$O/MeCN (0.1% Formic acid)] to produce a 1:1 mixture (by NMR) of 6-bromo-7-chloro-isoquinolin-3-amine (XXIII) and 6-bromo-5-chloroisoquinolin-3-amine (XXIV) (633.7 mg, 2.46 mmol, 53.9% yield). $^1$H NMR (499 MHz, DMSO-d$_6$) δ ppm 6.23 (2H, s), 6.46 (2H, s), 6.57 (1H, s), 6.83 (1H, s), 7.40 (1H, d, J=8.51 Hz), 7.74 (1H, d, J=8.51 Hz), 8.05 (1H, s), 8.09 (1H, s), 8.81 (1H, s), 8.88 (1H, s); ESIMS found for C$_9$H$_6$BrClN$_2$ m/z 256.9 ($^{79}$BrM+H).

Preparation of intermediates 6-bromo-7-methylisoquinolin-3-amine (XXVI) and 6-bromo-5-methylisoquinolin-3-amine (XXVII) is depicted below in Scheme 10.

Scheme 10

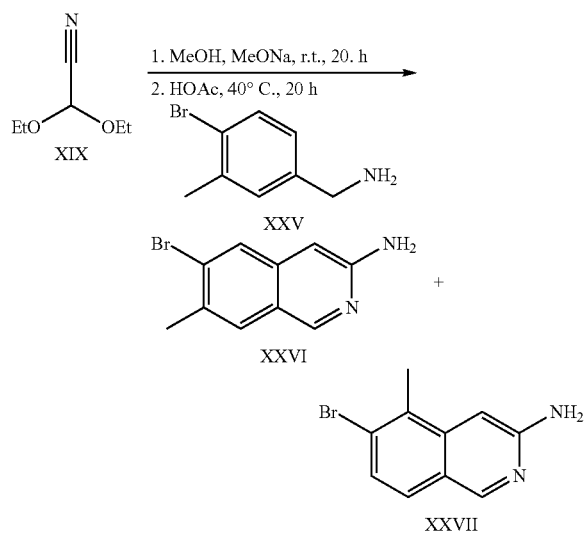

Step 1

To a stirred solution of 2,2-diethoxyacetonitrile (XIX) (0.33 g, 2.52 mmol) in a vial containing MeOH (2.52 mL) was added MeONa (0.23 mL, 0.25 mmol) dropwise. The reaction was stirred at 22° C. for 20 h. HOAc was added (14.4 µL, 0.25 mmol) (checked that the pH is 7-8 using pH strips) followed by (4-bromo-3-methyl-phenyl)methanamine (XXV) (0.5 g, 2.52 mmol). The mixture was stirred at 40° C. for 40 h. The solvent was removed under vacuum.

Sulfuric Acid (4.09 mL, 75.49 mmol) was then added and stirred at 40° C. for 16 h. NH$_4$OH (33.4 mL, 78 mmol) was added at 0° C. The reaction was filtered through Celite and purified by C18 silica gel (240 g) [0→30% H$_2$O/MeCN (0.1% Formic acid)] to produce a 1:1 mixture (by NMR) of 6-bromo-7-methylisoquinolin-3-amine (XXVI) and 6-bromo-5-methylisoquinolin-3-amine (XXVII) (378 mg, 1.59 mmol, 63.4% yield). $^1$H NMR (499 MHz, DMSO-d$_6$) δ ppm 2.40 (3H, s), 2.52 (3H, s), 5.96 (2H, s), 6.12 (1H, s), 6.54 (1H, s), 6.71 (1H, s), 7.27 (1H, d, J=8.78 Hz), 7.58 (1H, d, J=8.78 Hz), 7.73 (1H, s), 7.86 (1H, s), 8.74 (1H, s), 8.79 (1H, s); ESIMS found for C$_{10}$H$_9$BrN$_2$ m/z 237.0 ($^{79}$BrM+H).

Preparation of intermediate trans-4-((tert-butoxycarbonyl)(methyl)amino) cyclohexane-1-carboxylic acid (XXX) is depicted below in Scheme 11.

Scheme 11

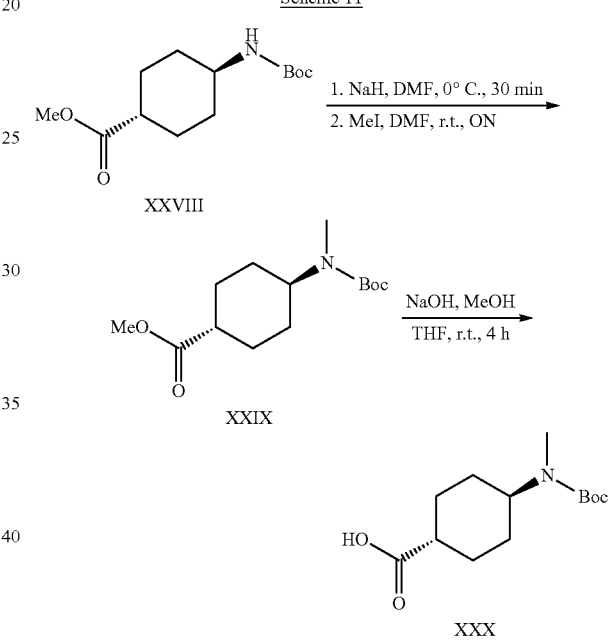

Step 1

To a solution of methyl trans-4-((tert-butoxycarbonyl)amino)cyclohexane-1-carboxylate (XXVIII) (1.3 g, 5 mmol) in DMF (15 mL) and cooled to 0° C. was added sodium hydride (60% in oil, 240 mg, 6 mmol) over 30 minutes. The mixture is stirred at room temperature for 1 h, then cooled to 0° C. and treated with iodomethane (0.38 mL, 6 mmol). After stirring overnight at room temperature, the mixture is poured into a saturated aqueous ammonium chloride and extracted with EtOAc. The combined organic phase is washed with water and brine, dried over anhydrous Na$_2$SO$_4$ and concentrated under reduced pressure. The obtained residue is purified by column chromatography on silica gel (eluent: n-hexane-EtOAc 10:1) to obtain methyl trans-4-((tert-butoxycarbonyl)(methyl)amino)cyclohexane-1-carboxylate (XXIX) (1.3 g, 4.79 mmol, 94.8% yield).

Step 2

To a stirred solution of methyl trans-4-((tert-butoxycarbonyl)(methyl)amino) cyclohexane-1-carboxylate (XXIX) (130 mg, 4.79 mmol) in a mixture of MeOH (10 mL) and THF (10 mL) was added 2 N aqueous NaOH (4.79 mL, 9.58 mmol) and the mixture was stirred for 4 h. The solvent was concentrated, the residue taken in water and acidified with 1N HCl and extracted with EtOAc. The organics were washed with 2× water then 1× brine. The organics were then separated and dried (MgSO$_4$) before concentration to dryness to obtain trans-4-((tert-butoxycarbonyl)(methyl)amino)cyclohexane-1-carboxylic acid (XXX) as a thick gum (1.198 g, 4.65 mmol, 97.2% yield) which was used for next step without purification.

Preparation of intermediate 2-(4-(tert-butoxycarbonyl)piperazin-1-yl) isonicotinic acid (XXXIV) is depicted below in Scheme 12.

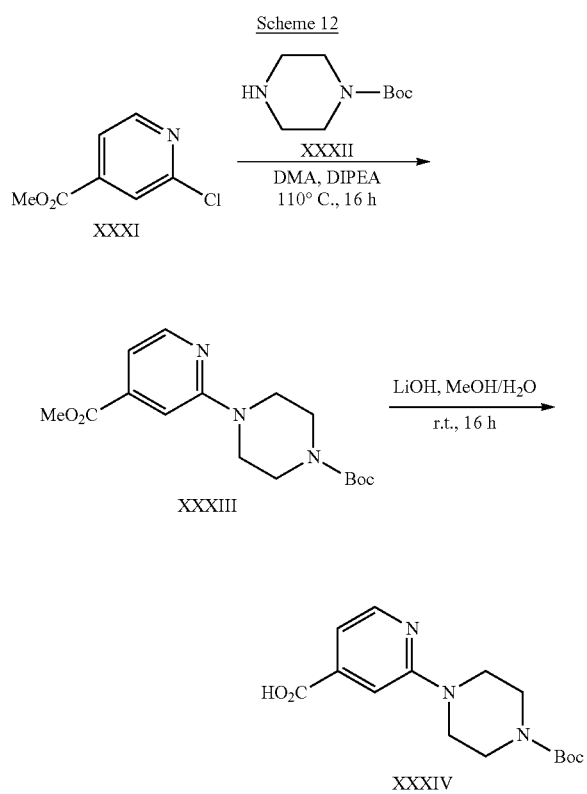

Step 1

To a solution of ethyl 2-chloroisonicotinate (XXXI) (10 g, 53.88 mmol) was added tert-butyl piperazine-1-carboxylate (XXXII) (0.32 mL, 2.89 mmol) and DIPEA (18.8 mL, 107.75 mmol). The reaction was stirred at 110° C. for 16 h. The mixture was poured into water, extracted with EtOAc, and dried over Na$_2$SO$_4$. The solvent was removed under high vacuum and the residue was purified on a silica gel column (120 g) (0-100% hexane/EtOAc) to give tert-butyl 4-(4-(ethoxycarbonyl)pyridin-2-yl)piperazine-1-carboxylate (XXXIII) as a brown oil (10.84 g, 32.32 mmol, 60.0% yield). ESIMS found for $C_{17}H_{25}N_3O_4$ m/z 336.15 (M+H).

Step 2

To a solution of tert-butyl 4-(4-(ethoxycarbonyl)pyridin-2-yl)piperazine-1-carboxylate (XXXIII) (10.7 g, 31.9 mmol) in MeOH (130 mL) and water (26 mL) was added 4 M aqueous lithium hydroxide (7.98 mL, 31.9 mmol). The reaction was stirred at room temperature for 16 h. The reaction was poured into water and neutralized with concentrated hydrogen chloride (31.9 mL, 31.9 mmol) and extracted with EtOAc, The organic layer was dried over Na$_2$SO$_4$ and evaporated under high vacuum to produce 2-(4-(tert-butoxycarbonyl)piperazin-1-yl)isonicotinic acid (XXXIV) as a white solid (8.79 g, 28.6 mmol, 89.7% yield) which was used without further purification. ESIMS found for $C_{15}H_{21}N_3O_4$ m/z 308.15 (M+H).

Example 1

Preparation of trans-N-(8-fluoro-6-(2-methyloxazol-5-yl)isoquinolin-3-yl)-4-morpholinocyclohexane-1-carboxamide (19) is depicted below in Scheme 13.

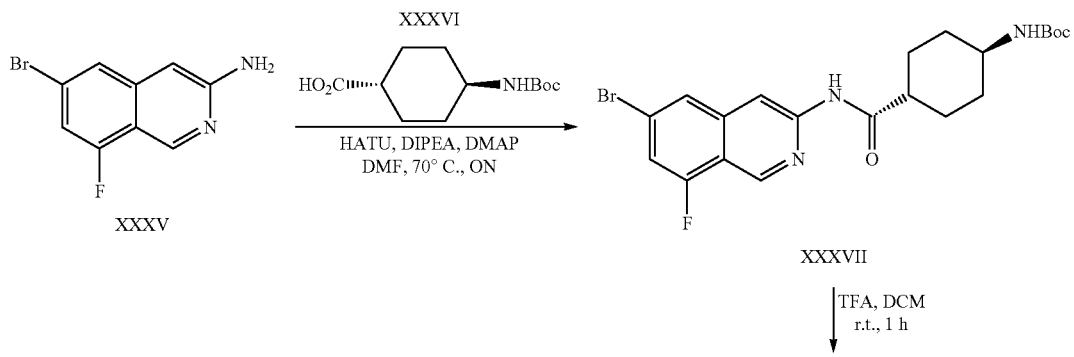

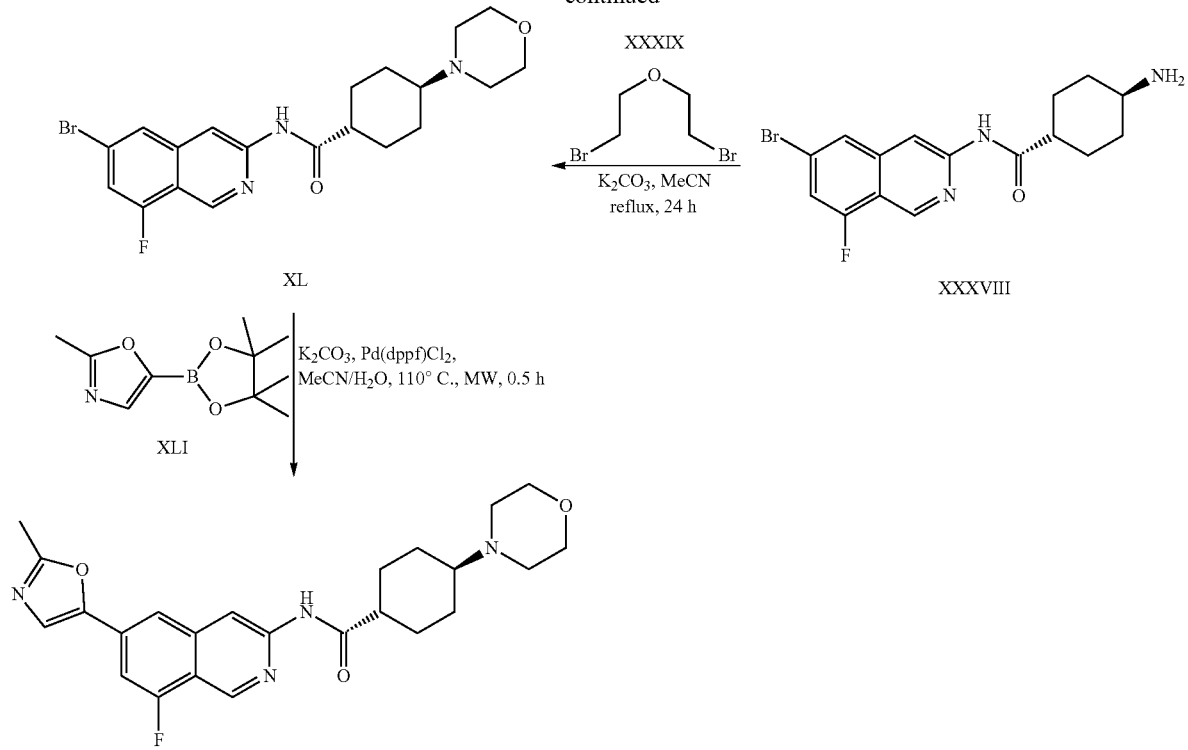

Step 1

To a stirred solution of 6-bromo-8-fluoroisoquinolin-3-amine (XXXV) (AbovChem-AC614182) (1.0 g, 4.15 mmol), DIPEA (1.81 mL, 10.37 mmol), HATU (1.97 g, 5.19 mmol) and DMAP (50.7 mg, 0.41 mmol) in DMF (16 mL) was added trans-4-((tert-butoxycarbonyl)(methyl)amino) cyclohexane-1-carboxylic acid (XXXVI) (1.26 g, 5.19 mmol). The mixture was heated to 70° C. overnight. An additional 0.5 equiv. of HATU was added and the mixture was stirred for another 5 h at 70° C. (repeated twice). The reaction mixture was poured into a saturated aqueous NaHCO$_3$ solution (~200 mL) and stirred for 20 min. The resulting solids were collected by filtration, washed with water and dried under high vacuo to obtain tert-butyl trans-4-((6-bromo-8-fluoroisoquinolin-3-yl)carbamoyl)cyclohexyl)carbamate (XXXVII) as a beige color solid (1.54 g, 3.30 mmol, 79.6% yield) which was used for next step without purification. ESIMS found for $C_{21}H_{25}BrFN_3O_3$ m/z 466.1 ($^{79}$BrM+H).

Step 2

To a stirred solution of tert-butyl trans-4-((6-bromo-8-fluoroisoquinolin-3-yl) carbamoyl)cyclohexyl)carbamate (XXXVII) (1.54 g, 3.3 mmol) in DCM (10 mL) was added TFA (6. mL, 77.9 mmol) and the mixture was stirred for 1 h. The reaction mixture was concentrated, treated with 7 N NH$_3$/MeOH, absorbed on silica gel and was purified by column chromatography (20→100% CHCl$_3$/10%7N NH$_3$/MeOH in CHCl$_3$). The pure fractions were combined and concentrated. The residue was suspended in EtOAc, sonicated and filtered. The solid was dried under high vacuo to obtain trans-4-amino-N-(6-bromo-8-fluoroisoquinolin-3-yl) cyclohexane-1-carboxamide (XXXVIII) as an off-white color solid (644 mg, 1.76 mmol, 53.2% yield). ESIMS found for $C_{16}H_{17}BrFN_3O$ m/z 366.1 ($^{79}$BrM+H).

Step 3

A stirred suspension of trans-4-amino-N-(6-bromo-8-fluoroisoquinolin-3-yl) cyclohexane-1-carboxamide (XXXVIII) (380 mg, 1.04 mmol), 1-bromo-2-(2-bromoethoxy)ethane (XXXIX) (0.16 mL, 1.25 mmol) and K$_2$CO$_3$ (430.2 mg, 3.11 mmol) in MeCN (5 mL) was heated to reflux for 24 h. The reaction mixture was concentrated and the residue was taken into DCM, washed with water and brine. The organics were then separated and dried (MgSO$_4$) before concentration to dryness. The crude was purified by column chromatography (0→30% CHCl$_3$/10% 7N NH$_3$MeOH in CHCl$_3$). The pure fractions were combined, concentrated and dried to obtain the desired product trans-N-(6-bromo-8-fluoroisoquinolin-3-yl)-4-morpholinocyclohexane-1-carboxamide (XL) as an off-white solid (205 mg, 0.47 mmol, 45.3% yield). ESIMS found for $C_{20}H_{23}BrFN_3O_2$ m/z 436.1 ($^{79}$BrM+H).

Step 4

To a solution of trans-N-(6-bromo-8-fluoroisoquinolin-3-yl)-4-morpholinocyclohexane-1-carboxamide (XL) (100 mg, 0.23 mmol), 2-methyl-5-(4,4,5,5-tetramethyl-1,3,2-dioxaborolan-2-yl)oxazole (XLI) (60 mg, 0.29 mmol), K$_2$CO$_3$ (0.29 mL, 0.57 mmol) in MeCN (1 mL) was added Pd(dppf)Cl$_2$ (18.7 mg, 0.02 mmol). N$_2$ gas was bubbled into the mixture for 10 min and then heated to 110° C. for 30 min using microwave (MW) irradiation. The organic layer was carefully separated, absorbed on silica gel and purified by column chromatography (0-60% CHCl$_3$/10% 7N NH₃MeOH in CHCl₃). The pure fractions were combined, concentrated and the product was suspended in EtOAc, sonicated and the solids were collected by filtration, washed with diethyl ether and dried under high vacuo to obtain trans-N-(8-fluoro-6-(2-methyloxazol-5-yl)isoquinolin-3-yl)-4-morpholinocyclohexane-1-carboxamide 19 as a white solid (30.0 mg, 0.068 mmol, 29.9% yield). ¹H NMR (499 MHz, DMSO-d₆) δ ppm 1.15-1.28 (2H, m), 1.42-1.54 (2H, m), 1.92 (4H, br t, J=12.76 Hz), 2.15-2.28 (1H, m), 2.46-2.49 (4H, m), 2.53 (3H, s), 3.52-3.60 (4H, m), 7.65 (1H, dd, J=11.53, 1.10 Hz), 7.84 (1H, s), 7.95 (1H, s), 8.56 (1H, s), 9.22 (1H, s), 10.66 (1H, s) ESIMS found for C₂₄H₂₇FN₄O₃ m/z 439.2 (M+1).

Example 2

Preparation of trans-4-(dimethylamino)-N-(8-fluoro-6-(2-methyloxazol-5-yl) isoquinolin-3-yl)cyclohexane-1-carboxamide (17) is depicted below in Scheme 14.

Scheme 14

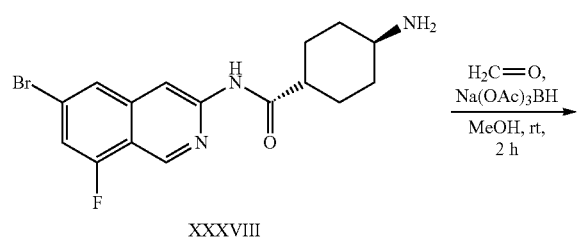

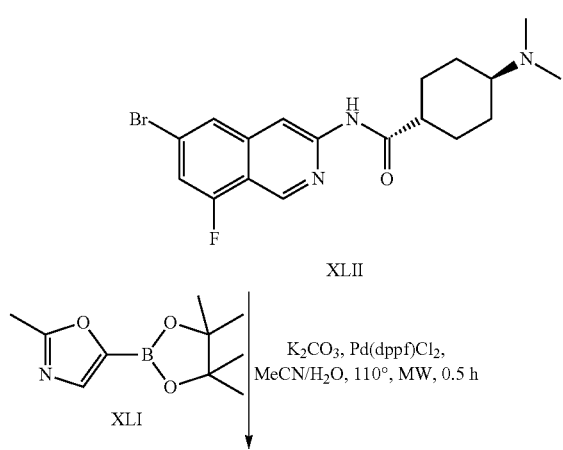

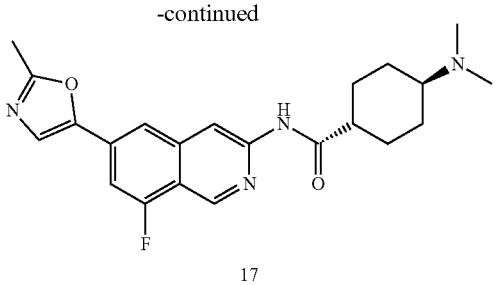

Step 1

To a solution of trans-4-amino-N-(6-bromo-8-fluoroisoquinolin-3-yl) cyclohexane-1-carboxamide (XXXVIII) (644 mg, 1.76 mmol) in MeOH (50 mL) was added formaldehyde (1.76 mL, 8.76 mmol). After 15 min, Na(OAc)₃BH (1.86 g, 8.76 mmol) was added and the mixture was stirred at room temperature 2 h. The solvents were removed in vacuo, the residue was partitioned between CHCl₃/1N aqueous NaOH. The organic layer was separated, washed with water and brine, dried over anhydrous Na₂SO₄ and the solvents were concentrated to obtain trans-N-(6-bromo-8-fluoro-3-isoquinolyl)-4-(dimethylamino)cyclohexanecarboxamide (XLII) as an off-white color solids (295 mg, 0.75 mmol, 42.5% yield) which was used for next step without purification. ESIMS found for C₁₈H₂₁BrFN₃O m/z 394.1 (⁷⁹BrM+H).

Step 2

To a solution of trans-N-(6-bromo-8-fluoro-3-isoquinolyl)-4-(dimethylamino) cyclohexanecarboxamide (XLII) (200 mg, 0.51 mmol), 2-methyl-5-(4,4,5,5-tetramethyl-1,3,2-dioxaborolan-2-yl)oxazole (XLI) (133 mg, 0.63 mmol), and K₂CO₃ (0.63 mL, 1.27 mmol) in MeCN (2.5 mL) was added Pd(dppf)Cl₂ (41.4 mg, 0.05 mmol). N₂ gas was bubbled into the mixture for 10 min and then heated to 110° C. for 30 min using microwave (MW) irradiation. The organic layer was carefully separated, absorbed on silica gel and purified by column chromatography (0→60% CHCl₃/10% 7N NH₃MeOH in CHCl₃). The pure fractions were combined, concentrated and the product was suspended in EtOAc, sonicated and the solids were collected by filtration, washed with diethyl ether and dried under high vacuo to obtain trans-4-(dimethylamino)-N-(8-fluoro-6-(2-methyloxazol-5-yl)isoquinolin-3-yl) cyclohexane-1-carboxamide 17 as a beige solid (115.0 mg, 0.290 mmol, 57.2% yield). ¹H NMR (499 MHz, DMSO-d₆) δ ppm 1.13-1.25 (2H, m), 1.47 (2H, qd, J=12.76, 2.61 Hz), 1.83-1.90 (2H, m), 1.90-1.96 (2H, m), 2.09-2.22 (1H, m), 2.18 (6H, s), 2.45-2.49 (1H, m), 2.53 (3H, s), 7.64 (1H, dd, J=11.39, 0.96 Hz), 7.83 (1H, s), 7.95 (1H, s), 8.56 (1H, s), 9.22 (1H, s), 10.65 (1H, s); ESIMS found for C₂₂H₂₅FN₄O₂ m/z 397.2 (M+1).

Example 3

Preparation of N-(6-(1-methyl-1H-pyrazol-4-yl)isoquinolin-3-yl-4-d) piperidine-4-carboxamide (5) and 1-isobutyl-N-(6-(1-methyl-1H-pyrazol-4-yl)isoquinolin-3-yl-4-d)piperidine-4-carboxamide (6) is depicted below in Scheme 15.

Scheme 15

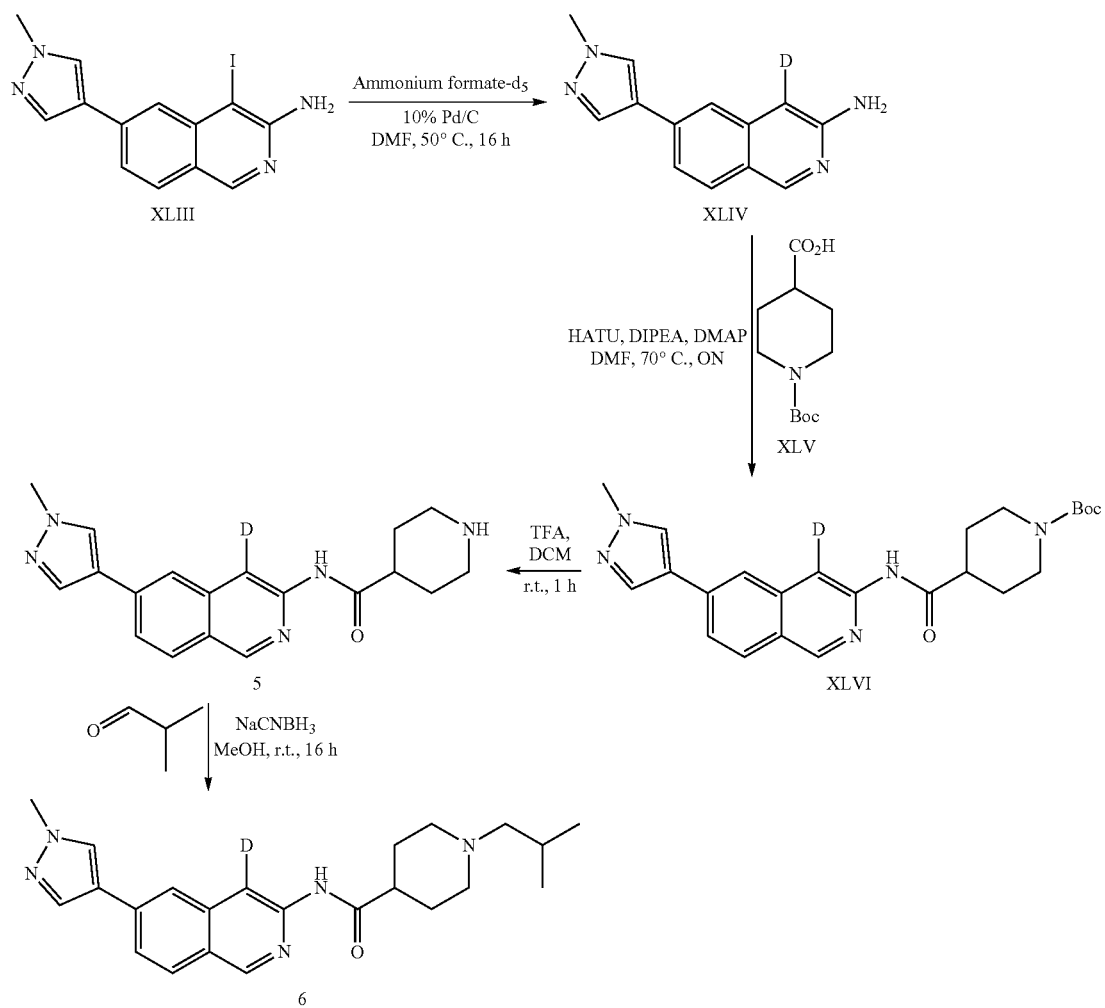

Step 1

A mixture of ammonium formate-d₅ (972.3 mg, 14.28 mmol), 10% Pd—C(50% w/w in water) (200 mg, 2.86 mmol) and 4-iodo-6-(1-methyl-1H-pyrazol-4-yl)isoquinolin-3-amine (XLIII)(synthesized using the procedure shown in scheme 13, step 4)(1.0 g, 2.86 mmol) in DMF (15 mL) was heated to 50° C. for 16 h. The reaction mixture was cooled, filtered through Celite, washed with water, then EtOH, and dried under high vacuo to obtain 6-(1-methyl-1H-pyrazol-4-yl)isoquinolin-4-d-3-amine (XLIV) as a pale green color solid (506 mg, 2.25 mmol, 78.7% yield). $^1$H NMR (499 MHz, DMSO-d₆) δ ppm 4.12 (3H, s), 5.94 (2H, s), 6.65 (1H, s), 7.61 (1H, dd, J=8.51, 1.65 Hz), 7.85 (1H, d, J=8.51 Hz), 7.96 (1H, s), 8.64 (1H, s), 8.79 (1H, s); ESIMS found for $C_{13}H_{11}DN_4$ m/z 226.1 (M+1).

Step 2

A mixture of 1-(tert-butoxycarbonyl)piperidine-4-carboxylic acid (XLV) (190.8 mg, 0.83 mmol), DIPEA (0.58 mL, 3.33 mmol) and HATU (316.5 mg, 0.83 mmol), 6-(1-methyl-1H-pyrazol-4-yl)isoquinolin-4-d-3-amine (XLIV) (150 mg, 0.67 mmol) and DMAP (8.13 mg, 0.07 mmol) in DMF (2 mL) was heated to 70° C. overnight. An additional 0.5 equiv. of HATU was added and the mixture was stirred for another 5 h at 70° C. (repeated twice). The reaction mixture was poured into a saturated aqueous NaHCO₃ solution (~100 mL), extracted with EtOAc, washed with water, brine and dried over anhydrous Na₂SO₄. The organic layer was concentrated and dried under high vacuo to obtain tert-butyl 4-((6-(1-methyl-1H-pyrazol-4-yl)isoquinolin-3-yl-4-d)carbamoyl)piperidine-1-carboxylate (XLVI) as a beige color solid (336 mg, 0.77 mmol, 115.6% yield) which was used for next step without purification. ESIMS found for $C_{24}H_{28}DN_5O_3$ m/z 437.2 (M+1).

Step 3

To a solution of tert-butyl 4-((6-(1-methyl-1H-pyrazol-4-yl)isoquinolin-3-yl-4-d)carbamoyl)piperidine-1-carboxylate (XLVI) (290.7 mg, 0.67 mmol) in DCM (2 mL) was added TFA (76 mg, 0.67 mmol) and the mixture was stirred at room temperature for 1 hr. The reaction mixture was concentrated, treated with 7 N NH₃/MeOH, absorbed on silica gel and purified by column chromatography (20→100% CHCl₃/ 10% 7N NH₃MeOH in CHCl₃). The pure fractions were combined, concentrated and dried under high vacuo to obtain N-(6-(1-methyl-1H-pyrazol-4-yl)isoquinolin-3-yl-4-d)piperidine-4-carboxamide 5 as an off-white color solid (130 mg, 0.39 mmol, 58.0% yield). $^1$H NMR (499 MHz, DMSO-d₆) δ ppm 1.53 (2H, qd, J=12.21, 3.98 Hz), 1.67-1.74 (2H, m), 2.13 (1H, br s), 2.43-2.49 (2H, m), 2.59-2.69

(1H, m), 2.94-3.01 (2H, m), 3.90 (3H, s), 7.74 (1H, dd, J=8.51, 1.65 Hz), 7.99 (1H, d, J=8.51 Hz), 8.03 (1H, s), 8.08 (1H, s), 8.35 (1H, s), 9.02 (1H, s), 10.40 (1H, s); ESIMS found for $C_{19}H_{20}DN_5O$ m/z 337.2 (M+1).

Step 4

To a solution of N-(6-(1-methyl-1H-pyrazol-4-yl)isoquinolin-3-yl-4-d)piperidine-4-carboxamide 5 (60 mg, 0.18 mmol) in MeOH (2 mL) was added 2-methylpropanal (0.02 mL, 0.27 mmol) and the mixture was stirred for 15 min. NaCNBH$_3$ (16.8 mg, 0.27 mmol) was then added and the mixture was stirred for 16 h. The solvent was concentrated and the residue taken into chloroform and washed with brine. The organic layer was then separated, dried (MgSO$_4$) and concentrated to dryness. The crude product was then purified by preparative TLC (50% CHCl$_3$/10% 7N NH$_3$MeOH in CHCl$_3$) to obtain 1-isobutyl-N-(6-(1-methyl-1H-pyrazol-4-yl)isoquinolin-3-yl-4-d)piperidine-4-carboxamide 6 as a white solid (35.0 mg, 0.089 mmol, 50.0% yield). $^1$H NMR (499 MHz, DMSO-d$_6$) δ ppm 0.86 (6H, d, J=6.59 Hz), 1.62-1.73 (2H, m), 1.73-1.81 (3H, m), 1.82-1.91 (2H, m), 2.02 (2H, d, J=7.41 Hz), 2.52-2.57 (1H, m), 2.86 (2H, br d, J=11.53 Hz), 3.90 (3H, s), 7.74 (1H, dd, J=8.64, 1.51 Hz), 8.00 (1H, d, J=8.51 Hz), 8.04 (1H, s), 8.08 (1H, s), 8.35 (1H, s), 9.02 (1H, s), 10.45 (1H, s); ESIMS found for $C_{23}H_{28}[^2H]N_5O$ m/z 393.25 (M+1).

Example 4

Preparation of trans-4-(hydroxymethyl)-N-(6-(2-methyloxazol-5-yl) isoquinolin-3-yl)cyclohexane-1-carboxamide (43) and trans-N-(6-(2-methyloxazol-5-yl) isoquinolin-3-yl)-4-(morpholinomethyl)cyclohexane-1-carboxamide (69) are depicted below in Scheme 16.

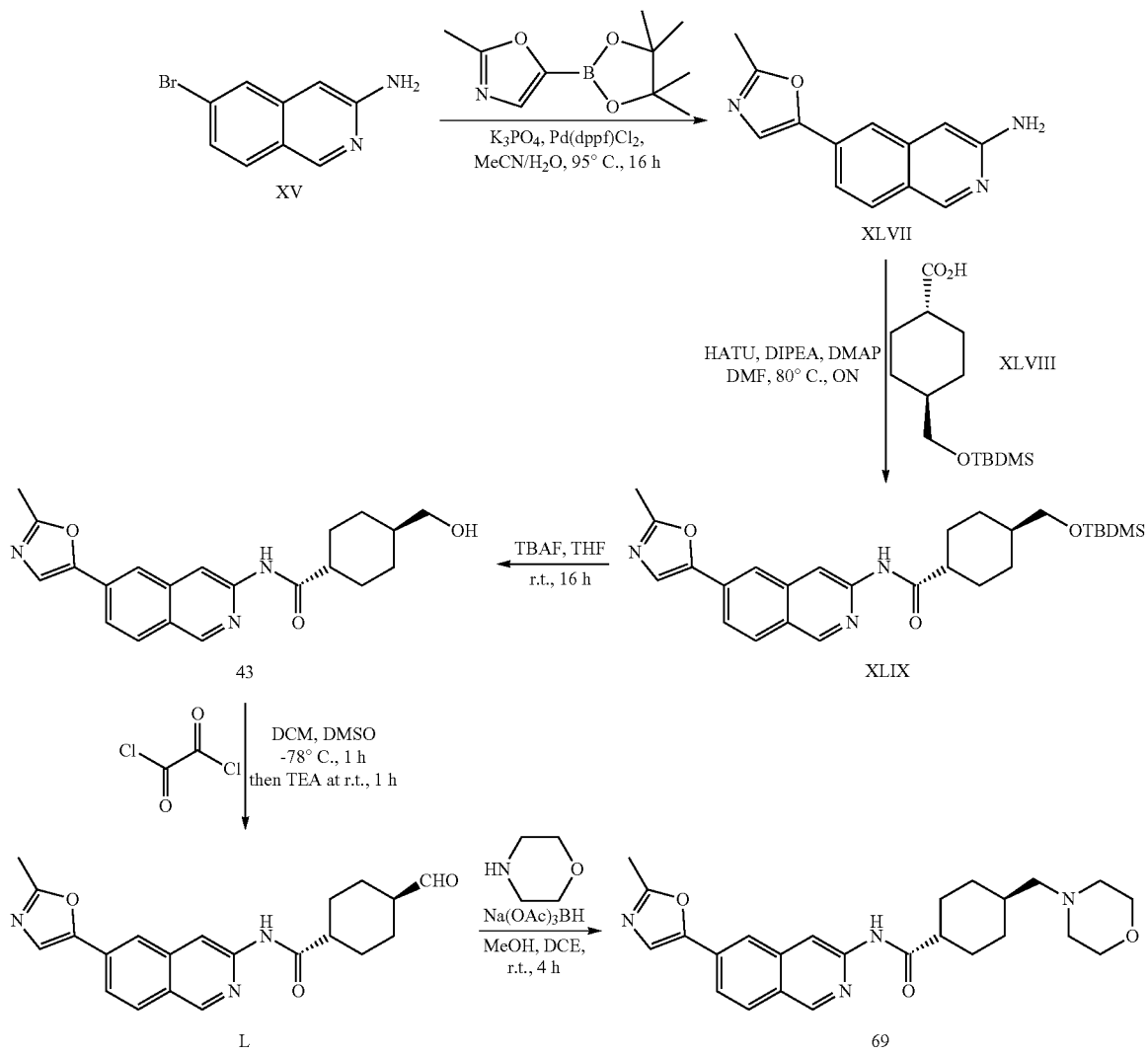

Step 1

To a mixture of 6-bromoisoquinolin-3-amine (XV) (1.0 g, 4.48 mmol) 2-methyl-5-(4,4,5,5-tetramethyl-1,3,2-dioxaborolan-2-yl)oxazole (XLI) (1.17 g, 5.6 mmol) Pd(dppf)Cl$_2$ (0.66 g, 0.81 mmol) in dioxane (20 mL) was added K$_3$PO$_4$ (56.0 mL, 112.07 mmol). N$_2$ gas was bubbled into the reaction mixture for 15 min and then heated to 90° C. for 16 h. The reaction mixture was poured into a mixture of DCM (30 mL) and water (30 mL) and adjusted the pH to 1-2 with concentrated HCl. The suspension was filtered and the aqueous layer was separated and adjusted the pH to 12 with adding 10 N aqueous NaOH solution. The resulting solid was collected by filtration, washed with water and dried under high vacuo at 60° C. for 24 h to obtain 6-(2-methyloxazol-5-yl)isoquinolin-3-amine (XLVII) as a yellow color solid (0.844 g, 3.75 mmol, 83.6% yield). $^1$H NMR (499 MHz, DMSO-$d_6$) δ ppm 2.53 (3H, s), 5.99 (2H, br s), 6.64 (1H, br s), 7.35-7.50 (1H, m), 7.67 (1H, br s), 7.75 (1H, br s), 7.80-7.91 (1H, m), 8.78 (1H, br s); ESIMS found for $C_{13}H_{11}N_3O$ m/z 226.1 (M+1).

Step 2

A mixture of 6-(2-methyloxazol-5-yl)isoquinolin-3-amine (XLVII) (0.5 g, 2.22 mmol), HATU (1.06 g, 2.77 mmol), trans-4-(((tert-butyldimethylsilyl)oxy)methyl)cyclohexane-1-carboxylic acid (XLVIII) (0.76 g, 2.77 mmol), DIPEA (1.16 mL, 6.66 mmol) and DMAP (0.05 g, 0.44 mmol) in DMF (6 mL) was heated to 80° C. overnight. The mixture was added to aqueous saturated NaHCO$_3$ and extracted with EtOAc. The organic layer was washed with water and then brine. The organic layer was separated and dried (MgSO$_4$) before concentration to dryness under high vacuum. The crude product was then purified by ISCO (10-70% EtOAc/hexanes) to obtain trans-4-(((tert-butyldimethylsilyl)oxy)methyl)-N-(6-(2-methyloxazol-5-yl)isoquinolin-3-yl)cyclohexane-1-carboxamide (XLIX) as a white color solid (970 mg, 2.02 mmol, 91.1% yield). ESIMS found for $C_{27}H_{37}N_3O_3Si$ m/z 480.25 (M+1).

Step 3

To a solution of trans-4-(((tert-butyldimethylsilyl)oxy)methyl)-N-(6-(2-methyloxazol-5-yl)isoquinolin-3-yl)cyclohexane-1-carboxamide (XLIX) (950 mg, 1.98 mmol) in THF (8 mL) was added 1 M solution of TBAF (2.97 mL, 2.97 mmol) and the mixture was stirred at 25° C. for 16 h. The reaction mixture was absorbed on silica gel and was purified by chromatography (0→5% CHCl$_3$/MeOH) to obtain trans-4-(hydroxymethyl)-N-(6-(2-methyloxazol-5-yl)isoquinolin-3-yl)cyclohexane-1-carboxamide 43 as a white solid (355.0 mg, 0.972 mmol, 49.1% yield). $^1$H NMR (500 MHz, DMSO-$d_6$) δ ppm 0.95 (2H, qd, J=12.76, 2.88 Hz), 1.31-1.40 (1H, m), 1.45 (2H, qd, J=12.67, 3.43 Hz), 1.80 (2H, br dd, J=13.17, 2.47 Hz), 1.88 (2H, br dd, J=13.04, 2.61 Hz), 2.42-2.48 (1H, m), 2.53 (3H, s), 3.24 (2H, t, J=5.76 Hz), 4.39 (1H, t, J=5.35 Hz), 7.79 (1H, s), 7.79-7.84 (1H, m), 8.09 (1H, s), 8.10 (1H, d, J=6.04 Hz), 8.50 (1H, s), 9.10 (1H, s), 10.49 (1H, s); ESIMS found for $C_{21}H_{23}N_3O_3$ m/z 366.2 (M+1).

Step 4

To a solution of DMSO (0.2 mL, 2.87 mmol) in DCM (3 mL) at −78° C. was added under Argon dropwise oxalyl chloride (0.13 mL, 1.44 mmol) in DCM (1 mL). After 15 min, trans-4-(hydroxymethyl)-N-(6-(2-methyloxazol-5-yl)isoquinolin-3-yl)cyclohexane-1-carboxamide 43 (350 mg, 0.96 mmol) in DCM (3 mL) was added and the mixture was stirred at -78° C. for 1 h. TEA (0.4 mL, 2.87 mmol) was then added and the mixture was continued to stir for 1 h and then warmed to room temperature for 1 h. The reaction mixture was diluted with H$_2$O and DCM, organic layer separated, washed with brine, dried over anhydrous Na$_2$SO$_4$ and the solvents were concentrated in vacuo to obtain trans-4-formyl-N-(6-(2-methyloxazol-5-yl)isoquinolin-3-yl)cyclohexane-1-carboxamide (L) as a pale yellow color solid (215.0 mg, 0.59 mmol, 108.1% yield) which was used for next step without purification. ESIMS found for $C_{21}H_{21}N_3O_3$ m/z 364.2 (M+1).

Step 5

To a solution of trans-4-formyl-N-(6-(2-methyloxazol-5-yl)isoquinolin-3-yl) cyclohexane-1-carboxamide (L) (100 mg, 0.28 mmol) in a mixture of MeOH (0.50 mL) and DCE (1 mL) was added morpholine hydrochloride (68 mg, 0.55 mmol)(pre-treated with TEA (0.08 mL, 0.55 mmol)). The mixture was stirred for 10 min before adding Na(OAc)$_3$BH (116.6 mg, 0.55 mmol) and stirring for another 4 h. The reaction mixture was diluted with DCM, washed with aqueous saturated NaHCO$_3$ and brine. The organic layer was separated and dried over anhydrous Na$_2$SO$_4$. The solvent evaporated under high vacuum and the crude product was then purified by preparative TLC (50% CHCl$_3$/10% 7N NH$_3$MeOH in CHCl$_3$) to obtain trans-N-(6-(2-Methyloxazol-5-yl)isoquinolin-3-yl)-4-(morpholinomethyl) cyclohexane-1-carboxamide 69 an off-white solid (21.0 mg, 0.048 mmol, 17.6% yield). $^1$H NMR (500 MHz, DMSO-$d_6$) δ ppm 0.81-0.94 (2H, m), 1.41-1.56 (3H, m), 1.80-1.91 (4H, m), 2.09 (2H, d, J=7.41 Hz), 2.31 (4H, br s), 2.51-2.56 (1H, m), 2.53 (3H, s), 3.56 (4H, t, J=4.53 Hz), 7.78 (1H, s), 7.79-7.84 (1H, m), 8.05-8.11 (2H, m), 8.50 (1H, s), 9.10 (1H, s), 10.49 (1H, s); ESIMS found for $C_{25}H_{30}N_4O_3$ m/z 435.2 (M+1).

Example 5

Preparation of trans-4-(methylamino)-N-(6-(2-methyloxazol-5-yl) isoquinolin-3-yl) cyclohexane-1-carboxamide (16) and trans-4-(methyl(oxetan-3-yl)amino)-N-(6-(2-methyloxazol-5-yl)isoquinolin-3-yl)cyclohexane-1-carboxamide (37) are depicted below in Scheme 17.

Scheme 17

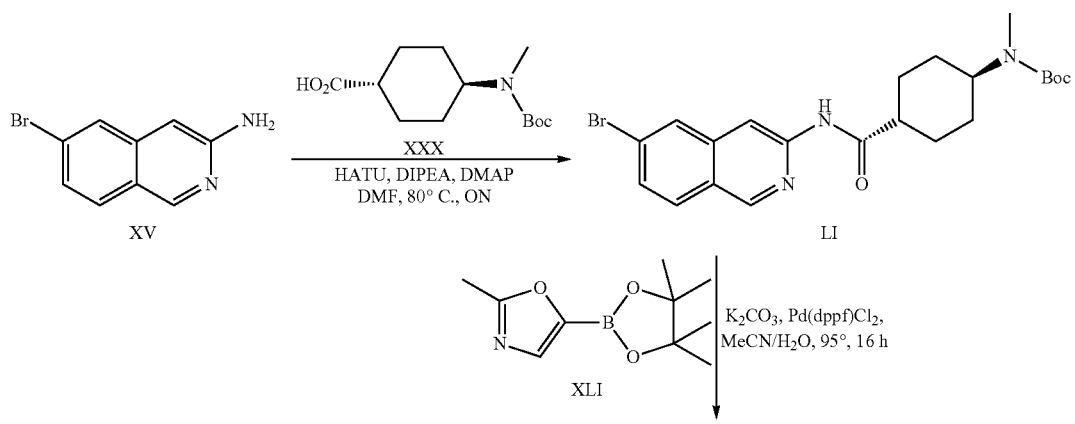

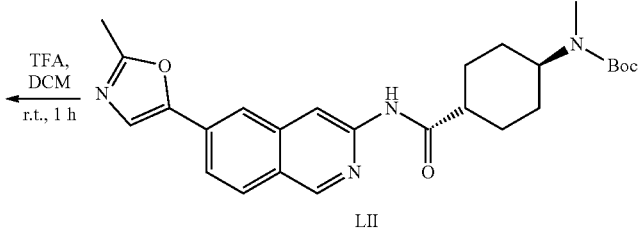

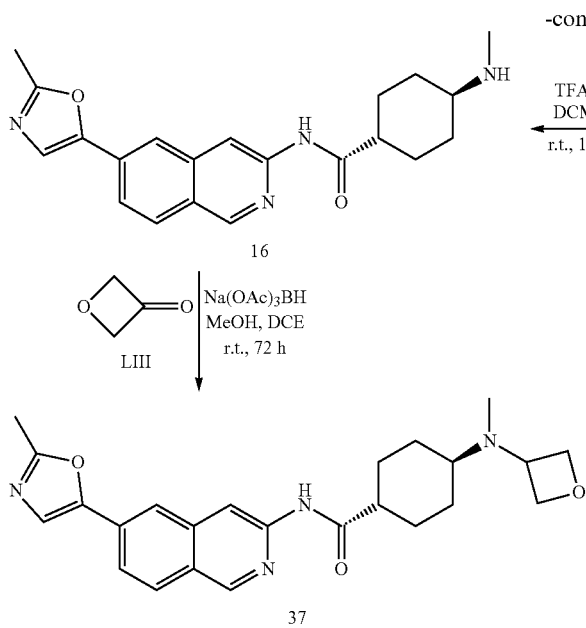

Step 1

A mixture of DIPEA (2.93 mL, 16.81 mmol), HATU (1.6 g, 4.2 mmol) DMAP (41 mg, 0.34 mmol), trans-4-((tert-butoxycarbonyl)(methyl)amino)cyclohexane--carboxylic acid (XXX) (1.2 g, 4.66 mmol) and 6-bromoisoquinolin-3-amine (XV) (750 mg, 3.36 mmol) in DMF (8 mL) was heated to 80° C. overnight. An additional 0.25 equiv. of HATU was added and the mixture was stirred for another 5 h at 80° C. The reaction mixture was poured into aqueous saturated NaHCO$_3$ solution (~200 mL), stirred for 20 min, the resulting solid was collected by filtration, washed with water and concentrated under high vacuum. The crude product was purified by column chromatography (0 to 40% EtOAc/hexanes). The pure fractions were combined, concentrated and dried under high vacuo to obtain tert-butyl (trans-4-(((6-bromoisoquinolin-3-yl)carbamoyl)cyclohexyl)(methyl)carbamate (LI) as a beige color solid (0.513 g, 1.11 mmol, 33.0% yield). ESIMS found for $C_{22}H_{28}BrN_3O_3$ m/z 462.1 ($^{79}$BrM+1).

Step 2

A mixture of 2-methyl-5-(4,4,5,5-tetramethyl-1,3,2-dioxaborolan-2-yl) oxazole (XLI) (283 mg, 1.35 mmol), Pd(dppf)Cl$_2$ (88.3 mg, 0.11 mmol), 2M aqueous K$_2$CO$_3$ (1.35 mL, 2.7 mmol) and tert-butyl (trans-4-((6-bromoisoquinolin-3-yl)carbamoyl) cyclohexyl)(methyl)carbamate (LI) (500 mg, 1.08 mmol) in MeCN (5 mL). N$_2$ gas was bubbled into the mixture for 10 min and then was heated to 95° C. for 16 h. The organic layer was carefully separated, absorbed on silica gel and purified by column chromatography (25-100% hexanes/EtOAc). The pure fractions were combined, concentrated and dried under high vacuo to obtain tert-butyl methyl(trans-4-((6-(2-methyloxazol-5-yl) isoquinolin-3-yl)carbamoyl) cyclohexyl)carbamate (LII) as an off-white color solid (228 mg, 0.49 mmol, 45.4% yield). ESIMS found for $C_{26}H_{32}N_4O_4$ m/z 465.3 (M+1).

Step 3

To a stirred solution of TFA (1.3 g, 11.42 mmol) in DCM (1 mL) was added tert-butyl methyl(trans-4-((6-(2-methyl-oxazol-5-yl)isoquinolin-3-yl)carbamoyl)cyclohexyl) carbamate (LII) (225 mg, 0.48 mmol) and the mixture was stirred for 1 h. The reaction mixture was concentrated, treated with 7 N NH$_3$/MeOH, absorbed on silica gel and purified by column chromatography (20-100% CHCl$_3$/10% 7N NH$_3$MeOH in CHCl$_3$). The pure fractions were combined, concentrated and dried under high vacuo to obtain trans-4-(methylamino)-N-(6-(2-methyloxazol-5-yl)isoquinolin-3-yl)cyclohexane-1-carboxamide 16 as an off-white solid (131.0 mg, 0.360 mmol, 74.2% yield). $^1$H NMR (499 MHz, DMSO-d$_6$) δ ppm 0.93-1.04 (2H, m), 1.48 (2H, qd, J=12.85, 3.16 Hz), 1.86 (2H, br d, J=11.25 Hz), 1.95 (2H, br dd, J=13.17, 3.02 Hz), 2.22 (1H, tt, J=10.94, 4.01 Hz), 2.28 (3H, s), 2.53 (3H, s), 7.78 (1H, s), 7.79-7.84 (1H, m), 8.06-8.12 (2H, m), 8.50 (1H, s), 9.10 (1H, s), 10.49 (1H, s); ESIMS found for $C_{21}H_{24}N_4O_2$ m/z 365.2 (M+1).

Step 4

To a stirred solution of Na(OAc)$_3$BH (52.3 mg, 0.25 mmol) and oxetan-3-one (LIII) (17.8 mg, 0.25 mmol) in a mixture of MeOH (0.50 mL) and DCE (1 mL) was added trans-4-(methylamino)-N-(6-(2-methyloxazol-5-yl)isoquinolin-3-yl)cyclohexane-1-carboxamide 16 (60 mg, 0.16 mmol) and the mixture was stirred for 72 h. The reaction mixture was absorbed on silica gel and purified by preparative TLC (60% CHCl$_3$/10% 7N NH$_3$MeOH in CHCl$_3$) to obtain trans-4-(Methyl(oxetan-3-yl)amino)-N-(6-(2-methyloxazol-5-yl)isoquinolin-3-yl)cyclohexane-1-carboxamide 37 as a white solid (6.0 mg, 0.014 mmol, 8.7% yield). $^1$H NMR (500 MHz, DMSO-d$_6$) δ ppm 1.16-1.30 (2H, m), 1.47 (2H, qd, J=12.72, 2.74 Hz), 1.68 (2H, br d, J=10.15 Hz), 1.85-1.94 (2H, m), 2.12 (3H, s), 2.30 (1H, tt, J=11.53, 3.02 Hz), 2.41-2.48 (1H, m), 2.53 (3H, s), 3.90 (1H, quin, J=6.86 Hz), 4.43-4.53 (4H, m), 7.78 (1H, s), 7.80 (1H, dd, J=8.64, 1.51 Hz), 8.05-8.12 (2H, m), 8.49 (1H, s), 9.10 (1H, s), 10.50 (1H, s); ESIMS found for $C_{24}H_{28}N_4O_3$ m/z 421.2 (M+1).

Example 6

Preparation of N-(6-(5-methyl-1,3,4-thiadiazol-2-yl)iso-quinolin-3-yl) piperidine-4-carboxamide (24), 1-(2,2-difluo-roethyl)-N-(6-(5-methyl-1,3,4-thiadiazol-2-yl) isoquinolin-3-yl)piperidine-4-carboxamide (27) and 1-(2,2- difluoropropyl)-N-(6-(5-methyl-1,3,4-thiadiazol-2-yl) isoquinolin-3-yl)piperidine-4-carboxamide (28) are depicted below in Scheme 18.

thiadiazol-2-yl)isoquinolin-3-amine (LVI) as a yellow solid (4.30 g, 17.75 mmol, 96.3% yield). ESIMS found for $C_{12}H_{10}N_4S$ m/z 243.0 (M+1).

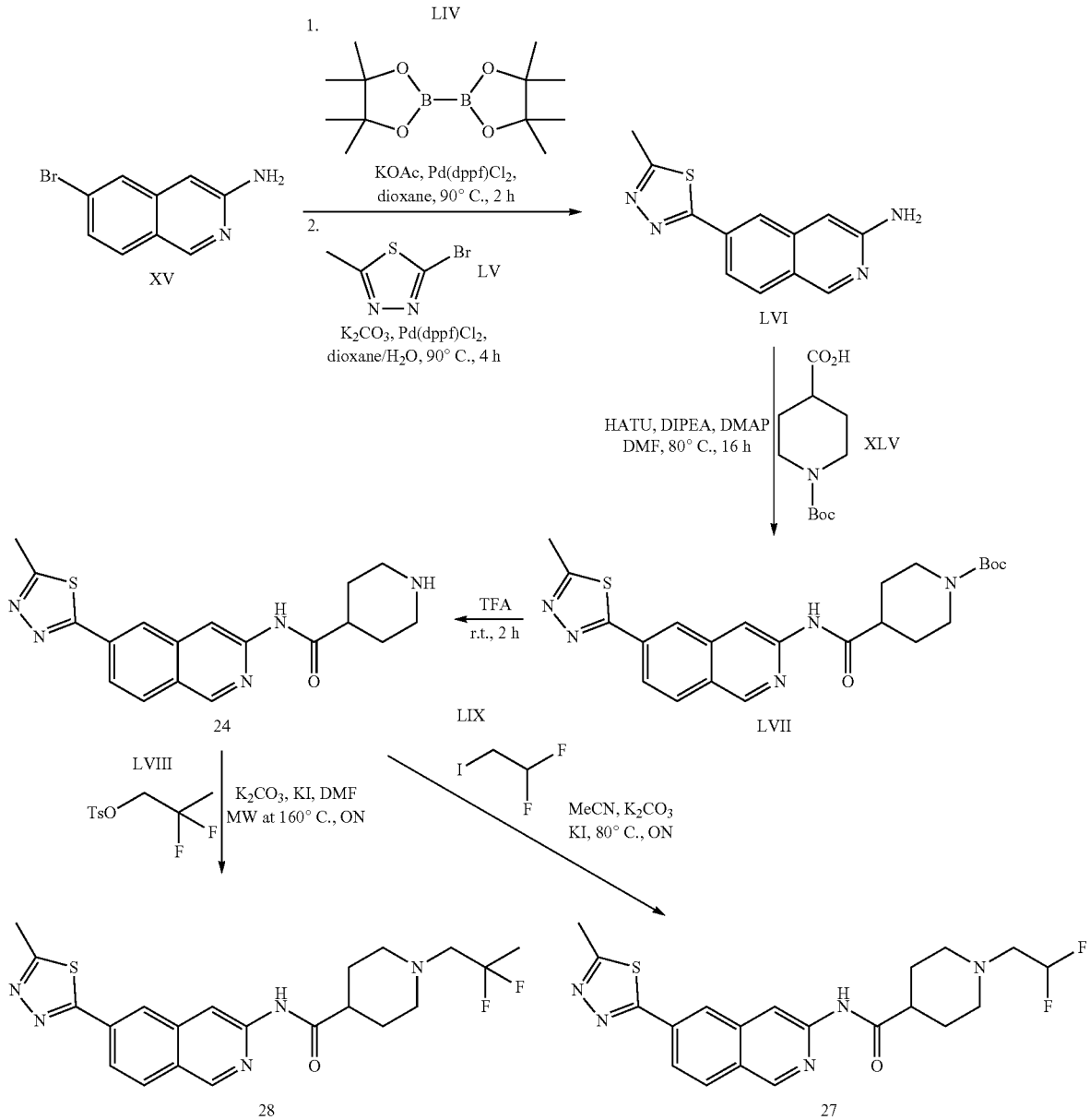

Scheme 18

Step 1-2

To a mixture of 6-bromoisoquinolin-3-amine (XV) (4.52 g, 20.27 mmol), 4,4,4',4',5,5,5',5'-octamethyl-2,2'-bi(1,3,2-dioxaborolane) (LIV) (5.62 g, 22.12 mmol), KOAc (5.43 g, 55.29 mmol), and Pd(dppf)Cl$_2$ (3.0 g, 3.69 mmol) in dioxane (10 mL) was purged with nitrogen and then heated at 90° C. for 2 h. The reaction was cooled to room temperature before adding the 2-bromo-5-methyl-1,3,4-thiadiazole (LV) (3.30 g, 18.43 mmol), K$_2$CO$_3$ (7.64 g, 55.29 mmol) and Pd(dppf) Cl$_2$ (3.0 g, 3.69 mmol). The mixture was heated at 90° C. for another 4 h. The solvent was removed under high vacuum and the residue was purified by column chromatography (0→100% EtOAc/hexanes) to produce 6-(5-methyl-1,3,4-

Step 3

To a suspension of 6-(5-methyl-1,3,4-thiadiazol-2-yl)isoquinolin-3-amine (LVII) (0.4 g, 1.65 mmol), 1-(tert-butoxycarbonyl)piperidine-4-carboxylic acid (XLV) (0.45 g, 1.98 mmol), DMAP (0.1 g, 0.83 mmol) and HATU (0.75 g, 1.98 mmol) in MeCN (4 mL) was added DIPEA (0.86 mL, 4.95 mmol). The resulting mixture was heated at 80° C. for 16 h. The reaction was concentrated under high vacuum and then purified via column chromatography (24 g of silica gel) (0→3% CHCl$_3$/10% 7N NH$_3$MeOH) to yield tert-butyl 4-((6-(5-methyl-1,3,4-thiadiazol-2-yl)isoquinolin-3-yl)carbamoyl)piperidine-1-carboxylate (LVII) as a light orange solid (590 mg, 1.30 mmol, 78.8% yield). ESIMS found for $C_{23}H_{27}N_5O_3S$ m/z 454.2 (M+1).

Step 4

A solution of tert-butyl 4-((6-(5-methyl-1,3,4-thiadiazol-2-yl)isoquinolin-3-yl)carbamoyl)piperidine-1-carboxylate (LVII (0.59 g, 1.3 mmol) in TFA (2.16 mL, 28.08 mmol) stirred at room temperature for 2 h. The reaction was concentrated under vacuum and neutralized with a $NH_3$ in $CHCl_3$ solution. The solution was concentrated and purified via column chromatography (12 g of silica gel) (0→1% $CHCl_3$/MeOH) to give N-(6-(5-methyl-1,3,4-thiadiazol-2-yl)isoquinolin-3-yl)piperidine-4-carboxamide 24 as a light green solid (105.0 mg, 0.297 mmol, 22.8% yield). $^1$H NMR (500 MHz, DMSO-$d_6$) δ ppm 1.93-2.02 (2H, m), 2.05-2.20 (5H, m), 2.22 (3H, s), 2.71-2.77 (2H, m), 2.83 (3H, s), 8.15 (1H, dd, J=8.64, 1.78 Hz), 8.24 (1H, d, J=8.51 Hz), 8.52 (1H, s), 8.59 (1H, s), 9.27 (1H, s), 10.08 (1H, d, J=4.12 Hz); ESIMS found for $C_{18}H_{19}N_5OS$ m/z 354.1 (M+1).

Step 5

A solution of N-(6-(5-methyl-1,3,4-thiadiazol-2-yl)isoquinolin-3-yl) piperidine-4-carboxamide 24 (50 mg, 0.14 mmol), $K_2CO_3$ (39.1 mg, 0.28 mmol), KI (46.5 mg, 0.28 mmol) and 2,2-difluoropropyl 4-methylbenzenesulfonate (LVIII) (70.8 mg, 0.28 mmol) in DMF (10 mL) heated at 160° C. overnight in a sealed vial. The reaction was partitioned between EtOAc/water. The organic phase was separated and the aqueous phase was washed again with EtOAc. The organic phases were combined, washed sequentially with water and brine, dried, and concentrated. The residue was purified via column chromatography (12 g of silica gel) (0→3% $CHCl_3$/10% 7 N $NH_3$MeOH) to yield 1-(2,2-difluoropropyl)-N-(6-(5-methyl-1,3,4-thiadiazol-2-yl)isoquinolin-3-yl)piperidine-4-carboxamide 28 as a beige solid (3.0 mg, 0.007 mmol, 4.9% yield). H NMR (500 MHz, DMSO-$d_6$) δ ppm 1.63 (3H, t, J=19.07 Hz), 1.67-1.75 (2H, m), 1.75-1.81 (2H, m), 2.22 (2H, td, J=11.73, 2.33 Hz), 2.52-2.60 (1H, m), 2.71 (2H, t, J=14.00 Hz), 2.83 (3H, s), 2.92-2.99 (2H, m), 8.09 (1H, dd, J=8.51, 1.65 Hz), 8.19 (1H, d, J=8.78 Hz), 8.45 (1H, d, J=0.82 Hz), 8.62 (1H, s), 9.21 (1H, s), 10.64 (1H, s); ESIMS found for $C_{21}H_{23}F_2N_5OS$ m/z 432.2 (M+1).

Step 6

To a suspension of N-(6-(5-methyl-1,3,4-thiadiazol-2-yl)isoquinolin-3-yl) piperidine-4-carboxamide 24 (45 mg, 0.13 mmol) and $K_2CO_3$ (22.9 mg, 0.38 mmol) in acetonitrile (20 mL) was added 1,1-difluoro-2-iodoethane (LIX) (29.3 mg, 0.15 mmol) and potassium iodide (41.5 mg, 0.25 mmol). The mixture was then heated to 80° C. overnight. The reaction mixture was absorbed on silica and was purified by ISCO (0→4% $CHCl_3$/10% 7 N $NH_3$MeOH). The pure fractions were combined, concentrated, suspended in diethyl ether, sonicated and the solids were collected by filtration and dried under high vacuo to obtain 1-(2,2-difluoroethyl)-N-(6-(5-methyl-1,3,4-thiadiazol-2-yl)isoquinolin-3-yl)piperidine-4-carboxamide 27 as a beige solid (20.0 mg, 0.048 mmol, 53.2% yield). $^1$H NMR (499 MHz, DMSO-$d_6$) δ ppm 1.62-1.74 (2H, m), 1.76-1.83 (2H, m), 2.14-2.25 (2H, m), 2.52-2.61 (1H, m), 2.73 (2H, td, J=15.71, 4.25 Hz), 2.83 (3H, s), 2.96 (2H, br d, J=11.53 Hz), 6.14 (1H, tt, J=56.10, 4.40 Hz), 8.09 (1H, dd, J=8.51, 1.65 Hz), 8.19 (1H, d, J=8.51 Hz), 8.45 (1H, s), 8.62 (1H, s), 9.21 (1H, s), 10.64 (1H, s); ESIMS found for $C_{20}H_{21}F_2N_5OS$ m/z 418.1 (M+1).

Example 7

Preparation of 1-methyl-3-(6-(5-methyl-1,3,4-thiadiazol-2-yl)isoquinolin-3-yl)-1-(1-methylpiperidin-4-yl)urea (29), (3S,4S)-4-amino-3-fluoro-N-(6-(5-methyl-1,3,4-thiadiazol-2-yl)isoquinolin-3-yl)piperidine-1-carboxamide (33) and (3S,4S)-4-(dimethylamino)-3-fluoro-N-(6-(5-methyl-1,3,4-thiadiazol-2-yl)isoquinolin-3-yl)piperidine-1-carboxamide (34) are depicted below in Scheme 19.

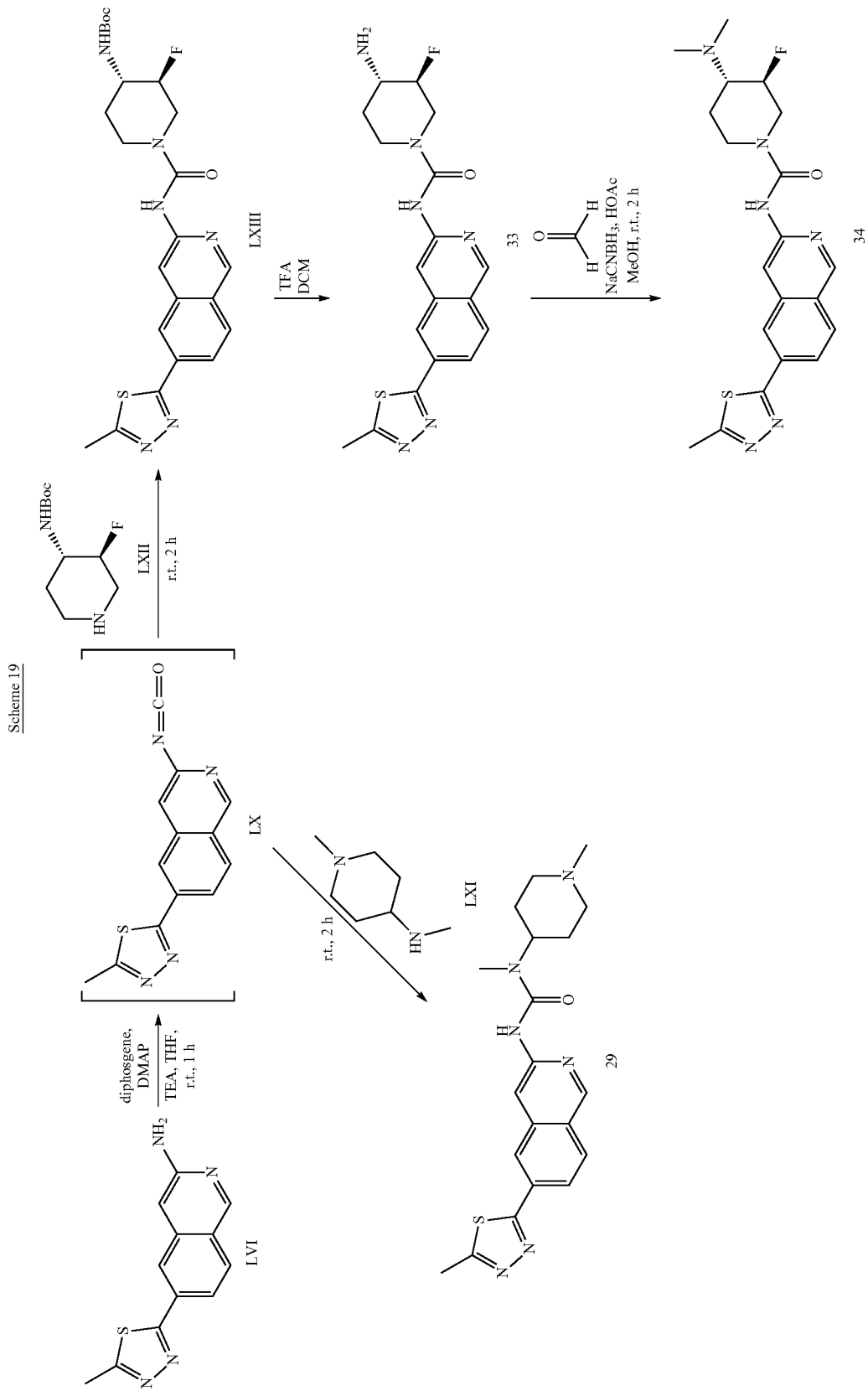

Step 1

To a stirred suspension of 6-(5-methyl-1,3,4-thiadiazol-2-yl)isoquinolin-3-amine (LVI) (400 mg, 1.65 mmol), DMAP (20.2 mg, 0.17 mmol) and TEA (0.92 mL, 6.6 mmol) in THF (20 mL) was added diphosgene (0.2 mL, 1.65 mmol). The mixture was stirred for 1 h at room temperature. LC-MS showed the formation of 2-(3-isocyanatoisoquinolin-6-yl)-5-methyl-1,3,4-thiadiazole (LX) which was not isolated and was used immediately for the next step.

Step 2

To the 2-(3-isocyanatoisoquinolin-6-yl)-5-methyl-1,3,4-thiadiazole (LX) (1.65 mmol) reaction solution from the procedure in Step 1 was added N,1-dimethylpiperidin-4-amine (LXI) (212 mg, 1.65 mmol) and the mixture was stirred for 2 h at room temperature. The solvents were removed under high vacuum and the crude was purified by column chromatography (0→10% CHCl$_3$/10% 7N NH$_3$MeOH) to obtain 1-Methyl-3-(6-(5-methyl-1,3,4-thiadiazol-2-yl)isoquinolin-3-yl)-1-(1-methylpiperidin-4-yl) urea 29 as a beige solid (70.0 mg, 0.177 mmol, 10.7% yield). $^1$H NMR (499 MHz, DMSO-d$_6$) δ ppm 1.58 (2H, br d, J=10.98 Hz), 1.73-1.85 (2H, m), 2.18 (2H, br s), 2.29 (3H, br s), 2.82 (3H, s), 2.89 (3H, s), 2.91-3.01 (2H, m), 4.10-4.20 (1H, m), 8.02 (1H, dd, J=8.51, 1.65 Hz), 8.15 (1H, d, J=8.78 Hz), 8.32 (1H, s), 8.36 (1H, s), 9.00 (1H, s), 9.16 (1H, s); ESIMS found for C$_{20}$H$_{24}$N$_6$OS m/z 397.2 (M+1).

Step 3

To the 2-(3-isocyanatoisoquinolin-6-yl)-5-methyl-1,3,4-thiadiazole (LX) (0.83 mmol) reaction solution from the procedure in Step 1 was added tert-butyl ((3S,4S)-3-fluoropiperidin-4-yl)carbamate (LXII) (216 mg, 0.99 mmol) and the mixture was stirred for 2 h at room temperature slowly until the orange color disappears. The solvents were removed under high vacuum and the crude was purified by column chromatography (0→10% CHCl$_3$/10% 7N NH$_3$MeOH) to produce tert-butyl ((3S,4S)-3-fluoro-1-((6-(5-methyl-1,3,4-thiadiazol-2-yl)isoquinolin-3-yl)carbamoyl)piperidin-4-yl)carbamate (LXIII) as a beige solid (55 mg, 0.11 mmol, 13.7% yield).

Step 4

To a solution of TFA (0.79 mL, 10.28 mmol) in DCM (1 mL) was added tert-butyl ((3 S,4S)-3-fluoro-1-((6-(5-methyl-1,3,4-thiadiazol-2-yl)isoquinolin-3-yl)carbamoyl) piperidin-4-yl)carbamate (LXIII) (50 mg, 0.10 mmol) and then stirred overnight at room temperature. The solvent was evaporated under high vacuum and the residue was adsorbed on silica gel, purified by column chromatography (0→10% 7N—NH$_3$-MeOH/CHCl$_3$). The pure fractions were concentrated and the solid was triturated with DCM/hexane, filtered and dried to obtain (3S,4S)-4-amino-3-fluoro-N-(6-(5-methyl-1,3,4-thiadiazol-2-yl)isoquinolin-3-yl)piperidine-1-carboxamide 33 as a beige solid (38.0 mg, 0.098 mmol, 95.7% yield). $^1$H NMR (499 MHz, DMSO-d$_6$) δ ppm 1.28-1.39 (1H, m), 1.84 (2H, dt, J=13.10, 4.01 Hz), 2.82 (3H, s), 2.85-2.94 (1H, m), 3.10-3.24 (2H, m), 3.84-3.94 (1H, m), 4.11-4.29 (2H, m), 8.03 (1H, dd, J=8.51, 1.65 Hz), 8.16 (1H, d, J=8.51 Hz), 8.30 (1H, s), 8.39 (1H, s), 9.17 (1H, s), 9.45 (1H, s); ESIMS found for C$_{18}$H$_{19}$FN$_6$OS m/z 387.1 (M+1).

Step 5

A mixture of (3S,4S)-4-amino-3-fluoro-N-(6-(5-methyl-1,3,4-thiadiazol-2-yl) isoquinolin-3-yl)piperidine-1-carboxamide 33 (35 mg, 0.09 mmol), formaldehyde (23.3 mg, 0.27 mmol) and catalytic HOAc in MeOH (5 mL) was stirred for 30 min at room temperature. NaCNBH$_3$ (28.5 mg, 0.45 mmol) was added and the stirring was continued at room temperature for 2 h. The reaction mixture was quenched with minimum amount of aqueous saturated ammonium chloride solution and concentrated under vacuum. The residue was adsorbed on silica gel, purified by chromatography (0→10% 7N.NH$_3$-MeOH/CHCl$_3$). The pure fractions were combined, concentrated and the residue triturated from DCM/hexanes. The solid was collected by filtration and further purified by HPLC using 0.1% Formic acid-MeCN/water. The pure fractions were dried and dissolved in MeOH filtered through basic resin to obtain the free base of (3S,4S)-4-(dimethylamino)-3-fluoro-N-(6-(5-methyl-1,3,4-thiadiazol-2-yl) isoquinolin-3-yl)piperidine-1-carboxamide 34 as an off-white solid (25.0 mg, 0.060 mmol, 66.6% yield). $^1$H NMR (499 MHz, DMSO-d$_6$) δ ppm 1.41-1.54 (1H, m), 1.74-1.84 (1H, m), 2.28 (6H, s), 2.64 (1H, tdd, J=10.94, 10.94, 8.71, 4.53 Hz), 2.82 (3H, s), 2.93-3.02 (1H, m), 3.05 (1H, ddd, J=12.97, 9.13, 5.63 Hz), 4.00-4.11 (1H, m), 4.25-4.35 (1H, m), 4.63 (1H, dsxt, J=49.00, 4.10, 4.10, 4.10, 4.10, 4.10 Hz), 8.03 (1H, dd, J=8.51, 1.65 Hz), 8.16 (1H, d, J=8.78 Hz), 8.30 (1H, s), 8.39 (1H, d, J=0.82 Hz), 9.17 (1H, s), 9.48 (1H, s); ESIMS found for C$_{20}$H$_{23}$FN$_6$OS m/z 415.2 (M+1).

Example 8

Preparation of N-(6-(1-methyl-1H-1,2,3-triazol-4-yl)isoquinolin-3-yl)-2-morpholinoacetamide (11) is depicted below in Scheme 20.

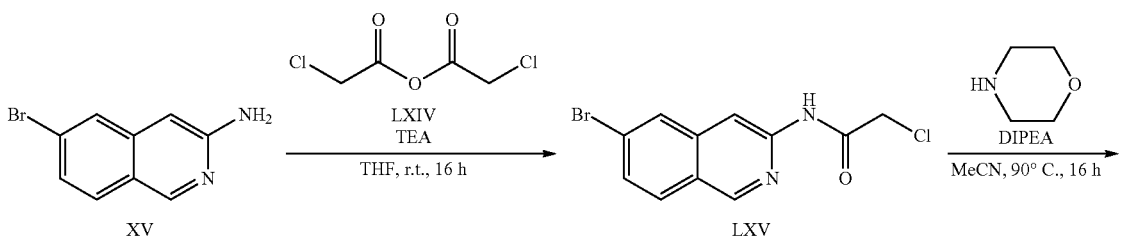

Scheme 20

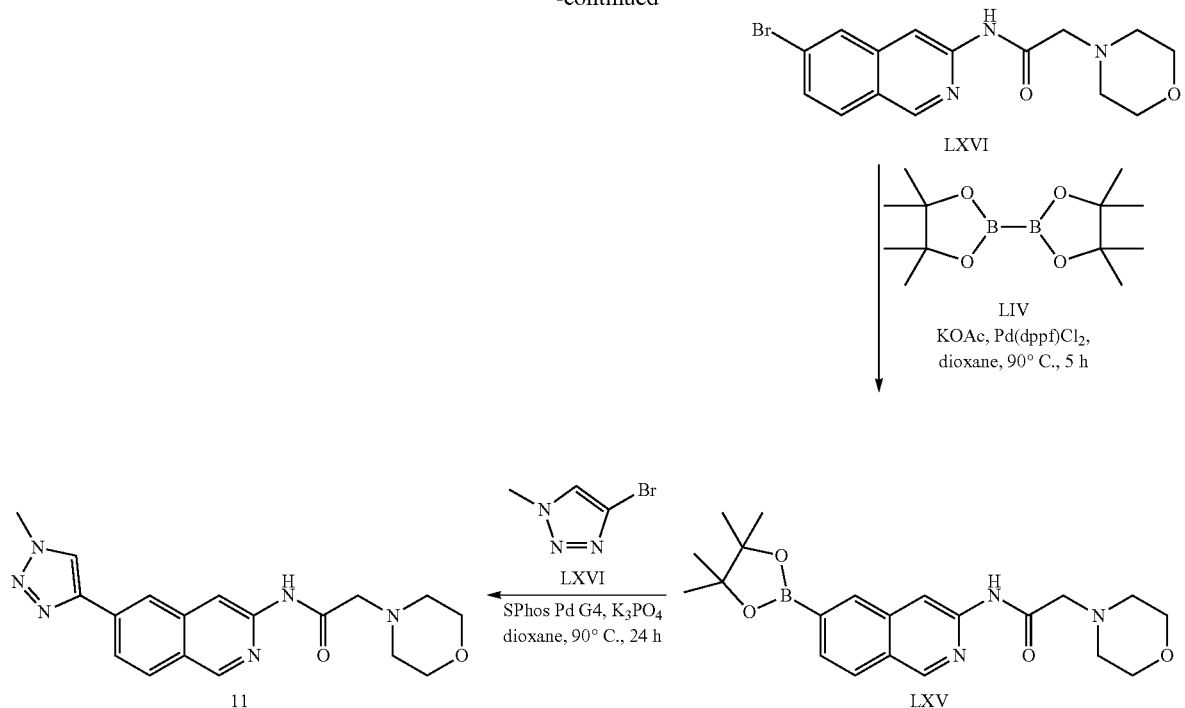

Steps 1

To a suspension of 6-bromoisoquinolin-3-amine (XV) (10 g, 44.83 mmol) and 2-chloroacetic anhydride (LXIV) (9.2 g, 53.79 mmol) in dry THF (100 mL) was added TEA (15.62 mL, 112.07 mmol). The mixture was stirred at room temperature for 16 h then poured into a mixture of aqueous saturated $NaHCO_3$ (200 mL) and water (300 mL). The mixture was stirred for an hour and the resulting solids were collected by filtration, air-dried and suspended in diethyl ether (400 mL), stirred for 30 min. The solid filtered and dried under high vacuo to obtain N-(6-bromoisoquinolin-3-yl)-2-chloroacetamide (LXV) as a brown solid (9.36 g, 31.25 mmol, 69.7% yield). ESIMS found for $C_{11}H_8BrClN_2O$ m/z 298.95 (M+1).

Step 2

A mixture of N-(6-bromoisoquinolin-3-yl)-2-chloroacetamide (LXV) (9.28 g, 30.98 mmol), morpholine (8.04 mL, 92.94 mmol), and DIPEA (10.79 mL, 61.96 mmol) in MeCN (100 mL) was heated to 90° C. for 16 h. The reaction mixture was filtered and the solid was dried under high vacuo to obtain 8.45 grams of the product. The filtrate was concentrated, absorbed on silica and purified by column chromatography (25→100% hexanes/EtOAc) to obtain another 1.75 g of N-(6-bromoisoquinolin-3-yl)-2-morpholinoacetamide (LXVI) as a brown solid (10.2 g, 28.05 mmol, 90.5% yield). ESIMS found for $C_{15}H_{16}BrN_3O_2$ m/z 350.1 (M+1).

Step 3-4

A mixture of N-(6-bromoisoquinolin-3-yl)-2-morpholinoacetamide (LXIV) (15 g, 42.83 mmol), 4,4,4',4',5,5,5',5'-octamethyl-2,2'-bi(1,3,2-dioxaborolane) (LIV) (16.3 g, 64.25 mmol), $Pd(dppf)Cl_2$ (3.5 g, 4.28 mmol) and KOAc (12.61 g, 128.49 mmol) was taken in dioxane (150 mL). $N_2$ gas was bubbled into the mixture for 10 min which was then heated to 90° C. for 5 h. The reaction mixture was filtered, washed with minimal dioxane and dried under vacuum to yield 2-morpholino-N-(6-(4,4,5,5-tetramethyl-1,3,2-dioxaborolan-2-yl)isoquinolin-3-yl)acetamide (LXV) which was used without further purification.

Step 4

To a mixture of 2-morpholino-N-(6-(4,4,5,5-tetramethyl-1,3,2-dioxaborolan-2-yl)isoquinolin-3-yl)acetamide (LXV) (675.4 mg, 1.7 mmol), 4-bromo-1-methyl-1H-1,2,3-triazole (LXVI) (0.55 g, 3.4 mmol) and SPhos Pd G4 (135 mg, 0.17 mmol) in dioxane (10 mL) was added 2 N aqueous $K_3PO_4$ (1.7 mL, 3.4 mmol). $N_2$ gas was bubbled into the mixture for 10 min and then heated to 90° C. for 24 h. The reaction mixture was partitioned between EtOAc and aqueous saturated $NaHCO_3$. Insoluble solids were removed by filtration and the organic layer separated and washed with water and brine. The organic layer was separated, dried ($MgSO_4$) and concentration to dryness under vacuum. The crude was then combined with the insoluble solid, dissolved in a mixture of chloroform/MeOH, absorbed on silica gel and was purified by column chromatography (0%→70% $CHCl_3$/10% 7N $NH_3MeOH$ in $CHCl_3$) to give N-(6-(1-Methyl-1H-1,2,3-triazol-4-yl)isoquinolin-3-yl)-2-morpholinoacetamide 11 as a brown solid (170.0 mg, 0.482 mmol, 28.4% yield). $^1H$ NMR (499 MHz, DMSO-$d_6$) δ ppm 2.55-2.61 (4H, m), 3.25 (2H, s), 3.63-3.69 (4H, m), 4.14 (3H, s), 8.04 (1H, dd, J=8.51, 1.65 Hz), 8.13 (1H, d, J=8.78 Hz), 8.33 (1H, s), 8.50 (1H, s), 8.74 (1H, s), 9.13 (1H, s), 10.07 (1H, s); ESIMS found for $C_{18}H_{20}N_6O_2$ m/z 353.2 (M+1).

Example 9

Preparation of 2-(4-isopropylpiperazin-1-yl)-N-(6-(1-methyl-1H-pyrazol-4-yl)isoquinolin-3-yl-1-d)isonicotinamide (9) is depicted below in Scheme 21.

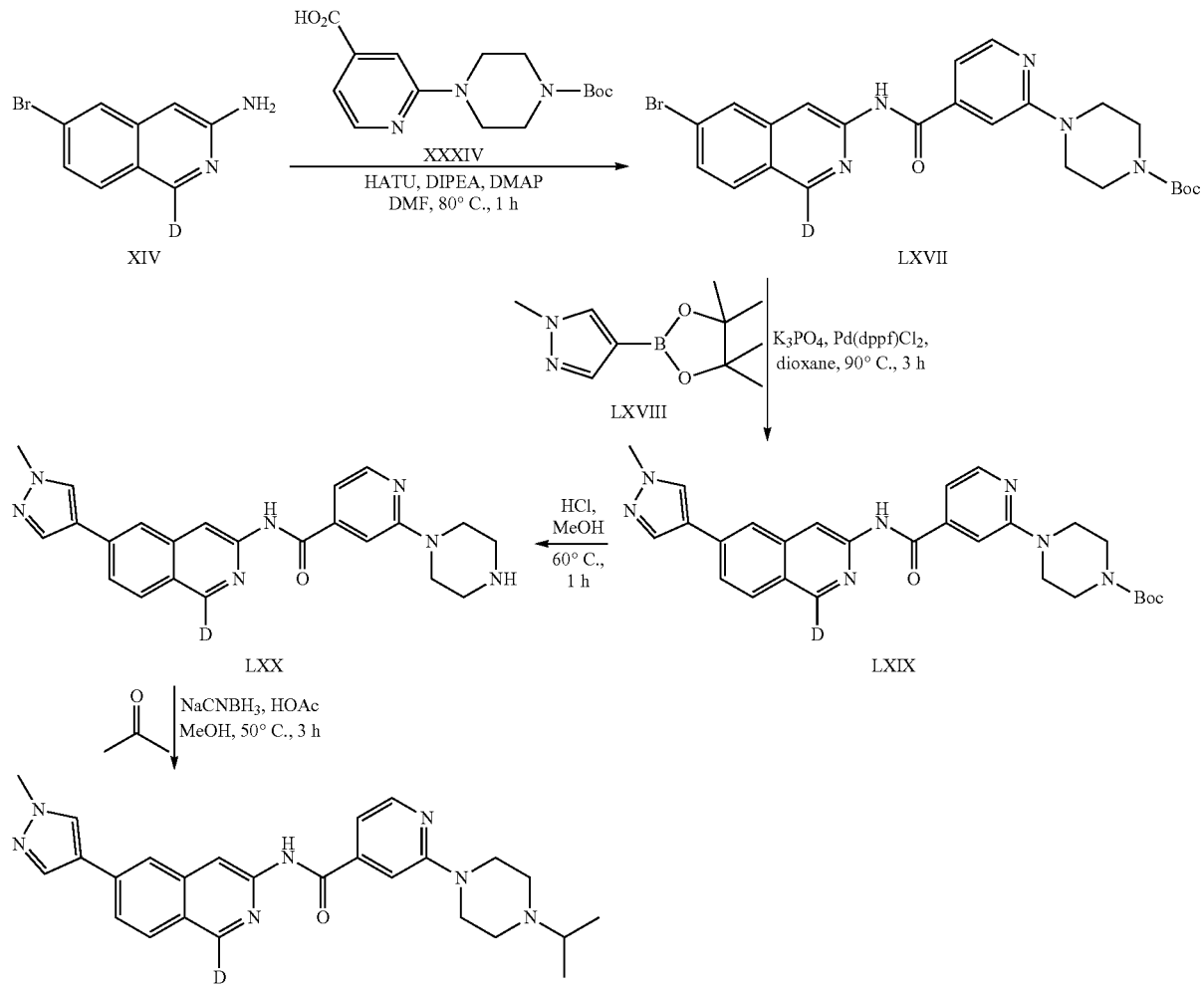

Scheme 21

Step 1
To a suspension of 6-bromoisoquinolin-1-d-3-amine (XIV) (200 mg, 0.89 mmol), 2-(4-(tert-butoxycarbonyl)piperazin-1-yl)isonicotinic acid (XXXIV) (329.1 mg, 1.07 mmol), DMAP (54.5 mg, 0.45 mmol) and HATU (407.2 mg, 1.07 mmol) in DMF (4 mL) was added DIPEA (0.39 mL, 2.23 mmol). The resulting mixture was at 80° C. for 1 h. Additional HATU (339 mg, 0.89 mmol) was added and the mixture heated at 80° C. for an additional 2 h. The reaction mixture was cooled to room temperature and poured into water. The resulting solid was filtered and dried under high vacuo to afford tert-butyl 4-(4-(((6-bromoisoquinolin-3-yl-1-d)carbamoyl)pyridin-2-yl)piperazine-1-carboxylate (LXVII) as a brown solid (445 mg, 0.89 mmol, 97.1% yield). ESIMS found for $C_{24}H_{25}DBrN_5O_3$ m/z 513.1 ($^{79}$BrM+H).

Step 2
A mixture of tert-butyl 4-(4-(((6-bromoisoquinolin-3-yl-1-d)carbamoyl)pyridin-2-yl)piperazine-1-carboxylate (LXVII) (440 mg, 0.86 mmol), 1-methyl-4-(4,4,5,5-tetramethyl-1,3,2-dioxaborolan-2-yl)-1H-pyrazole (LXVIII) (196.2 mg, 0.94 mmol), Pd(dppf)Cl$_2$ (49 mg, 0.06 mmol) and 2 M aqueous K$_3$PO$_4$ (1.07 mL, 2.14 mmol) in dioxane (5 mL) was purged with nitrogen and then stirred at 90° C. in a sealed tube for 3 h. The reaction was cooled to room temperature and concentrated under vacuum. The crude product was purified by flash column chromatography (0→5% MeOH/CHCl$_3$) to afford tert-butyl 4-(4-(((6-(1-methyl-1H-pyrazol-4-yl)isoquinolin-3-yl-1-d)carbamoyl)pyridin-2-yl)piperazine-1-carboxylate (LXIX) as a brown foam (410 mg, 0.80 mmol, 93.0% yield). ESIMS found for $C_{28}H_{30}DN_7O_3$ m/z 515.3 (M+H).

Step 3
To a suspension of tert-butyl 4-(4-((6-(1-methyl-1H-pyrazol-4-yl)isoquinolin-3-yl-1-d)carbamoyl)pyridin-2-yl)piperazine-1-carboxylate (LXIX) (410 mg, 0.80 mmol) in MeOH (5 mL) was added hydrogen chloride (4 M in dioxane) (1.0 mL, 3.98 mmol). The solution was stirred at 60° C. for 1 h and then the reaction mixture was concentrated under high vacuum. The crude product was purified by silica gel chromatography (0→10% 7 N NH$_3$-MeOH/CHCl$_3$) to give N-(6-(1-Methyl-1H-pyrazol-4-yl)isoquinolin-3-yl-1-d)-2-(piperazin-1-yl) isonicotinamide (LXX) as an off white solid (250 mg, 0.60 mmol, 75.7% yield). $^1$H NMR (499 MHz, DMSO-d$_6$) δ ppm 2.77-2.84 (4H, m), 3.48-3.57 (4H, m), 3.91 (3H, s), 7.13 (1H, dd, J=5.08, 1.24

Hz), 7.42 (1H, s), 7.81 (1H, dd, J=8.51, 1.65 Hz), 8.07 (1H, d, J=8.51 Hz), 8.11 (1H, s), 8.14 (1H, s), 8.25 (1H, d, J=5.21 Hz), 8.38 (1H, s), 8.59 (1H, s), 11.03 (1H, s); ESIMS found for $C_{23}H_{22}[^2H]N_7O$ m/z 415. (M+1).

Step 4

To a mixture of N-(6-(1-Methyl-1H-pyrazol-4-yl)isoquinolin-3-yl-1-d)-2-(piperazin-1-yl) isonicotinamide (LXX) (63 mg, 0.15 mmol) and HOAc (0.03 mL, 0.46 mmol) in a mixture of acetone (1 mL) and MeOH (2 mL) was added $NaCNBH_3$ (28.6 mg, 0.46 mmol). The mixture was stirred at 50° C. for 3 h. The mixture was concentrated and the residue purified by chromatography (0→6% 7N $NH_3$-MeOH/$CHCl_3$) to produce 2-(4-Isopropylpiperazin-1-yl)-N-(6-(1-methyl-1H-pyrazol-4-yl)isoquinolin-3-yl-1-d)isonicotinamide 9 as a white solid (53.0 mg, 0.116 mmol, 76.4% yield). $^1$H NMR (499 MHz, DMSO-$d_6$) δ ppm 1.01 (6H, d, J=6.59 Hz), 2.52-2.58 (4H, m), 2.66-2.76 (1H, m), 3.55-3.62 (4H, m), 3.91 (3H, s), 7.15 (1H, dd, J=5.21, 1.10 Hz), 7.44 (1H, s), 7.81 (1H, dd, J=8.51, 1.65 Hz), 8.07 (1H, d, J=8.51 Hz), 8.11 (1H, d, J=0.82 Hz), 8.14 (1H, s), 8.25 (1H, d, J=4.94 Hz), 8.38 (1H, s), 8.59 (1H, s), 11.04 (1H, s); ESIMS found for $C_{26}H_{28}[^2H]N_7O$ m/z 457.25 (M+1).

Example 10

Preparation of N-(6-(1-methyl-1H-imidazol-5-yl)isoquinolin-3-yl)-2-(pyrrolidin-1-yl-2,2,5,5-$d_4$)isonicotinamide (79) is depicted below in Scheme 22.

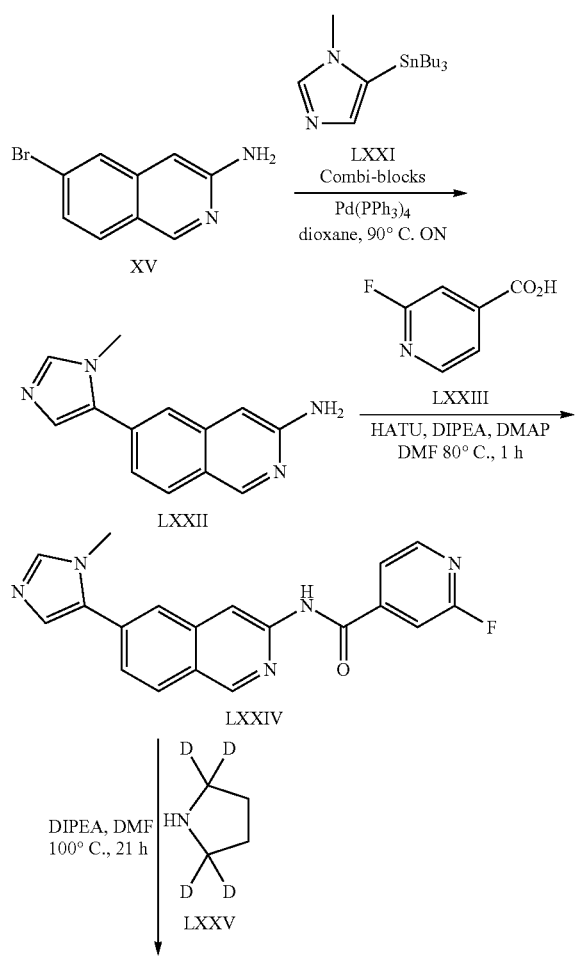

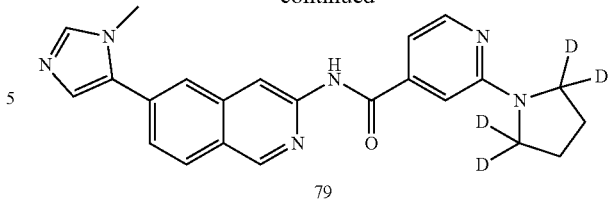

Step 1

A mixture of 6-bromoisoquinolin-3-amine (XV) (2.57 g, 11.52 mmol), 1-methyl-5-(tributylstannyl)-1H-imidazole (LXXI) (Combi-blocks) (4.28 g, 11.53 mmol), $Pd(PPh_3)_4$ (1.39 g, 1.2 mmol) in dioxane (57.6 mL) was purged with $N_2$ gas for 10 min and then heated to 90° C. overnight. The solvent was evaporated under high vacuum and the residue was purified by column chromatography (0→10% MeOH/$CHCl_3$) to give 6-(3-methylimidazol-4-yl)isoquinolin-3-amine (LXXII) as an olive green solid (2.32 g, 9.83 mmol, 85.3% yield). ESIMS found for $C_{13}H_{12}N_4$ m/z 225.1 (M+H).

Step 2

To a suspension of 6-(3-methylimidazol-4-yl)isoquinolin-3-amine (LXXII) (500 mg, 2.23 mmol), 2-fluoroisonicotinic acid (LXXIII) (377.5 mg, 2.68 mmol), DMAP (136 mg, 1.11 mmol) and HATU (1.02 g, 2.68 mmol) in DMF (8 mL) was added DIPEA (0.97 mL, 5.57 mmol). The resulting mixture was stirred at 80° C. for 1 h and then cooled to room temperature. Water was added and the resulting solid was filtered and dried under high vacuo to afford 2-fluoro-N-(6-(1-methyl-1H-imidazol-5-yl)isoquinolin-3-yl)isonicotinamide (LXXIV) as a beige solid (675 mg, 1.94 mmol, 87.2% yield). ESIMS found for $C_{19}H_{14}FN_5O$ m/z 348.1 (M+H).

Step 3

A mixture of 2-fluoro-N-(6-(1-methyl-1H-imidazol-5-yl) isoquinolin-3-yl) isonicotinamide (LXXIV) (80 mg, 0.23 mmol), DIPEA (0.12 mL, 0.69 mmol) and pyrrolidine-2,2,5,5-$d_4$ (LXXV) (0.06 mL, 0.69 mmol) in DMF (2 mL) was heated to 100° C. for 21 h. The reaction mixture was concentrated and the crude product purified by silica gel chromatography (0→6% 7 N $NH_3$-MeOH/$CHCl_3$). The fractions containing the product were concentrated and the residue triturated in ether. The resulting solid was filtered and dried under high vacuum to afford N-(6-(1-Methyl-1H-imidazol-5-yl)isoquinolin-3-yl)-2-(pyrrolidin-1-yl-2,2,5,5-$d_4$)isonicotinamide 79 as a beige solid (58.0 mg, 0.144 mmol, 62.6% yield). $^1$H NMR (500 MHz, DMSO-$d_6$) δ ppm 1.96 (4H, s), 3.85 (3H, s), 7.06 (1H, dd, J=5.21, 1.37 Hz), 7.07-7.12 (1H, m), 7.33 (1H, d, J=1.10 Hz), 7.74 (1H, dd, J=8.51, 1.65 Hz), 7.81 (1H, s), 8.10 (1H, d, J=0.82 Hz), 8.15 (1H, d, J=8.78 Hz), 8.18-8.24 (1H, m), 8.69 (1H, s), 9.22 (1H, s), 11.05 (1H, s); ESIMS found for $C_{23}H_{18}[^2H_4]N_6O$ m/z 403.15 (M+1).

Example 11

Preparation of trans-N-(8-fluoro-6-(2-methyloxazol-5-yl)isoquinolin-3-yl)-4-(4-methylpiperazine-1-carbonyl)cyclohexane-1-carboxamide (101) is depicted below in Scheme 23.

Scheme 23

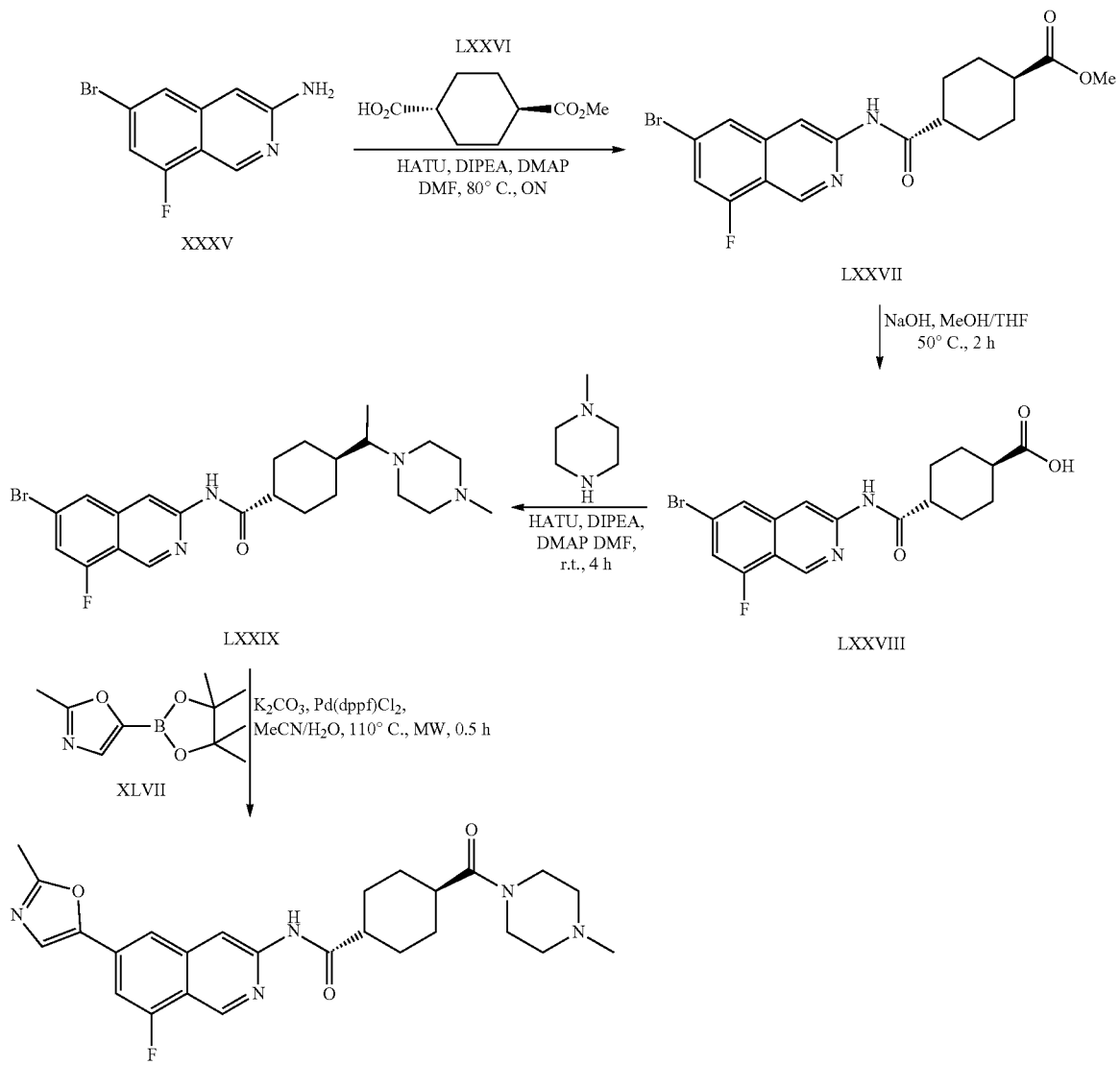

Step 1

A mixture of 6-bromo-8-fluoroisoquinolin-3-amine (XXXV) (300 mg, 1.24 mmol), DIPEA (1.08 mL, 6.22 mmol), HATU (591.5 mg, 1.56 mmol) and DMAP (15.2 mg, 0.12 mmol), and trans-4-(methoxycarbonyl)cyclohexane-1-carboxylic acid (LXXVI) (290 mg, 1.56 mmol) in DMF (5 mL). The reaction was heated to 80° C. overnight. Additional HATU (235 mg, 0.62 mmol) was added and the mixture was stirred for another 5 h at 80° C. The reaction mixture was concentrated and the residue partitioned between EtOAc and aqueous saturated $NaHCO_3$. The organic layer was separated and washed with water and brine. The crude was purified by column chromatography (10→80% EtOAc/hexanes) to obtain methyl trans-4-((6-bromo-8-fluoroisoquinolin-3-yl)carbamoyl)cyclohexane-1-carboxylate (LXXVII) as a beige solid (330 mg, 0.80 mmol, 64.8% yield). ESIMS found for $C_{18}H_{18}BrFN_2O_3$ m/z 409.05 ($^{79}$BrM+1).

Step 2

A suspension of methyl trans-4-((6-bromo-8-fluoroisoquinolin-3-yl)carbamoyl) cyclohexane-1-carboxylate (LXXVII) (330 mg, 0.81 mmol) in a mixture of MeOH (1 mL) and THF (2 mL) was added 2 M aqueous NaOH (0.81 mL, 1.61 mmol). The reaction was heated to 50° C. for 2 h. The mixture was concentrated and the residue taken in water and acidified with 1N HCl. The resulting solid was collected by filtration and dried under vacuum oven at 50° C. overnight to obtain trans-4-((6-bromo-8-fluoroisoquinolin-3-yl)carbamoyl)cyclohexane-1-carboxylic acid (LXXVIII) as an off-white solid (285 mg, 0.72 mmol, 89.4% yield). ESIMS found for $C_{17}H_{16}BrFN_2O_3$ m/z 395.0 ($^{79}$BrM+1).

Step 3

A mixture of trans-4-((6-bromo-8-fluoroisoquinolin-3-yl) carbamoyl)cyclohexane-1-carboxylic acid (LXXVIII) (280 mg, 0.71 mmol), HATU (255.9 mg, 0.67 mmol) and DIPEA (0.25 mL, 1.42 mmol) in DMF (3 mL) was stirred for 10 min. DMAP (108.6 mg, 0.89 mmol) was added and the mixture was stirred for 4 h at room temperature. The reaction mixture was poured into water (30 mL), the solid was collected by filtration, washed with aqueous saturated NaHCO$_3$, water and dried under vacuum over at 50° C. for 4 h to obtain trans-N-(6-bromo-8-fluoroisoquinolin-3-yl)-4-(4-methylpiperazine-1-carbonyl) cyclohexane-1-carboxamide (LXXIX) as a pale yellow solid (270 mg, 0.57 mmol, 79.8% yield) which was used for next step without purification. ESIMS found for C$_{22}$H$_{26}$BrFN$_4$O$_2$ m/z 477.15 ($^{79}$BrM+1).

Step 4

To a mixture of trans-N-(6-bromo-8-fluoroisoquinolin-3-yl)-4-(4-methylpiperazine-1-carbonyl) cyclohexane-1-carboxamide (LXXIX) (135 mg, 0.28 mmol), 2-methyl-5-(4,4,5,5-tetramethyl-1,3,2-dioxaborolan-2-yl)oxazole (XLVII) (73.9 mg, 0.35 mmol), and Pd(dppf)Cl$_2$ (23.1 mg, 0.03 mmol) in MeCN (1.5 mL) was added 2 M aqueous solution of K$_2$CO$_3$ (0.35 mL, 0.71 mmol). N$_2$ gas was bubbled into mmol, 61.2% yield). $^1$H NMR (499 MHz, DMSO-d$_6$) δ ppm 1.36-1.47 (2H, m), 1.51-1.62 (2H, m), 1.72 (2H, br d, J=11.25 Hz), 1.89 (2H, br d, J=10.15 Hz), 2.18 (3H, s), 2.23 (2H, br s), 2.30 (2H, br s), 2.53 (3H, s), 2.55-2.60 (1H, m), 2.61-2.68 (1H, m), 3.44 (2H, br s), 3.50 (2H, br s), 7.62-7.68 (1H, m), 7.84 (1H, s), 7.96 (1H, s), 8.57 (1H, s), 9.22 (1H, s), 10.67 (1H, s); ESIMS found for C$_{26}$H$_{30}$FN$_5$O$_3$ m/z 480.3 (M+1).

Example 12

Preparation of trans-4-amino-N-(6-(2-methyloxazol-5-yl)isoquinolin-3-yl)cyclohexane-1-carboxamide (149), trans-4-((1,3-difluoropropan-2-yl)amino)-N-(6-(2-methyloxazol-5-yl)isoquinolin-3-yl)cyclohexane-1-carboxamide (124) and trans-4-(2-(fluoromethyl)aziridin-1-yl)-N-(6-(2-methyloxazol-5-yl)isoquinolin-3-yl)cyclohexane-1-carboxamide (154) are depicted below in Scheme 24.

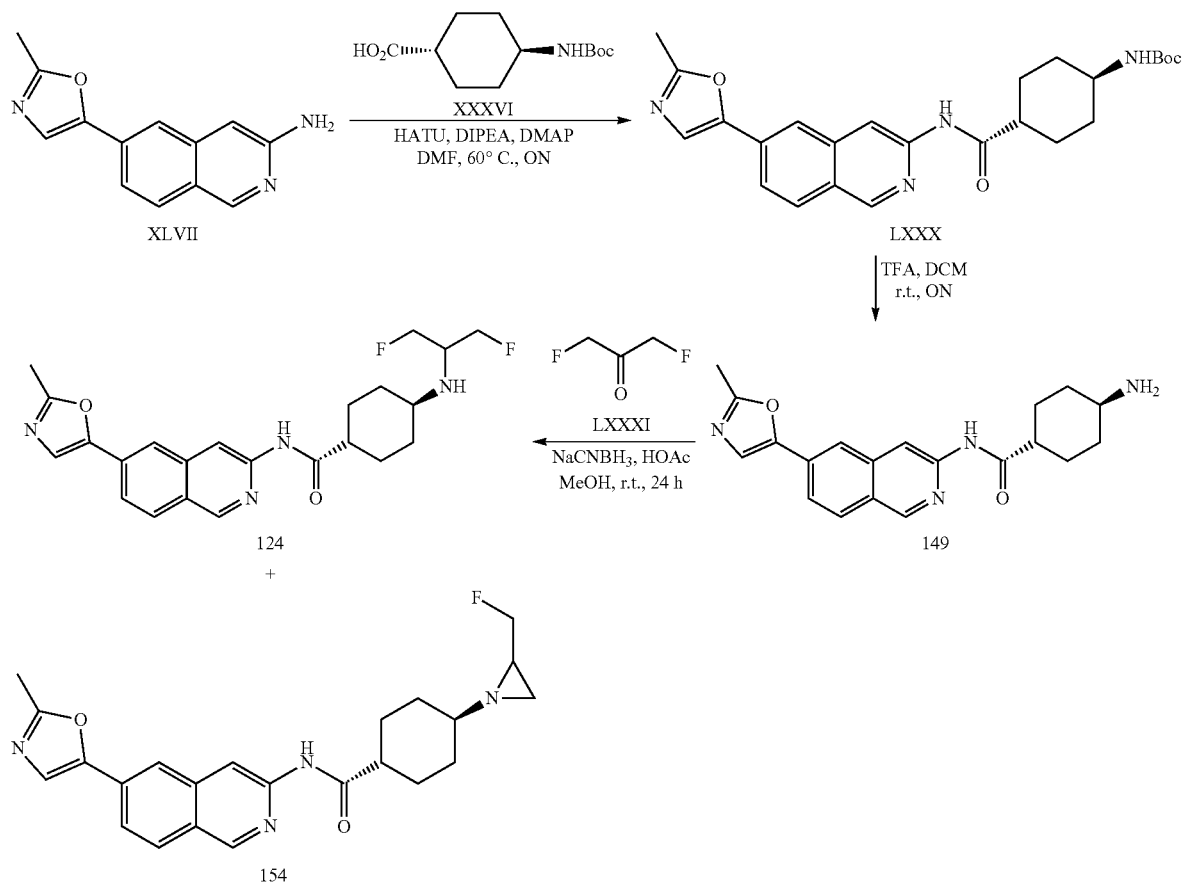

the mixture for 10 min followed by heating at 110° C. for 30 min using microwave (MW) irradiation. The organic layer was carefully separated, absorbed on silica gel and purified by flash column chromatography (10-80% CHCl$_3$/10% 7 N NH$_3$MeOH in CHCl$_3$). The pure fractions were combined, concentrated, the solid was suspended in EtOAc, sonicated and were collected by filtration, dried under high vacuo to obtain trans-N-(8-Fluoro-6-(2-methyloxazol-5-yl)isoquinolin-3-yl)-4-(4-methylpiperazine-1-carbonyl) cyclohexane-1-carboxamide 101 as an off-white solid (83.0 mg, 0.173

Step 1

To a mixture of 6-(2-methyloxazol-5-yl)isoquinolin-3-amine (XLVII) (370 mg, 1.64 mmol), HATU (0.94 g, 2.46 mmol), and DMAP (20.07 mg, 0.16 mmol) in DMF (5 mL) was stirred for 10 min before adding DIPEA (0.57 mL, 3.29 mmol) and trans-4-((tert-butoxycarbonyl)amino)cyclohexane-1-carboxylic acid (XXXVI) (400 mg, 1.64 mmol). The mixture was stirred at 60° C. overnight. The solvent was evaporated under high vacuum, the residue was taken up in EtOAc and washed with aqueous saturated NaHCO$_3$, water and then with brine. The organic layer was separated and dried (MgSO$_4$) before evaporation to dryness. The crude product was purified by silica gel chromatography (0→10% MeOH/CHCl$_3$). The fractions containing the product were concentrated and triturated with DCM/hexanes, filtered and dried under high vacuum to obtain tert-butyl (trans-4-((6-(2-methyloxazol-5-yl)isoquinolin-3-yl)carbamoyl)cyclohexyl)carbamate (LXXX) as a beige solid (723 mg, 1.60 mmol, 97.7% yield). ESIMS found for C$_{25}$H$_{30}$N$_4$O$_4$ m/z 451.3 (M+1).

Step 2

To a solution of TFA (1.71 mL, 22.2 mmol) in DCM (2 mL) was added tert-butyl (trans-4-((6-(2-methyloxazol-5-yl)isoquinolin-3-yl)carbamoyl)cyclohexyl)carbamate (LXXX) (500 mg, 1.11 mmol). The mixture was stirred overnight at room temperature. The solvent was evaporated under high vacuum and the residue was adsorbed on silica gel, purified by column chromatography (0→10% 7N—NH$_3$-MeOH/CHCl$_3$). The pure fractions were concentrated and the solid was triturated with DCM/hexane, filtered and dried to produce trans-4-Amino-N-(6-(2-methyloxazol-5-yl)isoquinolin-3-yl)cyclohexane-1-carboxamide 149 as a beige solid (370.0 mg, 1.056 mmol, 95.1% yield). $^1$H NMR (499 MHz, DMSO-d$_6$) δ ppm 0.98-1.11 (2H, m), 1.43-1.54 (2H, m), 1.82 (4H, br d, J=11.53 Hz), 2.43-2.49 (1H, m), 2.52 (1H, br s), 2.53 (3H, s), 7.78 (1H, s), 7.79-7.83 (1H, m), 8.06-8.12 (2H, m), 8.49 (1H, s), 9.10 (1H, s), 10.49 (1H, s); ESIMS found for C$_{20}$H$_{22}$N$_4$O$_2$ m/z 351.2 (M+1).

Step 3

A mixture of trans-4-Amino-N-(6-(2-methyloxazol-5-yl)isoquinolin-3-yl) cyclohexane-1-carboxamide 149 (115 mg, 0.33 mmol), 1,3-difluoropropan-2-one (LXXXI) (0.03 mL, 0.36 mmol) and catalytic HOAc in MeOH (1 mL) was stirred for 30 min at room temperature. NaCNBH$_3$ (45.4 mg, 0.72 mmol) was added and the reaction was stirred for 24 h at room temperature. Reaction mixture was quenched with minimum amount of aqueous saturated ammonium chloride solution, concentrated under vacuum. The residue was adsorbed on silica gel and purified by chromatography (0→10% 7N—NH$_3$-MeOH/CHCl$_3$). The pure fractions were combined, concentrated and further purified by preparative TLC (6% 7 N NH$_3$MeOH/CHCl$_3$) to obtain trans-4-((1,3-Difluoropropan-2-yl)amino)-N-(6-(2-methyloxazol-5-yl)isoquinolin-3-yl) cyclohexane-1-carboxamide 124 as an off-white solid (20.0 mg, 0.047 mmol, 14.2% yield). $^1$H NMR (500 MHz, DMSO-d$_6$) δ ppm 0.98-1.09 (2H, m), 1.42-1.54 (2H, m), 1.65 (1H, br s), 1.82-1.89 (2H, m), 1.91-1.98 (2H, m), 2.51-2.60 (1H, m), 2.53 (3H, s), 4.30-4.51 (4H, m), 7.78 (1H, s), 7.81 (1H, dd, J=8.64, 1.51 Hz), 8.09 (2H, dd, J=4.67, 3.84 Hz), 8.50 (1H, s), 9.10 (1H, s), 10.51 (1H, s); ESIMS found for C$_{23}$H$_{26}$F$_2$N$_4$O$_2$ m/z 429.2 (M+1) and trans-4-(2-(fluoromethyl)aziridin-1-yl)-N-(6-(2-methyloxazol-5-yl) isoquinolin-3-yl)cyclohexane-1-carboxamide 154 as an off-white solid (10.0 mg, 0.025 mmol, 7.4% yield). $^1$H NMR (500 MHz, DMSO-d$_6$) δ ppm 1.17-1.33 (4H, m), 1.35-1.45 (3H, m), 1.87 (4H, br d, J=9.88 Hz), 2.51-2.59 (1H, m), 2.53 (3H, s), 3.97-4.14 (2H, m), 4.36-4.50 (1H, m), 7.76-7.79 (1H, m), 7.80 (1H, dd, J=8.64, 1.51 Hz), 8.06-8.13 (2H, m), 8.49 (1H, s), 9.10 (1H, s), 10.51 (1H, s); ESIMS found for C$_{23}$H$_{25}$FN$_4$O$_2$ m/z 409.2 (M+1).

Example 13

Preparation of N-(6-(5-methyl-1,3,4-thiadiazol-2-yl)isoquinolin-3-yl)-4-(4-methylpiperazin-1-yl)piperidine-1-carboxamide (129) is depicted below in Scheme 25.

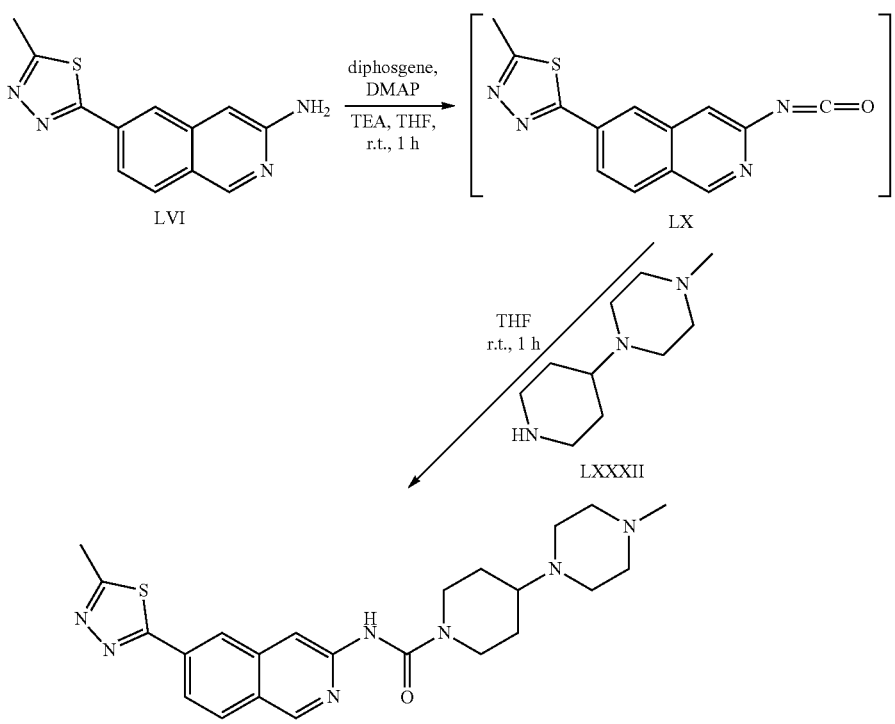

Step 1

To a suspension of 6-(5-methyl-1,3,4-thiadiazol-2-yl)isoquinolin-3-amine (LVI) (200 mg, 0.83 mmol), TEA (0.58 mL, 4.13 mmol), DMAP (10.1 mg, 0.08 mmol) in THF (20 mL) was added diphosgene (0.12 mL, 0.99 mmol) and the mixture was stirred at room temperature for 1 h. 1-Methyl-4-(piperidin-4-yl)piperazine (LXXXII) (454 mg, 2.48 mmol) was then added and the mixture was stirred at room temperature for 1 h. The reaction was filtered, and the filtrates were absorbed onto Celite and purified by column chromatography (10-60% $CHCl_3$/10% 7 N $NH_3$MeOH in $CHCl_3$) followed by preparative TLC to obtain N-(6-(5-Methyl-1,3,4-thiadiazol-2-yl)isoquinolin-3-yl)-4-(4-methylpiperazin-1-yl) piperidine-1-carboxamide 129 as an off-white solid (45.0 mg, 0.100 mmol, 12.1% yield). $^1$H NMR (499 MHz, DMSO-$d_6$) δ ppm 1.34 (2H, qd, J=11.94, 3.98 Hz), 1.77 (2H, br d, J=10.98 Hz), 2.13 (3H, s), 2.30 (4H, br s), 2.36-2.43 (1H, m), 2.43-2.54 (4H, m), 2.77-2.87 (2H, m), 2.82 (3H, s), 4.23 (2H, br d, J=13.17 Hz), 8.02 (1H, dd, J=8.78, 1.65 Hz), 8.15 (1H, d, J=8.51 Hz), 8.30 (1H, s), 8.37 (1H, d, J=0.82 Hz), 9.15 (1H, s), 9.30 (1H, s); ESIMS found for $C_{23}H_{29}N_7OS$ m/z 452.2 (M+1).

Example 14

Preparation of 1-methyl-4-(4-((6-(1-methyl-1H-1,2,3-triazol-4-yl)isoquinolin-3-yl) carbamoyl)pyridin-2-yl)piperazine 1-oxide (224) and 1-methyl-4-(4-((6-(1-methyl-1H-1,2,3-triazol-4-yl)isoquinolin-3-yl) carbamoyl)-1-oxidopyridin-2-yl)piperazine 1-oxide (225) are depicted below in Scheme 26.

(0-18% 7 N $NH_3$-MeOH/$CHCl_3$). The fractions containing the product were concentrated and the residue triturated in ether. The resulting solid was filtered and dried under high vacuo to afford 1-methyl-4-(4-((6-(1-methyl-1H-1,2,3-triazol-4-yl)isoquinolin-3-yl)carbamoyl)pyridin-2-yl)piperazine 1-oxide (224) as a beige solid (75 mg, 0.17 mmol, 72.3% yield). $^1$H NMR (499 MHz, DMSO-$d_6$) δ ppm 2.99 (2H, br d, J=10.70 Hz), 3.11 (3H, s), 3.41 (3H, td, J=11.46, 3.16 Hz), 3.62-3.73 (2H, m), 4.15 (3H, s), 4.25 (2H, br d, J=13.45 Hz), 7.21 (1H, dd, J=5.21, 1.10 Hz), 7.56 (1H, s), 8.08 (1H, dd, J=8.51, 1.37 Hz), 8.18 (1H, d, J=8.51 Hz), 8.29 (1H, d, J=5.21 Hz), 8.39 (1H, s), 8.67 (1H, s), 8.76 (1H, s), 9.22 (1H, s), 11.17 (1H, s); ESIMS found for $C_{23}H_{24}N_8O_2$ m/z 445.2 (M+1).

In addition, the double oxidation side product was isolated as a solid which was triturated in a saturated $NaHCO_3$ solution, filtered and dried under high vacuo to afford 1-methyl-4-(4-((6-(1-methyl-1H-1,2,3-triazol-4-yl)isoquinolin-3-yl) carbamoyl)-1-oxidopyridin-2-yl)piperazine 1-oxide (225) as a white solid (12 mg, 0.03 mmol, 11.2% yield). $^1$H NMR (499 MHz, DMSO-$d_6$) δ ppm 2.88 (2H, br d, J=11.25 Hz), 3.03 (2H, br d, J=11.53 Hz), 3.22 (3H, s), 4.13 (3H, s), 4.34 (2H, br t, J=10.98 Hz), 4.81-4.90 (2H, m), 7.85 (1H, br d, J=8.23 Hz), 7.98 (1H, br d, J=7.96 Hz), 8.12 (1H, br d, J=4.39 Hz), 8.15 (1H, br s), 8.54 (1H, s), 8.56 (1H, br d, J=4.94 Hz), 8.70 (1H, s), 9.04 (1H, s), 9.06 (1H, s), 11.44 (1H, br s); ESIMS found for $C_{23}H_{24}N_8O_3$ m/z 461.1 (M+1).

The following compounds were prepared in accordance with the procedures described in the above Examples 1-13.

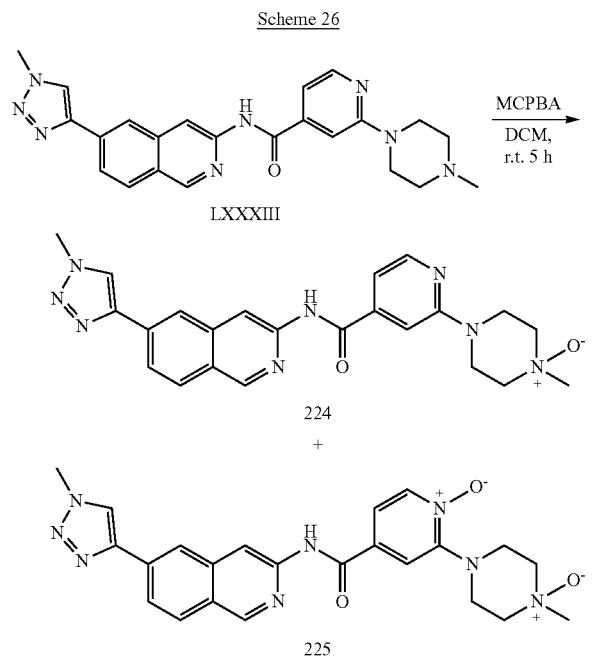

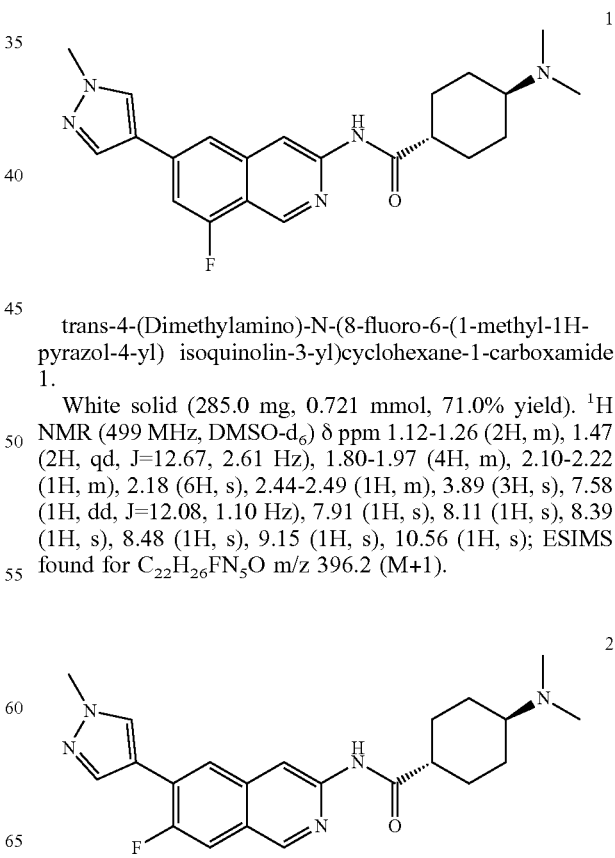

Step 1

To a suspension 2-(4-methylpiperazin-1-yl)-N-[6-(1-methyltriazol-4-yl)isoquinolin-3-yl]pyridine-4-carboxamide (LXXXIII) (100 mg, 0.23 mmol) in DCM (8 mL) was added MCPBA (78.5 mg, 0.35 mmol). The mixture was stirred at room temperature for 5 h and concentrated. The crude product was purified by silica gel chromatography trans-4-(Dimethylamino)-N-(8-fluoro-6-(1-methyl-1H-pyrazol-4-yl) isoquinolin-3-yl)cyclohexane-1-carboxamide 1.

White solid (285.0 mg, 0.721 mmol, 71.0% yield). $^1$H NMR (499 MHz, DMSO-$d_6$) δ ppm 1.12-1.26 (2H, m), 1.47 (2H, qd, J=12.67, 2.61 Hz), 1.80-1.97 (4H, m), 2.10-2.22 (1H, m), 2.18 (6H, s), 2.44-2.49 (1H, m), 3.89 (3H, s), 7.58 (1H, dd, J=12.08, 1.10 Hz), 7.91 (1H, s), 8.11 (1H, s), 8.39 (1H, s), 8.48 (1H, s), 9.15 (1H, s), 10.56 (1H, s); ESIMS found for $C_{22}H_{26}FN_5O$ m/z 396.2 (M+1).

trans-4-(Dimethylamino)-N-(7-fluoro-6-(1-methyl-1H-pyrazol-4-yl) isoquinolin-3-yl)cyclohexane-1-carboxamide 2.

Beige solid (4.0 mg, 0.010 mmol, 5.3% yield). $^1$H NMR (499 MHz, DMSO-d$_6$) δ ppm 1.14-1.26 (2H, m), 1.42-1.53 (2H, m), 1.83-1.96 (4H, m), 2.11-2.21 (1H, m), 2.18 (6H, s), 2.42-2.49 (1H, m), 3.93 (3H, s), 7.89 (1H, d, J=11.53 Hz), 8.10 (1H, s), 8.26 (1H, d, J=7.41 Hz), 8.30 (1H, d, J=2.74 Hz), 8.48 (1H, s), 9.03 (1H, s), 10.44 (1H, s); ESIMS found for C$_{22}$H$_{26}$FN$_5$O m/z 396.2 (M+1).

3

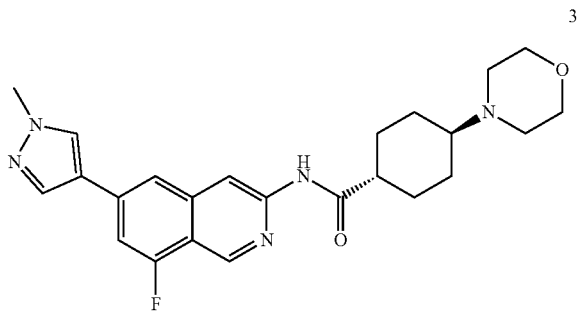 [SMILES: Cn1cc(-c2cc(F)c3cnc(NC(=O)[C@H]4CC[C@H](N5CCOCC5)CC4)cc3c2)cn1]

trans-N-(8-Fluoro-6-(1-methyl-1H-pyrazol-4-yl)isoquinolin-3-yl)-4-morpholinocyclohexane-1-carboxamide 3.

White solid (51.0 mg, 0.117 mmol, 50.9% yield). $^1$H NMR (499 MHz, DMSO-d$_6$) δ ppm 1.16-1.28 (2H, m), 1.42-1.55 (2H, m), 1.91 (4H, brt, J=12.35 Hz), 2.16-2.28 (1H, m), 2.44-2.49 (5H, m), 3.51-3.60 (4H, m), 3.89 (3H, s), 7.58 (1H, dd, J=12.08, 1.37 Hz), 7.91 (1H, s), 8.11 (1H, s), 8.39 (1H, s), 8.48 (1H, s), 9.15 (1H, s), 10.57 (1H, s); ESIMS found for C$_{24}$H$_{28}$FN$_5$O$_2$ m/z 438.2 (M+1).

4

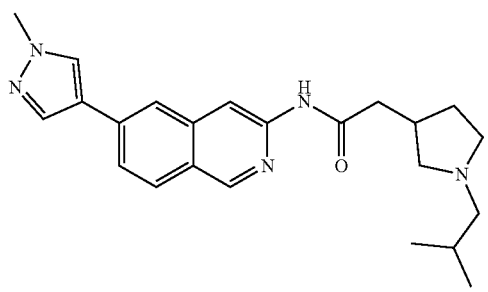

2-(1-Isobutylpyrrolidin-3-yl)-N-(6-(1-methyl-1H-pyrazol-4-yl)isoquinolin-3-yl)acetamide 4.

White solid (25.0 mg, 0.064 mmol, 14.3% yield). $^1$H NMR (499 MHz, DMSO-d$_6$) δ ppm 0.86 (6H, dd, J=6.59, 1.37 Hz), 1.43 (1H, dq, J=12.86, 6.32 Hz), 1.67 (1H, dquin, J=13.45, 6.66, 6.66, 6.66, 6.66 Hz), 1.88-2.01 (1H, m), 2.15 (3H, br s), 2.40-2.47 (1H, m), 2.52 (2H, s), 2.53-2.59 (1H, m), 2.67 (1H, br s), 3.90 (3H, s), 7.74 (1H, br s), 7.99 (1H, d, J=8.78 Hz), 8.05 (1H, d, J=0.82 Hz), 8.08 (1H, s), 8.35 (1H, s), 8.44 (1H, s), 9.02 (1H, s), 10.49 (1H, s); ESIMS found for C$_{23}$H$_{29}$N$_5$O m/z 392.2 (M+1).

5

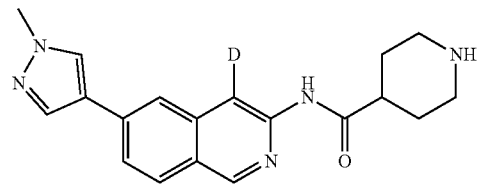

N-(6-(1-Methyl-1H-pyrazol-4-yl)isoquinolin-3-yl-4-d)piperidine-4-carboxamide 5.

Off-white solid (130.0 mg, 0.386 mmol, 58.0% yield). $^1$H NMR (499 MHz, DMSO-d$_6$) δ ppm 1.53 (2H, qd, J=12.21, 3.98 Hz), 1.67-1.74 (2H, m), 2.43-2.49 (2H, m), 2.60-2.68 (1H, m), 2.94-3.01 (2H, m), 3.90 (3H, s), 7.74 (1H, dd, J=8.51, 1.65 Hz), 7.99 (1H, d, J=8.51 Hz), 8.03 (1H, s), 8.08 (1H, s), 8.35 (1H, s), 9.02 (1H, s), 10.40 (1H, s); ESIMS found for C$_{19}$H$_{20}$[$^2$H]N$_5$O m/z 337.2 (M+1).

6

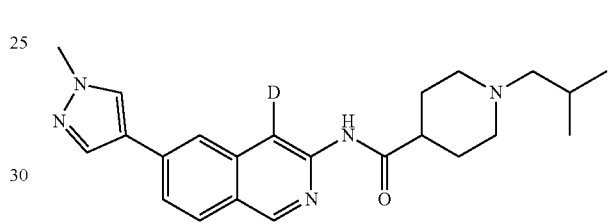

1-Isobutyl-N-(6-(1-methyl-1H-pyrazol-4-yl)isoquinolin-3-yl-4-d)piperidine-4-carboxamide 6.

White solid (35.0 mg, 0.089 mmol, 50.0% yield). $^1$H NMR (499 MHz, DMSO-d$_6$) δ ppm 0.86 (6H, d, J=6.59 Hz), 1.62-1.73 (2H, m), 1.73-1.81 (3H, m), 1.82-1.91 (2H, m), 2.02 (2H, d, J=7.41 Hz), 2.52-2.57 (1H, m), 2.86 (2H, br d, J=11.53 Hz), 3.90 (3H, s), 7.74 (1H, dd, J=8.64, 1.51 Hz), 8.00 (1H, d, J=8.51 Hz), 8.04 (1H, s), 8.08 (1H, s), 8.35 (1H, s), 9.02 (1H, s), 10.45 (1H, s); ESIMS found for C$_{23}$H$_{28}$[$^2$H]N$_5$O m/z 393.25 (M+1).

7

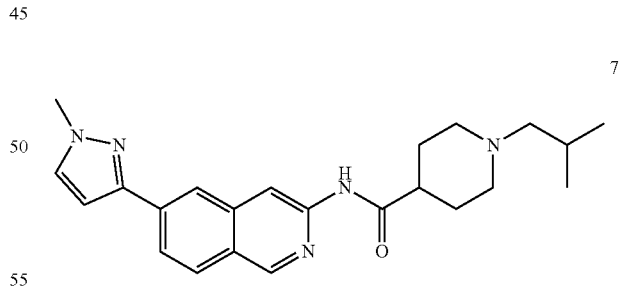

1-Isobutyl-N-(6-(1-methyl-1H-pyrazol-3-yl)isoquinolin-3-yl)piperidine-4-carboxamide 7.

White solid (10.0 mg, 0.026 mmol, 19.9% yield). $^1$H NMR (499 MHz, DMSO-d$_6$) δ ppm 0.86 (7H, d, J=6.59 Hz), 1.63-1.73 (2H, m), 1.74-1.81 (3H, m), 1.86 (2H, br t, J=10.84 Hz), 2.02 (2H, d, J=7.41 Hz), 2.51-2.60 (1H, m), 2.86 (2H, br d, J=11.25 Hz), 3.93 (3H, s), 6.93 (1H, d, J=2.20 Hz), 7.80 (1H, d, J=2.20 Hz), 7.96-8.01 (1H, m), 8.01-8.06 (1H, m), 8.21 (1H, s), 8.49 (1H, s), 9.07 (1H, s), 10.48 (1H, s); ESIMS found for C$_{23}$H$_{29}$N$_5$O m/z 392.2 (M+1).

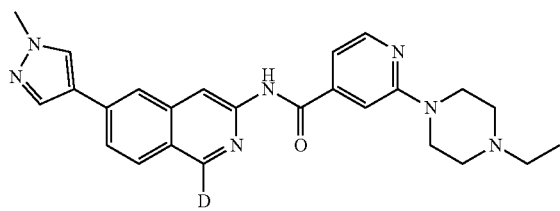

2-(4-Ethylpiperazin-1-yl)-N-(6-(1-methyl-1H-pyrazol-4-yl)isoquinolin-3-yl-1-d)isonicotinamide 8.

White solid (20.0 mg, 0.045 mmol, 28.0% yield). $^1$H NMR (499 MHz, DMSO-$d_6$) δ ppm 1.05 (3H, t, J=7.14 Hz), 2.38 (2H, q, J=7.14 Hz), 2.45-2.49 (4H, m), 3.57-3.64 (4H, m), 3.91 (3H, s), 7.16 (1H, dd, J=5.08, 0.96 Hz), 7.46 (1H, s), 7.81 (1H, dd, J=8.51, 1.37 Hz), 8.07 (1H, d, J=8.51 Hz), 8.11 (1H, s), 8.13 (1H, s), 8.25 (1H, d, J=4.94 Hz), 8.38 (1H, s), 8.59 (1H, s), 11.05 (1H, br s); ESIMS found for $C_{25}H_{26}[^2H]N_7O$ m/z 443.2 (M+1).

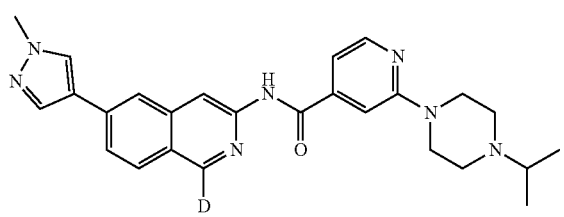

2-(4-Isopropylpiperazin-1-yl)-N-(6-(1-methyl-1H-pyrazol-4-yl)isoquinolin-3-yl-1-d)isonicotinamide 9.

White solid (53.0 mg, 0.116 mmol, 76.4% yield). $^1$H NMR (499 MHz, DMSO-$d_6$) δ ppm 1.01 (6H, d, J=6.59 Hz), 2.52-2.58 (4H, m), 2.66-2.76 (1H, m), 3.55-3.62 (4H, m), 3.91 (3H, s), 7.15 (1H, dd, J=5.21, 1.10 Hz), 7.44 (1H, s), 7.81 (1H, dd, J=8.51, 1.65 Hz), 8.07 (1H, d, J=8.51 Hz), 8.11 (1H, d, J=0.82 Hz), 8.14 (1H, s), 8.25 (1H, d, J=4.94 Hz), 8.38 (1H, s), 8.59 (1H, s), 11.04 (1H, s); ESIMS found for $C_{26}H_{28}[^2H]N_7O$ m/z 457.25 (M+1).

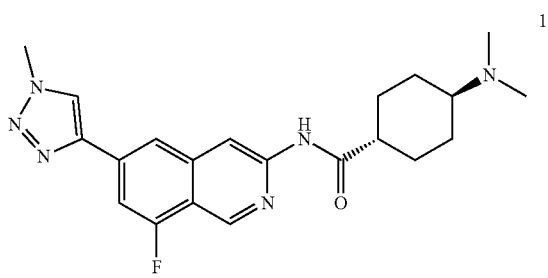

trans-4-(Dimethylamino)-N-(8-fluoro-6-(1-methyl-1H-1,2,3-triazol-4-yl) isoquinolin-3-yl)cyclohexane-1-carboxamide 10.

White solid (8.0 mg, 0.020 mmol, 4.0% yield). $^1$H NMR (499 MHz, DMSO-$d_6$) δ ppm 1.13-1.25 (2H, m), 1.48 (2H, qd, J=12.67, 2.88 Hz), 1.83-1.90 (2H, m), 1.90-1.97 (2H, m), 2.10-2.21 (1H, m), 2.18 (6H, s), 2.45-2.49 (1H, m), 4.14 (3H, s), 7.77 (1H, dd, J=11.53, 1.10 Hz), 8.16 (1H, s), 8.56 (1H, s), 8.76 (1H, s), 9.24 (1H, s), 10.65 (1H, s); ESIMS found for $C_{21}H_{25}FN_6O$ m/z 397.2 (M+1).

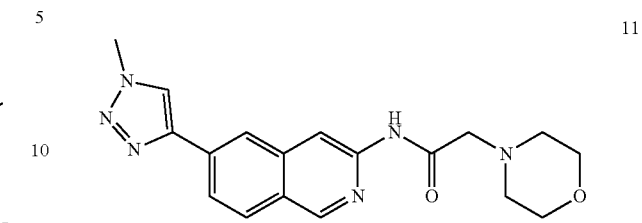

N-(6-(1-Methyl-1H-1,2,3-triazol-4-yl)isoquinolin-3-yl)-2-morpholinoacetamide 11.

Brown solid (170.0 mg, 0.482 mmol, 28.4% yield). $^1$H NMR (499 MHz, DMSO-$d_6$) δ ppm 2.55-2.61 (4H, m), 3.25 (2H, s), 3.63-3.69 (4H, m), 4.14 (3H, s), 8.04 (1H, dd, J=8.51, 1.65 Hz), 8.13 (1H, d, J=8.78 Hz), 8.33 (1H, s), 8.50 (1H, s), 8.74 (1H, s), 9.13 (1H, s), 10.07 (1H, s); ESIMS found for $C_{18}H_{20}N_6O_2$ m/z 353.2 (M+1).

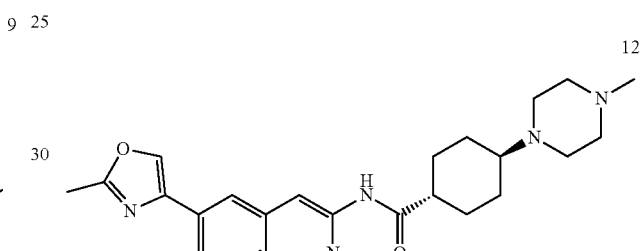

trans-N-(6-(2-Methyloxazol-4-yl)isoquinolin-3-yl)-4-(4-methylpiperazin-1-yl)cyclohexane-1-carboxamide 12.

Beige solid (2.5.0 mg, 0.006 mmol, 5.1% yield). $^1$H NMR (499 MHz, CHLOROFORM-d) δ ppm 0.81-0.92 (2H, m), 1.31-1.42 (2H, m), 1.63-1.73 (2H, m), 2.04-2.12 (2H, m), 2.12-2.21 (2H, m), 2.23-2.40 (2H, m), 2.31 (3H, s), 2.49 (3H, br s), 2.60 (3H, s), 2.65 (3H, br s), 7.40 (1H, s), 7.67 (1H, dd, J=8.51, 1.65 Hz), 7.90 (1H, d, J=8.51 Hz), 8.00 (1H, s), 8.02 (1H, s), 8.59 (1H, s), 8.92 (1H, s); ESIMS found for $C_{25}H_{31}N_5O_2$ m/z 434.25 (M+1).

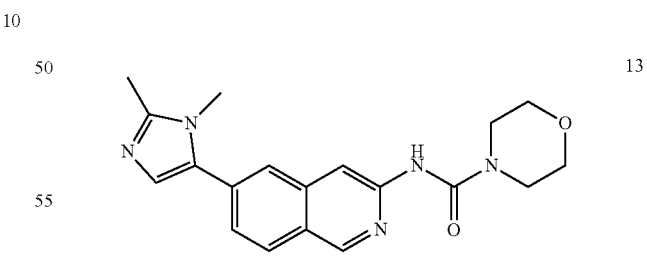

N-(6-(1,2-Dimethyl-1H-imidazol-5-yl)isoquinolin-3-yl)morpholine-4-carboxamide 13.

White solid (35.0 mg, 0.100 mmol, 15.8% yield). $^1$H NMR (499 MHz, DMSO-$d_6$) δ ppm 2.39 (3H, s), 3.46-3.55 (4H, m), 3.59-3.64 (4H, m), 3.65 (3H, s), 7.09 (1H, s), 7.54 (1H, dd, J=8.51, 1.65 Hz), 7.84 (1H, s), 8.05 (1H, d, J=8.51 Hz), 8.22 (1H, s), 9.07 (1H, s), 9.26 (1H, s); ESIMS found for $C_{19}H_{21}N_5O_2$ m/z 352.2 (M+1).

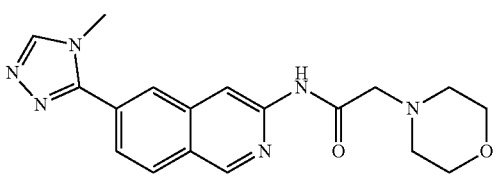

N-(6-(4-Methyl-4H-1,2,4-triazol-3-yl)isoquinolin-3-yl)-2-morpholinoacetamide 14.

Beige solid (34.0 mg, 0.097 mmol, 25.6% yield). $^1$H NMR (499 MHz, DMSO-$d_6$) δ ppm 2.55-2.63 (4H, m), 3.27 (2H, s), 3.63-3.69 (4H, m), 3.88 (3H, s), 7.93 (1H, dd, J=8.51, 1.65 Hz), 8.21 (1H, d, J=8.51 Hz), 8.33 (1H, d, J=0.82 Hz), 8.62 (1H, s), 8.66 (1H, s), 9.24 (1H, s), 10.16 (1H, s); ESIMS found for $C_8H_{20}N_6O_2$ m/z 353.2 (M+1).

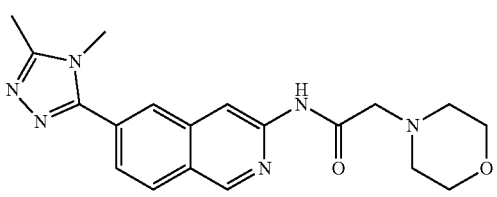

N-(6-(4,5-Dimethyl-4H-1,2,4-triazol-3-yl)isoquinolin-3-yl)-2-morpholinoacetamide 15.

White solid (51.0 mg, 0.139 mmol, 36.9% yield). $^1$H NMR (499 MHz, DMSO-$d_6$) δ ppm 2.45 (3H, s), 2.55-2.62 (4H, m), 3.27 (2H, s), 3.61-3.68 (4H, m), 3.71 (3H, s), 7.85 (1H, dd, J=8.51, 1.65 Hz), 8.21 (1H, d, J=8.51 Hz), 8.25 (1H, s), 8.61 (1H, s), 9.23 (1H, s), 10.16 (1H, s); ESIMS found for $C_{19}H_{22}N_6O_2$ m/z 367.2 (M+1).

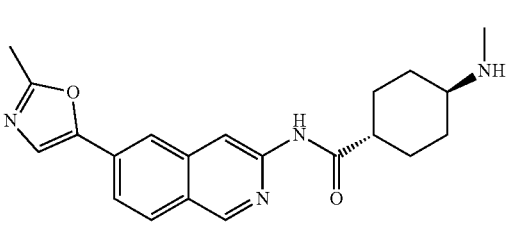

trans-4-(Methylamino)-N-(6-(2-methyloxazol-5-yl)isoquinolin-3-yl) cyclohexane-1-carboxamide 16.

Off-white solid (131.0 mg, 0.360 mmol, 74.2% yield). $^1$H NMR (499 MHz, DMSO-$d_6$) δ ppm 0.93-1.04 (2H, m), 1.48 (2H, qd, J=12.85, 3.16 Hz), 1.86 (2H, br d, J=11.25 Hz), 1.95 (2H, br dd, J=13.17, 3.02 Hz), 2.22 (1H, tt, J=10.94, 4.01 Hz), 2.28 (3H, s), 2.53 (3H, s), 7.78 (1H, s), 7.79-7.84 (1H, m), 8.06-8.12 (2H, m), 8.50 (1H, s), 9.10 (1H, s), 10.49 (1H, s); ESIMS found for $C_{21}H_{24}N_4O_2$ m/z 365.2 (M+1).

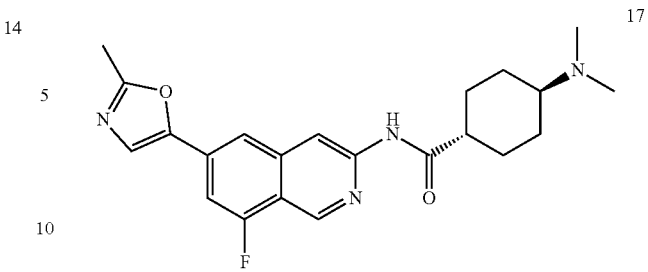

trans-4-(Dimethylamino)-N-(8-fluoro-6-(2-methyloxazol-5-yl)isoquinolin-3-yl)cyclohexane-1-carboxamide 17.

Beige solid (115.0 mg, 0.290 mmol, 57.2% yield). $^1$H NMR (499 MHz, DMSO-$d_6$) δ ppm 1.13-1.25 (2H, m), 1.47 (2H, qd, J=12.76, 2.61 Hz), 1.83-1.90 (2H, m), 1.90-1.96 (2H, m), 2.09-2.22 (1H, m), 2.18 (6H, s), 2.45-2.49 (1H, m), 2.53 (3H, s), 7.64 (1H, dd, J=11.39, 0.96 Hz), 7.83 (1H, s), 7.95 (1H, s), 8.56 (1H, s), 9.22 (1H, s), 10.65 (1H, s); ESIMS found for $C_{22}H_{25}FN_4O_2$ m/z 397.2 (M+1).

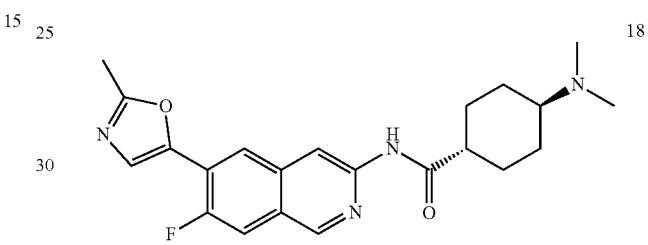

trans-4-(Dimethylamino)-N-(7-fluoro-6-(2-methyloxazol-5-yl)isoquinolin-3-yl)cyclohexane-1-carboxamide 18.

Beige solid (20.0 mg, 0.050 mmol, 26.5% yield). $^1$H NMR (499 MHz, DMSO-$d_6$) δ ppm 1.13-1.24 (2H, m), 1.41-1.54 (2H, m), 1.82-1.95 (4H, m), 2.09-2.20 (1H, m), 2.18 (6H, s), 2.43-2.49 (1H, m), 2.57 (3H, s), 7.59 (1H, d, J=4.67 Hz), 8.01 (1H, d, J=11.53 Hz), 8.23 (1H, d, J=6.86 Hz), 8.56 (1H, s), 9.10 (1H, s), 10.52 (1H, s); ESIMS found for $C_{22}H_{25}FN_4O_2$ m/z 397.2 (M+1).

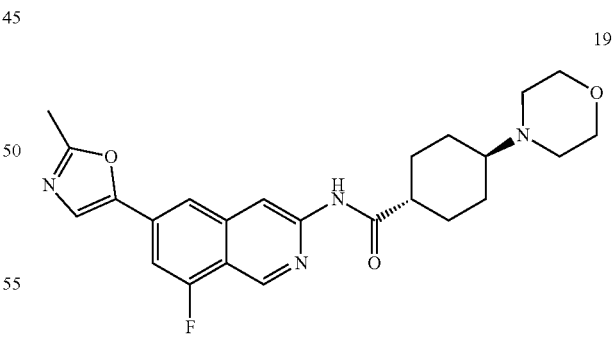

trans-N-(8-Fluoro-6-(2-methyloxazol-5-yl)isoquinolin-3-yl)-4-morpholinocyclohexane-1-carboxamide 19.

White solid (30.0 mg, 0.068 mmol, 29.9% yield). $^1$H NMR (499 MHz, DMSO-$d_6$) δ ppm 1.15-1.28 (2H, m), 1.42-1.54 (2H, m), 1.92 (4H, brt, J=12.76 Hz), 2.15-2.28 (1H, m), 2.46-2.49 (4H, m), 2.53 (3H, s), 3.52-3.60 (4H, m), 7.65 (1H, dd, J=11.53, 1.10 Hz), 7.84 (1H, s), 7.95 (1H, s), 8.56 (1H, s), 9.22 (1H, s), 10.66 (1H, s) ESIMS found for $C_{24}H_{27}FN_4O_3$ m/z 439.2 (M+1).

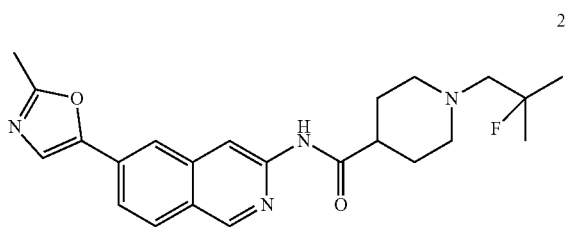

1-(2,2-Difluoropropyl)-N-(6-(2-methyloxazol-5-yl)isoquinolin-3-yl) piperidine-4-carboxamide 20.

White solid (26.0 mg, 0.063 mmol, 25.9% yield). $^1$H NMR (500 MHz, DMSO-$d_6$) δ ppm 1.63 (3H, t, J=19.21 Hz), 1.67-1.74 (2H, m), 1.75-1.80 (2H, m), 2.22 (2H, td, J=11.66, 2.47 Hz), 2.52-2.58 (1H, m), 2.53 (3H, s), 2.71 (2H, t, J=14.00 Hz), 2.91-2.99 (2H, m), 7.78 (1H, s), 7.81 (1H, dd, J=8.51, 1.65 Hz), 8.06-8.13 (2H, m), 8.51 (1H, s), 9.10 (1H, s), 10.55 (1H, s); ESIMS found for $C_{22}H_{24}F_2N_4O_2$ m/z 415.2 (M+1).

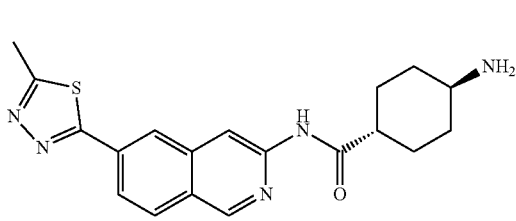

trans-4-Amino-N-(6-(5-methyl-1,3,4-thiadiazol-2-yl)isoquinolin-3-yl) cyclohexane-1-carboxamide 21.

White solid (210.0 mg, 0.572 mmol, 68.9% yield). $^1$H NMR (499 MHz, DMSO-$d_6$) δ ppm 0.99-1.12 (2H, m), 1.42-1.54 (2H, m), 1.57-1.72 (1H, m), 1.79-1.88 (4H, m), 2.45-2.55 (1H, m), 2.82 (3H, s), 8.08 (1H, dd, J=8.51, 1.65 Hz), 8.18 (1H, d, J=8.51 Hz), 8.43 (1H, s), 8.60 (1H, s), 9.20 (1H, s), 10.57 (1H, s); ESIMS found for $C_{19}H_{21}N_5OS$ m/z 368.2 (M+1).

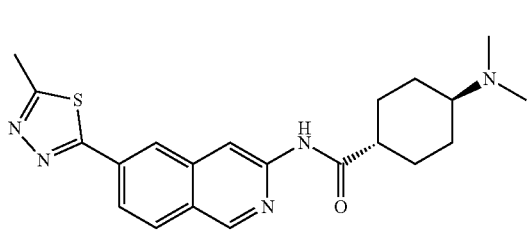

trans-4-(Dimethylamino)-N-(6-(5-methyl-1,3,4-thiadiazol-2-yl)isoquinolin-3-yl)cyclohexane-1-carboxamide 22.

White solid (22.0 mg, 0.056 mmol, 25.6% yield). $^1$H NMR (500 MHz, DMSO-$d_6$) δ ppm 1.13-1.26 (2H, m), 1.48 (2H, qd, J=12.67, 2.88 Hz), 1.83-1.90 (2H, m), 1.93 (2H, br d, J=11.53 Hz), 2.11-2.16 (1H, m), 2.18 (6H, s), 2.83 (3H, s), 8.08 (1H, dd, J=8.51, 1.65 Hz), 8.18 (1H, d, J=8.51 Hz), 8.43 (1H, d, J=0.82 Hz), 8.61 (1H, s), 9.21 (1H, s), 10.58 (1H, s); ESIMS found for $C_{21}H_{25}N_5OS$ m/z 396.2 (M+1).

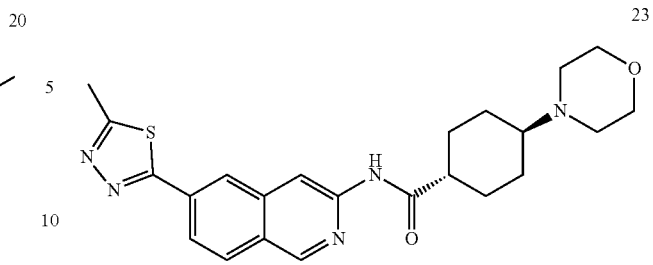

trans-N-(6-(5-Methyl-1,3,4-thiadiazol-2-yl)isoquinolin-3-yl)-4-morpholinocyclohexane-1-carboxamide 23.

Off-white solid (16.0 mg, 0.037 mmol, 13.4% yield). $^1$H NMR (499 MHz, DMSO-$d_6$) δ ppm 1.16-1.29 (2H, m), 1.43-1.56 (2H, m), 1.86-1.97 (4H, m), 2.17-2.26 (1H, m), 2.46-2.49 (4H, m), 2.51-2.54 (1H, m), 2.82 (3H, s), 3.52-3.60 (4H, m), 8.08 (1H, dd, J=8.51, 1.65 Hz), 8.18 (1H, d, J=8.51 Hz), 8.44 (1H, d, J=0.82 Hz), 8.61 (1H, s), 9.21 (1H, s), 10.59 (1H, s); ESIMS found for $C_{23}H_{27}N_5O_2S$ m/z 438.2 (M+1).

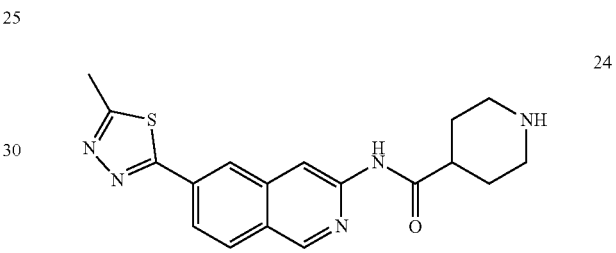

N-(6-(5-Methyl-1,3,4-thiadiazol-2-yl)isoquinolin-3-yl) piperidine-4-carboxamide 24.

Light green solid (105.0 mg, 0.297 mmol, 22.8% yield). $^1$H NMR (500 MHz, DMSO-$d_6$) δ ppm 1.93-2.02 (2H, m), 2.05-2.20 (5H, m), 2.22 (3H, s), 2.71-2.77 (2H, m), 2.83 (3H, s), 8.15 (1H, dd, J=8.64, 1.78 Hz), 8.24 (1H, d, J=8.51 Hz), 8.52 (1H, s), 8.59 (1H, s), 9.27 (1H, s), 10.08 (1H, d, J=4.12 Hz); ESIMS found for $C_{18}H_{19}N_5OS$ m/z 354.1 (M+1).

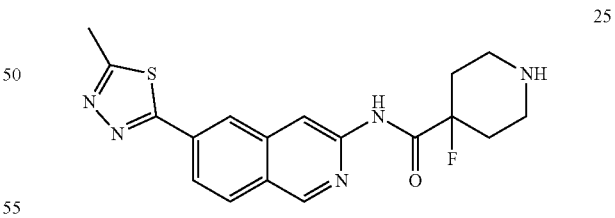

4-Fluoro-N-(6-(5-methyl-1,3,4-thiadiazol-2-yl)isoquinolin-3-yl)piperidine-4-carboxamide 25.

Beige solid (64.0 mg, 0.172 mmol, 45.1% yield). $^1$H NMR (499 MHz, DMSO-$d_6$) δ ppm 1.80-1.90 (2H, m), 1.98 (1H, td, J=12.97, 5.08 Hz), 2.06 (1H, td, J=12.97, 5.08 Hz), 2.19 (1H, br s), 2.75 (2H, td, J=12.21, 2.20 Hz), 2.83 (3H, s), 2.87-2.94 (2H, m), 8.15 (1H, dd, J=8.51, 1.65 Hz), 8.24 (1H, d, J=8.51 Hz), 8.53 (1H, d, J=0.82 Hz), 8.59 (1H, s), 9.26 (1H, s), 9.98 (1H, br d, J=3.57 Hz); ESIMS found for $C_{18}H_{18}FN_5OS$ m/z 372.1 (M+1).

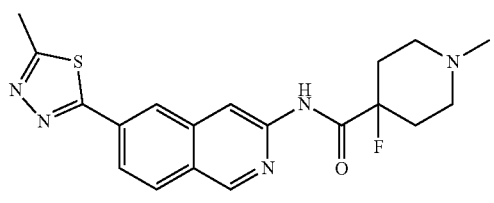

4-Fluoro-1-methyl-N-(6-(5-methyl-1,3,4-thiadiazol-2-yl)isoquinolin-3-yl) piperidine-4-carboxamide 26.

White solid (15.0 mg, 0.039 mmol, 24.1% yield). $^1$H NMR (499 MHz, METHANOL-d$_4$) δ ppm 2.02-2.10 (2H, m), 2.28-2.45 (4H, m), 2.36 (3H, s), 2.84-2.92 (2H, m), 2.86 (3H, s), 8.13-8.20 (2H, m), 8.42 (1H, s), 8.61 (1H, s), 9.15 (1H, s); ESIMS found for C$_{19}$H$_{20}$FN$_5$OS m/z 386.15 (M+1).

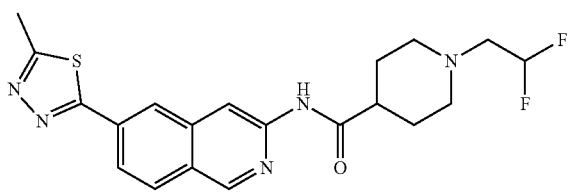

1-(2,2-Difluoroethyl)-N-(6-(5-methyl-1,3,4-thiadiazol-2-yl)isoquinolin-3-yl)piperidine-4-carboxamide 27.

Beige solid (20.0 mg, 0.048 mmol, 53.2% yield). $^1$H NMR (499 MHz, DMSO-d$_6$) δ ppm 1.62-1.74 (2H, m), 1.76-1.83 (2H, m), 2.14-2.25 (2H, m), 2.52-2.61 (1H, m), 2.73 (2H, td, J=15.71, 4.25 Hz), 2.83 (3H, s), 2.96 (2H, br d, J=11.53 Hz), 6.14 (1H, tt, J=56.10, 4.40 Hz), 8.09 (1H, dd, J=8.51, 1.65 Hz), 8.19 (1H, d, J=8.51 Hz), 8.45 (1H, s), 8.62 (1H, s), 9.21 (1H, s), 10.64 (1H, s); ESIMS found for C$_{20}$H$_{21}$F$_2$N$_5$OS m/z 418.1 (M+1).

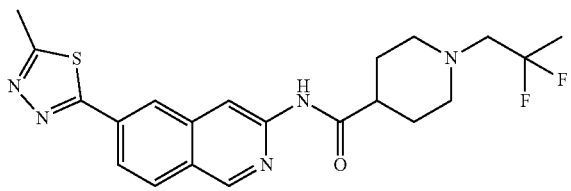

1-(2,2-Difluoropropyl)-N-(6-(5-methyl-1,3,4-thiadiazol-2-yl)isoquinolin-3-yl)piperidine-4-carboxamide 28.

Beige solid (3.0 mg, 0.007 mmol, 4.9% yield). $^1$H NMR (500 MHz, DMSO-d$_6$) δ ppm 1.63 (3H, t, J=19.07 Hz), 1.67-1.75 (2H, m), 1.75-1.81 (2H, m), 2.22 (2H, td, J=11.73, 2.33 Hz), 2.52-2.60 (1H, m), 2.71 (2H, t, J=14.00 Hz), 2.83 (3H, s), 2.92-2.99 (2H, m), 8.09 (1H, dd, J=8.51, 1.65 Hz), 8.19 (1H, d, J=8.78 Hz), 8.45 (1H, d, J=0.82 Hz), 8.62 (1H, s), 9.21 (1H, s), 10.64 (1H, s); ESIMS found for C$_{21}$H$_{23}$F$_2$N$_5$OS m/z 432.2 (M+1).

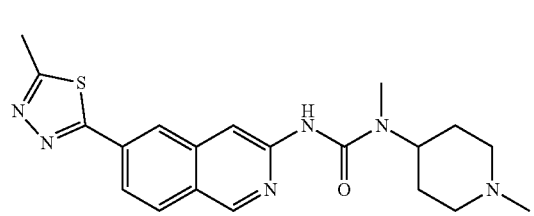

1-Methyl-3-(6-(5-methyl-1,3,4-thiadiazol-2-yl)isoquinolin-3-yl)-1-(1-methylpiperidin-4-yl)urea 29.

Beige solid (70.0 mg, 0.177 mmol, 10.7% yield). $^1$H NMR (499 MHz, DMSO-d$_6$) δ ppm 1.58 (2H, br d, J=10.98 Hz), 1.73-1.85 (2H, m), 2.18 (2H, br s), 2.29 (3H, br s), 2.82 (3H, s), 2.89 (3H, s), 2.91-3.01 (2H, m), 4.10-4.20 (1H, m), 8.02 (1H, dd, J=8.51, 1.65 Hz), 8.15 (1H, d, J=8.78 Hz), 8.32 (1H, s), 8.36 (1H, s), 9.00 (1H, s), 9.16 (1H, s); ESIMS found for C$_{20}$H$_{24}$N$_6$OS m/z 397.2 (M+1).

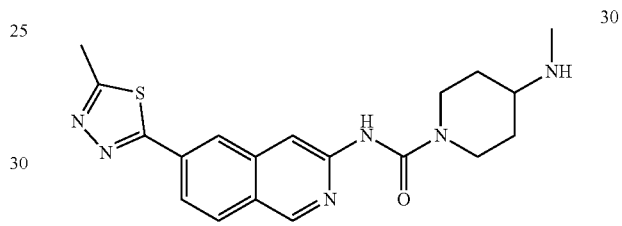

N-(6-(5-Methyl-1,3,4-thiadiazol-2-yl)isoquinolin-3-yl)-4-(methylamino) piperidine-1-carboxamide 30.

Beige solid (310.0 mg, 0.811 mmol, 96.6% yield). $^1$H NMR (499 MHz, DMSO-d$_6$) δ ppm 1.13-1.22 (2H, m), 1.77-1.86 (2H, m), 2.28 (3H, s), 2.43-2.49 (1H, m), 2.82 (3H, s), 2.92-3.02 (2H, m), 4.06 (2H, dt, J=13.45, 3.43 Hz), 8.01 (1H, dd, J=8.51, 1.65 Hz), 8.14 (1H, d, J=8.51 Hz), 8.30 (1H, s), 8.37 (1H, d, J=0.82 Hz), 9.15 (1H, s), 9.27 (1H, s); ESIMS found for C$_{19}$H$_{22}$N$_6$OS m/z 383.2 (M+1).

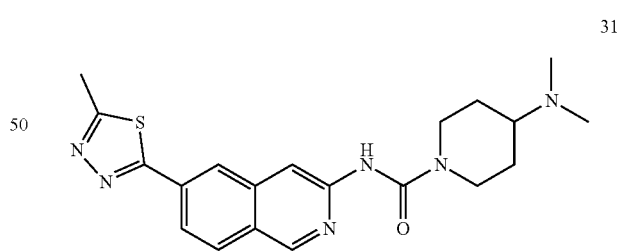

4-(Dimethylamino)-N-(6-(5-methyl-1,3,4-thiadiazol-2-yl)isoquinolin-3-yl) piperidine-1-carboxamide 31.

Off-white solid (55.0 mg, 0.139 mmol, 33.6% yield). $^1$H NMR (500 MHz, DMSO-d$_6$) δ ppm 1.32 (2H, qd, J=11.98, 3.84 Hz), 1.77 (2H, br d, J=10.70 Hz), 2.18 (6H, s), 2.29 (1H, tt, J=10.91, 3.50 Hz), 2.79-2.89 (2H, m), 2.82 (3H, s), 4.22 (2H, br d, J=13.17 Hz), 8.02 (1H, dd, J=8.64, 1.78 Hz), 8.15 (1H, d, J=8.51 Hz), 8.30 (1H, s), 8.37 (1H, d, J=0.82 Hz), 9.15 (1H, s), 9.31 (1H, s); ESIMS found for C$_{20}$H$_{24}$N$_6$OS m/z 397.2 (M+1).

32

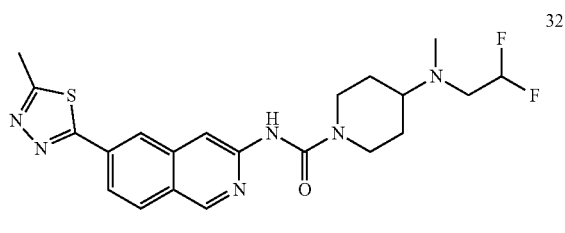 [SMILES: Cc1nnc(-c2ccc3cnc(NC(=O)N4CCC(N(C)CC(F)F)CC4)cc3c2)s1]

4-((2,2-Difluoroethyl)(methyl)amino)-N-(6-(5-methyl-1,3,4-thiadiazol-2-yl) isoquinolin-3-yl)piperidine-1-carboxamide 32.

Beige solid (25.0 mg, 0.056 mmol, 21.9% yield). $^1$H NMR (499 MHz, DMSO-d$_6$) δ ppm 1.55 (2H, br d, J=11.25 Hz), 1.75 (2H, qd, J=12.17, 3.84 Hz), 2.26-2.34 (2H, m), 2.74 (2H, td, J=15.64, 4.39 Hz), 2.82 (3H, s), 2.89 (3H, s), 2.98 (2H, br d, J=11.53 Hz), 4.07-4.18 (1H, m), 6.13 (1H, tt, J=55.80, 4.40 Hz), 8.02 (1H, dd, J=8.51, 1.65 Hz), 8.15 (1H, d, J=8.51 Hz), 8.33 (1H, s), 8.36 (1H, s), 9.00 (1H, s), 9.16 (1H, s); ESIMS found for C$_{21}$H$_{24}$F$_2$N$_6$OS m/z 447.2 (M+1).

33

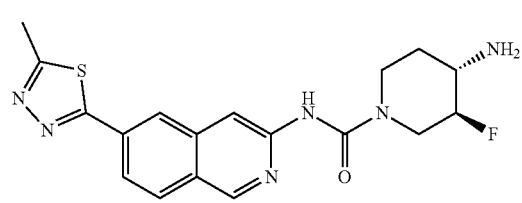

(3S,4S)-4-Amino-3-fluoro-N-(6-(5-methyl-1,3,4-thiadiazol-2-yl)isoquinolin-3-yl)piperidine-1-carboxamide 33.

Beige solid (38.0 mg, 0.098 mmol, 95.7% yield). $^1$H NMR (499 MHz, DMSO-d$_6$) δ ppm 1.28-1.39 (1H, m), 1.84 (2H, dt, J=13.10, 4.01 Hz), 2.82 (3H, s), 2.85-2.94 (1H, m), 3.10-3.24 (2H, m), 3.84-3.94 (1H, m), 4.11-4.29 (2H, m), 8.03 (1H, dd, J=8.51, 1.65 Hz), 8.16 (1H, d, J=8.51 Hz), 8.30 (1H, s), 8.39 (1H, s), 9.17 (1H, s), 9.45 (1H, s); ESIMS found for C$_{18}$H$_{19}$FN$_6$OS m/z 387.1 (M+1).

34

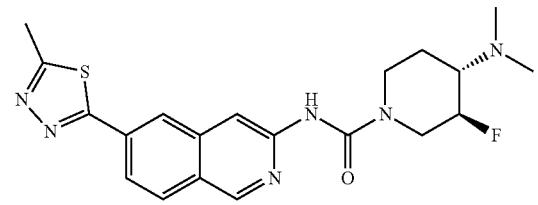

(3S,4S)-4-(Dimethylamino)-3-fluoro-N-(6-(5-methyl-1,3,4-thiadiazol-2-yl) isoquinolin-3-yl)piperidine-1-carboxamide 34.

Off-white solid (25.0 mg, 0.060 mmol, 66.6% yield). $^1$H NMR (499 MHz, DMSO-d$_6$) δ ppm 1.41-1.54 (1H, m), 1.74-1.84 (1H, m), 2.28 (6H, s), 2.64 (1H, tdd, J=10.94, 10.94, 8.71, 4.53 Hz), 2.82 (3H, s), 2.93-3.02 (1H, m), 3.05 (1H, ddd, J=12.97, 9.13, 5.63 Hz), 4.00-4.11 (1H, m), 4.25-4.35 (1H, m), 4.63 (1H, dsxt, J=49.00, 4.10, 4.10, 4.10, 4.10, 4.10 Hz), 8.03 (1H, dd, J=8.51, 1.65 Hz), 8.16 (1H, d, J=8.78 Hz), 8.30 (1H, s), 8.39 (1H, d, J=0.82 Hz), 9.17 (1H, s), 9.48 (1H, s); ESIMS found for C$_{20}$H$_{23}$FN$_6$OS m/z 415.2 (M+1).

35

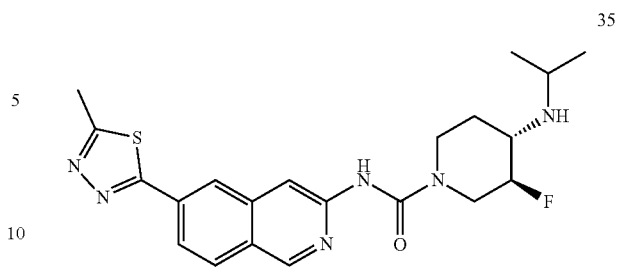

(3S,4S)-3-Fluoro-4-(isopropylamino)-N-(6-(5-methyl-1,3,4-thiadiazol-2-yl) isoquinolin-3-yl)piperidine-1-carboxamide 35.

Off-white solid (40.0 mg, 0.093 mmol, 56.4% yield). $^1$H NMR (500 MHz, DMSO-d$_6$) δ ppm 0.98 (3H, d, J=6.31 Hz), 1.01 (3H, d, J=6.04 Hz), 1.25-1.38 (1H, m), 1.86-1.95 (1H, m), 2.82 (3H, s), 2.86-2.97 (2H, m), 3.22-3.29 (1H, m), 3.34-3.44 (1H, m), 3.75-3.83 (1H, m), 4.04 (1H, ddd, J=17.91, 14.07, 3.43 Hz), 4.25-4.42 (1H, m), 8.03 (1H, dd, J=8.51, 1.65 Hz), 8.16 (1H, d, J=8.51 Hz), 8.29 (1H, s), 8.39 (1H, s), 9.17 (1H, s), 9.43 (1H, s); ESIMS found for C$_{21}$H$_{25}$FN$_6$OS m/z 429.2 (M+1).

36

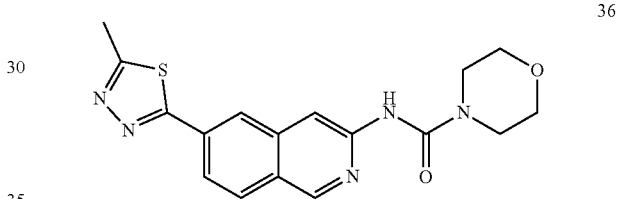

N-(6-(5-Methyl-1,3,4-thiadiazol-2-yl)isoquinolin-3-yl)morpholine-4-carboxamide 36.

Beige solid (30.0 mg, 0.084 mmol, 20.5% yield). $^1$H NMR (499 MHz, DMSO-d$_6$) δ ppm 2.82 (3H, s), 3.48-3.54 (4H, m), 3.59-3.66 (4H, m), 8.03 (1H, dd, J=8.51, 1.65 Hz), 8.16 (1H, d, J=8.78 Hz), 8.32 (1H, s), 8.39 (1H, s), 9.17 (1H, s), 9.37 (1H, s); ESIMS found for C$_{17}$H$_{17}$N$_5$O$_2$S m/z 356.1 (M+1).

37

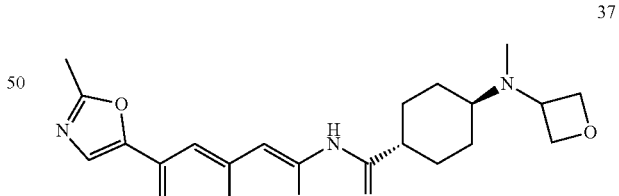

trans-4-(Methyl(oxetan-3-yl)amino)-N-(6-(2-methyloxazol-5-yl)isoquinolin-3-yl)cyclohexane-1-carboxamide 37.

White solid (6.0 mg, 0.014 mmol, 8.7% yield). $^1$H NMR (500 MHz, DMSO-d$_6$) δ ppm 1.16-1.30 (2H, m), 1.47 (2H, qd, J=12.72, 2.74 Hz), 1.68 (2H, br d, J=10.15 Hz), 1.85-1.94 (2H, m), 2.12 (3H, s), 2.30 (2H, tt, J=11.53, 3.02 Hz), 2.41-2.48 (1H, m), 2.53 (3H, s), 3.90 (1H, quin, J=6.86 Hz), 4.43-4.53 (4H, m), 7.78 (1H, s), 7.80 (1H, dd, J=8.64, 1.51 Hz), 8.05-8.12 (2H, m), 8.49 (1H, s), 9.10 (1H, s), 10.50 (1H, s); ESIMS found for C$_{24}$H$_{28}$N$_4$O$_3$ m/z 421.2 (M+1).

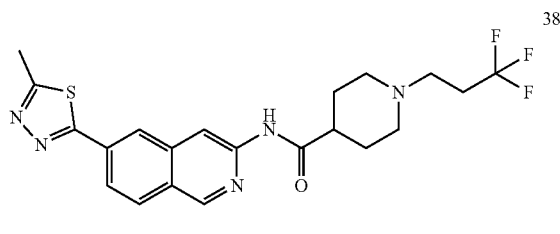 [SMILES: Cc1nnc(-c2ccc3cnc(NC(=O)C4CCN(CCC(F)(F)F)CC4)cc3c2)s1]

N-(6-(5-Methyl-1,3,4-thiadiazol-2-yl)isoquinolin-3-yl)-1-(3,3,3-trifluoropropyl)piperidine-4-carboxamide 38.

White solid (150.0 mg, 0.334 mmol, 41.7% yield). $^1$H NMR (499 MHz, DMSO-$d_6$) δ ppm 1.62-1.73 (2H, m), 1.81 (2H, br d, J=10.98 Hz), 1.93-2.01 (2H, m), 2.41-2.61 (5H, m), 2.83 (3H, s), 2.94 (2H, br d, J=11.53 Hz), 8.09 (1H, dd, J=8.51, 1.65 Hz), 8.19 (1H, d, J=8.51 Hz), 8.44 (1H, s), 8.62 (1H, s), 9.21 (1H, s), 10.64 (1H, s); ESIMS found for $C_{21}H_{22}F_3N_5OS$ m/z 450.2 (M+1).

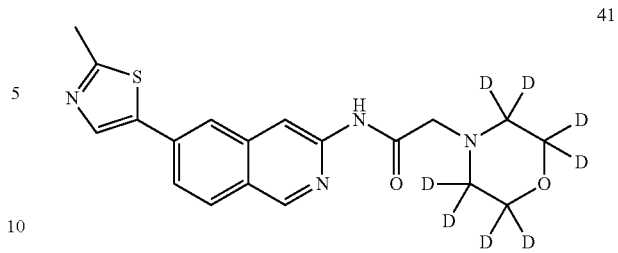

N-(6-(2-Methylthiazol-5-yl)isoquinolin-3-yl)-2-(morpholino-$d_8$)acetamide 41.

White solid (12.0 mg, 0.032 mmol, 11.4% yield). $^1$H NMR (499 MHz, DMSO-$d_6$) δ ppm 2.72 (3H, s), 3.25 (2H, s), 7.82 (1H, dd, J=8.51, 1.65 Hz), 8.10 (1H, d, J=8.51 Hz), 8.15 (1H, s), 8.30 (1H, s), 8.50 (1H, s), 9.12 (1H, s), 10.08 (1H, s); ESIMS found for $C_{19}H_{12}[^2H_8]N_4O_2S$ m/z 377.2 M+1).

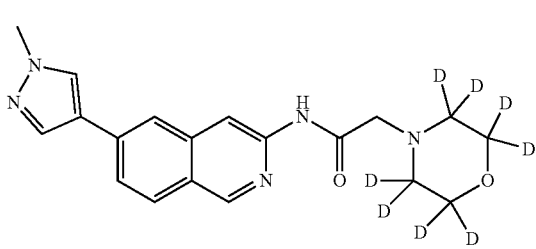

N-(6-(1-Methyl-1H-pyrazol-4-yl)isoquinolin-3-yl)-2-(morpholino-$d_8$) acetamide 39.

White solid (65.0 mg, 0.181 mmol, 64.8% yield). $^1$H NMR (499 MHz, DMSO-$d_6$) δ ppm 3.24 (2H, s), 3.90 (3H, s), 7.77 (1H, dd, J=8.51, 1.65 Hz), 8.02 (1H, d, J=8.51 Hz), 8.10 (2H, s), 8.37 (1H, s), 8.44 (1H, s), 9.04 (1H, s), 10.00 (1H, s); ESIMS found for $C_{19}H_{13}[^2H_8]N_5O_2$ m/z 360.2 (M+1).

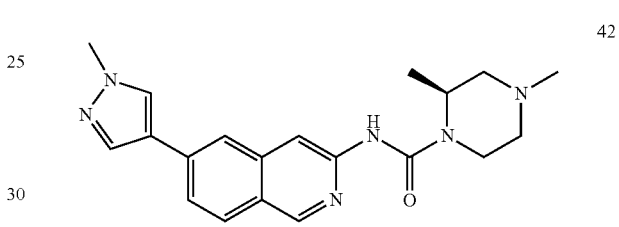

(S)-2,4-Dimethyl-N-(6-(1-methyl-1H-pyrazol-4-yl)isoquinolin-3-yl) piperazine-1-carboxamide 42.

Yellow solid (7.0 mg, 0.019 mmol, 4.3% yield). $^1$H NMR (500 MHz, DMSO-$d_6$) δ ppm 1.22 (3H, d, J=6.59 Hz), 1.85 (1H, td, J=11.66, 3.29 Hz), 2.04 (1H, dd, J=11.11, 3.70 Hz), 2.17 (3H, s), 2.63 (1H, br d, J=10.98 Hz), 2.72-2.79 (1H, m), 3.10 (1H, td, J=12.62, 3.29 Hz), 3.90 (3H, s), 3.95 (1H, br d, J=13.17 Hz), 4.38-4.46 (1H, m), 7.68 (1H, dd, J=8.37, 1.51 Hz), 7.96 (1H, d, J=8.51 Hz), 7.98 (1H, s), 8.06 (1H, s), 8.14 (1H, s), 8.33 (1H, s), 8.97 (1H, s), 9.01 (1H, s); ESIMS found for $C_{20}H_{24}N_6O$ m/z 365.2 (M+1).

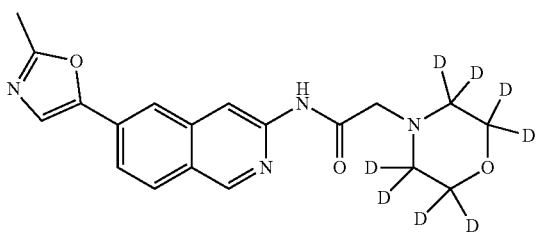

N-(6-(2-Methyloxazol-5-yl)isoquinolin-3-yl)-2-(morpholino-$d_8$)acetamide 40.

Off-white solid (72.0 mg, 0.200 mmol, 71.6% yield). $^1$H NMR (499 MHz, DMSO-$d_6$) δ ppm 2.53 (3H, s), 3.25 (2H, s), 7.80 (1H, s), 7.84 (1H, dd, J=8.51, 1.65 Hz), 8.12 (1H, d, J=8.78 Hz), 8.16 (1H, s), 8.51 (1H, s), 9.13 (1H, s), 10.08 (1H, s); ESIMS found for $C_{19}H_{12}[^2H_8]N_4O_3$ m/z 361.2 (M+1).

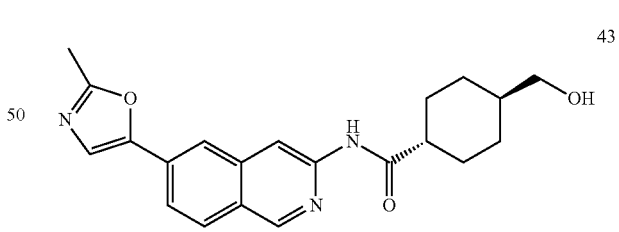

trans-4-(Hydroxymethyl)-N-(6-(2-methyloxazol-5-yl)isoquinolin-3-yl) cyclohexane-1-carboxamide 43.

White solid (355.0 mg, 0.972 mmol, 49.1% yield). $^1$H NMR (500 MHz, DMSO-$d_6$) δ ppm 0.95 (2H, qd, J=12.76, 2.88 Hz), 1.31-1.40 (1H, m), 1.45 (2H, qd, J=12.67, 3.43 Hz), 1.80 (2H, br dd, J=13.17, 2.47 Hz), 1.88 (2H, br dd, J=13.04, 2.61 Hz), 2.42-2.48 (1 H, m), 2.53 (3H, s), 3.24 (2H, t, J=5.76 Hz), 4.39 (1H, t, J=5.35 Hz), 7.79 (1H, s), 7.79-7.84 (1H, m), 8.09 (1H, s), 8.10 (1H, d, J=6.04 Hz), 8.50 (1H, s), 9.10 (1H, s), 10.49 (1H, s); ESIMS found for $C_{21}H_{23}N_3O_3$ m/z 366.2 (M+1).

44

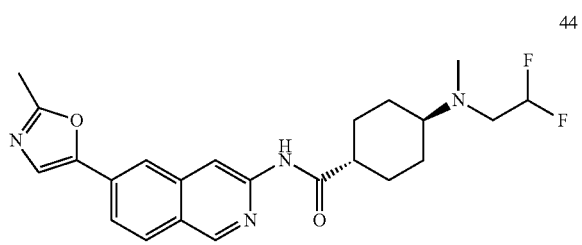 [SMILES: Cc1ncc(-c2ccc3cnc(NC(=O)[C@H]4CC[C@H](N(C)CC(F)F)CC4)cc3c2)o1]

trans-4-((2,2-Difluoroethyl)(methyl)amino)-N-(6-(2-methyloxazol-5-yl) isoquinolin-3-yl)cyclohexane-1-carboxamide 44.

White solid (35.0 mg, 0.082 mmol, 62.0% yield). $^1$H NMR (499 MHz, DMSO-d$_6$) δ ppm 1.24 (2H, qd, J=12.44, 3.29 Hz), 1.49 (2H, qd, J=12.67, 2.88 Hz), 1.80 (2H, br d, J=10.15 Hz), 1.92 (2H, br d, J=11.80 Hz), 2.30 (3H, s), 2.39-2.48 (2H, m), 2.53 (3H, s), 2.77 (2H, td, J=15.51, 4.39 Hz), 6.00 (1H, tt, J=56.40, 4.10 Hz), 7.78 (1H, s), 7.79-7.84 (1H, m), 8.07-8.12 (2H, m), 8.50 (1H, s), 9.10 (1H, s), 10.51 (1H, s); ESIMS found for C$_{23}$H$_{26}$F$_2$N$_4$O$_2$ m/z 429.2 (M+1).

45

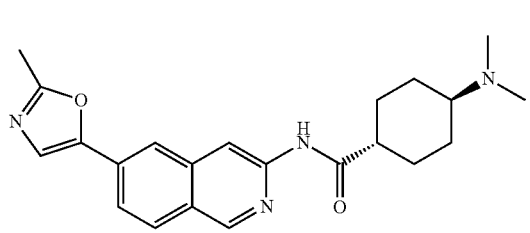

trans-4-(Dimethylamino)-N-(6-(2-methyloxazol-5-yl)isoquinolin-3-yl) cyclohexane-1-carboxamide 45.

Beige solid (92.0 mg, 0.243 mmol, 45.7% yield). $^1$H NMR (499 MHz, DMSO-d$_6$) δ ppm 1.13-1.23 (2H, m), 1.42-1.53 (2H, m), 1.82-1.95 (4H, m), 2.10-2.16 (1H, m), 2.18 (6H, s), 2.43-2.49 (1H, m), 2.53 (3H, s), 7.78 (1H, s), 7.79-7.84 (1H, m), 8.05-8.12 (2H, m), 8.50 (1H, s), 9.10 (1H, s), 10.49 (1H, s); ESIMS found for C$_{22}$H$_{26}$N$_4$O$_2$ m/z 379.2 (M+1).

46

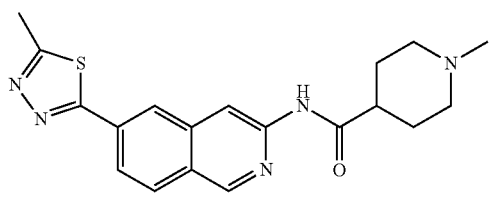

1-Methyl-N-(6-(5-methyl-1,3,4-thiadiazol-2-yl)isoquinolin-3-yl)piperidine-4-carboxamide 46.

Beige solid (102.0 mg, 0.278 mmol, 33.6% yield). $^1$H NMR (499 MHz, DMSO-d$_6$) δ ppm 1.61-1.73 (2H, m), 1.75-1.81 (2H, m), 1.83-1.92 (2H, m), 2.16 (3H, s), 2.51-2.56 (1H, m), 2.77-2.87 (2H, m), 2.83 (3H, s), 8.09 (1H, dd, J=8.51, 1.37 Hz), 8.19 (1H, d, J=8.51 Hz), 8.44 (1H, s), 8.62 (1H, s), 9.21 (1H, s), 10.63 (1H, s); ESIMS found for C$_{19}$H$_{21}$N$_5$OS m/z 368.15 (M+1).

47

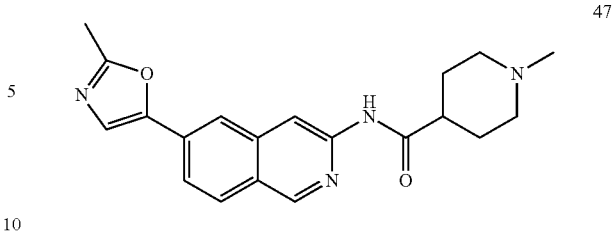

1-Methyl-N-(6-(2-methyloxazol-5-yl)isoquinolin-3-yl)piperidine-4-carboxamide 47.

Beige solid (240.0 mg, 0.685 mmol, 77.1% yield). $^1$H NMR (499 MHz, DMSO-d$_6$) δ ppm 1.61-1.73 (2H, m), 1.74-1.81 (2H, m), 1.86 (2H, td, J=11.66, 2.47 Hz), 2.16 (3H, s), 2.46-2.52 (1H, m), 2.53 (3H, s), 2.77-2.85 (2H, m), 7.78 (1H, s), 7.81 (1H, dd, J=8.64, 1.51 Hz), 8.05-8.12 (2H, m), 8.50 (1H, s), 9.10 (1H, s), 10.54 (1H, s); ESIMS found for C$_{20}$H$_{22}$N$_4$O$_2$ m/z 351.2 (M+1).

48

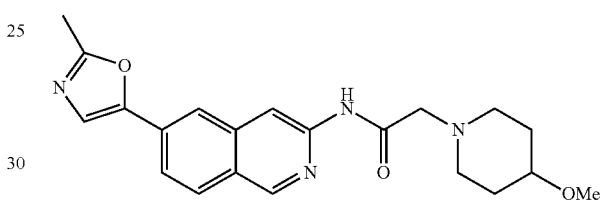

2-(4-Methoxypiperidin-1-yl)-N-(6-(2-methyloxazol-5-yl) isoquinolin-3-yl) acetamide 48.

White solid (45.0 mg, 0.118 mmol, 44.7% yield). $^1$H NMR (499 MHz, DMSO-d$_6$) δ ppm 1.46-1.58 (2H, m), 1.83-1.93 (2H, m), 2.32-2.41 (2H, m), 2.53 (3H, s), 2.73-2.82 (2H, m), 3.21 (2H, s), 3.22-3.24 (1H, m), 3.24 (3H, s), 7.80 (1H, s), 7.83 (1H, dd, J=8.64, 1.51 Hz), 8.12 (1H, d, J=8.51 Hz), 8.16 (1H, s), 8.50 (1H, s), 9.12 (1H, s), 10.01 (1H, s); ESIMS found for C$_{21}$H$_{24}$N$_4$O$_3$ m/z 381.2 (M+1).

49

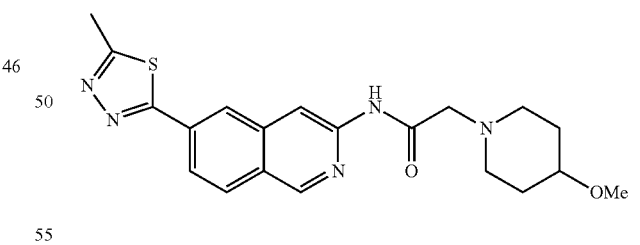

2-(4-Methoxypiperidin-1-yl)-N-(6-(5-methyl-1,3,4-thiadiazol-2-yl) isoquinolin-3-yl)acetamide 49.

Beige solid (50.0 mg, 0.126 mmol, 23.8% yield). $^1$H NMR (499 MHz, DMSO-d$_6$) δ ppm 1.47-1.57 (2H, m), 1.84-1.92 (2H, m), 2.34-2.42 (2H, m), 2.73-2.81 (2H, m), 2.83 (3H, s), 3.20-3.26 (1H, m), 3.23 (2H, s), 3.24 (3H, s), 8.12 (1H, dd, J=8.64, 1.78 Hz), 8.21 (1H, d, J=8.51 Hz), 8.50 (1H, d, J=0.82 Hz), 8.61 (1H, s), 9.23 (1H, s), 10.10 (1H, s); ESIMS found for C$_{20}$H$_{23}$N$_5$O$_2$S m/z 398.2 (M+1).

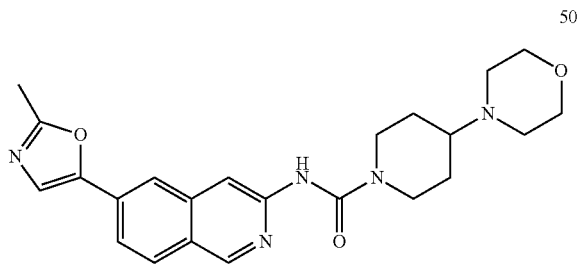 [SMILES: Cc1ncc(-c2ccc3cnc(NC(=O)N4CCC(N5CCOCC5)CC4)cc3c2)o1]

N-(6-(2-Methyloxazol-5-yl)isoquinolin-3-yl)-4-morpholinopiperidine-1-carboxamide 50.

Off-white solid (25.0 mg, 0.059 mmol, 13.4% yield). $^1$H NMR (499 MHz, DMSO-$d_6$) δ ppm 1.27-1.41 (2H, m), 1.76-1.84 (2H, m), 2.36 (1H, tt, J=10.94, 3.60 Hz), 2.44-2.49 (4H, m), 2.53 (3H, s), 2.83 (2H, brt, J=11.66 Hz), 3.52-3.60 (4H, m), 4.17-4.27 (2H, m), 7.74 (1H, dd, J=8.51, 1.65 Hz), 7.76 (1H, s), 8.04 (1H, s), 8.06 (1H, d, J=8.51 Hz), 8.19 (1H, s), 9.05 (1H, s), 9.20 (1H, s); ESIMS found for $C_{23}H_{27}N_5O_3$ m/z 422.2 (M+1).

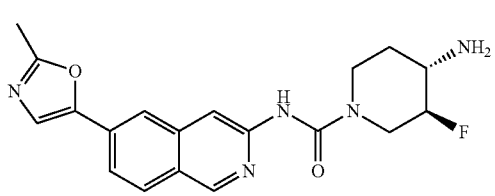

(3S,4S)-4-Amino-3-fluoro-N-(6-(2-methyloxazol-5-yl) isoquinolin-3-yl) piperidine-1-carboxamide 51.

Off-white solid (55.0 mg, 0.149 mmol, 61.9% yield). $^1$H NMR (500 MHz, DMSO-$d_6$) δ ppm 1.27-1.38 (1H, m), 1.77-1.88 (1H, m), 2.00 (2H, br s), 2.53 (3H, s), 2.83-2.94 (1H, m), 3.07-3.22 (2H, m), 3.85-3.95 (1H, m), 4.11-4.29 (2H, m), 7.75 (1H, dd, J=8.64, 1.78 Hz), 7.77 (1H, s), 8.05 (1H, s), 8.07 (1H, d, J=8.51 Hz), 8.19 (1H, s), 9.06 (1H, s), 9.37 (1H, s); ESIMS found for $C_{19}H_{20}FN_5O_2$ m/z 370.2 (M+1).

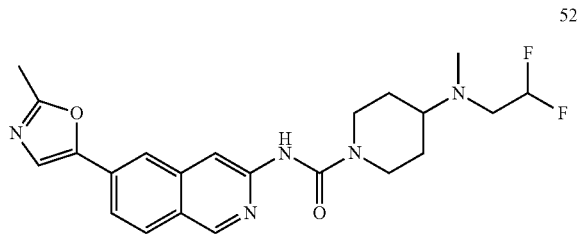 [SMILES: Cc1ncc(-c2ccc3cnc(NC(=O)N4CCC(N(C)CC(F)F)CC4)cc3c2)o1]

4-((2,2-Difluoroethyl)(methyl)amino)-N-(6-(2-methyloxazol-5-yl) isoquinolin-3-yl)piperidine-1-carboxamide 52.

Beige solid (35.0 mg, 0.082 mmol, 18.4% yield). $^1$H NMR (499 MHz, DMSO-$d_6$) δ ppm 1.29-1.41 (2H, m), 1.71 (2H, br dd, J=12.35, 1.37 Hz), 2.30 (3H, s), 2.53 (3H, s), 2.58-2.67 (2H, m), 2.73-2.85 (4H, m), 4.27 (2H, br d, J=13.72 Hz), 6.01 (1H, tt, J=56.10, 4.40 Hz), 7.74 (1H, dd, J=8.51, 1.65 Hz), 7.76 (1H, s), 8.04 (1H, s), 8.06 (1H, d, J=8.51 Hz), 8.20 (1H, s), 9.05 (1H, s), 9.20 (1H, s); ESIMS found for $C_{22}H_{25}F_2N_5O_2$ m/z 430.2 (M+1).

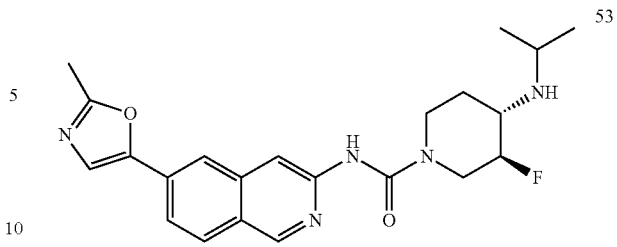

(3S,4S)-3-Fluoro-4-(isopropylamino)-N-(6-(2-methyloxazol-5-yl) isoquinolin-3-yl)piperidine-1-carboxamide 53.

Off-white solid (17.0 mg, 0.041 mmol, 47.7% yield). $^1$H NMR (499 MHz, DMSO-$d_6$) δ ppm 0.98 (3H, d, J=6.04 Hz), 1.01 (3H, d, J=6.31 Hz), 1.26-1.37 (1H, m), 1.55 (1H, br s), 1.85-1.95 (1H, m), 2.53 (3H, s), 2.83-2.97 (2H, m), 3.24 (1H, ddd, J=13.24, 9.67, 3.16 Hz), 3.35-3.40 (1H, m), 3.74-3.83 (1H, m), 3.98-4.10 (1H, m), 4.33 (1H, dsxt, J=48.10, 3.60, 3.60, 3.60, 3.60, 3.60 Hz), 7.75 (1H, dd, J=8.64, 1.51 Hz), 7.77 (1H, s), 8.05 (1H, br s), 8.06 (1H, d, J=8.51 Hz), 8.19 (1H, s), 9.06 (1H, s), 9.32 (1H, s); ESIMS found for $C_{22}H_{26}FN_5O_2$ m/z 412.2 (M+1).

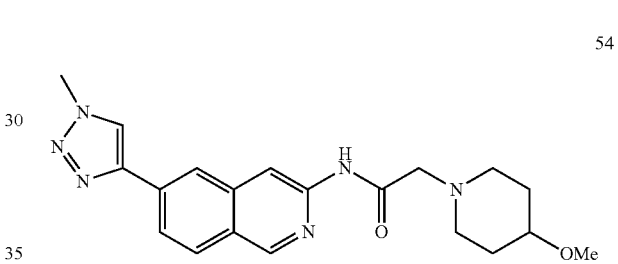

2-(4-Methoxypiperidin-1-yl)-N-(6-(1-methyl-1H-1,2,3-triazol-4-yl) isoquinolin-3-yl)acetamide 54.

White solid (60.0 mg, 0.158 mmol, 23.9% yield). $^1$H NMR (500 MHz, DMSO-$d_6$) δ ppm 1.47-1.58 (2H, m), 1.89 (2H, br dd, J=9.19, 3.98 Hz), 2.32-2.41 (2H, m), 2.74-2.82 (2H, m), 3.20-3.27 (1H, m), 3.22 (2H, s), 3.24 (3H, s), 4.14 (3H, s), 8.04 (1H, dd, J=8.51, 1.65 Hz), 8.13 (1H, d, J=8.51 Hz), 8.33 (1H, s), 8.50 (1H, s), 8.74 (1H, s), 9.13 (1H, s), 10.01 (1H, s); ESIMS found for $C_{20}H_{24}N_6O_2$ m/z 381.2 (M+1).

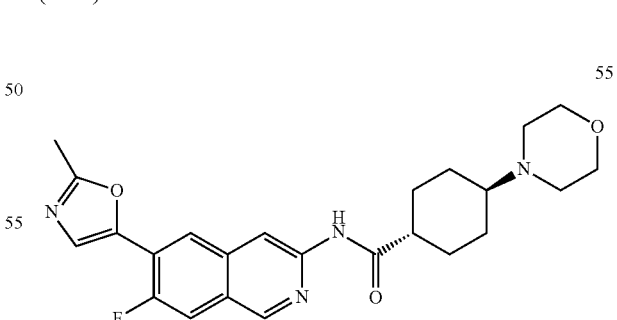

trans-N-(7-Fluoro-6-(2-methyloxazol-5-yl)isoquinolin-3-yl)-4-morpholinocyclohexane-1-carboxamide 55.

Beige solid (98.0 mg, 0.224 mmol, 82.3% yield). $^1$H NMR (500 MHz, DMSO-$d_6$) δ ppm 1.17-1.28 (2H, m), 1.43-1.54 (2H, m), 1.86-1.96 (4H, m), 2.16-2.26 (1H, m), 2.44-2.49 (5H, m), 2.56 (3H, s), 3.53-3.61 (4H, m), 7.60 (1H, d, J=4.39 Hz), 8.01 (1H, d, J=11.53 Hz), 8.23 (1H, d, J=6.86 Hz), 8.56 (1H, s), 9.10 (1H, s), 10.54 (1H, s); ESIMS found for C$_{24}$H$_{27}$FN$_4$O$_3$ m/z 439.2 (M+1).

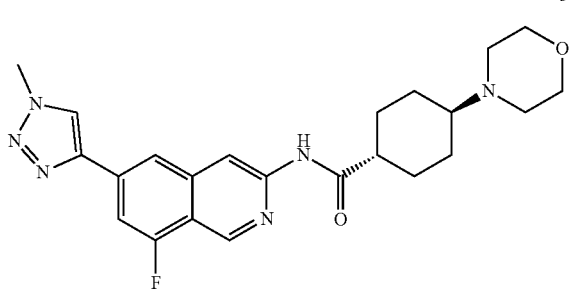

56 trans-N-(8-Fluoro-6-(1-methyl-1H-1,2,3-triazol-4-yl)isoquinolin-3-yl)-4-morpholinocyclohexane-1-carboxamide 56.

Off-white solid (54.0 mg, 0.123 mmol, 36.2% yield). $^1$H NMR (499 MHz, DMSO-d$_6$) δ ppm 1.16-1.31 (2H, m), 1.42-1.54 (2H, m), 1.86-1.99 (4H, m), 2.17-2.27 (1H, m), 2.48 (4H, br s), 2.52-2.55 (1H, m), 3.56 (4H, br s), 4.14 (3H, s), 7.77 (1H, dd, J=11.53, 1.10 Hz), 8.16 (1H, s), 8.56 (1H, s), 8.76 (1H, s), 9.24 (1H, s), 10.66 (1H, s); ESIMS found for C$_{23}$H$_{27}$FN$_6$O$_2$ m/z 439.2 (M+1).

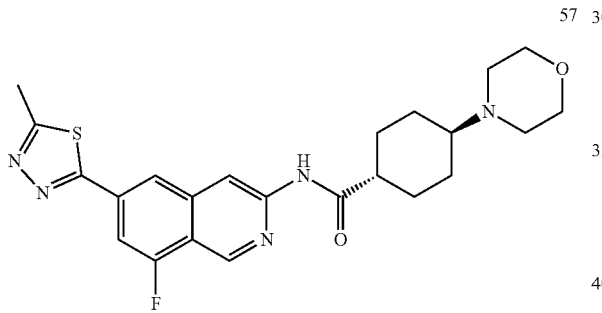

57 trans-N-(8-Fluoro-6-(5-methyl-1,3,4-thiadiazol-2-yl)isoquinolin-3-yl)-4-morpholinocyclohexane-1-carboxamide 57.

Off-white solid (46.0 mg, 0.155 mmol, 29.7% yield). $^1$H NMR (499 MHz, DMSO-d$_6$) δ ppm 1.17-1.30 (2H, m), 1.42-1.55 (2H, m), 1.86-1.99 (4H, m), 2.17-2.27 (1H, m), 2.48 (4H, br s), 2.51-2.56 (1H, m), 2.83 (3H, s), 3.52-3.62 (4H, m), 7.85 (1H, dd, J=11.11, 1.24 Hz), 8.34 (1H, s), 8.68 (1H, s), 9.32 (1H, s), 10.75 (1H, s); ESIMS found for C$_{23}$H$_{26}$FN$_5$O$_2$S m/z 456.2 (M+1).

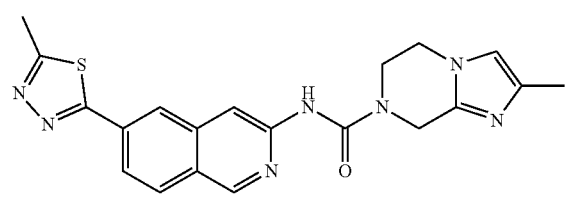

58

2-Methyl-N-(6-(5-methyl-1,3,4-thiadiazol-2-yl)isoquinolin-3-yl)-5,6-dihydroimidazo[1,2-a]pyrazine-7(8H)-carboxamide 58.

Beige solid (55.0 mg, 0.136 mmol, 32.9% yield). $^1$H NMR (499 MHz, DMSO-d$_6$) δ ppm 2.07 (3H, s), 2.82 (3H, s), 3.91-3.97 (2H, m), 3.97-4.03 (2H, m), 4.68 (2H, s), 6.79 (1H, s), 8.05 (1H, dd, J=8.51, 1.65 Hz), 8.17 (1H, d, J=8.78 Hz), 8.33 (1H, s), 8.40 (1H, s), 9.19 (1H, s), 9.71 (1H, s); ESIMS found for C$_{20}$H$_{19}$N$_7$OS m/z 406.15 (M+1).

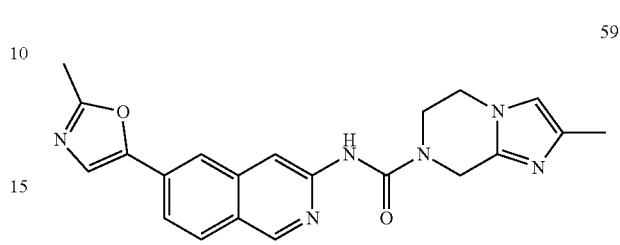

59

2-Methyl-N-(6-(2-methyloxazol-5-yl)isoquinolin-3-yl)-5,6-dihydroimidazo[1,2-a]pyrazine-7(8H)-carboxamide 59.

White solid (61.0 mg, 0.157 mmol, 35.4% yield). $^1$H NMR (499 MHz, DMSO-d$_6$) δ ppm 2.07 (3H, d, J=0.82 Hz), 2.53 (3H, s), 3.89-3.96 (2H, m), 3.96-4.02 (1H, m), 4.67 (2H, s), 6.78 (1H, d, J=0.82 Hz), 7.77 (1H, dd, J=8.51, 1.65 Hz), 7.77 (1H, s), 8.06 (1H, s), 8.08 (1H, d, J=8.51 Hz), 8.22 (1H, s), 9.09 (1H, s), 9.61 (1H, s); ESIMS found for C$_{21}$H$_{20}$N$_6$O$_2$ m/z 389.2 (M+1).

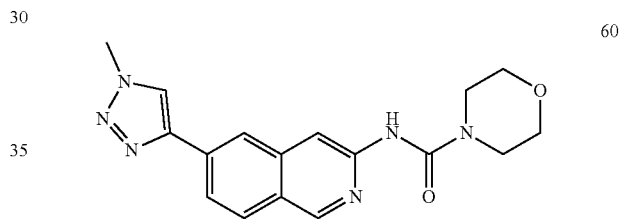

60

N-(6-(1-Methyl-1H-1,2,3-triazol-4-yl)isoquinolin-3-yl)morpholine-4-carboxamide 60.

Beige solid (40.0 mg, 0.118 mmol, 26.6% yield). $^1$H NMR (499 MHz, DMSO-d$_6$) δ ppm 3.49-3.54 (4H, m), 3.60-3.65 (4H, m), 4.14 (3H, s), 7.95 (1H, dd, J=8.51, 1.65 Hz), 8.08 (1H, d, J=8.51 Hz), 8.21 (1H, s), 8.23 (1H, s), 8.71 (1H, s), 9.07 (1H, s), 9.25 (1H, s); ESIMS found for C$_{17}$H$_{18}$N$_6$O$_2$ m/z 339.15 (M+1).

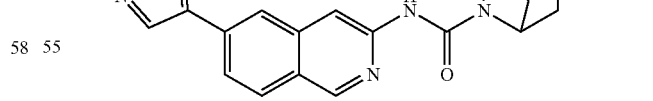

61

3-Methyl-N-(6-(1-methyl-1H-pyrazol-4-yl)isoquinolin-3-yl)-3,8-diazabicyclo[3.2.1]octane-8-carboxamide 61.

Yellow solid (25.0 mg, 0.066 mmol, 14.9% yield). $^1$H NMR (499 MHz, DMSO-d$_6$) δ ppm 1.73-1.86 (4H, m), 2.15 (3H, s), 2.16 (2H, br d, J=11.25 Hz), 2.61 (2H, dd, J=10.84, 2.33 Hz), 3.90 (3H, s), 4.48 (2H, br s), 7.68 (1H, dd, J=8.37, 1.51 Hz), 7.96 (1H, d, J=8.51 Hz), 7.98 (1H, s), 8.06 (1H, s), 8.22 (1H, s), 8.33 (1H, s), 8.97 (1H, s), 9.14 (1H, s); ESIMS found for C$_{21}$H$_{24}$N$_6$O m/z 377.2 (M+1).

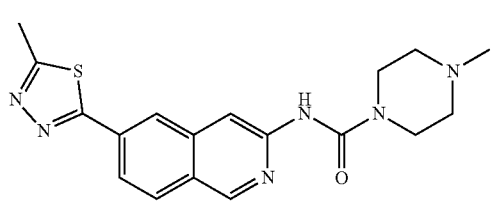

4-Methyl-N-(6-(5-methyl-1,3,4-thiadiazol-2-yl)isoquinolin-3-yl)piperazine-1-carboxamide 62.

Beige solid (20.0 mg, 0.054 mmol, 6.6% yield). $^1$H NMR (499 MHz, DMSO-$d_6$) δ ppm 2.20 (3H, s), 2.29-2.35 (4H, m), 2.82 (3H, s), 3.49-3.56 (4H, m), 8.02 (1H, dd, J=8.51, 1.65 Hz), 8.15 (1H, d, J=8.78 Hz), 8.31 (1H, s), 8.38 (1H, s), 9.16 (1H, s), 9.33 (1H, s); ESIMS found for $C_{18}H_{20}N_6OS$ m/z 369.1 (M+1).

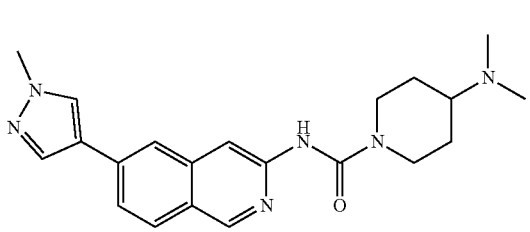

4-(Dimethylamino)-N-(6-(1-methyl-1H-pyrazol-4-yl)isoquinolin-3-yl) piperidine-1-carboxamide 63.

Beige solid (20.0 mg, 0.053 mmol, 5.9% yield). $^1$H NMR (499 MHz, DMSO-$d_6$) δ ppm 1.31 (2H, qd, J=11.98, 3.84 Hz), 1.76 (2H, br d, J=10.98 Hz), 2.18 (6H, s), 2.24-2.34 (1H, m), 2.78-2.87 (2H, m), 3.90 (3H, s), 4.21 (2H, br d, J=13.17 Hz), 7.67 (1H, dd, J=8.51, 1.65 Hz), 7.93-7.99 (2H, m), 8.06 (1H, s), 8.14 (1H, s), 8.33 (1H, s), 8.97 (1H, s), 9.10 (1H, s); ESIMS found for $C_{21}H_{26}N_6O$ m/z 379.2 (M+1).

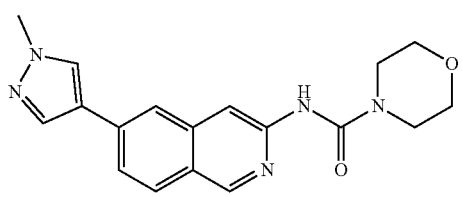

N-(6-(1-Methyl-1H-pyrazol-4-yl)isoquinolin-3-yl)morpholine-4-carboxamide 64.

Beige solid (25.0 mg, 0.074 mmol, 15.1% yield). $^1$H NMR (499 MHz, DMSO-$d_6$) δ ppm 3.47-3.54 (4H, m), 3.58-3.65 (4H, m), 3.90 (3H, s), 7.69 (1H, dd, J=8.51, 1.65 Hz), 7.94-8.00 (2H, m), 8.07 (1H, s), 8.15 (1H, s), 8.33 (1H, s), 8.98 (1H, s), 9.17 (1H, s); ESIMS found for $C_{18}H_{19}N_5O_2$ m/z 338.2 (M+1).

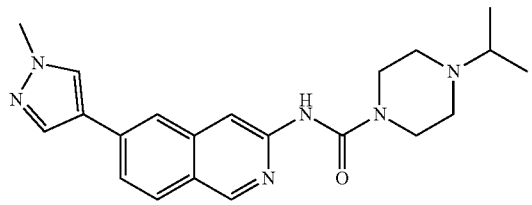

4-isopropyl-N-(6-(1-methyl-1H-pyrazol-4-yl)isoquinolin-3-yl)piperazine-1-carboxamide 65.

Beige solid (2.0 mg, 0.005 mmol, 0.6% yield). $^1$H NMR (500 MHz, DMSO-$d_6$) δ ppm 0.98 (6H, d, J=6.59 Hz), 2.43-2.47 (4H, m), 2.65-2.72 (1H, m), 3.46-3.52 (4H, m), 3.90 (3H, s), 7.68 (1H, dd, J=8.51, 1.65 Hz), 7.94-7.99 (2H, m), 8.06 (1H, s), 8.14 (1H, s), 8.33 (1H, s), 8.97 (1H, s), 9.09 (1H, s); ESIMS found for $C_{21}H_{26}N_6O$ m/z 379.2 (M+1).

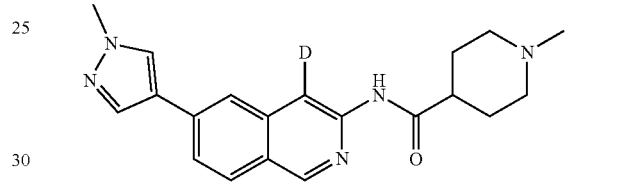

1-Methyl-N-(6-(1-methyl-1H-pyrazol-4-yl)isoquinolin-3-yl-4-d)piperidine-4-carboxamide 66.

White solid (32.0 mg, 0.091 mmol, 51.2% yield). $^1$H NMR (500 MHz, DMSO-$d_6$) δ ppm 1.61-1.73 (2H, m), 1.74-1.80 (2H, m), 1.86 (2H, td, J=11.66, 2.47 Hz), 2.16 (3H, s), 2.45-2.53 (1H, m), 2.77-2.84 (2H, m), 3.90 (3H, s), 7.74 (1H, dd, J=8.51, 1.65 Hz), 8.00 (1H, d, J=8.51 Hz), 8.02-8.04 (1H, m), 8.08 (1H, d, J=0.82 Hz), 8.35 (1H, s), 9.02 (1H, s), 10.46 (1H, s); ESIMS found for $C_{20}H_{22}[^2H]N_5O$ m/z 351.2 (M+1).

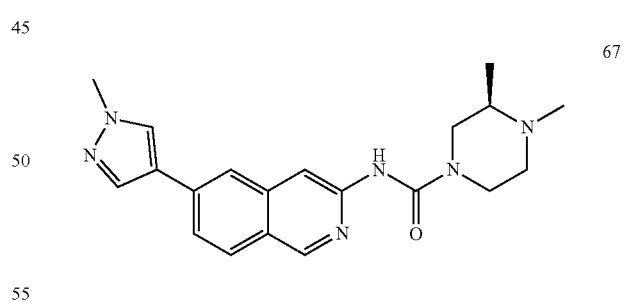

(R)-3,4-Dimethyl-N-(6-(1-methyl-1H-pyrazol-4-yl)isoquinolin-3-yl) piperazine-1-carboxamide 67.

Beige solid (26.0 mg, 0.071 mmol, % yield). $^1$H NMR (499 MHz, DMSO-$d_6$) δ ppm 1.01 (3H, d, J=6.31 Hz), 1.99 (1H, br s), 2.04-2.12 (1H, m), 2.19 (3H, s), 2.61 (1H, dd, J=12.76, 10.29 Hz), 2.74 (1H, br d, J=11.53 Hz), 2.93-3.02 (1H, m), 3.90 (3H, s), 3.99-4.10 (2H, m), 7.65-7.71 (1H, m), 7.93-7.99 (2H, m), 8.06 (1H, s), 8.14 (1H, s), 8.33 (1H, s), 8.97 (1H, s), 9.13 (1H, s); ESIMS found for $C_{20}H_{24}N_6O$ m/z 365.2 (M+1).

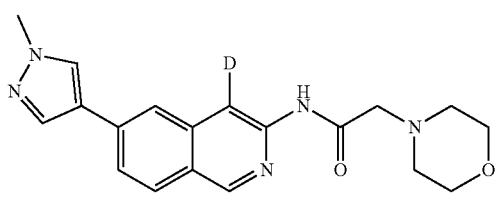

N-(6-(1-Methyl-1H-pyrazol-4-yl)isoquinolin-3-yl-4-d)-2-morpholinoacetamide 68.

Beige solid (4.0 mg, 0.011 mmol, 3.1% yield). $^1$H NMR (499 MHz, DMSO-d$_6$) δ ppm 2.55-2.61 (4H, m), 3.24 (2H, s), 3.62-3.69 (4H, m), 3.90 (3H, s), 7.77 (1H, dd, J=8.51, 1.37 Hz), 8.02 (1H, d, J=8.51 Hz), 8.10 (2H, s), 8.37 (1H, s), 9.04 (1H, s), 10.00 (1H, s); ESIMS found for C$_{19}$H$_{20}$[$^2$H]N$_5$O$_2$ m/z 352.2 (M+1).

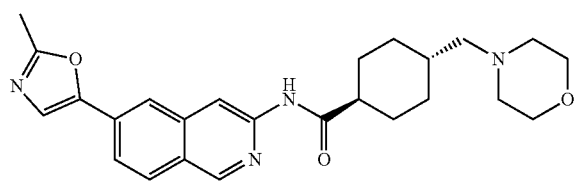

trans-N-(6-(2-Methyloxazol-5-yl)isoquinolin-3-yl)-4-(morpholinomethyl) cyclohexane-1-carboxamide 69.

Off-white solid (21.0 mg, 0.048 mmol, 17.6% yield). $^1$H NMR (500 MHz, DMSO-d$_6$) δ ppm 0.81-0.94 (2H, m), 1.41-1.56 (3H, m), 1.80-1.91 (4H, m), 2.09 (2H, d, J=7.41 Hz), 2.31 (4H, br s), 2.51-2.56 (1H, m), 2.53 (3H, s), 3.56 (4H, t, J=4.53 Hz), 7.78 (1H, s), 7.79-7.84 (1H, m), 8.05-8.11 (2H, m), 8.50 (1H, s), 9.10 (1H, s), 10.49 (1H, s); ESIMS found for C$_{25}$H$_{30}$N$_4$O$_3$ m/z 435.2 (M+1).

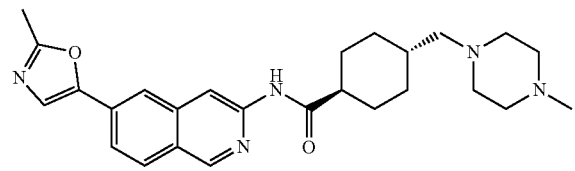

trans-N-(6-(2-Methyloxazol-5-yl)isoquinolin-3-yl)-4-((4-methylpiperazin-1-yl)methyl)cyclohexane-1-carboxamide 70.

White solid (38.0 mg, 0.085 mmol, 28.1% yield). H NMR (499 MHz, DMSO-d$_6$) δ ppm 0.83-0.94 (2H, m), 1.40-1.54 (3H, m), 1.79-1.90 (4H, m), 2.08 (2H, d, J=7.41 Hz), 2.14 (3H, s), 2.31 (8H, br s), 2.52 (1H, br s), 2.53 (3H, s), 7.78 (1H, s), 7.79-7.84 (1H, m), 8.06-8.12 (2H, m), 8.50 (1H, s), 9.10 (1H, s), 10.48 (1H, s); ESIMS found for C$_{26}$H$_{33}$N$_5$O$_2$ m/z 448.25 (M+1).

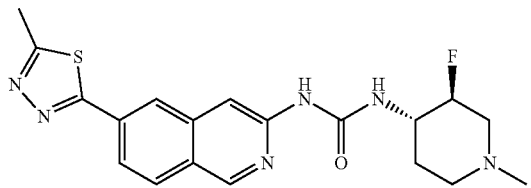

1-((3S,4S)-3-Fluoro-1-methylpiperidin-4-yl)-3-(6-(5-methyl-1,3,4-thiadiazol-2-yl)isoquinolin-3-yl)urea 71.

Pale yellow solid (40.0 mg, 0.100 mmol, 64.3% yield). $^1$H NMR (500 MHz, DMSO-d$_6$) δ ppm 1.46-1.56 (1H, m), 1.91-2.00 (1H, m), 2.06-2.13 (1H, m), 2.14-2.20 (1H, m), 2.23 (3H, s), 2.56-2.62 (1H, m), 2.82 (3H, s), 2.91-3.01 (1H, m), 3.67-3.78 (1H, m), 4.37-4.54 (1H, m), 7.25 (1H, br d, J=7.68 Hz), 8.01 (1H, dd, J=8.51, 1.65 Hz), 8.14 (1H, d, J=8.78 Hz), 8.19 (1H, s), 8.35 (1H, s), 9.13 (1H, s), 9.15 (1H, s); ESIMS found for C$_{19}$H$_{21}$FN$_6$OS m/z 401.2 (M+1).

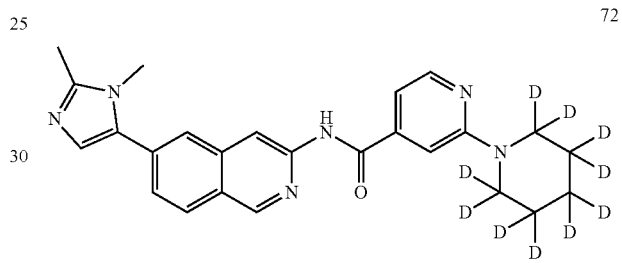

N-(6-(1,2-Dimethyl-1H-imidazol-5-yl)isoquinolin-3-yl)-2-(piperidin-1-yl-d$_{10}$)isonicotinamide 72.

Beige solid (72.0 mg, 0.175 mmol, 74.5% yield). $^1$H NMR (499 MHz, DMSO-d$_6$) δ ppm 2.40 (3H, s), 3.68 (3H, s), 7.09 (1H, dd, J=5.21, 1.37 Hz), 7.14 (1H, s), 7.43 (1H, s), 7.67 (1H, dd, J=8.51, 1.65 Hz), 8.00 (1H, s), 8.14 (1H, d, J=8.51 Hz), 8.23 (1H, d, J=5.21 Hz), 8.67 (1H, s), 9.22 (1H, s), 11.08 (1H, s); ESIMS found for C$_{25}$H$_{16}$[$^2$H$^{10}$]N$_6$O m/z 437.25 (M+1).

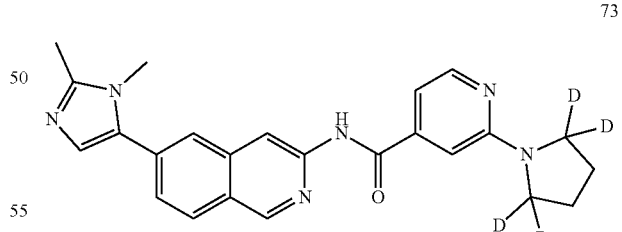

N-(6-(1,2-Dimethyl-1H-imidazol-5-yl)isoquinolin-3-yl)-2-(pyrrolidin-1-yl-2,2,5,5-d$_4$)isonicotinamide 73.

Beige solid (48.0 mg, 0.115 mmol, 52.1% yield). $^1$H NMR (499 MHz, DMSO-d$_6$) δ ppm 1.96 (4H, s), 2.40 (3H, s), 3.68 (3H, s), 7.06 (1H, dd, J=5.08, 1.51 Hz), 7.08 (1H, d, J=0.82 Hz), 7.14 (1H, s), 7.67 (1H, dd, J=8.51, 1.37 Hz), 8.00 (1H, s), 8.14 (1H, d, J=8.78 Hz), 8.20 (1H, d, J=4.94 Hz), 8.67 (1H, s), 9.21 (1H, s), 11.03 (1H, s); ESIMS found for C$_{24}$H$_{20}$[$^2$H$_4$]N$_6$O m/z 417.2 (M+1).

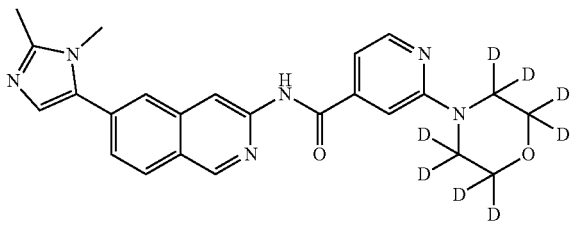

N-(6-(1,2-Dimethyl-1H-imidazol-5-yl)isoquinolin-3-yl)-2-(morpholino-d$_8$) isonicotinamide 74.

Beige solid (30.0 mg, 0.069 mmol, 59.1% yield). $^1$H NMR (499 MHz, DMSO-d$_6$) δ ppm 2.40 (3H, s), 3.68 (3H, s), 7.14 (1H, s), 7.20 (1H, dd, J=4.94, 1.37 Hz), 7.47 (1H, s), 7.67 (1H, dd, J=8.51, 1.65 Hz), 8.00 (1H, s), 8.15 (1H, d, J=8.78 Hz), 8.28 (1H, d, J=5.21 Hz), 8.68 (1H, s), 9.22 (1H, s), 11.10 (1H, s); ESIMS found for C$_{24}$H$_{16}$[$^2$H$_8$]N$_6$O$_2$ m/z 437.25 (M+1).

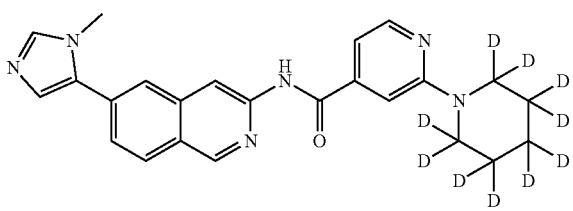

N-(6-(1-Methyl-1H-imidazol-5-yl)isoquinolin-3-yl)-2-(piperidin-1-yl-d$_{10}$) isonicotinamide 75.

Beige solid (68.0 mg, 0.161 mmol, 69.9% yield). $^1$H NMR (500 MHz, DMSO-d$_6$) δ ppm 3.85 (3H, s), 7.06-7.11 (1H, m), 7.33 (1H, d, J=1.10 Hz), 7.42-7.47 (1H, m), 7.74 (1H, dd, J=8.51, 1.65 Hz), 7.81 (1H, s), 8.10 (1H, d, J=0.82 Hz), 8.15 (1H, d, J=8.78 Hz), 8.23 (1H, d, J=5.76 Hz), 8.69 (1H, s), 9.22 (1H, s), 11.10 (1H, s); ESIMS found for C$_{24}$H$_{14}$[$^2$H$^{10}$]N$_6$O m/z 423.3 (M+1).

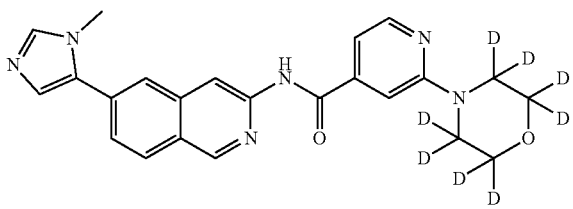

N-(6-(1-Methyl-1H-imidazol-5-yl)isoquinolin-3-yl)-2-(morpholino-d$_8$) isonicotinamide 76.

Beige solid (20.0 mg, 0.047 mmol, 20.6% yield). $^1$H NMR (499 MHz, DMSO-d$_6$) δ ppm 3.85 (3H, s), 7.20 (1H, dd, J=5.08, 1.24 Hz), 7.34 (1H, br s), 7.47 (1H, s), 7.74 (1H, dd, J=8.51, 1.65 Hz), 7.82 (1H, br s), 8.10 (1H, s), 8.15 (1H, d, J=8.51 Hz), 8.28 (1H, d, J=5.21 Hz), 8.70 (1H, s), 9.23 (1H, s), 11.11 (1H, s); ESIMS found for C$_{23}$H$_{14}$[$^2$H$_8$]N$_6$O$_2$ m/z 423.2 (M+1).

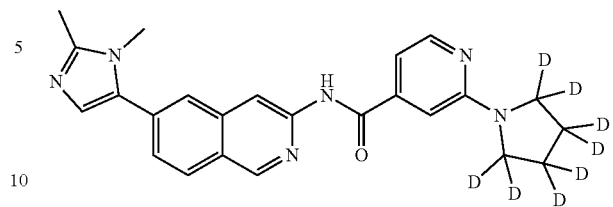

N-(6-(1,2-Dimethyl-1H-imidazol-5-yl)isoquinolin-3-yl)-2-(pyrrolidin-1-yl-d$_8$)isonicotinamide 77.

Beige solid (19.0 mg, 0.045 mmol, 38.9% yield). $^1$H NMR (499 MHz, DMSO-d$_6$) δ ppm 2.40 (3H, s), 3.68 (3H, s), 7.06 (1H, dd, J=5.08, 1.51 Hz), 7.08 (1H, s), 7.14 (1H, s), 7.67 (1H, dd, J=8.37, 1.51 Hz), 8.00 (1H, s), 8.14 (1H, d, J=8.51 Hz), 8.20 (1H, d, J=5.21 Hz), 8.67 (1H, s), 9.21 (1H, s), 11.03 (1H, s); ESIMS found for C$_{24}$H$_{16}$[$^2$H$_8$]N$_6$O m/z 421.25 (M+1).

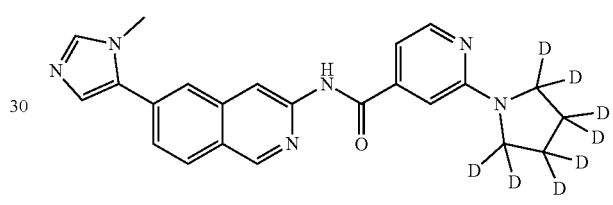

N-(6-(1-Methyl-1H-imidazol-5-yl)isoquinolin-3-yl)-2-(pyrrolidin-1-yl-d$_8$) isonicotinamide 78.

White solid (68.0 mg, 0.167 mmol, 72.3% yield). $^1$H NMR (500 MHz, DMSO-d$_6$) δ ppm 3.85 (3H, s), 7.06 (1H, dd, J=5.21, 1.37 Hz), 7.07-7.13 (1H, m), 7.33 (1H, d, J=1.10 Hz), 7.74 (1H, dd, J=8.51, 1.92 Hz), 7.81 (1H, s), 8.10 (1H, d, J=0.82 Hz), 8.15 (1H, d, J=8.78 Hz), 8.20 (1H, dd, J=5.21, 0.82 Hz), 8.69 (1H, s), 9.22 (1H, s), 11.05 (1H, s); ESIMS found for C$_{23}$H$_{14}$[$^2$H$_8$]N$_6$O m/z 407.3 (M+1).

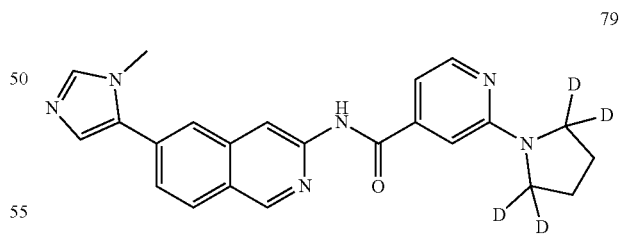

N-(6-(1-Methyl-1H-imidazol-5-yl)isoquinolin-3-yl)-2-(pyrrolidin-1-yl-2,2,5,5-d$_4$)isonicotinamide 79.

Beige solid (58.0 mg, 0.144 mmol, 62.6% yield). $^1$H NMR (500 MHz, DMSO-d$_6$) δ ppm 1.96 (4H, s), 3.85 (3H, s), 7.06 (1H, dd, J=5.21, 1.37 Hz), 7.07-7.12 (1H, m), 7.33 (1H, d, J=1.10 Hz), 7.74 (1H, dd, J=8.51, 1.65 Hz), 7.81 (1H, s), 8.10 (1H, d, J=0.82 Hz), 8.15 (1H, d, J=8.78 Hz), 8.18-8.24 (1H, m), 8.69 (1H, s), 9.22 (1H, s), 11.05 (1H, s); ESIMS found for C$_{23}$H$_{18}$[$^2$H$_4$]N$_6$O m/z 403.15 (M+1).

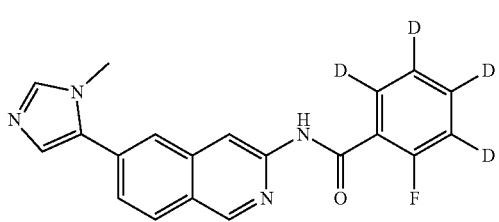

80

2-Fluoro-N-(6-(1-methyl-1H-imidazol-5-yl)isoquinolin-3-yl)benzamide-2,3,5,6-d₄ 80.

Off-white solid (15.4 mg, 0.044 mmol, 49.3% yield). ¹H NMR (499 MHz, DMSO-d₆) δ ppm 3.86 (3H, s), 7.33 (1H, s), 7.73 (1H, dd, J=8.51, 1.65 Hz), 7.81 (1H, s), 8.11 (1H, s), 8.14 (1H, d, J=8.51 Hz), 8.68 (1H, s), 9.18 (1H, s); ESIMS found for $C_{20}H_{11}[^2H_4]FN_4O$ m/z 351.2 (M+1).

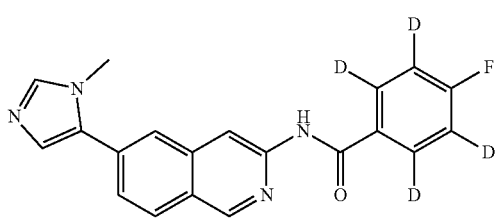

81

4-Fluoro-N-(6-(1-methyl-1H-imidazol-5-yl)isoquinolin-3-yl)benzamide-2,3,5,6-d₄ 81.

Off-white solid (15.1 mg, 0.043 mmol, 34.2% yield). ¹H NMR (499 MHz, DMSO-d₆) δ ppm 3.85 (3H, s), 7.33 (1H, d, J=0.82 Hz), 7.73 (1H, dd, J=8.51, 1.65 Hz), 7.81 (1 H, s), 8.09 (1H, s), 8.14 (1H, d, J=8.51 Hz), 8.69 (1H, s), 9.22 (1H, s), 10.95 (1H, s); ESIMS found for $C_{20}H_{11}[^2H_4]FN_4O$ m/z 351.15 (M+1).

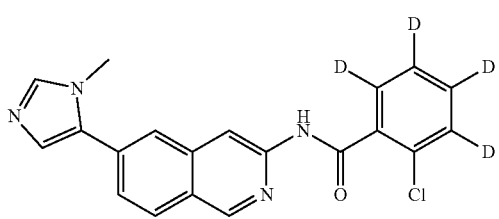

82

2-Chloro-N-(6-(1-methyl-1H-imidazol-5-yl)isoquinolin-3-yl)benzamide-2,3,5,6-d₄ 82.

Off-white solid (9.8 mg, 0.027 mmol, 30.0% yield). ¹H NMR (499 MHz, DMSO-d₆) δ ppm 3.86 (3H, s), 7.33 (1H, s), 7.73 (1H, dd, J=8.37, 1.78 Hz), 7.81 (1H, s), 8.09-8.17 (2H, m), 8.68 (1H, s), 9.17 (1H, s), 11.14 (1H, s); ESIMS found for $C_{20}H_{11}[^2H_4]ClN_4O$ m/z 367.1 (M+1).

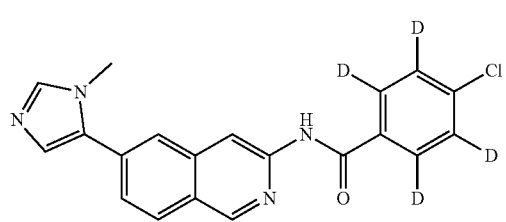

83

4-Chloro-N-(6-(1-methyl-1H-imidazol-5-yl)isoquinolin-3-yl)benzamide-2,3,5,6-d₄ 83.

Off-white solid (16.0 mg, 0.044 mmol, 34.6% yield). ¹H NMR (499 MHz, DMSO-d₆) δ ppm 3.85 (3H, s), 7.33 (1H, d, J=0.82 Hz), 7.73 (1H, dd, J=8.51, 1.65 Hz), 7.81 (1H, s), 8.10 (1H, s), 8.14 (1H, d, J=8.51 Hz), 8.69 (1H, s), 9.22 (1H, s), 11.02 (1H, s); ESIMS found for $C_{20}H_{11}[^2H_4]ClN_4O$ m/z 367.1 (M+1).

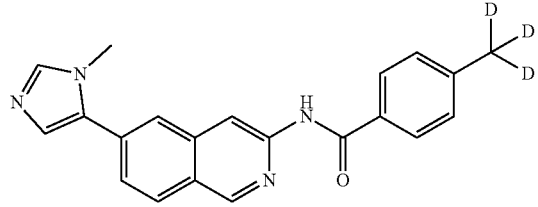

84

4-(Methyl-d₃)-N-(6-(1-methyl-1H-imidazol-5-yl)isoquinolin-3-yl)benzamide 84.

Off-white solid (9.0 mg, 0.026 mmol, 29.2% yield). ¹H NMR (499 MHz, DMSO-d₆) δ ppm 3.85 (3H, s), 7.31-7.37 (3H, m), 7.72 (1H, dd, J=8.51, 1.65 Hz), 7.81 (1H, s), 7.98-8.03 (2H, m), 8.08 (1H, s), 8.14 (1H, d, J=8.51 Hz), 8.69 (1H, s), 9.21 (1H, s), 10.79 (1H, s); ESIMS found for $C_{21}H_{15}[^2H_3]N_4O$ m/z 346.2 (M+1).

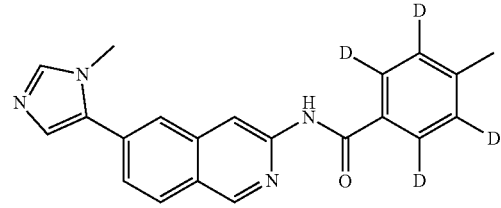

85

4-Methyl-N-(6-(1-methyl-1H-imidazol-5-yl)isoquinolin-3-yl)benzamide-2,3,5,6-d₄ 85.

Off-white solid (6.9 mg, 0.020 mmol, 22.3% yield). ¹H NMR (499 MHz, DMSO-d₆) δ ppm 2.40 (3H, s), 3.85 (3H, s), 7.33 (1H, s), 7.72 (1H, dd, J=8.51, 1.65 Hz), 7.81 (1H, s), 8.08 (1H, s), 8.14 (1H, d, J=8.51 Hz), 8.69 (1H, s), 9.21 (1H, s), 10.79 (1H, s); ESIMS found for $C_{21}H_{14}[^2H_4]N_4O$ m/z 347.2 (M+1).

86

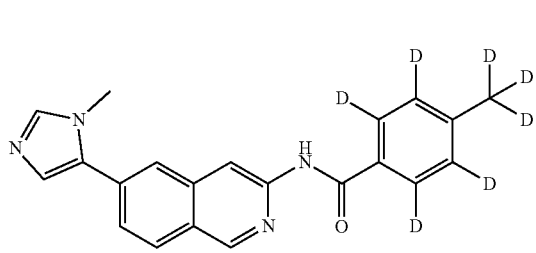

4-(Methyl-d₃)-N-(6-(1-methyl-1H-imidazol-5-yl)isoquinolin-3-yl) benzamide-2,3,5,6-d₄ 86.

Off-white solid (15.5 mg, 0.044 mmol, 35.2% yield). ¹H NMR (499 MHz, DMSO-d₆) δ ppm 3.85 (3H, s), 7.33 (1H, d, J=0.82 Hz), 7.72 (1H, dd, J=8.51, 1.65 Hz), 7.81 (1H, s), 8.08 (1H, d, J=0.82 Hz), 8.14 (1H, d, J=8.51 Hz), 8.69 (1H, s), 9.21 (1H, s), 10.79 (1H, s); ESIMS found for C₂₁H₁₁[²H₇]N₄O m/z 350.2 (M+1).

87

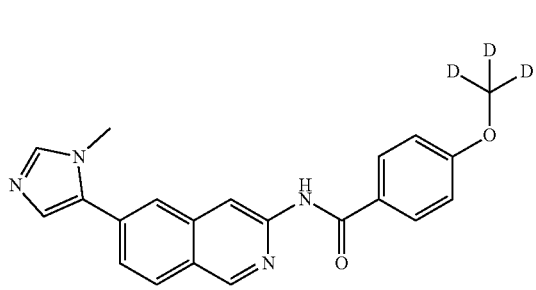

4-(Methoxy-d₃)-N-(6-(1-methyl-1H-imidazol-5-yl)isoquinolin-3-yl) benzamide 87.

Off-white solid (13.7 mg, 0.038 mmol, 42.5% yield). ¹H NMR (499 MHz, DMSO-d₆) δ ppm 3.85 (3H, s), 7.02-7.10 (2H, m), 7.32 (1H, s), 7.71 (1H, dd, J=8.51, 1.65 Hz), 7.81 (1H, s), 8.07 (1H, s), 8.08-8.12 (2H, m), 8.13 (1H, d, J=8.51 Hz), 8.68 (1H, s), 9.20 (1H, s), 10.72 (1H, s); ESIMS found for C₂₁H₁₅[²H₃]N₄O₂ m/z 362.1 (M+1).

88

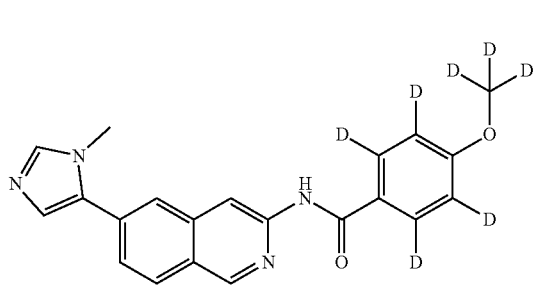

4-(Methoxy-d₃)-N-(6-(1-methyl-1H-imidazol-5-yl)isoquinolin-3-yl) benzamide-2,3,5,6-d₄ 88.

Off-white solid (8.4 mg, 0.023 mmol, 18.3% yield). ¹H NMR (499 MHz, DMSO-d₆) δ ppm 3.85 (3H, s), 7.33 (1H, br s), 7.71 (1H, dd, J=8.51, 1.65 Hz), 7.81 (1H, s), 8.07 (1H, s), 8.13 (1H, d, J=8.51 Hz), 8.68 (1H, s), 9.20 (1H, s), 10.72 (1H, s); ESIMS found for C₂₁H₁₁[²H₇]N₄O₂ m/z 366.2 (M+1).

89

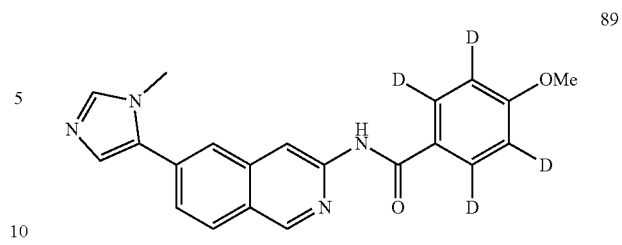

4-Methoxy-N-(6-(1-methyl-1H-imidazol-5-yl)isoquinolin-3-yl)benzamide-2,3,5,6-d₄ 89.

Off-white solid (8.1 mg, 0.022 mmol, 25.1% yield). ¹H NMR (499 MHz, DMSO-d₆) δ ppm 3.85 (6H, s), 7.33 (1H, s), 7.71 (1H, dd, J=8.51, 1.65 Hz), 7.81 (1H, s), 8.07 (1H, s), 8.13 (1H, d, J=8.51 Hz), 8.68 (1H, s), 9.20 (1H, s), 10.72 (1H, s); ESIMS found for C₂₁H₁₄[²H₄]N₄O₂ m/z 363.2 (M+1).

90

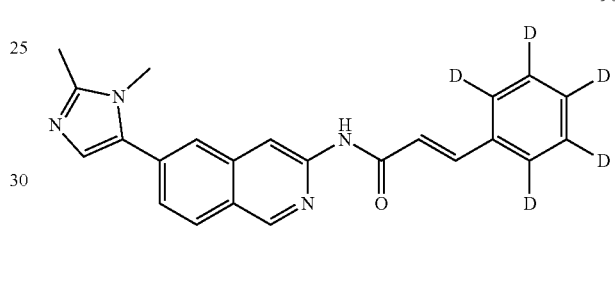

(E)-N-(6-(1,2-Dimethyl-1H-imidazol-5-yl)isoquinolin-3-yl)-3-(phenyl-2,3,4,5,6-d₅)acrylamide 90.

Brown solid (6.5 mg, 0.017 mmol, 13.8% yield). ¹H NMR (499 MHz, DMSO-d₆) δ ppm 2.40 (3H, s), 3.68 (3H, s), 7.13 (1H, br d, J=15.64 Hz), 7.14 (1H, s), 7.63 (1H, dd, J=8.51, 1.65 Hz), 7.66 (1H, d, J=15.64 Hz), 7.96 (1H, s), 8.11 (1H, d, J=8.51 Hz), 8.67 (1H, s), 9.16 (1H, s), 10.83 (1H, s); ESIMS found for C₂₃H₁₅[²H₅]N₄O m/z 374.2 (M+1).

91

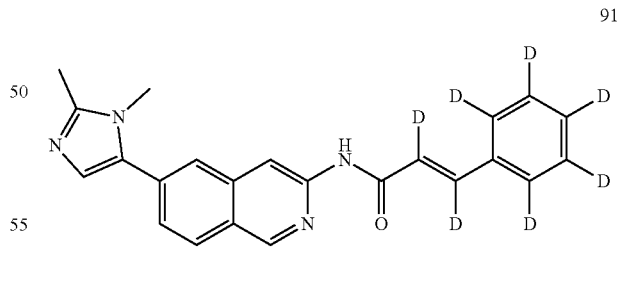

(E)-N-(6-(1,2-Dimethyl-1H-imidazol-5-yl)isoquinolin-3-yl)-3-(phenyl-2,3,4,5,6-d₅)acrylamide-2,3-d₂ 91.

Brown solid (5.9 mg, 0.016 mmol, 12.5% yield). ¹H NMR (499 MHz, DMSO-d₆) δ ppm 2.40 (3H, s), 3.68 (3H, s), 7.13 (1H, s), 7.63 (1H, dd, J=8.51, 1.65 Hz), 7.96 (1H, s), 8.11 (1H, d, J=8.51 Hz), 8.67 (1H, s), 9.16 (1H, s), 10.82 (1H, s); ESIMS found for C₂₃H₁₃[²H₇]N₄O m/z 376.2 (M+1).

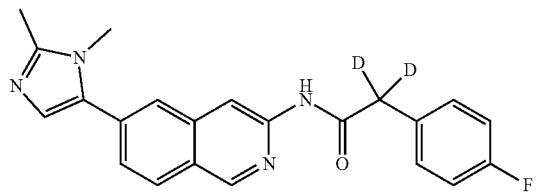

N-(6-(1,2-Dimethyl-1H-imidazol-5-yl)isoquinolin-3-yl)-2-(4-fluorophenyl) acetamide-2,2-d$_2$ 92.

Brown solid (18.1 mg, 0.048 mmol, 38.2% yield). $^1$H NMR (499 MHz, DMSO-d$_6$) δ ppm 2.38 (3H, s), 3.65 (3H, s), 7.11 (1H, s), 7.16 (2H, t, J=8.92 Hz), 7.41 (2H, dd, J=8.10, 5.63 Hz), 7.61 (1H, dd, J=8.51, 1.65 Hz), 7.89 (1H, s), 8.08 (1H, d, J=8.51 Hz), 8.47 (1H, s), 9.13 (1H, s), 10.83 (1H, s); ESIMS found for C$_{22}$H$_{17}$[$^2$H$_2$]FN$_4$O m/z 377.2 (M+1).

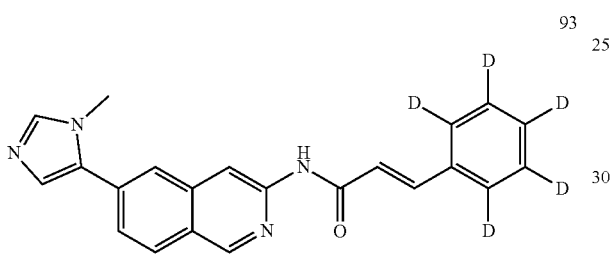

(E)-N-(6-(1-methyl-1H-imidazol-5-yl)isoquinolin-3-yl)-3-(phenyl-2,3,4,5,6-d$_5$)acrylamide 93.

Off-white solid (15.9 mg, 0.044 mmol, 35.1% yield). $^1$H NMR (499 MHz, DMSO-d$_6$) δ ppm 3.85 (3H, s), 7.13 (1H, d, J=15.92 Hz), 7.32 (1H, s), 7.67 (1H, d, J=15.64 Hz), 7.70 (1H, dd, J=8.37, 1.78 Hz), 7.81 (1H, s), 8.06 (1H, s), 8.12 (1H, d, J=8.78 Hz), 8.69 (1H, s), 9.17 (1H, s), 10.83 (1H, s); ESIMS found for C$_{22}$H$_{13}$[$^2$H$_5$]N$_4$O m/z 360.2 (M+1).

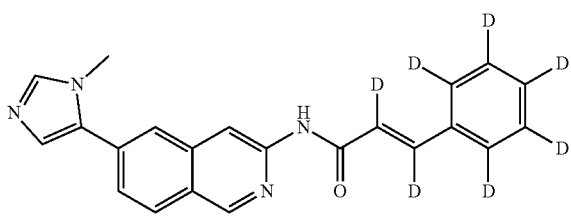

(E)-N-(6-(1-Methyl-1H-imidazol-5-yl)isoquinolin-3-yl)-3-(phenyl-2,3,4,5,6-d$_5$)acrylamide-2,3-d$_2$ 94.

Off-white solid (16.2 mg, 0.045 mmol, 35.6% yield). $^1$H NMR (499 MHz, DMSO-d$_6$) δ ppm 3.85 (3H, s), 7.32 (1H, s), 7.70 (1H, dd, J=8.37, 1.51 Hz), 7.80 (1H, s), 8.05 (1H, s), 8.12 (1H, d, J=8.51 Hz), 8.69 (1H, s), 9.17 (1H, s), 10.83 (1H, s); ESIMS found for C$_{22}$H$_{11}$[$^2$H$_7$]N$_4$O m/z 362.2 (M+1).

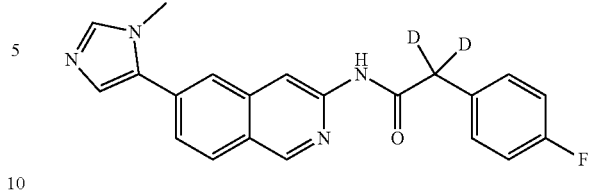

2-(4-Fluorophenyl)-N-(6-(1-methyl-1H-imidazol-5-yl)isoquinolin-3-yl) acetamide-2,2-d$_2$ 95.

Off-white solid (14.1 mg, 0.039 mmol, 30.9% yield). $^1$H NMR (499 MHz, DMSO-d$_6$) δ ppm 3.81 (3H, s), 7.12-7.20 (2H, m), 7.29 (1H, d, J=0.82 Hz), 7.41 (2H, dd, J=7.96, 5.76 Hz), 7.68 (1H, dd, J=8.51, 1.65 Hz), 7.78 (1H, s), 7.99 (1H, s), 8.09 (1H, d, J=8.51 Hz), 8.49 (1H, s), 9.14 (1H, s), 10.84 (1H, s); ESIMS found for C$_{21}$H$_{15}$[$^2$H$_2$]FN$_4$O m/z 363.2 (M+1).

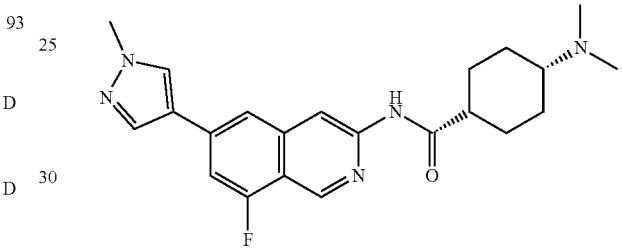

cis-4-(Dimethylamino)-N-(8-fluoro-6-(1-methyl-1H-pyrazol-4-yl) isoquinolin-3-yl)cyclohexane-1-carboxamide 96.

White solid (2.0 mg, 0.005 mmol, 1.9% yield). $^1$H NMR (499 MHz, DMSO-d$_6$) δ ppm 1.48-1.57 (4H, m), 1.81-1.93 (4H, m), 2.19 (6H, br s), 2.21-2.25 (1H, m), 2.67-2.73 (1H, m), 3.90 (3H, s), 7.56-7.61 (1H, m), 7.93 (1H, s), 8.12 (1H, s), 8.39 (1H, s), 8.48 (1H, s), 9.14 (1H, s), 10.51 (1H, s); ESIMS found for C$_{22}$H$_{26}$FN$_5$O m/z 396.2 (M+1).

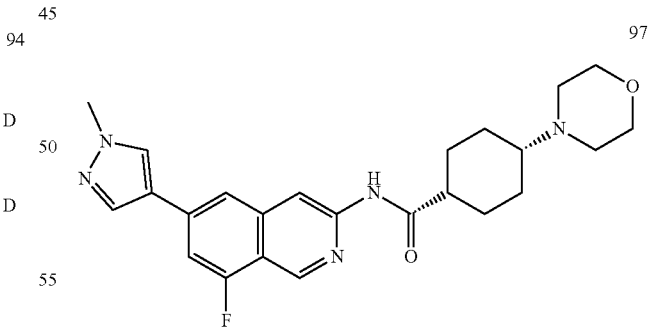

cis-N-(8-Fluoro-6-(1-methyl-1H-pyrazol-4-yl)isoquinolin-3-yl)-4-morpholinocyclohexane-1-carboxamide 97.

Off-white solid (20.0 mg, 0.046 mmol, 16.8% yield). $^1$H NMR (499 MHz, DMSO-d$_6$) δ ppm 1.42-1.57 (4H, m), 1.82-1.97 (4H, m), 2.13-2.20 (1H, m), 2.41 (4H, br s), 2.70 (1H, tt, J=7.82, 3.98 Hz), 3.59 (4H, t, J=4.39 Hz), 3.90 (3H, s), 7.58 (1H, dd, J=12.08, 1.10 Hz), 7.91 (1H, s), 8.11 (1H, s), 8.39 (1H, s), 8.48 (1H, s), 9.14 (1H, s), 10.51 (1H, s); ESIMS found for C$_{24}$H$_{28}$FN$_5$O$_2$ m/z 438.2 (M+1).

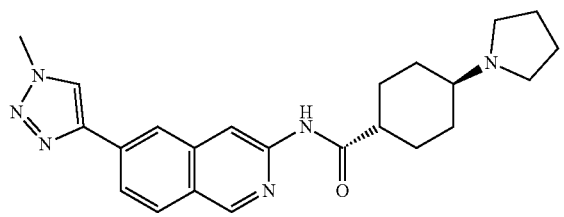

trans-N-(6-(1-Methyl-1H-1,2,3-triazol-4-yl)isoquinolin-3-yl)-4-(pyrrolidin-1-yl)cyclohexane-1-carboxamide 99.

Off-white solid (26.0 mg, 0.064 mmol, 30.0% yield). $^1$H NMR (499 MHz, DMSO-$d_6$) δ ppm 1.12-1.23 (2H, m), 1.44-1.55 (2H, m), 1.65 (4H, br t, J=3.16 Hz), 1.88 (2H, br d, J=12.35 Hz), 1.94-2.05 (3H, m), 2.46-2.49 (4H, m), 2.51-2.56 (1H, m), 4.14 (3H, s), 8.00 (1H, dd, J=8.51, 1.37 Hz), 8.10 (1H, d, J=8.78 Hz), 8.27 (1H, s), 8.50 (1H, s), 8.72 (1H, s), 9.10 (1H, s), 10.48 (1H, s); ESIMS found for $C_{23}H_{27}N_6O$ m/z 405.2 (M+1).

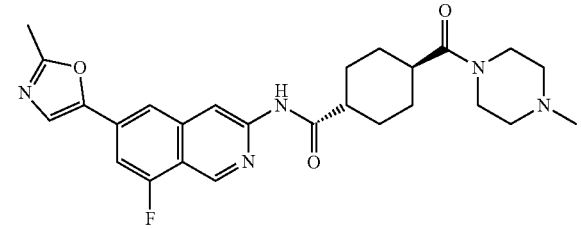

trans-N-(6-(1-Methyl-1H-1,2,3-triazol-4-yl)isoquinolin-3-yl)-4-morpholinocyclohexane-1-carboxamide 100.

Off-white solid (60.0 mg, 0.143 mmol, 66.7% yield). $^1$H NMR (499 MHz, DMSO-$d_6$) δ ppm 1.15-1.28 (2H, m), 1.42-1.56 (2H, m), 1.91 (4H, br t, J=12.62 Hz), 2.17-2.26 (1H, m), 2.45-2.49 (4H, m), 2.51-2.53 (1H, m), 3.53-3.59 (4H, m), 4.14 (3H, s), 8.01 (1H, dd, J=8.51, 1.65 Hz), 8.10 (1H, d, J=8.78 Hz), 8.27 (1H, s), 8.49 (1H, s), 8.72 (1H, s), 9.11 (1H, s), 10.50 (1H, s); ESIMS found for $C_{23}H_{28}N_6O_2$ m/z 421.2 (M+1).

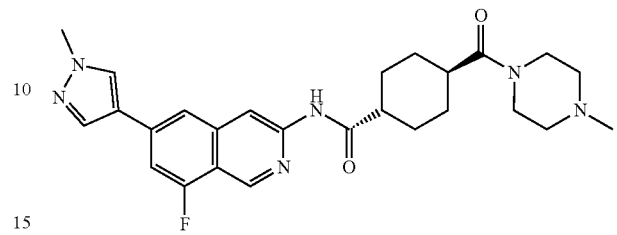

trans-N-(8-Fluoro-6-(2-methyloxazol-5-yl)isoquinolin-3-yl)-4-(4-methylpiperazine-1-carbonyl)cyclohexane-1-carboxamide 101.

Off-white solid (83.0 mg, 0.173 mmol, 61.2% yield). $^1$H NMR (499 MHz, DMSO-$d_6$) δ ppm 1.36-1.47 (2H, m), 1.51-1.62 (2H, m), 1.72 (2H, br d, J=11.25 Hz), 1.89 (2H, br d, J=10.15 Hz), 2.18 (3H, s), 2.23 (2H, br s), 2.30 (2H, br s), 2.53 (3H, s), 2.55-2.60 (1H, m), 2.61-2.68 (1H, m), 3.44 (2H, br s), 3.50 (2H, br s), 7.62-7.68 (1H, m), 7.84 (1H, s), 7.96 (1H, s), 8.57 (1H, s), 9.22 (1H, s), 10.67 (1H, s); ESIMS found for $C_{26}H_{30}FN_5O_3$ m/z 480.3 (M+1).

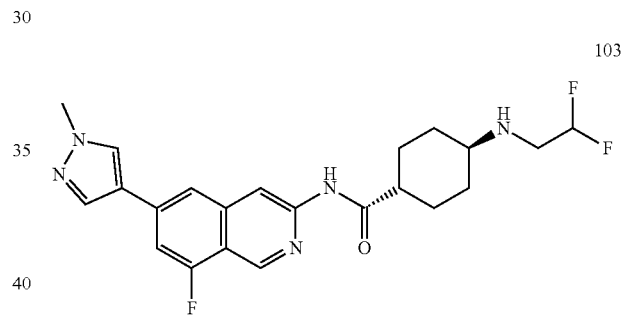

trans-N-(8-Fluoro-6-(1-methyl-1H-pyrazol-4-yl)isoquinolin-3-yl)-4-(4-methylpiperazine-1-carbonyl)cyclohexane-1-carboxamide 102.

Off-white solid (55.0 mg, 0.115 mmol, 40.6% yield). $^1$H NMR (499 MHz, DMSO-$d_6$) δ ppm 1.35-1.47 (2H, m), 1.57 (2H, qd, J=12.76, 2.88 Hz), 1.72 (2H, br d, J=10.98 Hz), 1.89 (2H, br d, J=10.43 Hz), 2.18 (3H, s), 2.23 (2H, br s), 2.30 (2H, br s), 2.52-2.60 (1H, m), 2.64 (1H, tt, J=11.53, 3.16 Hz), 3.44 (2H, br s), 3.50 (2H, br s), 3.90 (3H, s), 7.54-7.62 (1H, m), 7.92 (1H, s), 8.11 (1H, s), 8.39 (1H, s), 8.49 (1H, s), 9.15 (1H, s), 10.58 (1H, s); ESIMS found for $C_{26}H_{31}FN_6O_2$ m/z 479.25 (M+1).

trans-4-((2,2-Difluoroethyl)amino)-N-(8-fluoro-6-(1-methyl-1H-pyrazol-4-yl)isoquinolin-3-yl)cyclohexane-1-carboxamide 103.

White solid (7.0 mg, 0.016 mmol, 8.5% yield). $^1$H NMR (499 MHz, DMSO-$d_6$) δ ppm 0.96-1.07 (2H, m), 1.47 (2H, qd, J=12.90, 3.29 Hz), 1.87 (3H, br d, J=10.98 Hz), 1.93-2.00 (2H, m), 2.35-2.44 (1H, m), 2.51-2.56 (1H, m), 2.91 (2H, td, J=15.92, 4.39 Hz), 3.89 (3H, s), 5.94 (1H, tt, J=56.90, 4.40 Hz), 7.58 (1H, dd, J=12.08, 1.37 Hz), 7.91 (1H, s), 8.11 (1H, s), 8.39 (1H, s), 8.48 (1H, s), 9.14 (1H, s), 10.57 (1H, s); ESIMS found for $C_{22}H_{24}F_3N_5O$ m/z 432.2 (M+1).

trans-4-((2,2-Difluoroethyl)amino)-N-(6-(2-methyloxazol-5-yl)isoquinolin-3-yl)cyclohexane-1-carboxamide 104.

White solid (10.0 mg, 0.024 mmol, 8.5% yield). $^1$H NMR (500 MHz, DMSO-$d_6$) δ ppm 0.97-1.09 (2H, m), 1.47 (2H, qd, J=12.90, 3.02 Hz), 1.86 (3H, br d, J=11.53 Hz), 1.93-1.99 (2H, m), 2.34-2.43 (1H, m), 2.51-2.54 (1H, m), 2.53 (3H, s), 2.91 (2H, td, J=15.92, 4.12 Hz), 5.94 (1H, tt, J=56.80, 4.40 Hz), 7.78 (1H, s), 7.79-7.84 (1H, m), 8.06-8.13 (2H, m), 8.50 (1H, s), 9.10 (1H, s), 10.51 (1H, s); ESIMS found for $C_{22}H_{24}F_2N_4O_2$ m/z 415.2 (M+1).

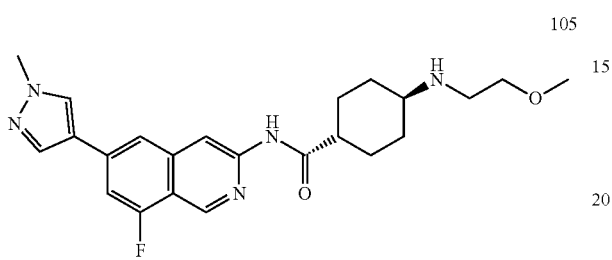

trans-N-(8-Fluoro-6-(1-methyl-1H-pyrazol-4-yl)isoquinolin-3-yl)-4-((2-methoxyethyl)amino)cyclohexane-1-carboxamide 105.

Beige solid (4.0 mg, 0.009 mmol, 4.9% yield). $^1$H NMR (499 MHz, DMSO-$d_6$) δ ppm 1.24-1.36 (2H, m), 1.44-1.55 (2H, m), 1.91-1.99 (2H, m), 2.02-2.15 (2H, m), 2.52 (1H, br d, J=1.92 Hz), 2.53-2.59 (1H, m), 3.04 (2H, br s), 3.29 (1H, br s), 3.53 (br s), 3.90 (3H, s), 7.59 (1H, dd, J=12.08, 1.10 Hz), 7.89-7.93 (1H, m), 8.11-8.14 (1H, m), 8.39 (1H, s), 8.46-8.50 (1H, m), 9.15 (1H, s), 10.61 (1H, s); ESIMS found for $C_{23}H_{28}FN_5O_2$ m/z 426.2 (M+1).

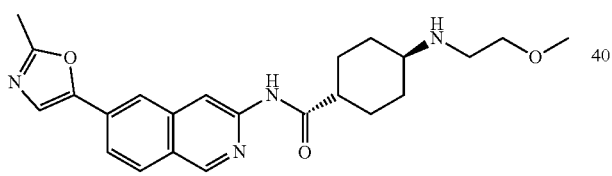

trans-4-((2-Methoxyethyl)amino)-N-(6-(2-methyloxazol-5-yl)isoquinolin-3-yl)cyclohexane-1-carboxamide 106.

White solid (8.0 mg, 0.020 mmol, 6.9% yield). $^1$H NMR (500 MHz, DMSO-$d_6$) δ ppm 0.97-1.07 (2H, m), 1.43-1.54 (2H, m), 1.86 (2H, br d, J=11.53 Hz), 1.91-1.98 (2H, m), 2.34-2.42 (1H, m), 2.51-2.53 (1H, m), 2.53 (3H, s), 2.70 (2H, t, J=5.63 Hz), 3.24 (3H, s), 3.37 (3H, t, J=5.76 Hz), 7.78 (1H, s), 7.81 (1H, dd, J=8.64, 1.51 Hz), 8.07-8.12 (2H, m), 8.50 (1H, s), 9.10 (1H, s), 10.50 (1H, s); ESIMS found for $C_{23}H_{28}N_4O_3$ m/z 409.2 (M+1).

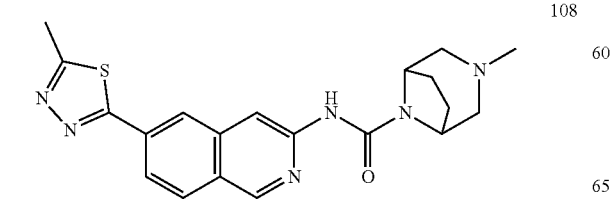

3-Methyl-N-(6-(5-methyl-1,3,4-thiadiazol-2-yl)isoquinolin-3-yl)-3,8-diazabicyclo[3.2.1]octane-8-carboxamide 108.

Pale yellow solid (23.0 mg, 0.058 mmol, 7.1% yield). $^1$H NMR (499 MHz, DMSO-$d_6$) δ ppm 1.75-1.87 (4H, m), 2.10-2.21 (2H, m), 2.15 (3H, s), 2.62 (2H, dd, J=10.84, 2.33 Hz), 2.82 (3H, s), 4.50 (2H, br s), 8.03 (1H, dd, J=8.51, 1.65 Hz), 8.15 (1H, d, J=8.78 Hz), 8.38 (1H, s), 8.40 (1H, s), 9.16 (1H, s), 9.35 (1H, s); ESIMS found for $C_{20}H_{22}N_6OS$ m/z 395.2 (M+1).

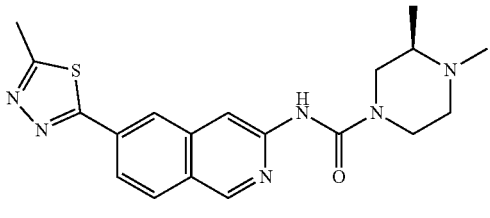

(R)-3,4-Dimethyl-N-(6-(5-methyl-1,3,4-thiadiazol-2-yl)isoquinolin-3-yl) piperazine-1-carboxamide 109.

Pale yellow solid (27.0 mg, 0.071 mmol, 8.6% yield). $^1$H NMR (499 MHz, DMSO-$d_6$) δ ppm 1.02 (3H, d, J=6.31 Hz), 1.98 (1H, dqd, J=9.67, 6.29, 6.29, 6.29, 3.29 Hz), 2.07 (1H, td, J=11.53, 3.02 Hz), 2.19 (3H, s), 2.62 (1H, dd, J=12.90, 10.15 Hz), 2.74 (1H, dt, J=11.53, 2.74 Hz), 2.82 (3H, s), 2.95-3.02 (1H, m), 4.00-4.10 (2H, m), 8.02 (1H, dd, J=8.51, 1.65 Hz), 8.15 (1H, d, J=8.78 Hz), 8.31 (1H, s), 8.38 (1H, d, J=0.82 Hz), 9.16 (1H, s), 9.32 (1H, s); ESIMS found for $C_{19}H_{22}N_6OS$ m/z 383.2 (M+1).

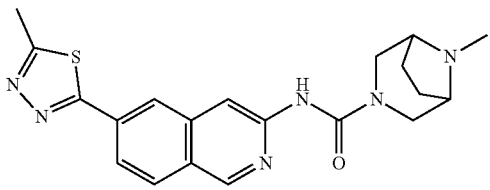

8-Methyl-N-(6-(5-methyl-1,3,4-thiadiazol-2-yl)isoquinolin-3-yl)-3,8-diazabicyclo[3.2.1]octane-3-carboxamide 110.

Beige solid (20.0 mg, 0.051 mmol, 6.1% yield). $^1$H NMR (499 MHz, DMSO-$d_6$) δ ppm 1.52-1.62 (2H, m), 1.87-1.95 (2H, m), 2.19 (3H, s), 2.82 (3H, s), 3.03 (2H, br d, J=11.53 Hz), 3.08-3.14 (2H, m), 3.80 (2H, dd, J=12.35, 2.47 Hz), 8.02 (1H, dd, J=8.51, 1.65 Hz), 8.15 (1H, d, J=8.78 Hz), 8.31 (1H, s), 8.38 (1H, d, J=0.82 Hz), 9.07 (1H, s), 9.15 (1H, s); ESIMS found for $C_{20}H_{22}N_6OS$ m/z 395.2 (M+1).

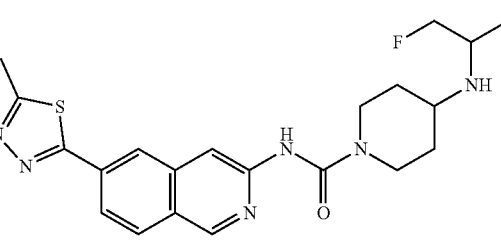

4-((1,3-Difluoropropan-2-yl)amino)-N-(6-(5-methyl-1,3,4-thiadiazol-2-yl) isoquinolin-3-yl)piperidine-1-carboxamide 121.

Off-white solid (20.0 mg, 0.045 mmol, 16.5% yield). $^1$H NMR (499 MHz, DMSO-d$_6$) δ ppm 1.16-1.27 (2H, m), 1.83 (2H, br dd, J=12.90, 3.02 Hz), 2.76-2.85 (1H, m), 2.82 (3H, s), 2.90-3.00 (2H, m), 3.11-3.23 (1H, m), 4.09 (2H, br d, J=13.45 Hz), 4.32-4.51 (4H, m), 8.02 (1H, dd, J=8.51, 1.65 Hz), 8.15 (1H, d, J=8.51 Hz), 8.30 (1H, s), 8.37 (1H, s), 9.15 (1H, s), 9.29 (1H, s); ESIMS found for C$_{21}$H$_{24}$F$_2$N$_6$OS m/z 447.2 (M+1).

N-(6-(2-Methyloxazol-5-yl)isoquinolin-3-yl)-5,6-dihydroimidazo[1,2-a]pyrazine-7(8H)-carboxamide 126.

Beige solid (53.0 mg, 0.142 mmol, 31.9% yield). $^1$H NMR (500 MHz, DMSO-d$_6$) δ ppm 2.53 (3H, s), 3.94-4.02 (2H, m), 4.04-4.11 (2H, m), 4.74 (2H, s), 6.89 (1H, d, J=1.37 Hz), 7.12 (1H, d, J=1.10 Hz), 7.77 (1H, dd, J=8.51, 1.65 Hz), 7.77 (1H, s), 8.03-8.12 (2H, m), 8.23 (1H, s), 9.09 (1H, s), 9.65 (1H, s); ESIMS found for C$_{20}$H$_{18}$N$_6$O$_2$ m/z 375.2 (M+1).

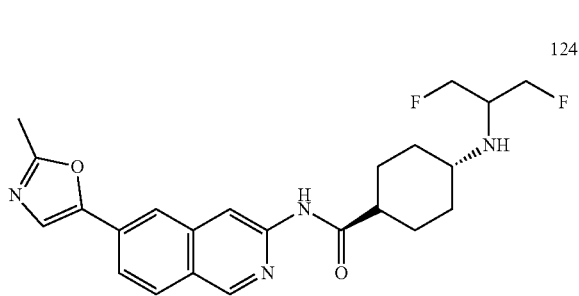

trans-4-((1,3-Difluoropropan-2-yl)amino)-N-(6-(2-methyloxazol-5-yl) isoquinolin-3-yl)cyclohexane-1-carboxamide 124.

Off-white solid (20.0 mg, 0.047 mmol, 14.2% yield). $^1$H NMR (500 MHz, DMSO-d$_6$) δ ppm 0.98-1.09 (2H, m), 1.42-1.54 (2H, m), 1.65 (1H, br s), 1.82-1.89 (2H, m), 1.91-1.98 (2H, m), 2.51-2.60 (1H, m), 2.53 (3H, s), 4.30-4.51 (4H, m), 7.78 (1H, s), 7.81 (1H, dd, J=8.64, 1.51 Hz), 8.09 (2H, dd, J=4.67, 3.84 Hz), 8.50 (1H, s), 9.10 (1H, s), 10.51 (1H, s); ESIMS found for C$_{23}$H$_{26}$F$_2$N$_4$O$_2$ m/z 429.2 (M+1).

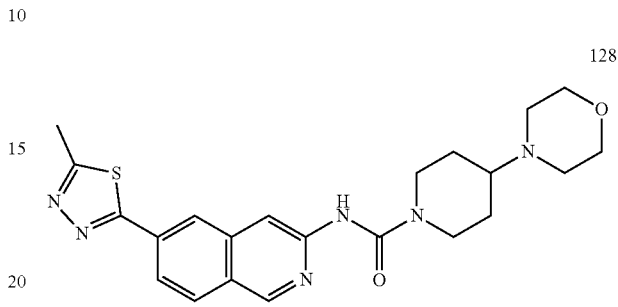

N-(6-(5-Methyl-1,3,4-thiadiazol-2-yl)isoquinolin-3-yl)-4-morpholinopiperidine-1-carboxamide 128.

Beige solid (55.0 mg, 0.125 mmol, 30.4% yield). $^1$H NMR (500 MHz, DMSO-d$_6$) δ ppm 1.28-1.40 (2H, m), 1.80 (2H, br d, J=10.70 Hz), 2.32-2.40 (1H, m), 2.44-2.49 (4H, m), 2.79-2.88 (2H, m), 2.82 (3H, s), 3.53-3.60 (4H, m), 4.23 (2H, br d, J=13.45 Hz), 8.02 (1H, dd, J=8.51, 1.65 Hz), 8.15 (1H, d, J=8.51 Hz), 8.30 (1H, s), 8.37 (1H, d, J=0.82 Hz), 9.15 (1H, s), 9.32 (1H, s); ESIMS found for C$_{22}$H$_{26}$N$_6$O$_2$S m/z 439.2 (M+1).

N-(6-(5-Methyl-1,3,4-thiadiazol-2-yl)isoquinolin-3-yl)-5,6-dihydroimidazo [1,2-a]pyrazine-7(8H)-carboxamide 125.

Beige solid (48.0 mg, 0.123 mmol, 29.7% yield). $^1$H NMR (500 MHz, DMSO-d$_6$) δ ppm 2.82 (3H, s), 3.95-4.01 (2H, m), 4.06-4.12 (2H, m), 4.75 (2H, s), 6.89 (1H, d, J=1.37 Hz), 7.12 (1H, d, J=1.37 Hz), 8.05 (1H, dd, J=8.51, 1.65 Hz), 8.17 (1H, d, J=8.51 Hz), 8.34 (1H, s), 8.41 (1H, d, J=0.82 Hz), 9.19 (1H, s), 9.74 (1H, s); ESIMS found for C$_{19}$H$_{17}$N$_7$OS m/z 392.1 (M+1).

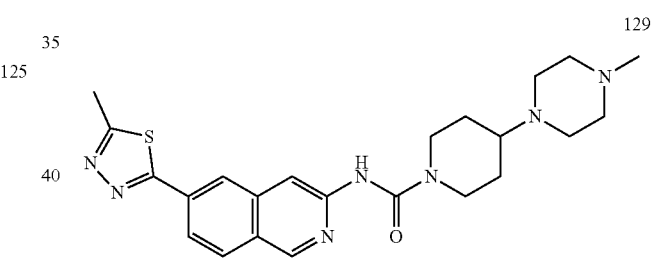

N-(6-(5-Methyl-1,3,4-thiadiazol-2-yl)isoquinolin-3-yl)-4-(4-methylpiperazin-1-yl)piperidine-1-carboxamide 129.

Off-white solid (45.0 mg, 0.100 mmol, 12.1% yield). $^1$H NMR (499 MHz, DMSO-d$_6$) δ ppm 1.34 (2H, qd, J=11.94, 3.98 Hz), 1.77 (2H, br d, J=10.98 Hz), 2.13 (3H, s), 2.30 (4H, br s), 2.36-2.43 (1H, m), 2.43-2.54 (4H, m), 2.77-2.87 (2H, m), 2.82 (3H, s), 4.23 (2H, br d, J=13.17 Hz), 8.02 (1H, dd, J=8.78, 1.65 Hz), 8.15 (1H, d, J=8.51 Hz), 8.30 (1H, s), 8.37 (1H, d, J=0.82 Hz), 9.15 (1H, s), 9.30 (1H, s); ESIMS found for C$_{23}$H$_{29}$N$_7$OS m/z 452.2 (M+1).

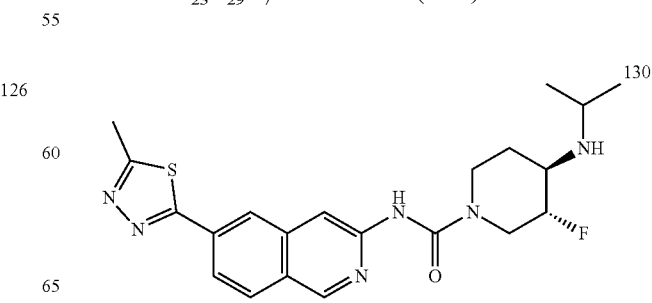

(3R,4R)-3-Fluoro-4-(isopropylamino)-N-(6-(5-methyl-1,3,4-thiadiazol-2-yl) isoquinolin-3-yl)piperidine-1-carboxamide 130.

Beige solid (20.0 mg, 0.04 mmol, 24.4% yield). $^1$H NMR (499 MHz, DMSO-$d_6$) δ ppm 0.98 (3H, d, J=6.31 Hz), 1.01 (3H, d, J=6.31 Hz), 1.27-1.36 (1H, m), 1.86-1.95 (1H, m), 2.82 (3H, s), 2.85-2.97 (2H, m), 3.22-3.29 (1H, m), 3.35-3.43 (1H, m), 3.75-3.84 (1H, m), 4.04 (1H, ddd, J=17.70, 13.86, 3.57 Hz), 4.33 (1H, dtd, J=47.8, 7.14, 3.84 Hz), 8.03 (1H, dd, J=8.51, 1.65 Hz), 8.16 (1H, d, J=8.51 Hz), 8.29 (1H, s), 8.39 (1H, s), 9.17 (1H, s), 9.43 (1H, s); ESIMS found for $C_{21}H_{25}FN_6OS$ m/z 429.2 (M+1).

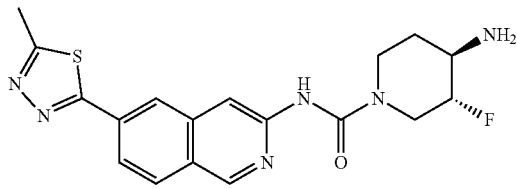

131

(3R,4R)-4-Amino-3-fluoro-N-(6-(5-methyl-1,3,4-thiadiazol-2-yl)isoquinolin-3-yl)piperidine-1-carboxamide 131.

Beige solid (200.0 mg, 0.518 mmol, 71.9% yield). $^1$H NMR (500 MHz, DMSO-$d_6$) δ ppm 1.28-1.39 (1H, m), 1.80-1.88 (1H, m), 2.82 (3H, s), 2.86-2.94 (1H, m), 3.14 (1H, ddd, J=13.17, 10.02, 2.61 Hz), 3.18-3.24 (1H, m), 3.86-3.94 (1H, m), 4.12-4.17 (1H, m), 4.18-4.29 (1H, m), 8.03 (1H, dd, J=8.51, 1.65 Hz), 8.16 (1H, d, J=8.78 Hz), 8.30 (1H, s), 8.39 (1H, s), 9.17 (1H, s), 9.47 (1H, s); ESIMS found for $C_{18}H_{19}FN_6OS$ m/z 387.2 (M+1).

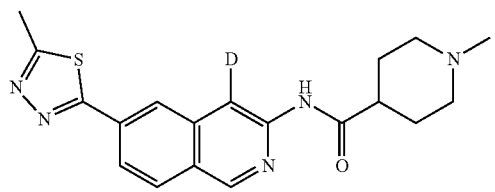

134

1-Methyl-N-(6-(5-methyl-1,3,4-thiadiazol-2-yl)isoquinolin-3-yl-4-d) piperidine-4-carboxamide 134.

Beige solid (10.0 mg, 0.027 mmol, 16.5% yield). $^1$H NMR (499 MHz, DMSO-$d_6$) δ ppm 1.63-1.74 (2H, m), 1.76-1.84 (2H, m), 1.86-1.96 (2H, m), 2.18 (3H, s), 2.52-2.58 (1H, m), 2.79-2.87 (5H, m), 8.09 (1H, dd, J=8.51, 1.65 Hz), 8.19 (1H, d, J=8.78 Hz), 8.44 (1H, s), 9.21 (1H, s), 10.64 (1H, s); ESIMS found for $C_{19}H_{20}[^2H]N_5OS$ m/z 369.15 (M+1).

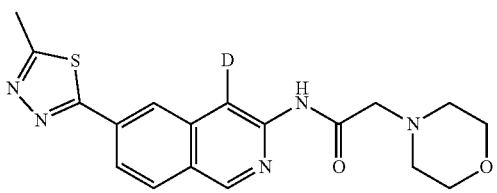

135

N-(6-(5-Methyl-1,3,4-thiadiazol-2-yl)isoquinolin-3-yl-4-d)-2-morpholinoacetamide 135.

Beige solid (3.0 mg, 0.008 mmol, 3.6% yield). 2.57-2.61 (4H, m), 2.83 (3H, s), 3.27 (2H, s), 3.63-3.69 (4H, m), 8.12 (1H, dd, J=8.51, 1.65 Hz), 8.21 (1H, d, J=8.51 Hz), 8.51 (1H, d, J=1.37 Hz), 9.23 (1H, s), 10.17 (1H, s); ESIMS found for $C_{18}H_{18}[^2H]N_5O_2S$ m/z 371.1 (M+1).

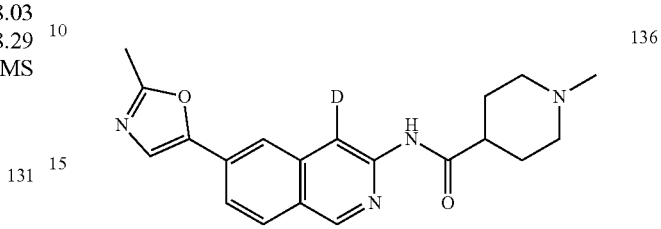

136

1-Methyl-N-(6-(2-methyloxazol-5-yl)isoquinolin-3-yl-4-d)piperidine-4-carboxamide 136.

Beige solid (20.0 mg, 0.057 mmol, 32.2% yield). $^1$H NMR (499 MHz, DMSO-$d_6$) δ ppm 1.64-1.75 (2H, m), 1.76-1.84 (2H, m), 1.89-1.99 (2H, m), 2.20 (3H, s), 2.51-2.57 (1H, m), 2.53 (3H, s), 2.85 (2H, br d, J=11.25 Hz), 7.78 (1H, s), 7.81 (1H, dd, J=8.78, 1.65 Hz), 8.06-8.12 (2H, m), 9.10 (1H, s), 10.56 (1H, s); ESIMS found for $C_{20}H_{21}[^2H]N_4O_2$ m/z 352.15 (M+1).

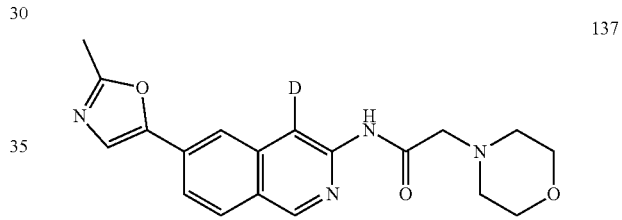

137

N-(6-(2-Methyloxazol-5-yl)isoquinolin-3-yl-4-d)-2-morpholinoacetamide 137.

Light orange solid (18.0 mg, 0.051 mmol, 32.0% yield). $^1$H NMR (499 MHz, DMSO-$d_6$) δ ppm 2.53 (3H, s), 2.55-2.60 (4H, m), 3.25 (2H, s), 3.63-3.69 (4H, m), 7.80 (1H, s), 7.83 (1H, dd, J=8.51, 1.65 Hz), 8.12 (1H, d, J=8.51 Hz), 8.16 (1H, s), 9.12 (1H, s), 10.08 (1H, s); ESIMS found for $C_{19}H_{19}[^2H]N_4O_3$ m/z 354.15 (M+1).

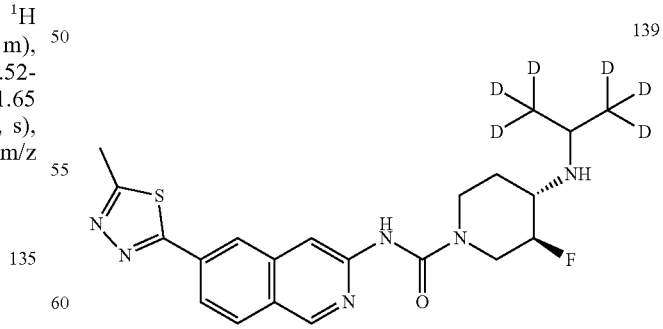

139

(3S,4S)-3-Fluoro-N-(6-(5-methyl-1,3,4-thiadiazol-2-yl)isoquinolin-3-yl)-4-((propan-2-yl-1,1,1,3,3,3-$d_6$)amino)piperidine-1-carboxamide 139.

Off-white solid (45.0 mg, 0.104 mmol, 80.0% yield). $^1$H NMR (499 MHz, DMSO-$d_6$) δ ppm 1.27-1.36 (1H, m), 1.60

(1H, br s), 1.86-1.95 (1H, m), 2.82 (3H, s), 2.83-2.93 (2H, m), 3.22-3.30 (1H, m), 3.36-3.42 (1H, m), 3.74-3.84 (1H, m), 3.98-4.09 (1H, m), 4.25-4.42 (1H, m), 8.03 (1H, dd, J=8.51, 1.65 Hz), 8.15 (1H, d, J=8.51 Hz), 8.29 (1H, s), 8.38 (1H, s), 9.16 (1H, s), 9.42 (1H, s); ESIMS found for $C_{21}H_{19}[^2H_6]FN_6OS$ m/z 435.2 (M+1).

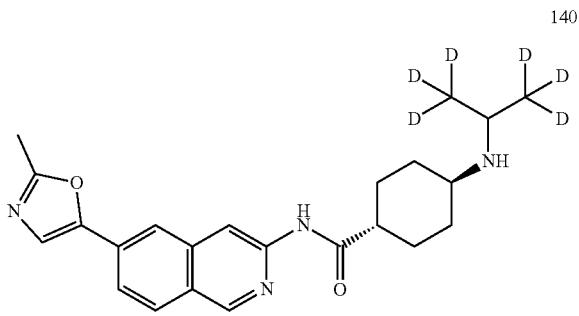 [SMILES: [2H]C([2H])([2H])C(N[C@H]1CC[C@H](C(=O)Nc2cc3cc(-c4cnc(C)o4)ccc3cn2)CC1)C([2H])([2H])[2H]]

140 trans-N-(6-(2-methyloxazol-5-yl)isoquinolin-3-yl)-4-((propan-2-yl-1,1,1,3,3,3-$d_6$)amino)cyclohexane-1-carboxamide 141.

Beige solid (48.0 mg, 0.120 mmol, 84.4% yield). $^1$H NMR (499 MHz, DMSO-$d_6$) δ ppm 0.96-1.05 (2H, m), 1.13 (1H, br s), 1.49 (2H, qd, J=12.90, 3.02 Hz), 1.85 (2H, br d, J=11.53 Hz), 1.92 (2H, br dd, J=12.76, 2.88 Hz), 2.41-2.47 (1H, m), 2.47-2.51 (1H, m), 2.53 (3H, s), 2.85-2.92 (1H, m), 7.78 (1H, s), 7.80 (1H, dd, J=8.78, 1.37 Hz), 8.06-8.12 (2H, m), 8.50 (1H, s), 9.10 (1H, s), 10.49 (1H, s); ESIMS found for $C_{23}H_{22}[^2H_6]N_4O_2$ m/z 399.25 (M+1).

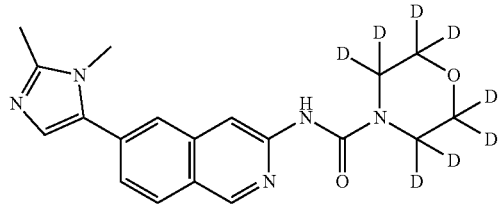

143

N-(6-(1,2-Dimethyl-1H-imidazol-5-yl)isoquinolin-3-yl) morpholine-$d_8$-4-carboxamide 143.

Off-white solid (35.0 mg, 0.10 mmol, 23.2% yield). $^1$H NMR (499 MHz, DMSO-$d_6$) δ ppm 2.39 (3H, s), 3.65 (3H, s), 7.09 (1H, s), 7.54 (1H, dd, J=8.51, 1.65 Hz), 7.84 (1H, s), 8.04 (1H, d, J=8.51 Hz), 8.22 (1H, s), 9.07 (1H, s), 9.24 (1H, s); ESIMS found for $C_{19}H_{13}[^2H_8]N_5O_2$ m/z 360.25 (M+1).

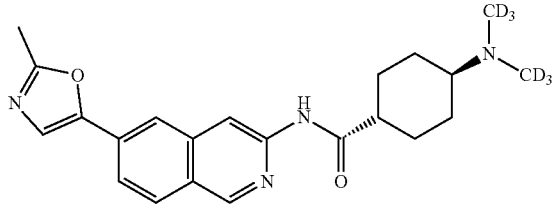

144 trans-4-(Bis(methyl-$d_3$)amino)-N-(6-(2-methyloxazol-5-yl)isoquinolin-3-yl) cyclohexane-1-carboxamide 144.

White solid (4.0 mg, 0.010 mmol, 6.1% yield). $^1$H NMR (499 MHz, DMSO-$d_6$) δ ppm 1.13-1.24 (2H, m), 1.41-1.54 (2H, m), 1.82-1.95 (4H, m), 2.09-2.20 (1H, m), 2.43-2.49 (1H, m), 2.53 (3H, s), 7.78 (1H, s), 7.79-7.82 (1H, m), 8.07-8.11 (2H, m), 8.50 (1H, s), 9.10 (1H, s), 10.50 (1H, s); ESIMS found for $C_{22}H_{20}[^2H_6]N_4O_2$ m/z 385.3 (M+1).

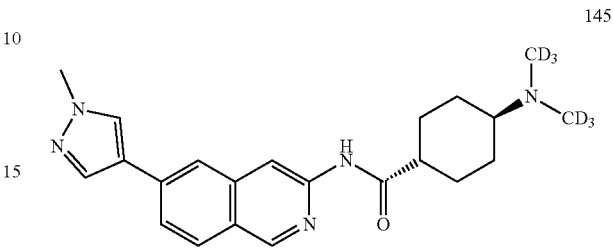

145 trans-4-(Bis(methyl-$d_3$)amino)-N-(6-(1-methyl-1H-pyrazol-4-yl)isoquinolin-3-yl)cyclohexane-1-carboxamide 145.

White solid (17.0 mg, 0.044 mmol, 10.3% yield). $^1$H NMR (499 MHz, DMSO-$d_6$) δ ppm 1.12-1.22 (2H, m), 1.42-1.54 (2H, m), 1.83-1.95 (4H, m), 2.14 (1H, tt, J=11.49, 3.33 Hz), 2.43-2.49 (1H, m), 3.90 (3H, s), 7.74 (1H, dd, J=8.51, 1.65 Hz), 7.99 (1H, d, J=8.51 Hz), 8.02 (1H, s), 8.07 (1H, s), 8.35 (1H, s), 8.42 (1H, s), 9.02 (1H, s), 10.41 (1H, s); ESIMS found for $C_{22}H_{21}[^2H_6]N_5O$ m/z 384.25 (M+1).

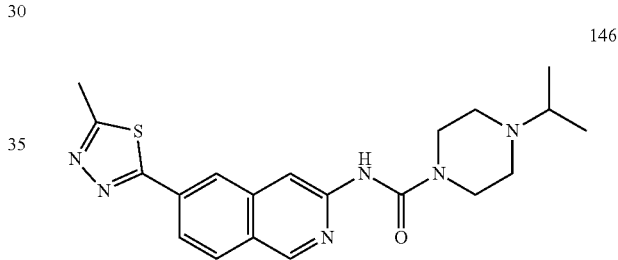

146

4-Isopropyl-N-(6-(5-methyl-1,3,4-thiadiazol-2-yl)isoquinolin-3-yl) piperazine-1-carboxamide 146.

Beige solid (4.0 mg, 0.010 mmol, 1.2% yield). $^1$H NMR (500 MHz, DMSO-$d_6$) δ ppm 0.98 (6H, d, J=6.59 Hz), 2.43-2.47 (4H, m), 2.62-2.72 (1H, m), 2.82 (3H, s), 3.47-3.54 (4H, m), 8.02 (1H, dd, J=8.51, 1.65 Hz), 8.15 (1H, d, J=8.51 Hz), 8.31 (1H, s), 8.37 (1H, s), 9.16 (1H, s), 9.29 (1H, s); ESIMS found for $C_{20}H_{24}N_6OS$ m/z 397.2 (M+1).

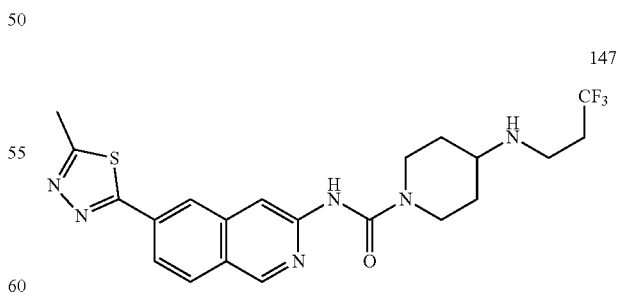

147

N-(6-(5-Methyl-1,3,4-thiadiazol-2-yl)isoquinolin-3-yl)-4-((3,3,3-trifluoropropyl)amino)piperidine-1-carboxamide 147.

Off-white solid (20.0 mg, 0.043 mmol, 24.4% yield). $^1$H NMR (499 MHz, DMSO-$d_6$) δ ppm 1.14-1.25 (2H, m), 1.77-1.85 (3H, m), 2.35-2.42 (2H, m), 2.59-2.67 (1H, m), 2.73-2.80 (2H, m), 2.82 (3H, s), 2.91-3.01 (2H, m), 4.05-4.12 (2H, m), 8.02 (1H, dd, J=8.51, 1.65 Hz), 8.15 (1H, d, J=8.78 Hz), 8.30 (1H, s), 8.37 (1H, d, J=0.82 Hz), 9.15 (1H, s), 9.29 (1H, s); ESIMS found for C$_{21}$H$_{23}$F$_3$N$_6$OS m/z 465.2 (M+1).

J=8.51, 1.65 Hz), 8.14 (1H, d, J=8.51 Hz), 8.30 (1H, s), 8.37 (1H, s), 9.15 (1H, s), 9.26 (1H, s); ESIMS found for C$_{18}$H$_{20}$N$_6$OS m/z 369.2 (M+1).

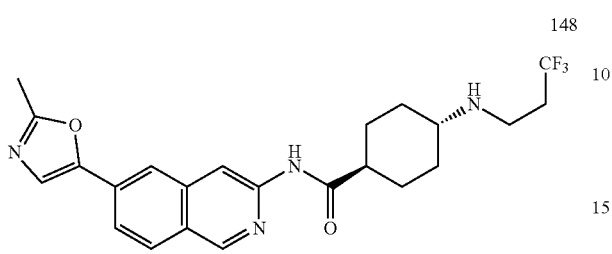

148

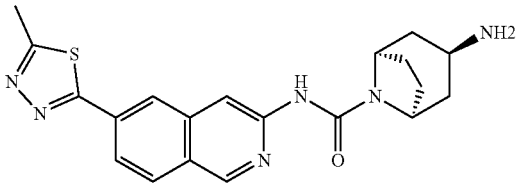

151 trans-N-(6-(2-Methyloxazol-5-yl)isoquinolin-3-yl)-4-((3,3,3-trifluoropropyl) amino)cyclohexane-1-carboxamide 148.

Off-white solid (25.0 mg, 0.056 mmol, 19.6% yield). $^1$H NMR (499 MHz, DMSO-d$_6$) δ ppm 0.97-1.09 (2H, m), 1.44-1.56 (2H, m), 1.83-1.90 (2H, m), 1.94 (2H, br dd, J=12.21, 2.33 Hz), 2.31-2.43 (3H, m), 2.52-2.55 (1H, m), 2.53 (3H, s), 2.76 (2H, t, J=7.41 Hz), 7.78 (1H, s), 7.81 (1H, dd, J=8.64, 1.51 Hz), 8.05-8.12 (2H, m), 8.50 (1H, s), 9.10 (1H, s), 10.50 (1H, s); ESIMS found for C$_{23}$H$_{25}$F$_3$N$_4$O$_2$ m/z 447.2 (M+1).

(1R,5S)-3-exo-Amino-N-(6-(5-methyl-1,3,4-thiadiazol-2-yl)isoquinolin-3-yl)-8-azabicyclo[3.2.1]octane-8-carboxamide 151.

Beige solid (100.0 mg, 0.254 mmol, 62.7% yield). $^1$H NMR (499 MHz, DMSO-d$_6$) δ ppm 1.35-1.43 (2H, m), 1.64-1.70 (2H, m), 1.70-1.76 (2H, m), 1.85-1.92 (2H, m), 2.82 (3H, s), 3.06 (1H, tt, J=10.94, 5.39 Hz), 4.49 (2H, br s), 8.02 (1H, dd, J=8.51, 1.65 Hz), 8.15 (1H, d, J=8.51 Hz), 8.37 (1H, s), 8.42 (1H, s), 9.16 (1H, s), 9.18 (1H, s); ESIMS found for C$_{20}$H$_{22}$N$_6$OS m/z 395.2 (M+1).

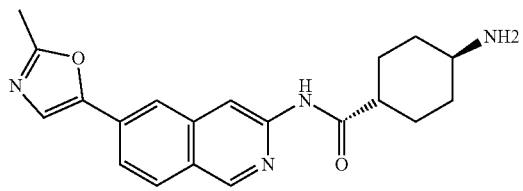

149

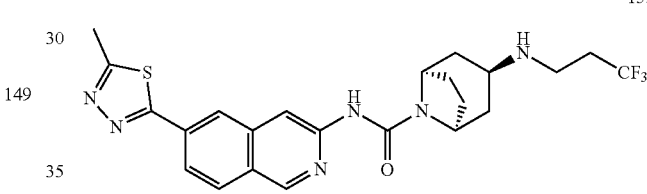

153 trans-4-Amino-N-(6-(2-methyloxazol-5-yl)isoquinolin-3-yl)cyclohexane-1-carboxamide 149.

Beige solid (370.0 mg, 1.056 mmol, 95.1% yield). $^1$H NMR (499 MHz, DMSO-d$_6$) δ ppm 0.98-1.11 (2H, m), 1.43-1.54 (2H, m), 1.82 (4H, br d, J=11.53 Hz), 2.43-2.49 (1H, m), 2.52 (1H, br s), 2.53 (3H, s), 7.78 (1H, s), 7.79-7.83 (1H, m), 8.06-8.12 (2H, m), 8.49 (1H, s), 9.10 (1H, s), 10.49 (1H, s); ESIMS found for C$_{20}$H$_{22}$N$_4$O$_2$ m/z 351.2 (M+1).

(1R,5S)-N-(6-(5-Methyl-1,3,4-thiadiazol-2-yl)isoquinolin-3-yl)-3-exo-((3,3,3-trifluoropropyl)amino)-8-azabicyclo[3.2.1]octane-8-carboxamide 153.

Beige solid (8.0 mg, 0.016 mmol, 19.5% yield). $^1$H NMR (499 MHz, DMSO-d$_6$) δ ppm 1.37 (2H, br t, J=10.98 Hz), 1.63 (1H, br s), 1.68-1.75 (2H, m), 1.79-1.86 (2H, m), 1.86-1.93 (2H, m), 2.26-2.39 (2H, m), 2.71 (2H, t, J=7.55 Hz), 2.82 (3H, s), 2.94 (1H, tt, J=10.74, 5.32 Hz), 4.52 (2H, br s), 8.02 (1H, dd, J=8.51, 1.65 Hz), 8.15 (1H, d, J=8.51 Hz), 8.37 (1H, s), 8.41 (1H, s), 9.16 (1H, s), 9.21 (1H, s); ESIMS found for C$_{23}$H$_{25}$F$_3$N$_6$OS m/z 491.2 (M+1).

150

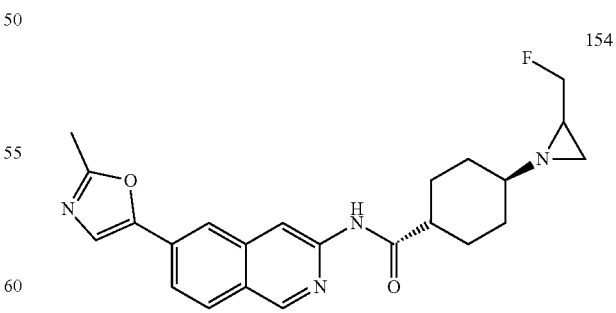

154

4-Amino-N-(6-(5-methyl-1,3,4-thiadiazol-2-yl)isoquinolin-3-yl)piperidine-1-carboxamide 150.

Beige solid (400.0 mg, 1.086 mmol, 53.5% yield). $^1$H NMR (499 MHz, DMSO-d$_6$) δ ppm 1.12-1.23 (2H, m), 1.72 (2H, br dd, J=12.90, 3.02 Hz), 2.72-2.80 (1H, m), 2.82 (3H, s), 2.88-2.96 (2H, m), 4.05-4.13 (2H, m), 8.02 (1H, dd, trans-4-(2-(fluoromethyl)aziridin-1-yl)-N-(6-(2-methyloxazol-5-yl) isoquinolin-3-yl)cyclohexane-1-carboxamide 154.

Off-white solid (10.0 mg, 0.025 mmol, 7.4% yield). $^1$H NMR (500 MHz, DMSO-d$_6$) δ ppm 1.17-1.33 (4H, m), 1.35-1.45 (3H, m), 1.87 (4H, br d, J=9.88 Hz), 2.51-2.59 (1H, m), 2.53 (3H, s), 3.97-4.14 (2H, m), 4.36-4.50 (1H, m), 7.76-7.79 (1H, m), 7.80 (1H, dd, J=8.64, 1.51 Hz), 8.06-8.13 (2H, m), 8.49 (1H, s), 9.10 (1H, s), 10.51 (1H, s); ESIMS found for $C_{23}H_{25}FN_4O_2$ m/z 409.2 (M+1).

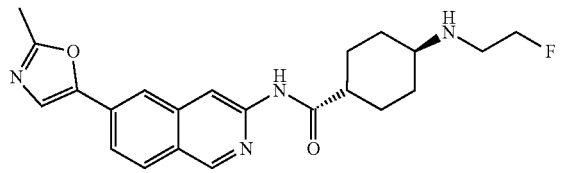

trans-4-((2-fluoroethyl)amino)-N-(6-(2-methyloxazol-5-yl)isoquinolin-3-yl) cyclohexane-1-carboxamide 155.

White solid (25.0 mg, 0.063 mmol, 34.5% yield). $^1$H NMR (499 MHz, DMSO-$d_6$) δ ppm 0.95-1.08 (2H, m), 1.49 (2H, qd, J=12.85, 3.16 Hz), 1.87 (2H, br d, J=11.25 Hz), 1.92-2.00 (1H, m), 2.37-2.43 (1H, m), 2.51-2.55 (1H, m), 2.53 (2H, s), 2.83 (2H, dt, J=27.00, 4.90 Hz), 4.44 (2H, dt, J=48.10, 5.00 Hz), 7.78 (1H, s), 7.80 (1H, dd, J=8.64, 1.51 Hz), 8.07-8.12 (2H, m), 8.50 (1H, s), 9.10 (1H, s), 10.50 (1H, s); ESIMS found for $C_{22}H_{25}FN_4O_2$ m/z 397.2 (M+1).

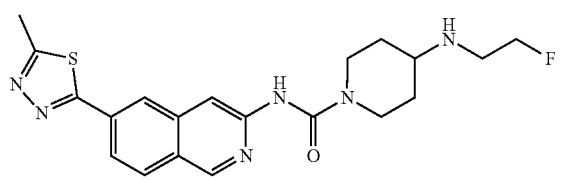

4-((2-Fluoroethyl)amino)-N-(6-(5-methyl-1,3,4-thiadiazol-2-yl)isoquinolin-3-yl)piperidine-1-carboxamide 156.

Beige solid (10.0 mg, 0.024 mmol, 15.6% yield). $^1$H NMR (500 MHz, DMSO-$d_6$) δ ppm 1.38-1.49 (2H, m), 1.82-1.90 (2H, m), 2.17-2.26 (2H, m), 2.58-2.68 (2H, m), 2.74-2.81 (2H, m), 2.82 (3H, s), 3.53-3.61 (1H, m), 4.53 (2H, dt, J=47.80, 5.00 Hz), 7.99 (1H, dd, J=8.51, 1.65 Hz), 8.12 (1H, d, J=8.78 Hz), 8.19 (1H, s), 8.33 (1H, d, J=0.82 Hz), 9.06 (1H, s), 9.11 (1H, s); ESIMS found for $C_{20}H_{23}FN_6OS$ m/z 415.2 (M+1).

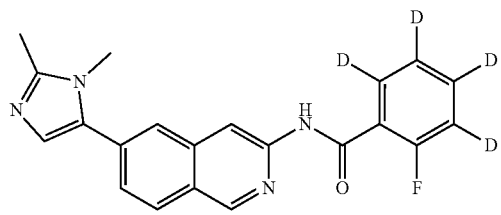

N-(6-(1,2-Dimethyl-1H-imidazol-5-yl)isoquinolin-3-yl)-2-fluorobenzamide-3,4,5,6-$d_4$ 157.

Brown solid (6.4.0 mg, 0.018 mmol, 20.9% yield). $^1$H NMR (500 MHz, DMSO-$d_6$) δ ppm 2.40 (3H, s), 3.69 (3H, s), 7.15 (1H, s), 7.66 (1H, dd, J=8.51, 1.65 Hz), 8.01 (1H, s), 8.13 (1H, d, J=8.78 Hz), 8.66 (1H, s), 9.18 (1H, s), 10.87 (1H, s); ESIMS found for $C_{21}H_{13}[^2H_4]FN_4O$ m/z 365.2 (M+1).

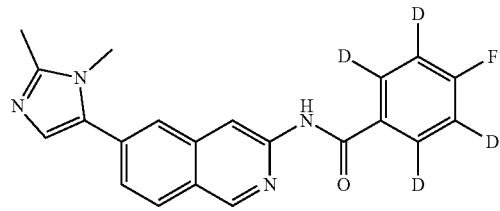

N-(6-(1,2-Dimethyl-1H-imidazol-5-yl)isoquinolin-3-yl)-4-fluorobenzamide-2,3,5,6-$d_4$ 158.

Brown solid (7.8 mg, 0.021 mmol, 17.0% yield). $^1$H NMR (499 MHz, DMSO-$d_6$) δ ppm 2.40 (3H, s), 3.69 (3H, s), 7.15 (1H, s), 7.66 (1H, dd, J=8.51, 1.65 Hz), 8.00 (1H, s), 8.14 (1H, d, J=8.51 Hz), 8.67 (1H, s), 9.21 (1H, s), 10.95 (1H, s); ESIMS found for $C_{21}H_{13}[^2H_4]FN_4O$ m/z 365.15 (M+1).

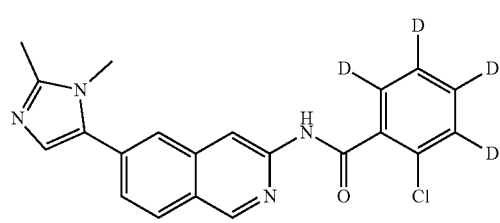

2-Chloro-N-(6-(1,2-dimethyl-1H-imidazol-5-yl)isoquinolin-3-yl)benzamide-3,4,5,6-$d_4$ 159.

Brown solid (10.1 mg, 0.027 mmol, 31.6% yield). $^1$H NMR (499 MHz, DMSO-$d_6$) δ ppm 2.40 (3H, s), 3.69 (3H, s), 7.15 (1H, s), 7.66 (1H, dd, J=8.51, 1.65 Hz), 8.02 (1H, s), 8.12 (1H, d, J=8.51 Hz), 8.66 (1H, s), 9.16 (1H, s), 11.12 (1H, s); ESIMS found for $C_{21}H_{13}[^2H_4]ClN_4O$ m/z 381. (M+1).

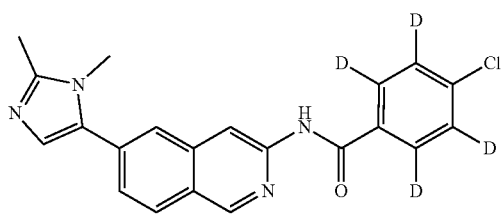

4-Chloro-N-(6-(1,2-dimethyl-1H-imidazol-5-yl)isoquinolin-3-yl)benzamide-2,3,5,6-$d_4$ 160.

Brown solid (15.0 mg, 0.039 mmol, 31.3% yield). $^1$H NMR (499 MHz, DMSO-$d_6$) δ ppm 2.40 (3H, s), 3.68 (3H, s), 7.14 (1H, s), 7.66 (1H, dd, J=8.51, 1.65 Hz), 8.00 (1H, s), 8.14 (1H, d, J=8.78 Hz), 8.67 (1H, s), 9.21 (1H, s), 11.01 (1H, s); ESIMS found for $C_{21}H_{13}[^2H_4]ClN_4O$ m/z 381.15 (M+1).

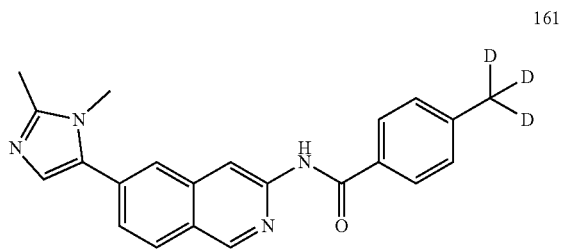 [SMILES: [2H]C([2H])([2H])c1ccc(C(=O)Nc2cc3cc(-c4cnc(C)n4C)ccc3cn2)cc1]

N-(6-(1,2-Dimethyl-1H-imidazol-5-yl)isoquinolin-3-yl)-4-(methyl-d₃) benzamide 161.

Brown solid (10.6 mg, 0.030 mmol, 35.1% yield). ¹H NMR (499 MHz, DMSO-d₆) δ ppm 2.41 (3H, s), 3.69 (3H, s), 7.15 (1H, s), 7.31-7.37 (2H, m), 7.65 (1H, dd, J=8.51, 1.65 Hz), 7.99 (1H, br s), 7.99-8.04 (2H, m), 8.11-8.16 (1H, m), 8.67 (1H, s), 9.20 (1H, s), 10.77 (1H, s); ESIMS found for $C_{22}H_{17}[^{2}H_{3}]N_{4}O$ m/z 360.2 (M+1).

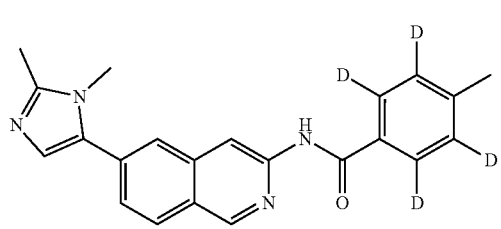

N-(6-(1,2-Dimethyl-1H-imidazol-5-yl)isoquinolin-3-yl)-4-methylbenzamide-2,3,5,6-d₄ 162.

Brown solid (9.3 mg, 0.026 mmol, 30.7% yield). ¹H NMR (499 MHz, DMSO-d₆) δ ppm 2.40 (3H, s), 2.40 (3H, s), 3.68 (3H, s), 7.14 (1H, s), 7.65 (1H, dd, J=8.23, 1.65 Hz), 7.99 (1H, s), 8.13 (1H, d, J=8.51 Hz), 8.67 (1H, s), 9.20 (1H, s), 10.77 (1H, s); ESIMS found for $C_{22}H_{16}[^{2}H_{4}]N_{4}O$ m/z 361. (M+1).

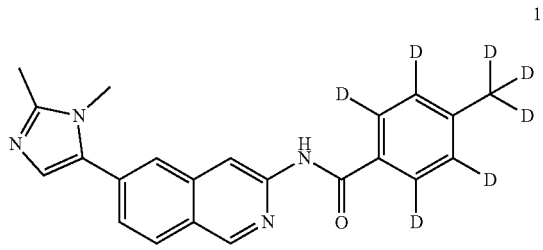

N-(6-(1,2-Dimethyl-1H-imidazol-5-yl)isoquinolin-3-yl)-4-(methyl-d₃) benzamide-2,3,5,6-d₄ 163.

Brown solid (8.4 mg, 0.023 mmol, 18.3% yield). ¹H NMR (499 MHz, DMSO-d₆) δ ppm 2.40 (3H, s), 3.68 (3H, s), 7.14 (1H, s), 7.65 (1H, dd, J=8.51, 1.65 Hz), 7.99 (1H, s), 8.13 (1H, d, J=8.51 Hz), 8.67 (1H, s), 9.20 (1H, s), 10.78 (1H, s); ESIMS found for $C_{22}H_{13}[^{2}H_{7}]N_{4}O$ m/z 364.2 (M+1).

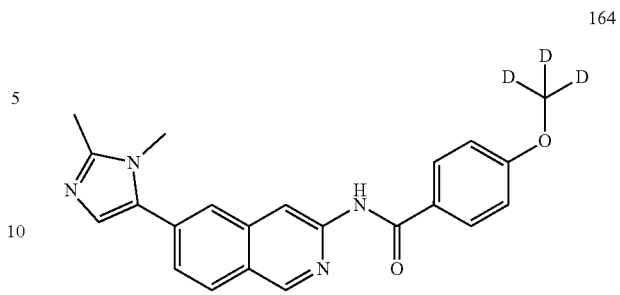

N-(6-(1,2-Dimethyl-1H-imidazol-5-yl)isoquinolin-3-yl)-4-(methoxy-d₃) benzamide 164.

Brown solid (10.5 mg, 0.028 mmol, 33.3% yield). ¹H NMR (499 MHz, DMSO-d₆) δ ppm 2.42 (3H, s), 3.69 (3H, s), 7.06 (2H, d, J=8.78 Hz), 7.19 (1H, s), 7.64 (1H, dd, J=8.37, 1.51 Hz), 7.99 (1H, s), 8.07-8.12 (2H, m), 8.13 (1H, d, J=8.51 Hz), 8.67 (1H, s), 9.20 (1H, s), 10.71 (1H, s); ESIMS found for $C_{22}H_{17}[^{2}H_{3}]N_{4}O_{2}$ m/z 376.2 (M+1).

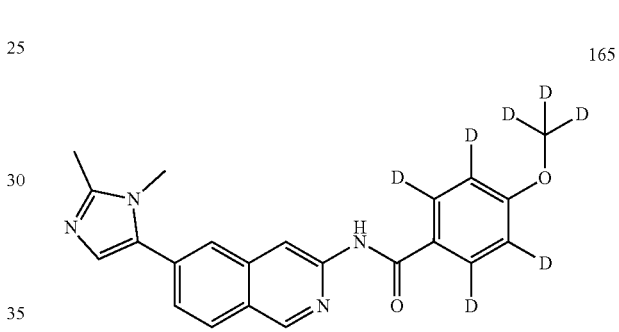

N-(6-(1,2-Dimethyl-1H-imidazol-5-yl)isoquinolin-3-yl)-4-(methoxy-d₃) benzamide-2,3,5,6-d4 165.

Brown solid (11.1 mg, 0.029 mmol, 23.3% yield). ¹H NMR (499 MHz, DMSO-d₆) δ ppm 2.40 (3H, s), 3.68 (3H, s), 7.14 (1H, s), 7.64 (1H, dd, J=8.51, 1.65 Hz), 7.98 (1H, s), 8.13 (1H, d, J=8.51 Hz), 8.66 (1H, s), 9.19 (1H, s), 10.71 (1H, s); ESIMS found for $C_{22}H_{13}[^{2}H_{7}]N_{4}O_{2}$ m/z 380.2 (M+1).

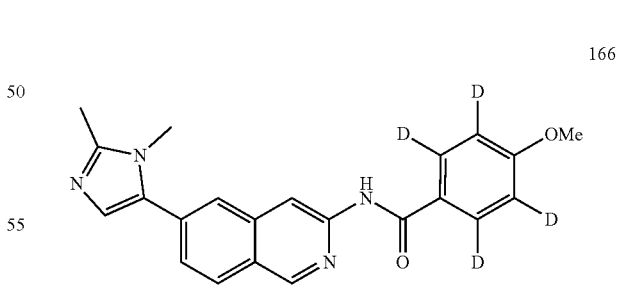

N-(6-(1,2-Dimethyl-1H-imidazol-5-yl)isoquinolin-3-yl)-4-methoxybenzamide-2,3,5,6-d₄ 166.

Brown solid (12.5 mg, 0.033 mmol, 39.6% yield). ¹H NMR (500 MHz, DMSO-d₆) δ ppm 2.44 (3H, s), 3.70 (3H, s), 3.85 (3H, s), 7.25 (1H, s), 7.65 (1H, dd, J=8.23, 1.65 Hz), 8.01 (1H, s), 8.12-8.18 (1H, m), 8.68 (1H, s), 9.21 (1H, s), 10.73 (1H, s); ESIMS found for $C_{22}H_{16}[^{2}H_{4}]N_{4}O_{2}$ m/z 377.2 (M+1).

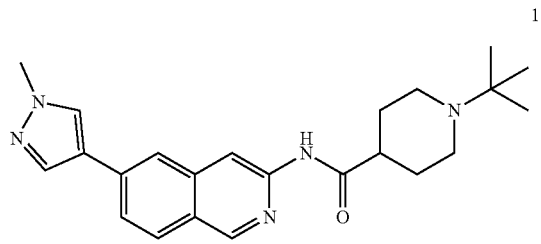

167

1-(tert-Butyl)-N-(6-(1-methyl-1H-pyrazol-4-yl)isoquinolin-3-yl)piperidine-4-carboxamide 167.

Off-white solid (48.0 mg, 0.123 mmol, 24.3% yield). $^1$H NMR (499 MHz, DMSO-d$_6$) δ ppm 1.02 (9H, s), 1.62 (2H, qd, J=12.17, 3.57 Hz), 1.79 (2H, br d, J=10.98 Hz), 1.98-2.09 (2H, m), 2.45-2.54 (1H, m), 3.03 (2H, br d, J=11.53 Hz), 3.90 (3H, s), 7.74 (1H, dd, J=8.51, 1.65 Hz), 7.99 (1H, d, J=8.51 Hz), 8.04 (1H, s), 8.08 (1H, s), 8.34 (1H, s), 8.45 (1H, s), 9.02 (1H, s), 10.43 (1H, s); ESIMS found for C$_{23}$H$_{29}$N$_5$O m/z 392.2 (M+1).

168

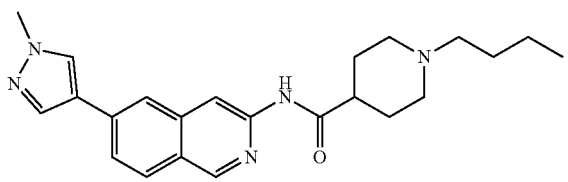

4-((2,2-Difluoroethyl)amino)-N-(6-(5-methyl-1,3,4-thiadiazol-2-yl) isoquinolin-3-yl)piperidine-1-carboxamide 168.

White solid (1.0 mg, 0.0 mmol, % yield). $^1$H NMR (499 MHz, DMSO-d$_6$) δ ppm 1.38-1.49 (2H, m), 1.81-1.89 (2H, m), 2.30-2.37 (2H, m), 2.73 (2H, td, J=15.64, 4.39 Hz), 2.81 (2H, br s), 2.82 (3H, s), 3.53-3.62 (1H, m), 6.13 (1H, tt, J=55.80, 4.40 Hz), 7.06 (1H, br d, J=6.59 Hz), 7.99 (1H, dd, J=8.51, 1.65 Hz), 8.13 (1H, d, J=8.51 Hz), 8.19 (1H, s), 8.33 (1H, s), 9.06 (1H, s), 9.11 (1H, s); ESIMS found for C$_{20}$H$_{22}$F$_2$N$_6$OS m/z 433. (M+1).

169

1-Butyl-N-(6-(1-methyl-1H-pyrazol-4-yl)isoquinolin-3-yl)piperidine-4-carboxamide 169.

White solid (1.0 mg, 0.0 mmol, % yield). $^1$H NMR (499 MHz, DMSO-d$_6$) δ ppm 0.89 (3H, t, J=7.41 Hz), 1.29 (2H, sxt, J=7.35 Hz), 1.37-1.45 (2H, m), 1.61-1.71 (2H, m), 1.73-1.80 (2H, m), 1.86 (2H, td, J=11.66, 2.20 Hz), 2.22-2.28 (2H, m), 2.51-2.57 (1H, m), 2.90 (2H, br d, J=11.25 Hz), 3.90 (3H, s), 7.74 (1H, dd, J=8.51, 1.65 Hz), 7.99 (1H, d, J=8.51 Hz), 8.03 (1H, s), 8.08 (1H, d, J=0.82 Hz), 8.35 (1H, s), 8.44 (1H, s), 9.02 (1H, s), 10.45 (1H, s); ESIMS found for C$_{23}$H$_{29}$N$_5$O m/z 392. (M+1).

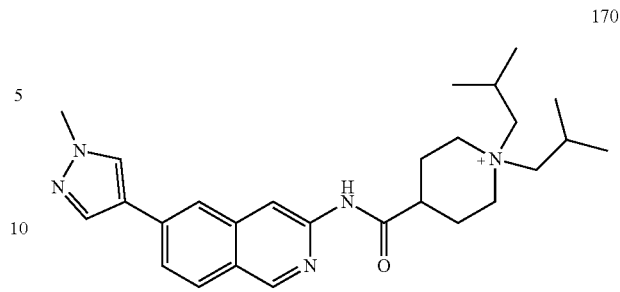

170

1,1-Diisobutyl-4-((6-(1-methyl-1H-pyrazol-4-yl)isoquinolin-3-yl) carbamoyl)piperidin-1-ium 170.

Yellow-white solid (10.0 mg, 0.022 mmol, 17.5% yield). $^1$H NMR (499 MHz, DMSO-d$_6$) δ ppm 1.07 (6H, d, J=6.6 Hz), 1.08 (6H, d, J=6.6 Hz), 2.12 (4H, br d, J=3.84 Hz), 2.18 (1H, br dd, J=13.31, 6.72 Hz), 2.21-2.28 (1H, m), 2.84-2.93 (1H, m), 3.32-3.41 (6H, m), 3.63 (2H, br d, J=12.90 Hz), 3.91 (3H, s), 7.77 (1H, dd, J=8.51, 1.65 Hz), 8.01-8.06 (2H, m), 8.09 (1H, s), 8.36 (1H, s), 8.40-8.47 (3H, m), 9.06 (1H, s), 10.72 (1H, s); ESIMS found for C$_{27}$H$_{38}$N$_5$O m/z 449.3 (M+1).

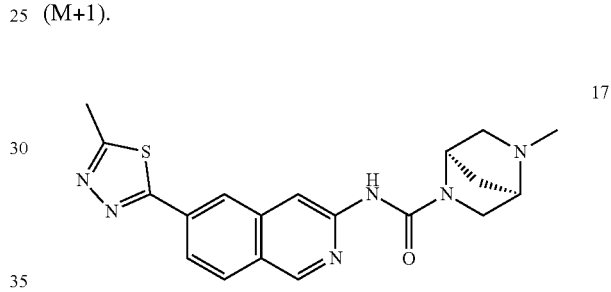

176

(1R,4R)-5-Methyl-N-(6-(5-methyl-1,3,4-thiadiazol-2-yl)isoquinolin-3-yl)-2,5-diazabicyclo[2.2.1]heptane-2-carboxamide 176.

White solid (55.0 mg, 0.145 mmol, 40.7% yield). $^1$H NMR (499 MHz, DMSO-d$_6$) δ ppm 1.66 (1H, br d, J=9.33 Hz), 1.81 (1H, br d, J=9.33 Hz), 2.31 (3H, s), 2.53 (1H, br d, J=9.61 Hz), 2.79 (1H, dd, J=9.47, 2.06 Hz), 2.82 (3H, s), 3.41 (1H, br s), 3.59 (1H, br d, J=9.61 Hz), 4.59 (1H, br s), 8.02 (1H, dd, J=8.51, 1.65 Hz), 8.15 (1H, d, J=8.78 Hz), 8.37 (1H, s), 8.38 (1H, s), 9.02 (1H, br s), 9.15 (1H, s); ESIMS found for C$_{19}$H$_{20}$N$_6$OS m/z 381. (M+1).

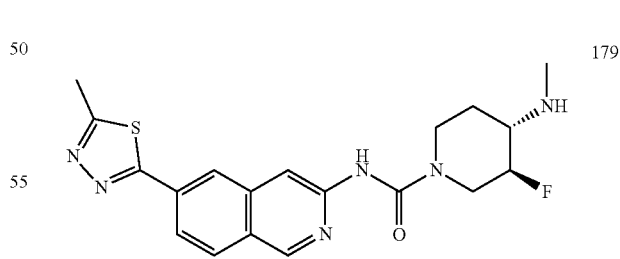

179

(3S,4S)-3-Fluoro-N-(6-(5-methyl-1,3,4-thiadiazol-2-yl)isoquinolin-3-yl)-4-(methylamino)piperidine-1-carboxamide 179.

Beige solid (8.0 mg, 0.020 mmol, 15.42% yield). $^1$H NMR (499 MHz, DMSO-d$_6$) δ ppm 1.30-1.40 (1H, m), 1.91 (1H, ddt, J=13.65, 9.95, 3.43, 3.43 Hz), 2.34 (3H, s), 2.62-2.72 (1H, m), 2.82 (3H, s), 3.21-3.29 (2H, m), 3.35-3.44 (2H, m), 3.75-3.84 (1H, m), 3.96-4.07 (1H, m), 4.32-

4.49 (1H, m), 8.03 (1H, dd, J=8.51, 1.65 Hz), 8.15 (1H, d, J=8.51 Hz), 8.29 (1H, s), 8.39 (1H, s), 9.16 (1H, s), 9.43 (1H, s); ESIMS found for $C_{19}H_{21}FN_6OS$ m/z 401.2 (M+1).

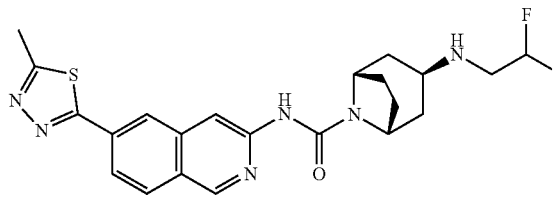

188

(1R,5S)-cis-3-((2,2-difluoroethyl)amino)-N-(6-(5-methyl-1,3,4-thiadiazol-2-yl)isoquinolin-3-yl)-8-azabicyclo[3.2.1]octane-8-carboxamide 188.

Off-white solid (10.0 mg, 0.022 mmol, 17.2% yield). $^1$H NMR (499 MHz, DMSO-$d_6$) δ ppm 1.56 (1H, s), 1.59 (1H, s), 1.95 (4H, s), 2.09 (2H, ddd, J=14.41, 6.72, 3.29 Hz), 2.71 (2H, td, J=15.64, 4.39 Hz), 2.82 (3H, s), 3.21 (2H, br s), 3.84-3.91 (1H, m), 6.02 (1H, tt, J=56.40, 4.70 Hz), 7.99 (1H, dd, J=8.51, 1.65 Hz), 8.03 (1H, s), 8.14 (1H, d, J=8.78 Hz), 8.32 (1H, s), 9.13 (1H, s), 9.41 (1H, s); ESIMS found for $C_{22}H_{24}F_2N_6OS$ m/z 459.2 (M+1).

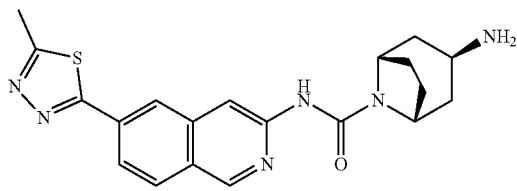

193

(1R,5S)-3-endo-Amino-N-(6-(5-methyl-1,3,4-thiadiazol-2-yl)isoquinolin-3-yl)-8-azabicyclo[3.2.1]octane-8-carboxamide 193.

Beige solid (203.0 mg, 0.515 mmol, 84.8% yield). $^1$H NMR (500 MHz, DMSO-$d_6$) δ ppm 1.43-1.49 (2H, m), 1.85 (2H, br dd, J=6.59, 1.37 Hz), 1.98-2.05 (2H, m), 2.25 (2H, br d, J=7.41 Hz), 2.82 (3H, s), 2.98 (1H, tt, J=10.92, 5.36 Hz), 4.44 (2H, br s), 8.02 (1H, dd, J=8.51, 1.65 Hz), 8.14 (1H, d, J=8.78 Hz), 8.37 (1H, s), 8.39 (1H, s), 9.14 (1H, s), 9.15 (1H, s); ESIMS found for $C_{20}H_{22}N_6OS$ m/z 395.2 (M+1).

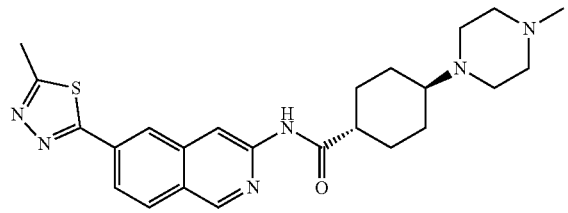

194 trans-N-(6-(5-methyl-1,3,4-thiadiazol-2-yl)isoquinolin-3-yl)-4-(4-methylpiperazin-1-yl)cyclohexane-1-carboxamide 194.

White solid (5.0 mg, 0.011 mmol, 4.1% yield). $^1$H NMR (499 MHz, METHANOL-$d_4$) δ ppm 1.33-1.44 (2H, m), 1.59-1.70 (2H, m), 2.08 (4H, dt, J=8.37, 4.32 Hz), 2.29 (3H, s), 2.37 (1H, tt, J=11.53, 3.02 Hz), 2.52 (4H, br s), 2.48 (1H, tt, J=12.04, 3.19 Hz), 2.69 (4H, br s), 2.86 (3H, s), 8.07-8.11 (1H, m), 8.11-8.14 (1H, m), 8.35 (1H, s), 8.55 (1H, s), 9.10 (1H, s); ESIMS found for $C_{24}H_{30}N_6OS$ m/z 451.2 (M+1).

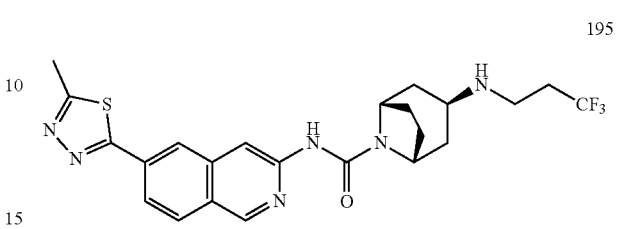

195

(1R,5S)-cis-N-(6-(5-methyl-1,3,4-thiadiazol-2-yl)isoquinolin-3-yl)-3-((3,3,3-trifluoropropyl)amino)-8-azabicyclo[3.2.1]octane-8-carboxamide 195.

White solid (10.0 mg, 0.020 mmol, 15.8% yield). $^1$H NMR (499 MHz, DMSO-$d_6$) δ ppm 1.57 (1H, s), 1.59 (1H, s), 1.90-1.98 (4H, m), 2.05 (2H, ddd, J=14.48, 6.93, 3.57 Hz), 2.37-2.46 (2H, m), 2.51-2.55 (2H, m), 2.82 (3H, s), 3.21 (2H, br s), 3.88 (1H, q, J=7.04 Hz), 7.66 (1H, br s), 7.99 (1H, dd, J=8.51, 1.65 Hz), 8.04 (1H, s), 8.14 (1H, d, J=8.78 Hz), 8.32 (1H, s), 9.13 (1H, s), 9.40 (1H, s); ESIMS found for $C_{23}H_{25}F_3N_6OS$ m/z 491.2 (M+1).

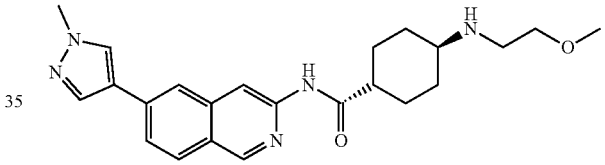

196 trans-4-((2-Methoxyethyl)amino)-N-(6-(1-methyl-1H-pyrazol-4-yl) isoquinolin-3-yl)cyclohexane-1-carboxamide 196.

Beige solid (3.0 mg, 0.007 mmol, 2.6% yield). $^1$H NMR (500 MHz, DMSO-$d_6$) δ ppm 0.96-1.08 (2H, m), 1.42-1.54 (3H, m), 1.85 (2H, br d, J=11.53 Hz), 1.90-1.97 (2H, m), 2.32-2.39 (1H, m), 2.69 (2H, t, J=5.76 Hz), 3.24 (3H, s), 3.37 (2H, t, J=5.63 Hz), 3.90 (3H, s), 7.74 (1H, dd, J=8.51, 1.65 Hz), 7.99 (1H, d, J=8.51 Hz), 8.02 (1H, s), 8.08 (1H, d, J=0.82 Hz), 8.35 (1H, s), 8.42 (1H, s), 9.02 (1H, s), 10.41 (1H, s); ESIMS found for $C_{23}H_{29}N_5O_2$ m/z 408.2 (M+1).

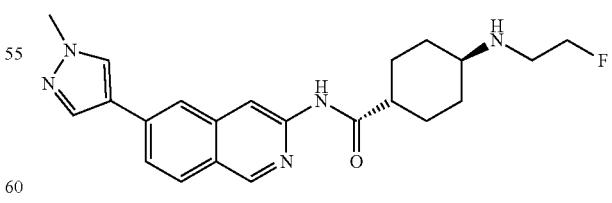

197 trans-4-((2-Fluoroethyl)amino)-N-(6-(1-methyl-1H-pyrazol-4-yl)isoquinolin-3-yl)cyclohexane-1-carboxamide 197.

White solid (41.0 mg, 0.10 mmol, 36.2% yield). $^1$H NMR (500 MHz, DMSO-$d_6$) δ ppm 0.97-1.07 (2H, m), 1.48 (2H, qd, J=12.90, 3.02 Hz), 1.82-1.91 (2H, m), 1.93-2.01 (2H, m), 2.39 (1H, tt, J=10.87, 3.53 Hz), 2.83 (2H, dt, J=26.70, 5.20

Hz), 3.90 (3H, s), 4.44 (2H, dt, J=47.80, 5.30 Hz), 7.74 (1H, dd, J=8.51, 1.65 Hz), 7.99 (1H, d, J=8.78 Hz), 8.02 (1H, d, J=0.82 Hz), 8.08 (1H, d, J=0.82 Hz), 8.35 (1H, s), 8.43 (1H, s), 9.02 (1H, s), 10.42 (1H, s); ESIMS found for $C_{22}H_{26}FN_5O$ m/z 396.2 (M+1).

3.11 (3H, s), 3.41 (3H, td, J=11.46, 3.16 Hz), 3.62-3.73 (2H, m), 4.15 (3H, s), 4.25 (2H, br d, J=13.45 Hz), 7.21 (1H, dd, J=5.21, 1.10 Hz), 7.56 (1H, s), 8.08 (1H, dd, J=8.51, 1.37 Hz), 8.18 (1H, d, J=8.51 Hz), 8.29 (1H, d, J=5.21 Hz), 8.39 (1H, s), 8.67 (1H, s), 8.76 (1H, s), 9.22 (1H, s), 11.17 (1H, s); ESIMS found for $C_{23}H_{24}N_8O_2$ m/z 445.2 (M+1).

199

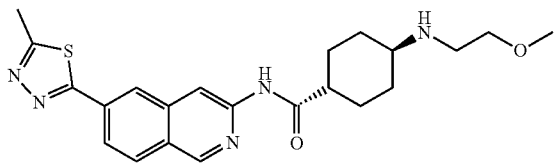

trans-4-((2-Methoxyethyl)amino)-N-(6-(5-methyl-1,3,4-thiadiazol-2-yl) isoquinolin-3-yl)cyclohexane-1-carboxamide 199.

White solid (12.0 mg, 0.03 mmol, 14.4% yield). $^1$H NMR (500 MHz, DMSO-$d_6$) δ ppm 0.96-1.06 (2H, m), 1.42-1.55 (3H, m), 1.87 (2H, br d, J=11.25 Hz), 1.91-1.98 (2H, m), 2.36 (1H, tt, J=10.84, 3.70 Hz), 2.51-2.57 (1H, m), 2.69 (2H, t, J=5.76 Hz), 2.82 (3H, s), 3.24 (3H, s), 3.37 (2H, t, J=5.63 Hz), 8.08 (1H, dd, J=8.51, 1.65 Hz), 8.18 (1H, d, J=8.51 Hz), 8.43 (1H, s), 8.61 (1H, s), 9.20 (1H, s), 10.58 (1H, s); ESIMS found for $C_{22}H_{27}N_5O_2S$ m/z 426.2 (M+1).

225

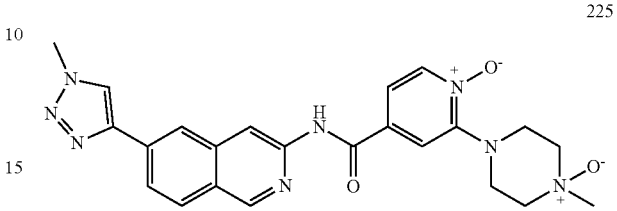

1-Methyl-4-(4-((6-(1-methyl-1H-1,2,3-triazol-4-yl)isoquinolin-3-yl) carbamoyl)-1-oxidopyridin-2-yl)piperazine 1-oxide 225.

White solid (12.0 mg, 0.03 mmol, 11.2% yield). $^1$H NMR (499 MHz, DMSO-$d_6$) δ ppm 2.88 (2H, br d, J=11.25 Hz), 3.03 (2H, br d, J=11.53 Hz), 3.22 (3H, s), 4.13 (3H, s), 4.34 (2H, br t, J=10.98 Hz), 4.81-4.90 (2H, m), 7.85 (1H, br d, J=8.23 Hz), 7.98 (1H, br d, J=7.96 Hz), 8.12 (1H, br d, J=4.39 Hz), 8.15 (1H, br s), 8.54 (1H, s), 8.56 (1H, br d, J=4.94 Hz), 8.70 (1H, s), 9.04 (1H, s), 9.06 (1H, s), 11.44 (1H, br s); ESIMS found for $C_{23}H_{24}N_8O_3$ m/z 461.1 (M+1).

200

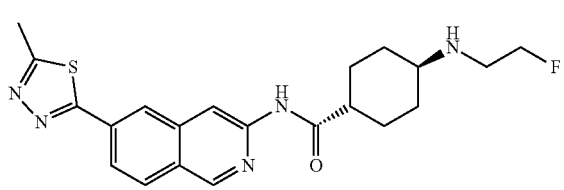

trans-4-((2-Fluoroethyl)amino)-N-(6-(5-methyl-1,3,4-thiadiazol-2-yl) isoquinolin-3-yl)cyclohexane-1-carboxamide 200.

White solid (10.0 mg, 0.02 mmol, 13.5% yield). $^1$H NMR (500 MHz, DMSO-$d_6$) δ ppm 0.99-1.09 (2H, m), 1.44-1.55 (2H, m), 1.85-1.92 (2H, m), 1.94-2.01 (2H, m), 2.39-2.46 (1H, m), 2.52-2.57 (1H, m), 2.82-2.91 (2H, m), 2.83 (3H, s), 4.46 (2H, dt, J=47.80, 5.20 Hz), 8.09 (1H, dd, J=8.51, 1.65 Hz), 8.19 (1H, d, J=8.78 Hz), 8.44 (1H, s), 8.61 (1H, s), 9.21 (1H, s), 10.59 (1H, s); ESIMS found for $C_{21}H_{24}FN_5OS$ m/z 414.2 (M+1).

226

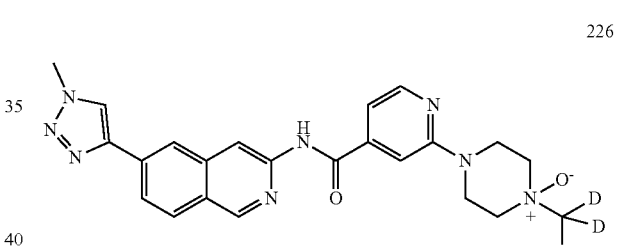

1-(Methyl-d3)-4-(4-((6-(1-methyl-1H-1,2,3-triazol-4-yl) isoquinolin-3-yl) carbamoyl)pyridin-2-yl)piperazine 1-oxide 226.

Beige solid (35.0 mg, 0.08 mmol, 33.8% yield). $^1$H NMR (499 MHz, DMSO-$d_6$) δ ppm 2.99 (2H, br d, J=10.43 Hz), 3.40 (2H, td, J=11.53, 3.02 Hz), 3.62-3.73 (2H, m), 4.15 (3H, s), 4.25 (2H, br d, J=13.45 Hz), 7.21 (1H, dd, J=5.21, 1.10 Hz), 7.56 (1H, s), 8.08 (1H, dd, J=8.51, 1.37 Hz), 8.18 (1H, d, J=8.51 Hz), 8.30 (1H, d, J=5.21 Hz), 8.39 (1H, s), 8.67 (1H, s), 8.76 (1H, s), 9.22 (1H, s), 11.16 (1H, s); ESIMS found for $C_{23}H_{21}[^2H_3]N_8O_2$ m/z 448.2 (M+1).

224

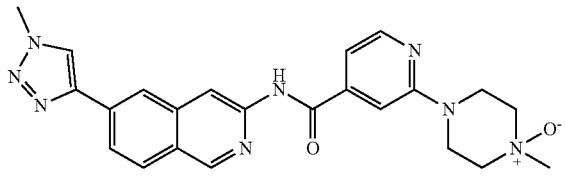

1-Methyl-4-(4-((6-(1-methyl-1H-1,2,3-triazol-4-yl)isoquinolin-3-yl) carbamoyl)pyridin-2-yl)piperazine 1-oxide 224.

Beige solid (75.0 mg, 0.17 mmol, 72.3% yield). $^1$H NMR (499 MHz, DMSO-$d_6$) δ ppm 2.99 (2H, br d, J=10.70 Hz),

227

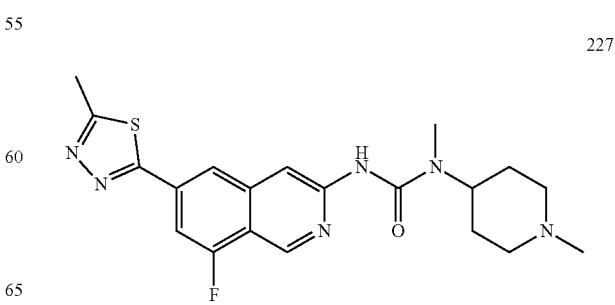

3-(8-Fluoro-6-(5-methyl-1,3,4-thiadiazol-2-yl)isoquinolin-3-yl)-1-methyl-1-(1-methylpiperidin-4-yl)urea 227.

Beige solid (95.0 mg, 0.23 mmol, 37.0% yield). $^1$H NMR (499 MHz, DMSO-$d_6$) δ ppm 1.50-1.58 (2H, m), 1.75 (2H, qd, J=12.08, 3.84 Hz), 1.97 (2H, br t, J=10.84 Hz), 2.17 (3H, s), 2.78-2.87 (5H, m), 2.89 (3H, s), 4.04-4.14 (1H, m), 7.78 (1H, d, J=10.98 Hz), 8.25 (1H, s), 8.40 (1H, s), 9.19 (1H, s), 9.26 (1H, s); ESIMS found for $C_{20}H_{23}FN_6OS$ m/z 415.2 (M+1).

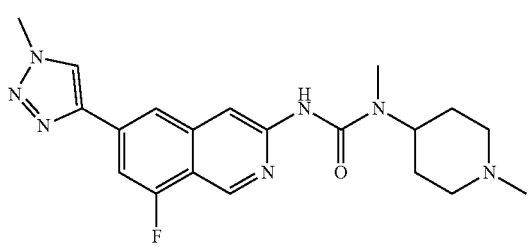

228

3-(8-Fluoro-6-(1-methyl-1H-1,2,3-triazol-4-yl)isoquinolin-3-yl)-1-methyl-1-(1-methylpiperidin-4-yl)urea 228.

Beige solid (92.0 mg, 0.23 mmol, 59.9% yield). $^1$H NMR (499 MHz, DMSO-$d_6$) δ ppm 1.53 (2H, br d, J=9.61 Hz), 1.74 (2H, qd, J=12.12, 3.70 Hz), 1.98 (2H, td, J=11.60, 1.78 Hz), 2.17 (3H, s), 2.83 (2H, br d, J=11.53 Hz), 2.89 (3H, s), 4.09 (1H, tt, J=11.94, 4.12 Hz), 4.14 (3H, s), 7.70 (1H, d, J=11.53 Hz), 8.09 (1H, s), 8.28 (1H, s), 8.74 (1H, s), 9.05 (1H, s), 9.18 (1H, s); ESIMS found for $C_{20}H_{24}FN_7O$ m/z 398.2 (M+1).

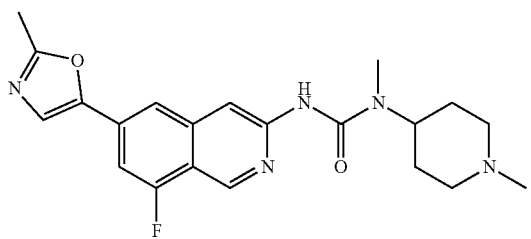

229

3-(8-Fluoro-6-(2-methyloxazol-5-yl)isoquinolin-3-yl)-1-methyl-1-(1-methylpiperidin-4-yl)urea 229.

White solid (140.0 mg, 0.35 mmol, 42.8% yield). $^1$H NMR (499 MHz, DMSO-d) δ ppm 1.49-1.57 (2H, m), 1.74 (2H, qd, J=12.08, 3.84 Hz), 1.97 (2H, td, J=11.73, 2.06 Hz), 2.17 (3H, s), 2.53 (3H, s), 2.82 (2H, br d, J=11.53 Hz), 2.88 (3H, s), 4.09 (1H, tt, J=11.90, 4.01 Hz), 7.57 (1H, dd, J=11.53, 1.10 Hz), 7.81 (1H, s), 7.88 (1H, s), 8.28 (1H, s), 9.06 (1H, s), 9.16 (1H, s); ESIMS found for $C_{21}H_{24}FN_5O_2$ m/z 398.2 (M+1).

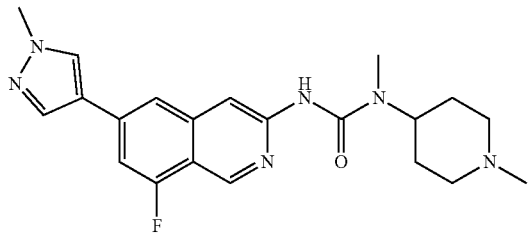

230

3-(8-Fluoro-6-(1-methyl-1H-pyrazol-4-yl)isoquinolin-3-yl)-1-methyl-1-(1-methylpiperidin-4-yl)urea 230.

Beige solid (110.0 mg, 0.28 mmol, 67.2% yield). $^1$H NMR (499 MHz, DMSO-$d_6$) δ ppm 1.49-1.57 (2H, m), 1.74 (2H, qd, J=12.12, 3.70 Hz), 1.97 (2H, td, J=11.66, 1.92 Hz), 2.17 (3H, s), 2.82 (2H, br d, J=11.25 Hz), 2.88 (3H, s), 3.90 (3H, s), 4.08 (1H, tt, J=11.94, 3.98 Hz), 7.51 (1H, dd, J=12.21, 1.23 Hz), 7.83 (1H, s), 8.09 (1H, s), 8.21 (1H, s), 8.37 (1H, s), 8.96 (1H, s), 9.09 (1H, s); ESIMS found for $C_{21}H_{25}FN_6O$ m/z 397.2 (M+1).

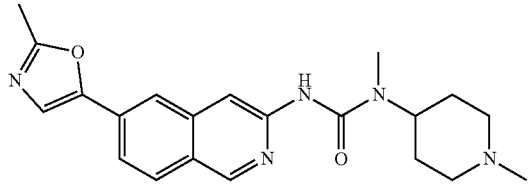

231

1-Methyl-3-(6-(2-methyloxazol-5-yl)isoquinolin-3-yl)-1-(1-methylpiperidin-4-yl)urea 231.

White solid (360.0 mg, 0.95 mmol, 71.2% yield). $^1$H NMR (499 MHz, DMSO-$d_6$) δ ppm 1.50-1.56 (2H, m), 1.74 (2H, qd, J=12.12, 3.98 Hz), 1.97 (2H, td, J=11.73, 2.06 Hz), 2.17 (3H, s), 2.53 (3H, s), 2.79-2.85 (2H, m), 2.88 (3H, s), 4.09 (1H, tt, J=12.01, 3.91 Hz), 7.74 (1H, dd, J=8.51, 1.65 Hz), 7.76 (1H, s), 8.02 (1H, s), 8.06 (1H, d, J=8.78 Hz), 8.22 (1H, s), 8.86 (1H, s), 9.05 (1H, s); ESIMS found for $C_{21}H_{25}N_5O_2$ m/z 380.2 (M+1).

Example 15

The screening assay for Wnt activity is described as follows. Reporter cell lines can be generated by stably transducing cancer cell lines (e.g., colon cancer) or primary cells (e.g., IEC-6 intestinal cells) with a lentiviral construct that includes a Wnt-responsive promoter driving expression of the firefly luciferase gene.

SW480 colon carcinoma cells were transduced with a lentiviral vector expressing luciferase with a human Sp5 promoter consisting of a sequence of eight TCF/LEF binding sites. SW480 cells stably expressing the Sp5-Luc reporter gene and a hygromycin resistance gene were selected by treatment with 150 μg/mL of hygromycin for 7 days. These stably transduced SW480 cells were expanded in cell culture and used for all further screening activities. Each compound was dissolved in DMSO as a 10 mM stock and used to prepare compound source plates. Serial dilution (1:3, 10-point dose-response curves starting from 10 μM) and compound transfer was performed using the ECHO 550 (Labcyte, Sunnyvale, Calif.) into 384-well white solid bottom assay plates (Greiner Bio-One) with appropriate DMSO backfill for a final DMSO concentration of 0.1%. For Sp5-Luc reporter gene assays, the cells were plated at 4,000 cells/well in 384-well plates with a DMEM medium containing 1% fetal bovine serum, and 1% Penicillin-Streptomycin and incubated for 36 to 48 hours at 37° C. and 5% $CO_2$. Following incubation, 15 µl of BriteLite Plus luminescence reagent (Perkin Elmer) was added to each well of the 384-well assay plates. The plates were placed on an orbital shaker for 2 min and then luminescence was quantified using the Envision (Perkin Elmer) plate reader. Readings were normalized to DMSO only treated cells, and normalized activities were utilized for $EC_{50}$ calculations using the dose-response log (inhibitor) vs. response -variable slope (four parameters) nonlinear regression feature available in GraphPad Prism 5.0 (or Dotmatics). For $EC_{50}$ of >10 µM, the percent inhibition at 10 µM is provided.

Table 2 shows the measured activity for representative compounds of Formula I as described herein.

TABLE 2

| Compound | $EC_{50}$ (µM) |
| --- | --- |
| 1 | 0.239 |
| 2 | 0.799 |
| 3 | 1.858 |
| 4 | 0.730 |
| 5 | 0.917 |
| 6 | 0.820 |
| 7 | >10 (32.9%) |
| 8 | 0.028 |
| 9 | 0.036 |
| 10 | 0.923 |
| 11 | 2.812 |
| 12 | 0.943 |
| 13 | 3.703 |
| 14 | 5.351 |
| 15 | >10 (40.1%) |
| 16 | 1.460 |
| 17 | 4.099 |
| 18 | 0.671 |
| 19 | >10 (22.4%) |
| 20 | 2.644 |
| 21 | 0.657 |
| 22 | 0.434 |
| 23 | 0.725 |
| 24 | 1.186 |
| 25 | >10 (34.3%) |
| 26 | 6.948 |
| 27 | 0.927 |
| 28 | 1.108 |
| 29 | >10 (45.6%) |
| 30 | 3.309 |
| 31 | 2.058 |
| 32 | >10 (30.5%) |
| 33 | 3.498 |
| 34 | 3.360 |
| 35 | 3.345 |
| 36 | 3.735 |
| 37 | 4.045 |
| 38 | 0.743 |
| 39 | >10 (36.3%) |
| 40 | >10 (29.6%) |
| 41 | >10 (29.7%) |
| 42 | >10 (25.5%) |
| 43 | 0.239 |
| 44 | 0.799 |
| 45 | 1.858 |
| 46 | 0.730 |
| 47 | 0.917 |
| 48 | 0.820 |
| 49 | >10 (32.9%) |
| 50 | 0.028 |
| 51 | 0.036 |
| 52 | 0.923 |
| 53 | 2.812 |
| 54 | 0.943 |
| 55 | 3.703 |
| 56 | 5.351 |
| 57 | >10 (40.1%) |
| 58 | 1.460 |
| 59 | 4.099 |
| 60 | 0.671 |
| 61 | >10 (22.4%) |
| 62 | 2.644 |
| 63 | 0.657 |
| 64 | 0.434 |
| 65 | 0.725 |
| 66 | 1.186 |
| 67 | >10 (34.3%) |
| 68 | 6.948 |
| 69 | 0.927 |
| 70 | 1.108 |
| 71 | >10 (45.6%) |
| 72 | 3.309 |
| 73 | 2.058 |
| 74 | >10 (30.5%) |
| 75 | 3.498 |
| 76 | 3.360 |
| 77 | 3.345 |
| 78 | 3.735 |
| 79 | 4.045 |
| 80 | 0.743 |
| 81 | >10 (36.3%) |
| 82 | >10 (29.6%) |
| 83 | >10 (29.7%) |
| 84 | >10 (25.5%) |
| 85 | 0.233 |
| 86 | 0.350 |
| 87 | 0.214 |
| 88 | 0.179 |
| 89 | 0.155 |
| 90 | 0.159 |
| 91 | 0.197 |
| 92 | 3.135 |
| 93 | 0.067 |
| 94 | 0.088 |
| 95 | 1.074 |
| 96 | >10 (0%) |
| 97 | 1.469 |
| 99 | 0.589 |
| 100 | 0.720 |
| 101 | >10 (6.3%) |
| 102 | 3.254 |
| 103 | 2.971 |
| 104 | 3.603 |
| 105 | >10 (15.8%) |
| 106 | 3.432 |
| 108 | >10 (19.9%) |

TABLE 2-continued

| Compound | EC$_{50}$ (µM) |
|---|---|
| 109 | 7.809 |
| 110 | >10 (24.5%) |
| 121 | 8.130 |
| 124 | 3.475 |
| 125 | 1.242 |
| 126 | 1.180 |
| 128 | 3.181 |
| 129 | 1.806 |
| 130 | 4.036 |
| 131 | 3.918 |
| 134 | 0.593 |
| 135 | 5.686 |
| 136 | 2.107 |
| 137 | >10 (38.5%) |
| 139 | 2.815 |
| 141 | 2.783 |
| 143 | 2.935 |
| 144 | >10 (35.8%) |
| 145 | 1.815 |
| 146 | 3.109 |
| 147 | 3.327 |
| 148 | 3.440 |
| 149 | 1.397 |
| 150 | 2.192 |
| 151 | >10 (4.4%) |
| 153 | >10 (3.4%) |
| 154 | 2.761 |
| 155 | 2.667 |
| 156 | 2.841 |
| 157 | 1.731 |
| 158 | 0.514 |
| 159 | 4.196 |
| 160 | 0.309 |
| 161 | 0.736 |
| 162 | 0.588 |
| 163 | 0.604 |
| 164 | 0.638 |
| 165 | 0.498 |
| 166 | 0.525 |
| 167 | 2.354 |
| 168 | >10 (42.2%) |
| 169 | 2.543 |
| 170 | >10 (23.1%) |
| 176 | 1.035 |
| 179 | 2.782 |
| 188 | 8.209 |
| 193 | >10 (8.4%) |
| 194 | 0.681 |
| 195 | >10 (13.8%) |
| 196 | 3.975 |
| 197 | 1.419 |
| 199 | 0.982 |
| 200 | 0.841 |
| 224 | >10 (43.8%) |
| 225 | 3.849 |
| 226 | >10 (31.6%) |
| 227 | 3.653 |
| 228 | >10 (46.3%) |
| 229 | >10 (0%) |
| 230 | >10 (0%) |
| 231 | 3.892 |

Example 16

Representative compounds were screened using the assay procedure for DYRK1A kinase activity as described below.

Each compound was dissolved in DMSO as a 10 mM stock and used to prepare compound source plates. Serial dilution (1:3, 11-point dose-response curves from 10 M to 0.00016 M) and compound transfer was performed using the ECHO 550 (Labcyte, Sunnyvale, Calif.) into 1536-well black-walled round bottom plates (Corning).

The DYRK1A kinase assay was run using the Ser/Thr 18 peptide Z-lyte assay kit according to manufacturer's instructions (Life Technologies—a Division of Thermo-Fisher). This is a non-radioactive assay using fluorescence resonance energy transfer (FRET) between coumarin and fluorescein to detect kinase activity which is represented as a ratio of coumarin emission/fluorescein emission.

Briefly, recombinant DYRK1A kinase, ATP and Ser/Thr peptide 18 were prepared in 1× Kinase buffer to final concentrations of 0.19 µg/mL, 30 µM, and 4 µM respectively. The mixture was allowed to incubate with the representative compounds for one hour at room temperature. All reactions were performed in duplicate. Unphosphorylated ("0% Control") and phosphorylated ("100% control") forms of Ser/Thr 18 served as control reactions. Additionally, an 11-point dose-response curve of Staurosporine (1 uM top) was run to serve as a positive compound control.

After incubation, Development Reagent A was diluted in Development Buffer then added to the reaction and allowed to further incubate for one hour at room temperature. The plate was read at Ex 400 Em 455 to detect the coumarin signal and Ex 400 Em 520 to measure the signal (EnVision Multilabel Plate Reader, PerkinElmer).

The Emission ratio (Em) was calculated as a ratio of the coumarin (C) emission signal (at 445 nm)/Fluorescein (F) emission signal (at 520 nm). The percent phosphorylation was then calculated using the following formula: [1−((Em ratio×F100%)−C100%)/((C0%−C100%)+(Em ratio×(F100%−F0%)))]. Dose-response curves were generated and inhibitory concentration (IC$_{50}$) values were calculated using non-linear regression curve fit in the Dotmatics' Studies Software (Bishops Stortford, UK).

Table 3 shows the measured activity for representative compounds of Formula I as described herein.

TABLE 3

| Compound | EC$_{50}$ (µM) |
|---|---|
| 1 | 0.004 |
| 2 | 0.004 |
| 3 | 0.004 |
| 4 | 0.004 |
| 5 | 0.003 |
| 6 | 0.003 |
| 7 | 0.376 |
| 8 | 0.002 |
| 9 | 0.002 |
| 10 | 0.004 |
| 11 | 0.010 |
| 12 | 0.016 |
| 13 | 0.013 |
| 14 | 0.033 |
| 15 | 0.061 |
| 16 | 0.005 |
| 17 | 0.018 |
| 18 | 0.003 |
| 19 | 0.110 |
| 20 | 0.005 |
| 21 | 0.006 |
| 22 | 0.005 |

TABLE 3-continued

| Compound | EC$_{50}$ (μM) |
|---|---|
| 23 | 0.004 |
| 24 | 0.007 |
| 25 | 0.014 |
| 26 | 0.038 |
| 27 | 0.006 |
| 28 | 0.004 |
| 29 | 0.018 |
| 30 | 0.027 |
| 31 | 0.024 |
| 32 | 0.017 |
| 33 | 0.009 |
| 34 | 0.015 |
| 35 | 0.026 |
| 36 | 0.012 |
| 37 | 0.007 |
| 38 | 0.006 |
| 39 | 0.015 |
| 40 | 0.029 |
| 41 | 0.027 |
| 42 | 0.012 |
| 43 | 0.002 |
| 44 | 0.005 |
| 45 | 0.003 |
| 46 | 0.006 |
| 47 | 0.006 |
| 48 | 0.020 |
| 49 | 0.021 |
| 50 | 0.020 |
| 51 | 0.014 |
| 52 | 0.009 |
| 53 | 0.038 |
| 54 | 0.007 |
| 55 | 0.006 |
| 56 | 0.004 |
| 57 | 0.009 |
| 58 | 0.006 |
| 59 | 0.003 |
| 60 | 0.007 |
| 61 | 0.007 |
| 62 | 0.007 |
| 63 | 0.017 |
| 64 | 0.008 |
| 65 | 0.070 |
| 66 | 0.003 |
| 67 | 0.007 |
| 68 | 0.007 |
| 69 | 0.003 |
| 70 | 0.002 |
| 71 | 0.006 |
| 72 | 0.003 |
| 73 | 0.003 |
| 74 | 0.006 |
| 75 | 0.003 |
| 76 | 0.002 |
| 77 | 0.006 |
| 78 | 0.002 |
| 79 | 0.002 |
| 80 | 0.003 |
| 81 | 0.002 |
| 82 | 0.003 |
| 83 | 0.002 |
| 84 | 0.002 |
| 85 | 0.002 |
| 86 | 0.002 |
| 87 | 0.003 |
| 88 | 0.002 |
| 89 | 0.002 |
| 90 | 0.004 |
| 91 | 0.005 |
| 92 | 0.010 |
| 93 | 0.002 |
| 94 | 0.002 |
| 95 | 0.004 |
| 96 | 0.846 |
| 97 | 0.014 |
| 99 | 0.004 |
| 100 | 0.003 |
| 101 | 0.022 |
| 102 | 0.005 |
| 103 | 0.005 |
| 104 | 0.008 |
| 105 | 0.034 |
| 106 | 0.017 |
| 108 | 0.010 |
| 109 | 0.010 |
| 110 | 0.017 |
| 121 | 0.035 |
| 124 | 0.035 |
| 125 | 0.004 |
| 126 | 0.005 |
| 128 | 0.016 |
| 129 | 0.018 |
| 130 | 0.037 |
| 131 | 0.013 |
| 134 | 0.006 |
| 135 | 0.041 |
| 136 | 0.006 |
| 137 | 0.018 |
| 139 | 0.022 |
| 141 | 0.009 |
| 143 | 0.011 |
| 144 | 0.020 |
| 145 | 0.002 |
| 146 | 0.022 |
| 147 | 0.018 |
| 148 | 0.014 |
| 149 | 0.007 |
| 150 | 0.013 |
| 151 | 0.009 |
| 153 | 0.028 |
| 154 | 0.005 |
| 155 | 0.008 |
| 156 | 0.007 |
| 157 | 0.019 |
| 158 | 0.005 |
| 159 | 0.027 |
| 160 | 0.004 |
| 161 | 0.010 |
| 162 | 0.011 |
| 163 | 0.005 |
| 164 | 0.011 |
| 165 | 0.006 |
| 166 | 0.009 |
| 167 | 0.007 |
| 168 | 0.004 |
| 169 | 0.003 |
| 170 | 0.015 |
| 176 | 0.023 |
| 179 | 0.018 |
| 188 | 0.003 |
| 193 | 0.033 |
| 194 | 0.003 |
| 195 | 0.005 |
| 196 | 0.006 |
| 197 | 0.003 |
| 199 | 0.004 |
| 200 | 0.006 |
| 224 | 0.001 |
| 225 | 0.002 |
| 226 | 0.004 |
| 227 | 0.024 |
| 228 | 0.012 |
| 229 | 1.000 |
| 230 | 0.021 |
| 231 | 0.016 |

Example 17

Representative compounds were screened using the assay procedure for GSK30 kinase activity as described below.

Each compound is dissolved in DMSO as a 10 mM stock and used to prepare compound source plates. Serial dilution (1:3, 11-point dose-response curves from 10 M to 0.0003 μM) and compound transfer was performed using the ECHO 550 (Labcyte, Sunnyvale, Calif.) into 1536-well black-walled round bottom plates (Corning).

The GSK3β kinase assay is run using the Ser/Thr 09 peptide Z-lyte assay kit according to manufacturer's instructions (Life Technologies—a Division of Thermo-Fisher). This is a non-radioactive assay using fluorescence resonance energy transfer (FRET) between coumarin and fluorescein to detect kinase activity which is represented as ratio of coumarin emission/fluorescein emission.

Briefly, recombinant GSK3β kinase, ATP and Ser/Thr peptide 09 are prepared in 1× Kinase buffer to final concentrations of 0.04 µg/mL, 46 µM, and 4 µM respectively. The mixture is allowed to incubate with the representative compounds for one hour at room temperature. All reactions were performed in duplicate. Unphosphorylated ("0% Control") and phosphorylated ("100% control") forms of Ser/Thr 18 serve as control reactions.

After incubation, diluted Development Buffer is added to the reaction and allowed to further incubate for one hour at room temperature. The plate is read at Ex 400 Em 455 to detect the coumarin signal and Ex 400 Em 520 to measure the signal (EnVision Multilabel Plate Reader, PerkinElmer).

The Emission ratio (Em) is calculated as a ratio of the coumarin (C) emission signal (at 445 nm)/Fluorescein (F) emission signal (at 520 nm). The percent phosphorylation is then calculated using the following formula: [1−((Em ratio× F100%)−C100%)/((C0%−C100%)+(Em ratio×(F100%− F0%)))].

Dose-response curves are generated and inhibitory concentration ($IC_{50}$) values are calculated using non-linear regression curve fit in the Dotmatics' Studies Software (Bishops Stortford, UK).

Table 4 shows the activity of representative compounds of Formula I as provided herein.

TABLE 4

| Compound | $EC_{50}$ (µM) |
|---|---|
| 1 | 0.107 |
| 2 | 0.246 |
| 3 | 0.131 |
| 4 | 0.022 |
| 5 | 0.115 |
| 6 | 0.051 |
| 7 | 1.899 |
| 8 | 6.579 |
| 9 | 7.707 |
| 10 | 0.018 |
| 11 | 0.010 |
| 12 | 0.189 |
| 13 | 1.246 |
| 14 | 0.048 |
| 15 | 0.059 |
| 16 | 0.122 |
| 17 | 0.188 |
| 18 | 0.068 |
| 19 | 1.162 |
| 20 | 0.041 |
| 21 | 0.035 |
| 22 | 0.022 |
| 23 | 0.017 |
| 24 | 0.030 |
| 25 | 0.313 |
| 26 | 0.524 |
| 27 | 0.011 |
| 28 | 0.008 |
| 29 | 0.337 |
| 30 | 0.099 |
| 31 | 0.117 |
| 32 | 0.210 |
| 33 | 0.023 |
| 34 | 0.046 |

TABLE 4-continued

| Compound | $EC_{50}$ (µM) |
|---|---|
| 35 | 0.084 |
| 36 | 0.079 |
| 37 | 0.138 |
| 38 | 0.009 |
| 39 | 0.096 |
| 40 | 0.120 |
| 41 | 0.203 |
| 42 | 4.674 |
| 43 | 0.066 |
| 44 | 0.065 |
| 45 | 0.076 |
| 46 | 0.023 |
| 47 | 0.065 |
| 48 | 0.054 |
| 49 | 0.006 |
| 50 | 0.218 |
| 51 | 0.349 |
| 52 | 0.156 |
| 53 | 0.366 |
| 54 | 0.006 |
| 55 | 0.088 |
| 56 | 0.009 |
| 57 | 0.016 |
| 58 | 0.007 |
| 59 | 0.015 |
| 60 | 0.073 |
| 61 | 9.210 |
| 62 | 0.068 |
| 63 | 0.473 |
| 64 | 0.530 |
| 65 | 2.836 |
| 66 | 0.053 |
| 67 | 1.866 |
| 68 | 0.066 |
| 69 | 0.070 |
| 70 | 0.073 |
| 71 | 0.014 |
| 72 | >10 |
| 73 | >10 |
| 74 | >10 |
| 75 | 3.802 |
| 76 | 2.068 |
| 77 | >10 |
| 78 | 7.673 |
| 79 | 4.458 |
| 80 | 2.584 |
| 81 | 1.051 |
| 82 | 1.508 |
| 83 | 0.874 |
| 84 | 1.046 |
| 85 | 0.847 |
| 86 | 1.744 |
| 87 | 1.454 |
| 88 | 1.006 |
| 89 | 0.533 |
| 90 | 0.388 |
| 91 | 0.454 |
| 92 | 0.066 |
| 93 | 0.238 |
| 94 | 0.276 |
| 95 | 0.038 |
| 96 | 5.423 |
| 97 | 0.020 |
| 99 | 0.008 |
| 100 | 0.011 |
| 101 | 1.027 |
| 102 | 0.434 |
| 103 | 0.030 |
| 104 | 0.149 |
| 105 | 0.550 |
| 106 | 0.320 |
| 108 | 0.671 |
| 109 | 0.175 |
| 110 | 0.314 |
| 121 | 0.082 |
| 124 | 0.217 |
| 125 | 0.005 |
| 126 | 0.024 |

TABLE 4-continued

| Compound | EC$_{50}$ (µM) |
|---|---|
| 128 | 0.025 |
| 129 | 0.090 |
| 130 | 0.142 |
| 131 | 0.006 |
| 134 | 0.019 |
| 135 | 0.022 |
| 136 | 0.080 |
| 137 | 0.068 |
| 139 | 0.033 |
| 141 | 0.050 |
| 143 | 1.782 |
| 144 | 0.021 |
| 145 | 0.080 |
| 146 | 0.062 |
| 147 | 0.037 |
| 148 | 0.257 |
| 149 | 0.128 |
| 150 | 0.023 |
| 151 | 0.103 |
| 153 | 0.532 |
| 154 | 0.124 |
| 155 | 0.668 |
| 156 | 0.034 |
| 157 | >10 |
| 158 | 2.596 |
| 159 | >10 |
| 160 | 3.034 |
| 161 | 5.669 |
| 162 | 5.061 |
| 163 | 4.266 |
| 164 | 4.582 |
| 165 | 3.735 |
| 166 | 6.378 |
| 167 | 0.096 |
| 168 | 0.020 |
| 169 | 0.047 |
| 170 | 0.052 |
| 176 | 0.207 |
| 179 | 0.026 |
| 188 | 0.154 |
| 193 | 0.330 |
| 194 | 0.012 |
| 195 | 1.254 |
| 196 | 0.194 |
| 197 | 0.087 |
| 199 | 0.017 |
| 200 | 0.014 |
| 224 | 0.703 |
| 225 | 0.407 |
| 226 | 1.188 |
| 227 | 4.500 |
| 228 | 0.255 |
| 229 | 6.707 |
| 230 | 3.640 |
| 231 | 2.825 |

Example 18

Representative compounds were screened using the assay procedure for tau phosphorylation activity described below.

SH-SY5Y cells (human neuroblastoma) were cultured in DMEM/F-12 medium supplemented with 15% FBS, Non-essential Amino Acid and Penicillin/Streptomycin. Two days before treatment, cells were seeded onto 96 well plates at $5 \times 10^4$ cells/well.

The above synthesized compounds were screened using the cell assay procedure to assess decrease Tau phosphorylation at Ser396 (pSer396) described below.

DMSO-resuspended compounds were dispensed to 8 wells as a serial titration from 10 µM to 4.6 nM final in medium and cells were exposed overnight (16-18 h) in a humidified incubator at 36.6c before harvest. Wells were visually checked for cell death or change in morphology and supernatants were tested for cytotoxicity by measurement of lactate dehydrogenase release (LDH, CytoToxOne kit, Promega) if necessary. As controls, commercially available DYRK1A inhibitors, Harmine and Indy which were shown to have good DYRK1A inhibition in the kinase assay with no CDK1 activity (EC$_{50}$ 18 and 53 nM respectively, 6 µM for CDK1) but weak EC$_{50}$ in the Tau assay>10 M.

Cells were lysed with RIPA buffer complemented with phosphatase and protease inhibitors then lysates were spun down at 12,000 g for 10 min to remove any cellular debris. Lysates are then either directly tested for pSer396 by ELISA (Life Technology, Kit KHB7031) or loaded on NuPage Bis-Tris gels for western blot analysis. Colorimetric detection of ELISA signal is performed by Cytation3 plate reader (Biotek) and the chemiluminescence signal for HRP-linked antibodies used in western blotting is detected using a Carestream Image Station. The same pSer396 antibody is used for detection of pTau in both assays.

Blot densitometry for pSer396 and β-actin were analyzed using ImageJ (NIH) and pSer396 Tau ELISA signal was used to plot, draw the curve fitting, and determine each compounds EC$_{50}$ in Prism (GraphPad).

Table 5 shows the activity of representative compounds as provided herein.

TABLE 5

| Compound | pSer396 Tau EC$_{50}$ (µM) |
|---|---|
| 1 | 0.368 |
| 2 | 0.559 |
| 3 | 0.458 |
| 4 | 0.069 |
| 5 | 0.511 |
| 6 | 0.103 |
| 8 | >10 |
| 9 | >10 |
| 10 | 0.119 |
| 11 | 0.190 |
| 12 | 0.436 |
| 13 | 4.700 |
| 14 | 0.382 |
| 15 | 0.981 |
| 16 | 0.286 |
| 17 | 0.743 |
| 18 | 0.186 |
| 20 | 0.524 |
| 21 | 0.566 |
| 22 | 0.126 |
| 23 | 0.161 |
| 24 | 0.127 |
| 25 | 0.430 |
| 26 | 0.167 |
| 27 | 0.104 |
| 28 | 0.089 |
| 29 | 3.400 |
| 30 | 0.453 |
| 31 | 0.386 |
| 32 | 0.891 |
| 33 | 0.321 |
| 34 | 0.456 |
| 35 | 0.543 |
| 36 | 0.843 |
| 37 | 0.497 |
| 38 | 0.067 |
| 39 | 0.538 |
| 40 | 0.688 |
| 41 | 0.869 |
| 42 | >10 |
| 43 | 0.362 |
| 44 | 0.445 |
| 45 | 0.320 |
| 46 | 0.091 |
| 47 | 0.174 |
| 48 | 0.359 |

TABLE 5-continued

| Compound | pSer396 Tau EC$_{50}$ (μM) |
|---|---|
| 49 | 0.135 |
| 50 | 0.779 |
| 51 | 0.656 |
| 52 | 1.100 |
| 53 | 2.300 |
| 54 | 0.097 |
| 55 | 0.178 |
| 56 | 0.092 |
| 57 | 0.136 |
| 58 | 0.058 |
| 59 | 0.035 |
| 60 | 1.100 |
| 61 | >10 |
| 62 | 1.200 |
| 63 | 3.100 |
| 64 | 2.900 |
| 65 | >10 |
| 66 | 0.168 |
| 67 | >10 |
| 68 | 0.948 |
| 69 | 0.516 |
| 70 | 0.307 |
| 71 | 0.250 |
| 72 | 2.600 |
| 73 | >10 |
| 74 | >10 |
| 75 | >10 |
| 76 | >10 |
| 77 | >10 |
| 78 | >10 |
| 79 | >10 |
| 80 | >10 |
| 81 | 2.828 |
| 82 | 5.900 |
| 83 | >10 |
| 84 | 1.400 |
| 85 | 1.400 |
| 86 | 3.041 |
| 87 | 0.896 |
| 88 | 0.016 |
| 89 | 0.594 |
| 90 | 0.171 |
| 91 | 0.068 |
| 92 | 0.769 |
| 93 | 0.259 |
| 94 | 0.244 |
| 95 | 0.076 |
| 96 | >10 |
| 97 | 0.184 |
| 99 | 0.208 |
| 100 | 0.113 |
| 101 | 5.400 |
| 102 | 2.600 |
| 103 | 1.300 |
| 104 | 0.712 |
| 105 | 2.200 |
| 106 | 0.323 |
| 108 | >10 |
| 109 | 3.100 |
| 110 | 2.100 |
| 121 | 0.953 |
| 124 | 0.612 |
| 125 | 0.114 |
| 126 | 0.197 |
| 128 | 0.491 |
| 129 | 0.656 |
| 130 | 1.500 |
| 131 | 0.337 |
| 134 | 0.093 |
| 135 | 0.365 |
| 136 | 0.309 |
| 137 | 0.573 |
| 139 | 1.400 |
| 141 | 0.594 |
| 143 | 7.200 |
| 144 | >10 |
| 145 | 0.503 |
| 146 | 1.000 |
| 147 | 1.100 |
| 148 | 0.599 |
| 149 | 1.100 |
| 150 | 0.272 |
| 151 | 2.600 |
| 153 | >10 |
| 154 | 0.580 |
| 155 | 0.384 |
| 156 | 0.615 |
| 157 | 0.720 |
| 158 | >10 |
| 159 | >10 |
| 160 | >10 |
| 161 | >10 |
| 162 | >10 |
| 163 | >10 |
| 164 | >10 |
| 165 | >10 |
| 166 | >10 |
| 167 | 0.288 |
| 168 | 0.578 |
| 169 | 0.154 |
| 170 | 9.911 |
| 176 | 4.000 |
| 179 | 1.300 |
| 188 | 4.800 |
| 193 | >10 |
| 194 | 0.218 |
| 195 | >10 |
| 197 | 0.570 |
| 199 | 0.234 |
| 200 | 0.095 |
| 204 | >10 |
| 225 | >10 |
| 226 | >10 |
| 227 | 4.500 |
| 228 | 6.400 |

Example 19

Representative compounds were screened using the cell-based assay procedure for signal of Tau phosphorylation at Threonine 212 (pT212Tau) in a transiently double transfected (Dyrk1a- and MAPT-overexpressing) cell type as described below.

HEK293T cells (transfectable human embryonic kidney cells) were cultured in DMEM medium supplemented with 10% FBS and 1% penicillin/streptomycin.

HEK293T cells were transiently transfected to overexpress Dyrk1a and microtubule-associated protein Tau (MAPT) genes. Specifically, Dyrk1a and MAPT expression vectors were obtained from OriGene (10 μg of each, catalog numbers SC314641 and RC216166, respectively). A Maxi-iPrep for each vector was ordered and received from GeneWiz, yielding 874.5 g (resuspended at 1.749 μg/L) of the Dyrk1a expression vector, and 898 μg (resuspended at 1.796 μg/μL) of MAPT.

HEK293T cells were seeded at 1.0×10$^7$ cells in 10 mL per T-75 flask. After overnight incubation, HEK293T cells in the T-75 flasks were transfected by creating a master mix of 10 μg of each expression vector per flask, with Lipofectamine™ 3000 Transfection Reagent (Invitrogen, L3000015) diluted in Opti-MEM medium according to the manufacturer's suggested protocol. One T-75 flask was designated as a no-vector negative control for pT212Tau signal.

After 4~6 hours of incubation in transfection reagents, transiently double transfected HEK293T cells were dissociated by treatment with trypsin EDTA and seeded at $1.0 \times 10^5$ cells in 100 μL per well in 96-well plates. No-vector negative controls were seeded in separate 96-well plates to avoid the risk of the negative control cells picking up the overexpression during incubation. At the time of seeding, DMSO-resuspended Samumed compounds were dispensed to eight wells as a serial dilution from 10 μM to 4.6 nM final concentration in medium, or at 0.12 μM to 0.05 nM with particularly potent compounds. Cells were exposed to the representative compounds overnight (16-18 hours) in a 37° C. incubator.

96-Well flat-bottom plates were coated with 100 μL per well anti-HT7 capture antibody (ThermoFisher, MN1000) diluted 1:300 in 1×PBS at 4° C. overnight, with shaking at 500 rpm. After overnight capture antibody incubation, coated plates were washed four times with 200 L per well of 1×PBS-0.05% Tween-20, and blocked for 1 hour with 200 μL per well of 1×PBS with 2% BSA. After 1 hour of blocking, plates were washed four times with 200 μL per well of 1×PBS-0.05% Tween-20, prior to sample loading.

Wells of compound-treated cells were visually checked for cell death before being washed with 200 μL per well of 1×DPBS supplemented with phosphatase inhibitor diluted to IX. Cells were then lysed with 100 μL 1×RIPA buffer supplemented with phosphatase and protease inhibitors (each diluted to a final 1×). Cells were shaken at 500 rpm, 4° C. for 20 minutes prior to further lysis (via manual scraping) and transfer to 96-well V-bottom collection plates (Corning, 3894). V-bottom plates were centrifuged at 4000 rpm, 4° C., for 15 minutes, and 100 μL of lysate supernatant from each well was directly tested for pT212Tau signal by sandwich ELISA.

Specifically, lysates were directly transferred to the coated and blocked ELISA plates for 2 hours before plates were washed four times with 200 μL per well of 1×PBS-0.05% Tween-20 and probed with 100 μL per well of anti-pT212Tau antibody (ThermoFisher, 44-740G) diluted 1:200 in 1×PBS for 2 hours. Plates were washed four times with 200 μL per well of 1×PBS-0.05% Tween-20 and probed with 100 μL per well of anti-rabbit/HRP conjugate (Cell Signaling Technology, 7074S) diluted 1:600 in 1×PBS for 1 hour. Plates were washed four times with 200 μL per well of 1×PBS-0.05% Tween-20 before 100 μL per well of TMB substrate solution (ThermoFisher, N301) was added. When colour development was observed, 100 μL per well of stop solution (ThermoFisher, N600) was added, and colorimetric detection of pT212Tau signal was read at 450 nm with the Cytation 3 Cell Imaging Multi-Mode Reader (BioTek). The signal was used to plot, draw the curves fitting, and determine the $EC_{50}$ values in GraphPad Prism for tested representative compounds.

Table 6 shows the activity of representative compounds as provided herein.

TABLE 6

| Compound | Thr212 $EC_{50}$ (μM) |
|---|---|
| 22 | 0.011 |
| 58 | 0.093 |
| 61 | 0.015 |
| 67 | 0.006 |
| 106 | 0.137 |
| 108 | 0.022 |
| 153 | 0.528 |
| 155 | 0.026 |

TABLE 6-continued

| Compound | Thr212 $EC_{50}$ (μM) |
|---|---|
| 195 | 0.046 |
| 196 | 0.019 |
| 227 | 0.691 |
| 228 | >10 |
| 230 | 0.056 |
| 231 | 0.110 |

Example 20

Representative compounds were screened using the assay procedure to assess the effect on cell viability as described below.

SW480 colon carcinoma cells were transduced with a lentiviral vector expressing luciferase with a human Sp5 promoter consisting of a sequence of eight TCF/LEF binding sites. SW480 cells stably expressing the Sp5-Luc reporter gene and a hygromycin resistance gene were selected by treatment with 150 μg/mL of hygromycin for 7 days. These stably transduced SW480 cells were expanded in cell culture and used for all further screening activities. Each compound was dissolved in DMSO as a 10 mM stock and used to prepare compound source plates. Serial dilution (1:3, 8-point dose-response curves from 10 μM to 0.0045 μM) and compound transfer was performed using the ECHO 550 (Labcyte, Sunnyvale, Calif.) into 384-well white solid bottom assay plates (Greiner Bio-One) with appropriate DMSO backfill for a final DMSO concentration of 0.1%.

For the Cell Viability Assays, the cells were plated at 2,000 cells/well in 384-well plates with a DMEM medium containing 1% fetal bovine serum, and 1% Penicillin-Streptomycin and incubated for four days hours at 37° C. and 5% $CO_2$. Eight replicates of DMSO-treated cells served as controls and cells treated with compound were performed in duplicate.

After incubation, 10 μL of CellTiter-Glo (Promega) was added to each well allowed to incubate for approximately 12 minutes. This reagent "results in cell lysis and generation of a luminescent signal proportional to the amount of ATP present. The amount of ATP is directly proportional to the number of cells present in culture, in agreement with previous reports. The CellTiter-Glo® Assay generates a "glow-type" luminescent signal, produced by the luciferase reaction (Promega.com)".

After incubation, the plates were read at Ex 560 nm Em 590 nm (Cytation 3, BioTek). Dose-response curves were generated and $EC_{50}$ concentration values were calculated using non-linear regression curve fit in the GraphPad Prism (San Diego, Calif.) or Dotmatics' Studies Software (Bishops Stortford, UK). For $EC_{50}$ of >10 μM, the percent inhibition at 10 μM is provided.

Table 7 shows the activity of representative compounds of Formula I as provided herein.

TABLE 7

| Compound | $EC_{50}$ (μM) |
|---|---|
| 1 | 0.839 |
| 2 | 4.450 |
| 3 | 6.670 |
| 4 | 0.907 |
| 5 | 0.738 |

TABLE 7-continued

| Compound | EC$_{50}$ (μM) |
|---|---|
| 6 | 1.239 |
| 7 | >10 |
|  | (42.5%) |
| 8 | 0.099 |
| 9 | 0.106 |
| 10 | 0.719 |
| 11 | >10 |
|  | (46.3%) |
| 12 | 0.713 |
| 13 | 3.507 |
| 14 | 5.554 |
| 15 | >10 |
|  | (38.0%) |
| 16 | 0.808 |
| 17 | 6.914 |
| 18 | 0.587 |
| 19 | >10 |
|  | (44.8%) |
| 20 | 3.067 |
| 21 | 1.064 |
| 22 | 2.053 |
| 23 | 2.124 |
| 24 | 3.644 |
| 25 | >10 |
|  | (40.3%) |
| 26 | 8.527 |
| 27 | 2.093 |
| 28 | >10 |
|  | (37.8%) |
| 29 | >10 |
|  | (28.2%) |
| 30 | 6.838 |
| 31 | 3.803 |
| 32 | >10 |
|  | (8.3%) |
| 33 | 4.627 |
| 34 | 3.765 |
| 35 | 4.548 |
| 36 | 5.699 |
| 37 | 6.890 |
| 38 | 1.078 |
| 39 | >10 |
|  | (27.3%) |
| 40 | >10 |
|  | (27.0%) |
| 41 | >10 |
|  | (10.7%) |
| 42 | >10 |
|  | (26.5%) |
| 43 | 4.980 |
| 44 | 2.804 |
| 45 | 0.659 |
| 46 | 1.042 |
| 47 | 0.751 |
| 48 | 3.892 |
| 49 | 2.896 |
| 50 | >10 |
|  | (43.0%) |
| 51 | 3.938 |
| 52 | 3.973 |
| 53 | 4.508 |
| 54 | 3.212 |
| 55 | 1.297 |
| 56 | 6.502 |
| 57 | 4.114 |
| 58 | 0.547 |
| 59 | 0.140 |
| 60 | 4.060 |
| 61 | >10 |
|  | (13.1%) |
| 62 | 3.640 |
| 63 | 2.572 |
| 64 | 3.534 |
| 65 | >10 |
|  | (7.3%) |
| 66 | 1.221 |
| 67 | 3.991 |
| 68 | >10 |
|  | (47.2%) |
| 69 | 1.704 |
| 70 | 1.721 |
| 71 | >10 |
|  | (46.7%) |
| 72 | 0.489 |
| 73 | 0.481 |
| 74 | 0.479 |
| 75 | 0.443 |
| 76 | 0.462 |
| 77 | 0.496 |
| 78 | 0.468 |
| 79 | 0.464 |
| 80 | 1.597 |
| 81 | 0.486 |
| 82 | 3.313 |
| 83 | 0.305 |
| 84 | 0.494 |
| 85 | 0.487 |
| 86 | 0.515 |
| 87 | 0.489 |
| 88 | 0.480 |
| 89 | 0.480 |
| 90 | 0.312 |
| 91 | 0.314 |
| 92 | 4.084 |
| 93 | 0.098 |
| 94 | 0.104 |
| 95 | 0.766 |
| 96 | >10 |
|  | (2.3%) |
| 97 | 0.806 |
| 99 | 1.081 |
| 100 | 1.531 |
| 101 | >10 |
|  | (18.8%) |
| 102 | 3.029 |
| 103 | 6.085 |
| 104 | 4.589 |
| 105 | >10 |
|  | (16.9%) |
| 106 | 2.956 |
| 108 | >10 |
|  | (7.8%) |
| 109 | 4.127 |
| 110 | >10 |
|  | (1.5%) |
| 121 | >10 |
|  | (36.5%) |
| 124 | 1.019 |
| 125 | 1.657 |
| 126 | 0.488 |
| 128 | 4.371 |
| 129 | 3.624 |
| 130 | 4.209 |
| 131 | >10 |
|  | (35.9%) |
| 134 | 2.736 |
| 135 | >10 |
|  | (27.8%) |
| 136 | 1.117 |
| 137 | >10 |
|  | (39.0%) |
| 139 | 7.354 |
| 141 | 1.569 |
| 143 | 3.362 |
| 144 | 3.769 |
| 145 | 1.494 |
| 146 | 3.835 |
| 147 | 4.141 |
| 148 | 1.201 |
| 149 | 1.335 |
| 150 | 3.922 |
| 151 | >10 |
|  | (0%) |
| 153 | >10 |
|  | (0%) |

TABLE 7-continued

| Compound | EC$_{50}$ (µM) |
|---|---|
| 154 | 0.761 |
| 155 | 0.807 |
| 156 | 2.552 |
| 157 | 2.382 |
| 158 | 0.781 |
| 159 | 7.997 |
| 160 | 0.415 |
| 161 | 0.660 |
| 162 | 0.653 |
| 163 | 0.795 |
| 164 | 0.782 |
| 165 | 0.752 |
| 166 | 0.671 |
| 167 | 3.343 |
| 168 | >10 (19.4%) |
| 169 | 1.127 |
| 170 | >10 (27.0%) |
| 176 | >10 (8.3%) |
| 179 | 5.059 |
| 188 | >10 (28.0%) |
| 193 | >10 (12.8%) |
| 194 | 1.260 |
| 195 | >10 (13.0%) |
| 196 | 6.112 |
| 197 | 1.270 |
| 199 | 1.645 |
| 200 | 1.388 |
| 224 | >10 (24.6%) |
| 225 | >10 (28.7%) |
| 226 | >10 (46.9%) |
| 227 | >10 ($ 1.9%) |
| 228 | >10 (178.4%) |
| 229 | >10 (49.5%) |
| 230 | >10 (31.9%) |
| 231 | >10 (41.6%) |

Example 21

Representative compounds were screened using primary human fibroblasts (derived from IPF patients) treated with TGF-β1 to determine their ability to inhibit the fibrotic process.

Human Fibroblast Cell Culture:

Primary human fibroblasts derived from IPF patients (LL29 cells) [[1]Xiaoqiu Liu, et. al., "Fibrotic Lung Fibroblasts Show Blunted Inhibition by cAMP Due to Deficient cAMP Response Element-Binding Protein Phosphorylation", *Journal of Pharmacology and Experimental Therapeutics* (2005), 315(2), 678-687; [2]Watts, K. L., et. al., "RhoA signaling modulates cyclin D1 expression in human lung fibroblasts; implications for idiopathic pulmonary fibrosis", *Respiratory Research* (2006), 7(1), 88] were obtained from American Type Culture Collection (ATCC) and expanded in F12 medium supplemented with 15% Fetal Bovine Serum and 1% Penicillin/Streptomycin.

Compound Screening:

Each compound was dissolved in DMSO as a 10 mM stock and used to prepare compound source plates. Serial dilution (1:2, 11-point dose-response curves from 10 M to 0.94 nM) and compound transfer was performed using the ECHO 550 (Labcyte, Sunnyvale, Calif.) into 384-well clear bottom assay plates (Greiner Bio-One) with appropriate DMSO backfill for a final DMSO concentration of 0.1%. LL29 cells were plated at 1,500 cells/well in 70 µL/well F12 medium supplemented with 1% Fetal Bovine Serum. TGF-β1 (Peprotech; 20 ng/mL) was added to the plates to induce fibrosis (ref. 1 and 2 above). Wells treated with TGF-31 and containing DMSO were used as positive control, and cells with only DMSO were negative control. Cells were incubated at 37° C. and 5% CO$_2$ for 4 days. Following incubation for 4 days, SYTOX green nucleic acid stain (Life Technologies [Thermo Fisher Scientific]) was added to the wells at a final concentration of 1 µM and incubated at room temperature for 30 min. Cells were then fixed using 4% formaldehyde (Electron Microscopy Sciences), washed 3 times with PBS followed by blocking and permeabilization using 3% Bovine Serum Albumin (BSA; Sigma) and 0.3% Triton X-100 (Sigma) in PBS. Cells were then stained with antibody specific to α-smooth muscle actin (αSMA; Abcam) (ref. 1 and 2 above) in 3% Bovine Serum Albumin (BSA; Sigma) and 0.3% Triton X-100 (Sigma) in PBS, and incubated overnight at 4° C. Cells were then washed 3 times with PBS, followed by incubation with Alexa Flor-647 conjugated secondary antibody (Life Technologies [Thermo Fisher Scientific]) and DAPI in 3% Bovine Serum Albumin (BSA; Sigma) and 0.3% Triton X-100 (Sigma) in PBS at room temperature for 1 hour. Cells were then washed 3 times with PBS and plates were sealed for imaging. αSMA staining was imaged by excitation at 630 nm and emission at 665 nm and quantified using the Compartmental Analysis program on the CellInsight CX5 (Thermo Scientific). Dead or apoptotic cells were excluded from analysis based on positive SYTOX green staining. % of total cells positive for αSMA were counted in each well and normalized to the average of 11 wells treated with TGF-β1 on the same plate using Dotmatics' Studies Software. The normalized averages (fold change over untreated) of 3 replicate wells for each compound concentration were used to create dose-responses curves and EC$_{50}$ values were calculated using non-linear regression curve fit in the Dotmatics' Studies Software. For EC$_{50}$ of >10 µM, the percent inhibition at 10 µM is provided.

Table 8 shows the activity of representative compounds of Formula I as provided herein.

TABLE 8

| Compound | EC$_{50}$ (µM) |
|---|---|
| 1 | 0.445 |
| 2 | 0.150 |
| 3 | 0.153 |
| 4 | 0.229 |
| 5 | 0.113 |
| 6 | 0.132 |
| 7 | 2.664 |
| 8 | 0.095 |
| 9 | 0.157 |
| 10 | 0.208 |
| 11 | >10 (3.8%) |
| 12 | 0.102 |
| 13 | >10 (38.2%) |
| 14 | 1.379 |
| 15 | 0.896 |
| 16 | 0.172 |
| 17 | 1.433 |

TABLE 8-continued

| Compound | EC$_{50}$ (μM) |
|---|---|
| 18 | 0.149 |
| 19 | >10 |
|  | (20.6%) |
| 20 | 0.480 |
| 21 | 0.340 |
| 22 | 0.602 |
| 23 | 0.489 |
| 24 | 0.573 |
| 25 | 3.866 |
| 26 | >10 |
|  | (48.4%) |
| 27 | 0.235 |
| 28 | 0.448 |
| 29 | >10 |
|  | (3.2%) |
| 30 | 4.112 |
| 31 | 3.709 |
| 32 | 0.771 |
| 33 | >10 |
|  | (49.9%) |
| 34 | >10 |
|  | (48.5%) |
| 35 | 1.022 |
| 36 | 5.202 |
| 37 | 0.244 |
| 38 | 0.112 |
| 39 | 2.589 |
| 40 | 3.713 |
| 41 | 1.220 |
| 42 | >10 |
|  | (6.4%) |
| 43 | 0.230 |
| 44 | 0.247 |
| 45 | 0.095 |
| 46 | 0.640 |
| 47 | 0.262 |
| 48 | 0.718 |
| 49 | 0.643 |
| 50 | 1.472 |
| 51 | 2.492 |
| 52 | 1.729 |
| 53 | 1.579 |
| 54 | 0.412 |
| 55 | 0.678 |
| 56 | 0.285 |
| 57 | 1.168 |
| 58 | 0.788 |
| 59 | 0.297 |
| 60 | 4.858 |
| 61 | 2.770 |
| 62 | 1.229 |
| 63 | 1.281 |
| 64 | 0.683 |
| 65 | 2.348 |
| 66 | 0.160 |
| 67 | >10 |
|  | (5.2%) |
| 68 | 1.525 |
| 69 | 0.210 |
| 70 | 0.124 |
| 71 | 4.658 |
| 72 | 0.937 |
| 73 | 1.706 |
| 74 | 1.253 |
| 75 | 0.450 |
| 76 | 0.611 |
| 77 | 2.149 |
| 78 | 0.526 |
| 79 | 0.572 |
| 80 | 2.714 |
| 81 | 0.309 |
| 82 | >10 |
|  | (31.2%) |
| 83 | 0.483 |
| 84 | 0.630 |
| 85 | 0.557 |
| 86 | 0.556 |
| 87 | 0.132 |
| 88 | 0.311 |
| 89 | 0.190 |
| 90 | 0.299 |
| 91 | 0.289 |
| 92 | 2.706 |
| 93 | 0.145 |
| 94 | 0.125 |
| 95 | 0.276 |
| 96 | >10 |
|  | (36.0%) |
| 97 | 0.200 |
| 99 | 0.072 |
| 100 | 0.064 |
| 101 | 3.074 |
| 102 | 2.400 |
| 103 | 0.392 |
| 104 | 0.220 |
| 105 | 0.812 |
| 106 | 0.707 |
| 108 | >10 |
|  | (18.2%) |
| 109 | >10 |
|  | (19.5%) |
| 110 | 1.968 |
| 121 | >10 |
|  | (10.4%) |
| 124 | 0.451 |
| 125 | 0.442 |
| 126 | 0.286 |
| 128 | 6.627 |
| 129 | 1.992 |
| 130 | 3.298 |
| 131 | 1.930 |
| 134 | 0.579 |
| 135 | 2.140 |
| 136 | 0.418 |
| 137 | 3.134 |
| 139 | 2.351 |
| 141 | 0.321 |
| 143 | >10 |
|  | (40.4%) |
| 144 | 1.379 |
| 145 | 0.072 |
| 146 | >10 |
|  | (35.1%) |
| 147 | 1.644 |
| 148 | 0.286 |
| 149 | 0.216 |
| 150 | >10 |
|  | (43.7%) |
| 151 | 2.687 |
| 153 | >10 |
|  | (9.0%) |
| 154 | 0.240 |
| 155 | 1.065 |
| 156 | 2.382 |
| 157 | 5.794 |
| 158 | 1.216 |
| 159 | >10 |
|  | (31.4%) |
| 160 | 1.010 |
| 161 | 3.004 |
| 162 | 2.004 |
| 163 | 0.876 |
| 164 | 1.479 |
| 165 | 0.998 |
| 166 | 1.880 |
| 167 | 0.293 |
| 168 | 1.295 |
| 169 | 0.148 |
| 170 | 7.091 |
| 176 | >10 |
|  | (8.4%) |
| 179 | >10 |
|  | (10.1%) |
| 188 | 2.476 |
| 193 | >10 |
|  | (6.5%) |

TABLE 8-continued

| Compound | EC$_{50}$ (μM) |
|---|---|
| 194 | 0.328 |
| 195 | >10 |
| | (23.4%) |
| 196 | 0.184 |
| 197 | 0.233 |
| 199 | 3.199 |
| 200 | 0.533 |
| 224 | >10 |
| | (13.1%) |
| 225 | >10 |
| | (24.8%) |
| 226 | >10 |
| | (33.2%) |
| 228 | 9.985 |
| 229 | 9.985 |
| 230 | 6.326 |
| 231 | 2.952 |

Example 22

Representative compounds were screened using the cell-based assay procedure for secreted cytokines in a Lipopolysaccharide-stimulated mouse glial cell line described below.

BV-2 cells (mouse microglial cells) were cultured in 1:1 DMEM medium supplemented with 10% FBS, and 1% penicillin/streptomycin.

BV-2 cells are plated at 35,000 cells/well in a volume of 100 μl for at least 4 hours before compounds are added. DMSO-resuspended compounds were first dispensed in a 96-well plate and serial diluted from 10 μM to 4.6 nM final concentration in medium. Compounds were added to cells overnight. 250 ng/mL of lipopolysaccharide (*Escherichia coli* O11:B4, SIGMA) was added for 5 hours. Supernatant is removed and saved for further cytokine detection. The original plates with seeded cells were tested for cytotoxicity by measure of adenosine triphosphate (ATP) release by adding CellTiter-Glo® diluted 1:4 in distilled water (G7573, Promega) and transferring lysed cells to a completely black 96-well plate to be read with the Cytation3. Supernatant was then diluted 1:2 with a diluent from V-PLEX cytokine Kit and directly tested for the secreted cytokines TNFα, IL-6 and KC-GRO using electrochemiluminescence (Meso Scale Discovery). The standard curve for each cytokine was used to convert the electrochemiluminescent signal into pg of protein per mL. The signal was used to plot, draw the curve fitting, and determine each compounds EC$_{50}$ in Prism (GraphPad).

Table 9 shows the activity of representative compounds of Formula I as provided herein.

TABLE 9

| Compound | EC$_{50}$ (μM) |
|---|---|
| 1 | 0.067 |
| 2 | 0.001 |
| 3 | 0.033 |
| 4 | 0.218 |
| 5 | 0.042 |
| 6 | 0.011 |
| 9 | 0.076 |
| 10 | 1.050 |
| 11 | 0.051 |
| 12 | 0.006 |
| 13 | 0.252 |
| 14 | 0.456 |
| 15 | 0.193 |
| 16 | 0.022 |
| 17 | 0.242 |
| 18 | 0.001 |
| 20 | 0.053 |
| 21 | 1.100 |
| 22 | 0.697 |
| 23 | 0.023 |
| 24 | 0.054 |
| 25 | 0.150 |
| 26 | 9.400 |
| 27 | 0.040 |
| 28 | 0.017 |
| 29 | 0.220 |
| 30 | 0.155 |
| 31 | 0.271 |
| 32 | 0.136 |
| 33 | 0.032 |
| 34 | 0.589 |
| 35 | 0.355 |
| 36 | 0.063 |
| 37 | 0.014 |
| 38 | 0.043 |
| 39 | 0.160 |
| 40 | 0.919 |
| 41 | 0.682 |
| 42 | 0.042 |
| 43 | 0.022 |
| 44 | 0.034 |
| 45 | 0.029 |
| 46 | 0.064 |
| 47 | 0.034 |
| 48 | 0.181 |
| 50 | 0.600 |
| 51 | 0.070 |
| 52 | 0.206 |
| 53 | 0.426 |
| 54 | 0.120 |
| 55 | 0.012 |
| 56 | 0.110 |
| 57 | 0.108 |
| 58 | 0.256 |
| 59 | 0.009 |
| 60 | 1.360 |
| 61 | 0.043 |
| 62 | 0.054 |
| 63 | 0.196 |
| 64 | 0.449 |
| 65 | 1.080 |
| 66 | 0.027 |
| 67 | 0.095 |
| 68 | 0.585 |
| 69 | 0.016 |
| 70 | 0.012 |
| 71 | 0.107 |
| 72 | 0.624 |
| 73 | 0.630 |
| 74 | 0.214 |
| 75 | 0.046 |
| 76 | 0.028 |
| 77 | 0.108 |
| 78 | 0.037 |
| 79 | 0.063 |
| 80 | 6.100 |
| 81 | 0.035 |
| 82 | 0.100 |
| 83 | 0.049 |
| 84 | 0.502 |
| 85 | 0.494 |
| 86 | 0.374 |
| 87 | 0.379 |
| 88 | 0.107 |
| 89 | 0.391 |
| 90 | 0.089 |
| 91 | 0.103 |
| 92 | 0.642 |
| 93 | 0.391 |
| 95 | 0.132 |

TABLE 9-continued

| Compound | EC$_{50}$ (μM) |
|---|---|
| 96 | 3.490 |
| 97 | 0.047 |
| 99 | 0.239 |
| 100 | 0.017 |
| 101 | 0.328 |
| 102 | 0.123 |
| 103 | 0.117 |
| 104 | 0.076 |
| 105 | 0.236 |
| 106 | 0.115 |
| 108 | 0.076 |
| 109 | 0.053 |
| 110 | 0.239 |
| 121 | 0.409 |
| 124 | 0.096 |
| 125 | 0.464 |
| 126 | 0.158 |
| 128 | 0.220 |
| 129 | 0.364 |
| 130 | 1.370 |
| 131 | 0.440 |
| 134 | 0.496 |
| 135 | 1.400 |
| 136 | 0.032 |
| 137 | 0.442 |
| 139 | 0.271 |
| 141 | 0.026 |
| 143 | 0.227 |
| 144 | 2.980 |
| 145 | 0.0420 |
| 146 | 0.189 |
| 147 | 0.248 |
| 148 | 0.047 |
| 149 | 0.055 |
| 150 | 0.097 |
| 151 | 0.250 |
| 153 | 2.060 |
| 155 | 0.139 |
| 156 | 0.369 |
| 157 | 0.854 |
| 158 | 0.776 |
| 159 | 0.118 |
| 161 | 1.500 |
| 163 | 0.122 |
| 164 | 0.145 |
| 165 | 0.181 |
| 166 | 0.119 |
| 167 | 0.033 |
| 168 | 0.066 |
| 169 | 0.108 |
| 170 | 3.100 |
| 176 | 0.3260 |
| 179 | 0.390 |
| 188 | 0.136 |
| 193 | 1.420 |
| 194 | 0.066 |
| 195 | 0.065 |
| 196 | 0.723 |
| 197 | 0.054 |
| 199 | 0.169 |
| 200 | 0.202 |
| 225 | >10 |
| 226 | >10 |
| 227 | 0.875 |
| 228 | 0.556 |
| 230 | 0.520 |
| 231 | 0.396 |

Example 23

Representative compounds were screened using the following assay procedure to determine their ability to inhibit IL-6 and therefore demonstrate their anti-inflammatory properties.

Human Peripheral Blood Mononuclear Cells:

Fresh Normal PB MNC (Catalog # PB001, AllCells, Alameda, Calif.) were shipped overnight at 4° C. and resuspended in Roswell Park Memorial Institute (RPMI) 1640 Medium, with GlutaMAX Supplement (Catalog #61870127, ThermoFisher Scientific, Waltham, Mass.) supplemented with 1% Penicillin-Streptomycin (Catalog #151401633 ThermoFisher Scientific, Waltham, Mass.) and 1% fetal bovine serum (FBS) (Catalog #16140089, ThermoFisher Scientific, Waltham, Mass.) assay media.

Compound Screening:

Fresh normal human peripheral blood mononuclear cells (huPBMCs) were resuspended in 1% FBS-RPMI assay media with 1% Penicillin-Streptomycin 1% to a cell concentration of 1×10e6 cells/mL. Each compound was dissolved in DMSO (Catalog # D8418-100 ml, Sigma-Aldrich, St. Louis, Mo.) as a 10 mM stock and used to prepare compound source plates. Serial dilution (1:3, 10-point dose-response curves starting from 10 μM) and compound transfer was performed using the ECHO 550 (Labcyte, Sunnyvale, Calif.) into 384-well white Proxiplate-Plus assay plates (Catalog #6008289, PerkinElmer, Shelton, Conn.) with appropriate DMSO backfill for a final DMSO concentration of 0.25%. huPBMCs were plated at 5000 cells/well in the 384-well Proxiplate-Plus assay plates and incubated at 37° C.-5% CO$_2$ for 2 hours. 50 ng/mL of Lipopolysaccharides from *Escherichia coli* O111:B4 (Catalog # L5293-2 ML, Sigma-Aldrich, St. Louis, Mo.) was added after 2 hours and cells were incubated for another 22 hours at 37° C.-5% CO$_2$. After 22 hour incubation, a mixture of anti-IL6 XL665 and anti-IL-6 Cryptate diluted in reconstitution buffer (Catalog #62IL6PEC, Cisbio Inc., Bedford, Mass.) was added to each well. Following incubation for 3 hours at room temperature, Homogeneous Time-Resolved Fluorescence (HTRF) was measured using the Envision (Perkin Elmer, Shelton, Conn.) at 665 nm and 620 nM. The ratio of fluorescence at 665 nm to 620 nm was used as a readout for IL-6 quantification. All samples were processed in duplicate. Readings were normalized to DMSO treated cells and normalized activities were utilized for EC$_{50}$ calculations. EC$_{50}$ was determined using software generated by Dotmatics Limited (Windhill Bishops Stortford Herts, UK) using the Levenberg-Marquardt 4 parameter fitting procedure with finite different gradients. For EC$_{50}$ of >10 μM, the percent inhibition at 10 μM is provided.

Table 10 shows the activity of representative compounds of Formula I as provided herein.

TABLE 10

| Compound | EC$_{50}$ (μM) |
|---|---|
| 1 | 3.040 |
| 2 | 1.284 |
| 3 | 1.123 |
| 4 | 0.489 |
| 5 | 1.050 |
| 6 | 0.967 |
| 7 | 9.417 |
| 8 | 0.932 |
| 9 | 1.874 |
| 10 | 9.219 |
| 11 | >10 (38.4%) |
| 12 | 1.122 |
| 13 | >10 (17.6%) |
| 14 | >10 (12.5%) |
| 15 | >10 (15.8%) |

TABLE 10-continued

| Compound | EC$_{50}$ (µM) |
|---|---|
| 16 | 1.035 |
| 17 | 3.436 |
| 18 | 1.250 |
| 19 | 3.217 |
| 20 | >10 |
|  | (13.4%) |
| 21 | 9.368 |
| 22 | 6.658 |
| 23 | 9.372 |
| 24 | 8.808 |
| 25 | >10 |
|  | (8.0%) |
| 26 | >10 |
|  | (5.6%) |
| 27 | >10 |
|  | (2.8%) |
| 28 | >10 |
|  | (4.3%) |
| 29 | >10 |
|  | (6.0%) |
| 30 | >10 |
|  | (9.3%) |
| 31 | >10 |
|  | (19.8%) |
| 32 | >10 |
|  | (10.1%) |
| 33 | 9.321 |
| 34 | >10 |
|  | (7.0%) |
| 35 | >10 |
|  | (9.6%) |
| 36 | >10 |
|  | (4.0%) |
| 37 | 1.342 |
| 38 | >10 |
|  | (3.2%) |
| 39 | 9.395 |
| 40 | 9.699 |
| 41 | >10 |
|  | (9.4%) |
| 42 | >10 |
|  | (6.4%) |
| 43 | 1.069 |
| 44 | 1.130 |
| 45 | 0.655 |
| 46 | 3.764 |
| 47 | 0.945 |
| 48 | 9.074 |
| 49 | >10 |
|  | (9.0%) |
| 50 | 9.204 |
| 51 | 3.239 |
| 52 | 3.698 |
| 53 | 9.359 |
| 54 | 9.626 |
| 55 | >10 |
|  | (18.3%) |
| 56 | 3.369 |
| 57 | >10 |
|  | (6.1%) |
| 58 | 9.569 |
| 59 | 0.129 |
| 60 | >10 |
|  | (5.7%) |
| 61 | >10 |
|  | (5.2%) |
| 62 | >10 |
|  | (8.5%) |
| 63 | 4.797 |
| 64 | 4.630 |
| 65 | >10 |
|  | (4.8%) |
| 66 | 0.997 |
| 67 | >10 |
|  | (29.6%) |
| 68 | 4.058 |
| 69 | 1.019 |
| 70 | 0.952 |

TABLE 10-continued

| Compound | EC$_{50}$ (µM) |
|---|---|
| 71 | 9.371 |
| 72 | 1.580 |
| 73 | 2.068 |
| 74 | 1.126 |
| 75 | 0.857 |
| 76 | 0.927 |
| 77 | 1.936 |
| 78 | 1.052 |
| 79 | 1.345 |
| 80 | 7.642 |
| 81 | 1.120 |
| 82 | >10 |
|  | (47.6%) |
| 83 | 1.126 |
| 84 | 1.301 |
| 85 | 1.224 |
| 86 | 2.170 |
| 87 | 1.174 |
| 88 | 1.196 |
| 89 | 1.051 |
| 90 | 0.606 |
| 91 | 0.679 |
| 92 | 3.178 |
| 93 | 0.280 |
| 94 | 0.319 |
| 95 | 0.339 |
| 96 | >10 |
|  | (3.6%) |
| 97 | 0.365 |
| 99 | 1.362 |
| 100 | 2.016 |
| 101 | 3.589 |
| 102 | 2.917 |
| 103 | 1.080 |
| 104 | 1.135 |
| 105 | 1.570 |
| 106 | 1.114 |
| 108 | >10 |
|  | (4.1%) |
| 109 | >10 |
|  | (6.9%) |
| 110 | >10 |
|  | (7.0%) |
| 121 | >10 |
|  | (5.4%) |
| 124 | 1.882 |
| 125 | 9.270 |
| 126 | 0.363 |
| 128 | >10 |
|  | (8.0%) |
| 129 | >10 |
|  | (4.5%) |
| 130 | >10 |
|  | (12.2%) |
| 131 | 1.930 |
| 134 | 7.132 |
| 135 | >10 |
|  | (0%) |
| 136 | 0.463 |
| 137 | 2.278 |
| 139 | >10 |
|  | (@6.6%) |
| 141 | 0.388 |
| 143 | >10 |
|  | (5.7%) |
| 144 | >10 |
|  | (14.3%) |
| 145 | 0.371 |
| 146 | >10 |
|  | (2.1%) |
| 147 | >10 |
|  | (36.8%) |
| 148 | 0.414 |
| 149 | 0.379 |
| 150 | >10 |
|  | (5.7%) |
| 151 | >10 |
|  | (13.1%) |

TABLE 10-continued

| Compound | EC$_{50}$ (µM) |
|---|---|
| 153 | >10 (9.0%) |
| 154 | 1.132 |
| 155 | 1.065 |
| 156 | >10 (28.8%) |
| 157 | >10 (0%) |
| 158 | 3.355 |
| 159 | >10 (1.6%) |
| 160 | 3.297 |
| 161 | >10 (42.2%) |
| 162 | >10 (44.7%) |
| 163 | 5.716 |
| 164 | 3.386 |
| 165 | 2.846 |
| 166 | 3.550 |
| 167 | 1.245 |
| 168 | >10 (14.2%) |
| 169 | 1.017 |
| 170 | >10 (4.4%) |
| 176 | >10 (8.4%) |
| 179 | >10 (10.1%) |
| 188 | 5.769 |
| 193 | >10 (6.5%) |
| 194 | 3.087 |
| 195 | >10 (23.4%) |
| 196 | 1.211 |
| 197 | 0.994 |
| 199 | 3.856 |
| 200 | 3.982 |
| 224 | >10 (13.7%) |
| 225 | >10 (6.9%) |
| 226 | >10 (4.5%) |
| 227 | >10 (4.9%) |
| 228 | >10 (3.3%) |
| 229 | 8.955 |
| 230 | >10 (36.6%) |
| 231 | 8.278 |

What is claimed is:

1. A compound, or a pharmaceutically acceptable salt thereof, of Formula I:

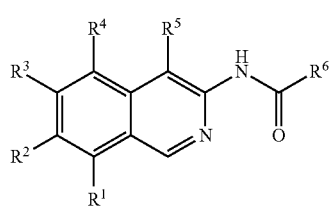

wherein:
R$^1$, R$^2$, R$^4$, and R$^5$ are independently selected from the group consisting of H and halide;

R$^3$ is a 5-membered heteroaryl substituted with 1-4 R$^{26}$; with the proviso that R$^3$ is not

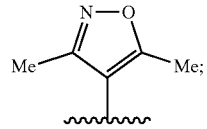 [SMILES: *c1c(C)noc1C]

R$^6$ is selected from the group consisting of —CH$_2$phenyl substituted with 1-5 R$^{41}$, —CH═CHphenyl optionally substituted with halide, —(C$_{1-4}$ alkylene)$_p$heterocyclyl optionally substituted with 1-5 R$^{27}$, -carbocyclyl substituted with 1-5 R$^{28}$, and

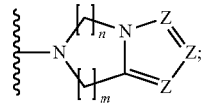

wherein —(C$_{1-4}$ alkylene) is, optionally substituted with one or more halides or one or more unsubstituted —(C$_{1-3}$ alkyl); wherein n is 1-4, m is 0-2 and each Z is independently selected from the group consisting of CR$^{32}$ and N;
  each R$^{26}$ is independently unsubstituted —(C$_{1-5}$ alkyl);
  each R$^{27}$ is independently selected from the group consisting of halide and —N(R$^{43}$)(R$^{44}$), with the proviso that if one or more R$^{27}$ is halide, at least one R$^{27}$ is —N(R$^{43}$)(R$^{44}$);
  each R$^{28}$ is independently —N(R$^{33}$)(R$^{34}$);
  each R$^{32}$ is independently selected from the group consisting of H, unsubstituted —(C$_{1-5}$ alkyl), unsubstituted —(C$_{2-5}$ alkenyl), unsubstituted —(C$_{2-5}$ alkynyl), and unsubstituted —(C$_{1-5}$ haloalkyl);
  R$^{33}$ is attached to the nitrogen and selected from the group consisting of H, unsubstituted —(C$_{1-5}$ alkyl), unsubstituted —(C$_{2-5}$ alkenyl), unsubstituted —(C$_{2-5}$ alkynyl), and unsubstituted —(C$_{1-5}$ haloalkyl);
  R$^{34}$ is attached to the nitrogen and is selected from the group consisting of unsubstituted —(C$_{1-5}$ haloalkyl), —(C$_{1-4}$ alkylene)$_p$heterocyclyl optionally substituted with 1-10 R$^{38}$, —(C$_{1-4}$ alkylene)$_p$carbocyclyl optionally substituted with 1-12 R$^{39}$, —(C$_{1-4}$ alkylene)OR$^{35}$; wherein each —(C$_{1-4}$ alkylene) is, independently, optionally substituted with one or more halides or one or more unsubstituted —(C$_{1-3}$ alkyl);
  each R$^{35}$ is independently selected from the group consisting of H and unsubstituted —(C$_{1-5}$ alkyl);
  each R$^{38}$ is independently selected from the group consisting of halide and unsubstituted —(C$_{1-5}$ alkyl);
  each R$^{39}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —CN, and —(C$_{1-4}$ alkylene)$_p$carbocyclyl optionally substituted with 1-12 R$^{40}$; wherein each —(C$_{1-4}$ alkylene) is, independently, optionally substituted with one or more halides or one or more unsubstituted —(C$_{1-3}$ alkyl);
  each R$^{40}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), and —CN;

each $R^{41}$ is halide;

each $R^{43}$ is attached to the nitrogen and selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

each $R^{44}$ is attached to the nitrogen and is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with 1-10 $R^{38}$, —($C_{1-4}$ alkylene)$_p$carbocyclyl optionally substituted with 1-12 $R^{39}$, and —($C_{1-4}$ alkylene)$OR^{35}$; wherein each —($C_{1-4}$ alkylene) is, independently, optionally substituted with one or more halides or one or more unsubstituted —($C_{1-3}$ alkyl);

each p is independently 0 or 1; and wherein one or more H are optionally replaced by D.

2. A compound, or a pharmaceutically acceptable salt thereof, of Formula I:

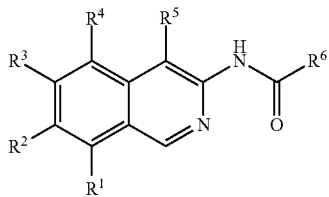

wherein:

$R^1$, $R^2$, $R^4$, and $R^5$ are independently selected from the group consisting of H and halide;

$R^3$ is selected from the group consisting of:

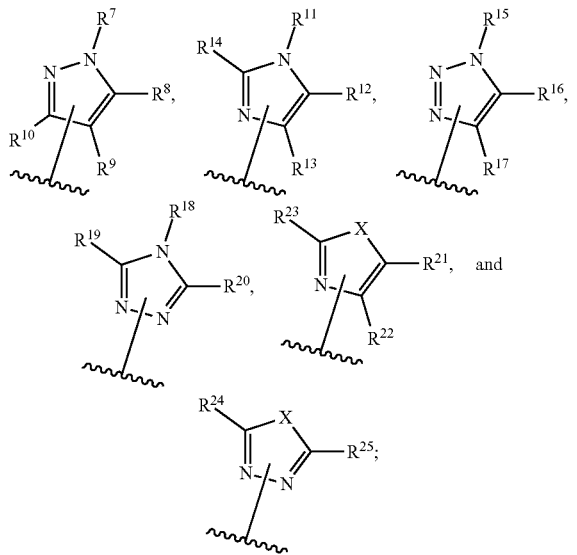

wherein each of $R^7$-$R^{25}$ is, independently, a substituent or a single bond connecting $R^3$ to the isoquinoline ring; wherein only one of $R^7$-$R^{10}$ (when present) is a bond, only one of $R^{11}$-$R^{14}$ (when present) is a bond, only one of $R^{15}$-$R^{17}$ (when present) is a bond, only one of $R^{18}$-$R^{20}$ (when present) is a bond, only one of $R^{21}$-$R^{23}$ (when present) is a bond, and only one of $R^{24}$-$R^{25}$ (when present) is a bond; for purposes of clarification, any one of the nitrogen atoms attached to $R^7$, $R^{11}$, $R^{15}$, or $R^{18}$ can serve as the point of attachment of $R^3$ to the isoquinoline ring; likewise, any one of the carbon atoms attached to $R^8$, $R^9$, $R^{10}$, $R^{12}$, $R^{13}$, $R^{14}$, $R^{16}$, $R^{17}$, $R^{19}$, $R^{20}$, $R^{21}$, $R^{22}$, $R^{23}$, $R^{24}$, and $R^{25}$ can serve as the point of attachment of $R^3$ to the isoquinoline ring; so that:

when the nitrogen atom to which $R^7$ is attached serves as the point of attachment of $R^3$ to the isoquinoline ring, then $R^7$ is a single bond connecting $R^3$ to the isoquinoline ring;

when the carbon atom to which $R^8$ is attached serves as the point of attachment of $R^3$ to the isoquinoline ring, then $R^8$ is a single bond connecting $R^3$ to the isoquinoline ring;

when the carbon atom to which $R^9$ is attached serves as the point of attachment of $R^3$ to the isoquinoline ring, then $R^9$ is a single bond connecting $R^3$ to the isoquinoline ring;

when the carbon atom to which $R^{10}$ is attached serves as the point of attachment of $R^3$ to the isoquinoline ring, then $R^{10}$ is a single bond connecting $R^3$ to the isoquinoline ring;

when the nitrogen atom to which $R^{11}$ is attached serves as the point of attachment of $R^3$ to the isoquinoline ring, then $R^{11}$ is a single bond connecting $R^3$ to the isoquinoline ring;

when the carbon atom to which $R^{12}$ is attached serves as the point of attachment of $R^3$ to the isoquinoline ring, then $R^{12}$ is a single bond connecting $R^3$ to the isoquinoline ring;

when the carbon atom to which $R^{13}$ is attached serves as the point of attachment of $R^3$ to the isoquinoline ring, then $R^{13}$ is a single bond connecting $R^3$ to the isoquinoline ring;

when the carbon atom to which $R^{14}$ is attached serves as the point of attachment of $R^3$ to the isoquinoline ring, then $R^{14}$ is a single bond connecting $R^3$ to the isoquinoline ring;

when the nitrogen atom to which $R^{15}$ is attached serves as the point of attachment of $R^3$ to the isoquinoline ring, then $R^{15}$ is a single bond connecting $R^3$ to the isoquinoline ring;

when the carbon atom to which $R^{16}$ is attached serves as the point of attachment of $R^3$ to the isoquinoline ring, then $R^{16}$ is a single bond connecting $R^3$ to the isoquinoline ring;

when the carbon atom to which $R^{17}$ is attached serves as the point of attachment of $R^3$ to the isoquinoline ring, then $R^{17}$ is a single bond connecting $R^3$ to the isoquinoline ring;

when the nitrogen atom to which $R^{18}$ is attached serves as the point of attachment of $R^3$ to the isoquinoline ring, then $R^{18}$ is a single bond connecting $R^3$ to the isoquinoline ring;

when the carbon atom to which $R^{19}$ is attached serves as the point of attachment of $R^3$ to the isoquinoline ring, then $R^{19}$ is a single bond connecting $R^3$ to the isoquinoline ring;

when the carbon atom to which $R^{26}$ is attached serves as the point of attachment of $R^3$ to the isoquinoline ring, then $R^{20}$ is a single bond connecting $R^3$ to the isoquinoline ring;

when the carbon atom to which $R^{21}$ is attached serves as the point of attachment of $R^3$ to the isoquinoline ring, then $R^{21}$ is a single bond connecting $R^3$ to the isoquinoline ring;

when the carbon atom to which $R^{22}$ is attached serves as the point of attachment of $R^3$ to the isoquinoline ring, then $R^{22}$ is a single bond connecting $R^3$ to the isoquinoline ring;

when the carbon atom to which $R^{23}$ is attached serves as the point of attachment of $R^3$ to the isoquinoline ring, then $R^{23}$ is a single bond connecting $R^3$ to the isoquinoline ring;

when the carbon atom to which $R^{24}$ is attached serves as the point of attachment of $R^3$ to the isoquinoline ring, then $R^{24}$ is a single bond connecting $R^3$ to the isoquinoline ring;

when the carbon atom to which $R^{25}$ is attached serves as the point of attachment of $R^3$ to the isoquinoline ring, then $R^{25}$ is a single bond connecting $R^3$ to the isoquinoline ring;

$R^6$ is selected from the group consisting of —CH$_2$phenyl substituted with 1-5 $R^{41}$, —CH=CHphenyl optionally substituted with halide, —(C$_{1-4}$ alkylene)$_p$heterocyclyl optionally substituted with 1-5 $R^{27}$, -carbocyclyl substituted with 1-5 $R^{28}$, and

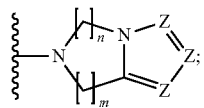

wherein —(C$_{1-4}$ alkylene) is, optionally substituted with one or more halides or one or more unsubstituted —(C$_{1-3}$ alkyl); wherein n is 1-4, m is 0-2 and each Z is independently selected from the group consisting of CR$^{32}$ and N;

$R^7$ is selected from the group consisting of a single bond and unsubstituted —(C$_{1-5}$ alkyl);

$R^8$, $R^9$, and $R^{10}$ are independently selected from the group consisting of a single bond, H, and unsubstituted —(C$_{1-5}$ alkyl);

$R^{11}$ is selected from the group consisting of a single bond, H, and unsubstituted —(C$_{1-5}$ alkyl);

$R^{12}$, $R^{13}$, and $R^{14}$ are independently selected from the group consisting of a single bond, H, and unsubstituted —(C$_{1-5}$ alkyl);

$R^{15}$ is selected from the group consisting of a single bond, H, and unsubstituted —(C$_{1-5}$ alkyl);

$R^{16}$ and $R^{17}$ are independently selected from the group consisting of a single bond, H, and unsubstituted —(C$_{1-5}$ alkyl);

$R^{18}$ is selected from the group consisting of a single bond, H, and unsubstituted —(C$_{1-5}$ alkyl);

$R^{19}$ and $R^{20}$ are independently selected from the group consisting of a single bond, H, and unsubstituted —(C$_{1-5}$ alkyl);

$R^{21}$, $R^{22}$, and $R^{23}$ are independently selected from the group consisting of a single bond, H, and unsubstituted —(C$_{1-5}$ alkyl);

$R^{24}$ and $R^{25}$ are independently selected from the group consisting of a single bond, H, and unsubstituted —(C$_{1-5}$ alkyl);

each $R^{27}$ is independently selected from the group consisting of halide, and —N(R$^{43}$)(R$^{44}$), with the proviso that if one or more $R^{27}$ is halide, at least one $R^{27}$ is —N(R$^{43}$)(R$^{44}$);

each $R^{28}$ is independently —N(R$^{33}$)(R$^{34}$);

each $R^{32}$ is independently selected from the group consisting of H, unsubstituted —(C$_{1-5}$ alkyl), unsubstituted —(C$_{2-5}$ alkenyl), unsubstituted —(C$_{2-5}$ alkynyl), and unsubstituted —(C$_{1-5}$ haloalkyl);

$R^{33}$ is attached to the nitrogen and selected from the group consisting of H, unsubstituted —(C$_{1-5}$ alkyl), unsubstituted —(C$_{2-5}$ alkenyl), unsubstituted —(C$_{2-5}$ alkynyl), and unsubstituted —(C$_{1-5}$ haloalkyl);

$R^{34}$ is attached to the nitrogen and is selected from the group consisting of unsubstituted —(C$_{1-5}$ haloalkyl), —(C$_{1-4}$ alkylene)$_p$heterocyclyl optionally substituted with 1-10 $R^{38}$, —(C$_{1-4}$ alkylene)$_p$carbocyclyl optionally substituted with 1-12 $R^{39}$, —(C$_{1-4}$ alkylene)OR$^{35}$; wherein each —(C$_{1-4}$ alkylene) is, independently, optionally substituted with one or more halides or unsubstituted —(C$_{1-3}$ alkyl);

each $R^{35}$ is independently selected from the group consisting of H and unsubstituted —(C$_{1-5}$ alkyl);

each $R^{38}$ is independently selected from the group consisting of halide and unsubstituted —(C$_{1-5}$ alkyl);

each $R^{39}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —CN, and —(C$_{1-4}$ alkylene)$_p$carbocyclyl optionally substituted with 1-12 $R^{40}$; wherein each —(C$_{1-4}$ alkylene) is, independently, optionally substituted with one or more halides or one or more unsubstituted —(C$_{1-3}$ alkyl);

each $R^{40}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), and —CN;

each $R^{41}$ is halide;

each $R^{43}$ is attached to the nitrogen and selected from the group consisting of H, unsubstituted -(C$_{1-5}$ alkyl), unsubstituted —(C$_{2-5}$ alkenyl), unsubstituted —(C$_{2-5}$ alkynyl), and unsubstituted —(C$_{1-5}$ haloalkyl);

each $R^{44}$ is attached to the nitrogen and is selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$heterocyclyl optionally substituted with 1-10 $R^{38}$, —(C$_{1-4}$ alkylene)$_p$carbocyclyl optionally substituted with 1-12 $R^{39}$, and —(C$_{1-4}$ alkylene)OR$^{35}$; wherein each —(C$_{1-4}$ alkylene) is, independently, optionally substituted with one or more halides or one or more unsubstituted —(C$_{1-3}$ alkyl);

each X is 0 or S;

each p is independently 0 or 1; and wherein one or more H are optionally replaced by D.

3. The compound of claim 1, wherein the compound of Formula I is selected from the group consisting of:

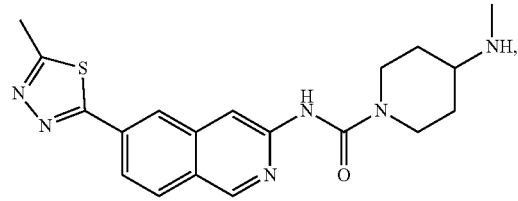

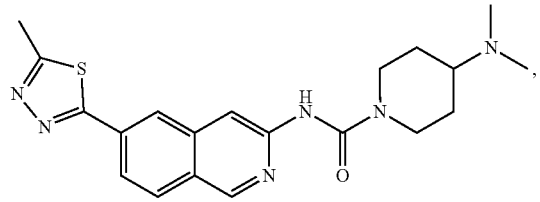

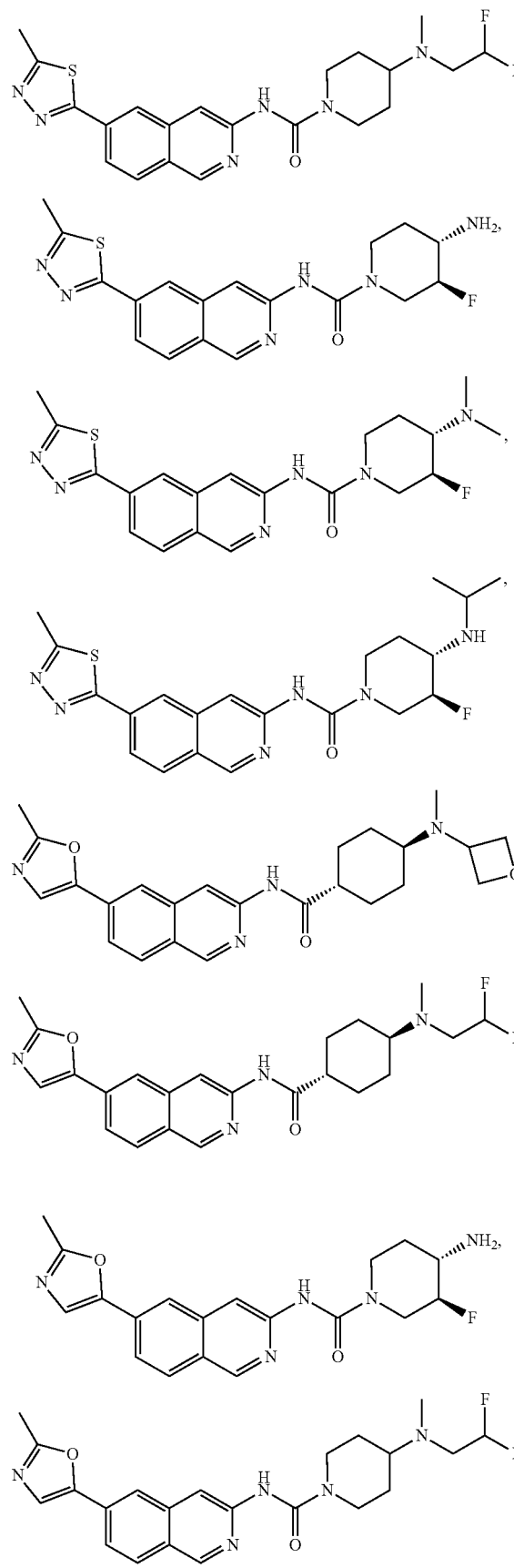
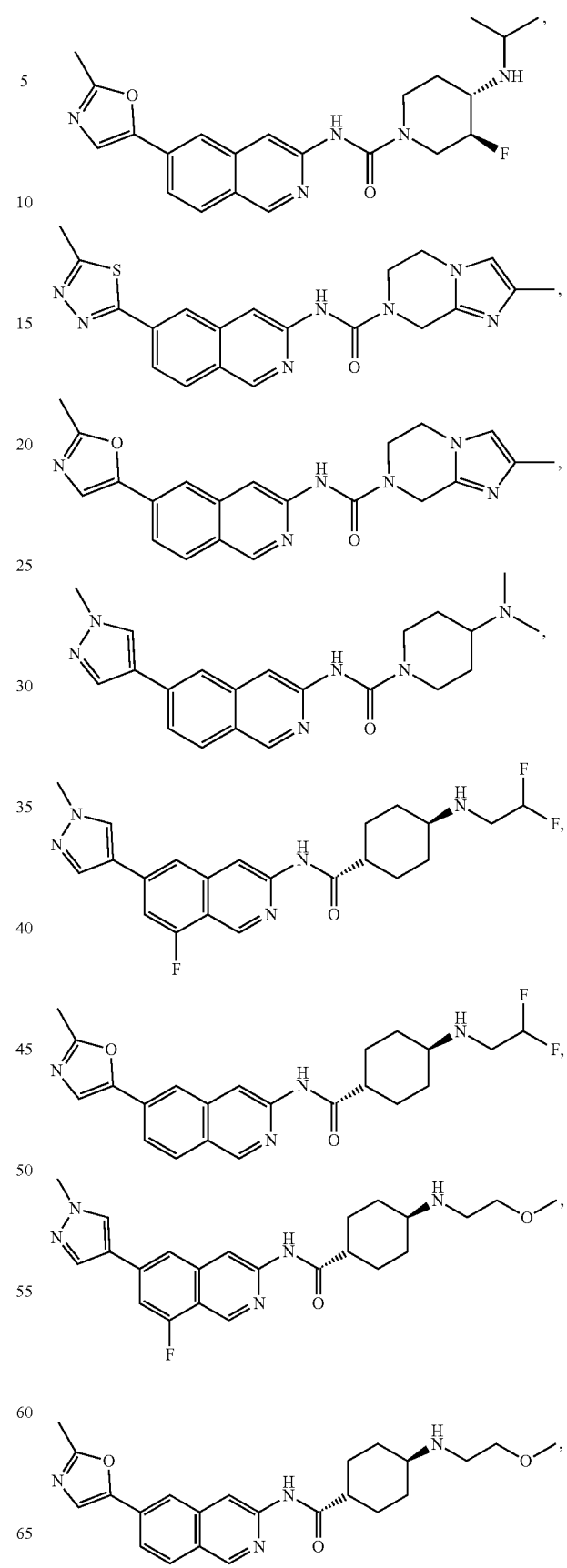

-continued
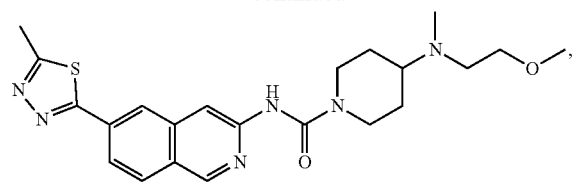
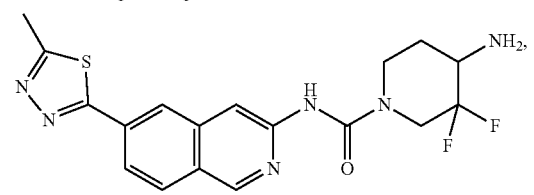
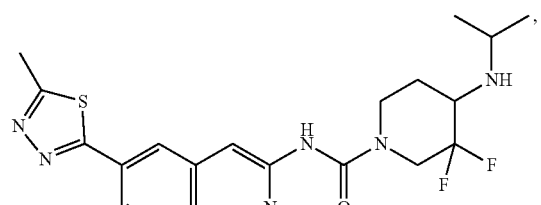
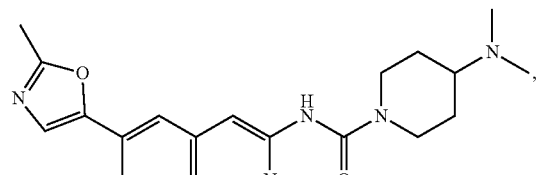
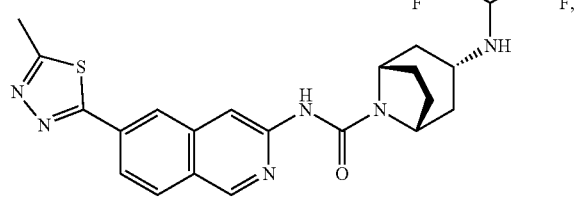
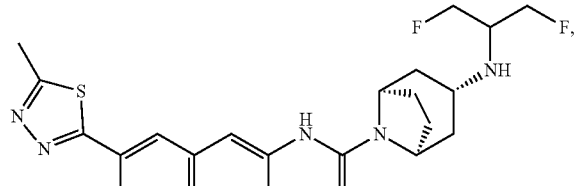
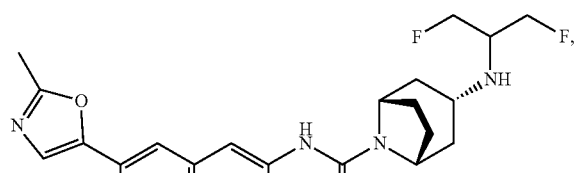
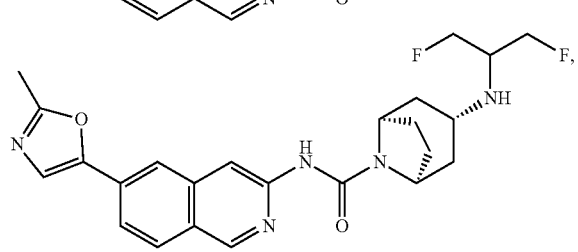
-continued
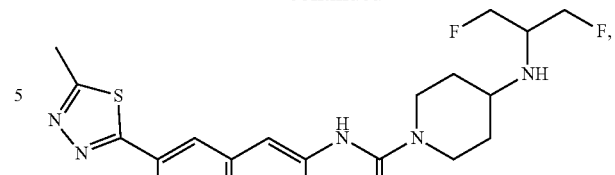
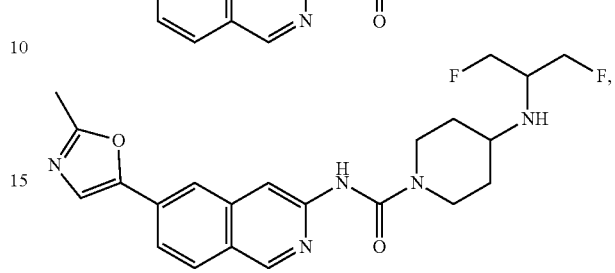
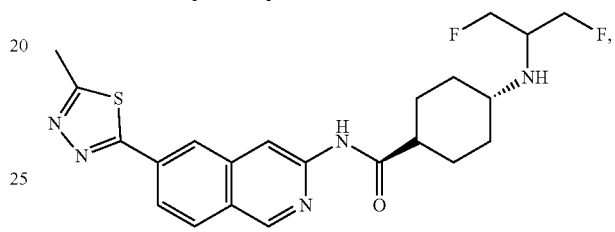
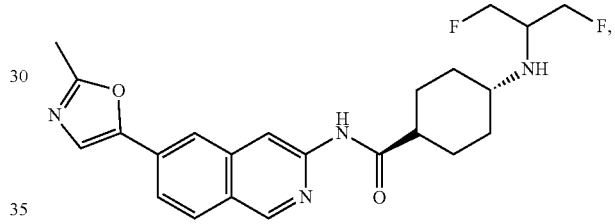
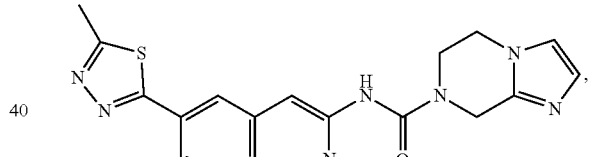
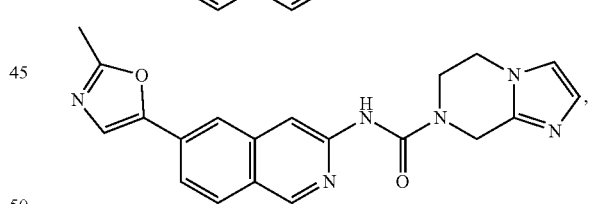
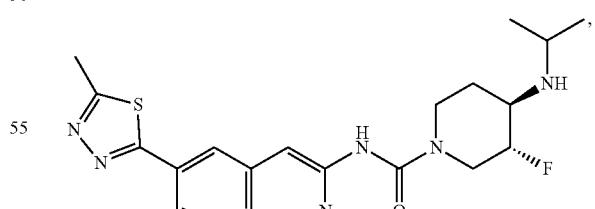
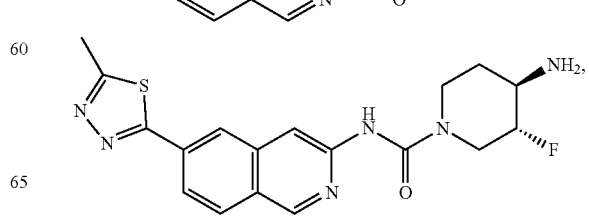

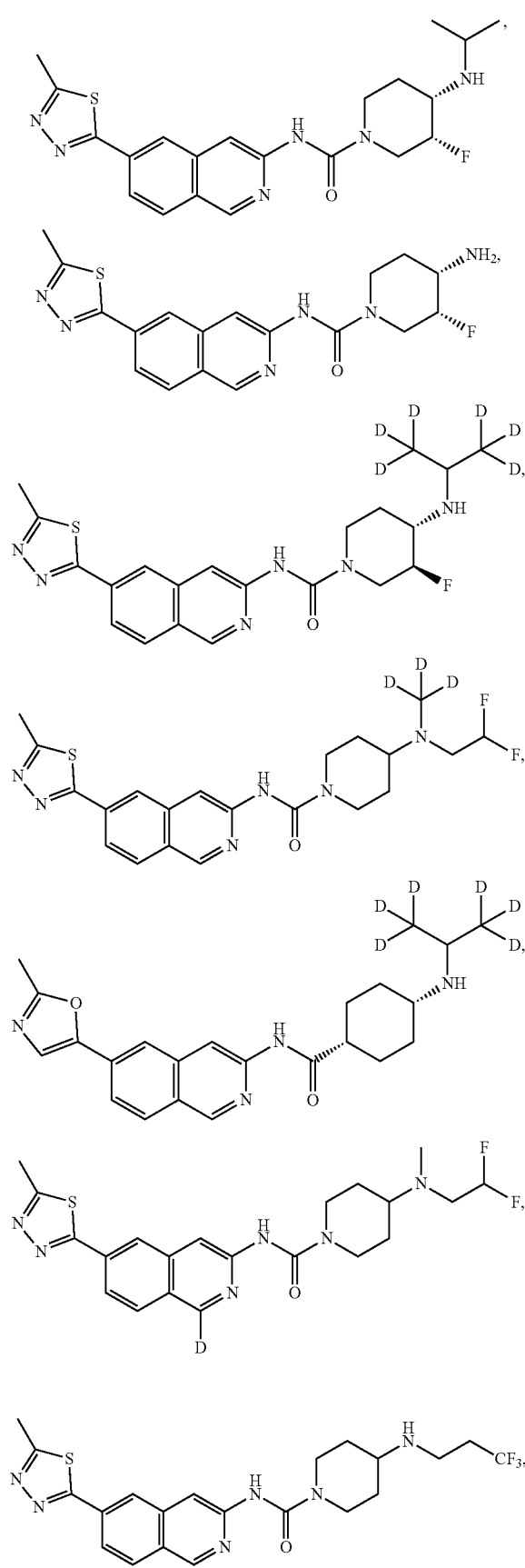
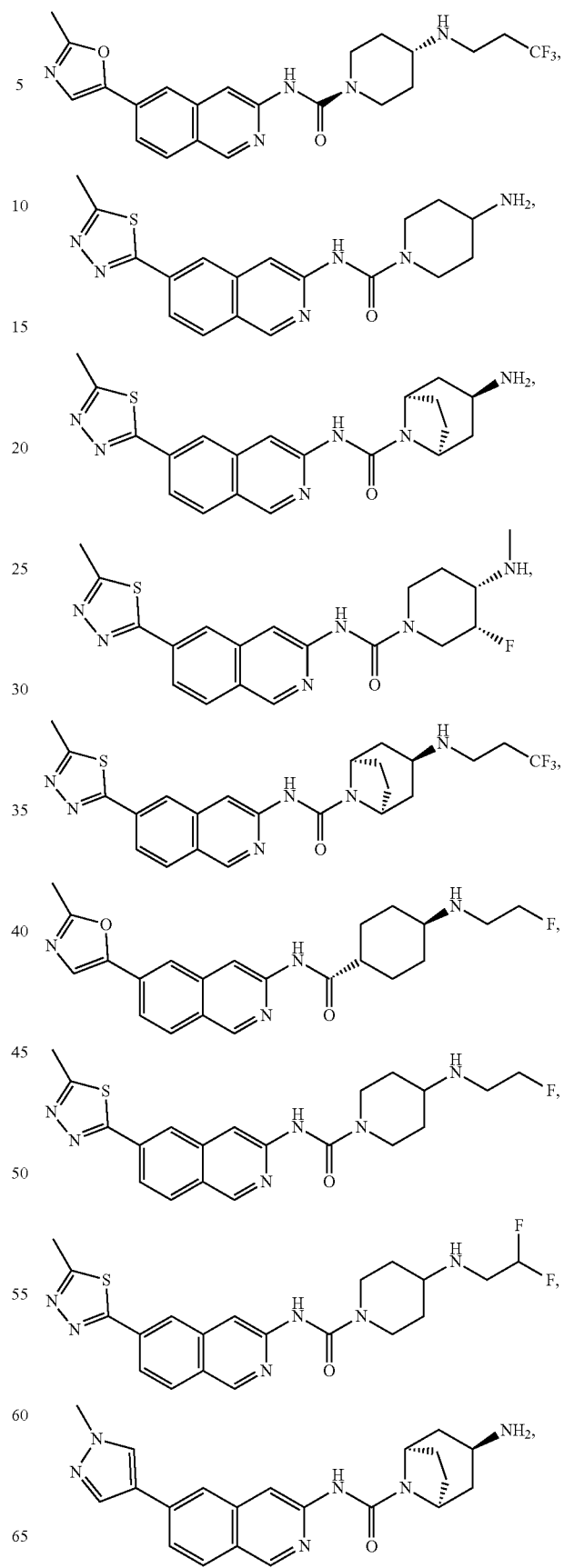

275
-continued
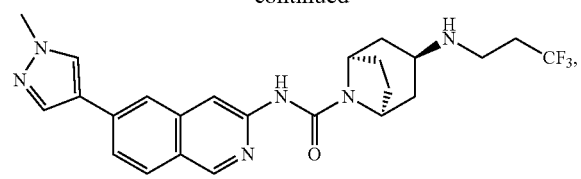
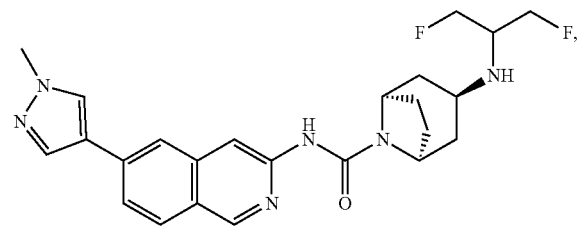
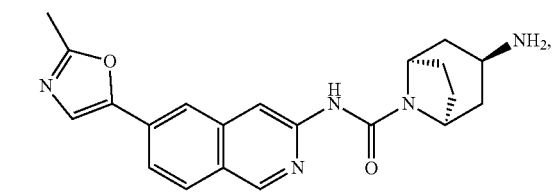
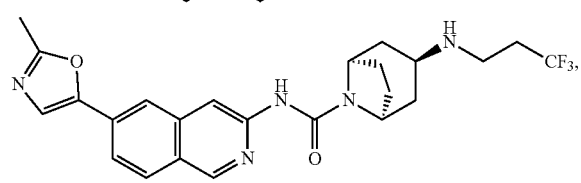
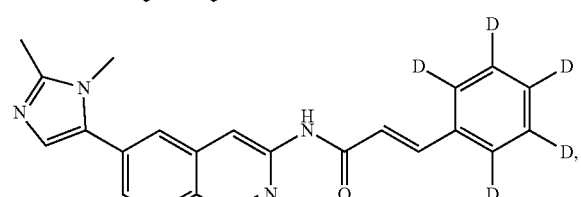
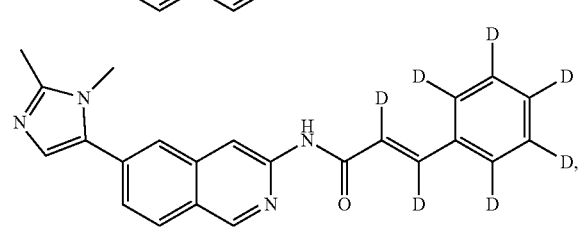
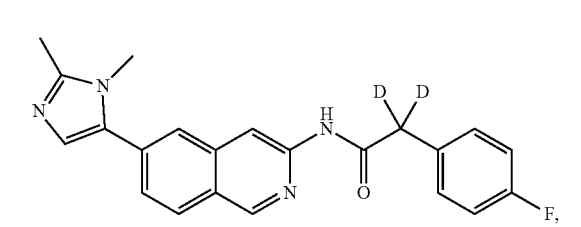
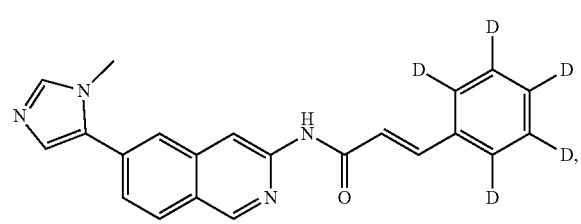
276
-continued
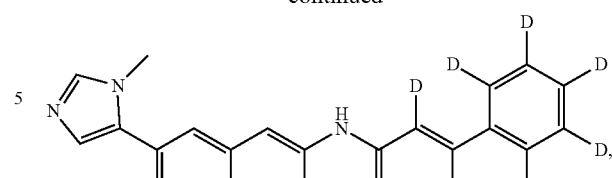
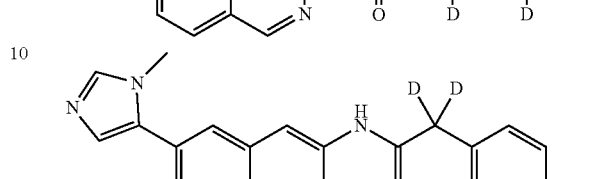
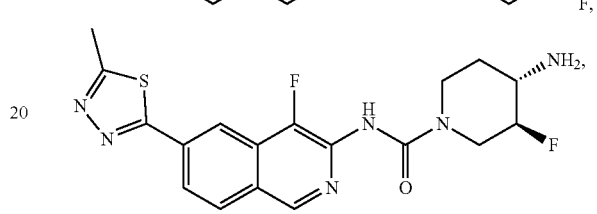
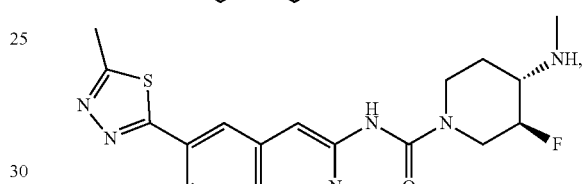
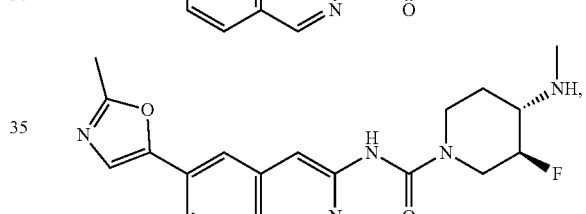
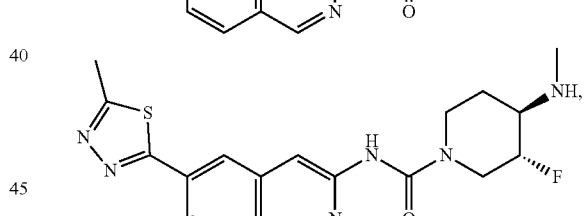
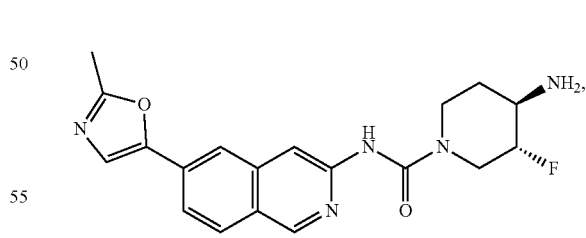
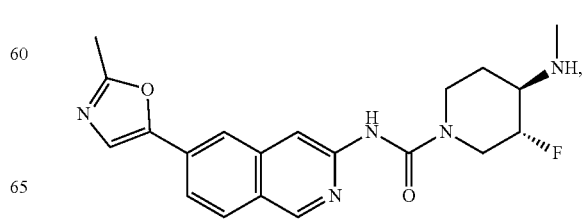

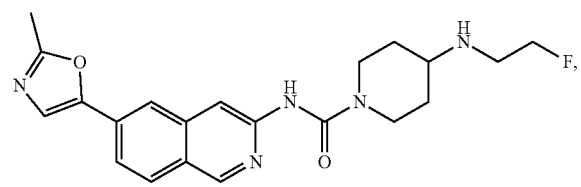
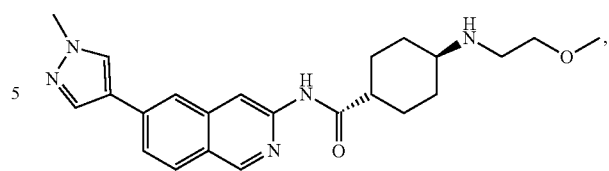
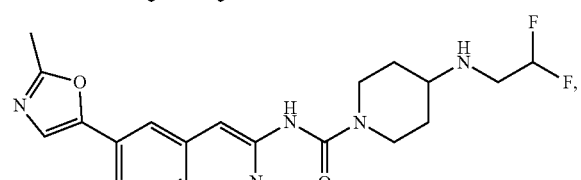
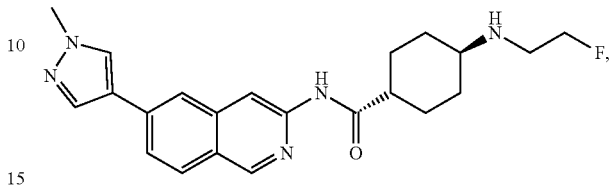
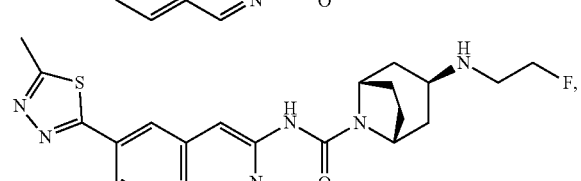
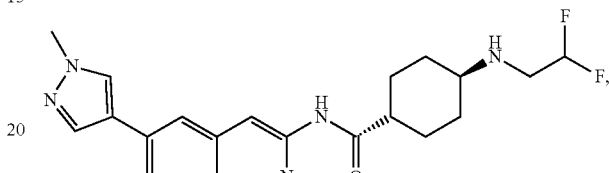
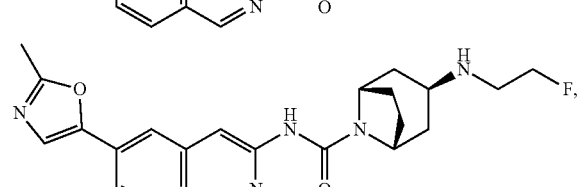
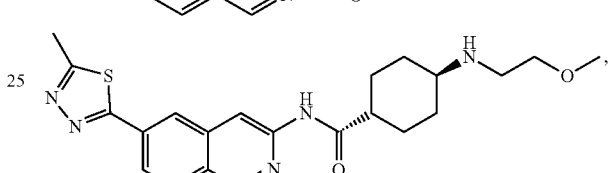
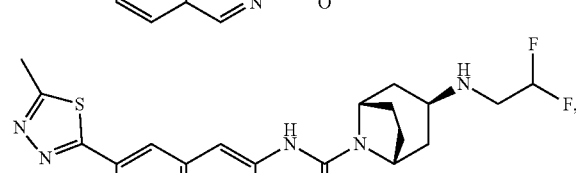
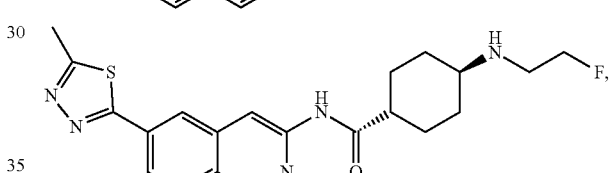
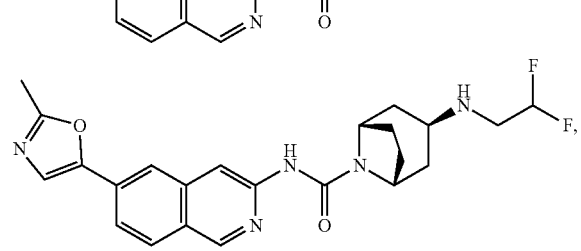
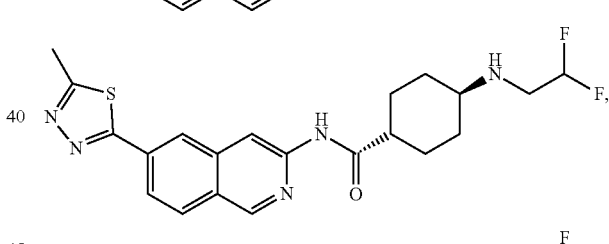
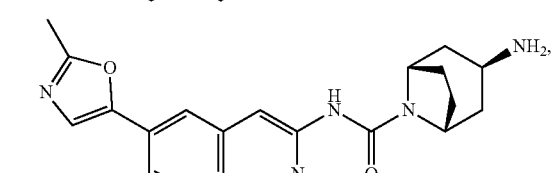
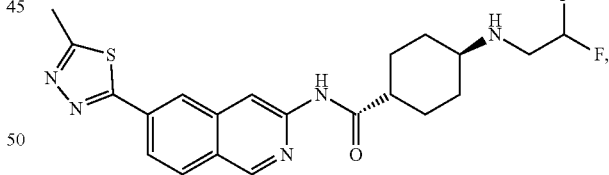
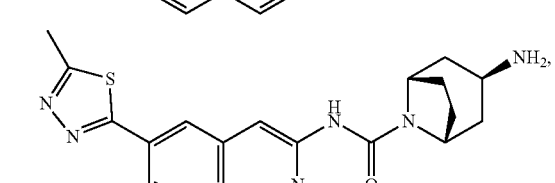
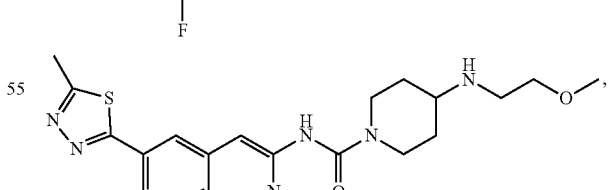
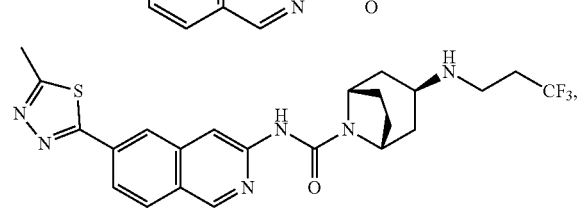
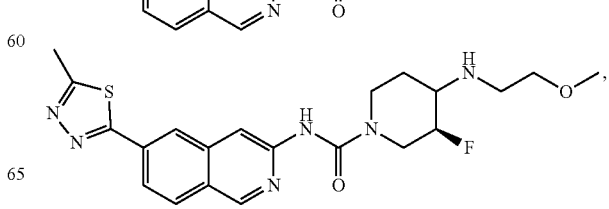

-continued

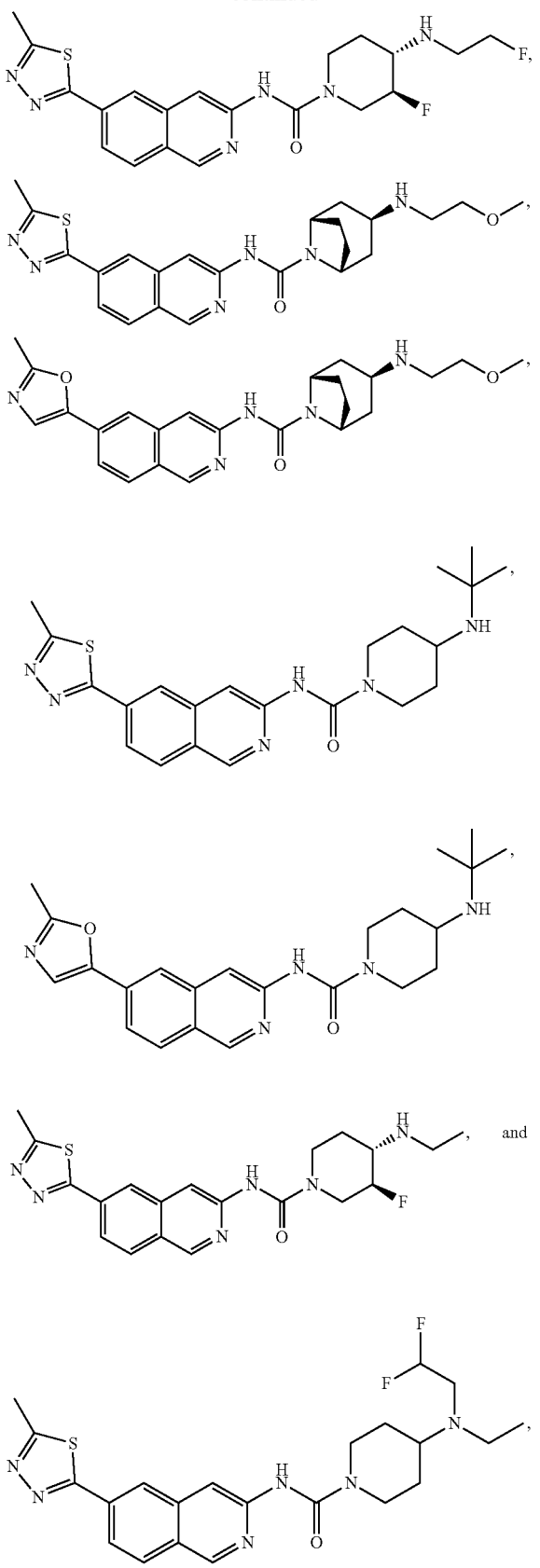

or a pharmaceutically acceptable salt thereof.

4. A compound, or a pharmaceutically acceptable salt thereof, of Formula I:

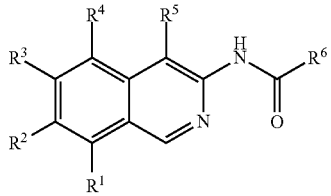

wherein:
$R^1$, $R^2$, $R^4$, and $R^5$ are independently selected from the group consisting of H and halide;
$R^3$ is a 5-membered heteroaryl substituted with 1-4 $R^{26}$; with the proviso that $R^3$ is not

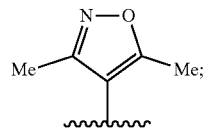

$R^6$ is selected from the group consisting of —($C_{1-4}$ alkylene)$_p$heterocyclyl optionally substituted with 1-5 $R^{27}$, -carbocyclyl optionally substituted with 1-5 $R^{28}$, and —N($R^{30}$)($R^{31}$); wherein —($C_{1-4}$ alkylene) is, optionally substituted with one or more halides or one or more unsubstituted —($C_{1-3}$ alkyl);
each $R^{26}$ is independently unsubstituted —($C_{1-5}$ alkyl);
each $R^{27}$ is independently selected from the group consisting of halide, unsubstituted —($C_{1-5}$ alkyl), unsubstituted —($C_{1-9}$ haloalkyl), —OR$^{35}$, and —($C_{1-4}$ alkylene)$_p$heterocyclyl optionally substituted with 1-5 $R^{36}$; wherein —($C_{1-4}$ alkylene) is, optionally substituted with one or more halides or one or more unsubstituted —($C_{1-3}$ alkyl);
each $R^{28}$ is independently selected from the group consisting of —N($R^{33}$)$_2$, —($C_{1-4}$ alkylene)OR$^{35}$, —C(=O)($R^{37}$), and —($C_{1-4}$ alkylene)$_p$heterocyclyl optionally substituted with 1-5 $R^{36}$; wherein each —($C_{1-4}$ alkylene) is independently, optionally substituted with one or more halides or one or more unsubstituted —($C_{1-3}$ alkyl);
$R^{30}$ is attached to the nitrogen and is selected from the group consisting of H and unsubstituted —($C_{1-5}$ alkyl);
$R^{31}$ is attached to the nitrogen and is heterocyclyl optionally substituted with 1-5 $R^{38}$;
$R^{33}$ is attached to the nitrogen and selected from the group consisting of H, unsubstituted —($C_{1-5}$ alkyl), unsubstituted —($C_{2-5}$ alkenyl), and unsubstituted —($C_{2-5}$ alkynyl);
each $R^{35}$ is independently selected from the group consisting of H and unsubstituted —($C_{1-5}$ alkyl);
each $R^{36}$ is selected from the group consisting of unsubstituted —($C_{1-5}$ alkyl) and unsubstituted —($C_{1-5}$ haloalkyl);
$R^{37}$ is -heterocyclyl optionally substituted with one or more halides or one or more unsubstituted —($C_{1-5}$ alkyl);
each $R^{38}$ is independently selected from the group consisting of halide and unsubstituted —($C_{1-5}$ alkyl);

each p is independently 0 or 1; and
wherein one or more H are optionally replaced by D.
5. The compound of claim 4, wherein the compound of Formula I is selected from the group consisting of:
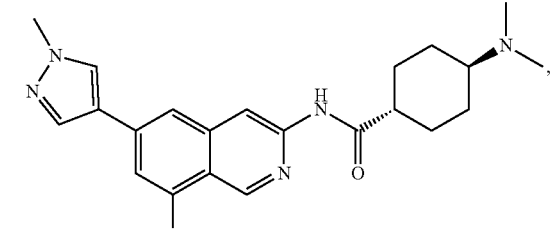
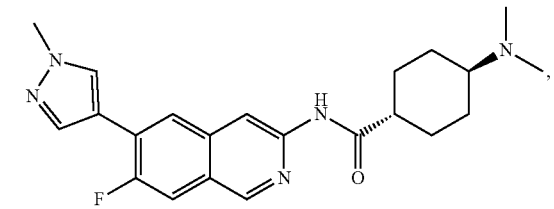
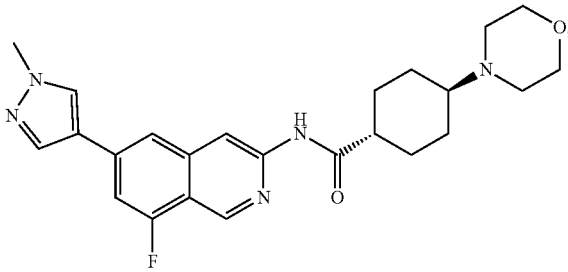
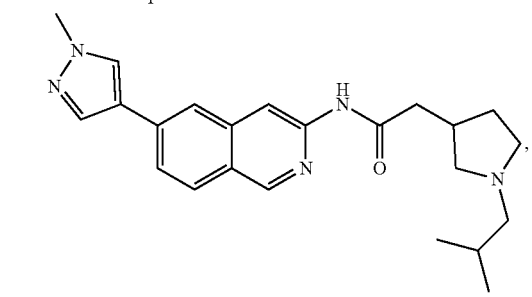
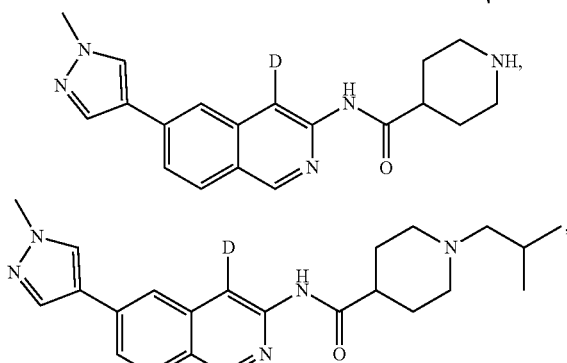
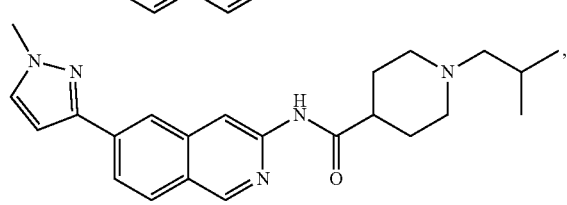
-continued
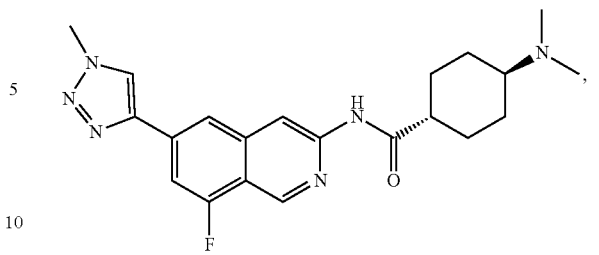
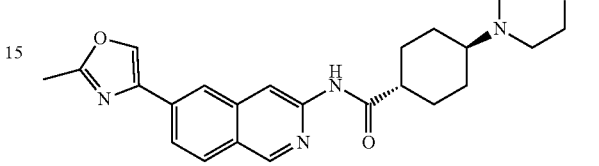
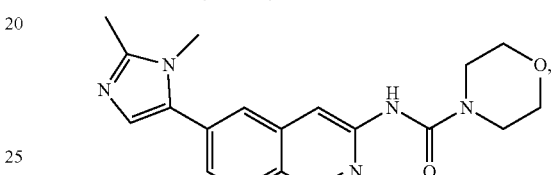
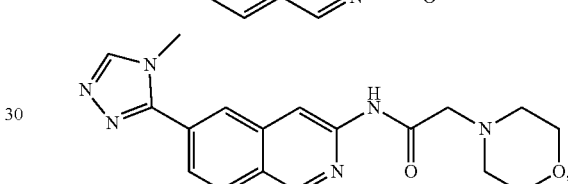
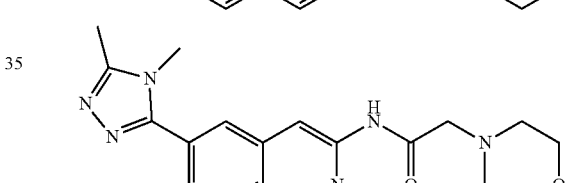
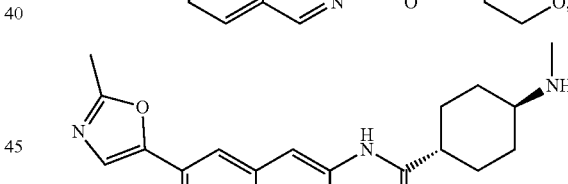
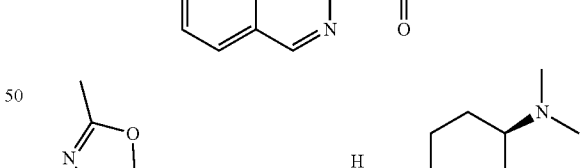
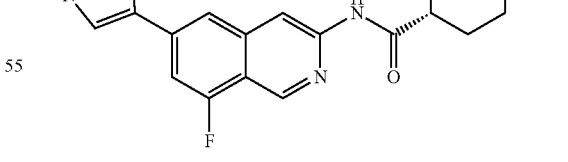
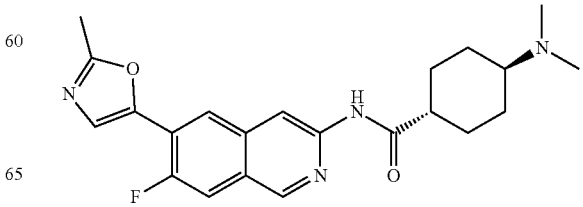

283
-continued
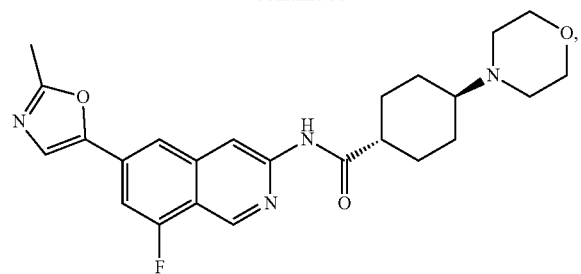
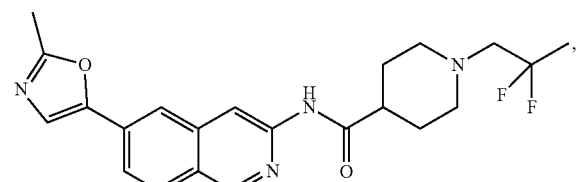
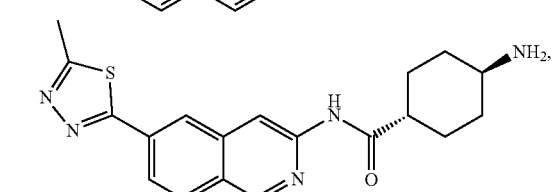
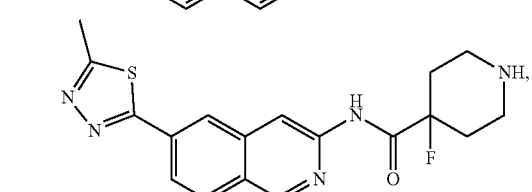
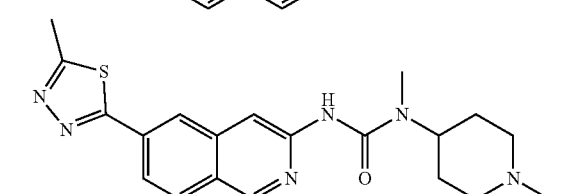
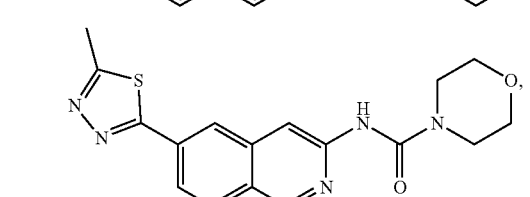
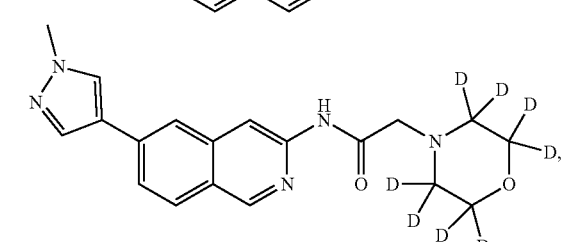
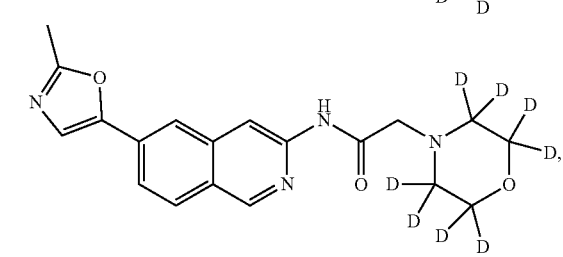
284
-continued
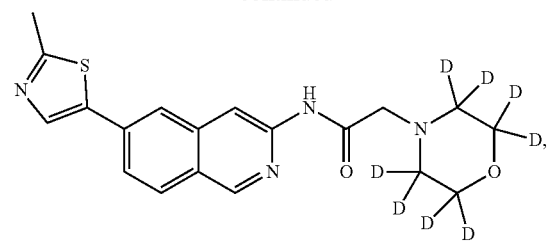
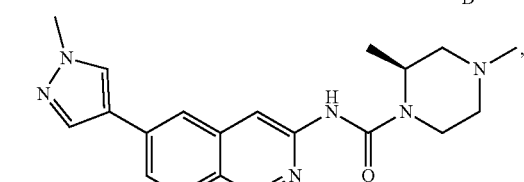
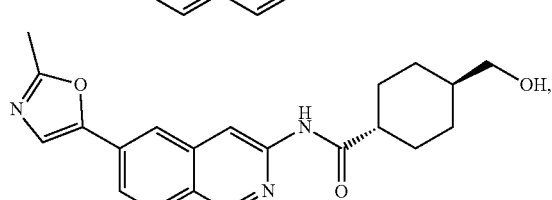
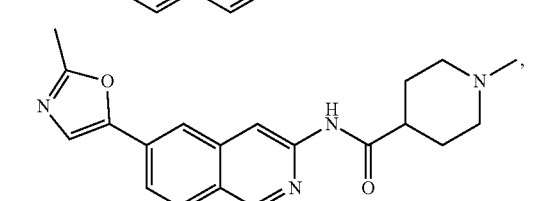
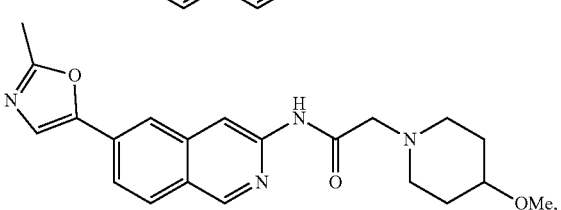
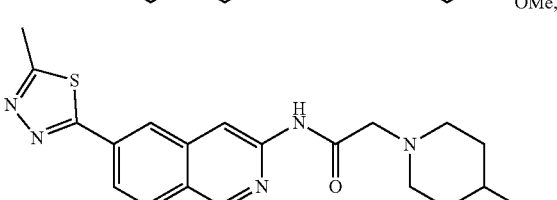
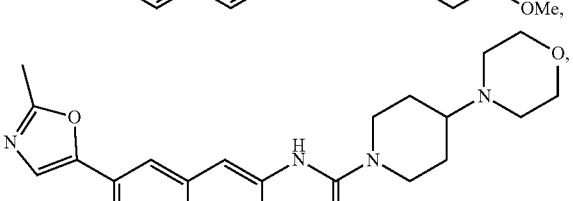
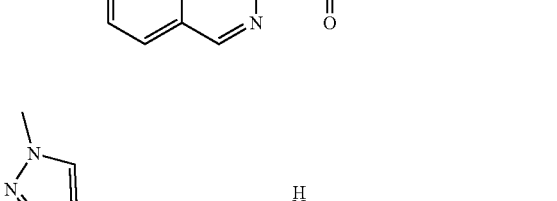

-continued
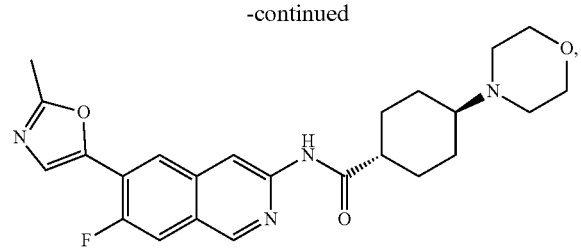
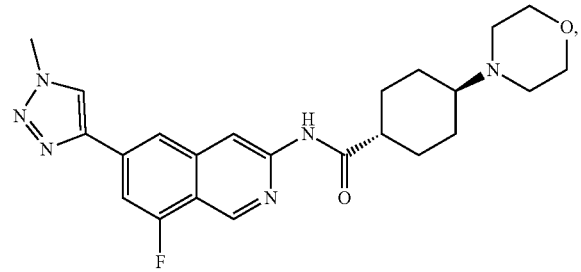
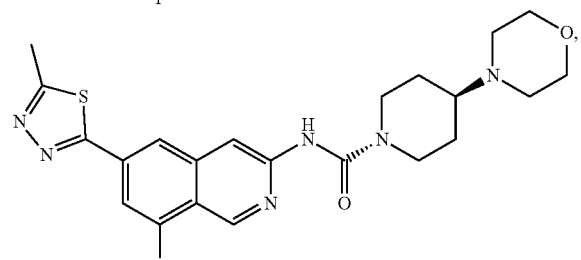
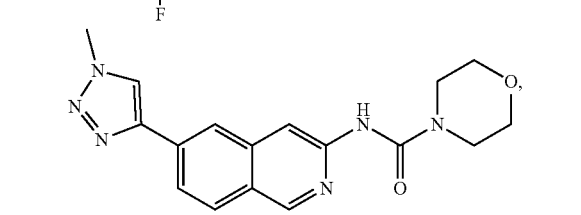
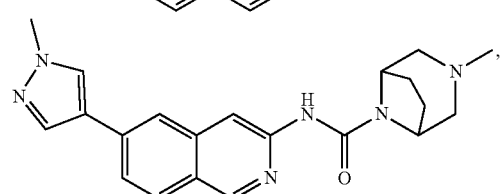
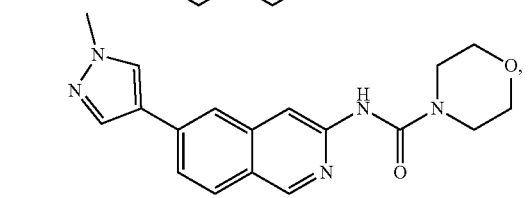
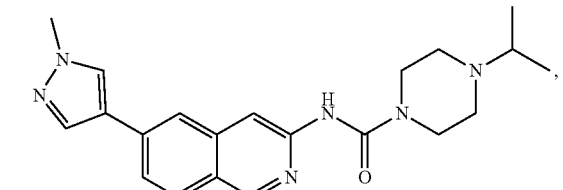
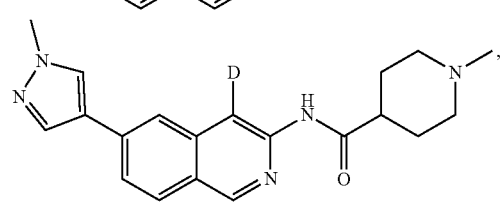
-continued
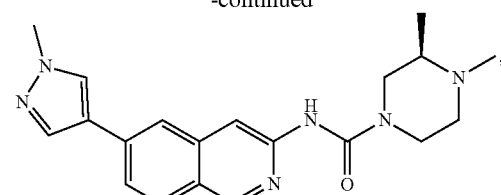
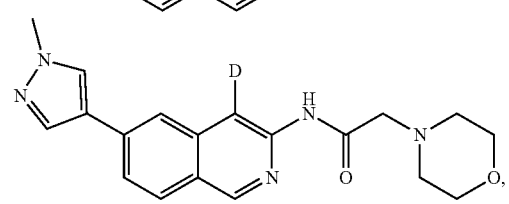
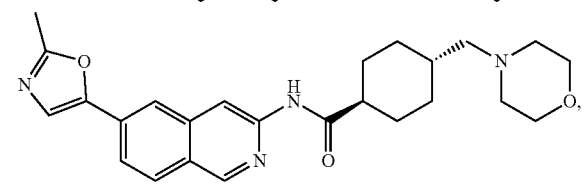
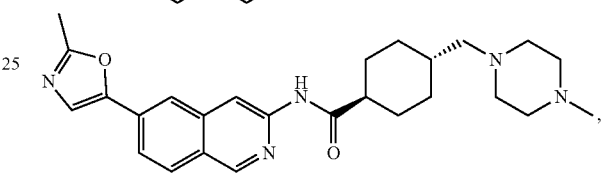
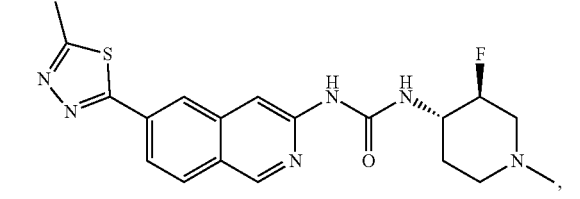
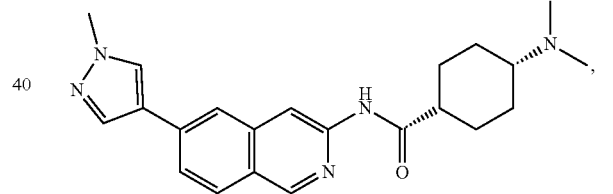
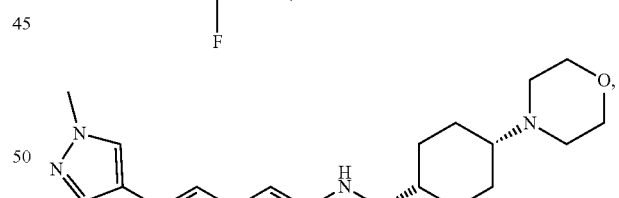
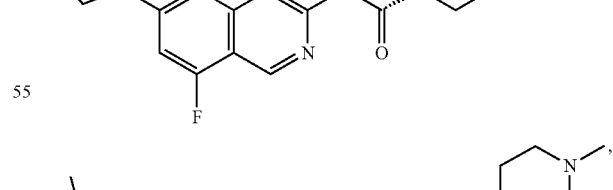
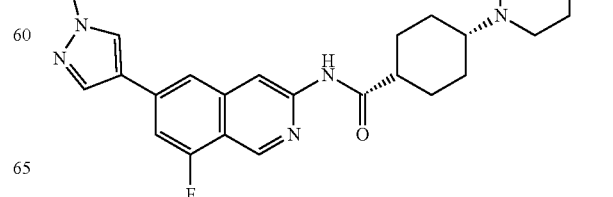

287
-continued
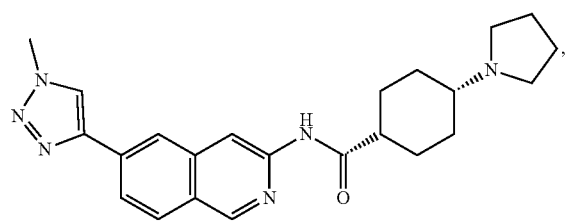
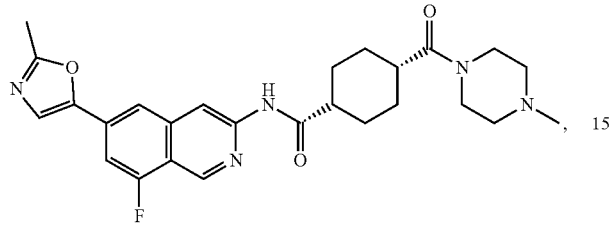
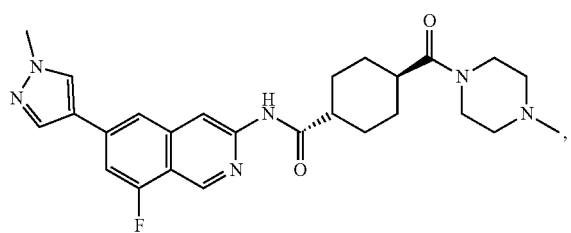
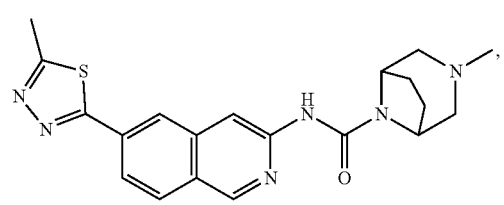
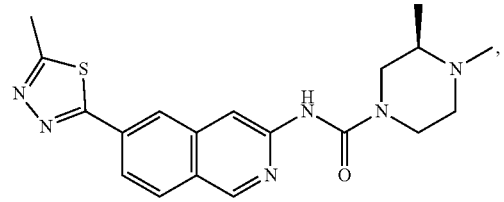
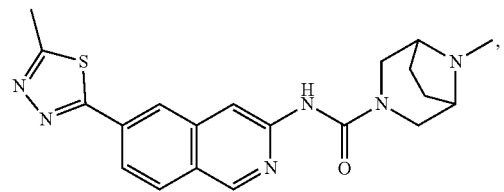
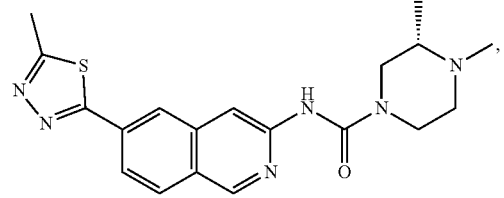
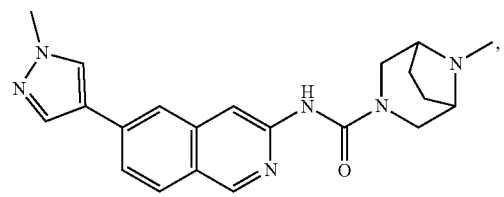
288
-continued
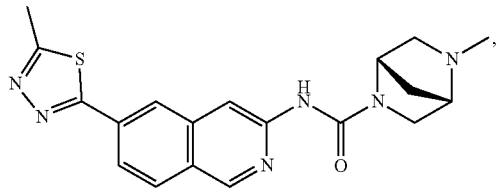
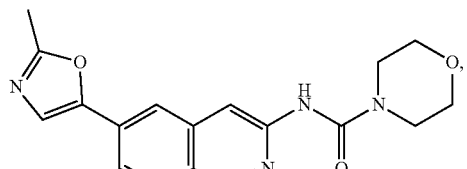
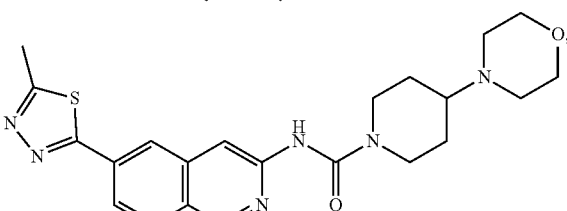
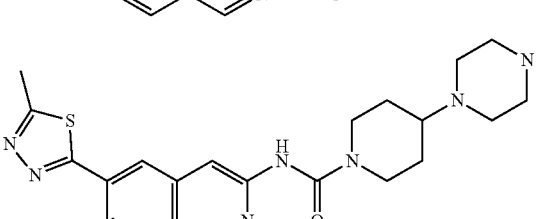
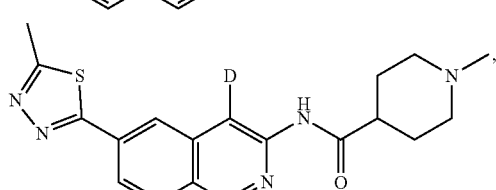
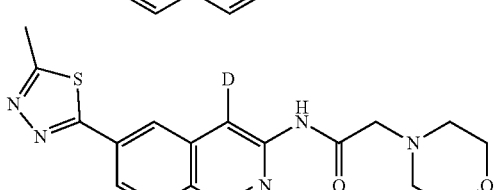
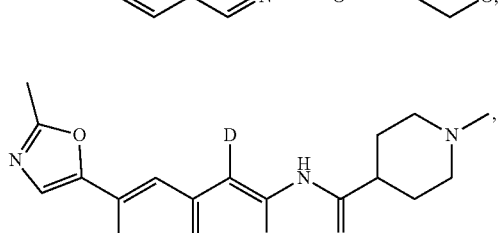
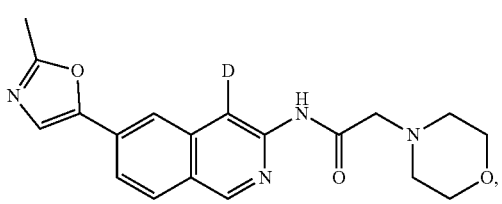

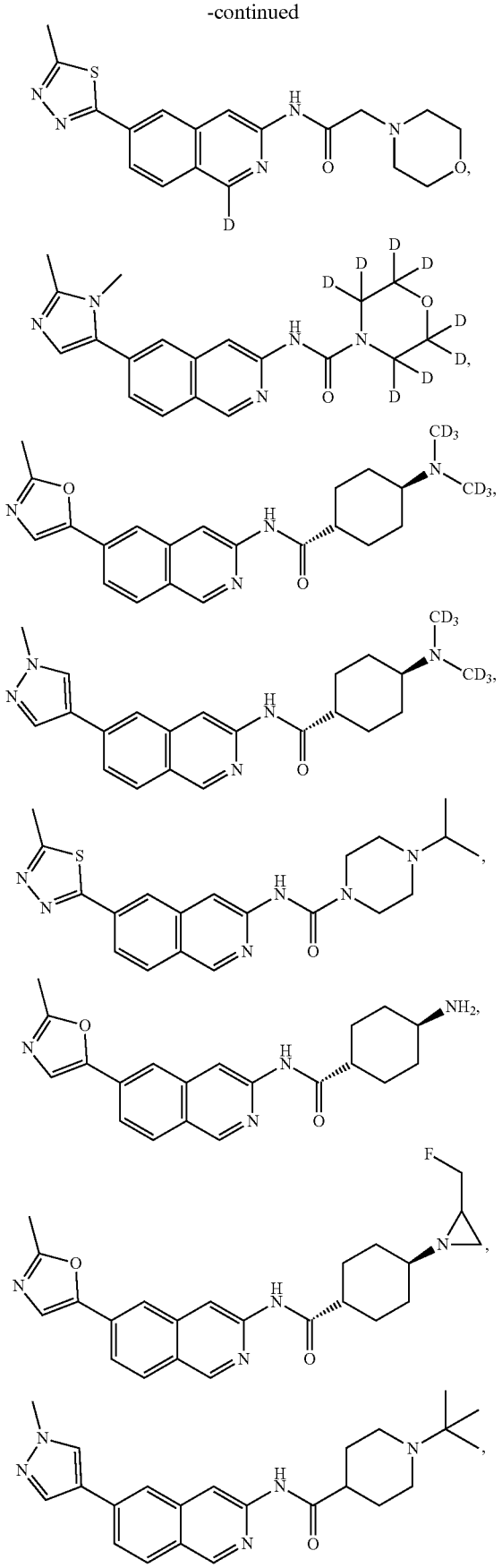
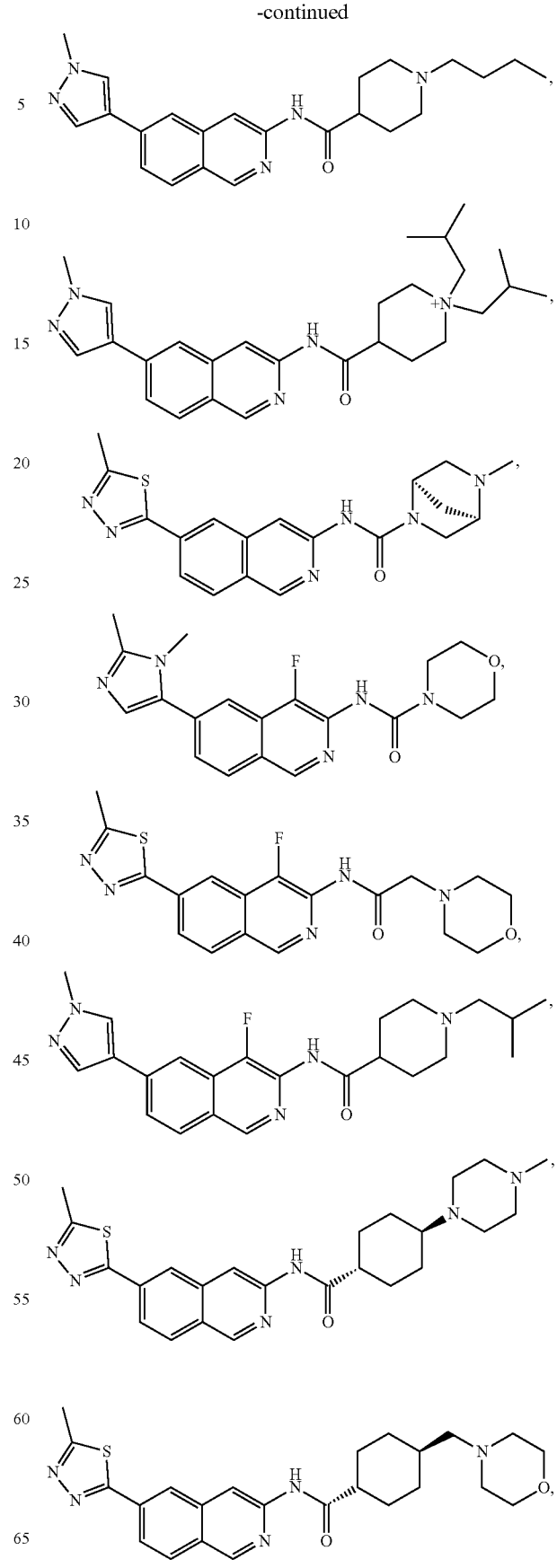

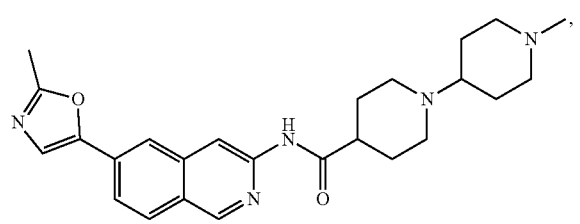
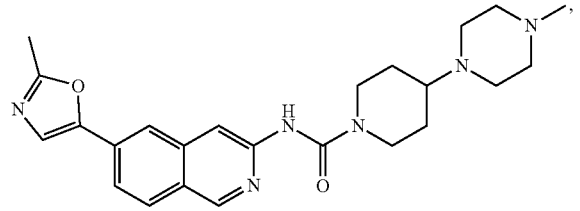
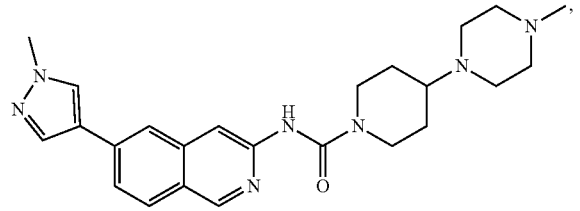
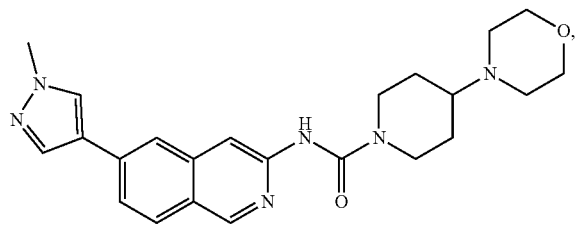
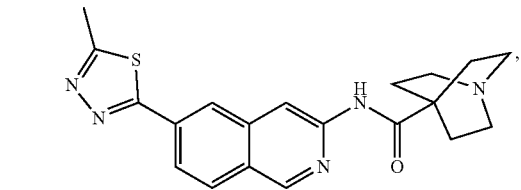
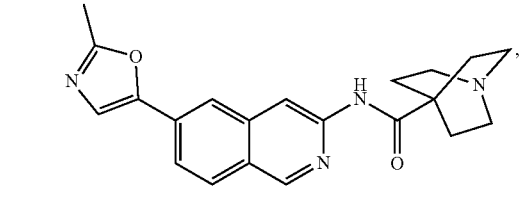
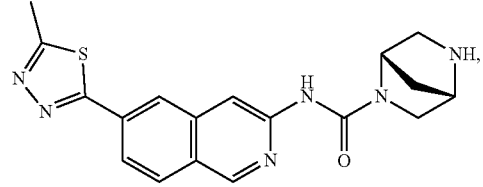
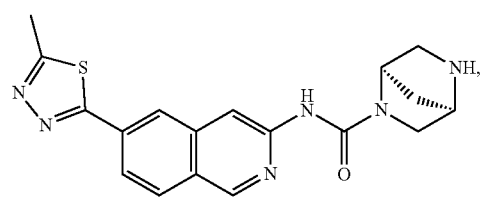
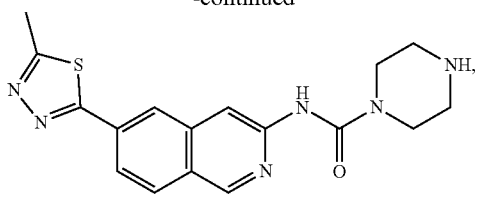
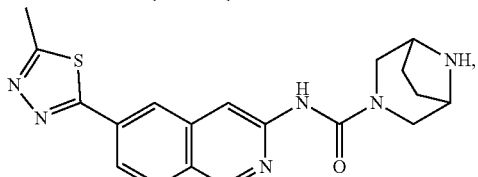
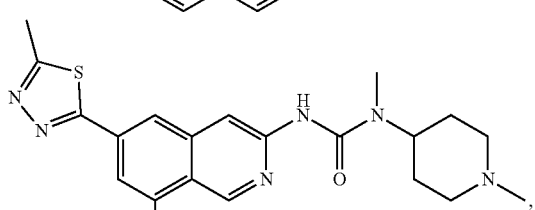
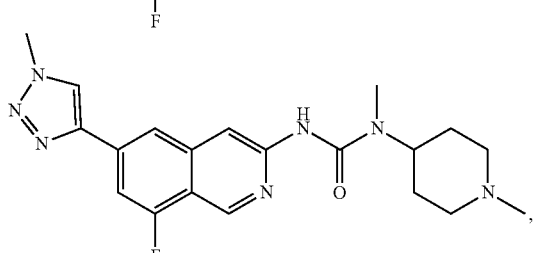
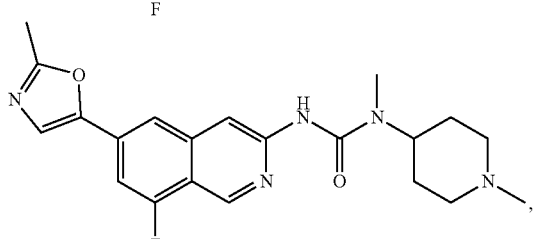
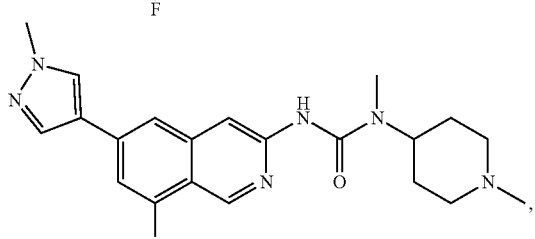
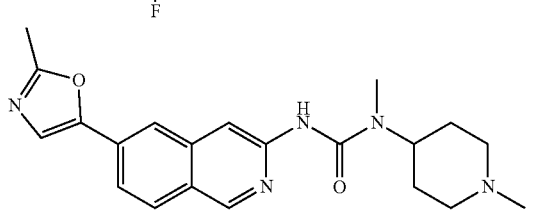
, and

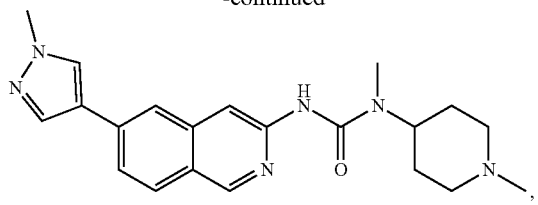

or a pharmaceutically acceptable salt thereof.

6. A compound, or a pharmaceutically acceptable salt thereof, of Formula I:

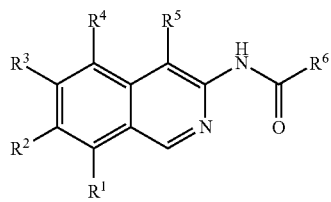

wherein:

$R^1$, $R^2$, $R^4$, and $R^5$ are independently selected from the group consisting of H and halide;

$R^3$ is a 5-membered heteroaryl optionally substituted with 1-4 $R^{26}$;

$R^6$ is a selected from the group consisting of -phenyl substituted with 1-5 $R^{42}$ and 6-membered heteroaryl optionally substituted with 1-6 $R^{29}$;

each $R^{26}$ is independently unsubstituted —($C_{1-5}$ alkyl);

each $R^{29}$ is independently selected from the group consisting of unsubstituted —($C_{1-5}$ alkyl) and heterocyclyl optionally substituted with 1-5 $R^{36}$;

each $R^{36}$ is independently unsubstituted ($C_{1-5}$ alkyl);

each $R^{42}$ is independently selected from the group consisting of halide, —OMe, and unsubstituted —($C_{1-5}$ alkyl); and wherein one or more H are optionally replaced by D.

7. The compound of claim 6, wherein the compound of Formula I is selected from the group consisting of:

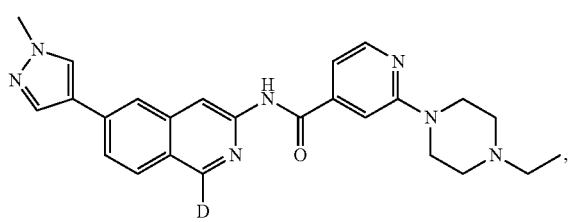

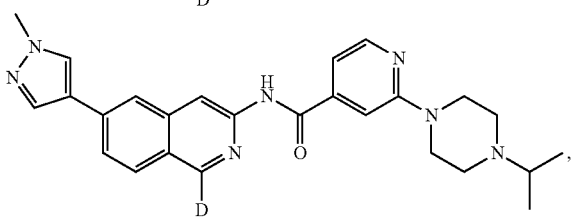

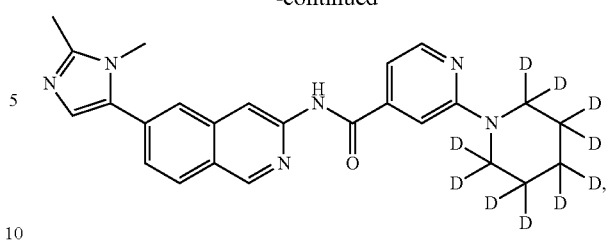

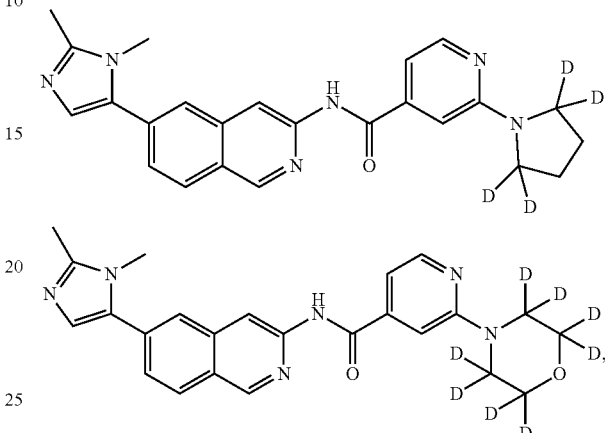

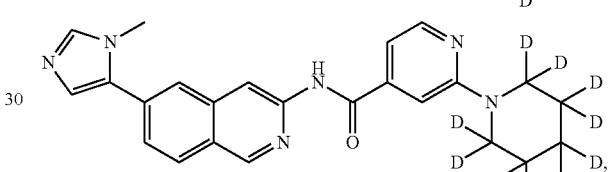

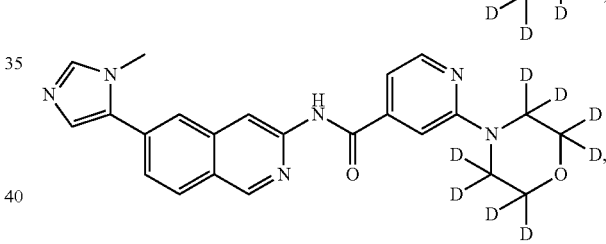

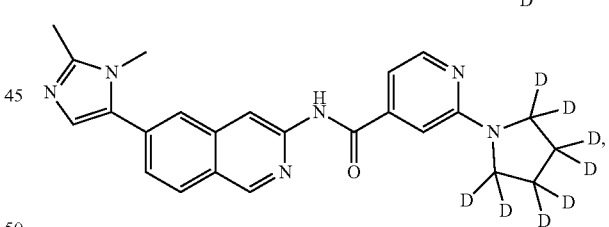

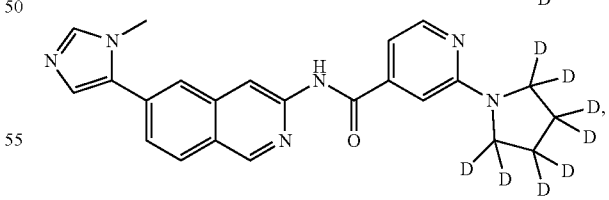

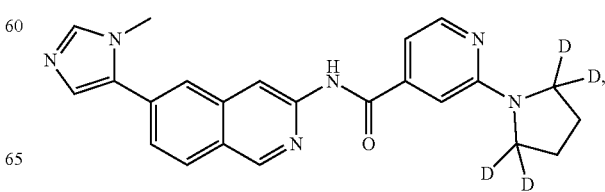

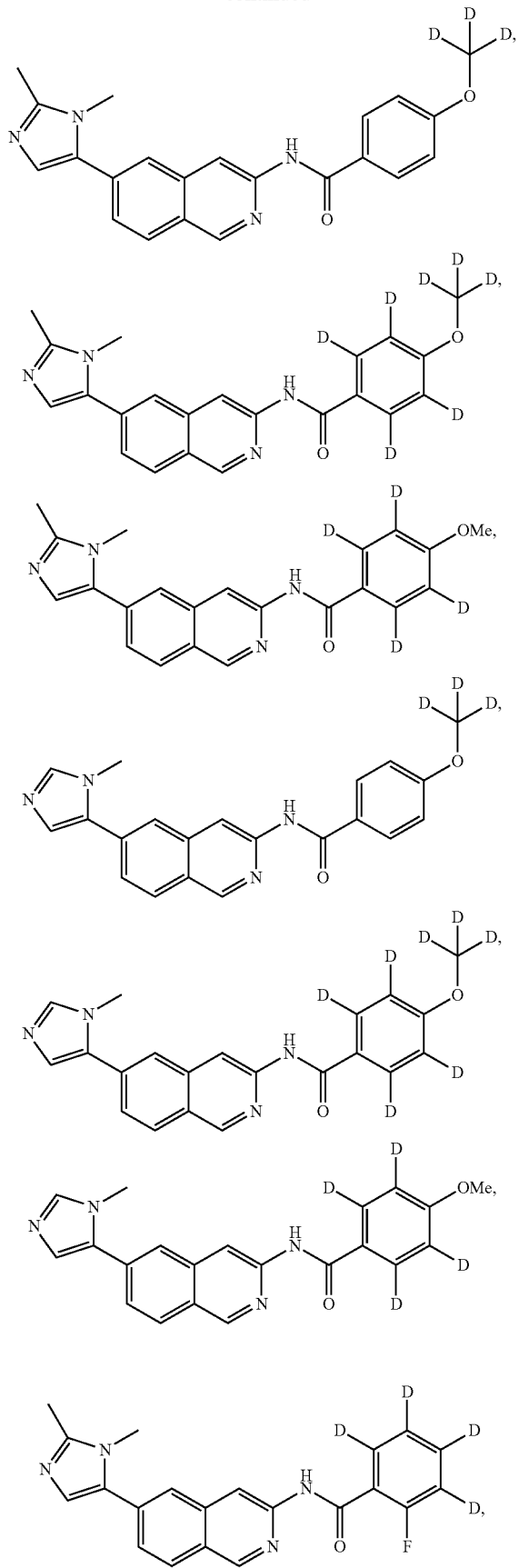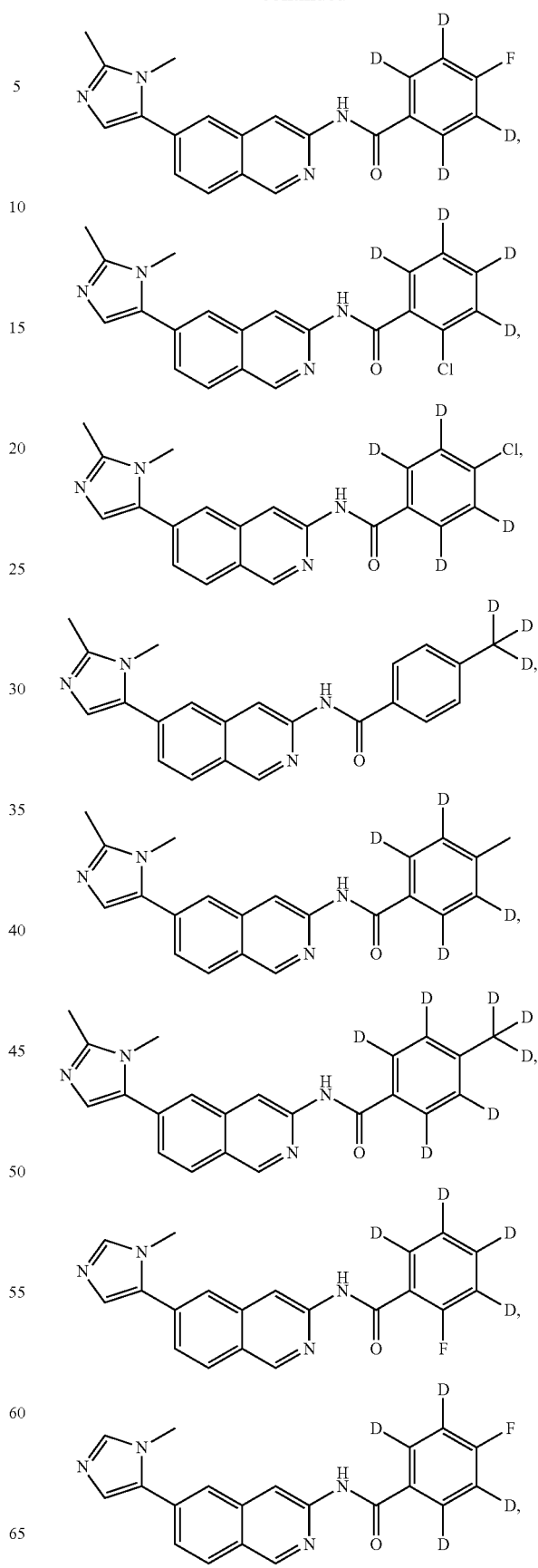

-continued

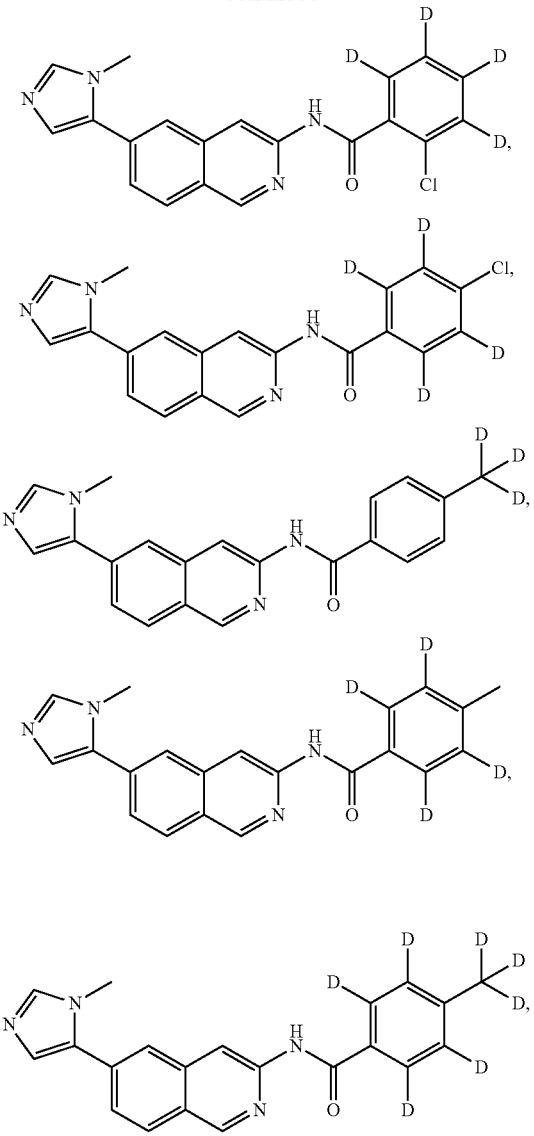

and or a pharmaceutically acceptable salt thereof.

8. A pharmaceutical composition comprising a therapeutically effective amount of a compound of claim 1, or a pharmaceutically acceptable salt thereof, and a pharmaceutically acceptable excipient.

9. A pharmaceutical composition comprising a therapeutically effective amount of a compound of claim 2, or a pharmaceutically acceptable salt thereof, and a pharmaceutically acceptable excipient.

10. A pharmaceutical composition comprising a therapeutically effective amount of a compound of claim 4, or a pharmaceutically acceptable salt thereof, and a pharmaceutically acceptable excipient.

11. A pharmaceutical composition comprising a therapeutically effective amount of a compound of claim 6, or a pharmaceutically acceptable salt thereof, and a pharmaceutically acceptable excipient.

12. The compound of claim 2, wherein $R^3$ is selected from the group consisting of:

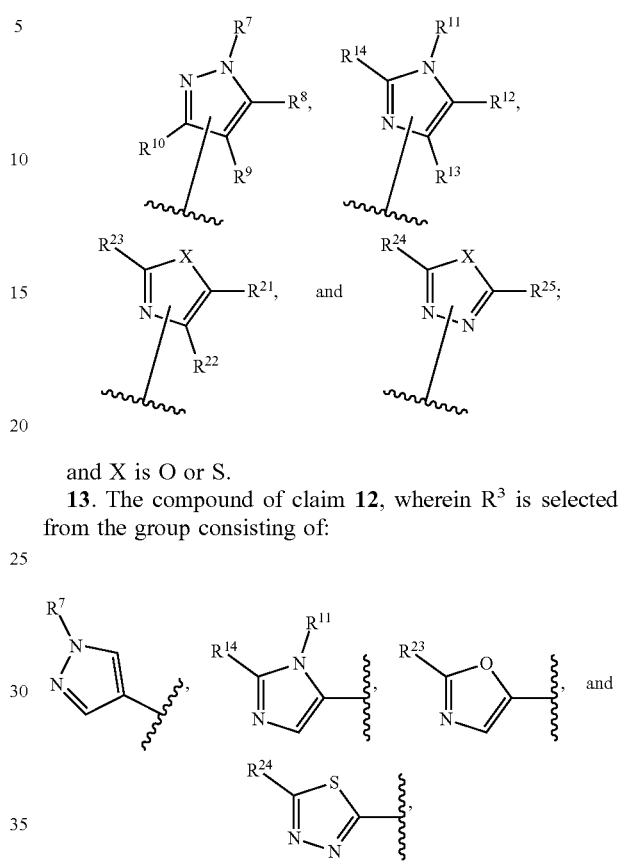

and X is O or S.

13. The compound of claim 12, wherein $R^3$ is selected from the group consisting of:

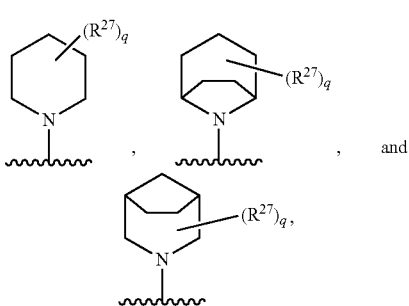

wherein $R^7$ is —$(C_{1-2}$ alkyl), and $R^{11}$, $R^{14}$, $R^{23}$, and $R^{24}$ are independently selected from the group consisting of H and —$(C_{1-2}$ alkyl).

14. The compound of claim 13, wherein $R^6$ is a -heterocyclyl optionally substituted with 1-2 $R^{27}$.

15. The compound of claim 13, wherein $R^6$ is a —$CH_2$heterocyclyl optionally substituted with 1-2 $R^{27}$.

16. The compound of claim 14, wherein $R^6$ is either a piperidinyl or a pyrrolidinyl both optionally substituted with 1-2 $R^{27}$.

17. The compound of claim 13, wherein $R^6$ is selected from the group consisting of

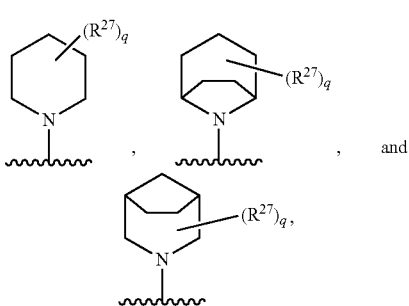

and q is 1.

18. The compound of claim 16, wherein $R^6$ is a piperidinyl substituted with one —$N(R^{43})(R^{44})$.

19. The compound of claim 17, wherein $R^{43}$ is H or Me and $R^{44}$ is —$C_{1-4}$ haloalkyl.

20. The compound of claim 13, wherein $R^6$ is —carbocyclyl substituted with 1-2 $R^{28}$.

21. The compound of claim 4, wherein $R^3$ is selected from the group consisting of a pyrazolyl substituted with one —($C_{1-2}$ alkyl), imidazolyl substituted with 1-2 —($C_{1-2}$ alkyl), oxazolyl substituted with one —($C_{1-2}$ alkyl), and thiadiazolyl substituted with one —($C_{1-2}$ alkyl).

22. The compound of claim 21, wherein $R^6$ is -heterocyclyl optionally substituted with 1-2 $R^{27}$.

23. The compound of claim 22, wherein $R^6$ is selected from the group consisting of

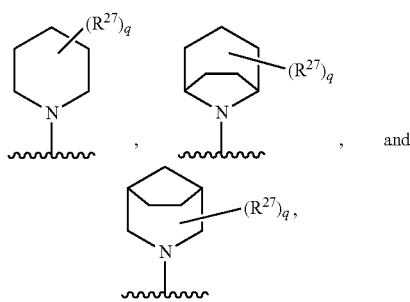

and q is 1.

24. A method of inhibiting one or more proteins in the Wnt pathway, the method comprising contacting a cell with an effective amount of a compound of claim 1, or a pharmaceutically acceptable salt, or a pharmaceutical composition.

25. A method of inhibiting one or more proteins in the Wnt pathway, the method comprising contacting a cell with an effective amount of a compound of claim 2, or a pharmaceutically acceptable salt, or a pharmaceutical composition.

26. A method of inhibiting one or more proteins in the Wnt pathway, the method comprising contacting a cell with an effective amount of a compound of claim 4, or a pharmaceutically acceptable salt, or a pharmaceutical composition.

27. A method of inhibiting one or more proteins in the Wnt pathway, the method comprising contacting a cell with an effective amount of a compound of claim 6, or a pharmaceutically acceptable salt, or a pharmaceutical composition.

28. The method of claim 24, wherein the cell is a human cancerous cell.

29. The method of claim 25, wherein the cell is a human cancerous cell.

30. The method of claim 26, wherein the cell is a human cancerous cell.

31. The method of claim 27, wherein the cell is a human cancerous cell.

32. The method of claim 24, wherein the protein is a kinase and the kinase is selected from the group consisting of DYRK or GSK families of kinases.

33. The method of claim 25, wherein the protein is a kinase and the kinase is selected from the group consisting of DYRK or GSK families of kinases.

34. The method of claim 26, wherein the protein is a kinase and the kinase is selected from the group consisting of DYRK or GSK families of kinases.

35. The method of claim 27, wherein the protein is a kinase and the kinase is selected from the group consisting of DYRK or GSK families of kinases.

* * * * *